US008852912B2

(12) United States Patent
Estell et al.

(10) Patent No.: US 8,852,912 B2
(45) Date of Patent: Oct. 7, 2014

(54) COMPOSITIONS AND METHODS COMPRISING ALPHA-AMYLASE VARIANTS WITH ALTERED PROPERTIES

(75) Inventors: David A. Estell, San Francisco, CA (US); Brian E. Jones, Leidschendam (NL); Marc Kolkman, Oegstgeest (NL); Christian D. Adams, San Francisco, CA (US); Edward M. Concar, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 241 days.

(21) Appl. No.: 13/260,146

(22) PCT Filed: Apr. 1, 2010

(86) PCT No.: PCT/US2010/029659
§ 371 (c)(1),
(2), (4) Date: Nov. 8, 2011

(87) PCT Pub. No.: WO2010/115021
PCT Pub. Date: Oct. 7, 2010

(65) Prior Publication Data
US 2012/0045817 A1    Feb. 23, 2012

Related U.S. Application Data

(60) Provisional application No. 61/165,813, filed on Apr. 1, 2009.

(51) Int. Cl.
| C12P 21/06 | (2006.01) |
| C12N 9/00 | (2006.01) |
| C12N 9/28 | (2006.01) |
| C07K 1/00 | (2006.01) |
| C07H 21/04 | (2006.01) |
| G01N 33/48 | (2006.01) |
| G01N 31/00 | (2006.01) |
| C11D 3/386 | (2006.01) |
| C12N 9/54 | (2006.01) |

(52) U.S. Cl.
CPC .......... *C12N 9/2417* (2013.01); *C11D 3/38681* (2013.01); *C12N 9/54* (2013.01)
USPC .......... 435/202; 435/69.1; 435/183; 530/350; 536/23.2; 702/19; 702/27

(58) Field of Classification Search
None
See application file for complete search history.

(56) References Cited

U.S. PATENT DOCUMENTS

| 3,912,590 A | 10/1975 | Slott et al. |
| 4,106,991 A | 8/1978 | Markussen et al. |
| 4,335,208 A | 6/1982 | Norman |
| 4,435,307 A | 3/1984 | Barbesgaard et al. |
| 4,536,182 A | 8/1985 | Tatin |
| RE32,153 E | 5/1986 | Tamura et al. |
| 4,587,215 A | 5/1986 | Hirsh |
| 4,643,736 A | 2/1987 | Cholley |
| 4,661,452 A | 4/1987 | Markussen et al. |
| 4,683,195 A | 7/1987 | Mullis et al. |
| 4,683,202 A | 7/1987 | Mullis |
| 4,689,297 A | 8/1987 | Good et al. |
| 4,760,025 A | 7/1988 | Estell et al. |
| 5,231,017 A | 7/1993 | Lantero et al. |
| RE34,606 E | 5/1994 | Estell et al. |
| 5,324,649 A | 6/1994 | Arnold et al. |
| 5,340,735 A | 8/1994 | Christianson et al. |
| 5,427,936 A | 6/1995 | Moeller et al. |
| 5,500,364 A | 3/1996 | Christianson et al. |
| 5,648,263 A | 7/1997 | Schulein et al. |
| 5,691,178 A | 11/1997 | Schulein et al. |
| 5,700,676 A | 12/1997 | Bott et al. |
| 5,776,757 A | 7/1998 | Schulein et al. |
| 5,801,039 A | 9/1998 | Maurer et al. |
| 5,814,501 A | 9/1998 | Becker et al. |
| 5,827,718 A | 10/1998 | Ishida et al. |
| 5,855,625 A | 1/1999 | Maurer et al. |
| 5,856,164 A | 1/1999 | Outtrup et al. |
| 5,942,431 A | 8/1999 | Yoneda et al. |
| 5,955,340 A | 9/1999 | Bott et al. |
| 6,077,316 A | 6/2000 | Lund et al. |
| 6,312,936 B1 | 11/2001 | Poulose et al. |
| 6,472,184 B1 | 10/2002 | Hegemann |
| 6,482,628 B1 | 11/2002 | Poulose et al. |
| 6,562,612 B2 | 5/2003 | Jones et al. |
| 7,122,334 B2 | 10/2006 | Schellenberger et al. |
| 8,080,401 B2 | 12/2011 | Bessler et al. |
| 8,153,412 B2 | 4/2012 | Chang et al. |
| 8,224,578 B2 | 7/2012 | Raab et al. |

(Continued)

FOREIGN PATENT DOCUMENTS

| CA | 2202553 | 4/1996 |
| CA | 2821537 | 8/1996 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
BPN' Swissprot Accession No. P00782, *Bacillus amyloliquefaciences (Bacillus velezensis)*, Vasantha, N., et al., Nov. 13, 2013.
Genbank Accession No. AAA63900, alpha-amylase (*Bacillus* sp. TS-23), Lin, L.-L., et al., Oct. 26, 1999.
Genbank Database Accession No. AAA22240, amyS (*Bacillus licheniformis*), Gray, G.L., et al., Apr. 26, 1993.
UniProt Accession No. AAA22241, *Geobacillus stearothermophilus*, Nakajima, R., et al., Oct. 16, 2013.
Genbank Accession No. AAA22191, alpha-amylase protein precursor (Ec 3.2.1.1) (*Bacillus amyloliquefaciens*), Takkinen, K., et al., Apr. 26, 1993.
Genbank Accession No. AAA22231, *Bacillus* sp., Tsukamoto, A., et al., Apr. 26, 1993.

(Continued)

*Primary Examiner* — Christian Fronda
(74) *Attorney, Agent, or Firm* — Danisco US Inc.

(57) ABSTRACT

Described are compositions and methods relating to variant alpha-amylases having altered biochemical properties and advantageous performance characteristics as compared to a reference alpha-amylase. The variants are suitable for use in various industrial applications such as starch conversion, ethanol production, laundry, dishwashing, pulp and paper production, textile desizing, and/or sweetener production.

23 Claims, 11 Drawing Sheets

(56) References Cited

U.S. PATENT DOCUMENTS

| | | |
|---|---|---|
| 8,236,545 B2 | 8/2012 | Cascao-Pereira et al. |
| 8,460,916 B2 | 6/2013 | Cascao-Pereira et al. |
| 8,507,244 B2 | 8/2013 | Shaw et al. |
| 2005/0048611 A1 | 3/2005 | Hoff et al. |
| 2007/0212768 A1 | 9/2007 | Bessler et al. |
| 2008/0090747 A1 | 4/2008 | Augustinus et al. |
| 2013/0344542 A1 | 12/2013 | Cascao-Pereira et al. |

FOREIGN PATENT DOCUMENTS

| | | |
|---|---|---|
| EP | 0063909 | 11/1982 |
| EP | 0135138 | 3/1985 |
| EP | 0200362 | 3/1986 |
| EP | 0201184 | 3/1986 |
| EP | 0218272 | 4/1987 |
| EP | 0260105 | 8/1987 |
| EP | 0238023 | 9/1987 |
| EP | 0238216 | 9/1987 |
| EP | 0252730 | 1/1988 |
| EP | 0258068 | 3/1988 |
| EP | 0305216 | 3/1989 |
| EP | 0331376 | 9/1989 |
| EP | 0407225 | 1/1991 |
| EP | 1199356 | 4/2002 |
| GB | 1240058 | 7/1971 |
| GB | 1296839 | 11/1972 |
| GB | 1372034 | 10/1974 |
| GB | 1483591 | 8/1977 |
| JP | 64/074992 | 3/1989 |
| WO | WO84/02921 | 8/1984 |
| WO | WO86/01831 | 3/1986 |
| WO | WO89/06270 | 7/1989 |
| WO | WO89/06279 | 7/1989 |
| WO | WO89/09259 | 10/1989 |
| WO | WO91/17243 | 11/1991 |
| WO | WO92/00381 | 1/1992 |
| WO | WO92/05249 | 4/1992 |
| WO | WO92/06154 | 4/1992 |
| WO | WO92/06165 | 4/1992 |
| WO | WO92/06221 | 4/1992 |
| WO | WO92/19708 | 11/1992 |
| WO | WO92/19709 | 11/1992 |
| WO | WO92/19729 | 11/1992 |
| WO | WO92/21760 | 12/1992 |
| WO | WO93/24618 | 12/1993 |
| WO | WO94/01541 | 1/1994 |
| WO | WO94/02597 | 2/1994 |
| WO | WO94/18314 | 8/1994 |
| WO | WO94/25578 | 11/1994 |
| WO | WO94/25583 | 11/1994 |
| WO | WO95/02044 | 1/1995 |
| WO | WO95/10602 | 4/1995 |
| WO | WO95/14783 | 6/1995 |
| WO | WO95/14807 | 6/1995 |
| WO | WO95/21247 | 8/1995 |
| WO | WO95/22615 | 8/1995 |
| WO | WO95/22625 | 8/1995 |
| WO | WO95/23221 | 8/1995 |
| WO | WO95/30744 | 11/1995 |
| WO | WO95/35381 | 12/1995 |
| WO | WO96/00292 | 1/1996 |
| WO | WO96/13580 | 5/1996 |
| WO | WO96/23873 | 8/1996 |
| WO | WO96/28567 | 9/1996 |
| WO | WO96/39528 | 12/1996 |
| WO | WO97/04079 | 2/1997 |
| WO | WO97/07202 | 2/1997 |
| WO | WO97/07205 | 2/1997 |
| WO | WO97/42825 | 11/1997 |
| WO | WO97/43424 | 11/1997 |
| WO | WO98/15257 | 4/1998 |
| WO | WO98/20115 | 5/1998 |
| WO | WO98/20116 | 5/1998 |
| WO | WO98/23732 | 6/1998 |
| WO | WO98/30669 | 7/1998 |
| WO | WO98/34946 | 8/1998 |
| WO | WO99/19467 | 4/1999 |
| WO | WO99/20723 | 4/1999 |
| WO | WO99/20770 | 4/1999 |
| WO | WO99/28448 | 6/1999 |
| WO | WO99/29876 | 6/1999 |
| WO | WO 99/29876 A2 * | 6/1999 |
| WO | WO00/04136 | 1/2000 |
| WO | WO00/60060 | 10/2000 |
| WO | WO01/14629 | 3/2001 |
| WO | WO01/34899 | 5/2001 |
| WO | WO01/88107 | 11/2001 |
| WO | WO02/08398 | 1/2002 |
| WO | WO02/14490 | 2/2002 |
| WO | WO02/068589 | 9/2002 |
| WO | WO02/077198 | 10/2002 |
| WO | WO2004/091544 | 10/2004 |
| WO | WO2004/096952 | 11/2004 |
| WO | WO2004/113551 | 12/2004 |
| WO | WO2005/045045 | 5/2005 |
| WO | WO2005/056782 | 6/2005 |
| WO | WO2005/056783 | 6/2005 |
| WO | WO2005/111203 | 11/2005 |
| WO | WO2007/044993 | 4/2007 |
| WO | WO2007/052309 | 5/2007 |
| WO | WO2007/144856 | 12/2007 |
| WO | WO2008/002472 | 1/2008 |
| WO | WO2008/153925 | 12/2008 |
| WO | WO2009/061378 | 5/2009 |
| WO | WO2009/061379 | 5/2009 |
| WO | WO2009/061380 | 5/2009 |
| WO | WO2009/100102 | 8/2009 |

OTHER PUBLICATIONS

Genbank Accession No. AAK00598, (*Bacillus megaterium*), Kim, Y.B., et al., Feb. 2, 2001.
Genbank Accession No. CAL48155, unnamed protein product, partial (*Bacillus* sp.), Bessler, C., et al., Sep. 22, 2006.
Genbank Accession No. AAE00432, Unknown, Outtrup, H., et al., Sep. 29, 1999 (Sequence 2 from Patent US 5856164).
Genbank Accession No. CAC16486, unnamed protein product, partial (*Bacillus* sp.), Borchert, T.V., et al., Nov. 16, 2000.
Genbank Accession No. CAD35985, unnamed protein product (*Bacillus sp.* KSM-AP1378), Araki, H.C., et al., Jun. 20, 2002.
Genbank Accession No. CAJ00040, unnamed protein product (*Bacillus* sp. pHSP-K38), Tohata, M., et al., Jun. 3, 2005.
Li, Y., et al., "Effect of introducing proline residues on the stability of *Aspergillus awamori*." *Protein Eng.* 10(10): 1199-1204, 1997.
Lin, L.-L., et al., "Production and properties of a raw-starch-degrading amylase from the thermophilic and alkaliphilic *Bacillus* sp. TS-23." *Biotechnol. Appl. Biochem.* 28: 61-68, 1998.
Lin, L.-L., et al., "A gene encoding for an α-amylase from thermophilic *Bacillus* sp. Strain TS-23 and its expression in *Escherichia coli*." *J. Appl. Microbiol.* 82:325-334, 1997.
International Search Report and the Written Opinion of the International Searching Authority for International Application No. PCT/US2010/029659 dated Oct. 27, 2010.
International Preliminary Report on Patentability for International Application No. PCT/US2010/029659 dated Oct. 4, 2011.
International Search Report and the Written Opinion of the International Searching Authority for International Application No. PCT/US2010/029666 dated Oct. 27, 2010.
International Preliminary Report on Patentability for International Application No. PCT/US2010/029666 dated Oct. 4, 2011.

\* cited by examiner

```
                    1         11        21        31        41        51
AAA63900   NTAPINETMMQYFEWDLPNDGTLWTKVKNEAANLSSLGITALWLPPAYKGTSQSDVGYGV
AAA22240   --ANLNGTLMQYFEWYMPNDGQHWKRLQNDSAYLAEHGITAVWIPPAYKGTSQADVGYGA
AAA22241   -AAPFNGTMMQYFEWYLPDDGTLWTKVANEANNLSSLGITALWLPPAYKGTSRSDVGYGV
AAA22191   ----VNGTLMQYFEWYTPNDGQHWKRLQNDAEHLSDIGITAVWIPPAYKGLSQSDNGYGP
AAA22231   HHNGTNGTMMQYFEWYLPNDGNHWNRLNSDASNLKSKGITAVWIPPAWKGASQNDVGYGA
AAK00598   -DTVNNGTLMQYFEWYAPNDGNHWNRLRTDAENLAQKGITSVWIPPAYKGTTQNDVGYGA
CAL48155   HHNGTNGTMMQYFEWYLPNDGNHWNRLRSDASNLKDKGITAVWIPPAWKGASQNDVGYGA
AAE00432   HHNGTNGTMMQYFEWHLPNDGNHWNRLRDDASNLRNRGITAIWIPPAWKGTSQNDVGYGA
CAC16486   HHNGTNGTMMQYFEWYLPNDGNHWNRLRSDASNLKDKGISAVWIPPAWKGASQNDVGYGA
CAD35985   HHNGTNGTMMQYFEWHLPNDGNHWNRLRDDAANLKSKGITAVWIPPAWKGTSQNDVGYGA
CAJ00040   ---DGLNGTMMQYYEWHLENDGQHWNRLHDDAAALSDAGITAIWIPPAYKGNSQADVGYGA 61        71        81        91       101       111
AAA63900   YDLYDLGEFNQKGTIRTKYGTKTQYIQAIQAAKAAGMQVYADVVFNHKAGADGTEFVDAV
AAA22240   YDLYDLGEFHQKGTVRTKYGTKGELQSAIKSLHSRDINVYGDVVINHKGADATEDVTAV
AAA22241   YDLYDLGEFNQKGTVRTKYGTKAQYLQAIQAAHAAGMQVYADVVFDHKGGADGTEWVDAV
AAA22191   YDLYDLGEFQQKGTVRTKYGTKSELQDAIGSLHSRNVQVYGDVVLNHKAGADATEDVTAV
AAA22231   YDLYDLGEFNQKGTVRTKYGTRSQLQAAVTSLKNNGIQVYGDVVMNHKGGADATEMVRAV
AAK00598   YDLYDLGEFNQKGTVRTKYGTKAQLKSAIDALHKKNIDVYGDVVMNHKGGADYTETVTAV
CAL48155   YDLYDLGEFNQKGTVRTKYGTRNQLQAAVTALKSNGIQVYGDVVMNHKGGADATEWVRAV
AAE00432   YDLYDLGEFNQKGTVRTKYGTRSQLESAIHALKNNGVQVYGDVVMNHKGGADATENVLAV
CAC16486   YDLYDLGEFNQKGTIRTKYGTRNQLQAAVNALKSNGIQVYGDVVMNHKGGADATEMVRAV
CAD35985   YDLYDLGEFNQKGTVRTKYGTRSQLQGAVTSLKNNGIQVYGDVVMNHKGGADGTEMVNAV
CAJ00040   YDLYDLGEFNQKGTVRTKYGTKAQLERAIGSLKSNDINVYGDVVMNHKMGADFTEAVQAV 121       131       141       151       161       171
AAA63900   EVDPSNRNQETSGTYQIQAWTKFDFPGRGNTYSSFKWRWYHFDGTDWDESRKL-NRIYKF
AAA22240   EVDPADRNRVISGEHLIKAWTHFHFPGRGSTYSDFKWHWYHFDGTDWDESRKL-NRIYKF
AAA22241   EVNPSDRNQEISGTYQIQAWTKFDFNGRGNTYSSFKWRWYHFDGVDWDESRKL-SRIYKF
AAA22191   EVNPANRNQETSEEYQIKAWTDFRFPGRGNTYSDFKWHWYHFDGADWDESRKI-SRIFKF
AAA22231   EVNPNNRNQEVTGEYTIEAWTRFDFPGRGNTHSSFKWRWYHFDGVDWDQSRRLNNRIYKF
AAK00598   EVDPSNRNVEVSGDYEISAWTGFNFPGRGDSYSNFKWKWYHFDGTDWDEGRKL-NRIYKF
CAL48155   EVNPSNRNQEVSGDYTIEAWTKFDFPGRGNTHSNFKWRWYHFDGVDWDQSRQLQNRIYKF
AAE00432   EVNPNRNQEISGDYTIEAWTKFDFPGRGNTYSDFKWRWYHFDGVDWDQSRQFQNRIYKF
CAC16486   EVNPNNRNQEVSGEYTIEAWTKFDFPGRGNTHSNFKWRWYHFDGVDWDQSRKLNNRIYKF
CAD35985   EVNRSNRNQEISGEYTIEAWTKFDFPGRGNTHSNFKWRWYHFDGTDWDQSRQLQNKIYKF
CAJ00040   QVNPTNRWQDISGAYTIDAWTGFDFSGRNNAYSDFKWRWFHFNGVDWDQRYQE-NHIFRF 181       191       201       211       221       231
AAA63900   RSTGKAWDWEVDTENGNYDYLMFADLDMDHPEVVTELKNWGTWYVNTTNIDGFRLDAVKH
AAA22240   QG--KAWDWEVSNENGNYDYLMYADIDYDHPDVAAEIKRWGTWYANELQLDGFRLDAVKH
AAA22241   RGIGKAWDWEVDTENGNYDYLMYADLDMDHPEVVTELKNWGKWYVNTTNIDGFRLDAVKH
AAA22191   RGEGKAWDWEVSSENGNYDYLMYADVDYDHPDVVAETKKWGIWYANELSLDGFRIDAAKH
AAA22231   RGHGKAWDWEVDTENGNYDYLMYADIDMDHPEVVNELRNWGVWYTNTLGLDGFRIDAVKH
AAK00598   RGIGKAWDWEVSSENGNYDYLMYADLDFDHPDVANEMKKWGTWYANELNLDGFRLDAVKH
CAL48155   RGDGKGWDWEVDTENGNYDYLMYADIDMDHPEVVNELRNWGVWYTNTLGLDGFRIDAVKH
AAE00432   RGDGKAWDWEVDSENGNYDYLMYADVDMDHPEVVNELRRWGEWYTNTLNLDGFRIDAVKH
CAC16486   RGDGKGWDWEVDTENGNYDYLMYADIDMDHPEVVNELRNWGVWYTNTLGLDGFRIDAVKH
CAD35985   RGTGKAWDWEVDIENGNYDYLMYADIDMDHPEVINELRNWGVWYTNTLNLDGFRIDAVKH
CAJ00040   AN--TNWNWRVDEENGNYDYLLGSNIDFSHPEVQDELKDWGSWFTDELDLDGYRLDAIKH
```

Figure 1

```
           241       251       261       271       281       291
AAA63900   IKYSFFPDWLTYVRNQTGKNLFAVGEFWSYDVNKLHNYITKTNGSMSLFDAPLHNNFYTA
AAA22240   IKFSFLRDWVNHVREKTGKEMFTVAEYWQNDLGALENYLNKTNFNHSVFDVPLHYQFHAA
AAA22241   IKFSFFPDWLSYVRSQTGKPLFTVGEYWSYDINKLHNYITKTNGTMSLFDAPLHNKFYTA
AAA22191   IKFSFLRDWVQAVRQATGKEMFTVAEYWQNNAGKLENYLNKTSFNQSVFDVPLHFNLQAA
AAA22231   IKYSFTRDWINHVRSATGKNMFAVAEFWKNDLGAIENYLQKTNWNHSVFDVPLHYNLYNA
AAK00598   IDHEYLRDWVNHVRQQTGKEMFAVAEYWQNDIQTLNNYLAKVNYNQSVFDAPLHYNFHYA
CAL48155   IKYSFTRDWLTHVRNTTGKNMFAVAEFWKNDIGAIENYLSKTNWNHSVFDVPLHYNLYNA
AAE00432   IKYSFTRDWLTHVRNATGKEMFAVAEFWKNDLGALENYLNKTNWNHSVFDVPLHYNLYNA
CAC16486   IKYSFTRDWINHVRSATGKNMFAVAEFWKNDLGAIENYLNKTNWNHSVFDVPLHYNLYNA
CAD35985   IKYSYTRDWLTHVRNTTGKPMFAVAEFWKNDLAAIENYLNKTSWNHSVFDVPLHYNLYNA
CAJ00040   IPFWYTSDWVRHQRNEADQDLFVVGEYWKDDVGALEFYLDEMNWEMSLFDVPLNYNFYRA 301       311       321       331       341       351
AAA63900   SKSSGYFDMRYLLNNTLMKDQPSLAVTLVDNHDTQPGQSLQSWVEPWFKPLAYAFILTRQ
AAA22240   STQGGGYDMRKLLNGTVVSKHPLKSVTFVDNHDTQPGQSLESTVQTWFKPLAYAFILTRE
AAA22241   SKSGGAFDMSTLMNNTLMKDQPTLAVTFVDNHDTEPGQALQSWVDPWFKPLAYAFILTRQ
AAA22191   SSQGGGYDMRRLLDGTVVSRHPEKAVTFVENHDTQPGQSLESTVQTWFKPLAYAFILTRE
AAA22231   SKSGGNYDMRNIFNGTVVQRHPSHAVTFVDNHDSQPBEALESFVEEWFKPLAYALTLTRE
AAK00598   SKGNGNYDMRNILKGTVVANHPTLAVTLVENHDSQPGQSLESVVSPWFKPLAYAFILTRA
CAL48155   SRSGGNYDMRQIFNGTVVQRHPTHAVTFVDNHDSQPEEALESFVEEWFKPLAYALTLTRD
AAE00432   SNSGGNYDMAKLLNGTVVQKHPMHAVTFVDNHDSQPGESLESFVQEWFKPLAYALILTRE
CAC16486   SKSGGNYDMRQIFNGTVVQRHPMHAVTFVDNHDSQPEEALESFVEEWFKPLAYALTLTRE
CAD35985   SNSGGYFDMRNILNGSVVQKHPIHAVTFVDNHDSQPGEALESFVQSWFKPLAYALILTRE
CAJ00040   SQQGGSYDMRNILRGSLVEAHPMHAVTFVDNHDTQPGESLESWVADWFKPLAYATILTRE 361       371       381       391       401       411
AAA63900   EGYPCVFYGDYYGI---PKYNIPGLKSKIDPLLIARRDYAYGTQRDYIDHQDIIGWTREG
AAA22240   SGYPQVFYGDMYGTKGDSQREIPALKHKIEPILKARKQYAYGAQHDYFDHHDIVGWTREG
AAA22241   EGYPCVFYGDYYGI---PQYNIPSLKSKIDPLLIARRDYAYGTQHDYLDHSDIIGWTREG
AAA22191   SGYPQVFYGDMYGTKGTSPKEIPSLKDNIEPILKARKEYAYGPQHDYIDHPDVIGWTREG
AAA22231   QGYPSVFYGDYYGI---PTHGVPAMRSKIDPILEARQKYAYGKQNDYLDHHNIIGWTREG
AAK00598   EGYPSVFYGDYYGTKGNSNYEIPALKDKIDPILTARKNYAYGTQRDYFDHPDVIGWTREG
CAL48155   QGYPSVFYGDYYGI---PTHGVPAMKSKIDPILEARQKYAYGKQNDYLDHHNMIGWTREG
AAE00432   QGYPSVFYGDYYGI---PTHSVPAMKAKIDPILEARQNFAYGTQHDYFDHHNIIGWTREG
CAC16486   QGYPSVFYGDYYGI---PTHGVPAMKSKIDPILEARQKYAYGRQNDYLDHHNIIGWTREG
CAD35985   QGYPSVFYGDYYGI---PTHGVPSMKSKIDPLLQARQTYAYGTQHDYFDHHDIIGWTREG
CAJ00040   GGYPNVFYGDYYGI---PNDNISAKKDMIDELLDARQNYAYGTQHDYFDHWDVVGWTREG 421       431       441       451       461       471
AAA63900   IDTKPNSGLAALITDGPGGSKWMYVGKKHAGKVFYDLTGNRSDTVTINADGWGEFKVNGG
AAA22240   DSSVANSGLAALITDGPGGAKRMYVGRQNAGETWHDITGNRSEPVVINSEGWGEFHVNGG
AAA22241   VTEKPGSGLAALITDGPGGSKWMYVGKQHAGKVFYDLTGNRSDTVTINSDGWGEFKVNGG
AAA22191   DSSAAKSGLAALITDGPGGSKRMYAGLKNAGETWYDITGNRSDTVKIGSDGWGEFHVNDG
AAA22231   NTAHPNSGLATIMSDGAGGSKWMFVGRNKAGQVWSDITGNRTGTVTINADGWGNFSVNGG
AAK00598   DSVHANSGLATLISDGPGGAKWMDVGKNNAGEIWYDITGNQTNTVTINKDGWGQFQVSGG
CAL48155   NTAHPNSGLATIMSDGPGGNKWMYVGRNKAGQVWRDITGNRSGTVTINADGWGNFSVNGG
AAE00432   NTTHPNSGLATIMSDGPGGEKWMYVGQNKAGQVWHDITGNKPGTVTINADGWANFSVNGG
CAC16486   NTAHPNSGLATIMSDGAGGNKWMFVGRNKAGQVWTDITGNRAGTVTINADGWGNFSVNGG
CAD35985   DSSHPNSGLATIMSDGPGGNKWMYVGKHHAGQVWRDITGNRSGTVTINADGWGNFTVNGG
CAJ00040   SSSRPNSGLATIMSNGPGGSKWMYVGRQNAGQTWTDLTGNNGASVTINGDGWGEFFTNGG
```

Figure 1 (cont.)

```
            481
AAA63900    SVSIWVAK--------------------------------  (SEQ ID NO: 2)
AAA22240    SVSIYVQR--------------------------------  (SEQ ID NO: 5)
AAA22241    SVSVWVPRKTTVSTIAWPITTRPWTGEFVRWTEPRLVAWP  (SEQ ID NO: 6)
AAA22191    SVSIYVQK--------------------------------  (SEQ ID NO: 7)
AAA22231    SVSIWVNK--------------------------------  (SEQ ID NO: 8)
AAK00598    SVSIYVQR--------------------------------  (SEQ ID NO: 9)
CAL48155    SVSIWVNN--------------------------------  (SEQ ID NO: 10)
AAE00432    SVSIWVKR--------------------------------  (SEQ ID NO: 11)
CAC16486    SVSIWVNK--------------------------------  (SEQ ID NO: 12)
CAD35985    AVSVWVKQ--------------------------------  (SEQ ID NO: 13)
CAJ00040    SVSVYVNQ--------------------------------  (SEQ ID NO: 14)
```

COMPOSITIONS AND METHODS COMPRISING ALPHA-AMYLASE VARIANTS WITH ALTERED PROPERTIES

PRIORITY

The present application claims priority to U.S. Provisional Application Ser. No. 61/165,813, filed on Apr. 1, 2009, and PCT Application No. PCT/US2010/029659, filed on Apr. 1, 2010, each of which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "31384US2A_SEQLIST", created on Sep. 19, 2011, which is 69,697 bytes in size.

TECHNICAL FIELD

Described are compositions and methods relating to variant alpha-amylases having altered biochemical properties and advantageous performance characteristics as compared to a reference alpha-amylase. The variants are suitable for use in various industrial applications such as starch conversion, ethanol production, laundry, dishwashing, pulp and paper production, textile desizing, and/or sweetener production.

BACKGROUND

Starch is of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units. Its MW may be as high as 100 million.

Sugars from starch, in the form of concentrated dextrose syrups, are currently produced by an enzyme catalyzed process involving: (1) liquefaction (or thinning) of solid starch with an α-amylase into dextrins having an average degree of polymerization of about 7-10; and (2) saccharification of the resulting liquefied starch (i.e., starch hydrolysate) with amyloglucosidase (also called glucoamylase or GA). The resulting syrup has a high glucose content. Much of the glucose syrup, which is commercially produced, is subsequently enzymatically isomerized to a dextrose/fructose mixture known as isosyrup.

Alpha (α)-Amylases (α-1,4-glucan-4-glucanohydrolases, E.C. 3.2.1.1) are a group of enzymes that hydrolyze starch, glycogen, and related polysaccharides by cleaving internal α-1,4-glucosidic bonds at random. This enzyme class has a number of important commercial applications in, for example, in the initial stages (liquefaction) of starch processing, in textile desizing, in deinking of recycled paper, in starch modification in the paper and pulp industry, in wet corn milling, in alcohol production, in sweetener (e.g., sugar) manufacture, in the beverage industry, in brewing, in oilfields, in animal feed, and as cleaning agents in detergent matrices. For example, such enzymes can be used to remove starchy stains during dishwashing and laundry washing.

α-amylases are isolated from a wide variety of bacterial, fungal, plant and animal sources. Industrially, many important α-amylases are those isolated from Bacilli. One characterized α-amylase is that of an alkaliphilic Bacillus sp. strain TS-23 which produces at least five kinds of enzymes exhibiting starch hydrolyzing activity. (Lin et al., Biotechnol Appl Biochem, 28:61-68, 1998). The α-amylase of Bacillus sp. no. TS-23 has a pH optimum of 9 although it is stable over a broad pH range (i.e., pH 4.7 to 10.8). Its temperature optimum is 45° C., although the enzyme has activity at lower temperatures, e.g., 15-20° C.

There remains a need for variant amylases (e.g., α-amylases) that possess altered biochemical characteristics and offer improved performance in industrial applications.

SUMMARY

Described are compositions and methods relating to variant alpha-amylases having altered biochemical properties and advantageous performance characteristics as compared to a reference alpha-amylase. The variants are suitable for use in various industrial applications such as starch conversion, ethanol production, laundry, dishwashing, pulp and paper production, textile desizing, and/or sweetener production.

In one aspect, an isolated alpha-amylase variant is provided, wherein the variant is a mature form of alpha-amylase having amylase activity, and comprising a substitution at one or more positions selected from the group consisting of 1, 2, 3, 4, 5, 7, 15, 16, 17, 18, 19, 22, 25, 26, 28, 29, 30, 32, 35, 36, 37, 50, 51, 52, 53, 54, 55, 56, 59, 60, 70, 71, 72, 73, 75, 78, 83, 87, 90, 91, 93, 94, 95, 104, 105, 107, 108, 110, 112, 113, 116, 118, 125, 126, 128, 129, 130, 131, 134, 136, 138, 142, 144, 147, 149, 150, 152, 154, 156, 158, 160, 161, 162, 165, 166, 168, 169, 170, 172, 174, 177, 178, 182, 183, 185, 189, 192, 195, 197, 201, 202, 203, 207, 210, 214, 217, 221, 228, 234, 236, 237, 246, 250, 254, 255, 257, 264, 267, 269, 270, 272, 275, 279, 283, 284, 298, 301, 303, 305, 306, 310, 311, 314, 318, 319, 320, 322, 323, 336, 337, 338, 339, 340, 344, 359, 374, 375, 376, 377, 379, 381, 382, 393, 394, 399, 401, 407, 408, 419, 433, 436, 438, 444, 447, 448, 451, 453, 459, 465, 470, 475, 476, 483, and 484; wherein the positions correspond to amino acid residues in the amino acid sequence set forth in SEQ ID NO: 2; and wherein the substitution of the naturally-occurring amino acid residue at the one or more positions for a different amino acid residue produces an alpha-amylase variant having a performance index >1.0 for a measure of stability, and a performance index >1.0 for a measure of activity.

In some embodiments, the alpha-amylase variant comprises a substitution at one or more positions selected from the group consisting of 7, 29, 35, 53, 60, 72, 87, 108, 116, 126, 128, 129, 130, 131, 134, 136, 138, 142, 156, 161, 165, 178, 182, 185, 189, 192, 195, 197, 202, 210, 214, 217, 221, 234, 246, 269, 303, 310, 337, 340, 374, 401, and 438, and wherein the substitution of the naturally-occurring amino acid residue for a different amino acid residue, produces an alpha-amylase variant having a performance index >1.5 for a measure of activity and a performance index >1.0 for a measure of stability.

In some embodiments, the alpha-amylase variant comprises a substitution at one or More positions selected from the group consisting of 2, 7, 22, 25, 28, 30, 37, 70, 75, 83, 87, 91, 93, 108, 128, 160, 165, 178, 182, 183, 217, 269, 270, 279, 283, 298, 305, 306, 310, 320, 374, 375, 376, 407, 419, 475, and 476, wherein the substitution of the naturally-occurring amino acid residue for a different amino acid residue, produces an alpha-amylase variant having a performance index >1.5 for a measure of stability and a performance index >1.0 for a measure of activity.

In some embodiments, the alpha-amylase variant comprises a substitution at one or more positions selected from the group consisting of 83, 125, 128, 131, 160, 178, 182, 183, 185, 189, 279, 305, 319, 320, 379, 407, 433, 453, 475, 476, and 483.

In a related aspect, an isolated alpha-amylase variant is provided, comprising a substitution at one or more positions selected from the group consisting of 83, 125, 128, 131, 160, 178, 182, 183, 185, 189, 279, 305, 319, 320, 379, 407, 433, 453, 475, 476, and 483, wherein the positions correspond to amino acid residues in the amino acid sequence set forth in SEQ ID NO: 2, and wherein the substitution provides at least one beneficial effect selected from the group consisting of improved cleaning performance, improved detergent stability, improved thermostability, and improved protein expression.

In another related aspect, an isolated alpha-amylase variant is provided, wherein the variant is a mature form of alpha-amylase having amylase activity and comprising a substitution at one or more positions selected from the group consisting of 5, 32, 83, 95, 154, 214, 221, 228, 322, 401, 407, 419, 444, 447, 459, 470, 483, and 484; wherein the positions correspond to amino acid residues in the amino acid sequence set forth in SEQ ID NO: 2; and wherein the substitution of the naturally-occurring amino acid residue for a different amino acid residue, produces an alpha-amylase variant having a performance index value of 0.5 or better for activity at pH 8, activity at pH 10, activity at 16° C., and activity at 32° C., and a performance index value of 0.5 or better for stability in detergent and for thermostability.

In some embodiments, the different amino acid residue is selected from the group consisting of A, C, D, E, F, G, H, I, K, L, M, N, P, Q, R, S, T, V, W, and Y, with the proviso that the different amino acid residue is different from the naturally-occurring amino acid residue.

In some embodiments, the alpha-amylase variant further comprises a substitution at position 243 corresponding to the amino acid sequence set forth in SEQ ID NO: 2. In some embodiments, any of the aforementioned alpha-amylase variants further comprise a deletion at position 180 and/or position 181, corresponding to the amino acid sequence set forth in SEQ ID NO: 2.

In some embodiments, the alpha-amylase variant is derived from a parent alpha-amylase having an amino acid sequence that is at least 75% identical to an amino acid sequence selected from the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

In some embodiments, the alpha-amylase variant has at least 75% sequence identity with the amino acid sequence set forth in SEQ ID NO: 2. In some embodiments, the alpha-amylase variant has at least 80% sequence identity with the amino acid sequence set forth in SEQ ID NO: 2. In some embodiments, the alpha-amylase variant has at least 90% sequence identity with the amino acid sequence set forth in SEQ ID NO: 2.

In some embodiments, the alpha-amylase variant comprises a substitution at one or more positions selected from the group consisting of 128, 178, 182, 185, and 189 corresponding to the amino acid sequence set forth in SEQ ID: 2, wherein the substitution provides improved cleaning performance or improved detergent stability.

In some embodiments, the alpha-amylase variant comprises:
  (a) an alanine at position 125,
  a cysteine at position 128,
  an isoleucine at position 131,
  an isoleucine at position 165,
  a leucine at position 178,
  a glycine at position 182,
  a tyrosine at position 202,
  an arginine at position 305,
  a threonine at position 319, or
  an arginine at position 475;
  (b) the substitutions N128C+K178L+T182G+Y305R+G475K, and
  at least one additional substitution selected from the group consisting of S125A, T131I, T165I, F202Y, and D319T; or
  (c) the substitutions
  N128C+K178L+T182G+F202Y+Y305R+D319T+G475K,
  S125A+N128C+K178L+T182G+Y305R+G475K, or
  S125A+N128C+T131I+T165I+K178L+T182G+Y305R+G475K;
  wherein the variant optionally further comprises a substitution at position 243 and/or a deletion at position 180 and/or position 181; and
  wherein the positions correspond to the amino acid sequence set forth in SEQ ID NO: 2.

In some embodiments, the alpha-amylase variant comprises a substitution at position 475. In some embodiments, the alpha-amylase variant comprises an arginine at position 475. In some embodiments, the alpha-amylase variant further comprising a substitution at position 243 and/or a deletion at position 180 and/or position 181.

In another aspect, an isolated alpha-amylase variant is provided, wherein the variant is a mature form having amylase activity and comprising a substitution at one or more positions selected from the group consisting of: 1, 2, 3, 4, 5, 7, 15, 16, 17, 18, 19, 22, 25, 26, 28, 29, 30, 32, 35, 36, 37, 50, 51, 52, 53, 54, 55, 56, 57, 59, 60, 70, 71, 72, 73, 75, 78, 82, 83, 87, 90, 91, 93, 94, 95, 103, 104, 105, 107, 108, 110, 112, 113, 114, 115, 116, 118, 121, 123, 125, 126, 127, 128, 129, 130, 131, 132, 134, 135, 136, 138, 140, 142, 144, 147, 149, 150, 152, 154, 156, 158, 159, 160, 161, 162, 164, 165, 166, 167, 168, 169, 170, 171, 172, 174, 175, 176, 177, 178, 179, 182, 183, 185, 186, 188, 189, 190, 191, 192, 193, 195, 197, 199, 200, 201, 202, 203, 207, 210, 214, 217, 221, 228, 234, 237, 238, 239, 240, 246, 250, 254, 255, 257, 264, 266, 267, 268, 269, 270, 272, 273, 275, 279, 283, 284, 298, 301, 303, 305, 306, 310, 311, 314, 318, 319, 320, 322, 323, 336, 337, 338, 339, 340, 344, 359, 374, 375, 376, 377, 379, 381, 382, 393, 394, 399, 401, 407, 408, 419, 433, 436, 438, 444, 447, 448, 451, 453, 459, 465, 479, 475, 483, and 484; wherein the positions are numbered by correspondence with the amino acid sequence of a reference alpha-amylase set forth as SEQ ID NO: 2. In some embodiments, the substitution at one or more positions is a substitution at 1, 2, 3, 4, 5, 6, 7, 8, 9, or 10 positions.

In some embodiments, the alpha-amylase variant is derived from a parent alpha-amylase selected from the group consisting of BASE, ACE, ACE-Q, and ACE-QK. In some embodiments, the alpha-amylase variant is derived from a parent alpha-amylase with the amino acid sequence at least 75% identical to a member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

In another aspect, an isolated nucleic acid encoding an alpha-amylase variant is provided. In a related aspect, an expression vector comprising the isolated nucleic acid in operable combination with a promoter is provided. In a further aspect, a host cell comprising the expression vector is provided.

In another aspect, a cleaning composition comprising the alpha-amylase variant is provided. In some embodiments, the cleaning composition further comprises at least one additional enzyme selected from the group consisting of a protease, a lipase, a cutinase, a carbohydrase, a cellulase, a pectinase, a mannanase, an arabinase, a galactanase, a xylanase, an oxidase, a perhydrolase, a pectate lyase, and a peroxidase. In some embodiments, the at least one additional enzyme is a protease. In some embodiments, the at least one additional enzyme is a subtilisin. In some embodiments, the at least one additional enzyme is subtilisin BPN' or a variant, thereof. In particular embodiments, the at least one additional enzyme is subtilisin BPN'Y217L or a variant, thereof.

In another aspect, a method of cleaning a fabric or hard surface is provided, comprising contacting the fabric or hard surface with the cleaning composition as described. In some embodiments, the cleaning composition further comprises at least one surfactant. In some embodiments, the cleaning composition further comprises at least one additional enzyme selected from the group consisting of a protease, a lipase, a cutinase, a carbohydrase, a cellulase, a pectinase, a mannanase, an arabinase, a galactanase, a xylanase, an oxidase, a perhydrolase, a pectate lyase, and a peroxidase. In some embodiments, the at least one additional enzyme is a protease. In some embodiments, the at least one additional enzyme is a subtilisin. In some embodiments, the at least one additional enzyme is BPN'Y217L subtilisin.

In particular embodiments, the alpha-amylase variant comprises the substitutions:

N128C+K178L+T182G+F202Y+S243Q+Y305R+ D319T+G475K;

S125A+N128C+K178L+T182G+S243Q+Y305R+ G475K; or

S125A+N128C+T131I+T165I+K178L+T182G+S243Q+ Y305R+G475K.

In some related embodiments, the disclosure provides an isolated alpha-amylase variant, wherein the variant is a mature form having amylase activity and comprising a substitution at one or more (preferably 1, 2, 3, 4, 5, 6, 7, 8, 9, 10 or more) positions selected from the group consisting of: 1, 2, 3, 4, 5, 7, 15, 16, 17, 18, 19, 22, 25, 26, 28, 29, 30, 32, 35, 36, 37, 50, 51, 52, 53, 54, 55, 56, 57, 59, 60, 70, 71, 72, 73, 75, 78, 82, 83, 87, 90, 91, 93, 94, 95, 103, 104, 105, 107, 108, 110, 112, 113, 114, 115, 116, 118, 121, 123, 125, 126, 127, 128, 129, 130, 131, 132, 134, 135, 136, 138, 140, 142, 144, 147, 149, 150, 152, 154, 156, 158, 159, 160, 161, 162, 164, 165, 166, 167, 168, 169, 170, 171, 172, 174, 175, 176, 177, 178, 179, 182, 183, 185, 186, 188, 189, 190, 191, 192, 193, 195, 197, 199, 200, 201, 202, 203, 207, 210, 214, 217, 221, 228, 234, 237, 238, 239, 240, 243, 246, 250, 254, 255, 257, 264, 266, 267, 268, 269, 270, 272, 273, 275, 279, 283, 284, 298, 301, 303, 305, 306, 310, 311, 314, 318, 319, 320, 322, 323, 336, 337, 338, 339, 340, 344, 359, 374, 375, 376, 377, 379, 381, 382, 393, 394, 399, 401, 407, 408, 419, 433, 436, 438, 444, 447, 448, 451, 453, 459, 465, 479, 475, 483, and 484, and wherein the positions are numbered by correspondence with the amino acid sequence of a reference alpha-amylase set forth as SEQ ID NO:2. In one embodiment, the alpha-amylase variant is derived from a parent alpha-amylase selected from the group consisting of BASE, ACE, ACE-Q, and ACE-QK. In another embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to a member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In a preferred embodiment, the positions are selected from the group consisting of: 1, 2, 3, 4, 5, 7, 16, 17, 18, 19, 22, 25, 26, 28, 29, 30, 32, 35, 36, 37, 57, 60, 70, 71, 72, 73, 75, 78, 82, 83, 87, 90, 91, 93, 94, 95, 103, 104, 105, 108, 112, 114, 115, 116, 118, 121, 123, 125, 126, 128, 129, 130, 131, 132, 134, 135, 136, 138, 140, 142, 144, 147, 149, 150, 152, 154, 156, 158, 159, 160, 161, 162, 164, 165, 166, 167, 168, 169, 171, 172, 174, 175, 176, 177, 178, 179, 182, 183, 185, 186, 189, 190, 191, 192, 193, 195, 197, 199, 202, 207, 214, 217, 221, 228, 234, 237, 238, 243, 246, 250, 254, 255, 257, 264, 266, 267, 268, 269, 270, 272, 273, 275, 279, 283, 284, 298, 301, 303, 305, 306, 310, 311, 318, 319, 320, 322, 323, 336, 337, 338, 339, 340, 344, 359, 374, 375, 376, 377, 379, 381, 382, 393, 394, 399, 401, 407, 408, 419, 433, 436, 438, 447, 451, 453, 459, 465, 479, 475, and 483, and wherein the positions are numbered by correspondence with the amino acid sequence of a reference alpha-amylase set forth as SEQ ID NO:2. In yet another embodiment, the positions are selected from the group consisting of: 1, 2, 3, 4, 5, 7, 16, 17, 18, 19, 22, 25, 26, 28, 29, 30, 32, 35, 36, 37, 57, 60, 70, 71, 72, 73, 75, 78, 82, 83, 90, 91, 93, 94, 95, 103, 104, 105, 108, 112, 114, 115, 116, 118, 121, 123, 125, 126, 128, 129, 130, 131, 132, 134, 135, 136, 138, 140, 142, 144, 147, 149, 150, 152, 154, 156, 158, 159, 160, 161, 162, 164, 165, 166, 167, 168, 169, 171, 172, 174, 175, 176, 177, 178, 179, 185, 186, 189, 190, 191, 192, 193, 195, 197, 199, 202, 207, 214, 217, 221, 228, 234, 237, 238, 246, 250, 254, 255, 257, 264, 266, 267, 268, 269, 270, 273, 275, 279, 283, 284, 298, 301, 303, 305, 306, 310, 311, 318, 319, 322, 323, 336, 337, 338, 339, 340, 344, 374, 375, 376, 377, 379, 381, 382, 393, 394, 399, 401, 407, 408, 419, 433, 436, 438, 447, 451, 453, 459, 465, 479, 475, and 483, and wherein the positions are numbered by correspondence with the amino acid sequence of a reference alpha-amylase set forth as SEQ ID NO:2. In a preferred embodiment, the alpha-amylase variant comprises a tyrosine at position 58 and an alanine at position 236, and wherein the positions are numbered by correspondence with the amino acid sequence of a reference alpha-amylase set forth as SEQ ID NO:2. In another embodiment, the alpha-amylase variant comprises a glutamine at position 243 and a lysine at position 475, and wherein the positions are numbered by correspondence with the amino acid sequence of a reference alpha-amylase set forth as SEQ ID NO:2.

The disclosure further provides an isolated alpha-amylase variant, wherein the variant is a mature form having amylase activity and comprising a substitution at from one to eight (e.g., 1, 2, 3, 4, 5, 6, 7, or 8) positions selected from the group consisting of: 182, 183, 305, 320, 379, 407, 419 and 475, and wherein the positions are numbered by correspondence with the amino acid sequence of a reference alpha-amylase set forth as SEQ ID NO:2. In another embodiment, the alpha-amylase variant is derived from a parent alpha-amylase selected from the group consisting of BASE, ACE, ACE-Q, and ACE-QK. In another embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In a preferred embodiment, the substitution comprises from one to eight of the group consisting of: X182N, X183N, X305Q, X320F, X379A, X407D, X419S and X475T. In a subset of these embodiments, the substitution comprises from one to eight (e.g., 1, 2, 3, 4, 5, 6, 7, or 8) of the group consisting of: T182N, G183N, Y305Q, Q320F, P379A, Q407D, T419S and G475T.

The disclosure provides an isolated alpha-amylase variant, wherein the variant is a mature form having amylase activity and comprising a substitution at from one to seven (e.g., 1, 2, 3, 4, 5, 6, or 7) positions selected from the group consisting of: 160, 182, 183, 189, 305, 379, and 475, and wherein the positions are numbered by correspondence with the amino acid sequence of a reference alpha-amylase set forth as SEQ ID NO:2. In another embodiment, the alpha-amylase variant is derived from a parent alpha-amylase selected from the group consisting of BASE, ACE, ACE-Q, and ACE-QK. In a preferred embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In another preferred embodiment, the substitution comprises from one to seven of the group consisting of: X160E, X182G, X183N, X189P, X305G, X379E, and X475T. In a subset of these embodiments, the substitution comprises from one to seven (e.g., 1, 2, 3, 4, 5, 6, or 7) of the group consisting of: Y160E, T182G, G183N, E189P, Y305G, P379E, and G475T.

The disclosure further provides an isolated alpha-amylase variant, wherein the variant is a mature form having amylase activity and comprising a substitution at from one to eight (e.g., 1, 2, 3, 4, 5, 6, 7, or 8) positions selected from the group consisting of: 125, 182, 214, 279, 305, 319, 320, and 475, and wherein the positions are numbered by correspondence with the amino acid sequence of a reference alpha-amylase set forth as SEQ ID NO:2. In another embodiment, the alpha-amylase variant is derived from a parent alpha-amylase selected from the group consisting of BASE, ACE, ACE-Q, and ACE-QK. In a preferred embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In another preferred embodiment, the substitution comprises from one to eight of the group consisting of: X125A, X182A, X214Q, X279N, X305R, X319T, X320N, and X475R. In a subset of these embodiments, the substitution comprises from one to eight (e.g., 1, 2, 3, 4, 5, 6, 7, or 8) of the group consisting of: S125A, T182A, T214Q, T279N, Y305R, D319T, Q320N, and G475R.

The disclosure provides another isolated alpha-amylase variant, wherein the variant is a mature form having amylase activity and comprising a substitution at from one to eight (e.g., 1, 2, 3, 4, 5, 6, 7, or 8) positions selected from the group consisting of: 7, 182, 298, 376, 379, 407, 419, and 453, and wherein the positions are numbered by correspondence with the amino acid sequence of a reference alpha-amylase set forth as SEQ ID NO:2. In another embodiment, the alpha-amylase variant is derived from a parent alpha-amylase selected from the group consisting of BASE, ACE, ACE-Q, and ACE-QK. In a preferred embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In another preferred embodiment, the substitution comprises from one to eight of the group consisting of: X7H, X182W, X298Q, X376R, X379K, X407W, X419S, and X453W. In a subset of these embodiments, the substitution comprises from one to eight (e.g., 1, 2, 3, 4, 5, 6, 7, or 8) of the group consisting of: E7H, T182W, T298Q, Y376R, P379K, Q407W, T419S, and L453W.

The disclosure provides an isolated alpha-amylase variant, wherein the variant is a mature form having amylase activity and comprising a substitution at from one to four (e.g., 1, 2, 3, or 4) positions selected from the group consisting of: 128, 178, 182 and 185, and the alpha-amylase variant comprises a serine or a glutamine at position 243, and wherein the positions are numbered by correspondence with the amino acid sequence of a reference alpha-amylase set forth as SEQ ID NO:2. In one embodiment, the alpha-amylase variant is derived from a parent alpha-amylase selected from the group consisting of BASE, ACE, ACE-Q, and ACE-QK. In a preferred embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In yet another embodiment, the substitution comprises from one to four (e.g., 1, 2, 3, or 4) of the group consisting of: N128C, K178L, T182G, and A185D.

The disclosure provides another isolated alpha-amylase variant, wherein the variant is a mature form having amylase activity and comprising a substitution at from one to nine (e.g., 1, 2, 3, 4, 5, 6, 7, 8 or 9) positions selected from the group consisting of: 125, 182, 183, 189, 279, 305, 319, 379 and 475, and the alpha-amylase variant comprises a glutamine, a phenylalanine or an asparagine at position 320, and wherein the positions are numbered by correspondence with the amino acid sequence of a reference alpha-amylase set forth as SEQ ID NO:2. In one embodiment, the alpha-amylase variant is derived from a parent alpha-amylase selected from the group consisting of BASE, ACE, ACE-Q, and ACE-QK. In a preferred embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In another embodiment, the alpha-amylase variant comprises: a serine or alanine at position 125; a threonine, an asparagine, a glycine or an alanine at position 182; a glycine or an asparagine at position 183; a glutamic acid or a proline at position 189; a threonine or an asparagine at position 279; a tyrosine, a glutamine, a glycine or an arginine at position 305; an aspartic acid or a threonine at position 319; a proline or an alanine at position 379; and a glycine, threonine or an arginine at position 475; and wherein the positions are numbered by correspondence with the amino acid sequence of a reference alpha-amylase set forth as SEQ ID NO:2.

The disclosure further provides an isolated alpha-amylase variant, wherein the variant is a mature form having amylase activity and comprising a substitution at from one to eleven (e.g., 1, 2, 3, 4, 5, 6, 7, 8, 9, 10 or 11) positions selected from the group consisting of: 125, 128, 178, 182, 183, 189, 279, 305, 319, 379 and 475, and the alpha-amylase variant comprises a serine or a glutamine at position 243, and a glutamine, a phenylalanine or an asparagine at position 320, and wherein the positions are numbered by correspondence with the amino acid sequence of a reference alpha-amylase set forth as SEQ ID NO:2. In one embodiment, the alpha-amylase variant is derived from a parent alpha-amylase selected from the group consisting of BASE, ACE, ACE-Q, and ACE-QK. In a preferred embodiment, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In another embodiment, the alpha-amylase variant comprises: a serine or alanine at position 125; an asparagine or a cysteine at position 128; a lysine or a leucine at position 178; a threonine, an asparagine, a glycine or an alanine at position 182; a glycine or an asparagine at position 183; a glutamic acid or a proline at position 189; a threonine or an asparagine at position 279; a tyrosine, a glutamine, a glycine or an arginine at position 305; an aspartic acid or a threonine at position 319; a proline or an alanine at position 379; and a glycine, threonine or an arginine at position 475; and wherein the positions are numbered by correspondence with the amino acid sequence of a reference alpha-amylase set forth as SEQ ID NO:2. In another preferred embodiment, the substitution is selected from the group consisting of: N128C, T131I, T134P, Q138E, Y160I, T165I, T165V, K178L, T182A, T182C, T182D, T182M, T182F, T182N, T182G, T182P, T182Q, A185D, A185E, E189P, S243D, S243E and S243Q.

The presently described amino acid mutations were made and tested using an exemplary alpha-amylase as a starting point, i.e., a "backbone;" however, it will be appreciated that equivalent amino acid mutations can be made in related alpha-amylases, where they are expected to produce a similar effect and yield similar advantages. Other exemplary alpha-amylases for use as a backbone include but are not limited to those identified, herein.

The disclosure further provides an isolated nucleic acid encoding an alpha-amylase variant of any of the preceding paragraphs. In one embodiment, an expression vector comprising the isolated nucleic acid in operable combination with a promoter is included. In another embodiment, a host cell comprising the expression vector is included. Another embodiment provides a method for producing an alpha-amylase variant, comprising: transforming a host cell with an expression vector comprising a nucleic acid encoding the alpha-amylase variant; and cultivating the transformed host cell under conditions suitable for the production of the alpha-amylase variant. Another embodiment further comprises the step of harvesting the produced alpha-amylase variant. Yet another embodiment includes as the host cell a *Bacillus* species, and in yet another embodiment the *Bacillus* species is *B. subtilis*.

The disclosure provides a cleaning composition comprising an alpha-amylase variant of any of the preceding paragraphs, further comprising at least one additional enzyme. In one embodiment, the additional enzyme is selected from the group consisting of a protease (including but not limited to a subtilisin, a neutral metalloprotease, an aspartyl protease, and the like), a lipase, a cutinase, a carbohydrase, a cellulase, a pectinase, a mannanase, an arabinase, a galactanase, a xylanase, an oxidase, a perhydrolase, a pectate lyase, and a peroxidase. In another embodiment, the cleaning composition is a laundry detergent, and in yet another embodiment, the cleaning composition is a dishwashing detergent. In another embodiment, the cleaning composition is a laundry and/or dish detergent with a bleaching agent. In another embodiment, the cleaning composition is a pretreatment for fabrics, e.g., for application prior to washing. In another embodiment, the cleaning composition is a laundry detergent or dishwashing detergent additive. The disclosure further provides a method of cleaning, comprising the step of contacting a surface and/or an article comprising a fabric with a cleaning composition comprising the alpha-amylase variant. In one embodiment, the method is a dishwashing method, comprising the steps of: providing i) the dishwashing composition, and ii) dishware in need of cleaning; and contacting the dishware with the dishwashing composition under conditions effective to provide cleaning of the dishware. In another embodiment, the method is a fabric cleaning method, comprising the steps of: providing i) the fabric cleaning composition, and ii) laundry in need of cleaning; and contacting the laundry with the fabric cleaning composition under conditions effective to provide cleaning of the laundry. In another embodiment, the method involves removing material from the yarns in woven fabrics, as in the case of textile desizing.

These and other aspects and embodiments of the compositions and methods will be apparent in view of the description.

BRIEF DESCRIPTION OF THE DRAWINGS

FIG. 1 provides an alignment of the mature form of various reference amylases set forth as SEQ ID NOS: 2 and 5-14 respectively. Sequences were aligned using the MUSCLE 3.7 multiple sequence alignment algorithm (Edgar, *Nucleic Acids Research*, 32:1792-1797, 2004).

DETAILED DESCRIPTION

Figure 2:
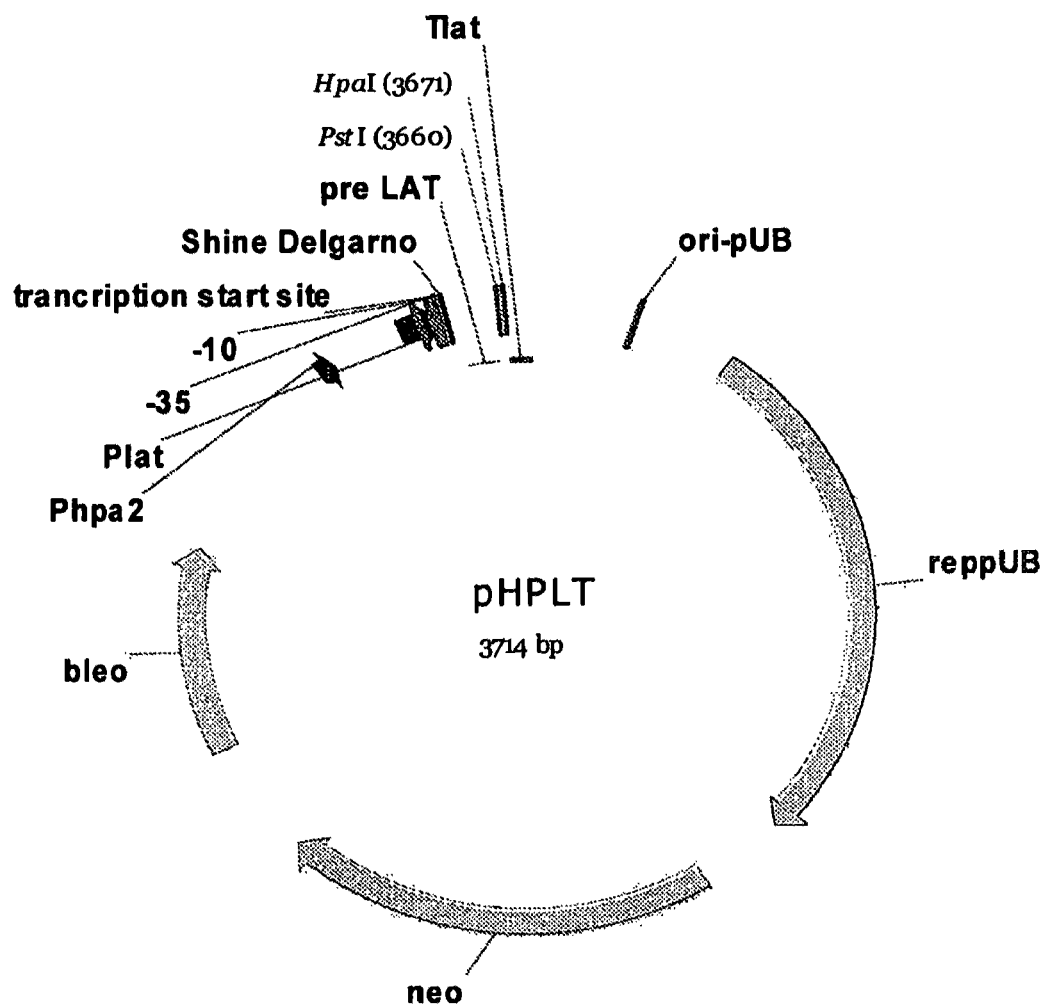
FIG. 2 provides a map of the pHPLT vector containing the *B. licheniformis* LAT promoter (Plat) and additional elements from pUB110 (McKenzie et al., *Plasmid*, 15: 93-103, 1986) including a replicase gene (reppUB), a neomycin/kanamycin resistance gene (neo) and a bleomycin resistance marker (bleo).

Described are compositions and methods involving amylase variants, and in particular variants of a *Bacillus* α-amylase. The amylase variants described herein have altered biochemical characteristics and demonstrate high performance in various industrial applications (e.g., laundry and dishwashing). These and other features of the variants, as well as methods for using the variants, are described in detail.

1. Definitions and Nomenclature for α-Amylase Variants

Unless defined otherwise herein, all technical and scientific terms used herein have the same meaning as commonly understood by one of ordinary skill in the art. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, NY (1991) provide one of skill with general dictionaries of many of the terms used herein.

Some aspects of the compostions and methods rely on routine techniques and methods used in the field of genetic engineering and molecular biology. The following resources include descriptions of general methodology useful in accordance with the present compositions and methods: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, it is not intended that the present compositions and methods be limited to any particular techniques, protocols, and reagents described, as these may vary. Although any methods and materials similar or equivalent to those described herein can be used in the practice or testing of the present compositions and methods, the preferred methods and materials are described.

When describing proteins and genes that encode them, the name of the gene is generally italicized and not capitalized, while the name of the protein is generally not italicized and the first letter is capitalized.

The singular forms "a", "an", and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

All patents and publications referred to herein, including all sequences disclosed within such patents and publications are expressly incorporated by reference.

1.1 Definitions

The following terms are defined for clarity.

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

As used herein, an "amylase" refers to an enzyme capable of catalyzing the degradation of starch. Generally, α-amylases (EC 3.2.1.1; α-D-(1→4)-glucan glucanohydrolase) are endo-acting enzymes that cleave α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase), and some product-specific amylases like maltogenic α-amylase (EC 3.2.1.133), cleave the starch molecule from the non-reducing end of the substrate. β-amylases, α-glucosidases (EC 3.2.1.20; α-D-glucoside glucohydrolase), glucoamylases (EC 3.2.1.3; α-D-(1→4)-glucan glucohydrolase), and product-specific amylases can produce malto-oligosaccharides of a specific length from starch. As used herein, amylases include any/all amylases, including glucoamylases, α-amylases, β-amylases and wild-type α-amylases, such as those of *Bacillus* sp., e.g., *B. licheniformis* and *B. subtilis*, while α-amylases include the aforementioned subset of these enzymes.

As used herein, "*Bacillus* sp. strain TS-23 α-amylase," and similar phrases, refer to an α-amylase derived from *Bacillus* sp. strain TS-23. The gene encoding the α-amylase can be the wild-type gene or a codon optimized polynucleotide that encodes the α-amylase. The mature α-amylase of *Bacillus* sp. strain TS-23 is (amino to carboxy orientation) (SEQ ID NO: 1):

```
NTAPINETMM QYFEWDLPND GTLWTKVKNE AANLSSLGIT ALWLPPAYKG    50

TSQSDVGYGV YDLYDLGEFN QKGTIRTKYG TKTQYIQAIQ AAKAAGMQVY   100

ADVVFNHKAG ADGTEFVDAV EVDPSNRNQE TSGTYQIQAW TKFDFPGRGN   150

TYSSFKWRWY HFDGTDWDES RKLNRIYKFR STGKAWDWEV DTENGNYDYL   200

MFADLDMDHP EVVTELKNWG TWYVNTTNID GFRLDAVKHI KYSFFPDWLT   250

YVRNQTGKNL FAVGEFWSYD VNKLHNYITK TNGSMSLFDA PLHNNFYTAS   300

KSSGYFDMRY LLNNTLMKDQ PSLAVTLVDN HDTQPGQSLQ SWVEPWFKPL   350

AYAFILTRQE GYPCVFYGDY YGIPKYNIPG LKSKIDPLLI ARRDYAYGTQ   400

RDYIDHQDII GWTREGIDTK PNSGLAALIT DGPGGSKWMY VGKKHAGKVF   450

YDLTGNRSDT VTINADGWGE FKVNGGSVSI WVAKTSNVTF TVNNATTTSG   500

QNVYVVANIP ELGNWNTANA IKMNPSSYPT WKATIALPQG KAIEFKFIKK   550

DQAGNVIWES TSNRTYTVPF SSTGSYTASW NVP                    583
```

As used herein, "α-amylase variants," and similar phrases, refer to variants/mutants of a reference α-amylase, which includes an amino acid substitution, insertion, and/or deletion with respect to the parent (wild-type; reference) amino acid sequence of the reference α-amylase. The term "variant" is used interchangeably with the term "mutant." The variant α-amylase may include mutations in the signal sequence with respect to parent signal sequence. In addition, the variant α-amylase can be in the form of a fusion protein containing a heterologous α-amylase signal sequence, such as from *B. licheniformis* (LAT).

As used herein, the phrases "parent *Bacillus* sp. strain TS-23 α-amylase," "wild-type *Bacillus* sp. strain TS-23 α-amylase," "reference *Bacillus* sp. strain TS-23 α-amylase," and similar phrases, refer to the polypeptide of *Bacillus* sp. strain TS-23. The term may be abbreviated "parent enzyme," "wild-type enzyme," "parent polypeptide," reference polypeptide," or the like, for convenience. The parent *Bacillus* sp. strain TS-23 α-amylase may include mutations in the signal sequence of the parent polypeptide. In addition, the parent *Bacillus* sp. strain TS-23 α-amylase can be in the form of a fusion protein containing a heterologous α-amylase signal sequence, such as from *B. licheniformis* (LAT).

As used herein, a "parent nucleic acid/polynucleotide," "wild-type nucleic acid/polynucleotide," or "reference nucleic acid/polynucleotide," refers to a nucleic acid sequence encoding a parent polypeptide, and a nucleic acid complementary thereto.

As used herein, a "variant nucleic acid/polynucleotide" refers to a nucleic acid sequence encoding a variant polypeptide or a nucleic acid complementary thereto, or a polynucleotide sequence having at least one base substitution, insertion, or deletion with respect to a parent polynucleotide sequence or a nucleic acid complementary thereto. Where specified such nucleic acids may include those having a specified degree of homology to a reference sequence, or that are capable of hybridizing to a reference sequence, for example, under stringent conditions [e.g., 50° C. and 0.2×SSC (1×SSC=0.15 M NaCl, 0.015 M Na$_3$ citrate, pH 7.0)] or highly stringent conditions [e.g., 65° C. and 0.1×SSC (1×SSC=0.15 M NaCl, 0.015 M Na$_3$ citrate, pH 7.0)]. A variant nucleic acid may be optimized to reflect preferred codon usage for a specified host organisms, such as the methylotrophic yeasts (e.g., *Pichia, Hansenula*, etc) or filamentous fungi (e.g., *Trichoderma* (e.g., *T. reesei*), etc) or other expression hosts (e.g., *Bacillus, Streptomyces*, etc.).

As used herein, the term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, the terms "recovered," "isolated," and "separated," refer to a compound, protein, cell, nucleic acid or amino acid that is removed from at least one component with which it is naturally associated and found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

As used herein, the terms, "thermostable" and "thermostability" refer to the ability of an enzyme to retain activity after exposure to an elevated temperature. The thermostability of an enzyme, such as an α-amylase enzymes, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

As used herein, a "pH range" refers to the range of pH values under which an enzyme exhibits catalytic activity.

As used herein, the terms "pH stable" and "pH stability" relate to the ability of an enzyme to retain activity over a wide range of pH values for a predetermined period of time (e.g., 15 min., 30 min., 1 hour, and the like).

As used herein, the term "amino acid sequence" is synonymous with the terms "polypeptide," "protein," and "peptide," and are used interchangeably. Where such amino acid sequence exhibit activity, they may be referred to as an "enzyme." The conventional one-letter or three-letter code for amino acid residues are used herein.

As used herein, the term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acids are written left to right in 5' to 3' orientation; amino acid sequences are written left to right in amino to carboxy orientation, respectively.

As used herein, the term "homologue" refers to an amino acid or nucleotide sequence having a certain degree of identity to a reference amino acid or nucleotide sequences, or another specified common structural or functional feature. A homologous sequence is taken to include an amino acid sequence that is at least 75%, 80%, 81%, 82%, 83%, 84%, 85%, 86%, 87%, 88%, 89%, 90%, 91%, 92%, 93%, 94%, 95%, 96%, 97%, 98%, or even 99% identical to the subject sequence, using conventional sequence alignment tools (e.g., Clustal, BLAST, and the like). Typically, homologues will include the same active site residues as the subject amino acid sequence, unless otherwise specified.

As used herein, "hybridization" refers to the process by which one strand of nucleic acid base pairs with a complementary strand, as occurs during blot hybridization techniques and PCR techniques.

As used herein, a "synthetic" molecule is produced by in vitro chemical or enzymatic synthesis rather than by an organism.

As used herein, the terms "transformed," "stably transformed," and "transgenic," used with reference to a cell means that the cell has a non-native (e.g., heterologous) nucleic acid sequence integrated into its genome or carried as an episomal plasmid that is maintained through multiple generations.

The term "introduced" in the context of inserting a nucleic acid sequence into a cell, means "transfection", "transformation" or "transduction," as known in the art.

As used herein, the terms "host strain" or "host cell" refer to an organism into which an expression vector, phage, virus, or other DNA construct including a polynucleotide encoding a polypeptide of interest (e.g., a variant α-amylase) has been introduced. Exemplary host strains are bacterial cells. The term "host cell" includes protoplasts created from cells, such as those of a *Bacillus* sp.

As used herein, the term "heterologous" with reference to a polynucleotide or protein refers to a polynucleotide or protein that does not naturally occur in a host cell.

As used herein, the term, "endogenous" with reference to a polynucleotide or protein refers to a polynucleotide or protein that occurs naturally in the host cell.

As used herein, the term "expression" refers to the process by which a polypeptide is produced based on the nucleic acid sequence of a gene. The process includes both transcription and translation.

As used herein, a "selective marker" or "selectable marker" refers to a gene capable of being expressed in a host to facilitate selection of host cells carrying the gene. Examples of selectable markers include but are not limited to antimicrobials (e.g., hygromycin, bleomycin, or neomycin) and/or genes that confer a metabolic advantage, such as a nutritional advantage on the host cell.

As used herein, "culturing" refers to growing a population of microbial cells under suitable conditions in a liquid or solid medium. Culturing includes fermentative bioconversion of a starch substrate containing granular starch to an end-product (typically in a vessel or reactor).

As used herein, "fermentation" is the enzymatic breakdown of organic substances by microorganisms to produce simpler organic compounds. While fermentation generally occurs under anaerobic conditions it is not intended that the term be solely limited to strict anaerobic conditions, as fermentation also occurs in the presence of oxygen.

As used herein, a "gene" refers to a DNA segment that is involved in producing a polypeptide, and includes coding regions, regions preceding and following the coding regions, and, intervening sequences (introns) between individual coding segments (exons).

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, an "expression vector" refers to a DNA construct comprising a DNA sequence encoding a polypeptide of interest, which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, a "promoter" is a regulatory sequence that is involved in binding RNA polymerase to initiate transcription of a gene. The promoter may be an inducible promoter or a constitutive promoter. An exemplary promoter is the *Bacillus licheniformis* α-amylase (AmyL) promoter.

As used herein, the term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

As used herein, the term, "under transcriptional control" means that transcription of a polynucleotide sequence, usually a DNA sequence, depends on its being operably linked to an element which contributes to the initiation of, or promotes transcription.

As used herein, the term, "under translational control" means that translation of a polynucleotide sequence, usually an RNA sequence, into a polypeptide depends on its being operably linked to an element which contributes to the initiation of, or promotes translation.

As used herein, a "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity. In the case of the present amylases, the activity is α-amylase activity.

As used herein, "water hardness" is a measure of the minerals (e.g., calcium and magnesium) present in water.

As used herein, the term, "cold water" refers to water at a temperature below about 25° C. Where specificied, cold water refers to water at a temperature below about 20° C. Exemplary cold water ranges are from about 15° C. to about 25° C. and from about 15° C. to about 20° C.

As used herein, the term "performance index (PI)" refers to the ratio of performance of a variant to a parent or reference amylase. Measures of performance (i.e., properties) include thermal stability, cleaning ability, expression levels, and the like, and will be apparent from context.

As used herein, mutations that improve performance are known as "up mutations," and have a PI>1 for a specified property. "Neutral mutations" have a PI>0.5 for a specified property. "Non-deleterious mutations" have a PI>0.05 for a specified property. "Deleterious mutations" have a PI≤0.05 for a specified property. "Combinable mutations" have a PI≥0.5 for at least one property, and >0.05 for all properties. Combinable mutations can be present together in the same variant to produce an enzyme having at least one beneficial property.

As used herein, the term "measure of activity" refers to a measure of enzymatic activity as described here. Such measures of activity include cleaning performance at pH 8, cleaning performance at pH 10, cleaning performance at 16° C., cleaning performance at 32° C., and activity using a synthetic substrate.

As used herein, the term "measure of stability" refers to a measure of enzymatic stability as described here. Such measures of stability include stability in detergents and thermostability.

As used herein, the term "co-formulation" means that subject ingredients, such as enzymes, are present together in the same liquid, semi-solid, or dry composition.

As used herein, "saccharification" refers to the enzymatic conversion of starch to glucose.

As used herein, "gelatinization" refers to solubilization of a starch molecule by cooking to form a viscous suspension.

As used herein, "liquefaction" refers to the stage in starch conversion in which gelatinized starch is hydrolyzed to give low molecular weight soluble dextrins.

As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from 200-300° F., e.g., 220-235° F. Subsequent to application to a heat exchange or jet temperature, the slurry is held for a period of 3-10 minutes at that temperature. This step of holding the slurry at 200-300° F. is primary liquefaction.

As used herein, the term "secondary liquefaction" refers the liquefaction step subsequent to primary liquefaction (heating to 200-300° F.), when the slurry is allowed to cool to atmospheric temperature. This cooling step can be 30 minutes to 180 minutes (3 hours), e.g. 90 minutes to 120 minutes (2 hours).

As used herein, the term "minutes of secondary liquefaction" refers to the time that has elapsed from the start of secondary liquefaction, to the time that the DE is measured.

As used herein, the term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

As used herein with respect to starch conversion, the terms "end-product" or "desired end-product" refer to specified carbon-source-derived molecules, which are enzymatically converted from a starch substrate.

As used herein, the term "dry solids content (ds)" refers to the total solids in a slurry, expressed in % dry weight.

As used herein, the term "slurry" refers to an aqueous mixture containing insoluble solids.

As used herein, the term, "residual starch" refers to the remaining starch (soluble or insoluble) in a composition after fermentation or enzymatic hydrolysis of a starch containing substrate.

As used herein "a recycling step" refers to the recycling of mash components, which may include residual starch, enzymes and/or microorganisms to ferment substrates comprising starch.

As used herein, the term "mash" refers to an aqueous mixture including a fermentable carbon source (e.g., carbohydrate), which may be used to produce a fermented product, such as an alcohol. The terms "beer" and "mash" may be used interchangeability.

As used herein, the term "stillage" refers to a mixture of non-fermented solids and water, which represents the residue following removal of alcohol from a fermented mash.

As used herein, the terms "distillers dried grain (DDG)" and "distillers dried grain with solubles (DDGS)" refer to a useful by-product of grain fermentation.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Sacchromyces*, particularly, *S. cerevisiae*.

As used herein with respect to amylase enzymes and their substrates, the term "contacting" refers to the placing of the enzyme in sufficiently close proximity to the substrate to enable the enzyme to convert the substrate to an end-product. Contacting may include mixing.

As used herein, the term "derived from" means "originated from," "based on," "obtained from," "obtainable from," or "isolated from," depending on context.

As used herein, the term "enzymatic conversion" generally refers to the modification of a substrate (e.g., starch) by enzyme action (e.g., amylase).

As used herein, the term "disintegration" refers to the hydrolysis of polysaccharides in a biofilm matrix connecting and binding together individual microbial cells in the biofilm, whereby the microbial cells can be released and removed from the biofilm.

As used herein, a "swatch" is a piece of material, such as a fabric, to which a stain may be applied for evaluating the cleaing efficiency of a composition.

As used herein the term "specific activity" refers to the number of moles of substrate converted to product by an enzyme preparation per unit time under specific conditions. Specific activity is expressed as units (U)/mg of protein.

As used herein, the term "yield" refers to the amount of end-product produced by a process, e.g., expressed in concentration, volume, amount, or a percentage of staring material.

As used herein, "ATCC" refers to American Type Culture Collection located at Manassas, Va. 20108 (ATCC).

As used herein, "NRRL" refers to the Agricultural Research Service Culture Collection, National Center for Agricultural Utilization Research (and previously known as USDA Northern Regional Research Laboratory), Peoria, Ill.

Numeric ranges are inclusive of the numbers defining the range.

Generally, headings are descriptive and are not intended as limitations.

1.2 Nomenclature

In the present description and claims, the conventional one-letter and three-letter codes for amino acid residues are used. For ease of reference, α-amylase variants of the present compositions and methods are described by use of the following nomenclature:

Original amino acid(s): position(s): substituted amino acid(s).

According to this nomenclature, for instance the substitution of serine by an alanine in position 242 is shown as: Ser242Ala or S242A. A deletion of alanine in position 30 is shown as: Ala30* or A30* or ΔA30. An insertion of an additional amino acid residue, such as lysine, is shown as: Ala30AlaLys or A30AK.

A deletion of a consecutive stretch of amino acid residues, such as amino acid residues 30-33, is indicated as (30-33)* or Δ(A30-N33) or Δ30-33. A deletion of two consecutive amino acids, such as amino acid residues R180-S181, is indicated as ΔRS or Δ180-181.

Where a specific α-amylase contains a "deletion" in comparison with other α-amylases and an insertion is made in such a position this is indicated as: *36Asp or *36D for insertion of an aspartic acid in position 36.

Multiple mutations are separated by plus or minus signs: Ala30Asp+Glu34Ser or A30N+E34S, Ala30Asp−Glu34Ser or A30N−E34S, representing mutations in positions 30 and 34 substituting alanine and glutamic acid for asparagine and serine, respectively.

When one or more alternative amino acid residues may be substituted for a residue in a given position it is indicated as: A30N,E or A30N or A30E.

Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of: R, N, D, A, C, Q, E, G, H, I, L, K, M, F, P, S, T, W, Y, V.

Further, "A30X" means any one of the following substitutions: A30R, A30N, A30D, A30C, A30Q, A30E, A30G, A30H, A30I, A30L, A30K, A30M, A30F, A30P, A30S, A30T, A30W, A30Y, or A30 V; or in short: A30R,N,D,C,Q,E,G,H, I,L,K,M,F,P,S,T,W,Y,V.

The following nomenclature is used to indicated an amino acid residue at a position of an unspecified parent amylase, where the position is numbered by correspondence with the amino acid sequence of a reference alpha-amylase set forth as SEQ ID NO: 2: "X30N" or "X30N,V" in the case where for instance one of N or V is present in the variant amylase in position 30, while one of the twenty standard amino acids is present in the parent amylase (e.g., wild type or variant enzyme)

1.3 Characteristics of Amino Acid Residues

Charged amino acids include: Asp, Glu, Arg, Lys, and His. Negatively charged amino acids (with the most negative residue first) are Asp and Glu. Positively charged amino acids (with the most positive residue first) are Arg, Lys, and His.

Neutral amino acids include: Gly, Ala, Val, Leu, lie, Phe, Tyr, Tip, Met, Cys, Asn, Gln, Ser, Thr, and Pro.

Hydrophobic amino acid residues (with the most hydrophobic residue listed last) include: Gly, Ala, Val, Pro, Met, Leu, lie, Tyr, Phe, and Trp.

Hydrophilic amino acids (with the most hydrophilic residue listed last) include: Thr, Ser, Cys, Gln, and Asn.

1.4 Homology (Identity)

A polynucleotide or a polypeptide having a certain percent (e.g., 75%, 80%, 81%, 82%, 83%, 84%, 85%, 86%, 87%, 88%, 89%, 90%, 91%, 92%, 93%, 94%, 95%, 96%, 97%, 98%, or even 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the Vector NTI Advance™ 9.0 (Invitrogen Corp. Carlsbad, Calif.), GCG Pileup program, FASTA (Pearson et al. (1988) *Proc. Natl, Acad. Sci USA* 85:2444-2448), and BLAST (BLAST Manual, Altschul et al., Natl Cent. Biotechnol. Inf., Natl Lib. Med. (NCIB NLM NIH), Bethesda, Md., and Altschul et al., (1997) *NAR* 25:3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

The homology may be determined as the degree of identity between the two sequences indicating a derivation of the first sequence from the second. The homology may suitably be determined by means of computer programs known in the art such as GAP provided in the GCG program package (described above). Thus, GAP GCG v8 may be used with the default scoring matrix for identity and the following default parameters: gap creation penalty of 5.0 and gap extension penalty of 0.3, respectively for nucleic acidic sequence comparison, and gap creation penalty of 3.0 and gap extension penalty of 0.1, respectively, for protein sequence comparison. GAP uses the method of Needleman and Wunsch, (1970), J. Mol. Biol. 48:443-453, to make alignments and to calculate the identity.

A structural alignment between BASE (SEQ ID NO: 2) or a BASE variant and, e.g., another α-amylase may be used to identify equivalent/corresponding positions in other α-amylases having a high degree of homology, e.g., about 75%, 80%, 81%, 82%, 83%, 84%, 85%, 86%, 87%, 88%, 89%, 90%, 91%, 92%, 93%, 94%, 95%, 96%, 97%, 98%, or even 99%, with AmyTS23. One method of obtaining the structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber and Torda, PROTEIN SCIENCE Vol. 7, No. 1 pp. 142-149 (1998).

An exemplary alignment of the mature form of various reference amylases is provided as FIG. 1. The reference amylases include: a truncated *Bacillus* sp. TS-23 alpha-amylase referred to herein as AmyTS23t or BASE, SEQ ID NO: 2 (GENBANK Accession No. AAA63900); *B. licheniformis* alpha-amylase referred to herein as AmyL or LAT, SEQ ID NO: 5 (GENBANK Accession No. AAA22240); *Geobacillus* (formerly *Bacillus*) *stearothermophilus* alpha-amylase AmyS, SEQ ID NO: 6 (GENBANK Accession No. AAA22241), *B. amyloliquefaciens* alpha-amylase BACAM, SEQ ID NO: 7 (GENBANK Accession No. AAA22191); *Bacillus* sp. #707 alpha-amylase referred to herein as AmyG6 or Amy#707, SEQ ID NO: 8 (GENBANK Accession No. AAA22231); *B. megaterium* alpha-amylase AmyG5 or AmyBm, SEQ ID NO: 9 (GENBANK Accession No. AAK00598); *Bacillus* sp. alpha-amylase ALBA, SEQ ID NO: 10 (GENBANK Accession No. CAL48155 and WO 2006/037484); *B. halmapalus* amylase AmyBh, SEQ ID NO: 11 (GENBANK Accession No. AAE00432 and U.S. Pat. No. 5,856,164); *Bacillus* sp. amylase AA560, SEQ ID NO: 12 (GENBANK Accession No. CAC16486 and WO 2000/060060); *Bacillus* sp. KSM-AP1378 alpha-amylase AmyKSM1378, SEQ ID NO: 13 (GENBANK Accession No. CAD35985 and EP No. 1199356 A); and *Bacillus* sp. pHSP-K38 amylase AmyK38, SEQ ID NO: 14 (GENBANK Accession No. CAJ00040 and WO 2005/045045). Sequences were aligned using the MUSCLE 3.7 multiple sequence alignment algorithm (Edgar, Nucleic Acids Research, 32:1792-1797, 2004). A matrix showing the percent identity of alpha-amylases of the sequence alignment of FIG. 1 is provided in Table 1.

TABLE 1

α-Amylase Percent Identity Matrix*

| Percent_ID | 2 | 5 | 6 | 7 | 8 | 9 | 10 | 11 | 12 | 13 | 14 |
|---|---|---|---|---|---|---|---|---|---|---|---|
| 2 | 100.0 | 64.6 | 88.0 | 65.2 | 67.6 | 66.7 | 68.2 | 68.6 | 67.6 | 69.5 | 59.4 |
| 5 | 64.6 | 100.0 | 65.5 | 80.9 | 68.2 | 74.2 | 68.0 | 70.7 | 68.4 | 69.4 | 62.7 |
| 6 | 88.0 | 65.5 | 100.0 | 65.2 | 66.5 | 65.5 | 67.5 | 67.3 | 66.3 | 67.9 | 59.0 |
| 7 | 65.2 | 80.9 | 65.2 | 100.0 | 66.9 | 71.9 | 66.7 | 68.6 | 66.9 | 67.1 | 60.3 |
| 8 | 67.6 | 68.2 | 66.5 | 66.9 | 100.0 | 69.4 | 93.2 | 86.2 | 95.5 | 86.4 | 64.2 |
| 9 | 66.7 | 74.2 | 65.5 | 71.9 | 69.4 | 100.0 | 70.4 | 71.1 | 69.6 | 70.0 | 61.5 |
| 10 | 68.2 | 68.0 | 67.5 | 66.7 | 93.2 | 70.4 | 100.0 | 87.5 | 95.1 | 87.7 | 65.0 |
| 11 | 68.6 | 70.7 | 67.3 | 68.6 | 86.2 | 71.1 | 87.5 | 100.0 | 86.8 | 86.6 | 66.9 |

TABLE 1-continued

α-Amylase Percent Identity Matrix*

| Percent_ID | 2 | 5 | 6 | 7 | 8 | 9 | 10 | 11 | 12 | 13 | 14 |
|---|---|---|---|---|---|---|---|---|---|---|---|
| 12 | 67.6 | 68.4 | 66.3 | 66.9 | 95.5 | 69.6 | 95.1 | 86.8 | 100.0 | 86.0 | 64.4 |
| 13 | 69.5 | 69.4 | 67.9 | 67.1 | 86.4 | 70.0 | 87.7 | 86.6 | 86.0 | 100.0 | 67.1 |
| 14 | 59.4 | 62.7 | 59.0 | 60.3 | 64.2 | 61.5 | 65.0 | 66.9 | 64.4 | 67.1 | 100.0 |

*Numbers in the top row and left column correspond to the SEQ ID NOS of the aligned sequences of FIG. 1.

1.5 Hybridisation

The oligonucleotide probe used in the characterization of AmyTS23, above, may suitably be prepared on the basis of the full or partial nucleotide or amino acid sequence of the α-amylase in question.

Suitable conditions for testing hybridization involve presoaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an α-amylase produced or producible by a strain of the organism in question, but also an α-amylase encoded by a DNA sequence isolated from such strain and produced in a host organism transformed with the DNA sequence. Finally, the term is intended to indicate an α-amylase, which is encoded by a DNA sequence of synthetic and/or cDNA origin and which has the identifying characteristics of the α-amylase in question. The term is also intended to indicate that the parent α-amylase may be a variant of a naturally occurring α-amylase, i.e., a variant, which is the result of a modification (insertion, substitution, deletion) of one or more amino acid residues of the naturally occurring α-amylase.

One skilled in the art will recognize that sequences encompassed by the present compositions and methods are also defined by the ability to hybridize under stringent hybridization conditions with the exemplified base sequence (e.g., SEQ ID NO: 4). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1×SSC, 0.1% SDS.

1.6 Parent α-Amylases

According to the present disclosure any α-amylase, may be used as the parent (i.e., backbone) α-amylase. In a preferred embodiment the parent α-amylase is BASE (AmyTS23t) having the amino acid sequence shown in SEQ ID NO: 2.

1.7 Altered Properties

The following section describes the relationship between mutations, which are present in the variant amylases described herein, and desirable alterations in properties (relative to those of a parent α-amylase), which may result therefrom. The variants encompassed by the present compositions and methods are described in detail throughout the specification, and merely summarized in the following paragraphs.

As described, above, as aspect of the compositions and methods relate to α-amylases derived or derivable from a Bacillus sp strain α-amylase, including variants/mutants having altered properties with respect to parent amylases. Parent amylases are the above-mentioned parent α-amylase and hybrid or chimeric amylases that include at least a portion of an α-amylase, such as amino acid sequences of the mature polypeptide.

While the BASE α-amylase (SEQ ID NO: 2) is used as a starting point for discussing variant amylases, it will be appreciated that other Bacillus α-amylases having a high degree of homology to the BASE α-amylase may serve as a parental amylase without defeating the scope of the compositions and methods. This is particularly true of other naturally-occurring Bacillus α-amylases that include only minor sequence differences in comparison to the BASE α-amylase, not including the substitutions, deletions, or insertions, that are the subject of the present disclosure.

In the first aspect of the present compositions and methods, a variant of a parent Bacillus sp. α-amylase is provided. In some embodiments, the alpha-amylase variant is a mature form having amylase activity and comprising a substitution at one or more (preferably 1, 2, 3, 4, 5, 6, 7, 8, 9, 10 or more) positions selected from the group consisting of: 1, 2, 3, 4, 5, 7, 15, 16, 17, 18, 19, 22, 25, 26, 28, 29, 30, 32, 35, 36, 37, 50, 51, 52, 53, 54, 55, 56, 57, 59, 60, 70, 71, 72, 73, 75, 78, 82, 83, 87, 90, 91, 93, 94, 95, 103, 104, 105, 107, 108, 110, 112, 113, 114, 115, 116, 118, 121, 123, 125, 126, 127, 128, 129, 130, 131, 132, 134, 135, 136, 138, 140, 142, 144, 147, 149, 150, 152, 154, 156, 158, 159, 160, 161, 162, 164, 165, 166, 167, 168, 169, 170, 171, 172, 174, 175, 176, 177, 178, 179, 182, 183, 185, 186, 188, 189, 190, 191, 192, 193, 195, 197, 199, 200, 201, 202, 203, 207, 210, 214, 217, 221, 228, 234, 237, 238, 239, 240, 243, 246, 250, 254, 255, 257, 264, 266, 267, 268, 269, 270, 272, 273, 275, 279, 283, 284, 298, 301, 303, 305, 306, 310, 311, 314, 318, 319, 320, 322, 323, 336, 337, 338, 339, 340, 344, 359, 374, 375, 376, 377, 379, 381, 382, 393, 394, 399, 401, 407, 408, 419, 433, 436, 438, 444, 447, 448, 451, 453, 459, 465, 479, 475, 483, and 484. Unless otherwise indicated, the positions are numbered by correspondence (e.g., same position in an alignment of alpha-amylase sequences such as that provided in FIG. 1) with the amino acid sequence of a reference alpha-amylase set forth as SEQ ID NO: 2 (BASE). In some preferred embodiments, the alpha-amylase variant is derived from a parent alpha-amylase selected from the group consisting of BASE, ACE, ACE-Q, and ACE-QK. In other preferred embodiments, the alpha-amylase variant is derived from a parent alpha-amylase with the amino acid sequence at least 75% (preferably 80%, 85%, 90%, 91%, 92%, 93%, 94%, 95%, 96%, 97%, 98% or 99%) identical to any member of the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. In some embodiments, the alpha-amylase variant comprises a tyrosine at position 58 and an alanine at position 236. In some embodiments, the alpha-amylase variant comprises a glutamine at position 243 and a lysine at position 475.

Also provided is an isolated alpha-amylase variant, wherein the variant is a mature form having amylase activity and comprising a substitution at from one to eight (e.g., 1, 2, 3, 4, 5, 6, 7, or 8) positions selected from the group consisting of: 182, 183, 305, 320, 379, 407, 419 and 475. In some preferred embodiments, the alpha-amylase variant is derived from a parent alpha-amylase selected from the group consisting of BASE, ACE, ACE-Q, and ACE-QK, and/or the substitution comprises from one to eight (e.g., 1, 2, 3, 4, 5, 6, 7, or 8) of the group consisting of: T182N, G183N, Y305Q, Q320F, P379A, Q407D, T419S and G475T (e.g., variants of BASE combinatorial library 1).

Moreover, the present disclosure provides an isolated alpha-amylase variant, wherein the variant is a mature form having amylase activity and comprising a substitution at from one to seven (e.g., 1, 2, 3, 4, 5, 6, or 7) positions selected from the group consisting of: 160, 182, 183, 189, 305, 379, and 475. In some preferred embodiments, the the alpha-amylase variant is derived from a parent alpha-amylase selected from the group consisting of BASE, ACE, ACE-Q, and ACE-QK, and/or the substitution comprises from one to seven (e.g., 1, 2, 3, 4, 5, 6, or 7) of the group consisting of: Y160E, T182G, G183N, E189P, Y305G, P379E, and G475T (e.g., variants of BASE combinatorial library 2).

The present disclosure provides an isolated alpha-amylase variant, wherein the variant is a mature form having amylase activity and comprising a substitution at from one to eight (e.g., 1, 2, 3, 4, 5, 6, 7, or 8) positions selected from the group consisting of: 125, 182, 214, 279, 305, 319, 320, and 475. In some preferred embodiments, the alpha-amylase variant is derived from a parent alpha-amylase selected from the group consisting of BASE, ACE, ACE-Q, and ACE-QK, and/or the substitution comprises from one to eight (e.g., 1, 2, 3, 4, 5, 6, 7, or 8) of the group consisting of: S125A, T182A, T214Q, T279N, Y305R, D319T, Q320N, and G475R (e.g., variants of BASE combinatorial library 3).

In addition, the present disclosure provides an isolated alpha-amylase variant, wherein the variant is a mature form having amylase activity and comprising a substitution at from one to eight (e.g., 1, 2, 3, 4, 5, 6, 7, or 8) positions selected from the group consisting of: 7, 182, 298, 376, 379, 407, 419, and 453. In some preferred embodiments, the alpha-amylase variant is derived from a parent alpha-amylase selected from the group consisting of BASE, ACE, ACE-Q, and ACE-QK, and/or the substitution comprises from one to eight (e.g., 1, 2, 3, 4, 5, 6, 7, or 8) of the group consisting of: E7H, T182W, T298Q, Y376R, P379K, Q407W, T419S, and L453W (e.g., variants of BASE combinatorial library 4).

The present disclosure provides an an isolated alpha-amylase variant, wherein the variant is a mature form having amylase activity and comprising a substitution at from one to four (e.g., 1, 2, 3, or 4) positions selected from the group consisting of: 128, 178, 182 and 185, and the alpha-amylase variant comprises a serine or a glutamine at position 243. In some preferred embodiments, the alpha-amylase variant is derived from a parent alpha-amylase selected from the group consisting of BASE, ACE, ACE-Q, and ACE-QK, and/or the substitution comprises from one to four (e.g., 1, 2, 3, or 4) of the group consisting of: N128C, K178L, T182G, and A185D (e.g., BASE-S1 to S32 variants).

In still further embodiments, the present disclosure provides an isolated alpha-amylase variant, wherein the variant is a mature form having amylase activity and comprising a substitution at from one to nine (e.g., 1, 2, 3, 4, 5, 6, 7, 8 or 9) positions selected from the group consisting of: 125, 182, 183, 189, 279, 305, 319, 379 and 475, and the alpha-amylase variant comprises a glutamine, a phenylalanine or an asparagine at position 320. In some preferred embodiments, the alpha-amylase variant is derived from a parent alpha-amylase selected from the group consisting of BASE, ACE, ACE-Q, and ACE-QK. In some preferred embodiments, the alpha-amylase variant comprises: a serine or alanine at position 125; a threonine, an asparagine, a glycine or an alanine at position 182; a glycine or an asparagine at position 183; a glutamic acid or a proline at position 189; a threonine or an asparagine at position 279; a tyrosine, a glutamine, a glycine or an arginine at position 305; an aspartic acid or a threonine at position 319; a proline or an alanine at position 379; and a glycine, threonine or an arginine at position 475; (e.g., BASE-P1 to P12 variants).

The present disclosure also provides an isolated alpha-amylase variant, wherein the variant is a mature form having amylase activity and comprising a substitution at from one to eleven (e.g., 1, 2, 3, 4, 5, 6, 7, 8, 9, 10 or 11) positions selected from the group consisting of: 125, 128, 178, 182, 183, 189, 279, 305, 319, 379 and 475, and the alpha-amylase variant comprises a serine or a glutamine at position 243, and a glutamine, a phenylalanine or an asparagine at position 320. In some preferred embodiments, the alpha-amylase variant is derived from a parent alpha-amylase selected from the group consisting of BASE, ACE, ACE-Q, and ACE-QK. In some preferred embodiments, the alpha-amylase variant comprises: a serine or alanine at position 125; an asparagine or a cysteine at position 128; a lysine or a leucine at position 178; a threonine, an asparagine, a glycine or an alanine at position 182; a glycine or an asparagine at position 183; a glutamic acid or a proline at position 189; a threonine or an asparagine at position 279; a tyrosine, a glutamine, a glycine or an arginine at position 305; an aspartic acid or a threonine at position 319; a proline or an alanine at position 379; and a glycine, threonine or an arginine at position 475 (e.g., BASE-W1 to W13 variants). Numerous exemplary alpha-amylase variants are disclosed for use in the claimed compositions and methods. The following alpha-amylase variants are exemplary alpha-amylase variants: BASE SEL variants, ACE-Q SEL variants, BASE combinatorial library 1 variants, BASE combinatorial library 2 variants, BASE combinatorial library 3 variants, BASE combinatorial library 4 variants, BASE-S1 to S32 combinatorial variants, BASE-Pi to P12 combinatorial variants, BASE-W1 to W13 combinatorial variants, and ACE-QK variant. The alpha-amylase variants of the present disclosure, however, are not limited to the exemplary variants, and include variants of other *Bacillus* sp. parent alpha-amylases having substitutions at corresponding positions. Based on the alignment and other data provided herein, it will also be appreciated that corresponding substitutions can be made in other alpha-amylase polypeptides, i.e., in other "backbones," and that the resulting amylase variants are expected to possess similar properties to those exemplified.

1.7.1 Stability

In the context of the variants described herein, mutations (including amino acid substitutions and deletions) of importance with respect to achieving altered stability (i.e., higher or lower), in particular improved stability, at especially high temperatures (i.e., 70-120° C.) and/or extreme pH (i.e., low or high pH, i.e., pH 4-6 or pH 8-11, respectively), in particular at free (i.e., unbound, therefore in solution) calcium concentrations below 60 ppm, include any of the mutations described herein. The stability may be determined as described in the "Methods" section below.

1.7.2 $Ca^{2+}$ Stability

Altered $Ca^{2+}$ stability means the stability of the enzyme under $Ca^{2+}$ depletion has been improved, i.e., higher or lower stability. In the context of the presently described variants, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations described herein.

1.7.3 Specific Activity

In a further aspect, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations described herein. The specific activity may be determined as described in the "Methods" section below.

1.7.4 Oxidation Stability

The described variants may have altered oxidation stability, in particular higher oxidation stability, in comparison to the parent α-amylase. Increased oxidation stability is advantageous in, e.g., detergent compositions and decreased oxidation stability may be advantageous in composition for starch liquefaction. Oxidation stability may be determined as described in the "Methods" section below.

1.7.5 Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues. Preferred mutations are the ones described herein. Suitable assays are described in the "Methods" section below.

1.7.6 Wash Performance

Important positions and mutations with respect to obtaining variants with improved wash performance at especially high pH (i.e., pH 8.5-11) include the specific mutations described herein. The wash performance may be tested as described below in the "Methods" section.

2. Methods for Preparing α-Amylase Variants

One aspect of the present compositions and methods is a method for preparing the present α-amylase variants having specified substitutions, deletions, transversions, insertions, and combinations, thereof. These variants may have possess advantageous features, such as, increased pH stability, increased temperature stability, reduced requirements for $Ca^{2+}$, increased specific activity, increased dishwashing or washing performance, increased solubility, increased storage stability, or combinations thereof.

Several methods for introducing mutations into genes and expressing mutated polypeptides encoded by these genes are known in the art. After a brief discussion of the cloning of α-amylase-encoding DNA sequences, methods for generating mutations at specific sites within the α-amylase-encoding sequence will be discussed.

2.1 Cloning a DNA Sequence Encoding an α-Amylase

DNA sequences encoding a parent α-amylase may be isolated from any cell or microorganism producing the α-amylase in question, using various methods well known in the art. First, a genomic DNA and/or cDNA library may be constructed using chromosomal DNA or messenger RNA from the organism that produces the α-amylase to be studied. Then, if the amino acid sequence of the α-amylase is known, homologous, labeled oligonucleotide probes may be synthesized and used to identify α-amylase-encoding clones from a genomic library prepared from the organism in question.

Alternatively, a labeled oligonucleotide probe containing sequences homologous to a known α-amylase gene could be used as a probe to identify α-amylase-encoding clones, using hybridization and washing conditions of lower stringency.

Yet another method for identifying α-amylase-encoding clones involves inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers (1981) or the method described by Matthes et al. (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

2.2 Site-Directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

2.3 Expression of α-Amylase Variants

A DNA sequence encoding an α-amylase variant produced by methods described above, or by any alternative methods known in the art, can be use to express a variant α-amylase (i.e., an enzyme) using an expression vector, which typically includes control sequences, such as a promoter, operator, ribosome binding site, translation initiation signal, and, optionally, a repressor gene or various activator genes.

A recombinant expression vector carrying DNA sequences encoding an α-amylase variant may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an α-amylase variant of the present compositions and methods, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Geobacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector may also comprise a suitable transcription terminator and, in eukaryotes, polyadenylation sequences operably connected to the DNA sequence encoding the α-amylase variant of the present compositions and methods. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, neomycin or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* α-amylases mentioned herein comprise a preregion or signal sequence permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct encoding an α-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell, either comprising a DNA construct or an expression vector, is advantageously used as a host cell in the recombinant production of an α-amylase variant. The cell may be transformed with the DNA construct of the present compositions and methods encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells. The cell may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis*, *Bacillus licheniformis*, *Bacillus lentus*, *Bacillus brevis*, *Geobacillus stearothermophilus*, *Bacillus alkalophilus*, *Bacillus amyloliquefaciens*, *Bacillus coagulans*, *Bacillus circulars*, *Bacillus lautus*, *Bacillus megaterium*, *Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

The medium used to cultivate the cells may be any conventional medium suitable for growing the host cell in question and obtaining expression of the α-amylase variant. Suitable media are available from commercial suppliers or may be prepared according to published recipes (e.g., as described in catalogues of the American Type Culture Collection).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

3. Industrial Applications

The present α-amylase variants possess advantageous properties allowing for a variety of industrial applications. In particular, the enzyme variants are applicable as a component in washing, dishwashing, and hard surface cleaning detergent compositions.

The variants may also be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are compositions for starch conversion purposes, which may beside the variant of the present compositions and methods also comprise a glucoamylase, pullulanase, and other α-amylases.

The variants may also be used in the production of sweeteners and ethanol (see, e.g., U.S. Pat. No. 5,231,017, hereby incorporated by reference), such as fuel or drinking/industrial ethanol, e.g., from starch or whole grains. One example is in beer making or brewing.

The variants may also be used for desizing of textiles, fabrics and garments (see, e.g., WO 95/21247, U.S. Pat. No. 4,643,736, EP 119,920, hereby incorporated by reference), in pulp and paper production.

3.1 Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference. The starch conversion process, which degrades starch to lower molecular weight carbohydrate components such as sugars or fat replacers, includes a debranching step.

3.2 Starch to Sugar Conversion

In the case of converting starch into a sugar the starch is depolymerized. Such a depolymerization process may consist of a pre-treatment step and two or three consecutive process steps, such as a liquefaction process, a saccharification process and (depending on the desired end product), an optional isomerization process.

3.3 Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation.

3.4 Liquefaction

During the liquefaction step, long-chain starch molecules are degraded into shorter branched and linear molecules (maltodextrins) by α-amylase. The liquefaction process is typically carried out at 105-110° C. for 5 to 10 minutes followed by 1-2 hours at 95° C. at a pH between 5.5 and 6.2. In order to ensure optimal enzyme stability under these conditions, 1 mM of calcium is added (40 ppm free calcium ions) is typically added. After this treatment the liquefied starch will have a "dextrose equivalent" (DE) of about 10-15.

3.5 Saccharification

After the liquefaction process the maltodextrins are converted into dextrose by addition of a glucoamylase (e.g., OPTIDEX® L-400) and a debranching enzyme, such as an isoamylase (U.S. Pat. No. 4,335,208) or a pullulanase. Before this step the pH is reduced to a value below 4.5, while maintaining the high temperature (above 95° C.) to inactivate the liquefying α-amylase, thereby reducing the formation of short oligosaccharides called "panose precursors," which cannot be hydrolyzed properly by the debranching enzyme. The temperature is lowered to 60° C., and glucoamylase and debranching enzyme are added. The saccharification process proceeds for 24-72 hours.

Normally, when denaturing the α-amylase after the liquefaction step, about 0.2-0.5% of the saccharification product is the branched trisaccharide Glc pα1-6Glc pα1-4Glc (panose), which cannot be degraded by a pullulanase. If active amylase from the liquefaction step is present during saccharification (i.e., no denaturing), this level can be as high as 1-2%, which is highly undesirable as it lowers the saccharification yield significantly.

3.6 Isomerization

When the desired final sugar product is, e.g., high fructose syrup, the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immobilized glucose isomerase (such as GENSWEET® IGI-HF).

3.7 Ethanol Production

In general alcohol production (ethanol) from whole grain can be separated into 4 main steps: milling; liquefaction; saccharification; and fermentation.

3.7.1 Milling

The grain is milled in order to open up the structure and allow for further processing. Two processes used are wet or dry milling. In dry milling the whole kernel is milled and used in the remaining part of the process. Wet milling gives a very good separation of germ and meal (starch granules and protein) and is with a few exceptions applied at locations where there is a parallel production of syrups.

3.7.2 Liquefaction

In the liquefaction process the starch granules are solubilized by hydrolysis to maltodextrins mostly of a DP higher than 4. The hydrolysis may be carried out by acid treatment or enzymatically by α-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

3.7.3 Saccharification

To produce low molecular sugars $DP_{1-3}$ that can be metabolized by yeast, the maltodextrin from the liquefaction must be further hydrolyzed. The hydrolysis is typically performed enzymatically by glucoamylases, alternatively α-glucosidases or acid α-amylases can be used. A full saccharification step may last up to 72 hours, however, it is common only to do a pre-saccharification of typically 40-90 minutes and then complete saccharification during fermentation (SSF). Saccharification is typically carried out at temperatures from 30-65° C., typically around 60° C., and at pH 4.5.

3.7.4 Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

The saccharification and fermentation steps may be carried out simultaneously or separately.

3.8 Distillation

Following the fermentation the mash is distilled to extract the ethanol. The ethanol obtained according to the process, may be used as, e.g., fuel ethanol; drinking ethanol, i.e., potable neutral spirits; or industrial ethanol.

3.9 By-Products

Left over from the fermentation is the grain, which is typically used for animal feed either in liquid form or dried. Further details on how to carry out liquefaction, saccharification, fermentation, distillation, and recovery of ethanol are well known to the skilled person.

3.10 Pulp and Paper Production

The present α-amylases may also be used in the production of lignocellulosic materials, such as pulp, paper and cardboard, from starch reinforced waste paper and cardboard, especially where repulping occurs at pH above 7 and where amylases facilitate the disintegration of the waste material through degradation of the reinforcing starch. The α-amylases are especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The α-amylases may also be used in modifying starch where enzymatically modified starch is used in papermaking together with alkaline fillers such as calcium carbonate, kaolin and clays. With the α-amylases of the present compositions and methods it becomes possible to modify the starch in the presence of the filler thus allowing for a simpler integrated process.

3.11 Desizing of Textiles, Fabrics and Garments

The present α-amylases may also be very useful in textile, fabric or garment desizing. In the textile processing industry, α-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. The non-enzymatic breakdown of the starch size does lead to some fiber damage because of the rather aggressive chemicals used. Accordingly, it would be desirable to use the α-amylases of the present compositions and methods as they have an improved performance in alkaline solutions. The α-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporated by reference, and commercially available products for desizing include OPTISIZE® FLEX from Genencor.

Also contemplated are compositions and methods of treating fabrics (e.g., to desize a textile) using one or more of the present α-amylase variants. The enzyme can be used in any fabric-treating method known in the art, see, e.g., U.S. Pat. No. 6,077,316. For example, in one aspect, the feel and appearance of a fabric is improved by a method comprising contacting the fabric with an α-amylase in solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. Also provided is a method of desizing comprising enzymatic hydrolysis of the size by the action of an -amylase.

The enzymes can be used alone or with other desizing chemical reagents and/or desizing enzymes to desize fabrics, including cotton-containing fabrics, as detergent additives, e.g., in aqueous compositions. An α-amylase can also be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The enzymes can be used in methods of finishing denim garments (e.g., a "bio-stoning process"), enzymatic desizing and providing softness to fabrics, and/or finishing process. Dosage of the amylase varies depending on the process type. Smaller dosages would require more time than larger dosages of the same enzyme. However, there is no upper limit on the amount of a desizing amylase present other than that dictated by the physical constraints of the solution. Thus, the limit of the enzyme may be the amount capable of solubilization in the solution. Typically, desizing enzymes, such as α-amylases, are incorporated in to the treating composition in an amount from about 0.00001% to about 2% of enzyme protein by weight of the fabric; or from about 0.0001% to about 1% of enzyme protein by weight of the fabric; or from about 0.001% to about 0.5% of enzyme protein by weight of the fabric; and in another example would be from about 0.01% to about 0.2% of enzyme protein by weight of the fabric.

3.12 Beer Making

As discussed above, the present α-amylases may also be useful in a beer-making process, wherein the enzymes are added during the mashing process.

3.13 Detergent Compositions

The present α-amylases may be added to and thus become a component of a detergent composition. The detergent composition may be formulated as a hand or machine laundry detergent composition, a laundry additive composition suitable for pretreatment of stained fabrics, a rinse added fabric softener composition, a detergent composition for general household hard surface cleaning, or a hand or machine dishwashing composition.

In one embodiment, there is provided for herein a detergent additive comprising a variant enzyme described herein. The detergent additive as well as the detergent composition may comprise one or more enzymes such as a protease, a lipase, a peroxidase, another amylolytic enzyme, e.g., another α-amylase, glucoamylase, maltogenic amylase, CGTase and/or a cellulose, mannanase (such as MANNASTAR™ from Danisco U.S.A., Inc., Genencor Division), pectinase, pectin lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease or a chymotrypsin-like protease. Examples of alkaline proteases are subtilisins, especially those derived from *Bacillus*, e.g., subtilisin *lentus*, subtilisin *amyloliquefaciens*, subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases also include but are not limited to the variants described in U.S. Pat. Nos. RE 34,606, 5,801,039, 5,340,735, 5,500,364, 5,855,625, 5,955,340, 5,700,676, 6,312,936, and 6,482,628, U.S. Pat. Publ. No. 2008/0090747, and International Patent Pub. Nos. WO98/23732, WO99/20770, WO 92/19729, WO 98/20115, WO 98/20116, WO 98/34946, WO95/23221, WO 92/21760, and WO 89/06270, especially variants with substitutions in one or more of the following positions: 27, 36, 57, 76, 87, 97, 101, 104, 120, 123, 167, 170, 194, 206, 218, 222, 224, 235 and 274.

Exemplary commercially available protease enzymes include ALCALASE®, SAVINASE®, PRIMASE®, DURALASE®, ESPERASE®, DURAZYM™, POLARZYME®, OVOZYME®, LIQUANASE®, NEUTRASE®, RELASE®, and KANNASE® (from Novozymes A/S), MAXATASE®, MAXACAL, MAXAPEM®, PROPERASE®, PURAFECT®, PURAFECT OXP®, FN2®, FN3® and FN4®, OPTICLEAN®, OPTIMASE®, PURAMAX™, EXCELLASE™, and PURAFAST™ (from Genencor), and BLAP™ (from Henkel Kommanditgesellschaft auf Aktien, Duesseldorf, Germany.

In some further embodiments, metalloproteases find use in the present invention, including but not limited to the neutral metalloprotease described in WO 07/044993.

Lipases:

Suitable lipases include those of bacterial or fungal origin. Chemically modified or protein engineered mutants are included. Examples of useful lipases include but are not limited to lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Additional exemplary lipase variants contemplated for use in the formulations include those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202. Commercially available lipase enzymes include LIPOLASE™ and LIPOLASE ULTRA™ (Novozymes A/S).

Polyesterases:

Suitable polyesterases can be included in composition. Suitable polyesterases include for example those described in WO 01/34899 and WO 01/14629.

Amylases:

One or more additional amylases (in addition to the variant amylase(s) described herein) may also be included. Suitable amylases (α and/or β) include those of bacterial or fungal origin. Chemically modified or protein engineered mutants are included. Amylases include, for example, α-amylases obtained from *Bacillus*, e.g., a special strain of *B. licheniformis*, described in more detail in GB 1,296,839. Examples of useful α-amylases are the variants described in WO 94/18314, WO 96/39528, WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available α-amylases are DURAMYL™, LIQUEZYME™ TERMAMYL™, NATALASE™, STAINZYME™ PLUS, STAINZYME™ ULTRA, FUNGAMYL™ and BAN™ (Novozymes A/S), RAPIDASE™ and PURASTAR™ (from Genencor).

Cellulases:

Cellulases may be added to the compositions. Suitable cellulases include those of bacterial or fungal origin. Chemically modified or protein engineered mutants are included. Suitable cellulases include but are not limited to cellulases from the genera *Bacillus, Pseudomonas, Trichoderma, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Exemplary *Trichoderma reesei* cellulases are disclosed in U.S. Pat. No. 4,689,297, U.S. Pat. No. 5,814,501, U.S. Pat. No. 5,324,649, WO 92/06221 and WO 92/06165. Exemplary *Bacillus* cellulases are disclosed in U.S. Pat. No. 6,562,612. Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME® (Novozymes A/S).

The detergent enzyme(s) may be included in a detergent composition by adding separate additives containing one or more enzymes, or by adding a combined additive comprising all of these enzymes. A detergent additive of the present compositions and methods, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Generally, the detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels contained for example about 30% water or less.

Persil, TIDE® 2X coldwater, and Ariel detergents are exemplary detergents used herein to test exemplary alpha-amylase variants. The present alpha-amylase variants are not restricted to the exemplary compositions, as they are contemplated to be functional in the presence of a broad range of commonly used cleaning compositions.

The detergent composition comprises one or more surfactants, which may be non-ionic including semi-polar and/or anionic and/or cationic and/or zwitterionic. The surfactants are typically present at a level of from 0.1% to 60% by weight. Exemplary alpha-amylase variants were tested in detergent compositions containing anionic and nonionic surfactants. The alpha-amylase variants described herein are contemplated to be active in compositions containing other surfactants that are commonly used in detergents.

When included therein the detergent will usually contain from about 1% to about 40% of an anionic surfactant such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system that may comprise a $H_2O_2$ source, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g. the amide, imide, or sulfone type peroxyacids). The bleaching system can also be an enzymatic bleaching system. See, for example, WO 05/056782.

The enzyme(s) of the detergent composition of the present compositions and methods may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

The present α-amylases may be added in an amount corresponding to about 0.01 to about 100 mg of enzyme protein per liter of wash liquor, for example about 0.05 to about 5.0 mg of enzyme protein per liter of wash liquor, or about 0.1 to about 1.0 mg of enzyme protein per liter of wash liquor.

The present α-amylases may additionally be incorporated in the detergent formulations disclosed in WO 97/07202, which is hereby incorporated as reference.

4. Compositions and Use

The present α-amylases may also be used in methods relating to detergent compositions and cleaning, in particular laundry detergent compositions, dishwashing detergent compositions, hard surface cleaning compositions, composition for desizing of textiles, fabrics or garments, compositions for production of pulp and paper, beer making, ethanol production, and starch conversion, and the like.

4.1 Laundry Detergent Compositions and Use

One embodiment, of the present α-amylases compositions and method is a laundry detergent composition and method of use, thereof. The detergent composition may be in the form of a non-dusting granulate, a stabilized liquid, or a protected enzyme. The dry formulations may be in the form of a granulate or a microgranulate. Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP Appln. No. 238,216. Polyols have long been recognized as stabilizers of proteins as well as improving solubility of proteins. See, e.g., J. K. Kaushik et al. *J. Biol. Chem.* 278: 26458-65 (2003) and the references cited therein; and Monica Conti et al. *J. Chromatography* 757: 237-245 (1997).

The composition may comprise one or more of the present amylases as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase, as well as other enzymes discussed below. The additional enzyme(s) may be producible by means of a microorganism belonging to the genera *Aspergillus, Trichoderma, Humicola* (e.g., *H. insolens*), and *Fusarium*. Exemplary members of the *Aspergillus* genus include *Aspergillus aculeatus, Aspergillus awamori, Aspergillus niger*, or *Aspergillus oryzae*. Exemplary members of the genus *Fusarium* include *Fusarium bactridioides, Fusarium cerealis, Fusarium crookwellense, Fusarium culmorum, Fusarium graminearum, Fusarium graminum, Fusarium heterosporum, Fusarium negundinis, Fusarium oxysporum, Fusarium reticulatum, Fusarium roseum, Fusarium sambucinum, Fusarium sarcochroum, Fusarium sulphureum, Fusarium torulosum, Fusarium trichothecioides*, and *Fusarium venenatum*.

The detergent composition may be in any useful form, e.g., powders, granules, pastes, or liquids. A liquid detergent may be aqueous, typically containing up to about 70% of water, and 0% to about 30% of organic solvent. It can also be a in the form of a compact gel type containing only about 30% water. Enzymes may be used in any detergent composition compatible with the stability of the enzyme. Enzymes can be protected against generally deleterious components by known forms of encapsulation as for example by granulation or sequestration in hydro gels. Enzymes and specifically α-amylases are not limited to laundry and dishwashing applications, but can also be used in surface cleaners, ethanol production from starch or biomass.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, cutinase, protease, cellulase, peroxidase, and/or laccase in any combination. See supra.

The detergent may optionally contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e., essentially free of detergent builder.

The detergent may optionally comprise one or more polymers. Examples include carboxymethylcellulose (CMC), polyvinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may optionally contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type. The bleaching system can also be an enzymatic bleaching system, where a perhydrolase activates peroxide, as described in for example WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) is usually neutral or alkaline, e.g., pH about 7.0 to about 11.0.

Particular forms of detergent compositions comprising a the α-amylase variants can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O, 2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O, 2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O, 2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O, 2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O, 2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., NaAlSiO$_4$) about 10% to about 20%; layered disilicate (e.g., SK56 from Hoechst) about 10% to about 20%; sodium carbonate (e.g., Na$_2$CO$_3$) about 3% to about 12%; soluble silicate (e.g., Na$_2$O, 2SiO$_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising (C$_{12}$-C$_{18}$) alkyl sulfate about 4% to about 8%; alcohol ethoxylate about 11% to about 15%; soap about 1% to about 4%; zeolite MAP or zeolite A about 35% to about 45%; sodium carbonate (as Na$_2$CO$_3$) about 2% to about 8%; soluble silicate (e.g., Na$_2$O, 2SiO$_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in Hage et al., Nature 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

One or more of the present α-amylases may be incorporated in concentrations conventionally employed in detergents. It is at present contemplated that, in the detergent composition, an α-amylase or variant thereof, may be added in an amount corresponding to 0.00001-1.0 mg (calculated as pure enzyme protein) of enzyme per liter of wash liquor.

In another embodiment, a 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for manual or machine laundry operations.

In a specific aspect, the detergent composition can further comprise 2,6-β-D-fructan hydrolase, one or more additional α-amylases in addition to one or more of the present α-amylase variants, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

4.2 Dishwash Detergent Compositions

The present α-amylases may also be used in dishwash detergent compositions, including the following:

| 1) POWDER AUTOMATIC DISHWASHING COMPOSITION | |
|---|---|
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

| 2) POWDER AUTOMATIC DISHWASHING COMPOSITION | |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10% |

| 3) POWDER AUTOMATIC DISHWASHING COMPOSITION | |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

| 4) POWDER AUTOMATIC DISHWASHING COMPOSITION | |
|---|---|
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) Polymer | 0-3% |
| | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

| 5) POWDER AUTOMATIC DISHWASHING COMPOSITION | |
|---|---|
| Nonionic surfactant | 1-7% |
| Sodium disilicate | 18-30% |
| Trisodium citrate | 10-24% |
| Sodium carbonate | 12-20% |
| Monopersulphate (2 KHSO$_5$•KHSO$_4$•K$_2$SO$_4$) | 15-21% |
| Bleach stabilizer | 0.1-2% |
| Maleic acid/acrylic acid copolymer | 0-6% |

| | |
|---|---|
| Diethylene triamine pentaacetate, pentasodium salt | 0-2.5% |
| Enzymes | 0.0001-0.1% |
| Sodium sulphate, water | Balance |
| 6) POWDER AND LIQUID DISHWASHING COMPOSITION WITH CLEANING SURFACTANT SYSTEM | |
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |
| 7) NON-AQUEOUS LIQUID AUTOMATIC DISHWASHING COMPOSITION | |
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |
| 8) NON-AQUEOUS LIQUID DISHWASHING COMPOSITION | |
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |
| 9) THIXOTROPIC LIQUID AUTOMATIC DISHWASHING COMPOSITION | |
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |

| | |
|---|---|
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |
| 10) LIQUID AUTOMATIC DISHWASHING COMPOSITION | |
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |
| Water | Balance |
| 11) LIQUID AUTOMATIC DISHWASHING COMPOSITION CONTAINING PROTECTED BLEACH PARTICLES | |
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

11) Automatic dishwashing compositions as described in 1), 2), 3), 4), 6) and 10), wherein perborate is replaced by percarbonate.

12) Automatic dishwashing compositions as described in 1)-6) which additionally contain a manganese catalyst. The manganese catalyst may, e.g., be one of the compounds described in Hage et al., Nature 369: 637-639 (1994).

4.3. Biofilm Removal Compositions and Use

In another embodiment, a composition for removing or disintegrating a biofilm is provided, comprising a one or more of the present α-amylases, is provided. The composition may include one or more of the present α-amylases as the only enzymatic activity, making it a mono-component composition for use in removing of disintegrating biofilms. Alternatively, the composition may comprise multiple enzymatic activities, such as multiple amylases, or a cocktail of enzymes including any combination of the following: aminopeptidase, amylase (β-, or α-, or gluco-amylase), carbohydrase, carboxypeptidase, catalase, cellulase, chitinase, cutinase, cyclodextrin glycosyltransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, and/or xylanase, or any combination thereof for removing biofilms. A particular enzyme is a 2,6-β-D-fructan hydrolase. The additional enzyme(s) may be producible by means of a microorganism belonging to the genera *Aspergillus, Trichoderma, Humicola* (e.g., *H. insolens*), and *Fusarium*. Exemplary members from the *Aspergillus* genus include *Aspergillus aculeatus, A. awamori, A. niger*, and *A. oryzae*. Exemplary members of the *Fusarium* genus include *F. bactridioides, F. cerealis, F. crookwellense, F. culmorum, F. graminearum, F. graminum, F. heterosporum, F. negundinis, F. oxysporum, F. reticulatum, F. roseum, F. sambucinum, F. sarcochroum, F. sulphureum, F. torulosum, F. trichothecioides*, and *F. venenatum*.

The biofilm removal or disintegration composition may be in the form of a liquid or a dry composition. For instance, the α-amylase may be in the form of a granulate or a microgranulate or may be stabilized in accordance with methods known in the art. The biofilm is typically present at a surface and the disintegration of the biofilm can be achieved by bringing the surface in contact, e.g., by immersing, covering or splashing the surface with an aqueous medium comprising one or more of the present α-amylases. The composition can be used to hydrolyse slime, e.g., in white waters in the pulping and paper industry.

The α-amylases may be present in the amount of 0.0001 to 10000 mg/L; 0.001-1000 mg/L; 0.01-100 mg/L; or 0.1-10 mg/L. Additional enzymes and enzyme variants may be present in similar amounts or less.

The process may suitably be performed at temperatures from about ambient temperature to about 70° C. Exemplary temperature ranges include from about 30° C. to about 60° C., e.g., about 40° C. to about 50° C.

A suitable pH for the hydrolyzing biofilms lies within from about 3.5 to about 8.5. Exemplary pH ranges include from about 5.5 to about 8, e.g. from about 6.5 to about 7.5. The contact time or reaction time for the enzyme to effectively removing a biofilm may vary considerably, depending on the biofilm properties and the frequency of which a surface is treated with the enzyme alone or in combination with other biofilm degrading enzymes. Exemplary reaction times include within about 0.25 to about 25 hours, and from about 1 to about 10 hours, e.g. about 2 hours.

The α-amylase can further be combined with antimicrobial agents such as enzymatic or non-enzymatic biocides. An enzymatic biocide may, e.g., be a composition comprising an oxidoreductase, e.g. a laccase or a peroxidase, especially haloperoxidase, and optionally an enhancing agent, such as an alkyl syringate, as described for example in International PCT applications WO 97/42825 and DK 97/1273.

The surface from which a biofilm for example can be removed and/or cleaned off is a hard surface, which by definition relates to any surface that is essentially non-permeable to microorganisms. Examples of surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like. Accordingly, the surface may be a member of a system holding, transporting, processing, or in contact with aqueous solutions such as water supply systems, food processing systems, cooling systems, chemical processing systems or pharmaceutical processing systems. The compositions and methods of using the compositions for removing biofilm in the wood processing industry, such as the pulp and/or paper industry. Accordingly, the enzyme and compositions containing the enzyme are useful in a conventional cleaning-in-place (C-I-P) system. The surface may a member of a system unit such as pipes, tanks, pumps, membranes, filters, heat exchangers, centrifuges, evaporators, mixers, spray towers, valves and reactors. The surface may also be or be a part of utensils used in the medical science and industry such as contaminated endoscopes, prosthetic devices or medical implants.

The compositions for biofilm removal is also contemplated for preventing so-called bio-corrosion occurring when a metal surface, e.g. a pipeline, is attacked by a microbial biofilm, that is by disintegrating the biofilm thereby preventing the microbial cells of the biofilm from creating a biofilm environment, which corrodes the metal surface to which it is attached.

Another application for anti-biofilm compositions is for oral care. The surface may however also be of biological origin, such as mucous membranes, skin, teeth, hair, nails etc.

Teeth with dental plaque, e.g., by incorporating the enzymes into toothpaste, and contaminated contact lenses are encompassed as surfaces. Accordingly, one or more of the present α-amylases can be used for compositions and processes for making a medicament for disintegration of plaque present on a human or animal tooth. A further use is disintegration of biofilm from mucous membranes, such as biofilm in lungs in patients suffering from cystic fibrosis.

Accordingly, in a still further aspect relates to an oral care composition comprising a recombinant enzyme, such as a purified enzyme that is essentially free of any active contaminants. An oral care composition may suitably comprise an amount of a recombinant enzyme.

Other biofilm degrading enzymes for use in oral care compositions include but are not limited to 2,6-β-D-fructan hydrolase activity in the oral care composition. Contemplated enzyme activities include activities from the group of enzymes comprising dextranase; mutanases; oxidases, such as glucose oxidase, L-amino acid oxidase, peroxidases, such as e.g. the *Coprinus* sp. peroxidases described in WO 95/10602, or lactoperoxidase, haloperoxidases, especially haloperoxidase derivable from *Curvularia* sp., in particular *C. verruculosa* and *C. inaequalis*; laccases; proteases such as papain, acidic protease (e.g. the acidic proteases described in WO 95/02044, endoglucosidases, lipases, amylases, including amyloglucosidases, such as AMG (Novo Nordisk A/S); anti-microbial enzymes, and mixtures thereof.

The oral care composition may have any suitable physical form (i.e., powder, paste, gel, liquid, ointment, tablet etc.). An "oral care composition" includes a composition, which can be used for maintaining or improving the oral hygiene in the mouth of humans and animals, by preventing dental caries, preventing the formation of dental plaque and tartar, removing dental plaque and tartar, preventing and/or treating dental diseases etc. At least in the context oral care compositions do also encompass products for cleaning dentures, artificial teeth and the like. Examples of such oral care compositions includes toothpaste, dental cream, gel or tooth powder, odontic mouth washes, pre- or post brushing rinse formulations, chewing gum, lozenges, and candy. Toothpastes and tooth gels typically include abrasive polishing materials, foaming agents, flavoring agents, humectants, binders, thickeners, sweetening agents, whitening/bleaching/stain removing agents, water, and optionally additional enzymes and enzyme combinations.

Mouthwashes, including plaque-removing liquids, typically comprise a water/alcohol solution, flavor, humectant, sweetener, foaming agent, colorant, and optionally additional enzymes or enzyme combinations.

Abrasive polishing material might also be incorporated into the oral care composition such as a dentifrice. Abrasive polishing materials include alumina and hydrates thereof, such as a alumina trihydrate; magnesium trisilicate; magnesium carbonate; kaolin; aluminosilicates, such as calcined aluminum silicate and aluminum silicate; calcium carbonate; zirconium silicate; and also powdered plastics, such as polyvinyl chloride; polyamides; polymethyl methacrylate; polystyrene; phenol-formaldehyde resins; melamine-formaldehyde resins; urea-formaldehyde resins; epoxy resins; powdered polyethylene; silica xerogels; hydrogels and aerogels and the like. Also suitable as abrasive agents are calcium pyrophosphate; water-insoluble alkali metaphosphates; dicalcium phosphate and/or its dihydrate, dicalcium orthophosphate; tricalcium phosphate; particulate hydroxyapatite and the like. It is also possible to employ mixtures of these substances.

Dependent on the oral care composition, the abrasive product may be present in from about 0% to about 70% by weight, or from about 1% to about 70%. For toothpastes, the abrasive material content typically lies in the range of from 10% to 70% by weight of the final toothpaste.

Humectants are employed to prevent loss of water from e.g. tooth pastes. Suitable humectants for use in oral care compositions include the following compounds and mixtures thereof: glycerol; polyol; sorbitol; polyethylene glycols (PEG); propylene glycol; 1,3-propanediol; 1,4-butanediol; hydrogenated partially hydrolyzed polysaccharides and the like. Humectants are in general present in from 0% to about 80%, or from about 5% to about 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing a dentifrice product. Thickeners may be present in toothpaste creams and gels in an amount of from about 0.1% to about 20% by weight, and binders to the extent of from about 0.01 to about 10% by weight of the final product.

As foaming agent soap, anionic, cationic, non-ionic, amphoteric and/or zwitterionic surfactants can be used. These may be present at levels of from 0% to about 15%, from about 0.1% to about 13%, or from about 0.25% to about 10% by weight of the final product.

Surfactants are suitable to the extent that they do not exert an inactivation effect on the α-amylase. Surfactants include fatty alcohol sulfates, salts of sulfonated mono-glycerides or fatty acids having 10 to 20 carbon atoms, fatty acid-albumen condensation products, salts of fatty acids amides and taurines and/or salts of fatty acid esters of isethionic acid.

Suitable sweeteners include saccharin for use in the formulations. Flavors, such as spearmint, are usually present in low amounts, such as from about 0.01% to about 5% by weight, especially from about 0.1% to about 5%. Whitening/bleaching agents include $H_2O_2$ and may be added in amounts less that about 5%, or from about 0.25% to about 4%, calculated by the weight of the final product. The whitening/bleaching agents may be an enzyme, such as an oxidoreductase. Examples of suitable teeth bleaching enzymes, such as those described in WO 97/06775.

Water is usually added in an amount giving e.g. toothpaste a flowable form. Further water-soluble anti-bacterial agents, such as chlorohexidine digluconate, hexetidine, alexidine, Triclosan®, quaternary ammonium anti-bacterial compounds and water-soluble sources of certain metal ions such as zinc, copper, silver and stannous (e.g., zinc, copper and stannous chloride, and silver nitrate) may also be included.

Also contemplated is the addition of compounds that can be used as fluoride source, dyes/colorants, preservatives, vitamins, pH-adjusting agents, anti-caries agents, desensitizing agents, etc.

Biofilm degrading enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids, which form the structural components of bacterial cell walls and membranes.

Dextranase and other carbohydrases, such as the 2,6-β-D-fructan hydrolase, break down the organic skeletal structure produced by bacteria that forms a matrix for bacterial adhesion. Proteases and amylases, not only prevent plaque formation, but also prevent the development of calculus by breaking-up the carbohydrate-protein complex that binds calcium, preventing mineralization.

A toothpaste may typically comprise the following ingredients (in weight % of the final toothpaste composition): abrasive material to about 70%; humectant: 0% to about 80%; thickener: about 0.1% to about 20%; binder: about 0.01% to about 10%; sweetener: about 0.1% to about 5%; foaming agent: 0% to about 15%; whitener: 0% to about 5%; and enzymes: about 0.0001% to about 20%.

In a specific embodiment, a toothpaste has a pH in the range from about 6.0 to about 8.0, and comprises: a) about 10% to about 70% abrasive material; b) 0% to about 80% humectant; c) 0.1% to about 20% thickener; d) 0.01% to about 10% binder; e) about 0.1% to about 5% sweetener; f) 0% to about 15% foaming agent; g) 0% to about 5% whitener; i) about 0.0001% to about 20% enzymes.

The enzymes referred to under i) include an α-amylase variants alone, or in combination with other biofilm degrading enzymes, such as 2,6-β-D-fructan hydrolase, and optionally other types of enzymes mentioned above known to be used in toothpastes and the like.

A mouth wash may typically comprise the following ingredients (in weight % of the final mouth wash composition): 0% to about 20% humectant; 0% to about 2% surfactant; 0% to about 5% enzymes; 0% to about 20% ethanol; 0% to about 2% other ingredients (e.g. flavor, sweetener active ingredients such as fluorides). The composition can also contain from about 0% to about 70% water.

The mouth wash composition may be buffered with an appropriate buffer e.g. sodium citrate or phosphate in the pH-range of about 6.0 to about 7.5. The mouth wash may be in non-diluted form (i.e., must be diluted before use).

The oral care compositions may be produced using any conventional method known to the art of oral care.

4.4 Starch Processing Compositions and Use

In another aspect, compositions comprising the present α-amylases can be utilized for starch liquefaction or saccharification.

In one embodiment, the compositions are used to produce sweeteners from starch. A "traditional" process for conversion of starch to fructose syrups normally consists of three consecutive enzymatic processes, viz. a liquefaction process followed by a saccharification process, and an isomerization process. During the liquefaction process, starch is degraded to dextrins by an α-amylase, at pH values between about 5.5 and about 6.2, and at temperatures of about 95° C. to about 160° C. for a period of approximately 2 hours. In order to ensure optimal enzyme stability under these conditions, 1 mM of calcium is added (40 ppm free calcium ions). Starch processing is useful for producing alcohol (e.g., cereal liquefaction for fuel and potable alcohol, alcohol brewing), starch liquefaction for sweetener production, cane sugar processing, and other food related starch processing goals. Other conditions can be used for different α-amylase or variants thereof.

After the liquefaction process, the dextrins are converted into dextrose by addition of a glucoamylase (e.g., AMG™) and a debranching enzyme, such as an isoamylase or a pullulanase (e.g., PROMOZYME®). Before this step, the pH is reduced to a value below about 4.5, maintaining the high temperature (above 95° C.), and the liquefying α-amylase activity is denatured. The temperature is lowered to 60° C., and a glucoamylase and a debranching enzyme can be added. The saccharification process proceeds typically for about 24 to about 72 hours.

After the saccharification process, the pH is increased to a value in the range of about 6.0 to about 8.0, e.g., pH 7.5, and the calcium is removed by ion exchange. The dextrose syrup is then converted into high fructose syrup using, e.g., an immobilized glucose isomerase (such as Sweetzyme®).

In some embodiments, the compositions and methods involve reduced calcium dependency of the liquefying α-amylase. Addition of free calcium is required to ensure adequately stability of the α-amylase but free calcium strongly inhibits the activity of the glucose isomerase and needs to be removed, by means of an expensive unit operation, to an extent that reduces the level of free calcium to below 3-5 ppm. Cost savings can be obtained if such an operation could be avoided, and the liquefaction process could be performed without addition of free calcium ions.

α-Amylases having reduced calcium-dependence, and which are stable and active at low concentrations of free calcium (<40 ppm), can be utilized in the composition and procedures. Such an α-amylase or variant thereof should have a pH optimum at a pH in the range of about 4.5 to about 6.5, or in the range of about 4.5 to about 5.5.

One of more of the present α-amylases can be used in laboratory and in industrial settings to hydrolyze starch or any maltodextrine-comprising compound for a variety of purposes. The α-amylases can be used alone to provide specific hydrolysis or can be combined with other amylases to provide a "cocktail" with a broad spectrum of activity. Exemplary uses include the removal or partial or complete hydrolysis of starch or any maltodextrine-comprising compound from biological, food, animal feed, pharmaceutical, or industrial samples.

One of more of the present α-amylases can be used in a fermentation process, wherein a starch substrate is liquefied and/or saccharified to produce glucose and/or maltose suitable for conversion into a fermentation product by a fermenting organism, such as a yeast. Such fermentation processes include a process for producing ethanol for fuel or drinking ethanol (potable alcohol), a process for producing a beverage, a process for producing desired organic compounds (e.g., such as citric acid, itaconic acid, lactic acid, gluconic acid, sodium gluconate, calcium gluconate, potassium gluconate, glucono delta lactone, or sodium erythorbate), ketones, amino acids (such as glutamic acid, sodium monoglutaminate), but also more complex compounds (e.g., antibiotics, such as penicillin, tetracyclin), enzymes, vitamins (e.g., riboflavin, vitamin $B_{12}$, β-carotene), and hormones, which are difficult to produce synthetically.

The starch to be processed may be a highly refined starch quality, such as at least 90%, at least 95%, at least 97%, or at least 99.5% pure. Alternatively, the starch can be a more crude starch containing material comprising milled whole grain including non-starch fractions such as germ residues and fibers. The raw material, such as whole grain, is milled in order to open up the structure and allowing for further processing. Two milling processes can be used: wet and dry milling. Also, corn grits such as milled corn grits may be applied.

Dry milled grain will, in addition to starch, comprise significant amounts of non-starch carbohydrate compounds. When such a heterogeneous material is processed by jet cooking only a partial gelatinization of the starch is achieved. As the present α-amylases have high activity towards ungelatinized starch, they may be advantageously applied in a process involving the liquefaction and/or saccharification of jet-cooked, dry-milled starch.

Furthermore, due to the superior hydrolysis activity of the present α-amylases, the need for glucoamylase during the saccharification step is greatly reduced, allowing saccharification to be performed at very low levels of glucoamylase activity. Glucoamylase activity is either absent or present in an amount of no more than or even less than 0.5 AGU/g DS, or no more than or even less than 0.4 AGU/g DS, or no more than or even less than about 0.3 AGU/g DS, or less than 0.1 AGU, such as no more than or even less than about 0.05 AGU/g DS of starch substrate. "DS" is the unit of enzyme added per gram of dry solid substrate. Expressed in mg enzyme protein, the enzyme having glucoamylase activity is either absent or present in an in an amount of no more than or even less than about 0.5 mg EP/g DS, or no more than or even less than about 0.4 mg EP/g DS, or no more than or even less than about 0.3 mg EP/g DS, or no more than or even less than about 0.1 mg EP/g DS (e.g., no more than or even less than about 0.05 mg EP/g DS or no more than or even less than 0.02 mg EP/g DS of starch substrate). The glucoamylase may be derived from an Aspergillus spp., a Talaromyces spp., a Pachykytospora spp., or a Trametes spp., with exemplary examples being Aspergillus niger, Talaromyces emersonii, Trametes cingulata, and Pachykytospora papyracea.

The process may comprise a) contacting a starch substrate with one or more of the present α-amylases comprising a catalytic module having α-amylase activity and a carbohydrate-binding module, e.g., the polypeptide of the first aspect; b) incubating the starch substrate with the enzyme for a time and at a temperature sufficient to achieve conversion of at least 90%, at least 91%, at least 92%, at least 93%, at least 94%, at least 95%, at least 96%, at least 97%, at least 98%, at least 99%, or even at least 99.5% w/w of the starch substrate into fermentable sugars; c) fermenting to produce a fermentation product; and d) optionally recovering the fermentation product. During the process steps b) and/or c), an enzyme having glucoamylase activity is either absent or present in an amount from 0.001 to 2.0 AGU/g DS, from 0.01 to 1.5 AGU/g DS, from 0.05 to 1.0 AGU/g DS, from 0.01 to 0.5 AGU/g DS. The enzyme having glucoamylase activity can either absent or present in an amount of no more than or even less than 0.5 AGU/g DS, or no more than or even less than 0.4 AGU/g DS, or no more than or even less than 0.3 AGU/g DS, or no more than or even less than 0.1 AGU/g DS (e.g., no more than or even less than 0.05 AGU/g DS of starch substrate). Expressed in mg enzyme protein, the enzyme having glucoamylase activity is either absent or present in an in an amount of no more than or even less than 0.5 mg EP/g DS, or no more than or even less than 0.4 mg EP/g DS, or no more than or even less than 0.3 mg EP/g DS, or no more than or even less than 0.1 mg EP/g DS (e.g., no more than or even less than 0.05 mg EP/g DS or no more than or even less than 0.02 mg EP/g DS of starch substrate). In the process steps a), b), c), and/or d) may be performed separately or simultaneously.

In some embodiments, the process comprises: a) contacting a starch substrate with a yeast cell transformed to express one or more of the present α-amylases comprising a catalytic module having α-amylase activity and a carbohydrate-binding module; b) incubating the starch substrate with the yeast for a time and at a temperature sufficient to achieve conversion of at least 90% w/w of the starch substrate into fermentable sugars; c) fermenting to produce ethanol; d) optionally recovering ethanol. The steps a), b), and c) may performed separately or simultaneously.

In some embodiments, the process comprising hydrolysis of a slurry of gelatinized or granular starch, in particular hydrolysis of granular starch into a soluble starch hydrolysate at a temperature below the initial gelatinization temperature of the granular starch. In addition to being contacted with a polypeptide comprising a catalytic module having α-amylase activity and a carbohydrate-binding module. The starch can be contacted with any one or more of the following a fungal α-amylase (EC 3.2.1.1) and one or more of the following: a β-amylase (EC 3.2.1.2), and a glucoamylase (EC 3.2.1.3). In a further aspect, another amylolytic enzyme or a debranching enzyme, such as an isoamylase (EC 3.2.1.68), or a pullulanases (EC 3.2.1.41) may be combined with the present α-amylase(s).

In some embodiments, the process is conducted at a temperature below the initial gelatinization temperature. Such processes are oftentimes conducted at least at 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or at least 60° C. The pH at which the process is conducted may in be in the range of about 3.0 to about 7.0, or from about 3.5 to about 6.0, or from about 4.0 to about 5.0. One aspect contemplates a process comprising fermentation, e.g. with a yeast to produce ethanol, e.g., at a temperature around 32° C., such as from 30° C. to 35° C.

In another aspect, the process comprises simultaneous saccharification and fermentation, e.g., with a yeast to produce ethanol, or another suitable fermentation organism to produce a desired organic compound, such as at a temperature from 30° C. to 35° C., e.g., at around 32° C.

In the above fermentation processes, the ethanol content reaches at least about 7%, at least about 8%, at least about 9%, at least about 10%, at least about 11%, at least about 12%, at least about 13%, at least about 14%, at least about 15% such as at least about 16% ethanol.

The starch slurry to be used in any of the above aspects may have about 20% to about 55% dry solids granular starch, about 25% to about 40% dry solids granular starch, or from about 30% to about 35% dry solids granular starch. After being contacted with an α-amylase, the enzyme converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, an α-amylase comprises a catalytic module having α-amylase activity and a carbohydrate-binding module is used in a process for liquefaction, saccharification of a gelatinized starch, e.g., but not limited to gelatinization by jet cooking. The process may comprise fermentation to produce a fermentation product, e.g., ethanol. Such a process for producing ethanol from starch-containing material by fermentation comprises: (i) liquefying the starch-containing material with a polypeptide comprising a catalytic module having α-amylase activity and a carbohydrate-binding module, e.g., the polypeptide of the first aspect; (ii) saccharifying the liquefied mash obtained; and (iii) fermenting the material obtained in step (ii) in the presence of a fermenting organism. Optionally the process further comprises recovery of the ethanol. The saccharification and fermentation processes may be carried out as a simultaneous saccharification and fermentation process (SSF process). During the fermentation, the ethanol content reaches at least about 7%, at least about 8%, at least about 9%, at least about 10% such as at least about 11%, at least about 12%, at least about 13%, at least about 14%, at least 15% such as at least about 16% ethanol.

The starch to be processed in the processes of the above aspects may in particular be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Also contemplated are both waxy and non-waxy types of corn and barley.

The composition described above may be used for liquefying and/or saccharifying a gelatinized or a granular starch, and a partly gelatinized starch. A partly gelatinized starch is a starch that to some extent is gelatinized, i.e., wherein part of the starch has irreversibly swelled and gelatinized and part of the starch is still present in a granular state.

The composition described above may comprise an acid α-amylase variant present in an amount of 0.01 to 10.0 AFAU/g DS, or 0.1 to 5.0 AFAU/g DS, or 0.5 to 3.0 AFAU/AGU, or 0.3 to 2.0 AFAU/g DS. The composition may be applied in any of the starch processes described above.

A β-amylase (EC 3.2.1.2), i.e., an exo-acting maltogenic amylase, may be added to catalyze the hydrolysis of 1,4-α-glucosidic linkages in amylose, amylopectin, and related glucose polymers, thereby releasing maltose. β-amylases have been isolated from various plants and microorganisms (W. M. Fogarty and C. T. Kelly, PROGRESS IN INDUSTRIAL MICROBIOLOGY, vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley SPEZYME® BBA 1500, SPEZYME® DBA, OPTIMALT® ME, OPTIMALT® BBA (Genencor International Inc.) and NOVOZYM™ WBA (Novozymes A/S).

A glucoamylase (EC 3.2.1.3) may also be included in the compositions. The glucoamylases may be derived from a microorganism or a plant. Exemplary glucoamylases are of fungal or bacterial origin. Exemplary fungal glucoamylases are *Aspergillus* glucoamylases, in particular *A. niger* G1 or G2 glucoamylase (Boel et al., *EMBO J.* 3(5): 1097-1102 (1984), or variants thereof, such as disclosed in WO 92/00381; and WO 00/04136; the *A. awamori* glucoamylase (WO 84/02921); *A. oryzae* (*Agric. Biol. Chem.*, 55(4): 941-949 (1991)), or variants or fragments thereof.

Other *Aspergillus* glucoamylase variants include variants to enhance the thermal stability: G137A and G139A (Chen et al., *Prot. Eng.* 9: 499-505 (1996)); D257E and D293E/Q (Chen et al., *Prot. Eng.* 8: 575-582 (1995)); N182 (Chen et al., *Biochem. J.* 301: 275-281 (1994)); disulfide bonds, A246C (Fierobe et al., *Biochemistry*, 35: 8698-8704 (1996)); and introduction of Pro residues in positions A435 and S436 (Li et al., *Protein Eng.* 10: 1199-1204 (1997)). Other contemplated glucoamylases include and *Talaromyces* glucoamylases, in particular derived from *Talaromyces emersonii* (WO 99/28448), *Talaromyces leycettanus* (U.S. Pat. No. RE 32,153), *Talaromyces duponti, Talaromyces thermophilus* (U.S. Pat. No. 4,587,215).

Bacterial glucoamylases include glucoamylases from the genus *Clostridium*, in particular *C. thermoamylolyticum* (EP 135138) and *C. thermohydrosulfuricum* (WO 86/01831). Also contemplated are the commercial glucoamylases such as AMG 200L; AMG 300 L; SAN™ SUPER and AMG™ E (Novozymes); OPTIDEX®300 (from Genencor International, Inc.); AMIGASE® and AMIGASE® PLUS (DSM); G-ZYME® G900 (Enzyme Bio-Systems); G-ZYME® G990 ZR (*A. niger* glucoamylase and low protease content).

In some embodiments, glucoamylases may be added in an amount of 0.02-2.0 AGU/g DS, or 0.1-1.0 AGU/g DS, such as 0.2 AGU/g DS.

Another enzyme that can optionally be added is a debranching enzyme, such as an isoamylase (EC 3.2.1.68) or a pullulanase (EC 3.2.1.41). Isoamylase hydrolyses α-1,6-D-glucosidic branch linkages in amylopectin and β-limit dextrins and can be distinguished from pullulanases by the inability of isoamylase to attack pullulan, and by the limited action on α-limit dextrins. Debranching enzymes may be added in effective amounts well known to the person skilled in the art.

The exact composition of the products of the process depends on the combination of enzymes applied as well as the type of granular starch processed. For example, the soluble hydrolysate can be maltose with a purity of at least about 85%, at least about 90%, at least about 95.0%, at least about 95.5%, at least about 96.0%, at least about 96.5%, at least about 97.0%, at least about 97.5%, at least about 98.0%, at least about 98.5, at least about 99.0% or at least about 99.5%. Alternatively, the soluble starch hydrolysate can be glucose or the starch hydrolysate has a DX (glucose percent of total solubilized dry solids) of at least 94.5%, at least 95.0%, at least 95.5%, at least 96.0%, at least 96.5%, at least 97.0%, at least 97.5%, at least 98.0%, at least 98.5, at least 99.0% or at least 99.5%. The process can include a product which is a specialty syrup, such as a specialty syrup containing a mixture of glucose, maltose, DP3 and DPn for use in the manufacture of ice creams, cakes, candies, canned fruit.

Two milling processes are: wet and dry milling. In dry milling, the whole kernel is milled and used. Wet milling gives a good separation of germ and meal (starch granules and protein), and is with a few exceptions, applied at locations where the starch hydrolysate is used in production of syrups. Both dry and wet milling are well known in the art of starch processing and are equally contemplated for use with the compositions and methods disclosed. The process may be conducted in an ultrafiltration system where the retentate is held under recirculation in presence of enzymes, raw starch and water and where the permeate is the soluble starch hydrolysate. Equally contemplated is the process conducted in a continuous membrane reactor with ultrafiltration membranes and where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

In some embodiments, the soluble starch hydrolysate of the process is subjected to conversion into high fructose starch-based syrup (HFSS), such as high fructose corn syrup (HFCS). This conversion can be achieved using a glucose isomerase, and by an immobilized glucose isomerase supported on a solid support. Exemplary isomerases include the commercial products Sweetzyme®, IT (Novozymes A/S); G-ZYME® IMGI, and G-ZYME® G993, KETOMAX™, G-ZYME® G993 (Rhodia); G-ZYME® G993 liquid, GENSWEET® IGI (Genencor International, Inc.).

In other embodiments, the soluble starch hydrolysate produced by these methods can be used in the production of fuel or potable ethanol. Fermentation may be carried out simultaneously or separately/sequential with respect to hydrolysis. When the fermentation is performed simultaneous to hydrolysis, the temperature is between 30° C. and 35° C., or between 31° C. and 34° C. The process may be conducted in an ultrafiltration system where the retentate is held under recirculation in presence of enzymes, raw starch, yeast, yeast nutrients and water and where the permeate is an ethanol containing liquid. The process may also be conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta lactone, or sodium erythorbate.

The amylolytic activity of one of more of the present α-amylases may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch, the blue color gets weaker and gradually turns into a reddish-brown, which is compared to a colored glass standard.

5. Methods 5.1 Filter Screening Assays

The assays discussed below may be used in the screening of the present α-amylases to identify variants having altered stability at high or low pH and/or under $Ca^{2+}$ depleted conditions compared to a parent or reference α-amylase.

5.2 High pH Filter Assay

*Bacillus* libraries are plated on a sandwich of cellulose acetate (OE 67, Schleicher & Schuell, Dassel, Germany) and nitrocellulose filters (Protran-Ba 85, Schleicher & Schuell, Dassel, Germany) on TY agar plates with 10 µg/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

5.3 Low Calcium Filter Assay

*Bacillus* libraries are plated on a sandwich of cellulose acetate (OE 67, Schleicher & Schuell, Dassel, Germany) and nitrocellulose filters (Protran-Ba 85, Schleicher & Schuell, Dassel, Germany) on TY agar plates with a relevant antibiotic, e.g., kanamycin or neomycin, at 37° C. for at least 21 hours. The cellulose-acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

5.4 Low pH Filter Assay

*Bacillus* libraries are plated on a sandwich of cellulose acetate (OE 67, Schleicher & Schuell, Dassel, Germany) and nitrocellulose filters (Protran-Ba 85, Schleicher & Schuell, Dasseli Germany) on TY agar plates with 10 micro g/ml neomycin at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild type backbone) or 85° C. for 60 minutes (when screening for variants of the parent α-amylase). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are re-screened twice under the same conditions as the first screen.

5.5 Secondary Screening

Positive transformants after rescreening are picked from the storage plate and tested in a secondary plate assay. Positive transformants are grown for 22 hours at 37° C. in 5 ml LB+neomycin. The *Bacillus* culture of each positive transformant and as a control a clone expressing the corresponding backbone are incubated in citrate buffer, pH 4.5 at 90° C. and samples are taken at 0, 10, 20, 30, 40, 60 and 80 minutes. A 3 micro liter sample is spotted on an assay plate. The assay plate is stained with 10% Lugol solution. Improved variants are seen as variants with higher residual activity (detected as halos on the assay plate) than the backbone. The improved variants are determined by nucleotide sequencing.

5.6 Stability Assay of Unpurified Variants

The stability of the variants may be assayed as follows: *Bacillus* cultures expressing the variants to be analyzed are grown for 21 hours at 37° C. in 10 ml LB+neomycin. 800 micro liter culture is mixed with 200 μL citrate buffer, pH 4.5. A number of 70 μL aliquots corresponding to the number of sample time points are made in PCR tubes and incubated at 70° C. or 90° C. for various time points (typically 5, 10, 15, 20, 25 and 30 minutes) in a PCR machine. The 0 min sample is not incubated at high temperature. Activity in the sample is measured by transferring 20 μL to 200 μL of the α-amylase PNP-G$_7$ substrate MPR3 ((Boehringer Mannheim Cat. no. 1660730) as described below under "Assays for Alpha-amylase Activity". Results are plotted as percentage activity (relative to the 0 time point) versus time, or stated as percentage residual activity after incubation for a certain period of time.

5.7 Fermentation and Purification of α-Amylase Variants

A *B. subtilis* strain harboring the relevant expression plasmid may be fermented and purified as follows: The strain is streaked on a LB-agar plate with 10 μg/ml kanamycin from −80° C. stock, and grown overnight at 37° C. The colonies are transferred to 100 ml PS-1 media supplemented with 10 μg/ml neomycin in a 500 ml shaking flask.

| Composition of PS-1 medium: | |
|---|---|
| Pearl sugar | 100 g/l |
| Soy Bean Meal | 40 g/l |
| Na$_2$HPO$_4$, 12H$_2$O | 10 g/l |
| Pluronic ™ PE 6100 | 0.1 g/l |
| CaCO$_3$ | 5 g/l |

The culture is shaken at 37° C. at 270 rpm for 5 days. Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10,000 MW cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialysed against 10 mM Tris, pH 9.0 and applied on a Q-sepharose F.F. and eluted with a linear gradient from 0-0.3 M NaCl over 6 column volumes. The fractions that contain the activity (measured by the Phadebas assay) are pooled, pH was adjusted to pH 7.5 and remaining color was removed by a treatment with 0.5% W/vol. active charcoal in 5 minutes.

5.8 Specific Activity Determination

The specific activity is determined using the PHADEBAS® assay (Pharmacia) as activity/mg enzyme. The manufacturer's instructions are followed (see also below under "Assay for Alpha-amylase Activity").

5.9 Determination of Isoelectric Point

The pI is determined by isoelectric focusing (ex: Pharmacia, Ampholine, pH 3.5-9.3).

5.10 Accelerated Stability Assay

In 50 ml Propylene tubes, 10 ml of detergent of interest was added. Appropriate dilutions were made so that 180 ppm of each α-amylase was measured with a pipette into separate tubes containing the detergent. The detergent with each α-amylase was vortex for 30 sec and then placed on a Rota-Mix (ATR RKVS Model) for 10 minutes. 100 μL of the detergent with the mutant enzyme were measured with a pipette and diluted 1:651. The initial activity of the mutants was assayed using Blocked P-Nitro-Phenyl-Maltoheptaose (Blocked PBNPG7) substrate on a Konelab, Model 20XT. The detergent samples were then incubated in a constant temperature incubator set at 37° C. Samples were removed at 1, 2, 4, 7 and 17 days and the enzyme activity assayed.

5.11 Assays for α-Amylase Activity 5.11.1 Phadebas Assay

α-Amylase activity is determined by a method employing PHADEBAS® tablets as substrate. Phadebas tablets (PHADEB AS® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric add, 50 mM boric acid, 0.1 mM CaCl$_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolyzed by the α-amylase giving soluble blue fragments. The absorbance of the resulting blue solution, measured spectrophotometrically at 620 nm, is a function of the α-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given α-amylase will hydrolyze a certain amount of substrate and a blue color will be produced. The color intensity is measured at 620 nm. The measured absorbance is directly proportional to the specific activity (activity/mg of pure α-amylase protein) of the α-amylase in question under the given set of conditions.

5.11.2 Alternative Method

α-Amylase activity is determined by a method employing p-nitrophenyl-α-D-maltoheptaoside (PNP-$G_7$) substrate, which is a blocked oligosaccharide that can be cleaved by an endo-amylase. Following the cleavage, the α-glucosidase included in the kit digests the substrate to liberate a free PNP molecule which has a yellow color and thus can be measured by visible spectophometry at λ=405 nm (400-420 nm). Kits containing PNP-$G_7$ substrate and α-glucosidase are manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring a 20 µL sample to a 96 well microtitre plate and incubating at 25° C. 200 µL reagent solution pre-equilibrated to 25° C. is added. The solution is mixed and pre-incubated 1 minute and absorption is measured every 30 seconds over 4 minutes at OD 405 nm in an ELISA reader.

The slope of the time dependent absorption-curve is directly proportional to the activity of the α-amylase in question under the given set of conditions.

5.12 Determination of Enzyme Performance in Detergent Compositions 5.12.1 US Conditions A Terg-o-tometer (United States Testing, Hoboken, N.J.) was used to simulate washing conditions typical in the U.S. A dose efficiency curve (DEC) was conducted at 20° C. using standard detergents such as Liquid AATCC 2003 Without Optical Brightener and/or Powder AATCC 1993 (American Association of Textile Chemists and Colorists). A corresponding DEC of a comparative α-amylase was then conducted to compare the stain removal performance of the inventive mutant enzyme. This process was repeated at 40° C. Typically, 4 swatches of CS-28 Rice Starch stain (CFT of Holland) were placed in a steel container of the Terg-o-tometer, which was filled with 1 Liter of DI water and 1.5 g of Liquid AATCC. When Powder AATCC was used, 1.5 g of the detergent powder was weighed out on an analytical balance (Model PM4800, Mettler Instrument Corp., Highstown, N.J. 08520 and added to the Terg-o-tometer. Two replicates were run at the same time. Unless otherwise stated, the tests were carried out for 12 minutes and rinsed for 3 minutes. After washing, the swatches were air-dried and the reflectance of the test swatches was measured with a Chroma Meter Model CR-410 manufactured by Konica Minolta. The data collected were treated with appropriate statistical analysis.

5.12.2 European Conditions

A Launder-O-meter (Atlas Company, Atlanta, Ga.) was used to simulate washing conditions typical in Europe. A dose efficiency curve (DEC) of the mutant enzyme of interest was conducted at 40° C. using standard European testing detergents, IEC A and IEC A with Bleach (TAED-Tetra-Acetyl-ethylene-diamine acetate) and Sodium Perborate. A corresponding DEC curve of a comparative mutant enzyme was then conducted to compare the stain removal performance of the inventive mutant enzyme. This process was repeated at higher wash temperature if desirable. Typically, 4 swatches of EMPA 161, Maize starch (EMPA, Switzerland) were placed in a steel container with 250 ml of DI water containing 6.8 g/L of the IEC A detergent or 8.0 g/L of the IEC A with Bleach detergent. Two replicates were run at the same time. Unless otherwise stated the tests were carried out for 45 minutes and rinsed for 5 minutes. After washing, the swatches were air-dried and the reflectance of the test swatches was measured with a Chroma Meter Model CR-410. The data collected were treated with appropriate statistical analysis.

5.12.3 Microswatch Method of Assessing Detergent Compositions

Numerous α-amylase cleaning assays are known in the art. Exemplary cleaning assays involve swatches, which are pieces of material, such as a fabric, to which a stain may be applied. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

Some assays may utilize a smaller portion of a larger swatch that has been cut with a single-hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. Smaller swatches can also be made by applying a stain to a small piece of material. For example, a smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate for use in testing cleaning compositions for materials other than textiles. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay can be to deliver and secure a swatch, for example an indigo dyed denim, to a well of a multi-well plate, and add particles such as sand or larger particles such as for example garnet sieved to include particle 6 to 8, or 9 gauge, and agitate the plate so as to cause abrasion of the swatch by the added particles. This assay has found use in the assessment of cellulases in stone washing applications. The effectiveness of the enzyme can be judged by either color release (e.g., released indigo is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. One aspect provides a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk-Testgewebe GmbH, Krefeld Germany; or Center for Test Materials, Vlaardingen, The Netherlands) and/or can be made by the practitioner (Morris and Prato, *Textile Research Journal* 52(4): 280 286 (1982)). Other test swatches include but are not limited to blood/milk/ink (BMI) stain(s) on a cotton-containing fabric, a spinach stain on a cotton-containing fabric, or grass on a cotton-containing fabric, and chocolate/milk/soot on a cotton-containing fabric.

A BMI stain can be fixed to cotton with 0.0003% to 0.3% hydrogen peroxide. Other combinations include grass or spinach fixed with 0.001% to 1% glutaraldehyde, gelatin and Coomassie Brilliant Blue stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see e.g., Cayot and Tainturier, *Anal. Biochem.* 249: 184-200 (1997)). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink or other stain that is based on ink release. Proteolysis of protein on the swatches leads to the release of ink particles that can be quantified by measuring the absorbance of the wash liquor. The absorbance can be measured at any wavelength between 350 and 800 nm. The wavelength is measured at 410 nm or 620 nm. The wash liquor can also be examined to determine the wash performance on stains containing grass, spinach, gelatin or Coomassie Brilliant Blue stain. Exemplary wavelengths for these stains include and 670 nm for spinach or grass and 620 nm for gelatin or Coomassie Brilliant Blue. For example, an aliquot of the wash liquor (typically 100 to 150 µL from a 96-well microplate, for example) is removed and placed in a cuvette or multiwell microplate. This is then placed in a spectrophotometer and the absorbance is read at an appropriate wavelength.

The system can also be used to determine an enhanced enzyme and/or detergent composition for dishwashing, for example, using a blood/milk/ink stain on a suitable substrate such as cloth, plastic or ceramic.

In one aspect, the a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tested with spinach stains or grass stains fixed to cotton by applying 0.01% glutaraldehyde to the spinach/cotton swatch or grass/cotton swatch for 30 minutes at 25° C. The same can be performed with chocolate, milk, and/or soot stains. Additional blood/milk/ink assays and conditions are provided in U.S. Pat. No. 7,122,334 (Genencor International, Inc.).

5.13 Determination of LAS Sensitivity

The variant is incubated with different concentrations of LAS (linear alkyl benzene sulphonate; Nansa 1169/P) for 10 minutes at 40° C. The residual activity is determined using the Phadebas® assay method or the alternative method employing the PNP-G$_7$ substrate. LAS is diluted in 0.1 M phosphate buffer pH 7.5. The following concentrations are used: 500 ppm, 250 ppm, 100 ppm, 50 ppm, 25 ppm, and 10 ppm or no LAS.

The variant is diluted in the different LAS buffers to concentration of 0.01-5 mg/l in a total volume of 10 ml and incubated for 10 minutes in a temperature controlled water bath. The incubation is stopped by transferring a small aliquot into cold assay buffer. It is important that during activity measurement the LAS concentration is below 1 ppm, in order not to affect the activity measurement.

Then the residual activity is determined in duplicate using the above mentioned PHADEBAS® assay or alternative method. The activity is measured after subtraction of the blank. The activity with no LAS is 100%.

The present application is organized into a number of sections for ease of reading; however, the reader will appreciate that statements made in one section may apply to other sections. In this manner, the headings used for different sections of the disclosure should not be construed as limiting.

In order to further illustrate the present compositions and methods and advantages thereof, the following specific examples are given with the understanding that they are being offered to illustrate the present compositions and methods and should not be construed in any way as limiting its scope.

EXPERIMENTAL

The present disclosure is described in further detail in the following examples, which are not in any way intended to limit the scope of the disclosure as claimed.

The following abbreviations apply throughout the disclosure: AE (alcohol ethoxylate); AEO (alcohol ethoxylate); AEOS (alcohol ethoxysulfate); AES (alcohol ethoxysulfate); AFAU (acid fungal α-amylase units); AGU (glucoamylase activity unit); AOS (α-olefinsulfonate); AS (alcohol sulfate); BAA (*Bacillus amyloliquefaciens* α-amylase); BLA (*Bacillus licheniformis* or LAT); BPNPG7 (p-nitrophenyl maltoheptaoside); BSA (bovine serum albumin); cDNA (complementary DNA); CMC (carboxymethylcellulose): DNA (deoxyribonucleic acid); DP3 (degree of polymerization with three subunits); DPn (degree of polymerization with n subunits); DTMPA (diethyltriaminepentaacetic acid); EC (enzyme commission for enzyme classification); EDTA (ethylenediaminetetraacetic acid); EO (ethylene oxide); F&HC (fabric and household care); FAU (fungal amylase unit); GA (glucoamylase); gpg (grains per gallon); HFCS (high fructose corn syrup); HFSS (high fructose starch based syrup); IPTG (isopropyl β-D-1-thiogalactopyranoside0); LAS (linear alkylbenezenesulfonate); LOM (Launder-O-meter); LU (Liquiphon unit); MTP (microtiter plate); MW (molecular weight); MWU (modified Wohlgemuth unit); NOBS (nonanoyloxybenzenesulfonate); NTA (nitrilotriacetic acid); PCR (polymerase chain reaction); PEG (polyethyleneglycol); PI (performance index); PVA (poly(vinyl alcohol); PVP (poly (vinylpyrrolidone)); RNA (ribonucleic acid); SAS (secondary alkane sulfonates); SEL (site evaluation library); TAED (tetraacetylethylenediamine); TCA (trichloroacetic acid); TSB (tryptic soy broth); UFC (ultrafiltration concentrate); ° C. (degrees Centigrade); $H_2O$ (water); $dH_2O$ or DI (deionized water); $dIH_2O$ (deionized water, Milli-Q filtration); ETOH (ethanol); eq (equivalents); N (normal); DS (dry solids); g or gm (grams); μg (micrograms); mg (milligrams); kg (kilograms); μL and μl (microliters); mL and ml (milliliters); mm (millimeters); μm (micrometer); M (molar); mM (millimolar); μM (micromolar); U (units); sec (seconds); min(s) (minute/minutes); hr(s) (hour/hours); DO (dissolved oxygen); WT % (weight percent); W/V (weight to volume); W/W (weight to weight); V/V (volume to volume); GENEART (GENEART GmbH, Regensburg, Germany); and Genencor (Danisco US Inc, Genencor Division, Palo Alto, Calif.).

Example 1

Assays

In the following examples, various assays were used as set forth below for ease in reading. Any deviations from the protocols provided below are indicated. In these experiments, a spectrophotometer was used to measure the absorbance of the products formed after the completion of the reactions.

A. Protein Content Assay

This assay was performed using filtered culture supernatant from microtiter plates (MTPs) grown 3 days at 37° C. with shaking at 300 rpm and 80% humidity. A fresh 96-well flat bottom MTP containing 50 μl supernatant per well was used for the protein assay by a High Performance Liquid Chromatography method. Supernatants were diluted three fold into 10 mM potassium phosphate buffer pH 7.25 containing 5% acetonitrile and 10% sodium chloride and 100 of each diluted sample was analzyed. An Agilent 1100 (Hewlet Packard) HPLC equipped with a Swift™ RP-all PN 68-1030-041 (Teledyne Isco, Inc.) column was used. The solvent system consisted of 0.1% trifluoroacetic acid in aqueous phase and 0.07% trifluoroacetic acid in acetonitrile. Absorbance was read at 222 nm and protein concentration of samples was determined based on a standard curve of purified BASE (AmyTS23t) protein.

B. Ceralpha Amylase Assay

The principle of this α-amylase assay is based on the hydrolysis of a defined oligosaccharide (BPNPG7) in the presence of excess levels of a thermostable α-glucosidase to glucose and free p-nitrophenol. The absorbance at 400 nm is measured and this relates directly to the level of active amylase in the sample analysed.

The equipment used was a Biomek FX Robot (Beckman Coulter); a SpectraMAX MTP Reader (type 340-Molecular Devices) and iEMS incubator/shaker (Thermo/Labsystems). In this assay system, the reagent and solutions used were:
1) p-nitrophenyl maltoheptaoside (BPNPG7) substrate (Megazyme HR kit);
2) 50 mM MOPS, 50 mM NaCl, 0.1 mM $CaCl_2$, 0.005% TWEEN® 80 buffer, pH 7.15; and
3) 200 mM Boric acid/NaOH buffer, pH 10.2 (STOP buffer).

A vial containing 54.5 mg BPNPG7 substrate was dissolved in 10 ml of milliQ water. The amylase samples (fermentation supernatant) were diluted in MOPS buffer. The assay was performed by adding 25 μl of diluted amylase solution into the wells of a MTP followed by the addition of 25 μl 5.45 mg/ml BPNPG7 substrate solution. The solutions were mixed and the microtiter plate was sealed with a plate seal and placed in an incubator/shaker (iEMS-Thermo/Labsystems) for 30 minutes at 25° C. and 900 rpm. The reaction was terminated by adding 50 μl STOP buffer and the absorbance was read at wavelength 400 nm in an MTP-Reader. A non-enzyme control was used to correct for background absorbance values.

C. CS-28 Rice Starch Microswatch Assay

The principle of this α-amylase assay is based on the liberation of an orange-dye due to the hydrolysis of rice starch incorporated in a microswatch. The absorbance at 488 nm is measured and this relates to the level of amylase activity in the sample analysed, at the desired conditions (pH, temperature, and buffer).

The equipment used was a Biomek FX Robot (Beckman Coulter), a SpectraMAX MTP Reader (type 340-Molecular Devices) and iEMS incubator/shaker (Thermo/Labsystems). In this assay system the reagent and solutions used were:
1) CS-28 Microswatches (rice starch, colored);
2) 25 mM HEPES, 2 mM $CaCl_2$, 0.005% TWEEN 80 buffer, pH 8.0;
3) 25 mM CAPS, 2 mM $CaCl_2$, 0.005% TWEEN 80 buffer, pH 10.0; and
4) 10 mM NaCl, 0.1 mM $CaCl_2$, 0.005% TWEEN 80 (Dilution buffer).

CS-28 Microswatches of ¼" circular diameter were delivered by the Center for Testmaterials (CFT, Vlaardingen, The Netherlands). Two microswatches were placed in each well of a 96-well microtiter plate vertically to expose the whole surface area (e.g., not flat on the bottom of the well). The amylase samples (fermentation supernatant) were tested at appropriate concentrations in several conditions, pre-diluted in 10 mM NaCl, 0.1 mM $CaCl_2$, 0.005% TWEEN®80 solution:
1) pH 8 (25 mM HEPES buffer) and 16° C.; final amylase conc. in assay <0.025 μg/ml;
2) pH 8 (25 mM HEPES buffer) and 32° C.; final amylase conc. in assay <0.012 μg/ml;
3) pH 10 (25 mM CAPS buffer) and 32° C.; final amylase conc. in assay <0.025 μg/ml; and
4) pH 10 (25 mM CAPS buffer) and 50° C.; final amylase conc. in assay <0.012 μg/ml.

The incubator/shaker was set at the desired temperature, 16° C. (cold storage chamber or refrigerator), 32° C. or 50° C. The microswatches were placed into the wells of a 96-well MTP. The culture supernatant samples were diluted in 10 mM NaCl, 0.1 mM CaCl$_2$, 0.005% TWEEN® 80 to 20× the desired final concentration. 190 µl of either HEPES or CAPS buffer was added to each well of a microswatch-MTP and subsequently 10 µl of enzyme solution was added to each well resulting in a total volume of 200 µl/well. The MTP was sealed with a plate seal and placed in the incubator/shaker and incubated for 60 minutes at 1150 rpm at the desired temperature (16°, 32° or 50° C.). Following incubation under the appropriate conditions, 100 µl of solution from each well was transferred to a new MTP, and the absorbance at 488 nm was measured using a MTP-spectrophotometer. Controls containing two microswatches and buffer but no enzyme were included for background subtraction.

The obtained absorbance value was corrected for the blank value (obtained after incubation of microswatches in the absence of enzyme), and the resulting absorbance is a measure of hydrolytic activity. For each sample (variants) the performance index (PI) was calculated. The performance index compares the performance of the variant (actual value) and the reference enzyme (theoretical value) at the same protein concentration. The theoretical values can be calculated, using the parameters of the Langmuir equation of the reference enzyme. A PI that is greater than 1 (PI>1) identifies a better variant (as compared to the reference or standard enzyme [e.g., wild-type]), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

D. Thermostability Assay—Determination of Initial and Residual Activities

The thermostability of the amylase variant in relation to a reference amylase was determined by incubating the amylase samples under defined conditions in MOPS buffer, pH 7.15. The temperature of the incubation was chosen such that approximately 70% of the initial reference amylase activity was lost. The initial and residual amylase activities were determined using the Ceralpha method.

The equipment used was a Biomek FX Robot (Beckman Coulter); a SpectraMAX MTP Reader (type 340-Molecular Devices) and iEMS incubator/shaker (Thermo/Labsystems). In this assay system, the reagent solutions used were:
1) p-nitrophenyl maltoheptaoside (BPNPG7) substrate (Megazyme HR kit);
2) 10 mM NaCl, 10 mM CaCl$_2$, 0.005% TWEEN® 80 buffer (Dilution buffer);
3) 50 mM MOPS, 50 mM NaCl, 0.1 mM CaCl$_2$, 0.005% TWEEN®80 buffer, pH 7.15;
4) 200 mM Boric acid/NaOH buffer, pH 10.2 (STOP buffer); and
5) amylase culture supernatants, containing 50-150 µg/ml protein.

A "master dilution" plate was prepared by diluting the culture supernatant 20× in 10 mM NaCl, 0.1 mM CaCl$_2$, 0.005% TWEEN®80 buffer, followed by a 42× dilution step in MOPS buffer. From the master dilution 25 µl was used to determine the initial amylase activity and 100 µl was used for heat incubation. The 100 µl sample was put in a MTP (Greiner 655.101) that was sealed with aluminum tape and incubated at 65.5° C. for 60 minutes with agitation at 900 rpm in an iEMS incubator. After incubation the MTP was cooled on ice water before determining the residual amylase activity. To determine the initial ($t_{00}$) and residual ($t_{60}$) activity, a 25 µl sample was transferred into a new MTP, containing 25 µl BPNPG7 solution per well and incubated at 25° C. for 30 minutes. The Ceralpha amylase assay was performed as described above in Section B.

The ratio of the residual and initial amylase activities was used to calculate thermostability as follows: Thermostability=[$t_{60}$ value]/[$t_{00}$ value]. For each variant the performance index, which compares the thermostability of the variant to the reference (standard) enzyme, was also calculated. A performance index (PI) that is greater than 1 (PI>1) identifies a better variant (as compared to the reference or standard [e.g., wild-type or backbone]), while a PI of 1 (PI=1) identifies a variant that is as stable as the standard, and a PI that is less than 1 (PI<1) identifies a variant that is less stable than the standard. Thus, the PI identifies winners, as well as variants that are less stable for use under certain circumstances.

E. Thermostability Assay—Determination of T$_{50}$ Values

The thermostability assay described in Section D above, can only rank variants that lose activity under given conditions. Variants that are 100% stable at the given condition cannot be distinguished from one another. Thus, determination of the T$_{50}$ value, the incubation temperature by which 50% of the initial activity is lost, is a more suitable assay to rank variants with significantly increased thermostability.

The equipment used was a Biomek FX Robot (Beckman Coulter); a SpectraMAX MTP Reader (type 340-Molecular Devices) and Eppendorf Mastercycler. Culture supernatant containing the amylase variant was diluted 1000× in MOPS buffer and the initial amylase activity was determined using the Ceralpha amylase assay described above in Section B. Using the diluted amylase sample, PCR plates were prepared containing 100 µl/well. The plates were incubated for 60 min on a Eppendorf Mastercycler on temperature gradient spanning 60° C.-80° C. (single site mutants) or 60° C.-100° C. (combinatorial mutants). After incubation the MTPs were cooled down to 4° C. before determining the residual amylase activity.

The ratio of the residual and initial amylase activities was plotted against the incubation temperature, and the data was fitted using the following equation: $y=a_0+a_1/(1+(x/a_2)^{a_3})$. Subsequently, the T$_{50}$-value for each amylase variant was calculated (e.g., temperature at which the residual activity is 50%). Thus the T$_{50}$ value is a measure for the thermostability of the variant, and can rank the variants in relation to the reference amylase and to one another.

F. 10% Detergent Stability Assay

The stability of the reference amylase and variants thereof was measured after incubation under defined conditions in the presence of 10% detergent (commercial detergent; heat inactivated), and the initial and residual amylase activities were determined using the Ceralpha amylase assay.

The equipment used was a Biomek FX Robot (Beckman Coulter); a SpectraMAX MTP Reader (type 340-Molecular Devices) and iEMS incubator/shaker (Thermo/Labsystems). In this assay system, the reagent solutions used were:
1) p-nitrophenyl maltoheptaoside (BPNPG7) substrate (Megazyme HR kit):
2) liquid detergent (HDL commercial product, enzyme-inactivated, 2 hrs at 95° C.);
3) 10.5% detergent in 25 mM HEPES buffer, pH 8.0;
4) 50 mM MOPS, 50 mM NaCl, 0.1 mM CaCl$_2$, 0.005% TWEEN®80 buffer, pH 7.15;
5) 200 mM Boric acid/NaOH buffer, pH 10.2 (STOP buffer); and
6) amylase culture supernatants containing 50-150 µg/ml protein.

Briefly, 95 μl of a 10.5% detergent solution was transferred to a microtiter plate (MTP) and mixed with 5 μl of culture supernatant. A 3 μl aliquot was removed for determination of the initial amylase activity. The MTP was incubated in an iEMS incubator at 40° (or 50° C. in the case of BASE combinatorial variants with higher stability) for 30 minutes with 900 rpm agitation. After incubation the residual amylase activity was measured using 3 μl of the detergent-enzyme mixture. Initial ($t_0$) and residual ($t_{30}$) amylase activity: 3 μl 'detergent-enzyme' mix was diluted in 122 μl MOPS buffer and subsequently 25 μl was used to determine the amylase activity using the Ceralpha amylase assay described above.

The ratio of the residual and initial amylase activities was used to calculate the '10% Detergent' Stability as follows: Stability=[$t_{30}$ value]/[$t_0$ value]. For each variant the performance index was also calculated. The performance index compares the 10% Detergent stability of the amylase variants to a reference amylase. A performance index (PI) that is greater than 1 (PI>1) identifies a more stable variant (as compared to the reference or standard [e.g., wild-type]), while a PI of 1 (PI=1) identifies a variant that is as stable as the standard, and a PI that is less than 1 (PI<1) identifies a variant that is less stable than the standard. Thus, the PI identifies winners, as well as variants that are less stable for use under certain circumstances.

G. 100% Detergent Stability Assay—Temperature Gradient Curve

The HDL Detergent stability of BASE-backbone and BASE-variants were measured after incubation under defined conditions in the presence of 100% detergent (commercial detergent; enzyme-inactivated), and the initial and residual amylase activity were determined using the Ceralpha amylase assay.

The equipment used was a Biomek FX Robot (Beckman Coulter); a SpectraMAX MTP Reader (type 340-Molecular Devices); Eppendorf PCR Mastercycler and iEMS incubator/shaker (Thermo/Labsystems). In this assay system, the reagent solutions used were:
1) p-nitrophenyl maltoheptaoside (BPNPG7) substrate (Megazyme HR kit);
2) Liquid Detergent (HDL commercial product—inactivated by heating at 95° C. for 2 hrs);
3) 50 mM MOPS, 50 mM NaCl, 0.1 mM CaCl2, 0.005% TWEEN®80 buffer, pH 7.15;
4) 200 mM Boric acid/NaOH buffer, pH 10.2 (STOP buffer); and
5) amylase culture supernatants containing 50-150 μg/ml protein.

Amylase culture supernatants were diluted 20× in HDL Detergent and mixed thoroughly. The initial amylase activity was determined using the Ceralpha amylase assay described above in Section B. Using the diluted amylase-HDL sample, PCR plates were prepared containing 100 μl/well. The plates were incubated for 30 min on an Eppendorf Master cycler on a temperature gradient spanning 30° C.-70° C. After incubation the MTPs were cooled down to 4° C. before determining the residual amylase activity as described above.

To calculate the HDL T50 value, the ratio of the residual and initial amylase activities was plotted against the incubation temperature, and the data was fitted using the following equation: $y=a_0+a_1/(1+(x/a_2)^{a_3})$. Subsequently, the $T_{50}$-value for each BASE-variant was calculated (e.g., temperature at which the residual activity is 50%). Thus the $T_{50}$-value is a measure of the thermostability of the variant, and can rank the variants with regards to the reference amylase as well as to each other.

H. AAPF Protease

In order to determine the protease activity of the subtilisin proteases of the present disclosure, the hydrolysis of N-succinyl-L-alanyl-L-alanyl-L-prolyl-L-phenyl-p-nitroanilide (AAPF) was measured. The reagent solutions used were:
1) 100 mM Tris/HCl, pH 8.6, containing 0.005% TWEEN®-80 (Tris dilution buffer);
2) 100 mM Tris buffer, pH 8.6, containing 10 mM CaCl2 and 0.005% TWEEN®-80 (Tris/Ca buffer); and
3) 160 mM suc-AAPF-pNA in DMSO (suc-AAPF-pNA stock solution) (Sigma: S-7388).

To prepare a suc-AAPF-pNA working solution, 1 ml AAPF stock was added to 100 ml Tris/Ca buffer and mixed well for at least 10 seconds. The assay was performed by adding 10 μl of diluted protease solution to each well, immediately followed by the addition of 190 μl 1 mg/ml AAPF-working solution. The solutions were mixed for 5 sec., and the absorbance change in kinetic mode (20 readings in 5 minutes) was read at 410 nm in an MTP reader, at 25° C. The protease activity was expressed as AU (activity=▩ OD·min-1 ml-1).

Example 2

Generation of *B. subtilis* Strains Expressing BASE (AmyTS23t) and Variants Thereof In this example, the construction of *Bacillus subtilis* strains expressing BASE (a truncated form of *Bacillus* sp. TS-23 alpha-amylase or AmyTS23t) and variants thereof are described. BASE, the mature form of a truncated amylase originated from the TS-23 alpha-amylase (AmyTS23) of an alkaliphilic and thermophilic *Bacillus* sp. strain TS-23 (Lin et al., J Appl Microbiol, 82:325-334, 1997).

The amino acid sequence of the mature form of AmyTS23 is set forth as SEQ ID NO:1:

```
NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYSFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAKTSNVTFTVNNATTTSG

QNVYVVANIPELGNWNTANAIKMNPSSYPTWKATIALPQGKAIEFKFIKK

DQAGNVIWESTSNRTYTVPFSSTGSYTASWNVP.
```

A codon-modified nucleic acid sequence encoding the mature form of AmyTS23 is set forth as SEQ ID NO:3:

```
aatacggcgccgatcaacgaaacgatgatgcagtattttgaatgggatct gccgaatgatggaacgctgtggacgaaagtcaaaaacgaagcggcgaatc ttagcagcctgggaatcacagcactttggcttccgccggcatataaagga acgagccaaagcgatgtcggctatggcgtctatgatctgtatgacctggg
``` cgaatttaaccaaaaaggcacgatccggacgaaatatggcacgaaaacac agtatatccaagcgatccaggcagcaaaagcagcaggcatgcaagtctat gccgacgtcgtctttaatcataaagcgggagcggatggcacagaatttgt cgatgccgtcgaagttgatccgagcaacagaaaccaagaaacgagcggca cgtatcaaatccaagcgtggacgaaatttgattttccgggcagaggcaat acgtatagcagctttaaatggcgctggtatcattttgacggcacggattg ggatgaaagcagaaaactgaaccggatctataaatttcggagcacgggca aagcatgggattgggaagtcgatacggaaaacggcaactatgactatctg atgtttgccgatctggatatggatcatccggaagtcgtcacggaactgaa aaattggggcacgtggtatgttaatacgacgaacatcgatggctttagac tggatgccgtcaaacatatcaaatatagcttttttccggactggctgacg tatgtcagaaaccagacgggcaaaaaccttttttgccgtcggcgaattttg gagctatgacgtcaacaaacttcataactatatcacgaaaacgaacggca gcatgagccttttgatgcccgcttcataacaactttatacggcgagc aaaagctcaggctattttgatatgagatatctgctgaacaacacgctgat gaaagatcaaccgagcctggcagtcacactggtcgataaccatgatacac aaccgggccaaagccttcaaagctgggtcgaaccgtggtttaaaccgctg gcgtatgcctttatcctgacgagacaagaagggtatccttgcgtcttta tggcgactattatggcatcccgaaatataatatcccgggcctgaaaagca aaatcgatccgctgctgatcgccagacgggattatgcctatggcacacag cgggattatatcgaccatcaggacatcatcggctggacaagagaaggcat cgatacgaaaccgaatagcggactggcagcactgattacagatggaccgg gcggaagcaaatggatgtatgtcggcaaaaaacatgccggcaaagtcttt tatgatctgacgggcaacagaagcgatacggtcacgatcaatgctgatgg ctggggagaatttaaagtcaatggcggcagcgtttcaatctgggtcgcca aaacgagcaatgtcacgtttaCggtcaacaatgccacgacaacgagcggc caaaatgtctatgtcgtcgccaatatcccggaactgggcaattggaatac ggcgaacgcaatcaaaatgaacccgagcagctatccgacatggaaagcga caatcgctctgccgcaaggaaaagcgatcgaatttaaatttatcaaaaaa gaccaggcgggcaatgttatttgggaaagcacgagcaatagaacgtatac ggtcccgtttagcagcacaggaagctatacagcgagctggaatgttccgt ga.

BASE was created by deleting both the first 90 bp of the 5'-sequence region encoding the signal peptide and 297 bp of the 3'-sequence encoding the carboxyl-terminal end of the enzyme, yielding a truncated alpha-amylase. The amino acid sequence of the mature form of BASE (AmyTS23t) is set forth as SEQ ID NO:2:

NTAPINETMMQYFEWDLPNDGTLWTKVKNEAANLSSLGITALWLPPAYKG

TSQSDVGYGVYDLYDLGEFNQKGTIRTKYGTKTQYIQAIQAAKAAGMQVY

ADVVFNHKAGADGTEFVDAVEVDPSNRNQETSGTYQIQAWTKFDFPGRGN

TYSSFKWRWYHFDGTDWDESRKLNRIYKFRSTGKAWDWEVDTENGNYDYL

MFADLDMDHPEVVTELKNWGTWYVNTTNIDGFRLDAVKHIKYSFFPDWLT

YVRNQTGKNLFAVGEFWSYDVNKLHNYITKTNGSMSLFDAPLHNNFYTAS

KSSGYFDMRYLLNNTLMKDQPSLAVTLVDNHDTQPGQSLQSWVEPWFKPL

AYAFILTRQEGYPCVFYGDYYGIPKYNIPGLKSKIDPLLIARRDYAYGTQ

RDYIDHQDIIGWTREGIDTKPNSGLAALITDGPGGSKWMYVGKKHAGKVF

YDLTGNRSDTVTINADGWGEFKVNGGSVSIWVAK.

A synthetic DNA fragment (0723013) produced by GENEART and containing a codon-modified BASE gene for expression in *B. subtilis* served as template DNA (SEQ ID NO: 4) for the construction of *Bacillus subtilis* strains expressing BASE and variants thereof. To express BASE, the BASE DNA fragment was cloned into the pHPLT vector (Solingen et al., Extremophiles 5:333-341, 2001) by GENEART using the unique PstI and HpaI restriction sites. The pHPLT expression vector contains the *B. licheniformis* LAT promoter (Plat) and additional elements from pUB110 (McKenzie et al., Plasmid, 15: 93-103, 1986) including a replicase gene (reppUB), a neomycin/kanamycin resistance gene (neo) and a bleomycin resistance marker (bleo).

The coding region for the LAT signal peptide is set forth as SEQ ID NO: 15: atgaaacaacaaaaacggattacgc-ccgattgctgacgctgttatttgcgct-catcttcttgctgcctcattctgcagatcagca.

The amino acid sequence of the LAT signal peptide is set forth as SEQ ID NO: 16: MKQQKRLYARLLTLLFALIFLL-PHSAASA.

Figure 3:
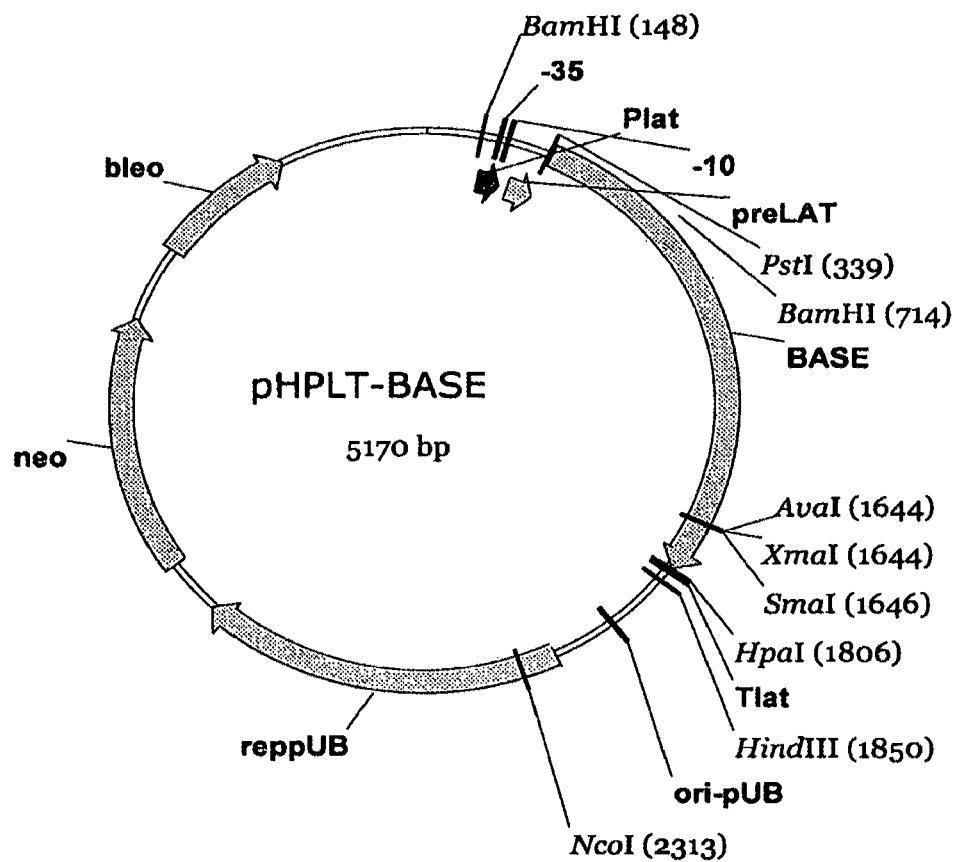
FIG. 3 provides a map of the pHPLT-BASE plasmid.

A map of the pHPLT expression vector is shown in FIG. 2, while a map of the pHPLT vector containing the BASE gene is shown in FIG. 3. The codon-modified nucleic acid sequence produced by GENEART, encoding the mature form of BASE (AmyTS23t), is set forth as SEQ ID NO: 4, with the N001 N-terminal codon and the K484 C-terminal codon shown in bold:

```
   1  tctgcagct tcagcaaac accgcgccg attaacgaa accatgatg cagtatttc gaatgggat ctgccgaac 73  gatggcacc ctgtggacc aaagtgaaa aacgaagcg gcgaacctg agcagcctg ggcattacc gcgctgtgg 145  ctgccgccg gcatataaa ggcaccagc cagagcgat gtgggctat ggcgtgtat gatctgtac gatctgggc 217  gaatttaac cagaaaggc accattcgt accaaatat ggcaccaaa acccagtat attcaggcg atccaggcg 289  gcgaaagcg gcgggtatg caggtgtat gcggatgtg gtgtttaac cataaagcg ggtgcggat ggcaccgaa 361  tttgtggat gcggtggaa gtggatccg agcaaccgt aaccaggaa accagcggc acctatcag attcaggcg 433  tggaccaaa tttgatttt cccggccgt ggcaacacc tatagcagc tttaaatgg cgctggtat cattttgat 505  ggcaccgat tgggatgaa agccgtaaa ctgaaccgc atctataaa tttcgtagc accggcaaa gcgtgggat 577  tgggaagtg gataccgaa aacggcaac tatgattac ctgatgttc gcagacctg gatatggat catccggaa 649  gtggtgacc gaactgaaa aactggggc acctggtat gtgaacacc accaacatt gatggcttt cgtctggat 721  gcggtgaaa cacatcaaa tacagcttt tttccggat tggctgacc tatgtgcgt aaccagacc ggcaaaaac 793  ctgtttgcg gtgggcgaa ttttggagc tatgatgtg aacaaactg cacaactac atcaccaaa accaacggc 865  agcatgagc ctgtttgat gcgccgctg cataacaac ttttatacc gcgagcaaa agcagcggc tattttgat 937  atgcgttat ctgctgaac aacaccctg atgaaagat cagccgagc ctggccgtg accctggtg gataaccat 1009  gatacccag ccgggccag agcctgcaa agctgggtg gaaccgtgg tttaaaccg ctggcctac gcgtttatt 1081  ctgacccgt caagagggc tatccgtgc gtttttat ggcgattat tacggcatc ccgaaatat aacattccg 1153  ggcctgaaa agcaaaatt gatccgctg ctgattcgc gtcgtgat tatgcgtat ggcacccag cgtgattat 1225  attgatcac caggatatt attggctgg acccgtgaa ggcattgat accaaaccg aacagcggc ctggccgcg 1297  ctgattacc gatgcccg ggtggcagc aaatggatg tatgtgggc aaaaaacat gcgggcaaa gtgttttat 1369  gatctgacc ggcaaccgt agcgatacc gtgaccatt aacgcggat ggctggggt gagtttaaa gtgaacggc 1441  ggcagcgtg agcatttgg gtggcgaaa taagttaac aga.
```

GENEART transformed a *B. subtilis* strain (genotype: ΔaprE, ΔnprE, Δepr, ΔispA, Δbpr) and (degU$^{Hy}$32, oppA, ΔspoIIE3501, amyE::xylRPxylAcomK-ermC), using the pHPLT-BASE vector DNA. Transformation of *B. subtilis* was performed as known in the art (WO 02/14490). The *B. subtilis* transformants were selected on agar plates containing Heart infusion agar (Difco, Catalog No. 244400) and 10 mg/L neomycin sulfate (Sigma, Catalog No. N-1876; contains 732 μs neomycin per mg). Selective growth of *B. subtilis* transformants harboring the pHPLT-BASE GENEART vector was performed in shake flasks containing MBD medium (a MOPS based defined medium), 5 mM CaCl$_2$ and 10 mg/L neomycin. MBD medium was made essentially as known in the art (Neidhardt et al., J Bacteriol, 119: 736-747, 1974), except that NH$_4$Cl$_2$, FeSO$_4$, and CaCl$_2$ were omitted from the base medium, 3 mM K$_2$HPO$_4$ was used, and the base medium was supplemented with 60 mM urea, 75 g/L glucose, and 1% soytone. The micronutrients were made up as a 100× stock solution containing in one liter, 400 mg FeSO$_4$ 7H$_2$O, 100 mg MnSO$_4$.H$_2$O, 100 mg ZnSO$_4$ 7H$_2$O, 50 mg CuCl$_2$ 2H$_2$O, 100 mg CoCl$_2$ 6H$_2$O, 100 mg NaMoO$_4$ 2H$_2$O, 100 mg Na$_2$B$_4$O$_7$ 10H$_2$O, 10 ml of 1M CaCl$_2$, and 10 ml of 0.5 M sodium citrate. Growth resulted in the production of secreted BASE amylase with starch hydrolyzing activity.

Example 3

Generation of BASE (AmyTS23t) Site Evaluation Libraries

Site evaluation library (SEL) production was performed by GENEART using a proprietary process (WO 2004/059556A3). Methods and devices for optimizing a nucleotide sequence for the purpose of expression of a protein by PCR, and the manufacture of DNA molecules utilized technology owned by or licensed to GENEART (European Patent Nos. 0 200 362 and 0 201 184; and U.S. Pat. Nos. 4,683,195, 4,683, 202 and 6,472,184). The construction of BASE SELs described in this example was performed by GENEART using their technology platform for gene optimization, gene synthesis and library generation under proprietary GENEART know how and/or intellectual property. The sequential permutation approach of GENEART, to produce SELs, is described in general on the company's web site.

The pHPLT-BASE plasmid DNA served as template to produce the SELs. BASE SELs were produced by GENEART at positions (Table 3-1) pre-selected by the inventors. The corresponding DNA codons were each substituted with codons for at least 16 (out of a possible 19) different amino acids. The codon mutagenized pHPLT-BASE mixes were used to transform competent *B. subtilis* cells (genotype: ΔaprE, ΔnprE, oppA, ΔspoIIE, degUHy32, ΔamyE:[xylR, pxylA-comK]) as known in the art (WO 2002/014490) to generate the BASE SELs. Transformation mixes were plated on HI-agar plates (Heart Infusion agar) containing 10 mg/L neomycin sulfate. For each library, single colonies were picked and grown in TSB (tryptone and soy based broth) liquid medium with 10 mg/ml neomycin selection for subsequent DNA isolation and gene sequence analysis. Sequence analysis data revealed a maximum of 19 BASE mature variants per library. The BASE variants that identified in the BASE SELs are listed in Table 3-2. To generate BASE and BASE variant enzyme samples for biochemical characterization, selective growth of the BASE SEL variants was performed in 96 well MTPs at 37° C. for 68 hours in MBD medium.

TABLE 3-1

BASE (AmyTS23t) Site Evaluation Library Positions

| N001 | G057 | F116 | H161 | Y197 | Y269 | P374 |
|------|------|------|------|------|------|------|
| T002 | Y058 | D118 | F162 | Y199 | D270 | K375 |
| A003 | G059 | E121 | G164 | L200 | N272 | Y376 |
| P004 | V060 | D123 | T165 | M201 | K273 | N377 |
| I005 | N070 | S125 | D166 | F202 | H275 | P379 |
| E007 | Q071 | N126 | W167 | A203 | T279 | L381 |
| W015 | K072 | R127 | D168 | M207 | G283 | K382 |
| D016 | G073 | N128 | E169 | P210 | S284 | R393 |
| L017 | I075 | Q129 | S170 | T214 | T298 | D394 |
| P018 | K078 | E130 | R171 | K217 | K301 | T399 |
| N019 | K082 | T131 | K172 | T221 | S303 | R401 |
| T022 | T083 | S132 | N174 | N228 | Y305 | Q407 |

TABLE 3-1-continued

BASE (AmyTS23t) Site Evaluation Library Positions

| T025 | Q087 | T134 | R175 | L234 | F306 | D408 |
|------|------|------|------|------|------|------|
| K026 | Q090 | Y135 | I176 | A236 | Y310 | T419 |
| K028 | A091 | Q136 | Y177 | V237 | L311 | P433 |
| N029 | K093 | Q138 | K178 | K238 | N314 | S436 |
| E030 | A094 | W140 | F179 | H239 | K318 | W438 |
| A032 | A095 | K142 | T182 | Q243 | D319 | K444 |
| S035 | V103 | D144 | G183 | I240 | Q320 | G447 |
| S036 | V104 | G147 | A185 | P246 | S322 | K448 |
| L037 | F105 | G149 | W186 | T250 | L323 | Y451 |
| G050 | H107 | N150 | W188 | N254 | G336 | L453 |
| T051 | K108 | Y152 | E189 | Q255 | Q337 | D459 |
| S052 | G110 | S154 | V190 | G257 | S338 | A465 |
| Q053 | D112 | K156 | D191 | G264 | L339 | E470 |
| S054 | G113 | R158 | T192 | F266 | Q340 | G475 |
| D055 | T114 | W159 | E193 | W267 | E344 | A483 |
| V056 | E115 | Y160 | G195 | S268 | Q359 | K484 |

TABLE 3-2

BASE Variants of the SELs

| Pos. | Amino Acid Substitutions Generated in the BASE Amylase Background |
|------|---|---|---|---|---|---|---|---|---|---|---|---|---|---|---|---|---|---|---|
| N001 | A | C | D | E | F | G | H | I | K | L | M | P | Q | R | S | T | V | W | Y |
| T002 | A | D | E | F | H | I | K | L | M | N | P | Q | R | S | Y | — | — | — | — |
| A003 | C | D | E | F | G | H | I | K | L | M | N | P | Q | R | S | T | V | W | Y |
| P004 | A | C | D | E | G | H | I | K | L | M | N | Q | R | S | V | Y | — | — | — |
| I005 | C | D | E | F | G | H | K | L | M | N | R | S | T | V | W | Y | — | — | — |
| E007 | A | C | D | F | G | H | I | K | L | M | N | P | Q | R | S | T | V | W | Y |
| W015 | A | C | D | E | F | G | H | I | K | L | M | P | Q | R | S | T | V | Y | — |
| D016 | A | C | E | F | G | H | I | K | L | M | N | P | Q | R | T | V | W | Y | — |
| L017 | A | C | D | E | F | G | H | I | K | M | N | P | Q | R | S | T | V | W | Y |
| P018 | A | C | D | E | F | G | H | I | K | L | M | N | Q | R | S | T | V | Y | — |
| N019 | A | C | D | E | F | G | H | I | K | L | M | P | Q | R | S | T | V | W | Y |
| T022 | A | C | D | E | F | G | H | I | K | L | M | N | P | Q | S | V | W | Y | — |
| T025 | A | C | D | E | F | G | H | I | K | L | M | N | P | Q | S | V | W | Y | — |
| K026 | A | C | D | E | F | G | H | I | L | M | N | P | Q | R | S | T | V | W | Y |
| K028 | A | C | D | E | G | H | I | L | M | N | P | Q | R | S | T | V | W | Y | — |
| N029 | A | C | D | E | F | G | H | I | K | L | M | P | Q | R | S | T | V | W | Y |
| E030 | A | C | D | G | H | I | K | L | N | P | Q | R | S | T | V | W | Y | — | — |
| A032 | E | F | G | H | K | L | M | N | P | Q | R | S | T | V | W | Y | — | — | — |
| S035 | A | C | D | E | F | G | H | K | L | N | P | Q | R | T | V | W | Y | — | — |
| S036 | A | C | D | E | F | G | I | K | L | M | N | P | Q | R | T | V | W | Y | — |
| L037 | C | D | E | F | G | H | I | K | M | N | P | Q | R | S | T | V | W | Y | — |
| G050 | A | C | D | E | F | H | I | K | L | M | N | P | Q | R | S | T | V | W | Y |
| T051 | A | C | D | E | F | G | H | K | M | N | P | Q | R | S | V | W | Y | — | — |
| S052 | A | C | D | E | F | G | H | I | K | L | M | N | P | Q | R | T | V | W | Y |
| Q053 | A | C | D | E | F | G | H | I | K | L | M | N | P | R | S | T | V | W | — |
| S054 | A | C | D | E | F | G | H | I | K | L | M | N | P | Q | R | T | V | W | Y |
| D055 | A | C | E | F | G | H | I | K | M | N | P | R | S | T | V | W | Y | — | — |
| V056 | A | C | D | E | F | G | H | I | K | L | M | N | P | Q | R | S | T | W | Y |
| G057 | A | C | D | E | F | I | L | M | N | P | Q | R | S | T | W | Y | — | — | — |
| Y058 | A | C | D | E | F | G | H | I | K | L | M | N | P | Q | R | S | T | V | W |
| G059 | A | C | D | E | F | I | K | L | M | N | P | Q | R | S | T | V | W | Y | — |
| V060 | A | C | D | E | F | G | H | I | K | L | M | N | P | Q | R | S | T | W | Y |
| N070 | A | C | D | E | F | G | H | I | K | L | M | P | Q | R | S | T | V | W | Y |
| Q071 | A | C | D | E | F | G | H | I | K | L | M | N | P | R | S | T | V | W | Y |
| K072 | A | C | D | E | G | I | L | M | P | Q | R | S | T | V | W | Y | — | — | — |
| G073 | A | C | D | E | F | H | I | K | L | M | N | P | Q | R | S | T | V | W | Y |
| I075 | A | C | E | F | G | H | K | L | M | N | P | Q | R | S | T | V | W | Y | — |
| K078 | A | C | D | E | F | G | H | I | L | M | N | P | Q | R | S | T | V | W | Y |
| K082 | A | C | D | E | F | G | H | I | L | M | N | P | Q | S | T | V | W | Y | — |
| T083 | A | C | D | E | F | G | H | I | K | L | M | N | P | Q | R | S | V | W | Y |
| Q087 | A | C | D | E | F | G | H | I | K | L | M | N | P | R | S | T | V | W | Y |
| Q090 | A | C | D | E | F | G | H | I | K | L | M | N | P | R | S | T | V | W | Y |
| A091 | C | D | E | F | G | H | I | K | L | M | N | Q | R | S | T | V | W | Y | — |
| K093 | A | C | D | E | F | G | I | M | N | Q | R | S | T | V | W | Y | — | — | — |
| A094 | C | D | E | F | G | H | I | K | L | M | N | P | Q | R | S | T | V | W | Y |
| A095 | C | D | E | F | G | H | I | K | L | M | N | P | Q | R | S | T | V | W | Y |
| V103 | A | C | D | E | F | G | H | I | K | L | M | N | P | R | S | W | Y | — | — |
| V104 | A | C | D | E | F | G | H | I | K | L | M | N | P | Q | R | S | T | W | Y |
| F105 | C | D | E | G | H | I | K | L | M | N | P | Q | R | S | T | V | W | Y | — |
| H107 | A | C | D | E | F | G | I | K | L | M | N | P | Q | R | S | T | V | W | Y |
| K108 | A | C | E | F | G | I | L | M | N | R | S | V | W | Y | — | — | — | — | — |
| G110 | A | C | D | E | F | H | I | K | L | M | P | Q | R | S | V | W | Y | — | — |

TABLE 3-2-continued

BASE Variants of the SELs

| Pos. | Amino Acid Substitutions Generated in the BASE Amylase Background | | | | | | | | | | | | | | | | | |
|---|---|---|---|---|---|---|---|---|---|---|---|---|---|---|---|---|---|---|
| D112 | A | C | E | F | G | H | K | L | M | N | P | R | S | T | V | W | Y | — | — |
| G113 | A | C | D | E | F | H | I | K | L | M | N | P | Q | R | S | T | V | W | Y |
| T114 | A | C | D | E | F | G | H | I | K | L | M | N | P | Q | R | S | V | W | Y |
| E115 | A | C | D | G | I | K | L | M | N | Q | R | S | T | V | W | Y | — | — |
| F116 | A | C | D | E | G | H | I | K | L | M | N | P | Q | R | S | T | V | W | Y |
| D118 | A | C | E | F | G | H | I | K | L | M | N | P | Q | R | S | T | V | W | Y |
| E121 | A | C | D | F | G | H | I | K | L | M | N | P | Q | S | T | V | Y | — | — |
| D123 | A | C | E | F | G | H | I | K | L | M | P | Q | R | S | T | V | W | Y | — |
| S125 | A | C | D | E | F | G | H | I | K | L | M | N | P | Q | R | T | V | W | Y |
| N126 | A | C | D | E | G | H | I | K | L | M | Q | R | S | T | V | W | Y | — | — |
| R127 | A | C | E | F | G | I | K | L | M | N | P | Q | T | V | — | — | — | — | — |
| N128 | A | C | D | E | F | G | H | K | L | M | P | Q | R | S | T | V | W | Y | — |
| Q129 | A | C | D | E | F | G | H | I | K | L | M | N | P | R | S | T | V | W | — |
| E130 | A | C | D | F | G | H | I | K | L | M | N | P | Q | R | S | T | V | W | Y |
| T131 | A | C | D | E | F | G | H | I | K | M | N | P | Q | R | S | V | W | Y | — |
| S132 | A | C | D | E | F | G | H | I | K | L | M | N | Q | R | T | V | W | Y | — |
| T134 | A | C | D | E | F | G | H | I | K | L | M | N | P | Q | R | S | W | Y | — |
| Y135 | A | C | D | E | F | G | H | I | K | L | M | N | P | Q | R | S | T | V | W |
| Q136 | A | C | D | E | F | G | H | I | K | L | M | N | P | R | S | T | V | W | Y |
| Q138 | A | C | D | E | F | G | H | K | L | M | N | P | R | S | T | V | W | Y | — |
| W140 | A | C | D | E | F | G | H | I | K | M | N | P | Q | R | S | T | V | Y | — |
| K142 | A | C | D | E | F | G | H | I | L | M | N | P | Q | R | S | T | V | W | Y |
| D144 | A | C | E | F | G | H | I | K | L | M | N | P | R | S | T | V | W | Y | — |
| G147 | A | C | D | E | F | H | K | L | M | N | P | Q | R | S | T | V | W | Y | — |
| G149 | A | C | D | E | F | H | I | K | L | M | N | P | Q | R | S | T | V | W | Y |
| N150 | A | C | D | E | F | G | H | I | K | L | M | P | Q | S | T | V | W | — | — |
| Y152 | A | D | E | G | H | I | K | L | M | N | P | Q | R | S | T | V | W | — | — |
| S154 | A | C | D | E | F | G | H | I | K | L | M | N | Q | R | T | V | W | Y | — |
| K156 | A | C | D | E | F | G | H | I | L | M | N | P | Q | R | V | W | Y | — | — |
| R158 | A | C | D | E | G | H | I | K | L | M | Q | S | T | V | W | Y | — | — | — |
| W159 | A | D | E | F | H | I | K | L | M | N | P | Q | R | S | T | V | — | — | — |
| Y160 | A | D | E | F | I | K | L | M | N | P | Q | R | S | T | V | W | — | — | — |
| H161 | A | C | D | E | F | G | I | K | L | M | N | Q | R | S | T | V | Y | — | — |
| F162 | A | C | D | E | G | H | I | K | M | N | Q | S | T | W | Y | — | — | — | — |
| G164 | A | C | N | S | T | — | — | — | — | — | — | — | — | — | — | — | — | — | — |
| T165 | A | C | D | E | F | G | H | I | L | M | N | P | Q | R | S | V | W | Y | — |
| D166 | A | C | F | G | H | K | L | M | N | P | Q | R | S | T | V | W | — | — | — |
| W167 | A | C | D | E | F | G | I | K | L | N | P | Q | R | S | T | V | Y | — | — |
| D168 | A | C | E | F | H | K | L | M | N | P | Q | R | S | T | V | W | Y | — | — |
| E169 | A | C | D | F | G | H | I | K | L | M | N | P | Q | R | S | T | V | W | Y |
| S170 | A | C | D | E | F | G | H | I | K | L | M | N | P | Q | R | T | V | W | Y |
| R171 | A | C | D | E | F | G | H | K | L | M | N | P | Q | S | T | V | W | Y | — |
| K172 | A | C | D | E | F | G | H | I | L | N | P | Q | R | S | T | V | W | Y | — |
| N174 | A | C | D | E | F | H | I | L | M | Q | R | S | T | V | W | Y | — | — | — |
| R175 | A | C | D | E | F | G | H | I | K | L | M | N | P | Q | S | T | V | W | Y |
| I176 | A | C | D | E | F | G | H | K | L | M | N | P | Q | R | S | T | V | W | Y |
| Y177 | A | C | E | F | G | H | I | L | M | N | Q | R | S | V | W | — | — | — | — |
| K178 | A | C | E | F | G | H | I | L | M | N | P | Q | R | S | T | V | W | Y | — |
| F179 | A | C | E | G | H | I | K | L | M | N | P | T | V | W | Y | — | — | — | — |
| T182 | A | C | D | E | F | G | H | I | K | L | M | N | P | Q | R | V | W | Y | — |
| G183 | A | C | E | F | I | K | L | M | N | P | Q | R | S | T | V | W | — | — | — |
| A185 | C | D | E | F | G | I | K | L | M | N | Q | R | S | T | V | W | Y | — | — |
| W186 | D | F | G | H | I | K | L | M | N | Q | R | S | T | V | Y | — | — | — | — |
| W188 | A | C | D | E | F | G | H | I | K | L | M | N | P | Q | R | S | T | V | — |
| E189 | C | D | F | G | H | I | K | L | M | N | P | Q | R | S | T | V | W | Y | — |
| V190 | A | C | D | E | F | G | H | L | M | N | P | Q | S | T | W | Y | — | — | — |
| D191 | A | C | F | G | H | I | L | M | N | P | Q | S | T | V | W | Y | — | — | — |
| T192 | A | C | D | E | F | G | H | I | K | L | M | N | P | Q | R | S | V | W | Y |
| E193 | A | C | D | F | I | K | L | M | N | P | Q | R | S | T | V | W | Y | — | — |
| G195 | A | C | D | F | H | I | L | M | N | P | Q | R | S | T | V | W | Y | — | — |
| Y197 | A | C | D | E | F | G | H | K | M | N | P | Q | R | S | T | V | W | — | — |
| Y199 | A | C | D | E | F | G | H | I | K | L | M | N | P | Q | R | S | T | V | W |
| L200 | A | C | D | E | F | G | H | K | M | N | Q | R | T | V | Y | — | — | — | — |
| M201 | A | C | D | E | F | G | H | I | K | L | N | P | Q | R | S | T | V | W | Y |
| F202 | A | C | D | E | G | H | I | K | L | M | N | P | Q | R | S | T | V | W | Y |
| A203 | C | D | E | F | G | H | I | K | L | M | N | P | Q | R | S | T | V | W | Y |
| M207 | A | C | E | F | H | I | K | L | N | Q | S | T | V | W | Y | — | — | — | — |
| P210 | C | D | E | F | G | H | I | K | L | M | N | Q | R | S | T | V | W | — | — |
| T214 | A | C | D | E | F | G | I | K | L | P | Q | R | S | V | W | Y | — | — | — |
| K217 | A | C | D | E | G | F | G | H | L | M | N | P | Q | R | S | T | V | W | Y |
| T221 | A | C | D | E | F | G | H | K | M | N | P | Q | R | S | V | W | Y | — | — |
| N228 | A | C | D | E | F | G | H | I | L | M | P | Q | R | S | T | V | W | Y | — |
| L234 | A | C | D | G | H | I | M | N | P | Q | S | T | V | W | Y | — | — | — | — |
| A236 | C | E | F | G | H | I | K | L | M | N | P | Q | R | S | T | V | W | Y | — |
| V237 | A | C | D | E | F | G | H | I | K | L | M | N | P | Q | R | S | T | W | Y |
| K238 | A | C | D | E | F | G | H | I | M | N | Q | R | S | T | V | W | Y | — | — |

TABLE 3-2-continued

BASE Variants of the SELs

| Pos. | Amino Acid Substitutions Generated in the BASE Amylase Background |
|---|---|
| H239 | A C D F G I K L M N Q R S T V W Y — — |
| I240 | A C E F G H K L M N Q S T W Y — — — |
| S243 | A C D E F G H I K L M P Q R T V — — |
| P246 | A C D E F G H I K L M N Q R S T V W Y |
| T250 | A C D E F G H I K L P Q R W Y — — — |
| N254 | A C D E F G H I K L M P Q R S T V W Y |
| Q255 | A C D E F I K L M N P R S T V W Y — — |
| G257 | C D E F H I K L M N P R S T V W Y — — |
| N259 | A C D E G H K P Q R S T Y — — — — — |
| G264 | D E F H I K L M N P Q R S T V W Y — — |
| F266 | A C D E G H I K L M N P Q R S T V W Y |
| W267 | F I M V — — — — — — — — — — — — — — |
| S268 | A C D E F G H I K L M N P Q R T V W Y |
| Y269 | A C D E F G H I K L M N P Q R S T V W |
| D270 | A C E G H K N R S T — — — — — — — — |
| N272 | A C D E F H I K L M P Q R S T V W Y — |
| K273 | A D E F G H I L M N Q R T V Y — — — |
| H275 | A C D E F G I K L M N Q R S T V W Y — |
| T279 | A C D E H I K L M N Q R S V W Y — — |
| G283 | A C D E F H K M N P Q R S T V Y — — |
| S284 | C D E F G H I K L M N P Q R T V W Y — |
| T298 | C D E F G H I K L M N Q R S V W Y — |
| K301 | C D E F G H I L M N Q R S T V W Y — |
| S303 | A C D E F G H I K L M N P Q R T V Y — |
| Y305 | A C D E F G H I K L M N P Q R S T V W |
| F306 | A C D E G H I K L M N Q R S T V W Y — |
| Y310 | A C D E F GH I K L M N P Q R S T V W — |
| L311 | C F G I M Q S T V — — — — — — — — — |
| N314 | A C D E F G H I K L M P Q R S T V W Y |
| K318 | A C D E G H I L M N P Q R S T Y — — |
| D319 | A C E F H I K M N P Q R S T V W Y — |
| Q320 | A C D E F G H I K L M N R S T V W Y — |
| S322 | A D E F G H I L M N P Q R T V W Y — |
| L323 | A C D E F G H K M N P Q R S T V W — — |
| G336 | A C E F H I K M N P Q R S T W Y — — |
| Q337 | A D E F G H L M N P R S T V W Y — — |
| S338 | A C D E F G H K L M N P Q R T V Y — |
| L339 | A C D E F G H I K M N Q R S T V W Y — |
| Q340 | A C D E F G H I K L M N P R S T V W Y |
| E344 | A C D F G H K L M N P Q R S T V — — |
| Q359 | A C D E F G I M N S T V W Y — — — — |
| P374 | A D E F H I K L M N Q R S T V W Y — |
| K375 | A C D E F G H I L M N P Q R S T V W Y |
| Y376 | A C D E F G H I K M N P Q R S T V W — |
| N377 | A C D E F G H K L M P Q R S T V W Y — |
| P379 | A C E F G H I K L M Q R T V W Y — — |
| L381 | A C D E F G H I K M N P Q R S T V W Y |
| K382 | A C D E F G H I L M N P Q R S T V W Y |
| R393 | A C D E F G H I K L M N P Q T V W — — |
| D394 | A C E F G H K L M N Q R S T V W — — |
| T399 | A C D E F G H I K L M P Q R S W Y — |
| R401 | A C D E G H I K L M N Q S T W Y — — |
| Q407 | A C D E F G I K M N P R S T V W — — |
| D408 | A C F G H I K M N Q R S T — — — — — |
| T419 | A C D E F G H I K L M N P Q R S V W Y |
| P433 | A C D E H I K L M N Q R S T V W — — |
| S436 | A C D E F G H I K L M N P Q R T V W Y |
| W438 | C F G H I K L M N P Q R S T V Y — — |
| K444 | C D F G H I L M N P Q R S T V W Y — |
| G447 | A C D F H I K L M N P Q R S T V W Y — |
| K448 | A C D E F G H L N P Q R S T V W — — |
| Y451 | A C D E F G K L M N P Q R S T V — — |
| L453 | A C D E F G H I K M N P Q R S T V W Y |
| D459 | A C E F G H I K L M N P Q R S T V W Y |
| A465 | C F G H I K L M N P Q S T V W Y — — |
| E470 | A C D F G H I K L N P Q R S T W Y — |
| G475 | A C D E F H I K L N P Q R S T V W — |
| G476 | A C D E H I K L M N P Q T V W Y — — |
| A483 | C D E F G H I K M N P Q R S T V W Y — |
| K484 | A C D E F G H I L M N — — — — — — — |

Example 4

Generation of BASE (AmyTS23t) Combinatorial Libraries

Synthetic BASE combinatorial libraries contain a mix of synthetic BASE genes in which two or more selected codons of the mature sequence are replaced by specific DNA sequences. Four synthetic BASE combinatorial libraries were produced by GENEART under contract to Genencor, using GENEART's technology platform for gene optimization, gene synthesis and library generation under proprietary GENEART know how and/or intellectual property. The advanced mutagenesis approach of GENEART to produce combinatorial libraries is described in general on the company's web site.

Tables 4-1 to 4-4 list the substitutions that could be present in members of the synthetic BASE combinatorial libraries (numbered according to the BASE mature amino acid sequence of SEQ ID NO: 2). In each library the targeted BASE positions have an equal chance to remain wild type (wt) or to be substituted with the specific amino acid listed in Tables 4-1 to 4-4. The BASE combinatorial libraries were produced by cloning the mutagenized BASE genes in the pHPLT vector to create variants of pHPLT-BASE plasmid DNA, and subsequently transforming *B. subtilis* cells. Transformation mixes were plated on HI-agar plates (Heart Infusion agar) containing 10 mg/L neomycin sulfate and 0.5% RBB-starch (Sigma-Aldrich Product No. S7629, Potato starch covalently linked with Remazol Brilliant Blue R). For each library, clear zone producing single colonies were picked and grown in TSB (tryptone and soy based broth) liquid medium containing 10 mg/ml neomycin. To generate BASE combinatorial variant enzyme samples for biochemical characterization, selective growth of the BASE combinatorial libraries members was performed in 96 well MTPs at 37° C. for 68 hours in MBD medium.

TABLE 4-1

BASE (AmyTS23t) Combinatorial Library 1

| Targeted Position | Wild Type Residue | Substitution |
|---|---|---|
| 182 | T | N |
| 183 | G | N |
| 305 | Y | Q |
| 320 | Q | F |
| 379 | P | A |
| 407 | Q | D |
| 419 | T | S |
| 475 | G | T |

TABLE 4-2

BASE (AmyTS23t) Combinatorial Library 2

| Targeted Position | Wild Type Residue | Substitution |
|---|---|---|
| 160 | Y | E |
| 182 | T | G |
| 183 | G | N |
| 189 | E | P |
| 305 | Y | G |
| 379 | P | E |
| 475 | G | T |

TABLE 4-3

BASE (AmyTS23t) Combinatorial Library 3

| Targeted Position | Wild Type Residue | Substitution |
|---|---|---|
| 125 | S | A |
| 182 | T | A |
| 214 | T | Q |
| 279 | T | N |
| 305 | Y | R |
| 319 | D | T |
| 320 | Q | N |
| 475 | G | R |

TABLE 4-4

BASE (AmyTS23t) Combinatorial Library 4

| Targeted Position | Wild Type Residue | Substitution |
|---|---|---|
| 7 | E | H |
| 182 | T | W |
| 298 | T | Q |
| 376 | Y | R |
| 379 | P | K |
| 407 | Q | W |
| 419 | T | S |
| 453 | L | W |

Example 5

Generation of BASE Combinatorial Variants

In this example, the construction of *Bacillus subtilis* strains expressing BASE combinatorial variants is described. To express BASE combinatorial variants, BASE variant DNA fragments were cloned in the pHPLT vector, by using the unique PstI and HindIII restriction sites, and subsequently introduced into a *Bacillus subtilis* strain. The BASE DNA variant fragments were constructed as described below. For each BASE combinatorial variant listed in Table 5-1 (S1 to S32), PCR reactions were performed using the primers listed in Table 5-2 and Table 5-3.

For the PCR reactions described below, final concentrations of 0.2 µM DNA primers and 0.1-10 ng of plasmid DNA template were used. Table 5-2 lists the specific pDNA template and primer pairs used to construct each of the variants. In addition, all PCR reactions were completed in a volume of 50 µL, using Finnzymes (Finnzymes O Y, Espoo, Finland) Phusion High-Fidelity DNA Polymerase (Catalog No. F-530L). All PCR reaction mixes contained 10 µL of 5× Phusion HF buffer, 1 µL of 10 mM dNTP mixture, 0.75 µL of Phusion DNA polymerase (2 units/µL), 1 µL of 100% DMSO and de-ionised, autoclaved water for a total volume of 50 µL. The PCR programs were run using a MJ Research PTC-200 Peltier thermal cycler (MJ Research, Waltham, Mass.) as follows: 30 sec at 98° C., 25× (10 sec at 98° C., 20 sec at 55° C., 25 sec at 72° C.), and finally 5 min at 72° C.

For BASE combinatorial variants S1 to S16, the amplified DNA fragments generated by PCR 1 and 2 were fused by a third PCR. A 0.5 µL aliquot of the amplified DNA fragments of both PCR1 and PCR 2 were added to the third reaction mixture containing primers PstI-FW and HindIII-RV. The amplified linear 1.5 kb DNA fragments were purified (Qiagen® Qiaquick PCR purification kit, Catalog No. 28106) and digested with PstI and HindIII restriction enzymes. Subsequently, the BASE combinatorial variant DNA fragments S1 to S16 and pHPLT pDNA (50 ng/µL digested with PstI and HindIII restriction enzymes) were purified (Qiagen® Qiaquick PCR purification kit, Catalog No. 28106) and ligated. The reaction conditions were as follows: 4 μL of purified, PstI and HpaI digested BASE variant fragment, 2 μL of purified, PstI and HindIII digested pHPLT DNA fragment, 8 μL T4 DNA Ligase buffer (Invitrogen® Catalog No. 46300-018), 25 μL de-ionised, autoclaved water and 1 μL T4 DNA Ligase, 1 unit/μL (Invitrogen® Catalog No. 15224-017). The ligation reaction was performed for 16-20 hours at 20° C.

To transform the ligation reaction mix directly into *B. subtilis* cells, the ligated pHPLT-BASE variant DNA was amplified using the TempliPhi kit (Amersham Catalog No. 25-6400). For this purpose 1 μL of the ligation reaction mix was mixed with 5 μL of sample buffer from the TempliPhi kit and heated for 3 minutes at 95° C. to denature the DNA. The reaction mixture was placed on ice to cool for 2 minutes and then spun down briefly. Next, 5 μL of reaction buffer and 0.2 μL of phi29 polymerase from the TempliPhi kit were added, and the reactions were incubated at 30° C. in an MJ Research PCR machine for 4 hours. The phi29 enzyme was heat inactivated by incubation at 65° C. for 10 min.

For introducing of the BASE variants into *B. subtilis*, 0.1 μL of the TempliPhi amplification reaction product was mixed with 500 μL of competent *B. subtilis* cells [(genotype: ΔaprE, ΔnprE, oppA, ΔspoIIE, degUHy32, ΔamyE::(xylR, prxylA-comK)] followed by vigorous shaking at 37° C. for 1 hour and 100 μL and 500 μL was plated on Heart infusion agar (Difco, Cat. no 244400) plates containing 10 mg/L neomycin sulfate and 0.5% RBB-starch. For each variant, clearing zone producing single colonies were picked and grown in TSB (tryptone and soy based broth) liquid medium with 10 mg/L neomycin selection for subsequent plasmid DNA isolation and gene sequence analysis. The identities of the BASE combinatorial variants were determined by sequence analysis. The pHPLT-BASE S1 to S16 plasmid DNA served as template DNA to construct BASE combinatorial variants S17 to S32 as described herein. To generate BASE combinatorial variant enzyme samples for biochemical characterization, the BASE combinatorial variants were grown in 96 well MTPs at 37° C. for 68 hours in MBD medium.

TABLE 5-1

BASE Combinatorial Variants S1-S32*

| Variants | N128 | K178 | T182 | A185 | S243 |
|---|---|---|---|---|---|
| BASE-S1 | — | — | G | D | — |
| BASE-S3 | — | L | G | D | — |
| BASE-S4 | — | L | G | — | — |
| BASE-S8 | — | L | — | D | — |
| BASE-S9 | — | — | G | D | Q |
| BASE-S10 | — | — | G | — | Q |
| BASE-S11 | — | L | G | D | Q |
| BASE-S12 | — | L | G | — | Q |
| BASE-S14 | — | — | — | D | Q |
| BASE-S15 | — | L | — | — | Q |
| BASE-S16 | — | L | — | D | Q |
| BASE-S17 | C | — | G | D | — |
| BASE-S18 | C | — | G | — | — |
| BASE-S19 | C | L | G | D | — |
| BASE-S20 | C | L | G | — | — |
| BASE-S21 | C | — | — | D | — |
| BASE-S23 | C | L | — | — | — |
| BASE-S24 | C | L | — | D | — |
| BASE-S25 | C | — | G | D | Q |
| BASE-S26 | C | — | G | — | Q |
| BASE-S27 | C | L | G | D | Q |
| BASE-S28 | C | L | G | — | Q |
| BASE-S29 | C | — | — | — | Q |
| BASE-S31 | C | L | — | — | Q |
| BASE-S32 | C | L | — | D | Q |

*minus sign = wild type residue

TABLE 5-2

Plasmid DNA Templates and Primer Pairs

| Variants | Plasmid DNA Template | PCR1 | PCR2 |
|---|---|---|---|
| BASE-S1 | pHPLT-BASE | KGA/D-FW + HindIII-Rv | KGA/D-RV + PstI-Fw |
| BASE-S3 | pHPLT-BASE | LGA/D-FW + HindIII-Rv | LGA/D-RV + PstI-Fw |
| BASE-S4 | pHPLT-BASE | LGA/D-FW + HindIII-Rv | LGA/D-RV + PstI-Fw |
| BASE-S8 | pHPLT-BASE | LTA/D-FW + HindIII-Rv | LTA/D-RV + PstI-Fw |
| BASE-S9 | pHPLT-BASE-S243Q | KGA/D-FW + HindIII-Rv | KGA/D-RV + PstI-Fw |
| BASE-S10 | pHPLT-BASE-S243Q | KGA/D-FW + HindIII-Rv | KGA/D-RV + PstI-Fw |
| BASE-S11 | pHPLT-BASE-S243Q | LGA/D-FW + HindIII-Rv | LGA/D-RV + PstI-Fw |
| BASE-S12 | pHPLT-BASE-S243Q | LGA/D-FW + HindIII-Rv | LGA/D-RV + PstI-Fw |
| BASE-S14 | pHPLT-BASE-S243Q | KTA/D-FW + HindIII-Rv | KTA/D-RV + PstI-Fw |
| BASE-S15 | pHPLT-BASE-S243Q | LTA/D-FW + HindIII-Rv | LTA/D-RV + PstI-Fw |
| BASE-S16 | pHPLT-BASE-S243Q | LTA/D-FW + HindIII-Rv | LTA/D-RV + PstI-Fw |
| BASE-S17 | pHPLT-BASE-S1 | 128-FW + HindIII-Rv | 128-RV + PstI-Fw |
| BASE-S18 | pHPLT-BASE-T182G | 128-FW + HindIII-Rv | 128-RV + PstI-Fw |
| BASE-S19 | pHPLT-BASE-S3 | 128-FW + HindIII-Rv | 128-RV + PstI-Fw |
| BASE-S20 | pHPLT-BASE-S4 | 128-FW + HindIII-Rv | 128-RV + PstI-Fw |
| BASE-S21 | pHPLT-BASE-A185D | 128-FW + HindIII-Rv | 128-RV + PstI-Fw |
| BASE-S23 | pHPLT-BASE-K178L | 128-FW + HindIII-Rv | 128-RV + PstI-Fw |
| BASE-S24 | pHPLT-BASE-S8 | 128-FW + HindIII-Rv | 128-RV + PstI-Fw |
| BASE-S25 | pHPLT-BASE-S9 | 128-FW + HindIII-Rv | 128-RV + PstI-Fw |
| BASE-S26 | pHPLT-BASE-S10 | 128-FW + HindIII-Rv | 128-RV + PstI-Fw |
| BASE-S27 | pHPLT-BASE-S11 | 128-FW + HindIII-Rv | 128-RV + PstI-Fw |
| BASE-S28 | pHPLT-BASE-S12 | 128-FW + HindIII-Rv | 128-RV + PstI-Fw |
| BASE-S29 | pHPLT-BASE-S243Q | 128-FW + HindIII-Rv | 128-RV + PstI-Fw |
| BASE-S31 | pHPLT-BASE-S15 | 128-FW + HindIII-Rv | 128-RV + PstI-Fw |
| BASE-S32 | pHPLT-BASE-S16 | 128-FW + HindIII-Rv | 128-RV + PstI-Fw |

TABLE 5-3

Primers Used to Construct BASE Combinatorial Variants S1-S32*

| Primer Name | Alternate Name | Primer Sequence (SEQ ID NO) |
|---|---|---|
| N128C_FW | 128-FW | GATCCGAGCAACCGTTGCCAGGAAACCAGCGGC (SEQ ID NO: 17) |
| N128C_RV | 128-RV | GCCGCTGGTTTCCTGGCAACGGTTGCTCGGATC (SEQ ID NO: 18) |
| KGA/D_FW | KGA/D-FW | CCGCATCTATAAATTTCGTAGCGGAGGCAAAGMYTGGGATTGGG (SEQ ID NO: 19) |
| KGA/D_RV | KGA/D-RV | CCCAATCCCARKCTTTGCCTCCGCTACGAAATTTATAGATGCGG (SEQ ID NO: 20) |
| LGA/D_FW | LGA/D-FW | CCGCATCTATTTATTTCGTAGCGGAGGCAAAGMYTGGGATTGGG (SEQ ID NO: 21) |
| LGA/D_RV | LGA/D-RV | CCCAATCCCARKCTTTGCCTCCGCTACGAAATAAATAGATGCGG (SEQ ID NO: 22) |
| KTA/D_FW | KTA/D-FW | CCGCATCTATAAATTTCGTAGCACCGGCAAAGMYTGGGATTGGG (SEQ ID NO: 23) |
| KTA/D_RV | KTA/D-RV | CCCAATCCCARKCTTTGCCGGTGCTACGAAATTTATAGATGCGG (SEQ ID NO: 24) |
| LTA/D_FW | LTA/D-FW | CCGCATCTATTTATTTCGTAGCACCGGCAAAGMYTGGGATTGGG (SEQ ID NO: 25) |
| LTA/D_RV | LTA/D-RV | CCCAATCCCARKCTTTGCCGGTGCTACGAAATAAATAGATGCGG (SEQ ID NO: 26) |
| BASE-PstI-FW | PstI-Fw | GCTGCCTCATTCTGCAGCTTCAGCA (SEQ ID NO: 27) |
| BASE-HindIII-RV | HindIII-Rv | CTGTTTTATCCTTTACCTTGTCTC (SEQ ID NO: 28) |

*M = DNA A or C; Y = DNA C or T; R = DNA G or A; and K = DNA G or T.

BASE combinatorial variants W1 to W13 were constructed by making use of BASE combinatorial variants P1 to P12. The P1-P12 variants of Table 5-4 were selected from the BASE combinatorial libraries 1-4 described in Example 4. For each BASE combinatorial variant listed in Table 5-5 (W1 to W32), PCR reactions were performed using the primers listed in Table 5-6. All PCR reaction conditions were similar to the protocol used for generating BASE combinatorial variants S1 to S32, set forth above.

TABLE 5-4

Amino Acid Substitutions of BASE Variants P1-P12*

| Variant | S125 | T182 | G183 | E189 | T279 | Y305 | D319 | Q320 | P379 | G475 |
|---|---|---|---|---|---|---|---|---|---|---|
| BASE-P1 (9) | — | — | — | — | — | Q | — | — | A | — |
| BASE-P2 (3) | — | N | — | — | — | Q | — | F | A | — |
| BASE-P3 (17) | — | N | — | — | — | — | — | — | A | T |
| BASE-P4 (18) | — | N | N | — | — | Q | — | F | — | T |
| BASE-P5 (29) | — | G | — | — | — | G | — | — | — | — |
| BASE-P6 (23) | — | G | — | P | — | G | — | — | — | — |
| BASE-P7 (33) | — | G | — | — | — | — | — | — | — | T |
| BASE-P8 (41) | A | — | — | — | N | — | T | N | — | R |
| BASE-P9 (51) | — | — | — | — | — | — | R | T | — | R |
| BASE-P10 (45) | A | — | — | — | — | — | R | — | — | R |

TABLE 5-4-continued

Amino Acid Substitutions of BASE Variants P1-P12*

| Variant | S125 | T182 | G183 | E189 | T279 | Y305 | D319 | Q320 | P379 | G475 |
|---|---|---|---|---|---|---|---|---|---|---|
| BASE-P11 (59) | — | A | — | — | N | R | — | N | — | — |
| BASE-P12 (62) | — | — | — | — | — | R | T | N | — | — |

*BASE Performance Variant No. is shown in parenthesis. BASE P1-P12 variants have wild type residues at positions Y160, T214, Q407 and T149.

TABLE 5-5

Amino Acid Substitutions of BASE Variants W1-W13

| Variant | S125 | N128 | K178 | T182 | G183 | E189 | S243 | T279 | Y305 | D319 | Q320 | P379 | G475 |
|---|---|---|---|---|---|---|---|---|---|---|---|---|---|
| W1 | — | C | L | G | — | — | Q | — | Q | — | — | A | — |
| W2 | — | C | L | G | — | — | Q | — | Q | — | F | A | — |
| W3 | — | C | — | N | — | — | Q | — | Q | — | F | A | — |
| W4 | — | C | L | G | — | — | Q | — | — | — | — | A | T |
| W5 | — | C | L | G | N | — | Q | — | Q | — | F | — | T |
| W6 | — | C | L | G | — | — | Q | — | G | — | — | — | — |
| W7 | — | C | L | G | — | P | Q | — | G | — | — | — | — |
| W8 | — | C | L | G | — | — | Q | — | — | — | — | — | T |
| W9 | A | C | L | G | — | — | Q | N | — | T | N | — | R |
| W10 | — | C | L | G | — | — | Q | — | R | T | — | — | R |
| W11 | A | C | L | G | — | — | Q | — | R | — | — | — | R |
| W12 | — | C | L | A | — | — | Q | N | R | — | N | — | — |
| W13 | — | C | L | G | — | — | Q | — | R | T | N | — | — |

TABLE 5-6

Primers Used to Construct BASE Combinatorial Variants W1-W13

| Primer Name (Alternate) | Primer Sequence (SEQ ID NO) |
|---|---|
| BASE-N128C-FW (Pr1) | GGATCCGAGCAACCGTTGCCAGGAAACCAGCGGC (SEQ ID NO: 29) |
| BASE-N128C-RV (Pr2) | GCCGCTGGTTTCCTGGCAACGGTTGCTCGGATCC (SEQ ID NO: 30) |
| BASE-S125A-N128C-FW (Pr3) | GGATCCGGCCAACCGTTGCCAGGAAACCAGCGGC (SEQ ID NO: 31) |
| BASE-S125A-N128C-RV (Pr4) | GCCGCTGGTTTCCTGGCAACGGTTGGCCGGATCC (SEQ ID NO: 32) |
| BASE-K178L-T182G-FW (Pr5) | GAACCGCATCTATCTATTTCGTAGCGGCGGCAAAGCGTGGGAT (SEQ ID NO: 33) |
| BASE-K178L-T182G-RV (Pr6) | ATCCCACGCTTTGCCGCCGCTACGAAATAGATAGATGCGGTTC (SEQ ID NO: 34) |
| BASE-K178L-T182G-G183N-FW (Pr7) | GAACCGCATCTATCTATTTCGTAGCGGCAACAAAGCGTGGGAT (SEQ ID NO: 35) |
| BASE-K178L-T182G-G183N-RV (Pr8) | ATCCCACGCTTTGTTGCCGCTACGAAATAGATAGATGCGGTTC (SEQ ID NO: 36) |
| BASE-K178L-T182A-FW (Pr9) | GAACCGCATCTATCTATTTCGTAGCGCCGGCAAAGCGTGGGAT (SEQ ID NO: 37) |
| BASE-K178L-T182A-RV (Pr10) | ATCCCACGCTTTGCCGGCGCTACGAAATAGATAGATGCGGTTC (SEQ ID NO: 38) |
| BASE-S243Q-FW (Pr11) | GGTGAAACACATCAAATACCAATTTTTTCCGGATTGGCTG (SEQ ID NO: 39) |
| BASE-S243Q-RV (Pr12) | CAGCCAATCCGGAAAAAATTGGTATTTGATGTGTTTCACC (SEQ ID NO: 40) |
| BASE-T182G-FW (Pr13) | GAACCGCATCTATAAATTTCGTAGCGGCGGCAAAGCGTGGGAT (SEQ ID NO: 41) |

TABLE 5-6-continued

Primers Used to Construct BASE Combinatorial Variants W1-W13

| Primer Name (Alternate) | Primer Sequence (SEQ ID NO) |
|---|---|
| BASE-T182G-RV (Pr14) | ATCCCACGCTTTGCCGCCGCTACGAAATTTATAGATGCGGTTC (SEQ ID NO: 42) |
| BASE-T182G-G182N-FW (Pr15) | GAACCGCATCTATAAATTTCGTAGCGGCAACAAAGCGTGGGAT (SEQ ID NO: 43) |
| BASE-T182G-G182N-RV (Pr16) | ATCCCACGCITTGTTGCCGCTACGAAATTTATAGATGCGGTTC (SEQ ID NO: 44) |
| BASE-T182A-FW (Pr17) | GAACCGCATCTATAAATTTCGTAGCGCCGGCAAAGCGTGGGAT (SEQ ID NO: 45) |
| BASE-T182A-RV (Pr18) | ATCCCACGCTTTGCCGGCGCIACGAAATTTATAGATGCGGTTC (SEQ ID NO: 46) |
| BASE-PstI-FW (Pr19) | GCTGCCTCATTCTGCAGCTTCAGCA (SEQ ID NO: 47) |
| BASE-HindIII-RV (Pr20) | GCTGTTTTATCCTTTACCTTGTCTC (SEQ ID NO: 48) |

The PCR scheme to construct BASE combinatorial variants W1 to W13 is shown in Tables 5-7 and 5-8. Variant production begins with five PCR reactions (series A to E), and continues with two fusion PCR reactions (series F and G). All PCR fragments were purified using Qiagen® Qiaquick PCR purification kit (Catalog No. 28106). As described for construction of variants S1 to S32, fusion DNA fragments of PCR G1 to G13 were digested with PstI and HindIII and ligated to PstI and HindIII-digested pHPLT vector DNA. Subsequently, a phi29 polymerase amplified ligation mixture was introduced into *B. subtilis*. For each variant, clear zone producing single colonies were picked and grown in TSB (tryptone and soy based broth) liquid medium containing 10 mg/L neomycin for subsequent plasmid DNA isolation and gene sequence analysis. Identity of the BASE combinatorial variants was confirmed by sequence analysis. To generate enzyme samples of combinatorial variants W1 to W13 for biochemical characterization, selective growth of the BASE combinatorial variants was performed in 96 well MTPs at 37° C. for 68 hours in MBD medium.

TABLE 5-7

PCR Reactions For Construction of BASE Combinatorial Variants W1-W13

| BASE Variants | Template DNA | PCR A1 to A13 | PCR B1 to B12 | PCR C13 | PCR D1 to D12 | PCR E1 to E13 |
|---|---|---|---|---|---|---|
| BASE-W1 | BASE-P1 | Pr19 + Pr2 | Pr1 + Pr6 | — | Pr5 + Pr12 | Pr11 + Pr20 |
| BASE-W2 | BASE-P2 | Pr19 + Pr2 | Pr1 + Pr6 | — | Pr5 + Pr12 | Pr11 + Pr20 |
| BASE-W3 | BASE-P3 | Pr19 + Pr2 | Pr1 + Pr6 | — | Pr5 + Pr12 | Pr11 + Pr20 |
| BASE-W4 | BASE-P4 | Pr19 + Pr2 | Pr1 + Pr8 | — | Pr7 + Pr12 | Pr11 + Pr20 |
| BASE-W5 | BASE-P5 | Pr19 + Pr2 | Pr1 + Pr6 | — | Pr5 + Pr12 | Pr11 + Pr20 |
| BASE-W6 | BASE-P6 | Pr19 + Pr2 | Pr1 + Pr6 | — | Pr5 + Pr12 | Pr11 + Pr20 |
| BASE-W7 | BASE-P7 | Pr19 + Pr2 | Pr1 + Pr6 | — | Pr5 + Pr12 | Pr11 + Pr20 |
| BASE-W8 | BASE-P8 | Pr19 + Pr4 | Pr3 + Pr6 | — | Pr5 + Pr12 | Pr11 + Pr20 |
| BASE-W9 | BASE-P9 | Pr19 + Pr2 | Pr1 + Pr6 | — | Pr5 + Pr12 | Pr11 + Pr20 |
| BASE-W10 | BASE-P10 | Pr19 + Pr4 | Pr3 + Pr6 | — | Pr5 + Pr12 | Pr11 + Pr20 |
| BASE-W11 | BASE-P11 | Pr19 + Pr2 | Pr1 + Pr10 | — | Pr9 + Pr12 | Pr11 + Pr20 |
| BASE-W12 | BASE-P12 | Pr19 + Pr2 | Pr1 + Pr6 | — | Pr5 + Pr12 | Pr11 + Pr20 |
| BASE-W13 | BASE-P2 | Pr19 + Pr2 | — | Pr1 + Pr2 | — | Pr11 + Pr20 |
| Size | | 424 bp | 196 bp | 382 bp | 229 bp | 826 bp |

TABLE 5-8

Series 1 (F) and Series 2 (G) Fusion Reactions For BASE Variants W1-W13

| BASE Variants | Template DNA | PCR F1 to F12 | Template DNA | PCR G1 to G12 |
|---|---|---|---|---|
| BASE-W1 | B1 + D1 | Pr1 + Pr6 | A1 + F1 + E1 | Pr19 + Pr20 |
| BASE-W2 | B2 + D2 | Pr1 + Pr6 | A2 + F2 + E2 | Pr19 + Pr20 |
| BASE-W3 | B3 + D3 | Pr1 + Pr6 | A3 + F3 + E3 | Pr19 + Pr20 |
| BASE-W4 | B4 + D4 | Pr1 + Pr8 | A4 + F4 + E4 | Pr19 + Pr20 |
| BASE-W5 | B5 + D5 | Pr1 + Pr6 | A5 + F5 + E5 | Pr19 + Pr20 |
| BASE-W6 | B6 + D6 | Pr1 + Pr6 | A6 + F6 + E6 | Pr19 + Pr20 |
| BASE-W7 | B7 + D7 | Pr1 + Pr6 | A7 + F7 + E7 | Pr19 + Pr20 |
| BASE-W8 | B8 + D8 | Pr3 + Pr6 | A8 + F8 + E8 | Pr19 + Pr20 |
| BASE-W9 | B9 + D9 | Pr1 + Pr6 | A9 + F9 + E9 | Pr19 + Pr20 |
| BASE-W10 | B10 + D10 | Pr3 + Pr6 | A10 + F10 + E10 | Pr19 + Pr20 |
| BASE-W11 | B11 + D11 | Pr1 + Pr10 | A11 + F11 + E11 | Pr19 + Pr20 |
| BASE-W12 | B12 + D12 | Pr1 + Pr6 | A12 + F12 + E12 | Pr19 + Pr20 |
| BASE-W13 | — | — | A13 + F13 + E13 | Pr19 + Pr20 |
| | size | 382 bp | Size | 382 bp |

Example 6

Generation of ACE (AmyTS23tΔRS) Site Evaluation Libraries

In this example, the construction of *Bacillus subtilis* strains expressing the BASE variants: BASE-ΔR180-ΔS181 (also known as AmyTS23tΔRS or ACE); and BASE-ΔR180-ΔS181-S243Q (also known as AmyTS23tΔRS-S243Q, named ACE-S243Q or ACE-Q) are described. In addition, the generation of ACE-Q site evaluation libraries (SELs) is described.

Synthetic DNA fragment 056426 (produced by Geneart, Regensburg, Germany) containing a DNA codon-modified BASE gene served as template DNA. This BASE DNA fragment was cloned into the pHPLT vector (Solingen et al., *Extremophiles*, 5:333-341, 2001) using the unique PstI and HpaI restriction sites. The pHPLT expression vector contains the *B. licheniformis* LAT promoter (Plat) followed by PstI and HpaI restriction sites for cloning BASE, and additional elements from pUB110 (McKenzie et al., *Plasmid*, 15: 93-103, 1986) including a replicase gene (reppUB), a neomycin/kanamycin resistance gene (neo) and a bleomycin resistance marker (bleo). A map of the pHPLT-BASE plasmid is shown in FIG. 3. BASE DNA with codons 180 (CGG) and 181 (AGC) deleted (BASE-ΔR180-ΔS181, also named ACE) was generated using pHPLT-BASE as template DNA and the DNA primers listed in Table 6-1. The DNA primers were synthesized and desalted by Sigma (Sigma-Aldrich Chemie B. V., Zwijndrecht, The Netherlands).

Two PCR reactions were performed using pHPLT-BASE template DNA using primer pairs TS-delRS-FW/pHPLT-HpaI-RV and TS-delRS-RV/pHPLT-PstI-FW. In order to fuse the two PCR generated fragments, 1 µl unpurified PCR mix from both reactions was added to a third PCR reaction in which primers pHPLT-PstI-FW and pHPLT-HpaI-RV were added. The amplified linear 1.5 kb DNA fragment was purified (using Qiagen® Qiaquick PCR purification kit Cat. no. 28106) and digested with PstI and HpaI restriction enzymes. For all the PCR reactions described, final concentrations of 0.2 µM DNA primer were used, and 0.1-10 ng of DNA template was used. In addition, all PCR reactions were completed in a volume of 50 using Finnzymes (Finnzymes O Y, Espoo, Finland) Phusion High-Fidelity DNA Polymerase (Cat. no. F-530L). Also, all PCR reaction mixes contained 10 µL of 5× Phusion HF buffer, 1 µL of 10 mM dNTP mixture, 0.75 µL of Phusion DNA polymerase (2 units/µL), 1 µL of 100% DMSO and de-ionised, autoclaved water to give a final volume of 50 µL. The PCR programs, using a MJ Research PTC-200 Peltier thermal cycler (MJ Research, Waltham, Mass.) were performed as described by Finnzymes (30 sec at 98° C., 30×[10 sec at 98° C., 20 sec at 55° C., 22 sec/kb at 72° C.] with a final step of 5 min at 72° C.).

Subsequently, the BASE-ΔR180-ΔS181 DNA fragment and pHPLT plasmid DNA (50 ng/µL, digested with PstI and HpaI restriction enzymes) were both purified (using Qiagen® Qiaquick PCR purification kit Cat. no. 28106) and then ligated at the PstI and HpaI ends using the following reaction conditions: 4 µL of purified, PstI and HpaI digested BASE-ΔR180-ΔS181 DNA fragment, 2 µL of purified, PstI and HpaI digested pHPLT DNA fragment, 8 µL T4 DNA Ligase buffer (Invitrogen® Cat. no. 46300-018), 25 µl di-ionised, autoclaved water and 1 µL T4 DNA Ligase, 1 unit/µL (Invitrogen® Cat. no. 15224-017). The ligation reaction was performed for 16-20 hours at 20° C.

The ligation mixture was transformed into a *B. subtilis* strain (genotype: ΔaprE, ΔnprE, Δepr, ΔispA, Δbpr) and (degUHy32, oppA, ΔspoIIE3501, amyE::xylRPxylAcomK-ermC, (Δvpr, ΔwprA, Δmpr-ybfJ, ΔnprB)) as described in WO 02/14490, incorporated herein by reference for the teaching of bacterial transformation. The *B. subtilis* transformants were selected on agar plates containing Heart infusion agar (Difco, Cat. no 244400) and 10 mg/L neomycin. Selective growth of *B. subtilis* transformants harboring the pHPLT-BASE-ΔR180-ΔS181 plasmid was performed in shake flasks containing 25 ml MBD medium (MOPS based defined medium) and 10 mg/L neomycin. This resulted in the production of secreted BASE-ΔR180-ΔS181 amylase with starch hydrolyzing activity. The pHPLT-BASE-ΔR180-ΔS181 plasmid is also referred to herein as pHPLT-ACE.

Figure 4:
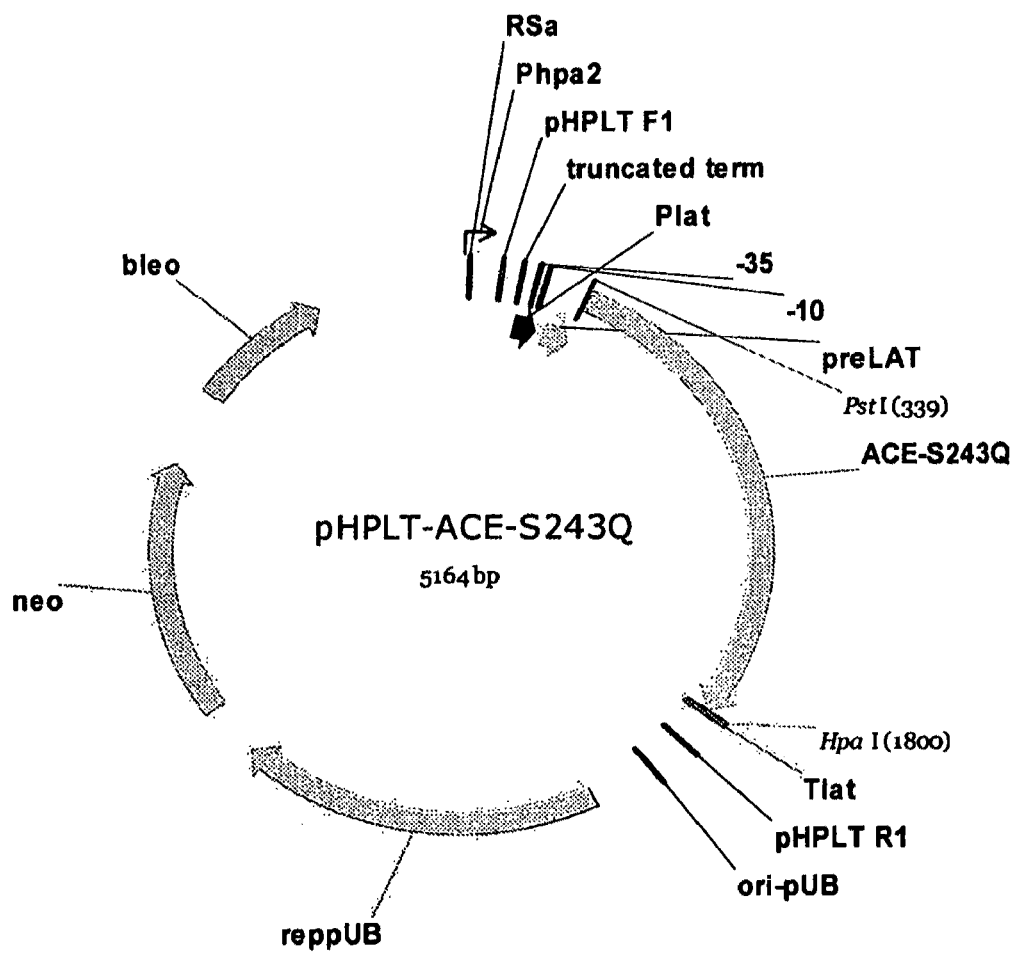
FIG. 4 provides a map of the pHPLT-ACE-S243Q plasmid.

For the generation of a *Bacillus subtilis* strain expressing the BASE-ΔR180-ΔS181-S243Q amylase, a similar protocol was used. The first two PCR reactions were performed using primers ACE-S243Q-FW and pHPLT-HpaI-RV, and primers ACE-S243Q-RV and pHPLT-PstI-FW, pHPLT-ACE template DNA. Primer sequences are listed in Table 6-1. The *B. subtilis* transformants harboring the pHPLT-BASE-ΔR180-ΔS181-S243Q produced and secreted BASE ΔR180-ΔS181-S234Q amylase with starch hydrolyzing activity. A map of the pHPLT-BASE-ΔR180-ΔS181-S243Q plasmid, also termed pHPLT-ACE-S243Q, is shown in FIG. 4.

TABLE 6-1

Primers for Generation of the BASE-ΔR180-ΔS181 (ACE) and ACE-Q Amylases

| Primer name | DNA sequence (SEQ ID NO) |
|---|---|
| pHPLT-PstI-FW | CTCATTCTGCAGCTTCAGCAAATACGGCG (SEQ ID NO: 49) |
| pHPLT-HpaI-RV | CTCTGTTAACTCATTTGGCGACCCAGATTGAAACG (SEQ ID NO: 50) |
| TS-delRS-FW | CTATAAATTTACGGGCAAAGCATGGGATTGG (SEQ ID NO: 51) |
| TS-delRS-RV | TGCTTTGCCCGTAAATTTATAGATCCGGTTCAG (SEQ ID NO: 52) |

TABLE 6-1-continued

Primers for Generation of the BASE-ΔR180-ΔS181 (ACE) and ACE-Q Amylases

| Primer name | DNA sequence (SEQ ID NO) |
|---|---|
| ACE-S243Q-FW | CAAACATATCAAATATCAATTTTTCCGGACTG (SEQ ID NO: 53) |
| ACE-S243Q-RV | CAGTCCGGAAAAAATTGATATTTGATATGTTTG (SEQ ID NO: 54) |

The pHPLT-ACE-S243Q plasmid DNA served as a template for the production of site evaluation libraries (SELs). The amino acid positions selected for the ACE-Q SELs are numbered according to the mature BASE amino acid sequence (SEQ ID NO: 2) and include: R127, Y305, Q320, P379, T419, L453 and G475. The corresponding DNA codons were each replaced with mutated codons encoding a maximum of 20 different amino acids. This pHPLT-ACE-S243Q plasmid contained a unique BglII restriction site, which was utilized during SEL construction. Sequences of the primers (commercially synthesized and desalted) used to generate the libraries are listed in Table 6-2.

To construct ACE-Q SELs, three reactions were performed: two mutagenesis reactions to introduce the mutated codon of interest in the ACE-Q DNA sequence, and a third reaction to fuse the two PCR fragments. The method of mutagenesis was based on the codon-specific mutation approach. In this method, the creation of all possible mutations in a specific DNA triplet is accomplished using a forward and reverse oligonucleotide primer encoding a specific designed triplet DNA sequence NNS ((A, C, T or G), (A, C, T or G), (C or G)) that corresponds with the sequence of the codon to be mutated and guarantees random incorporation of nucleotides at the codon of interest. The number listed in the primer names of Table 6-2 corresponds with the specific ACE-Q codon position (based on the numbering of the mature BASE amino acid sequence). Two additional oligonucleotide primers that were used to construct the SEL encode the unique BglII restriction site and pHPLT DNA sequence flanking the BglII restriction site.

TABLE 6-2

Primers for Generation of ACE-Q SEL Variants

| Primer name | DNA sequence (SEQ ID NO) |
|---|---|
| ACE-Q-R127-FW | GTTGATCCGAGCAACNNSAACCAAGAAACGAG (SEQ ID NO: 55) |
| ACE-Q-R127-RV | CTCGTTTCTTGGTTSNNGTTGCTCGGATCAAC (SEQ ID NO: 56) |
| ACE-Q-Y305-FW | GCAAAAGCTCAGGCNNSTTTGATATGAGATATC (SEQ ID NO: 57) |
| ACE-Q-Y305-RV | GATATCTCATATCAAASNNGCCTGAGCTTTTGC (SEQ ID NO: 58) |
| ACE-Q-Q320-FW | CGCTGATGAAAGATNNSCCGAGCCTGGCAGTC (SEQ ID NO: 59) |
| ACE-Q-Q320-RV | GACTGCCAGGCTCGGSNNATCTTTCATCAGCG (SEQ ID NO: 60) |
| ACE-Q-P379-FW | CGAAATATAATATCNNSGGCCTGAAAAGC (SEQ ID NO: 61) |

TABLE 6-2-continued

Primers for Generation of ACE-Q SEL Variants

| Primer name | DNA sequence (SEQ ID NO) |
|---|---|
| ACE-Q-P379-RV | GCTTTTCAGGCCSNNGATATTATATTTCG (SEQ ID NO: 62) |
| ACE-Q-T419-FW | GAGAAGGCATCGATNNSAAACCGAATAGCG (SEQ ID NO: 63) |
| ACE-Q-T419-RV | CGCTATTCGGTTTSNNATCGATGCCTTCTC (SEQ ID NO: 64) |
| ACE-Q-L453-FW | CAAAGTCTTTTATGATNNSACGGGCAACAGAAGC (SEQ ID NO: 65) |
| ACE-Q-L453-RV | GCTTCTGTTGCCCGTSNNATCATAAAAGACTTTG (SEQ ID NO: 66) |
| ACE-Q-G475-FW | GAATTTAAAGTCAATNNSGGCAGCGTTTCAATC (SEQ ID NO: 67) |
| ACE-Q-G475-RV | GATTGAAACGCTGCCSNNATTGACTTTAAATTC (SEQ ID NO: 68) |
| pHPLT-BglII-FW | GCAATCAGATCTTCCTTCAGGTTATGACC (SEQ ID NO: 69) |
| pHPLT-BglII-RV | GCATCGAAGATCTGATTGCTTAACTGCTTC (SEQ ID NO: 70) |

Construction of each SEL began with two primary amplification reactions: a first PCR using the pHPLT-BglII-FW primer and a specific ACE-Q reverse mutagenesis primer; and a second PCR using the pHPLT-BglII-RV primer and a specific ACE-Q forward mutagenesis primer. The introduction of the mutations in the mature ACE-Q sequence was performed using Finnzymes Phusion High-Fidelity DNA Polymerase (Finnzymes O Y, Espoo, Finland) (Cat. no. F-530L). All reactions were performed according to the protocol supplied by the manufacturer The PCR conditions for the primary reactions were as follows. For primary PCR 1: the pHPLT-BglII-FW primer and a specific ACE-Q reverse mutagenesis primer—both 1 µL (10 µM), and 0.1-10 ng of DNA template (pHPLT-ACE-S243Q), 10 µL of 5× Phusion HF buffer, 1 µL of 10 mM dNTP mixture, 0.75 µL of Phusion DNA polymerase (2 units/µL), 1 µL of 100% DMSO and de-ionised, autoclaved water to a total final volume of 50 µL. For primary PCR 2: the pHPLT-BglII-RV primer and a specific ACE-Q forward mutagenesis primer—both 1 µL (10 µM), and 0.1-10 ng of DNA template (pHPLT-ACE-S243Q), 10 µL of 5× Phusion HF buffer, 1 µL of 10 mM dNTP mixture, 0.75 µL of Phusion DNA polymerase (2 units/µL), 1 µL of 100% DMSO and de-ionised, autoclaved water to a total final volume of 50 µL.

A PTC-200 Peltier thermal cycler (MJ Research, Inc. Waltham, Mass.) with the following program was used: 30 seconds 98° C., 30× cycles (10 seconds 98° C., 20 seconds 55° C., 1 minute 72° C.) and 5 min 72° C. For each SEL primary amplification reaction two DNA fragments of approximately 2-3 kb with an approximately 30 nucleotide overlap around the ACE-Q codon of interest were produced. In order to fuse the two DNA fragments, 1 µL unpurified PCR mix from both reactions was added to a third amplification reaction to which primers pHPLT-BglII-FW and pHPLT-BglII-RV were added. The amplified linear 5.2 kb DNA fragments were purified (using Qiagen® Qiaquick PCR purification kit Cat. no. 28106) and digested with a BclI restriction enzyme to create cohesive ends on both sides of the fusion fragment. The restriction digest contained 35 µL purified linear DNA fragment, 4 µL React® 3 buffer (Invitrogen, Paisley PA4 9RF, UK) and 1 µL BglII, 10 units/ml (Invitrogen, Paisley PA4 9RF, UK) as was incubated at 30° C. for 1 hour.

The codon mutagenized pHPLT-ACE-S243Q ligation mixtures were used to transform competent *B. subtilis* cells (genotype: ΔaprE, ΔnprE, oppA, ΔspoIIE, degUHy32, ΔamyE:[xylR,pxylA-comK]) as described in WO 2002/014490, in order to generate the ACE-Q SELs. Transformation mixes were plated on HI-agar plates (Heart Infusion agar) containing 10 mg/ml neomycin sulfate (Sigma, Catalog No. N-1876; contains 732 µg neomycin per mg). For each library, single colonies were picked and grown in tryptone and soy based broth liquid media under 10 mg/ml neomycin selection for subsequent plasmid DNA isolation and DNA sequence analysis of the ACE-Q gene variants. DNA sequence analysis was performed by BaseClear B.V. (Leiden, The Netherlands). Sequence analysis data revealed a maximum of 18 ACE-Q variants per library. All ACE-Q variants that were identified in the seven ACE-Q SELs are listed in Table 6-3. To generate ACE-Q variant enzyme samples for biochemical characterization selective growth of the ACE-Q SEL members was done in 96 well MTPs at 37° C. for 68 hours in MBD medium (MOPS based defined medium).

TABLE 6-3

ACE-S243Q (ACE-Q) Variants Identified in the Seven ACE-Q SELs

| Position | Amino Acid Substitutions Generated in the ACE-Q Amylase Background | | | | | | | | | | | | | | | | |
|---|---|---|---|---|---|---|---|---|---|---|---|---|---|---|---|---|---|
| R127 | A | C | D | E | F | G | H | I | K | L | M | P | Q | S | T | V | W | Y |
| Y305 | A | C | D | E | G | H | L | N | P | Q | R | S | T | V | W | — | — | — |
| Q320 | A | C | D | E | F | G | H | I | L | M | N | P | R | S | T | V | W | Y |
| P379 | A | C | E | E | G | H | L | N | Q | R | S | T | V | W | Y | — | — | — |
| T419 | A | C | D | E | F | G | H | K | L | M | N | P | Q | R | S | V | W | Y |
| L453 | A | C | D | F | G | H | I | K | M | N | P | Q | R | S | T | V | W | Y |
| G475 | A | D | E | H | I | K | L | M | N | P | Q | R | S | T | V | W | — | — |

Example 7

Performance Index Values for BASE Variants

In this example, results of experiments conducted to determine cleaning performance (CS-28 microswatch assay at pH 10/32° C., pH 10/50° C., pH 8/16° C. and pH 8/32° C.), detergent stability, thermostability, BPNPG7 amylase activity and HPLC protein concentration (tests of properties of interest) of BASE and variants thereof are described. The results were obtained using the methods of Example 1. As described throughout, functionality of BASE variants was quantified as a performance index (PI), which is the ratio of performance of a variant to a parent protein. Table 10-1 shows the PI values for numerous BASE variants for the properties tested. The mutations introduced at the various amino acid positions are indicated. Performance indices less than or equal to 0.05 were fixed to 0.05. For every variant with an HPLC protein PI less than or equal to 0.05, all values were fixed at 0.05. Also, for the two stability measures, if the PI of the initial activity in the stability assays was less than or equal to 0.05, the associated stability PI was fixed to 0.05. Table 7-1 provides performance indices of BASE variants having combinable mutations, which are defined herein as mutations in variants with PI values ≥0.5 for at least one property, and PI values of >0.05 for all properties.

TABLE 7-1

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 1 | N001A | 0.81 | 0.71 | 2.75 | 0.26 | 0.88 | 0.83 | 0.83 | 0.78 | 0.79 |
| 1 | N001C | 0.75 | 0.34 | 2.72 | 0.11 | 0.70 | 1.03 | 0.75 | 0.67 | 0.28 |
| 1 | N001D | 0.92 | 0.72 | 2.91 | 0.28 | 0.88 | 0.83 | 0.80 | 0.85 | 0.78 |
| 1 | N001E | 0.93 | 0.87 | 3.10 | 0.29 | 0.90 | 0.77 | 0.82 | 0.75 | 0.87 |
| 1 | N001F | 0.68 | 0.48 | 2.96 | 0.19 | 0.98 | 0.77 | 0.69 | 0.76 | 0.53 |
| 1 | N001H | 0.67 | 0.62 | 2.59 | 0.33 | 0.94 | 0.87 | 0.77 | 0.93 | 0.84 |
| 1 | N001K | 0.64 | 0.87 | 2.54 | 0.37 | 0.97 | 1.00 | 1.21 | 0.91 | 1.04 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 1 | N001L | 0.81 | 0.51 | 2.67 | 0.20 | 0.80 | 0.79 | 0.80 | 0.68 | 0.59 |
| 1 | N001M | 0.91 | 0.59 | 3.02 | 0.23 | 0.82 | 0.74 | 0.73 | 0.64 | 0.67 |
| 1 | N001Q | 0.47 | 0.49 | 2.66 | 0.34 | 0.79 | 0.94 | 0.88 | 0.96 | 0.88 |
| 1 | N001R | 0.79 | 1.09 | 2.63 | 0.35 | 0.97 | 1.20 | 0.92 | 0.90 | 0.96 |
| 1 | N001S | 0.90 | 0.77 | 2.72 | 0.29 | 0.94 | 0.88 | 0.91 | 0.80 | 0.84 |
| 1 | N001T | 0.90 | 0.72 | 2.87 | 0.29 | 0.86 | 0.82 | 1.02 | 0.80 | 0.81 |
| 1 | N001Y | 0.66 | 0.46 | 2.70 | 0.25 | 0.89 | 0.81 | 0.79 | 0.80 | 0.69 |
| 2 | T002A | 0.79 | 1.06 | 1.02 | 0.96 | 0.90 | 1.04 | 0.98 | 0.73 | 1.02 |
| 2 | T002D | 0.98 | 1.01 | 1.19 | 1.00 | 0.90 | 1.04 | 0.99 | 1.00 | 1.04 |
| 2 | T002E | 0.86 | 1.14 | 1.24 | 0.98 | 1.03 | 0.90 | 1.14 | 1.02 | 1.10 |
| 2 | T002F | 0.90 | 0.54 | 1.23 | 0.54 | 0.80 | 0.89 | 1.80 | 1.01 | 0.55 |
| 2 | T002H | 0.94 | 0.97 | 1.16 | 0.93 | 0.99 | 1.03 | 0.76 | 1.01 | 0.98 |
| 2 | T002I | 0.71 | 0.63 | 1.04 | 0.60 | 1.11 | 1.44 | 0.52 | 0.95 | 0.64 |
| 2 | T002K | 0.96 | 1.06 | 1.09 | 1.01 | 1.00 | 1.12 | 0.85 | 1.00 | 1.07 |
| 2 | T002L | 0.85 | 0.50 | 1.18 | 0.48 | 0.90 | 1.22 | 0.47 | 0.88 | 0.56 |
| 2 | T002M | 0.94 | 0.65 | 1.27 | 0.65 | 0.93 | 1.01 | 0.54 | 0.88 | 0.76 |
| 2 | T002N | 0.95 | 1.16 | 1.25 | 1.09 | 1.04 | 1.05 | 1.05 | 1.03 | 1.20 |
| 2 | T002P | 1.21 | 0.39 | 1.35 | 0.41 | 1.52 | 1.20 | 0.97 | 1.41 | 0.25 |
| 2 | T002Q | 1.00 | 1.10 | 1.22 | 1.07 | 1.10 | 1.15 | 1.05 | 1.06 | 0.82 |
| 2 | T002R | 0.92 | 0.97 | 0.96 | 1.01 | 1.20 | 1.48 | 1.06 | 1.09 | 0.90 |
| 2 | T002S | 0.92 | 0.97 | 1.09 | 0.94 | 1.02 | 1.00 | 0.86 | 0.97 | 0.97 |
| 2 | T002Y | 0.93 | 0.64 | 1.21 | 0.69 | 0.93 | 1.07 | 0.67 | 0.98 | 0.68 |
| 3 | A003C | 0.68 | 0.66 | 0.94 | 0.55 | 1.11 | 0.99 | 0.89 | 1.00 | 0.31 |
| 3 | A003D | 0.92 | 1.06 | 1.10 | 0.95 | 0.77 | 0.75 | 0.94 | 0.85 | 0.76 |
| 3 | A003E | 0.97 | 1.15 | 1.20 | 1.11 | 0.91 | 0.82 | 1.02 | 0.78 | 0.94 |
| 3 | A003F | 0.91 | 0.84 | 1.10 | 0.82 | 0.96 | 1.05 | 1.05 | 0.92 | 0.58 |
| 3 | A003G | 0.86 | 0.94 | 1.30 | 0.93 | 0.81 | 1.02 | 0.99 | 0.67 | 0.74 |
| 3 | A003H | 1.06 | 0.94 | 1.22 | 0.95 | 0.95 | 0.90 | 0.90 | 0.91 | 0.79 |
| 3 | A003I | 0.81 | 0.77 | 0.99 | 0.75 | 1.10 | 1.20 | 0.88 | 1.01 | 0.48 |
| 3 | A003K | 0.83 | 0.93 | 1.12 | 0.86 | 0.91 | 1.06 | 0.87 | 0.71 | 0.67 |
| 3 | A003M | 0.89 | 0.38 | 1.31 | 0.40 | 0.97 | 1.20 | 1.13 | 1.10 | 0.24 |
| 3 | A003N | 0.94 | 1.06 | 1.22 | 0.97 | 1.03 | 1.00 | 1.12 | 0.87 | 0.77 |
| 3 | A003P | 0.97 | 1.16 | 1.23 | 1.16 | 0.97 | 0.94 | 0.82 | 0.83 | 0.85 |
| 3 | A003Q | 0.96 | 1.09 | 1.20 | 1.06 | 1.03 | 0.97 | 1.17 | 0.81 | 0.84 |
| 3 | A003R | 0.82 | 1.01 | 0.96 | 0.90 | 1.05 | 1.19 | 1.14 | 0.80 | 0.67 |
| 3 | A003S | 0.89 | 1.01 | 1.02 | 1.03 | 1.03 | 1.23 | 1.31 | 0.92 | 0.66 |
| 3 | A003T | 0.82 | 1.44 | 1.13 | 1.18 | 0.70 | 0.98 | 0.94 | 0.82 | 0.94 |
| 3 | A003V | 0.81 | 0.86 | 1.25 | 0.82 | 0.92 | 0.77 | 0.97 | 0.82 | 0.69 |
| 3 | A003W | 0.85 | 0.52 | 1.19 | 0.55 | 0.98 | 0.96 | 0.72 | 0.92 | 0.42 |
| 3 | A003Y | 0.90 | 0.77 | 1.25 | 0.76 | 0.95 | 0.99 | 0.96 | 0.91 | 0.57 |
| 4 | P004A | 0.91 | 0.78 | 0.90 | 0.77 | 1.03 | 0.94 | 0.90 | 0.90 | 0.73 |
| 4 | P004C | 0.77 | 0.41 | 1.01 | 0.39 | 1.13 | 1.28 | 0.90 | 1.18 | 0.23 |
| 4 | P004D | 0.94 | 0.82 | 0.97 | 0.85 | 0.92 | 0.92 | 1.09 | 1.02 | 0.74 |
| 4 | P004E | 0.99 | 0.81 | 1.01 | 0.87 | 0.91 | 1.13 | 0.90 | 0.89 | 0.79 |
| 4 | P004G | 1.04 | 0.69 | 1.02 | 0.74 | 1.00 | 0.89 | 0.83 | 0.97 | 0.65 |
| 4 | P004H | 0.96 | 0.92 | 0.91 | 0.84 | 0.99 | 0.94 | 0.89 | 0.89 | 0.84 |
| 4 | P004I | 0.77 | 0.65 | 0.90 | 0.61 | 0.95 | 1.61 | 0.89 | 0.83 | 0.50 |
| 4 | P004K | 0.99 | 0.90 | 0.91 | 0.93 | 1.01 | 1.28 | 1.21 | 0.89 | 0.89 |
| 4 | P004L | 0.79 | 0.54 | 0.97 | 0.55 | 0.96 | 0.85 | 0.90 | 0.88 | 0.46 |
| 4 | P004M | 0.86 | 0.61 | 1.04 | 0.60 | 0.97 | 0.71 | 0.99 | 0.92 | 0.51 |
| 4 | P004N | 0.82 | 0.69 | 1.03 | 0.70 | 0.86 | 0.68 | 0.83 | 0.85 | 0.65 |
| 4 | P004Q | 0.95 | 0.87 | 0.93 | 0.90 | 0.94 | 1.14 | 1.05 | 0.94 | 0.79 |
| 4 | P004R | 0.92 | 0.94 | 0.82 | 0.89 | 0.95 | 1.13 | 1.02 | 0.88 | 0.86 |
| 4 | P004S | 0.92 | 0.70 | 0.92 | 0.72 | 0.91 | 0.71 | 0.94 | 0.87 | 0.66 |
| 4 | P004V | 0.89 | 0.63 | 1.03 | 0.67 | 1.06 | 0.61 | 1.00 | 0.95 | 0.56 |
| 4 | P004Y | 0.93 | 0.58 | 0.97 | 0.66 | 1.01 | 0.86 | 0.73 | 0.99 | 0.52 |
| 5 | I005C | 1.16 | 0.77 | 0.85 | 0.84 | 0.84 | 0.78 | 0.68 | 0.81 | 0.85 |
| 5 | I005D | 1.22 | 0.98 | 0.74 | 1.13 | 0.96 | 0.97 | 0.83 | 0.98 | 1.12 |
| 5 | I005E | 1.13 | 1.20 | 0.79 | 1.22 | 0.86 | 0.95 | 0.91 | 0.87 | 1.46 |
| 5 | I005F | 1.13 | 0.76 | 1.00 | 0.85 | 0.90 | 0.97 | 0.90 | 0.96 | 0.90 |
| 5 | I005G | 1.23 | 0.90 | 0.95 | 0.99 | 0.93 | 0.97 | 0.74 | 0.93 | 1.02 |
| 5 | I005H | 1.24 | 1.09 | 1.03 | 1.23 | 0.95 | 0.93 | 0.93 | 1.00 | 1.28 |
| 5 | I005K | 1.20 | 1.00 | 1.06 | 1.14 | 0.97 | 0.96 | 0.88 | 0.89 | 1.13 |
| 5 | I005L | 1.28 | 0.78 | 0.92 | 0.89 | 0.89 | 0.81 | 0.76 | 0.96 | 0.96 |
| 5 | I005M | 1.16 | 1.03 | 1.05 | 1.09 | 0.88 | 0.84 | 0.84 | 0.95 | 1.11 |
| 5 | I005N | 1.19 | 1.18 | 0.94 | 1.25 | 0.86 | 1.09 | 1.01 | 1.01 | 1.23 |
| 5 | I005R | 1.08 | 0.99 | 1.05 | 1.17 | 1.04 | 0.97 | 0.81 | 1.03 | 1.11 |
| 5 | I005S | 1.09 | 1.09 | 0.81 | 1.16 | 0.88 | 0.76 | 1.02 | 0.96 | 1.17 |
| 5 | I005T | 1.18 | 1.10 | 0.91 | 1.24 | 0.98 | 0.94 | 0.83 | 0.95 | 1.28 |
| 5 | I005V | 1.12 | 1.07 | 1.01 | 1.10 | 1.01 | 0.72 | 0.80 | 0.94 | 1.16 |
| 5 | I005W | 1.27 | 0.57 | 1.00 | 0.67 | 0.72 | 0.89 | 0.77 | 0.91 | 0.73 |
| 5 | I005Y | 1.10 | 0.90 | 1.01 | 1.02 | 0.93 | 0.86 | 0.88 | 0.97 | 1.01 |
| 7 | E007A | 0.87 | 0.92 | 1.37 | 0.85 | 0.89 | 1.17 | 0.61 | 0.87 | 1.17 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 7 | E007C | 0.78 | 0.58 | 1.29 | 0.49 | 0.98 | 0.93 | 0.50 | 0.82 | 0.53 |
| 7 | E007D | 0.86 | 0.90 | 0.96 | 0.83 | 1.03 | 1.05 | 0.77 | 1.00 | 1.02 |
| 7 | E007F | 0.92 | 0.68 | 0.96 | 0.63 | 0.69 | 1.28 | 0.55 | 0.82 | 0.78 |
| 7 | E007G | 0.97 | 0.99 | 0.92 | 0.92 | 0.38 | 0.67 | 0.77 | 0.72 | 1.07 |
| 7 | E007H | 0.99 | 0.98 | 1.07 | 1.03 | 0.87 | 1.60 | 0.98 | 0.88 | 1.33 |
| 7 | E007I | 0.83 | 0.79 | 1.02 | 0.71 | 0.98 | 1.14 | 0.83 | 1.06 | 0.93 |
| 7 | E007K | 1.00 | 1.14 | 1.10 | 1.19 | 1.01 | 1.21 | 0.99 | 1.02 | 1.52 |
| 7 | E007L | 1.01 | 0.66 | 0.99 | 0.69 | 0.81 | 1.06 | 0.59 | 0.75 | 0.97 |
| 7 | E007M | 0.90 | 0.81 | 1.41 | 0.77 | 0.87 | 1.04 | 0.74 | 0.83 | 1.02 |
| 7 | E007N | 0.92 | 0.96 | 1.14 | 0.94 | 0.92 | 1.18 | 0.93 | 0.89 | 1.18 |
| 7 | E007P | 1.03 | 0.95 | 1.51 | 1.00 | 1.00 | 1.07 | 0.80 | 1.01 | 1.19 |
| 7 | E007Q | 1.00 | 0.98 | 1.35 | 0.99 | 1.07 | 1.10 | 1.11 | 0.98 | 1.24 |
| 7 | E007R | 0.76 | 1.08 | 1.38 | 1.00 | 1.19 | 1.00 | 1.11 | 1.00 | 1.30 |
| 7 | E007S | 0.83 | 1.01 | 1.14 | 0.89 | 0.79 | 1.06 | 0.82 | 0.90 | 1.09 |
| 7 | E007T | 0.99 | 0.90 | 0.90 | 0.95 | 0.97 | 1.12 | 0.93 | 0.99 | 1.25 |
| 7 | E007V | 0.85 | 0.79 | 0.97 | 0.70 | 0.92 | 1.03 | 0.96 | 0.72 | 0.96 |
| 7 | E007W | 0.96 | 0.52 | 0.97 | 0.51 | 0.57 | 1.25 | 0.64 | 0.79 | 0.57 |
| 7 | E007Y | 0.96 | 0.88 | 0.97 | 0.88 | 0.76 | 1.21 | 0.84 | 0.82 | 1.08 |
| 15 | W015A | 0.60 | 0.41 | 1.80 | 0.24 | 0.40 | 0.19 | 0.44 | 0.80 | 1.16 |
| 15 | W015C | 0.93 | 0.13 | 0.98 | 0.11 | 0.29 | 0.21 | 0.51 | 0.61 | 0.78 |
| 15 | W015F | 0.89 | 1.06 | 0.74 | 0.83 | 0.57 | 0.50 | 0.90 | 1.01 | 0.86 |
| 15 | W015G | 1.70 | 0.31 | 0.98 | 0.28 | 0.38 | 0.06 | 0.66 | 0.78 | 0.99 |
| 15 | W015N | 0.61 | 0.18 | 0.71 | 0.08 | 0.12 | 0.09 | 0.51 | 0.63 | 1.06 |
| 15 | W015P | 0.95 | 0.21 | 0.54 | 0.18 | 0.32 | 0.10 | 0.71 | 0.79 | 1.09 |
| 15 | W015S | 0.81 | 0.43 | 1.12 | 0.35 | 0.35 | 0.08 | 0.46 | 1.07 | 0.99 |
| 15 | W015Y | 0.92 | 0.87 | 0.86 | 0.79 | 0.75 | 0.35 | 0.90 | 1.11 | 1.01 |
| 16 | D016A | 0.84 | 0.19 | 0.56 | 0.23 | 0.71 | 0.67 | 0.74 | 0.60 | 0.46 |
| 16 | D016C | 0.87 | 0.19 | 1.03 | 0.19 | 0.89 | 0.18 | 0.56 | 0.95 | 0.30 |
| 16 | D016E | 1.12 | 0.87 | 0.93 | 0.91 | 0.92 | 0.61 | 0.95 | 0.90 | 0.82 |
| 16 | D016F | 0.92 | 0.09 | 1.26 | 0.10 | 0.87 | 0.53 | 1.24 | 1.02 | 0.18 |
| 16 | D016G | 0.94 | 0.37 | 0.51 | 0.47 | 0.70 | 0.81 | 0.88 | 0.68 | 0.69 |
| 16 | D016H | 0.82 | 0.38 | 1.03 | 0.42 | 0.47 | 0.86 | 0.61 | 0.62 | 0.63 |
| 16 | D016I | 0.88 | 0.06 | 0.43 | 0.06 | 0.75 | 0.23 | 0.93 | 0.91 | 0.22 |
| 16 | D016K | 0.87 | 0.17 | 0.52 | 0.19 | 0.70 | 0.49 | 0.57 | 0.62 | 0.71 |
| 16 | D016L | 1.27 | 0.11 | 0.53 | 0.12 | 0.80 | 1.12 | 1.06 | 1.17 | 0.15 |
| 16 | D016M | 0.97 | 0.12 | 0.66 | 0.13 | 0.78 | 0.60 | 1.08 | 0.95 | 0.26 |
| 16 | D016N | 1.12 | 0.29 | 0.82 | 0.34 | 0.81 | 1.29 | 0.84 | 0.80 | 0.29 |
| 16 | D016P | 0.98 | 0.07 | 0.23 | 0.08 | 0.58 | 0.22 | 0.34 | 0.86 | 0.14 |
| 16 | D016Q | 0.84 | 0.26 | 0.45 | 0.30 | 0.75 | 1.01 | 0.72 | 0.69 | 0.56 |
| 16 | D016R | 0.87 | 0.13 | 0.29 | 0.15 | 0.60 | 0.50 | 0.44 | 0.45 | 0.69 |
| 16 | D016T | 0.94 | 0.23 | 0.71 | 0.25 | 0.74 | 0.55 | 1.25 | 0.73 | 0.52 |
| 16 | D016V | 0.84 | 0.06 | 0.56 | 0.06 | 0.67 | 0.15 | 0.80 | 0.96 | 0.27 |
| 16 | D016W | 1.01 | 0.21 | 1.25 | 0.27 | 0.64 | 0.72 | 0.74 | 0.98 | 0.32 |
| 16 | D016Y | 0.89 | 0.48 | 1.29 | 0.51 | 0.73 | 1.16 | 0.61 | 0.87 | 0.46 |
| 17 | L017A | 0.85 | 0.83 | 0.51 | 0.80 | 1.06 | 1.04 | 1.04 | 1.09 | 1.00 |
| 17 | L017C | 0.98 | 0.80 | 0.59 | 0.83 | 1.08 | 0.67 | 0.99 | 0.94 | 0.83 |
| 17 | L017D | 0.98 | 1.14 | 0.38 | 1.08 | 1.01 | 0.72 | 1.00 | 1.01 | 0.92 |
| 17 | L017E | 0.97 | 1.23 | 0.52 | 1.16 | 0.98 | 0.76 | 0.94 | 1.02 | 0.98 |
| 17 | L017F | 1.04 | 0.98 | 0.65 | 0.94 | 0.90 | 0.68 | 0.93 | 0.94 | 0.89 |
| 17 | L017G | 1.02 | 0.73 | 0.46 | 0.76 | 1.00 | 0.76 | 0.88 | 0.92 | 0.89 |
| 17 | L017H | 1.09 | 0.72 | 0.53 | 0.76 | 0.91 | 0.91 | 1.03 | 1.02 | 0.82 |
| 17 | L017I | 0.86 | 1.04 | 0.62 | 1.04 | 0.95 | 0.99 | 0.92 | 1.00 | 0.91 |
| 17 | L017K | 0.96 | 0.95 | 0.46 | 1.00 | 0.94 | 1.00 | 0.92 | 1.00 | 0.89 |
| 17 | L017M | 0.88 | 0.61 | 0.96 | 0.63 | 0.78 | 0.75 | 0.86 | 1.02 | 0.86 |
| 17 | L017N | 1.14 | 1.07 | 0.46 | 1.10 | 0.92 | 0.80 | 1.03 | 1.04 | 1.10 |
| 17 | L017P | 1.00 | 0.49 | 0.21 | 0.53 | 0.85 | 0.23 | 0.82 | 0.98 | 0.49 |
| 17 | L017Q | 0.80 | 0.85 | 0.49 | 0.78 | 1.03 | 0.86 | 1.19 | 1.09 | 1.06 |
| 17 | L017R | 0.75 | 0.72 | 0.37 | 0.71 | 1.04 | 1.18 | 1.09 | 1.03 | 0.99 |
| 17 | L017S | 0.92 | 0.77 | 0.53 | 0.80 | 0.92 | 0.79 | 0.91 | 0.96 | 0.97 |
| 17 | L017T | 1.04 | 0.94 | 0.54 | 0.99 | 0.95 | 0.86 | 1.04 | 0.91 | 0.88 |
| 17 | L017V | 1.02 | 1.03 | 0.59 | 1.06 | 0.98 | 0.91 | 0.88 | 1.06 | 0.97 |
| 17 | L017W | 1.07 | 0.44 | 0.40 | 0.51 | 0.85 | 0.34 | 0.85 | 0.93 | 0.55 |
| 17 | L017Y | 1.13 | 1.11 | 0.77 | 1.13 | 0.89 | 0.91 | 0.93 | 1.01 | 0.94 |
| 18 | P018A | 0.66 | 0.82 | 0.57 | 0.71 | 0.96 | 0.85 | 1.04 | 1.02 | 0.91 |
| 18 | P018C | 0.91 | 0.39 | 0.72 | 0.38 | 1.13 | 0.59 | 0.59 | 1.01 | 0.36 |
| 18 | P018D | 0.96 | 1.05 | 0.70 | 0.95 | 1.02 | 0.81 | 1.04 | 1.00 | 0.98 |
| 18 | P018E | 0.96 | 1.11 | 0.73 | 1.02 | 0.91 | 0.76 | 0.91 | 0.98 | 1.12 |
| 18 | P018F | 0.73 | 0.49 | 0.59 | 0.45 | 1.01 | 0.87 | 0.30 | 0.99 | 0.64 |
| 18 | P018G | 0.91 | 0.79 | 0.57 | 0.74 | 1.00 | 0.94 | 0.86 | 1.01 | 0.99 |
| 18 | P018H | 0.95 | 0.74 | 0.43 | 0.74 | 0.94 | 0.91 | 0.84 | 1.04 | 1.02 |
| 18 | P018I | 0.75 | 0.57 | 0.55 | 0.56 | 0.87 | 0.92 | 0.92 | 1.00 | 0.77 |
| 18 | P018K | 0.82 | 0.90 | 0.50 | 0.85 | 0.89 | 1.01 | 0.84 | 1.00 | 1.06 |
| 18 | P018L | 0.77 | 0.64 | 0.53 | 0.60 | 0.98 | 0.85 | 0.68 | 0.88 | 0.72 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 18 | P018M | 0.86 | 0.62 | 0.60 | 0.64 | 0.89 | 0.84 | 0.71 | 0.98 | 0.77 |
| 18 | P018N | 1.02 | 0.90 | 0.59 | 0.92 | 0.99 | 1.02 | 0.91 | 1.03 | 1.02 |
| 18 | P018Q | 0.82 | 1.07 | 0.56 | 0.93 | 1.01 | 0.99 | 1.10 | 1.01 | 1.04 |
| 18 | P018R | 0.76 | 1.01 | 0.40 | 0.90 | 1.10 | 1.31 | 0.86 | 0.90 | 1.01 |
| 18 | P018S | 0.86 | 0.79 | 0.54 | 0.75 | 1.09 | 0.94 | 0.91 | 1.09 | 0.89 |
| 18 | P018T | 0.86 | 1.14 | 0.56 | 0.97 | 1.08 | 1.07 | 1.08 | 1.12 | 1.20 |
| 18 | P018V | 0.78 | 0.69 | 0.64 | 0.62 | 0.89 | 0.82 | 0.61 | 0.97 | 0.87 |
| 18 | P018Y | 0.80 | 0.62 | 0.58 | 0.60 | 0.93 | 0.89 | 0.66 | 0.91 | 0.83 |
| 19 | N019A | 0.81 | 0.63 | 0.55 | 0.69 | 0.97 | 1.01 | 0.76 | 1.00 | 0.91 |
| 19 | N019C | 0.94 | 0.34 | 0.46 | 0.38 | 0.89 | 0.54 | 1.12 | 0.84 | 0.48 |
| 19 | N019D | 0.87 | 0.75 | 0.61 | 0.79 | 0.91 | 0.66 | 0.99 | 0.95 | 0.91 |
| 19 | N019E | 0.95 | 0.70 | 0.48 | 0.69 | 0.91 | 0.86 | 0.78 | 0.91 | 0.93 |
| 19 | N019F | 0.93 | 0.37 | 0.45 | 0.43 | 0.82 | 0.61 | 0.92 | 0.96 | 0.52 |
| 19 | N019G | 0.93 | 0.48 | 0.42 | 0.57 | 0.97 | 0.88 | 1.10 | 1.00 | 0.73 |
| 19 | N019H | 0.91 | 0.56 | 0.44 | 0.65 | 0.99 | 0.87 | 0.98 | 0.99 | 0.90 |
| 19 | N019I | 0.80 | 0.33 | 0.43 | 0.40 | 0.94 | 0.91 | 0.94 | 0.89 | 0.57 |
| 19 | N019K | 0.95 | 0.53 | 0.35 | 0.66 | 0.87 | 0.96 | 0.96 | 0.98 | 0.93 |
| 19 | N019L | 0.79 | 0.31 | 0.34 | 0.35 | 0.90 | 0.79 | 1.04 | 0.87 | 0.52 |
| 19 | N019M | 0.91 | 0.39 | 0.43 | 0.48 | 0.85 | 0.90 | 0.86 | 0.91 | 0.63 |
| 19 | N019P | 0.91 | 0.53 | 0.60 | 0.64 | 0.99 | 0.97 | 1.00 | 0.94 | 0.76 |
| 19 | N019R | 0.95 | 0.48 | 0.29 | 0.62 | 0.89 | 1.23 | 0.76 | 0.95 | 0.91 |
| 19 | N019S | 0.82 | 0.64 | 0.62 | 0.66 | 0.69 | 0.98 | 0.93 | 0.96 | 0.89 |
| 19 | N019T | 1.04 | 0.52 | 0.50 | 0.62 | 0.91 | 1.03 | 0.99 | 0.90 | 0.86 |
| 19 | N019V | 1.00 | 0.40 | 0.54 | 0.49 | 1.03 | 0.87 | 0.51 | 0.92 | 0.66 |
| 19 | N019W | 0.89 | 0.30 | 0.46 | 0.36 | 0.89 | 0.81 | 0.71 | 0.83 | 0.50 |
| 19 | N019Y | 0.96 | 0.46 | 0.46 | 0.57 | 0.93 | 0.87 | 0.91 | 0.95 | 0.72 |
| 22 | T022A | 0.84 | 1.00 | 0.74 | 0.96 | 0.97 | 0.87 | 0.95 | 0.76 | 1.44 |
| 22 | T022C | 0.97 | 0.68 | 1.03 | 0.71 | 0.85 | 0.78 | 0.90 | 0.93 | 0.90 |
| 22 | T022D | 0.97 | 1.04 | 0.72 | 0.98 | 0.93 | 0.83 | 1.08 | 1.00 | 1.51 |
| 22 | T022E | 1.08 | 1.02 | 0.88 | 1.08 | 0.90 | 0.73 | 1.00 | 0.98 | 1.58 |
| 22 | T022F | 0.98 | 0.75 | 0.79 | 0.80 | 0.96 | 0.78 | 0.91 | 0.93 | 1.20 |
| 22 | T022G | 1.15 | 0.85 | 0.81 | 0.96 | 1.01 | 0.91 | 0.93 | 0.96 | 1.37 |
| 22 | T022H | 1.13 | 0.97 | 0.68 | 1.06 | 0.90 | 1.05 | 0.99 | 1.02 | 1.58 |
| 22 | T022I | 0.95 | 0.75 | 0.60 | 0.85 | 0.90 | 0.91 | 0.95 | 0.94 | 1.28 |
| 22 | T022K | 1.05 | 1.08 | 0.74 | 1.06 | 1.08 | 1.01 | 1.17 | 1.02 | 1.60 |
| 22 | T022L | 0.81 | 0.86 | 0.84 | 0.80 | 0.98 | 0.75 | 0.93 | 0.89 | 1.18 |
| 22 | T022N | 1.03 | 1.03 | 0.87 | 1.02 | 0.96 | 1.03 | 0.96 | 0.95 | 1.51 |
| 22 | T022P | 0.91 | 0.51 | 0.35 | 0.56 | 0.99 | 0.92 | 1.06 | 0.99 | 1.39 |
| 22 | T022Q | 1.08 | 0.97 | 0.87 | 1.05 | 0.95 | 1.05 | 0.92 | 0.99 | 1.55 |
| 22 | T022R | 0.91 | 1.11 | 0.61 | 1.03 | 1.08 | 1.26 | 1.26 | 1.09 | 1.34 |
| 22 | T022S | 1.03 | 0.95 | 0.91 | 1.04 | 0.90 | 0.87 | 0.85 | 1.02 | 1.40 |
| 22 | T022V | 1.00 | 0.78 | 0.66 | 0.88 | 2.67 | 6.35 | 3.80 | 3.67 | 0.99 |
| 22 | T022Y | 0.96 | 0.74 | 0.78 | 0.81 | 0.96 | 0.95 | 0.93 | 0.94 | 1.13 |
| 25 | T025A | 0.90 | 0.96 | 0.65 | 0.97 | 0.85 | 0.94 | 0.99 | 0.81 | 1.35 |
| 25 | T025C | 1.09 | 0.73 | 1.26 | 0.77 | 0.74 | 0.69 | 0.83 | 1.67 | 0.88 |
| 25 | T025D | 1.10 | 0.88 | 1.05 | 1.01 | 0.78 | 0.77 | 0.92 | 0.41 | 1.22 |
| 25 | T025E | 0.91 | 0.88 | 1.22 | 0.94 | 0.77 | 0.74 | 0.82 | 1.26 | 1.18 |
| 25 | T025F | 0.95 | 0.82 | 0.67 | 0.80 | 0.81 | 1.10 | 0.87 | 0.93 | 0.90 |
| 25 | T025H | 1.10 | 1.07 | 0.62 | 1.07 | 0.89 | 0.98 | 1.03 | 1.07 | 1.37 |
| 25 | T025I | 0.67 | 0.61 | 0.89 | 0.60 | 0.80 | 0.81 | 0.72 | 1.14 | 0.76 |
| 25 | T025K | 1.17 | 1.06 | 0.58 | 1.05 | 0.78 | 0.93 | 0.96 | 0.97 | 1.31 |
| 25 | T025L | 0.87 | 0.91 | 0.90 | 0.83 | 0.87 | 1.05 | 0.91 | 1.63 | 0.98 |
| 25 | T025M | 0.89 | 0.79 | 0.89 | 0.76 | 0.88 | 0.89 | 0.89 | 1.43 | 0.94 |
| 25 | T025N | 1.12 | 1.06 | 0.83 | 1.03 | 1.03 | 1.05 | 1.03 | 0.80 | 1.18 |
| 25 | T025P | 1.15 | 1.15 | 0.52 | 1.23 | 0.89 | 1.00 | 1.08 | 0.69 | 1.43 |
| 25 | T025Q | 0.95 | 0.26 | 0.53 | 0.25 | 0.89 | 0.52 | 1.04 | 1.20 | 1.03 |
| 25 | T025S | 0.90 | 1.07 | 0.72 | 1.00 | 0.91 | 0.91 | 0.98 | 1.21 | 1.30 |
| 25 | T025V | 1.01 | 0.64 | 0.93 | 0.71 | 0.78 | 0.73 | 0.82 | 0.71 | 1.11 |
| 25 | T025W | 1.00 | 0.97 | 0.64 | 0.97 | 0.97 | 1.13 | 0.85 | 1.15 | 1.01 |
| 25 | T025Y | 0.93 | 0.65 | 0.72 | 0.60 | 0.82 | 0.81 | 0.76 | 1.05 | 0.67 |
| 26 | K026A | 0.80 | 0.95 | 0.67 | 0.95 | 0.97 | 0.76 | 0.90 | 0.91 | 0.82 |
| 26 | K026C | 0.96 | 0.44 | 0.63 | 0.52 | 0.78 | 0.39 | 0.88 | 0.79 | 0.46 |
| 26 | K026D | 0.71 | 0.49 | 0.56 | 0.43 | 0.82 | 0.65 | 0.74 | 0.58 | 0.43 |
| 26 | K026E | 1.04 | 1.19 | 0.67 | 1.24 | 0.94 | 0.65 | 0.90 | 0.87 | 1.09 |
| 26 | K026F | 0.86 | 0.60 | 0.67 | 0.64 | 0.95 | 0.63 | 1.34 | 0.88 | 0.54 |
| 26 | K026G | 1.06 | 1.17 | 0.59 | 1.30 | 1.02 | 0.75 | 1.03 | 1.00 | 1.06 |
| 26 | K026H | 1.00 | 0.93 | 0.59 | 1.07 | 0.91 | 0.66 | 0.86 | 0.91 | 0.93 |
| 26 | K026I | 0.81 | 0.63 | 0.69 | 0.69 | 0.97 | 0.55 | 0.94 | 0.89 | 0.60 |
| 26 | K026L | 0.90 | 0.66 | 0.70 | 0.73 | 0.93 | 0.55 | 0.83 | 0.84 | 0.59 |
| 26 | K026M | 0.78 | 0.68 | 0.96 | 0.73 | 1.07 | 0.61 | 1.01 | 0.88 | 0.60 |
| 26 | K026N | 0.96 | 1.26 | 0.66 | 1.29 | 1.07 | 0.81 | 0.97 | 0.96 | 1.03 |
| 26 | K026P | 1.07 | 0.32 | 0.37 | 0.33 | 0.95 | 0.10 | 0.56 | 0.82 | 0.27 |
| 26 | K026Q | 0.92 | 0.94 | 0.80 | 0.99 | 1.03 | 0.73 | 1.05 | 1.06 | 0.84 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 26 | K026R | 0.82 | 0.89 | 0.79 | 0.89 | 0.99 | 0.90 | 0.62 | 0.73 | 0.82 |
| 26 | K026S | 0.92 | 1.05 | 0.67 | 1.08 | 0.99 | 0.69 | 0.94 | 0.94 | 0.87 |
| 26 | K026T | 0.89 | 0.94 | 0.73 | 0.98 | 0.88 | 0.80 | 0.89 | 0.89 | 0.93 |
| 26 | K026V | 0.81 | 0.82 | 0.72 | 0.83 | 0.85 | 0.59 | 0.85 | 0.91 | 0.68 |
| 26 | K026W | 1.00 | 0.52 | 0.65 | 0.62 | 1.11 | 0.67 | 0.88 | 0.87 | 0.49 |
| 26 | K026Y | 0.91 | 0.74 | 0.65 | 0.82 | 0.92 | 0.66 | 0.86 | 0.85 | 0.66 |
| 28 | K028A | 0.96 | 0.89 | 1.08 | 0.87 | 0.98 | 0.79 | 1.22 | 1.00 | 0.81 |
| 28 | K028C | 0.87 | 0.52 | 0.87 | 0.50 | 0.93 | 0.69 | 0.84 | 0.93 | 0.43 |
| 28 | K028D | 1.03 | 1.28 | 0.67 | 1.26 | 1.02 | 0.79 | 1.60 | 1.03 | 1.03 |
| 28 | K028G | 1.15 | 1.20 | 0.88 | 1.18 | 1.09 | 0.93 | 1.07 | 1.09 | 0.98 |
| 28 | K028H | 1.04 | 1.18 | 0.73 | 1.15 | 1.07 | 0.76 | 1.22 | 0.88 | 1.05 |
| 28 | K028I | 0.79 | 0.59 | 0.97 | 0.57 | 1.10 | 0.98 | 0.90 | 1.11 | 0.54 |
| 28 | K028L | 0.93 | 0.55 | 0.80 | 0.57 | 0.97 | 0.79 | 0.99 | 1.05 | 0.53 |
| 28 | K028M | 1.01 | 0.63 | 1.15 | 0.68 | 0.73 | 0.77 | 0.91 | 1.04 | 0.68 |
| 28 | K028N | 1.09 | 1.22 | 0.74 | 1.24 | 1.16 | 0.95 | 1.57 | 1.13 | 0.95 |
| 28 | K028Q | 1.08 | 1.05 | 1.07 | 1.06 | 0.99 | 0.80 | 1.47 | 1.01 | 0.94 |
| 28 | K028R | 0.88 | 1.07 | 0.73 | 0.96 | 1.01 | 1.04 | 1.12 | 1.08 | 0.89 |
| 28 | K028S | 0.99 | 1.00 | 0.90 | 1.01 | 0.96 | 0.82 | 1.32 | 1.00 | 0.86 |
| 28 | K028T | 0.99 | 0.91 | 1.00 | 0.89 | 0.96 | 0.93 | 1.28 | 1.12 | 0.69 |
| 28 | K028V | 0.88 | 0.67 | 1.17 | 0.65 | 0.82 | 0.70 | 0.84 | 0.94 | 0.65 |
| 28 | K028W | 0.89 | 0.78 | 0.73 | 0.74 | 0.99 | 0.70 | 0.70 | 1.10 | 0.69 |
| 28 | K028Y | 0.92 | 0.86 | 0.82 | 0.86 | 1.01 | 0.77 | 1.16 | 1.08 | 0.77 |
| 29 | N029A | 1.26 | 0.67 | 0.73 | 0.92 | 0.82 | 0.83 | 0.85 | 0.74 | 0.88 |
| 29 | N029D | 0.86 | 0.79 | 0.96 | 1.06 | 0.80 | 0.80 | 0.97 | 0.89 | 0.97 |
| 29 | N029E | 1.21 | 0.97 | 1.15 | 0.97 | 0.83 | 0.67 | 0.83 | 0.85 | 0.85 |
| 29 | N029G | 1.08 | 1.31 | 0.74 | 1.15 | 0.91 | 0.94 | 0.94 | 1.02 | 1.01 |
| 29 | N029H | 0.63 | 0.47 | 0.81 | 0.75 | 0.66 | 0.62 | 0.67 | 0.70 | 0.91 |
| 29 | N029I | 1.20 | 0.54 | 0.69 | 0.74 | 0.94 | 0.84 | 0.90 | 0.90 | 0.57 |
| 29 | N029K | 2.74 | 0.45 | 0.64 | 0.71 | 0.67 | 0.68 | 0.63 | 0.66 | 0.93 |
| 29 | N029L | 1.03 | 0.68 | 0.78 | 0.69 | 0.67 | 0.59 | 0.94 | 0.81 | 0.63 |
| 29 | N029M | 1.09 | 0.72 | 0.98 | 0.72 | 0.83 | 0.86 | 0.88 | 0.79 | 0.62 |
| 29 | N029P | 1.52 | 1.09 | 0.54 | 1.16 | 0.93 | 0.88 | 0.89 | 0.92 | 1.12 |
| 29 | N029Q | 1.19 | 0.91 | 1.00 | 0.92 | 0.87 | 0.72 | 0.82 | 0.86 | 0.80 |
| 29 | N029R | 1.08 | 0.97 | 0.61 | 0.95 | 0.90 | 1.00 | 0.86 | 0.96 | 0.88 |
| 29 | N029S | 1.23 | 0.91 | 0.74 | 0.95 | 0.84 | 0.96 | 0.77 | 0.90 | 0.89 |
| 29 | N029T | 1.29 | 0.84 | 0.81 | 0.90 | 0.88 | 0.63 | 0.92 | 0.94 | 0.81 |
| 29 | N029V | 0.93 | 0.53 | 0.82 | 0.73 | 0.78 | 0.73 | 0.88 | 0.86 | 0.65 |
| 29 | N029W | 1.24 | 0.52 | 0.70 | 0.54 | 0.79 | 1.07 | 1.01 | 0.75 | 0.40 |
| 29 | N029Y | 1.98 | 0.56 | 0.85 | 0.82 | 0.77 | 0.97 | 0.75 | 0.94 | 0.68 |
| 30 | E030A | 0.79 | 0.46 | 0.68 | 0.49 | 0.91 | 0.56 | 0.89 | 0.95 | 0.37 |
| 30 | E030C | 0.92 | 0.30 | 0.91 | 0.35 | 0.85 | 0.35 | 1.12 | 1.03 | 0.25 |
| 30 | E030D | 0.93 | 1.14 | 0.85 | 1.07 | 0.93 | 1.06 | 1.29 | 0.98 | 0.71 |
| 30 | E030G | 1.21 | 0.88 | 0.69 | 0.98 | 0.87 | 0.95 | 1.00 | 0.98 | 0.74 |
| 30 | E030I | 0.84 | 0.33 | 0.54 | 0.35 | 0.87 | 0.57 | 0.73 | 0.89 | 0.25 |
| 30 | E030K | 1.00 | 1.11 | 0.60 | 1.15 | 1.02 | 1.20 | 1.50 | 1.04 | 0.74 |
| 30 | E030L | 0.85 | 0.31 | 0.66 | 0.33 | 0.79 | 0.78 | 1.36 | 0.81 | 0.27 |
| 30 | E030N | 1.10 | 1.09 | 0.88 | 1.08 | 0.89 | 1.11 | 1.14 | 0.99 | 0.86 |
| 30 | E030P | 1.31 | 1.08 | 0.60 | 1.06 | 0.86 | 1.04 | 1.20 | 0.89 | 0.89 |
| 30 | E030Q | 1.04 | 0.88 | 0.77 | 0.93 | 0.97 | 1.21 | 1.12 | 0.99 | 0.76 |
| 30 | E030R | 0.93 | 1.06 | 0.53 | 1.05 | 0.98 | 1.42 | 1.50 | 0.94 | 0.85 |
| 30 | E030S | 0.82 | 0.83 | 0.66 | 0.80 | 0.92 | 1.12 | 1.18 | 0.93 | 0.60 |
| 30 | E030T | 0.94 | 0.61 | 0.69 | 0.64 | 0.90 | 1.02 | 1.04 | 0.84 | 0.54 |
| 30 | E030V | 1.05 | 0.36 | 0.71 | 0.41 | 0.80 | 0.75 | 1.02 | 0.76 | 0.36 |
| 30 | E030W | 0.83 | 0.29 | 0.69 | 0.28 | 0.85 | 0.63 | 0.81 | 1.02 | 0.23 |
| 30 | E030Y | 1.02 | 0.32 | 0.75 | 0.35 | 0.92 | 0.29 | 0.75 | 0.90 | 0.26 |
| 32 | A032E | 1.12 | 0.99 | 1.13 | 0.98 | 0.78 | 0.94 | 0.71 | 0.96 | 1.14 |
| 32 | A032F | 0.88 | 0.83 | 1.10 | 0.74 | 0.80 | 0.97 | 0.82 | 1.00 | 0.90 |
| 32 | A032G | 1.03 | 1.09 | 1.06 | 1.05 | 0.86 | 1.16 | 0.77 | 0.99 | 1.27 |
| 32 | A032H | 1.03 | 0.81 | 1.06 | 0.78 | 0.76 | 1.00 | 0.80 | 1.02 | 0.95 |
| 32 | A032K | 0.88 | 1.02 | 1.13 | 0.92 | 1.01 | 1.11 | 0.80 | 1.06 | 1.13 |
| 32 | A032L | 0.90 | 0.76 | 0.97 | 0.73 | 0.92 | 1.00 | 0.88 | 0.80 | 0.83 |
| 32 | A032M | 0.89 | 0.82 | 1.14 | 0.75 | 0.87 | 1.16 | 0.69 | 0.98 | 0.83 |
| 32 | A032N | 0.97 | 1.14 | 1.08 | 1.02 | 0.96 | 1.17 | 0.97 | 1.05 | 1.25 |
| 32 | A032P | 1.12 | 1.12 | 1.18 | 1.12 | 0.96 | 1.19 | 0.87 | 1.03 | 1.42 |
| 32 | A032Q | 0.92 | 0.71 | 1.16 | 0.69 | 0.98 | 1.13 | 0.92 | 1.00 | 0.72 |
| 32 | A032R | 0.90 | 0.89 | 1.02 | 0.88 | 0.93 | 1.38 | 0.85 | 0.98 | 1.01 |
| 32 | A032S | 0.92 | 0.95 | 1.02 | 0.95 | 0.84 | 1.10 | 0.81 | 0.99 | 1.08 |
| 32 | A032T | 0.92 | 0.83 | 0.94 | 0.75 | 0.95 | 1.05 | 0.90 | 0.98 | 0.84 |
| 32 | A032V | 1.09 | 0.77 | 1.09 | 0.81 | 0.84 | 1.02 | 0.95 | 0.87 | 0.88 |
| 32 | A032W | 0.96 | 0.77 | 1.07 | 0.74 | 0.98 | 1.15 | 0.82 | 0.95 | 0.74 |
| 32 | A032Y | 1.03 | 0.79 | 1.07 | 0.77 | 0.89 | 1.09 | 0.87 | 1.01 | 0.87 |
| 35 | S035A | 0.74 | 0.61 | 2.26 | 0.58 | 0.96 | 0.97 | 1.09 | 0.80 | 0.50 |
| 35 | S035C | 0.74 | 0.39 | 0.79 | 0.38 | 0.81 | 0.57 | 1.09 | 0.66 | 0.33 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 35 | S035D | 1.02 | 1.38 | 0.64 | 1.29 | 1.15 | 1.06 | 1.14 | 0.74 | 1.11 |
| 35 | S035E | 0.99 | 1.09 | 0.70 | 1.01 | 0.88 | 0.89 | 1.18 | 0.76 | 1.12 |
| 35 | S035F | 0.66 | 0.33 | 0.93 | 0.44 | 0.74 | 0.79 | 0.83 | 0.77 | 0.44 |
| 35 | S035G | 0.99 | 0.89 | 0.76 | 0.91 | 0.98 | 0.89 | 1.01 | 0.84 | 0.79 |
| 35 | S035H | 1.01 | 0.89 | 0.84 | 0.90 | 1.01 | 0.90 | 1.05 | 0.85 | 0.81 |
| 35 | S035K | 0.92 | 0.90 | 0.93 | 0.90 | 0.96 | 0.84 | 1.11 | 0.78 | 0.96 |
| 35 | S035L | 0.80 | 0.37 | 0.65 | 0.36 | 0.73 | 0.63 | 0.96 | 0.80 | 0.36 |
| 35 | S035N | 1.01 | 1.07 | 0.80 | 1.00 | 0.88 | 0.99 | 0.71 | 0.71 | 0.99 |
| 35 | S035P | 0.82 | 1.10 | 0.08 | 1.75 | 0.90 | 0.77 | 0.84 | 0.75 | 1.01 |
| 35 | S035Q | 1.16 | 0.85 | 0.73 | 0.98 | 0.98 | 0.95 | 1.00 | 0.82 | 0.87 |
| 35 | S035R | 0.86 | 0.86 | 1.11 | 0.82 | 0.95 | 1.06 | 1.04 | 0.87 | 0.80 |
| 35 | S035T | 0.84 | 0.66 | 0.81 | 0.65 | 1.00 | 0.79 | 1.16 | 0.75 | 0.74 |
| 35 | S035V | 0.86 | 0.39 | 0.98 | 0.39 | 0.88 | 0.62 | 0.81 | 0.74 | 0.38 |
| 35 | S035W | 0.82 | 0.48 | 0.84 | 0.46 | 0.95 | 0.75 | 1.00 | 0.71 | 0.47 |
| 35 | S035Y | 0.83 | 0.61 | 0.94 | 0.59 | 0.80 | 0.69 | 0.98 | 0.80 | 0.64 |
| 36 | S036C | 1.00 | 0.60 | 0.76 | 0.58 | 0.82 | 0.88 | 0.67 | 0.78 | 0.61 |
| 36 | S036D | 1.18 | 1.16 | 0.78 | 1.17 | 1.04 | 1.05 | 1.05 | 0.94 | 1.27 |
| 36 | S036E | 1.03 | 1.26 | 0.96 | 1.16 | 0.98 | 0.95 | 0.83 | 0.97 | 1.43 |
| 36 | S036F | 1.01 | 0.61 | 0.86 | 0.60 | 0.87 | 0.73 | 0.66 | 0.92 | 0.68 |
| 36 | S036G | 1.05 | 0.68 | 0.89 | 0.70 | 0.93 | 0.94 | 0.94 | 0.92 | 0.73 |
| 36 | S036I | 0.86 | 0.58 | 0.89 | 0.57 | 1.00 | 0.86 | 0.62 | 0.79 | 0.64 |
| 36 | S036K | 1.11 | 0.99 | 0.95 | 0.98 | 0.97 | 1.10 | 0.81 | 0.94 | 1.09 |
| 36 | S036L | 1.01 | 0.81 | 0.95 | 0.79 | 0.99 | 1.18 | 1.05 | 0.90 | 0.74 |
| 36 | S036M | 1.02 | 0.69 | 0.96 | 0.72 | 1.00 | 0.98 | 0.90 | 0.96 | 0.78 |
| 36 | S036N | 1.16 | 1.10 | 0.91 | 1.07 | 0.99 | 1.03 | 0.74 | 1.01 | 1.18 |
| 36 | S036P | 1.40 | 1.15 | 0.83 | 1.20 | 1.01 | 0.98 | 0.80 | 0.97 | 1.29 |
| 36 | S036Q | 1.06 | 1.07 | 1.01 | 1.06 | 1.08 | 0.95 | 0.84 | 0.95 | 1.13 |
| 36 | S036R | 0.86 | 0.45 | 0.93 | 0.39 | 1.02 | 1.04 | 0.55 | 0.95 | 0.42 |
| 36 | S036T | 1.04 | 1.11 | 0.84 | 1.04 | 1.10 | 1.02 | 0.71 | 0.98 | 1.09 |
| 36 | S036V | 1.08 | 0.86 | 0.90 | 0.78 | 1.03 | 0.85 | 0.56 | 0.89 | 0.84 |
| 36 | S036W | 0.92 | 0.49 | 0.85 | 0.47 | 0.88 | 0.87 | 0.56 | 0.73 | 0.53 |
| 36 | S036Y | 1.08 | 0.75 | 0.90 | 0.76 | 0.99 | 0.96 | 0.60 | 0.95 | 0.81 |
| 37 | L037C | 1.19 | 0.35 | 0.78 | 0.40 | 0.99 | 1.36 | 1.12 | 1.53 | 0.21 |
| 37 | L037D | 1.30 | 0.64 | 0.74 | 0.69 | 0.86 | 1.06 | 1.33 | 1.07 | 0.45 |
| 37 | L037E | 1.23 | 0.84 | 0.74 | 0.82 | 0.82 | 0.86 | 0.95 | 1.19 | 0.60 |
| 37 | L037F | 1.24 | 1.01 | 0.80 | 1.02 | 0.81 | 1.37 | 1.18 | 1.10 | 0.80 |
| 37 | L037G | 1.44 | 0.69 | 0.76 | 0.78 | 0.89 | 1.08 | 1.10 | 1.17 | 0.57 |
| 37 | L037H | 1.14 | 1.32 | 0.70 | 1.17 | 0.96 | 0.93 | 1.05 | 0.88 | 1.09 |
| 37 | L037I | 1.10 | 1.03 | 0.92 | 1.03 | 0.88 | 1.07 | 1.06 | 0.96 | 0.92 |
| 37 | L037K | 0.91 | 0.80 | 0.75 | 0.66 | 0.92 | 1.32 | 0.97 | 1.15 | 0.49 |
| 37 | L037M | 1.15 | 1.01 | 1.04 | 0.97 | 0.87 | 0.92 | 1.21 | 1.00 | 0.89 |
| 37 | L037N | 1.39 | 1.18 | 0.75 | 1.14 | 0.72 | 1.01 | 1.04 | 1.04 | 0.96 |
| 37 | L037P | 1.29 | 0.32 | 0.66 | 0.30 | 1.46 | 2.41 | 1.34 | 2.39 | 0.11 |
| 37 | L037Q | 1.35 | 1.19 | 0.76 | 1.20 | 0.83 | 1.01 | 1.11 | 1.10 | 0.97 |
| 37 | L037R | 1.00 | 1.28 | 0.71 | 1.20 | 0.90 | 1.21 | 0.87 | 1.10 | 1.05 |
| 37 | L037S | 1.22 | 1.03 | 0.79 | 1.10 | 0.88 | 1.05 | 1.12 | 0.90 | 0.94 |
| 37 | L037T | 1.11 | 1.12 | 0.82 | 1.06 | 0.93 | 1.06 | 1.09 | 1.00 | 0.88 |
| 37 | L037V | 1.21 | 1.06 | 0.92 | 1.07 | 0.91 | 1.10 | 0.97 | 1.04 | 0.88 |
| 37 | L037W | 1.35 | 0.80 | 0.92 | 0.86 | 0.88 | 1.02 | 1.02 | 1.63 | 0.65 |
| 37 | L037Y | 1.22 | 1.03 | 0.82 | 1.06 | 0.91 | 1.08 | 1.24 | 1.01 | 0.88 |
| 50 | G050A | 0.99 | 1.50 | 0.95 | 1.28 | 1.16 | 0.94 | 0.98 | 0.89 | 1.12 |
| 50 | G050C | 1.04 | 1.03 | 0.57 | 0.96 | 0.84 | 0.54 | 0.76 | 0.78 | 0.75 |
| 50 | G050E | 0.64 | 0.25 | 0.07 | 0.23 | 0.07 | 0.11 | 0.47 | 0.77 | 0.34 |
| 50 | G050L | 0.33 | 0.15 | 0.09 | 0.15 | 0.28 | 0.09 | 0.80 | 0.89 | 0.63 |
| 50 | G050M | 0.54 | 1.19 | 0.07 | 0.98 | 0.47 | 0.22 | 0.77 | 0.90 | 0.92 |
| 50 | G050N | 0.79 | 0.14 | 0.25 | 0.14 | 0.36 | 0.43 | 0.80 | 0.83 | 1.10 |
| 50 | G050P | 1.06 | 0.94 | 0.44 | 0.81 | 0.99 | 0.61 | 0.85 | 0.91 | 1.01 |
| 50 | G050Q | 0.56 | 0.64 | 0.11 | 0.59 | 0.56 | 0.34 | 0.76 | 0.88 | 0.86 |
| 50 | G050S | 0.97 | 1.74 | 0.45 | 1.51 | 1.03 | 0.99 | 1.09 | 0.95 | 1.12 |
| 50 | G050T | 0.88 | 0.76 | 0.21 | 0.67 | 0.94 | 0.49 | 0.51 | 0.89 | 0.92 |
| 50 | G050V | 0.64 | 0.60 | 0.06 | 0.55 | 0.63 | 0.28 | 0.77 | 0.81 | 0.65 |
| 51 | T051A | 0.62 | 0.83 | 1.00 | 0.81 | 0.84 | 0.54 | 0.71 | 0.97 | 1.00 |
| 51 | T051C | 1.20 | 0.38 | 1.60 | 0.32 | 0.36 | 0.09 | 0.63 | 0.78 | 0.40 |
| 51 | T051D | 0.78 | 0.37 | 0.29 | 0.29 | 0.68 | 0.37 | 0.85 | 0.95 | 0.61 |
| 51 | T051E | 1.15 | 0.60 | 0.67 | 0.55 | 0.61 | 0.22 | 0.85 | 1.05 | 0.95 |
| 51 | T051G | 0.69 | 0.29 | 0.31 | 0.31 | 0.85 | 0.54 | 0.79 | 0.97 | 0.62 |
| 51 | T051H | 0.75 | 0.11 | 0.69 | 0.13 | 0.75 | 0.43 | 0.69 | 0.79 | 1.04 |
| 51 | T051K | 0.89 | 0.35 | 1.37 | 0.38 | 0.70 | 0.53 | 0.56 | 0.70 | 0.66 |
| 51 | T051M | 1.30 | 0.81 | 1.88 | 0.75 | 0.79 | 0.77 | 0.89 | 0.86 | 0.88 |
| 51 | T051N | 0.84 | 0.44 | 0.40 | 0.43 | 0.90 | 0.68 | 0.83 | 0.97 | 1.00 |
| 51 | T051Q | 2.19 | 0.26 | 1.75 | 0.27 | 0.85 | 0.54 | 0.84 | 0.86 | 0.96 |
| 51 | T051R | 0.79 | 0.29 | 1.18 | 0.28 | 0.90 | 0.70 | 0.63 | 0.85 | 1.00 |
| 51 | T051S | 0.70 | 0.71 | 0.67 | 0.72 | 0.86 | 0.58 | 0.69 | 0.83 | 0.93 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 51 | T051V | 0.96 | 0.60 | 1.17 | 0.69 | 0.86 | 0.55 | 0.82 | 0.90 | 0.88 |
| 51 | T051W | 0.58 | 0.08 | 0.70 | 0.07 | 0.48 | 0.78 | 0.58 | 0.49 | 0.70 |
| 51 | T051Y | 0.82 | 0.13 | 0.90 | 0.30 | 0.84 | 0.75 | 0.59 | 0.75 | 0.83 |
| 52 | S052A | 0.81 | 1.13 | 0.62 | 1.10 | 0.95 | 0.91 | 0.94 | 0.99 | 0.93 |
| 52 | S052C | 0.94 | 0.93 | 0.67 | 0.83 | 0.50 | 0.35 | 0.66 | 0.88 | 0.63 |
| 52 | S052D | 1.13 | 1.08 | 0.79 | 1.15 | 0.86 | 0.45 | 0.89 | 0.87 | 0.99 |
| 52 | S052E | 1.20 | 1.53 | 0.72 | 1.42 | 0.87 | 0.50 | 1.02 | 0.94 | 1.01 |
| 52 | S052F | 0.82 | 0.83 | 0.84 | 0.78 | 0.80 | 0.77 | 0.90 | 0.87 | 0.86 |
| 52 | S052G | 0.97 | 0.79 | 0.62 | 0.84 | 0.87 | 0.82 | 0.96 | 0.86 | 1.01 |
| 52 | S052H | 0.95 | 1.15 | 0.76 | 1.12 | 0.93 | 0.94 | 1.07 | 0.95 | 1.15 |
| 52 | S052I | 0.82 | 1.18 | 0.42 | 1.20 | 0.89 | 0.61 | 0.68 | 0.92 | 0.88 |
| 52 | S052K | 0.77 | 1.59 | 0.53 | 1.36 | 1.01 | 0.96 | 1.01 | 0.77 | 0.97 |
| 52 | S052L | 0.81 | 0.94 | 0.35 | 1.06 | 0.93 | 0.49 | 1.05 | 1.05 | 0.80 |
| 52 | S052M | 0.96 | 1.11 | 0.61 | 1.05 | 0.86 | 0.85 | 0.77 | 0.93 | 0.65 |
| 52 | S052N | 0.97 | 0.80 | 0.74 | 0.91 | 0.98 | 0.87 | 0.99 | 0.92 | 1.00 |
| 52 | S052P | 0.60 | 0.14 | 0.12 | 0.13 | 0.48 | 0.17 | 0.79 | 0.78 | 0.74 |
| 52 | S052Q | 0.92 | 1.08 | 0.58 | 1.08 | 0.91 | 0.82 | 0.89 | 0.91 | 0.98 |
| 52 | S052R | 0.83 | 1.47 | 0.42 | 1.51 | 1.08 | 1.24 | 0.79 | 0.98 | 0.95 |
| 52 | S052T | 0.96 | 1.24 | 0.74 | 1.32 | 0.98 | 0.71 | 1.21 | 0.92 | 0.89 |
| 52 | S052V | 0.95 | 1.27 | 0.52 | 1.29 | 0.94 | 0.61 | 0.79 | 0.81 | 0.86 |
| 52 | S052W | 0.77 | 0.45 | 0.27 | 0.46 | 0.96 | 1.06 | 0.83 | 0.78 | 0.75 |
| 52 | S052Y | 0.88 | 1.58 | 0.30 | 1.67 | 0.86 | 0.68 | 0.95 | 0.91 | 0.80 |
| 53 | Q053A | 0.90 | 0.81 | 0.50 | 0.86 | 1.12 | 1.17 | 0.90 | 1.12 | 1.17 |
| 53 | Q053C | 0.71 | 0.46 | 0.48 | 0.61 | 0.77 | 0.65 | 0.96 | 0.85 | 0.82 |
| 53 | Q053D | 0.90 | 0.64 | 0.58 | 0.88 | 0.93 | 0.68 | 1.06 | 0.82 | 1.20 |
| 53 | Q053E | 4.42 | 0.70 | 0.48 | 0.91 | 0.95 | 0.71 | 1.07 | 0.82 | 1.13 |
| 53 | Q053F | 2.83 | 0.57 | 0.31 | 0.76 | 0.95 | 1.13 | 1.02 | 0.89 | 1.02 |
| 53 | Q053G | 0.76 | 0.68 | 0.42 | 0.91 | 1.02 | 1.04 | 0.82 | 0.93 | 1.14 |
| 53 | Q053K | 0.95 | 0.69 | 0.24 | 0.75 | 0.92 | 1.13 | 1.03 | 0.94 | 1.25 |
| 53 | Q053N | 0.96 | 0.89 | 0.45 | 0.87 | 1.06 | 1.11 | 0.93 | 0.99 | 1.23 |
| 53 | Q053P | 0.43 | 0.42 | 0.37 | 0.79 | 1.02 | 1.10 | 0.73 | 1.04 | 1.21 |
| 53 | Q053R | 0.89 | 0.78 | 0.21 | 0.78 | 0.95 | 1.60 | 0.99 | 0.73 | 1.14 |
| 53 | Q053S | 6.10 | 0.56 | 0.57 | 0.84 | 1.04 | 1.17 | 0.97 | 1.03 | 1.24 |
| 53 | Q053T | 0.90 | 0.70 | 0.29 | 0.73 | 1.02 | 1.09 | 1.20 | 1.03 | 1.10 |
| 53 | Q053V | 1.09 | 0.64 | 0.51 | 0.72 | 1.13 | 1.27 | 1.20 | 0.97 | 1.08 |
| 53 | Q053W | 0.98 | 0.63 | 0.29 | 0.68 | 0.99 | 1.00 | 1.05 | 0.98 | 0.91 |
| 53 | Q053Y | 0.88 | 0.69 | 0.31 | 0.75 | 1.00 | 1.03 | 0.91 | 0.90 | 0.98 |
| 54 | S054A | 0.91 | 0.88 | 0.89 | 0.91 | 0.95 | 0.88 | 0.70 | 0.99 | 0.88 |
| 54 | S054C | 0.95 | 0.66 | 1.01 | 0.60 | 0.62 | 0.57 | 0.90 | 1.00 | 0.49 |
| 54 | S054D | 1.00 | 1.04 | 1.36 | 0.92 | 0.77 | 0.70 | 0.80 | 0.92 | 0.95 |
| 54 | S054E | 1.14 | 0.98 | 1.38 | 0.92 | 0.87 | 0.63 | 0.87 | 0.88 | 0.92 |
| 54 | S054F | 1.10 | 0.92 | 0.52 | 0.92 | 0.87 | 0.94 | 0.91 | 0.86 | 0.81 |
| 54 | S054H | 0.91 | 0.89 | 0.83 | 0.87 | 1.03 | 0.84 | 0.91 | 0.86 | 0.89 |
| 54 | S054I | 0.91 | 0.52 | 0.57 | 0.54 | 0.94 | 0.87 | 0.72 | 0.99 | 0.60 |
| 54 | S054K | 0.79 | 0.87 | 0.51 | 0.91 | 0.78 | 0.93 | 0.88 | 0.90 | 0.88 |
| 54 | S054L | 0.84 | 0.77 | 0.62 | 0.71 | 0.99 | 0.94 | 0.86 | 0.93 | 0.70 |
| 54 | S054M | 1.07 | 0.76 | 0.83 | 0.75 | 0.89 | 0.94 | 0.65 | 0.86 | 0.79 |
| 54 | S054N | 0.91 | 0.87 | 0.98 | 0.85 | 0.75 | 0.87 | 0.81 | 0.86 | 1.02 |
| 54 | S054P | 1.06 | 0.95 | 0.48 | 0.98 | 0.91 | 0.78 | 0.82 | 0.82 | 0.90 |
| 54 | S054Q | 0.90 | 1.00 | 0.90 | 0.93 | 0.91 | 0.87 | 0.93 | 0.89 | 0.91 |
| 54 | S054R | 0.83 | 0.84 | 0.45 | 0.82 | 0.92 | 1.10 | 0.51 | 0.84 | 0.92 |
| 54 | S054T | 0.87 | 0.89 | 0.71 | 0.75 | 0.87 | 0.87 | 0.68 | 0.91 | 0.79 |
| 54 | S054V | 1.03 | 0.69 | 0.75 | 0.69 | 0.96 | 0.79 | 0.71 | 0.81 | 0.72 |
| 54 | S054W | 1.06 | 0.73 | 0.94 | 0.67 | 0.77 | 1.09 | 0.78 | 0.88 | 0.72 |
| 54 | S054Y | 0.99 | 0.85 | 0.81 | 0.79 | 0.93 | 0.93 | 0.50 | 0.88 | 0.75 |
| 55 | D055E | 1.14 | 1.18 | 0.35 | 1.21 | 0.84 | 0.54 | 0.83 | 0.85 | 0.95 |
| 55 | D055G | 0.89 | 0.08 | 0.11 | 0.15 | 0.48 | 0.45 | 0.55 | 0.66 | 0.94 |
| 55 | D055I | 0.64 | 0.25 | 0.08 | 0.27 | 0.33 | 0.29 | 0.55 | 0.67 | 0.62 |
| 55 | D055N | 0.90 | 0.32 | 0.27 | 0.37 | 0.98 | 0.79 | 0.65 | 0.74 | 1.02 |
| 55 | D055P | 0.55 | 0.09 | 0.06 | 0.09 | 0.38 | 0.14 | 0.47 | 0.70 | 0.75 |
| 55 | D055S | 0.62 | 0.07 | 0.13 | 0.15 | 0.59 | 0.36 | 0.53 | 0.74 | 0.81 |
| 55 | D055T | 0.84 | 0.19 | 0.10 | 0.26 | 0.61 | 0.87 | 0.59 | 0.70 | 0.85 |
| 56 | V056A | 0.83 | 0.98 | 0.59 | 0.89 | 0.92 | 0.74 | 0.92 | 0.86 | 1.02 |
| 56 | V056C | 0.94 | 0.58 | 0.58 | 0.62 | 0.71 | 0.66 | 0.78 | 0.79 | 0.80 |
| 56 | V056E | 1.35 | 1.71 | 0.62 | 1.63 | 0.60 | 0.51 | 0.80 | 0.86 | 1.03 |
| 56 | V056F | 0.87 | 0.12 | 0.11 | 0.12 | 0.06 | 0.08 | 0.65 | 0.52 | 0.82 |
| 56 | V056G | 0.98 | 0.29 | 0.33 | 0.31 | 0.69 | 0.51 | 0.84 | 0.61 | 0.61 |
| 56 | V056H | 1.13 | 0.68 | 0.32 | 0.65 | 0.70 | 0.44 | 0.94 | 0.82 | 1.15 |
| 56 | V056I | 0.93 | 0.39 | 0.45 | 0.37 | 0.84 | 0.68 | 0.66 | 0.86 | 0.95 |
| 56 | V056K | 0.83 | 0.11 | 0.24 | 0.11 | 0.70 | 0.60 | 0.84 | 0.83 | 1.05 |
| 56 | V056M | 1.19 | 0.43 | 0.29 | 0.48 | 0.76 | 0.41 | 1.45 | 0.84 | 0.91 |
| 56 | V056N | 1.12 | 0.82 | 0.63 | 0.85 | 0.91 | 0.89 | 1.00 | 0.90 | 1.09 |
| 56 | V056P | 1.01 | 0.90 | 0.68 | 0.88 | 0.75 | 0.57 | 0.88 | 0.91 | 1.16 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 56 | V056Q | 1.08 | 1.08 | 0.58 | 1.08 | 0.73 | 0.57 | 1.10 | 0.89 | 1.09 |
| 56 | V056R | 0.62 | 0.18 | 0.39 | 0.26 | 0.62 | 0.80 | 0.95 | 0.80 | 1.18 |
| 56 | V056S | 0.79 | 1.07 | 0.53 | 0.99 | 0.76 | 0.70 | 1.16 | 0.92 | 0.97 |
| 56 | V056T | 1.03 | 1.18 | 0.80 | 1.30 | 0.83 | 0.83 | 0.75 | 0.92 | 1.06 |
| 56 | V056W | 1.18 | 0.20 | 0.22 | 0.20 | 0.37 | 0.29 | 0.49 | 0.54 | 0.76 |
| 56 | V056Y | 0.97 | 0.21 | 0.18 | 0.23 | 0.48 | 0.13 | 0.69 | 0.66 | 0.64 |
| 58 | Y058F | 0.93 | 0.61 | 0.29 | 0.68 | 0.91 | 0.84 | 0.39 | 0.50 | 0.91 |
| 58 | Y058W | 0.64 | 0.16 | 0.11 | 0.16 | 0.65 | 0.27 | 0.34 | 0.49 | 0.93 |
| 59 | G059A | 1.00 | 0.75 | 1.14 | 0.75 | 0.88 | 0.43 | 0.68 | 0.93 | 0.84 |
| 59 | G059E | 2.22 | 0.80 | 0.91 | 0.74 | 0.42 | 0.15 | 0.55 | 0.64 | 0.89 |
| 59 | G059P | 1.20 | 0.06 | 0.44 | 0.07 | 0.30 | 0.08 | 0.38 | 0.51 | 0.57 |
| 59 | G059Q | 1.39 | 0.37 | 0.72 | 0.36 | 0.58 | 0.44 | 0.57 | 0.81 | 0.92 |
| 59 | G059S | 1.11 | 0.23 | 0.90 | 0.23 | 0.79 | 0.29 | 0.67 | 0.88 | 0.85 |
| 60 | V060A | 0.96 | 0.63 | 2.01 | 0.60 | 0.96 | 1.04 | 1.01 | 0.97 | 0.83 |
| 60 | V060C | 1.10 | 0.46 | 1.11 | 0.49 | 0.97 | 1.09 | 0.71 | 1.00 | 0.50 |
| 60 | V060D | 1.04 | 0.34 | 0.71 | 0.38 | 0.86 | 1.12 | 0.66 | 0.91 | 0.52 |
| 60 | V060E | 0.89 | 0.39 | 1.02 | 0.40 | 0.88 | 1.10 | 0.84 | 0.89 | 0.57 |
| 60 | V060G | 1.73 | 0.48 | 0.67 | 0.58 | 0.78 | 0.55 | 0.89 | 0.88 | 0.86 |
| 60 | V060H | 0.92 | 0.67 | 0.20 | 0.72 | 0.79 | 0.73 | 0.76 | 0.90 | 0.82 |
| 60 | V060I | 1.11 | 0.83 | 1.06 | 0.81 | 0.98 | 0.93 | 0.70 | 0.94 | 0.78 |
| 60 | V060K | 0.81 | 0.53 | 0.20 | 0.56 | 0.84 | 0.85 | 0.65 | 0.79 | 0.54 |
| 60 | V060L | 1.18 | 0.77 | 0.50 | 0.78 | 1.04 | 0.78 | 0.79 | 0.98 | 0.71 |
| 60 | V060M | 0.97 | 0.80 | 0.30 | 0.87 | 0.85 | 0.89 | 0.84 | 1.01 | 0.80 |
| 60 | V060N | 0.92 | 0.61 | 0.35 | 0.60 | 0.69 | 0.65 | 0.96 | 0.91 | 0.91 |
| 60 | V060P | 0.65 | 0.60 | 0.80 | 0.61 | 0.89 | 0.89 | 0.89 | 1.02 | 1.02 |
| 60 | V060Q | 0.57 | 0.75 | 0.60 | 0.79 | 0.88 | 0.89 | 0.76 | 0.94 | 0.92 |
| 60 | V060R | 0.43 | 0.37 | 0.19 | 0.33 | 0.77 | 0.78 | 0.83 | 0.86 | 0.36 |
| 60 | V060S | 1.25 | 0.56 | 1.37 | 0.64 | 0.87 | 0.94 | 0.59 | 0.92 | 0.86 |
| 60 | V060T | 1.14 | 0.80 | 1.25 | 0.78 | 0.76 | 0.90 | 0.94 | 0.98 | 0.91 |
| 70 | N070A | 1.08 | 0.91 | 0.65 | 0.89 | 1.07 | 1.03 | 0.93 | 0.90 | 0.69 |
| 70 | N070C | 1.01 | 0.81 | 2.09 | 0.77 | 0.74 | 0.60 | 0.83 | 0.80 | 0.62 |
| 70 | N070D | 1.00 | 1.06 | 1.41 | 0.98 | 0.72 | 0.72 | 0.98 | 0.80 | 0.73 |
| 70 | N070E | 1.00 | 0.65 | 1.15 | 0.63 | 0.80 | 0.72 | 0.93 | 0.56 | 0.48 |
| 70 | N070F | 1.25 | 0.83 | 1.40 | 0.85 | 0.95 | 1.03 | 1.24 | 0.86 | 0.58 |
| 70 | N070G | 1.19 | 0.87 | 0.64 | 0.93 | 0.84 | 0.95 | 1.08 | 0.82 | 0.79 |
| 70 | N070H | 0.85 | 0.67 | 1.03 | 0.98 | 0.81 | 1.01 | 0.96 | 0.85 | 0.79 |
| 70 | N070I | 1.25 | 0.63 | 0.57 | 0.70 | 0.95 | 0.97 | 0.82 | 0.87 | 0.57 |
| 70 | N070K | 1.21 | 0.85 | 0.61 | 0.92 | 0.84 | 1.54 | 0.96 | 0.66 | 0.77 |
| 70 | N070L | 1.10 | 0.75 | 0.98 | 0.72 | 0.86 | 0.73 | 0.89 | 0.72 | 0.64 |
| 70 | N070M | 1.18 | 0.94 | 0.64 | 0.94 | 0.80 | 0.89 | 0.81 | 0.82 | 0.70 |
| 70 | N070P | 1.43 | 0.89 | 0.96 | 1.09 | 0.89 | 0.91 | 0.93 | 0.75 | 1.01 |
| 70 | N070Q | 1.02 | 1.10 | 0.87 | 1.05 | 0.90 | 0.96 | 0.89 | 0.88 | 0.76 |
| 70 | N070R | 1.19 | 0.89 | 0.51 | 0.95 | 0.91 | 1.39 | 1.11 | 0.85 | 0.78 |
| 70 | N070S | 1.01 | 0.91 | 0.69 | 0.86 | 0.91 | 0.94 | 1.13 | 0.85 | 0.68 |
| 70 | N070T | 1.13 | 0.74 | 0.67 | 0.78 | 0.82 | 0.92 | 1.01 | 0.91 | 0.66 |
| 70 | N070V | 1.16 | 0.71 | 0.70 | 0.75 | 1.01 | 1.02 | 1.13 | 0.89 | 0.53 |
| 70 | N070W | 1.30 | 0.96 | 1.01 | 0.95 | 0.83 | 1.03 | 0.99 | 0.76 | 0.81 |
| 70 | N070Y | 1.33 | 0.82 | 1.49 | 0.87 | 0.89 | 0.95 | 0.88 | 0.96 | 0.71 |
| 71 | Q071A | 0.78 | 1.09 | 0.56 | 1.01 | 0.99 | 0.93 | 0.58 | 1.07 | 0.65 |
| 71 | Q071C | 0.95 | 0.79 | 0.44 | 0.74 | 0.92 | 0.67 | 1.04 | 1.08 | 0.46 |
| 71 | Q071D | 0.89 | 0.99 | 0.38 | 0.92 | 0.99 | 0.65 | 1.17 | 0.97 | 0.56 |
| 71 | Q071E | 1.02 | 1.03 | 0.31 | 1.02 | 0.85 | 0.65 | 0.91 | 1.07 | 0.60 |
| 71 | Q071F | 0.81 | 1.10 | 0.22 | 0.94 | 1.06 | 0.69 | 0.92 | 1.10 | 0.48 |
| 71 | Q071G | 0.89 | 0.87 | 0.41 | 0.79 | 0.94 | 0.82 | 0.94 | 0.95 | 0.68 |
| 71 | Q071H | 0.75 | 0.88 | 0.32 | 0.80 | 0.82 | 0.67 | 0.89 | 0.88 | 0.47 |
| 71 | Q071I | 0.83 | 1.06 | 0.51 | 0.90 | 1.01 | 0.84 | 0.99 | 1.12 | 0.57 |
| 71 | Q071K | 0.77 | 0.82 | 0.25 | 0.75 | 0.88 | 0.80 | 0.90 | 1.07 | 0.36 |
| 71 | Q071L | 0.83 | 0.67 | 0.25 | 0.64 | 0.99 | 0.79 | 0.88 | 1.02 | 0.43 |
| 71 | Q071M | 0.92 | 0.86 | 0.34 | 0.84 | 1.03 | 0.82 | 1.07 | 0.96 | 0.58 |
| 71 | Q071N | 0.94 | 0.93 | 0.36 | 0.87 | 0.86 | 0.83 | 1.05 | 0.89 | 0.76 |
| 71 | Q071P | 0.71 | 0.24 | 0.24 | 0.22 | 1.01 | 0.37 | 1.20 | 0.90 | 0.19 |
| 71 | Q071R | 0.78 | 0.96 | 0.22 | 0.92 | 1.04 | 1.11 | 1.03 | 1.07 | 0.46 |
| 71 | Q071S | 0.92 | 0.78 | 0.44 | 0.82 | 0.97 | 0.83 | 0.65 | 1.00 | 0.64 |
| 71 | Q071T | 0.86 | 1.23 | 0.30 | 1.18 | 0.93 | 0.73 | 0.94 | 1.02 | 0.60 |
| 71 | Q071V | 1.02 | 1.07 | 0.42 | 1.02 | 1.02 | 0.83 | 0.88 | 1.14 | 0.62 |
| 71 | Q071W | 0.90 | 1.18 | 0.27 | 0.98 | 1.05 | 0.94 | 0.91 | 1.01 | 0.73 |
| 71 | Q071Y | 0.84 | 0.89 | 0.24 | 0.84 | 0.98 | 0.55 | 0.93 | 1.15 | 0.55 |
| 72 | K072A | 0.99 | 1.66 | 0.33 | 1.69 | 0.89 | 0.56 | 1.11 | 1.20 | 1.01 |
| 72 | K072C | 2.12 | 0.99 | 0.18 | 1.03 | 0.78 | 0.40 | 0.93 | 0.96 | 0.51 |
| 72 | K072D | 0.76 | 1.12 | 0.21 | 1.00 | 0.78 | 0.28 | 0.97 | 0.89 | 0.68 |
| 72 | K072E | 0.93 | 1.99 | 0.38 | 1.82 | 0.87 | 0.42 | 1.03 | 0.90 | 0.97 |
| 72 | K072G | 1.05 | 1.49 | 0.29 | 1.54 | 0.89 | 0.55 | 1.17 | 1.07 | 0.91 |
| 72 | K072I | 0.91 | 1.68 | 0.22 | 1.62 | 0.88 | 0.57 | 1.01 | 0.93 | 0.75 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 72 | K072L | 0.86 | 1.65 | 0.19 | 1.61 | 0.85 | 0.70 | 0.90 | 0.88 | 0.80 |
| 72 | K072M | 0.92 | 1.74 | 0.25 | 1.68 | 0.94 | 0.79 | 1.14 | 0.91 | 0.90 |
| 72 | K072P | 1.12 | 1.62 | 0.31 | 1.63 | 0.77 | 0.41 | 1.12 | 0.86 | 0.89 |
| 72 | K072Q | 1.09 | 1.87 | 0.43 | 1.83 | 0.98 | 0.78 | 1.09 | 1.04 | 1.07 |
| 72 | K072R | 0.71 | 1.46 | 0.45 | 1.45 | 0.89 | 0.58 | 1.10 | 1.08 | 1.07 |
| 72 | K072S | 1.11 | 1.47 | 0.38 | 1.49 | 0.98 | 0.42 | 0.90 | 1.07 | 1.07 |
| 72 | K072T | 0.78 | 1.43 | 0.08 | 1.34 | 0.81 | 0.47 | 1.18 | 0.97 | 0.77 |
| 72 | K072V | 0.88 | 1.91 | 0.29 | 1.77 | 0.83 | 0.47 | 1.08 | 0.97 | 0.85 |
| 72 | K072Y | 1.01 | 1.26 | 0.11 | 1.23 | 0.96 | 0.60 | 1.19 | 0.97 | 0.82 |
| 73 | G073A | 0.84 | 1.04 | 0.55 | 0.91 | 1.06 | 0.98 | 0.74 | 0.93 | 0.88 |
| 73 | G073C | 0.87 | 0.83 | 0.71 | 0.70 | 0.83 | 0.65 | 0.81 | 0.75 | 0.66 |
| 73 | G073D | 1.02 | 1.11 | 0.81 | 1.03 | 1.00 | 0.66 | 0.88 | 0.86 | 0.87 |
| 73 | G073E | 0.99 | 1.09 | 0.82 | 1.01 | 0.80 | 0.88 | 0.81 | 0.92 | 0.79 |
| 73 | G073F | 0.82 | 0.74 | 0.61 | 0.58 | 0.93 | 0.95 | 0.76 | 0.78 | 0.69 |
| 73 | G073H | 0.93 | 0.89 | 0.60 | 0.84 | 1.04 | 0.95 | 0.91 | 0.85 | 0.84 |
| 73 | G073I | 0.84 | 0.56 | 0.50 | 0.51 | 0.86 | 0.92 | 0.48 | 0.81 | 0.50 |
| 73 | G073K | 1.00 | 0.90 | 0.46 | 0.92 | 0.87 | 1.04 | 0.78 | 0.92 | 0.80 |
| 73 | G073L | 1.00 | 0.64 | 0.53 | 0.64 | 0.89 | 0.76 | 0.86 | 0.77 | 0.68 |
| 73 | G073M | 0.91 | 0.78 | 0.64 | 0.70 | 0.83 | 1.11 | 0.89 | 0.86 | 0.71 |
| 73 | G073P | 0.72 | 0.19 | 0.24 | 0.17 | 0.65 | 0.68 | 0.84 | 0.62 | 0.20 |
| 73 | G073Q | 0.83 | 1.11 | 0.66 | 0.93 | 1.03 | 0.89 | 0.80 | 0.96 | 0.81 |
| 73 | G073R | 0.88 | 0.86 | 0.39 | 0.86 | 0.95 | 1.17 | 0.73 | 0.84 | 0.89 |
| 73 | G073S | 0.92 | 0.97 | 0.58 | 0.91 | 1.04 | 1.07 | 0.86 | 0.81 | 0.81 |
| 73 | G073V | 0.94 | 0.88 | 0.50 | 0.87 | 1.17 | 1.06 | 1.10 | 1.06 | 0.53 |
| 73 | G073Y | 0.96 | 0.68 | 0.60 | 0.62 | 0.93 | 1.21 | 0.74 | 0.83 | 0.66 |
| 75 | I075A | 0.97 | 0.90 | 0.51 | 0.87 | 1.01 | 1.01 | 0.87 | 0.89 | 1.22 |
| 75 | I075C | 0.93 | 0.72 | 0.77 | 0.65 | 0.97 | 0.61 | 0.92 | 0.86 | 0.88 |
| 75 | I075E | 0.92 | 1.08 | 0.66 | 0.95 | 1.05 | 0.83 | 0.95 | 1.04 | 1.12 |
| 75 | I075F | 0.86 | 1.24 | 0.74 | 1.00 | 1.05 | 1.03 | 0.79 | 1.00 | 1.30 |
| 75 | I075G | 0.99 | 1.00 | 0.53 | 0.90 | 0.92 | 0.89 | 0.88 | 0.91 | 1.31 |
| 75 | I075H | 1.01 | 1.31 | 0.55 | 1.17 | 1.02 | 1.11 | 0.96 | 1.03 | 1.42 |
| 75 | I075K | 0.96 | 1.10 | 0.57 | 0.93 | 0.97 | 1.20 | 1.08 | 0.95 | 1.33 |
| 75 | I075L | 0.92 | 0.90 | 0.64 | 0.86 | 1.09 | 0.91 | 0.72 | 0.96 | 1.15 |
| 75 | I075M | 0.94 | 1.08 | 0.65 | 0.90 | 0.99 | 0.99 | 0.87 | 0.98 | 1.14 |
| 75 | I075N | 1.02 | 1.04 | 0.60 | 0.95 | 1.01 | 1.06 | 1.09 | 0.95 | 1.20 |
| 75 | I075P | 1.01 | 0.76 | 0.43 | 0.74 | 1.02 | 1.79 | 0.90 | 0.90 | 1.10 |
| 75 | I075Q | 0.96 | 1.05 | 0.59 | 1.00 | 1.04 | 0.91 | 0.87 | 1.02 | 1.22 |
| 75 | I075R | 0.94 | 1.11 | 0.53 | 0.93 | 1.09 | 1.58 | 0.86 | 1.15 | 1.32 |
| 75 | I075S | 0.99 | 0.89 | 0.52 | 0.88 | 1.07 | 0.93 | 0.87 | 1.02 | 1.14 |
| 75 | I075T | 0.94 | 1.02 | 0.75 | 0.92 | 1.05 | 1.03 | 0.97 | 1.08 | 1.19 |
| 75 | I075V | 0.97 | 1.01 | 1.13 | 0.93 | 1.00 | 0.93 | 1.04 | 1.06 | 1.12 |
| 75 | I075W | 1.00 | 1.13 | 0.71 | 1.01 | 1.01 | 1.06 | 0.89 | 1.06 | 1.19 |
| 75 | I075Y | 0.99 | 1.03 | 0.74 | 0.93 | 1.03 | 0.92 | 0.95 | 1.01 | 1.17 |
| 78 | K078C | 0.79 | 0.57 | 0.17 | 0.51 | 0.73 | 0.16 | 0.82 | 0.75 | 0.47 |
| 78 | K078F | 1.21 | 0.72 | 0.37 | 0.62 | 0.70 | 0.21 | 0.72 | 0.77 | 0.40 |
| 78 | K078G | 0.82 | 0.40 | 0.13 | 0.40 | 0.58 | 0.10 | 0.79 | 0.82 | 0.53 |
| 78 | K078H | 0.86 | 0.53 | 0.22 | 0.53 | 0.80 | 0.50 | 0.83 | 0.90 | 0.72 |
| 78 | K078I | 0.76 | 0.55 | 0.17 | 0.49 | 0.79 | 0.32 | 0.70 | 0.79 | 0.59 |
| 78 | K078L | 0.87 | 0.70 | 0.24 | 0.61 | 0.76 | 0.26 | 0.92 | 0.78 | 0.76 |
| 78 | K078M | 0.97 | 0.95 | 0.26 | 0.89 | 0.78 | 1.34 | 0.89 | 0.82 | 0.74 |
| 78 | K078N | 0.83 | 0.79 | 0.17 | 0.72 | 0.77 | 0.31 | 0.99 | 0.78 | 0.64 |
| 78 | K078Q | 0.76 | 0.73 | 0.14 | 0.67 | 0.93 | 0.54 | 1.08 | 0.88 | 0.66 |
| 78 | K078S | 0.74 | 0.49 | 0.17 | 0.46 | 0.76 | 0.23 | 0.76 | 0.59 | 0.56 |
| 78 | K078T | 0.75 | 0.84 | 0.13 | 0.75 | 0.77 | 0.69 | 0.84 | 0.90 | 0.72 |
| 78 | K078Y | 0.99 | 0.92 | 0.20 | 0.81 | 0.77 | 0.07 | 0.82 | 0.67 | 0.46 |
| 82 | K082A | 0.70 | 0.91 | 0.65 | 0.83 | 1.03 | 0.91 | 1.32 | 0.99 | 0.81 |
| 82 | K082C | 0.77 | 0.68 | 0.69 | 0.65 | 0.99 | 0.67 | 1.04 | 0.86 | 0.68 |
| 82 | K082D | 0.69 | 0.86 | 0.72 | 0.74 | 0.89 | 0.72 | 1.06 | 0.80 | 0.79 |
| 82 | K082E | 0.90 | 1.11 | 0.68 | 0.96 | 0.90 | 0.75 | 0.99 | 1.00 | 1.00 |
| 82 | K082F | 0.80 | 1.03 | 0.88 | 0.88 | 1.04 | 0.77 | 1.31 | 1.00 | 0.92 |
| 82 | K082G | 0.82 | 0.84 | 0.64 | 0.72 | 0.86 | 0.72 | 1.22 | 0.86 | 0.89 |
| 82 | K082H | 0.91 | 0.95 | 0.80 | 0.86 | 0.81 | 0.86 | 1.36 | 0.86 | 0.93 |
| 82 | K082I | 0.61 | 0.99 | 0.70 | 0.81 | 1.03 | 0.86 | 1.06 | 0.96 | 0.79 |
| 82 | K082L | 0.70 | 0.86 | 0.69 | 0.79 | 1.02 | 0.81 | 1.16 | 0.89 | 0.80 |
| 82 | K082M | 0.84 | 0.80 | 0.79 | 0.83 | 1.12 | 0.81 | 0.92 | 0.97 | 0.90 |
| 82 | K082N | 0.80 | 1.32 | 0.72 | 1.15 | 1.26 | 0.99 | 1.42 | 1.05 | 1.07 |
| 82 | K082P | 0.87 | 0.33 | 0.63 | 0.29 | 0.59 | 0.63 | 0.66 | 0.66 | 0.49 |
| 82 | K082Q | 0.91 | 0.90 | 0.68 | 0.87 | 1.09 | 1.31 | 1.25 | 0.92 | 0.91 |
| 82 | K082S | 0.73 | 0.86 | 0.66 | 0.80 | 1.00 | 0.98 | 1.09 | 0.91 | 0.83 |
| 82 | K082T | 0.76 | 0.66 | 0.60 | 0.63 | 1.04 | 0.84 | 1.08 | 0.91 | 0.74 |
| 82 | K082V | 0.71 | 0.80 | 0.81 | 0.73 | 1.03 | 0.86 | 1.41 | 0.96 | 0.77 |
| 82 | K082W | 0.75 | 0.58 | 0.64 | 0.50 | 1.08 | 0.78 | 1.03 | 0.83 | 0.54 |
| 82 | K082Y | 0.88 | 0.97 | 0.83 | 0.91 | 1.02 | 0.79 | 1.16 | 0.91 | 0.95 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 83 | T083A | 0.89 | 0.84 | 1.07 | 0.83 | 1.09 | 0.82 | 1.47 | 1.00 | 0.81 |
| 83 | T083C | 0.99 | 0.82 | 1.13 | 0.76 | 0.92 | 0.74 | 1.35 | 1.00 | 0.74 |
| 83 | T083D | 0.98 | 0.95 | 1.92 | 0.85 | 1.10 | 0.78 | 0.96 | 0.84 | 0.89 |
| 83 | T083E | 1.02 | 0.91 | 1.99 | 0.86 | 0.96 | 0.80 | 1.22 | 0.91 | 0.89 |
| 83 | T083F | 1.23 | 1.03 | 0.80 | 1.05 | 1.13 | 1.05 | 1.51 | 0.97 | 0.91 |
| 83 | T083G | 1.10 | 0.83 | 0.96 | 0.86 | 1.09 | 0.84 | 1.49 | 1.03 | 0.87 |
| 83 | T083H | 1.04 | 1.06 | 0.97 | 1.05 | 1.05 | 0.95 | 1.40 | 0.87 | 1.05 |
| 83 | T083I | 1.13 | 0.96 | 0.77 | 0.96 | 1.19 | 1.36 | 1.06 | 1.03 | 0.84 |
| 83 | T083K | 1.28 | 0.93 | 0.71 | 0.97 | 1.18 | 0.96 | 1.22 | 1.02 | 1.04 |
| 83 | T083L | 1.05 | 1.08 | 0.81 | 1.03 | 1.07 | 0.82 | 1.29 | 0.86 | 1.09 |
| 83 | T083M | 1.16 | 1.02 | 0.91 | 1.06 | 0.94 | 0.93 | 1.46 | 0.75 | 0.78 |
| 83 | T083N | 1.24 | 1.07 | 1.01 | 1.06 | 1.16 | 0.90 | 1.09 | 0.96 | 1.17 |
| 83 | T083P | 1.22 | 0.97 | 0.72 | 1.04 | 1.09 | 0.76 | 1.32 | 0.92 | 1.28 |
| 83 | T083Q | 0.95 | 1.19 | 1.25 | 1.06 | 1.02 | 0.78 | 1.44 | 0.85 | 1.15 |
| 83 | T083R | 0.92 | 1.12 | 0.67 | 0.92 | 1.27 | 1.27 | 1.07 | 0.91 | 0.94 |
| 83 | T083S | 1.08 | 1.04 | 0.90 | 0.99 | 1.04 | 0.97 | 1.38 | 0.86 | 0.99 |
| 83 | T083V | 1.12 | 0.76 | 0.90 | 0.81 | 1.09 | 0.99 | 1.36 | 1.02 | 0.72 |
| 83 | T083W | 1.20 | 1.09 | 0.85 | 1.05 | 1.08 | 1.13 | 1.55 | 0.98 | 0.96 |
| 83 | T083Y | 1.18 | 0.93 | 0.81 | 1.00 | 0.97 | 0.93 | 1.22 | 1.00 | 0.97 |
| 87 | Q087A | 0.70 | 0.97 | 0.85 | 0.91 | 1.19 | 1.92 | 0.80 | 1.01 | 0.84 |
| 87 | Q087C | 0.84 | 0.70 | 0.97 | 0.72 | 0.91 | 0.18 | 0.63 | 0.99 | 0.74 |
| 87 | Q087D | 0.83 | 0.89 | 1.20 | 0.85 | 1.06 | 0.80 | 0.80 | 0.85 | 0.94 |
| 87 | Q087E | 0.97 | 0.78 | 1.81 | 0.83 | 1.02 | 1.10 | 0.77 | 0.94 | 0.94 |
| 87 | Q087F | 0.87 | 1.17 | 0.68 | 0.97 | 1.21 | 1.47 | 1.06 | 1.03 | 0.91 |
| 87 | Q087G | 0.97 | 0.65 | 0.82 | 0.61 | 1.02 | 0.26 | 0.90 | 0.95 | 0.64 |
| 87 | Q087H | 0.92 | 1.02 | 0.83 | 0.93 | 1.11 | 1.24 | 1.21 | 1.02 | 0.98 |
| 87 | Q087I | 0.70 | 0.72 | 0.65 | 0.72 | 1.19 | 1.00 | 0.91 | 1.02 | 0.73 |
| 87 | Q087K | 0.97 | 0.91 | 0.75 | 0.86 | 1.15 | 1.46 | 0.92 | 1.09 | 0.84 |
| 87 | Q087L | 0.86 | 0.88 | 0.72 | 0.86 | 1.13 | 1.40 | 0.86 | 1.09 | 0.82 |
| 87 | Q087M | 0.84 | 0.92 | 0.86 | 0.85 | 1.13 | 1.26 | 0.93 | 0.92 | 0.92 |
| 87 | Q087N | 1.03 | 0.98 | 0.88 | 0.99 | 1.16 | 1.61 | 1.07 | 0.91 | 1.08 |
| 87 | Q087P | 0.95 | 0.86 | 0.60 | 0.85 | 1.06 | 1.04 | 0.93 | 0.90 | 1.04 |
| 87 | Q087R | 0.84 | 0.87 | 0.62 | 0.87 | 1.21 | 1.72 | 1.23 | 1.02 | 0.96 |
| 87 | Q087S | 0.72 | 0.98 | 0.76 | 0.91 | 1.04 | 1.18 | 0.86 | 0.88 | 0.97 |
| 87 | Q087T | 0.91 | 0.77 | 0.80 | 0.80 | 1.12 | 0.98 | 0.84 | 1.01 | 0.88 |
| 87 | Q087W | 0.97 | 0.95 | 0.71 | 0.93 | 1.22 | 1.37 | 0.94 | 1.03 | 0.94 |
| 87 | Q087Y | 1.00 | 0.82 | 0.69 | 0.90 | 0.95 | 0.98 | 0.89 | 1.11 | 0.88 |
| 90 | Q090A | 0.69 | 1.25 | 0.86 | 1.04 | 0.92 | 1.10 | 1.16 | 0.69 | 0.82 |
| 90 | Q090C | 0.80 | 0.81 | 0.87 | 0.78 | 0.76 | 0.92 | 1.05 | 0.83 | 0.58 |
| 90 | Q090D | 0.91 | 0.92 | 0.93 | 0.89 | 0.92 | 0.81 | 1.02 | 0.74 | 0.78 |
| 90 | Q090E | 0.85 | 0.96 | 1.15 | 0.90 | 0.98 | 1.19 | 1.00 | 0.92 | 0.75 |
| 90 | Q090F | 0.87 | 0.83 | 0.71 | 0.85 | 1.13 | 1.24 | 1.07 | 0.94 | 0.61 |
| 90 | Q090G | 0.93 | 0.87 | 0.77 | 0.91 | 0.92 | 0.92 | 1.06 | 0.93 | 0.77 |
| 90 | Q090H | 0.83 | 1.03 | 0.79 | 0.92 | 0.96 | 1.04 | 1.03 | 0.95 | 0.79 |
| 90 | Q090I | 0.92 | 0.88 | 0.77 | 0.90 | 0.93 | 1.05 | 0.92 | 0.94 | 0.72 |
| 90 | Q090K | 0.82 | 0.93 | 0.85 | 0.89 | 0.86 | 0.92 | 0.89 | 0.82 | 0.83 |
| 90 | Q090L | 0.84 | 0.89 | 0.78 | 0.87 | 0.91 | 0.94 | 1.20 | 0.85 | 0.80 |
| 90 | Q090M | 1.00 | 0.85 | 0.89 | 0.90 | 0.89 | 0.95 | 0.89 | 0.97 | 0.84 |
| 90 | Q090N | 1.01 | 0.91 | 0.99 | 0.96 | 0.86 | 1.03 | 0.85 | 0.90 | 0.96 |
| 90 | Q090P | 1.02 | 0.30 | 0.63 | 0.31 | 0.92 | 0.77 | 0.69 | 0.69 | 0.36 |
| 90 | Q090R | 0.86 | 0.99 | 0.73 | 0.94 | 1.08 | 1.27 | 0.59 | 0.71 | 0.82 |
| 90 | Q090S | 0.77 | 0.97 | 0.79 | 0.94 | 1.06 | 1.13 | 0.86 | 0.89 | 0.75 |
| 90 | Q090T | 0.91 | 0.89 | 0.84 | 0.88 | 1.02 | 1.27 | 0.89 | 0.87 | 0.79 |
| 90 | Q090V | 0.96 | 0.83 | 0.80 | 0.87 | 0.90 | 1.21 | 1.10 | 0.86 | 0.70 |
| 90 | Q090W | 0.88 | 0.91 | 0.72 | 0.84 | 1.03 | 1.16 | 1.00 | 0.99 | 0.65 |
| 90 | Q090Y | 0.87 | 0.92 | 0.72 | 0.92 | 0.98 | 1.15 | 1.00 | 1.01 | 0.72 |
| 91 | A091C | 1.04 | 0.84 | 0.78 | 0.80 | 0.98 | 0.81 | 0.59 | 0.91 | 0.81 |
| 91 | A091D | 1.07 | 1.12 | 0.68 | 1.07 | 0.97 | 0.75 | 0.57 | 0.81 | 1.22 |
| 91 | A091E | 1.00 | 1.20 | 0.73 | 1.11 | 1.02 | 0.88 | 0.58 | 0.95 | 1.12 |
| 91 | A091F | 1.22 | 1.03 | 0.66 | 1.07 | 1.02 | 0.85 | 0.62 | 0.99 | 1.03 |
| 91 | A091G | 1.20 | 1.14 | 0.69 | 1.15 | 0.99 | 0.87 | 0.63 | 0.93 | 1.15 |
| 91 | A091H | 1.14 | 1.05 | 0.62 | 1.14 | 0.94 | 0.87 | 0.78 | 0.97 | 1.21 |
| 91 | A091I | 1.08 | 1.05 | 0.62 | 1.06 | 1.01 | 0.84 | 0.37 | 1.03 | 1.04 |
| 91 | A091K | 1.13 | 1.11 | 0.67 | 1.15 | 1.01 | 0.87 | 0.65 | 0.91 | 1.34 |
| 91 | A091L | 1.08 | 1.04 | 0.57 | 1.02 | 1.12 | 0.88 | 0.67 | 1.00 | 0.98 |
| 91 | A091M | 1.13 | 1.06 | 0.66 | 1.02 | 0.90 | 0.84 | 0.59 | 0.82 | 1.07 |
| 91 | A091N | 1.24 | 1.17 | 0.64 | 1.17 | 0.96 | 0.84 | 0.59 | 0.89 | 1.30 |
| 91 | A091Q | 1.07 | 1.02 | 0.63 | 1.03 | 0.84 | 0.88 | 0.59 | 0.94 | 0.96 |
| 91 | A091R | 0.99 | 1.16 | 0.65 | 1.15 | 1.07 | 1.01 | 0.49 | 0.91 | 1.23 |
| 91 | A091S | 1.00 | 0.29 | 0.80 | 0.28 | 2.28 | 4.29 | 0.96 | 2.11 | 0.12 |
| 91 | A091T | 1.21 | 1.02 | 0.74 | 1.03 | 1.11 | 1.00 | 0.61 | 0.98 | 0.94 |
| 91 | A091V | 1.15 | 0.94 | 0.66 | 0.97 | 1.02 | 1.00 | 0.63 | 1.06 | 0.84 |
| 91 | A091W | 1.14 | 1.13 | 0.63 | 1.09 | 1.00 | 0.94 | 0.65 | 0.84 | 1.05 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 91 | A091Y | 1.19 | 1.00 | 0.64 | 1.02 | 0.92 | 1.07 | 0.67 | 1.01 | 0.94 |
| 93 | K093C | 0.79 | 0.24 | 0.55 | 0.22 | 1.87 | 1.19 | 1.35 | 3.01 | 0.09 |
| 93 | K093D | 1.06 | 0.73 | 0.59 | 0.71 | 0.99 | 1.24 | 0.91 | 1.17 | 0.48 |
| 93 | K093E | 1.05 | 0.56 | 0.60 | 0.59 | 1.10 | 0.86 | 0.79 | 1.13 | 0.43 |
| 93 | K093G | 1.00 | 0.56 | 0.61 | 0.56 | 1.16 | 0.92 | 0.86 | 1.23 | 0.34 |
| 93 | K093I | 0.90 | 0.18 | 0.49 | 0.20 | 1.43 | 0.97 | 1.05 | 0.98 | 0.11 |
| 93 | K093M | 0.91 | 0.18 | 0.56 | 0.17 | 1.92 | 1.33 | 2.36 | 3.18 | 0.06 |
| 93 | K093N | 1.04 | 0.67 | 0.61 | 0.66 | 1.16 | 1.11 | 0.85 | 1.18 | 0.38 |
| 93 | K093Q | 0.97 | 0.40 | 0.89 | 0.38 | 1.21 | 0.96 | 0.83 | 1.20 | 0.22 |
| 93 | K093R | 0.84 | 0.85 | 0.59 | 0.80 | 1.11 | 0.98 | 0.88 | 0.77 | 0.65 |
| 93 | K093S | 0.94 | 0.40 | 0.52 | 0.41 | 1.41 | 0.59 | 1.16 | 1.75 | 0.22 |
| 93 | K093T | 0.96 | 0.36 | 0.58 | 0.36 | 1.25 | 1.09 | 0.99 | 1.41 | 0.23 |
| 93 | K093V | 0.90 | 0.24 | 0.54 | 0.22 | 1.25 | 1.31 | 1.22 | 1.69 | 0.11 |
| 93 | K093W | 1.03 | 0.23 | 0.55 | 0.23 | 1.81 | 1.59 | 1.25 | 2.39 | 0.08 |
| 93 | K093Y | 1.00 | 0.35 | 0.50 | 0.34 | 1.34 | 1.09 | 0.91 | 1.85 | 0.16 |
| 94 | A094C | 0.92 | 0.79 | 0.75 | 0.77 | 0.95 | 0.73 | 0.67 | 0.87 | 0.73 |
| 94 | A094D | 0.88 | 0.65 | 1.01 | 0.64 | 0.93 | 0.66 | 0.85 | 0.83 | 0.63 |
| 94 | A094E | 0.96 | 0.92 | 1.08 | 0.91 | 0.94 | 0.87 | 1.02 | 0.88 | 0.79 |
| 94 | A094F | 1.04 | 0.98 | 0.75 | 0.98 | 0.99 | 0.95 | 0.84 | 0.89 | 0.93 |
| 94 | A094G | 1.04 | 0.68 | 0.84 | 0.71 | 0.90 | 0.71 | 0.89 | 0.82 | 0.69 |
| 94 | A094H | 1.06 | 0.88 | 0.82 | 0.92 | 0.92 | 0.83 | 0.86 | 0.93 | 0.92 |
| 94 | A094I | 0.82 | 1.02 | 0.63 | 0.93 | 1.10 | 0.87 | 0.83 | 0.74 | 0.94 |
| 94 | A094L | 0.98 | 0.93 | 0.78 | 0.94 | 1.06 | 0.92 | 0.79 | 0.78 | 0.89 |
| 94 | A094M | 1.00 | 0.06 | 0.75 | 0.07 | 0.19 | 0.08 | 0.41 | 0.55 | 0.66 |
| 94 | A094P | 1.15 | 0.24 | 0.63 | 0.24 | 0.72 | 0.68 | 0.83 | 0.66 | 0.23 |
| 94 | A094Q | 0.86 | 0.08 | 1.02 | 0.07 | 0.50 | 0.32 | 0.58 | 0.66 | 0.09 |
| 94 | A094R | 0.85 | 0.98 | 0.71 | 0.94 | 1.11 | 1.01 | 0.73 | 0.90 | 0.98 |
| 94 | A094S | 1.02 | 0.85 | 0.82 | 0.90 | 0.97 | 0.97 | 0.95 | 0.83 | 0.90 |
| 94 | A094T | 0.99 | 0.89 | 0.78 | 0.91 | 0.96 | 1.32 | 0.90 | 0.83 | 0.86 |
| 94 | A094V | 1.03 | 0.82 | 0.74 | 0.89 | 0.96 | 0.94 | 1.06 | 0.90 | 0.83 |
| 94 | A094W | 1.05 | 0.89 | 0.72 | 0.90 | 0.95 | 1.07 | 0.95 | 0.91 | 0.86 |
| 94 | A094Y | 0.92 | 0.93 | 0.75 | 0.88 | 0.96 | 0.85 | 1.03 | 0.89 | 0.84 |
| 95 | A095C | 1.02 | 0.75 | 0.76 | 0.78 | 0.88 | 0.92 | 0.86 | 0.97 | 0.79 |
| 95 | A095D | 1.02 | 0.82 | 0.62 | 0.80 | 0.96 | 0.87 | 0.77 | 1.00 | 0.84 |
| 95 | A095E | 1.13 | 1.00 | 0.70 | 0.98 | 0.86 | 0.95 | 0.86 | 0.95 | 1.04 |
| 95 | A095F | 0.78 | 0.80 | 0.65 | 1.05 | 0.96 | 1.08 | 0.91 | 1.11 | 1.00 |
| 95 | A095G | 1.17 | 1.20 | 0.53 | 1.25 | 0.96 | 0.97 | 0.86 | 1.09 | 1.35 |
| 95 | A095I | 0.98 | 1.02 | 0.55 | 0.97 | 1.06 | 0.90 | 0.57 | 1.11 | 1.00 |
| 95 | A095K | 1.12 | 0.99 | 0.62 | 1.06 | 0.98 | 0.89 | 0.94 | 1.03 | 1.33 |
| 95 | A095L | 1.02 | 0.99 | 0.56 | 1.04 | 0.91 | 0.93 | 0.68 | 1.05 | 1.16 |
| 95 | A095M | 1.08 | 1.04 | 0.68 | 1.03 | 0.91 | 0.97 | 0.79 | 1.08 | 1.16 |
| 95 | A095N | 1.06 | 1.04 | 0.73 | 1.03 | 0.85 | 0.98 | 0.94 | 1.13 | 1.15 |
| 95 | A095P | 1.16 | 0.50 | 0.51 | 0.52 | 0.91 | 0.98 | 0.65 | 0.79 | 0.51 |
| 95 | A095Q | 0.97 | 1.16 | 0.60 | 1.12 | 1.03 | 1.04 | 0.92 | 1.14 | 1.08 |
| 95 | A095R | 0.88 | 1.20 | 0.54 | 1.13 | 0.91 | 1.09 | 0.82 | 1.20 | 1.27 |
| 95 | A095S | 1.07 | 0.99 | 0.67 | 1.04 | 0.99 | 1.03 | 0.88 | 1.10 | 1.10 |
| 95 | A095T | 1.08 | 0.99 | 0.66 | 0.98 | 1.00 | 0.93 | 0.96 | 1.19 | 1.06 |
| 95 | A095V | 1.06 | 0.92 | 0.80 | 0.94 | 0.89 | 1.05 | 0.69 | 1.06 | 0.98 |
| 95 | A095W | 1.16 | 0.93 | 0.63 | 0.92 | 0.93 | 1.09 | 0.98 | 1.04 | 0.90 |
| 95 | A095Y | 1.03 | 0.91 | 0.65 | 0.99 | 0.92 | 1.01 | 0.78 | 1.11 | 1.03 |
| 103 | V103A | 0.74 | 0.88 | 0.29 | 0.95 | 1.14 | 0.98 | 1.13 | 1.00 | 1.42 |
| 103 | V103C | 0.78 | 0.80 | 0.42 | 0.81 | 1.00 | 1.01 | 0.81 | 0.99 | 0.88 |
| 103 | V103D | 0.67 | 0.13 | 0.29 | 0.13 | 1.18 | 0.78 | 0.61 | 0.78 | 0.16 |
| 103 | V103E | 0.90 | 0.36 | 0.16 | 0.39 | 0.82 | 0.88 | 0.80 | 0.81 | 0.40 |
| 103 | V103F | 0.71 | 0.78 | 0.07 | 0.75 | 0.99 | 1.00 | 0.85 | 0.81 | 1.16 |
| 103 | V103G | 0.86 | 0.99 | 0.19 | 1.09 | 1.10 | 1.09 | 1.39 | 0.99 | 1.01 |
| 103 | V103H | 0.51 | 0.49 | 0.07 | 0.48 | 1.02 | 0.66 | 0.96 | 0.78 | 0.58 |
| 103 | V103I | 0.99 | 0.87 | 1.00 | 0.87 | 0.98 | 1.08 | 1.03 | 0.95 | 0.95 |
| 103 | V103K | 0.66 | 0.31 | 0.06 | 0.34 | 0.88 | 0.75 | 0.27 | 0.73 | 0.36 |
| 103 | V103L | 0.67 | 1.08 | 0.26 | 0.97 | 1.00 | 0.80 | 1.28 | 0.97 | 0.97 |
| 103 | V103M | 0.89 | 0.84 | 0.13 | 0.85 | 1.03 | 0.99 | 1.12 | 0.86 | 1.05 |
| 103 | V103N | 0.69 | 1.22 | 0.23 | 1.07 | 1.06 | 1.05 | 1.18 | 0.94 | 0.90 |
| 103 | V103S | 0.71 | 1.08 | 0.17 | 1.16 | 1.28 | 1.17 | 1.21 | 1.10 | 1.01 |
| 104 | V104A | 0.56 | 0.10 | 0.35 | 0.09 | 0.46 | 0.09 | 0.75 | 0.54 | 1.04 |
| 104 | V104G | 1.55 | 0.16 | 0.47 | 0.18 | 0.63 | 0.37 | 0.41 | 0.27 | 0.99 |
| 104 | V104I | 1.06 | 1.17 | 0.37 | 1.16 | 0.89 | 0.83 | 0.87 | 0.84 | 0.88 |
| 104 | V104L | 0.75 | 0.22 | 0.14 | 0.20 | 0.51 | 0.25 | 0.49 | 0.39 | 0.83 |
| 104 | V104T | 0.84 | 0.32 | 0.31 | 0.31 | 0.87 | 0.64 | 0.64 | 0.63 | 0.94 |
| 105 | F105C | 0.78 | 0.87 | 0.33 | 0.82 | 0.86 | 0.67 | 1.04 | 0.92 | 0.83 |
| 105 | F105E | 0.58 | 1.00 | 0.08 | 0.87 | 0.98 | 0.90 | 1.06 | 0.96 | 0.69 |
| 105 | F105G | 0.86 | 1.01 | 0.12 | 0.98 | 0.97 | 0.77 | 1.05 | 0.87 | 0.81 |
| 105 | F105H | 1.26 | 0.96 | 0.39 | 0.91 | 0.92 | 1.20 | 0.90 | 0.84 | 0.99 |
| 105 | F105I | 0.41 | 0.86 | 0.09 | 0.86 | 0.82 | 0.74 | 0.82 | 0.93 | 0.82 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 105 | F105K | 0.71 | 0.79 | 0.07 | 0.81 | 0.77 | 0.82 | 1.01 | 0.88 | 0.70 |
| 105 | F105L | 0.80 | 0.91 | 0.46 | 0.97 | 0.96 | 0.81 | 1.06 | 0.94 | 0.85 |
| 105 | F105M | 0.72 | 0.90 | 0.25 | 0.89 | 0.84 | 0.86 | 0.73 | 0.88 | 0.89 |
| 105 | F105N | 0.92 | 0.92 | 0.12 | 0.89 | 0.86 | 0.84 | 1.16 | 0.89 | 0.94 |
| 105 | F105Q | 0.71 | 0.92 | 0.09 | 0.91 | 1.02 | 0.82 | 0.88 | 0.91 | 0.87 |
| 105 | F105S | 0.61 | 0.89 | 0.06 | 0.95 | 0.95 | 0.99 | 0.65 | 0.93 | 0.86 |
| 105 | F105T | 0.70 | 0.82 | 0.09 | 0.85 | 0.92 | 0.90 | 0.86 | 1.00 | 0.94 |
| 105 | F105V | 0.71 | 0.65 | 0.43 | 0.69 | 0.87 | 1.03 | 0.98 | 0.91 | 0.74 |
| 105 | F105Y | 0.62 | 0.80 | 0.06 | 0.85 | 0.94 | 0.84 | 1.04 | 0.91 | 0.98 |
| 108 | K108A | 1.32 | 1.11 | 0.21 | 1.21 | 1.22 | 1.06 | 1.86 | 1.08 | 0.62 |
| 108 | K108C | 1.80 | 0.57 | 0.26 | 0.65 | 1.04 | 0.88 | 1.24 | 0.99 | 0.48 |
| 108 | K108E | 1.78 | 0.41 | 0.38 | 0.42 | 1.27 | 0.81 | 1.67 | 1.06 | 0.17 |
| 108 | K108F | 1.44 | 0.84 | 0.20 | 0.83 | 0.76 | 0.41 | 1.38 | 0.97 | 0.52 |
| 108 | K108G | 1.46 | 0.69 | 0.18 | 0.83 | 1.01 | 0.79 | 1.15 | 0.93 | 0.59 |
| 108 | K108I | 1.77 | 1.25 | 0.29 | 1.33 | 1.17 | 0.77 | 1.22 | 0.83 | 0.57 |
| 108 | K108L | 2.05 | 1.14 | 0.52 | 1.19 | 0.95 | 0.63 | 1.61 | 0.90 | 0.56 |
| 108 | K108M | 1.64 | 1.15 | 0.55 | 1.20 | 0.84 | 0.50 | 1.50 | 0.99 | 0.64 |
| 108 | K108N | 1.56 | 0.69 | 0.20 | 0.75 | 0.84 | 0.63 | 1.03 | 0.92 | 0.51 |
| 108 | K108R | 0.97 | 0.74 | 0.46 | 0.83 | 1.00 | 0.88 | 1.12 | 1.04 | 0.78 |
| 108 | K108S | 1.56 | 0.91 | 0.20 | 1.04 | 0.92 | 0.95 | 1.31 | 0.96 | 0.58 |
| 108 | K108V | 1.93 | 0.92 | 0.24 | 1.08 | 0.95 | 0.91 | 1.46 | 0.98 | 0.53 |
| 108 | K108Y | 1.26 | 0.73 | 0.11 | 0.79 | 0.79 | 0.57 | 1.35 | 0.83 | 0.51 |
| 110 | G110A | 1.04 | 1.48 | 0.53 | 1.69 | 1.23 | 0.83 | 1.18 | 1.09 | 0.88 |
| 110 | G110C | 0.82 | 0.21 | 0.28 | 0.18 | 0.28 | 0.06 | 0.64 | 0.99 | 0.35 |
| 110 | G110D | 0.98 | 0.47 | 0.18 | 0.39 | 1.07 | 0.71 | 1.11 | 0.90 | 0.55 |
| 110 | G110E | 0.94 | 0.82 | 0.26 | 0.69 | 1.04 | 0.31 | 1.12 | 1.00 | 0.97 |
| 110 | G110F | 0.65 | 0.70 | 0.14 | 0.54 | 0.79 | 1.02 | 0.60 | 0.84 | 0.71 |
| 110 | G110H | 0.74 | 0.17 | 0.18 | 0.15 | 0.75 | 1.08 | 0.70 | 0.69 | 0.99 |
| 110 | G110I | 0.49 | 0.58 | 0.12 | 0.56 | 0.54 | 0.06 | 0.69 | 1.31 | 0.52 |
| 110 | G110K | 0.68 | 0.46 | 0.17 | 0.50 | 1.00 | 0.26 | 0.91 | 1.18 | 0.86 |
| 110 | G110L | 0.61 | 0.37 | 0.11 | 0.32 | 0.78 | 0.22 | 0.88 | 0.93 | 0.71 |
| 110 | G110M | 0.81 | 0.53 | 0.19 | 0.48 | 1.14 | 0.66 | 1.06 | 1.03 | 0.78 |
| 110 | G110P | 0.32 | 0.09 | 0.08 | 0.10 | 0.33 | 0.08 | 0.86 | 1.27 | 0.76 |
| 110 | G110Q | 0.87 | 0.92 | 0.21 | 0.83 | 1.15 | 0.60 | 1.05 | 1.15 | 0.85 |
| 110 | G110R | 0.53 | 0.76 | 0.15 | 1.17 | 0.73 | 0.27 | 0.92 | 1.12 | 0.83 |
| 110 | G110S | 0.91 | 0.97 | 0.27 | 0.95 | 0.95 | 0.96 | 0.96 | 1.01 | 0.86 |
| 110 | G110V | 0.73 | 0.64 | 0.10 | 0.68 | 1.00 | 0.53 | 0.85 | 0.96 | 0.65 |
| 110 | G110W | 0.69 | 0.34 | 0.19 | 0.28 | 0.59 | 0.68 | 0.35 | 0.67 | 0.66 |
| 110 | G110Y | 0.70 | 0.48 | 0.13 | 0.44 | 0.74 | 0.96 | 0.65 | 0.67 | 0.78 |
| 112 | D112A | 0.56 | 0.22 | 0.08 | 0.25 | 0.84 | 0.18 | 0.92 | 0.89 | 0.64 |
| 112 | D112E | 1.28 | 0.46 | 0.21 | 0.49 | 1.14 | 1.05 | 1.13 | 1.12 | 1.13 |
| 112 | D112G | 0.93 | 0.54 | 0.44 | 0.53 | 1.10 | 0.87 | 1.18 | 1.20 | 1.23 |
| 112 | D112H | 0.71 | 0.22 | 0.10 | 0.25 | 0.68 | 0.13 | 0.66 | 0.81 | 0.64 |
| 112 | D112L | 0.65 | 0.20 | 0.10 | 0.20 | 0.95 | 0.44 | 0.92 | 0.91 | 0.65 |
| 112 | D112M | 0.69 | 0.17 | 0.13 | 0.20 | 0.72 | 0.21 | 0.81 | 1.08 | 0.67 |
| 112 | D112N | 0.80 | 0.45 | 0.16 | 0.41 | 1.06 | 1.13 | 1.17 | 0.96 | 1.10 |
| 112 | D112S | 0.68 | 0.37 | 0.08 | 0.40 | 1.07 | 0.26 | 1.00 | 1.02 | 0.90 |
| 112 | D112W | 0.77 | 0.12 | 0.06 | 0.13 | 0.66 | 0.09 | 0.53 | 0.98 | 0.36 |
| 112 | D112Y | 0.72 | 0.20 | 0.19 | 0.22 | 0.74 | 0.07 | 0.90 | 1.08 | 0.51 |
| 113 | G113A | 1.08 | 0.95 | 0.77 | 0.94 | 1.02 | 1.29 | 1.07 | 0.90 | 0.95 |
| 113 | G113D | 0.75 | 0.48 | 1.34 | 0.95 | 0.91 | 0.71 | 0.94 | 0.87 | 0.96 |
| 113 | G113E | 1.41 | 1.07 | 1.44 | 0.95 | 0.92 | 0.69 | 1.03 | 0.84 | 0.95 |
| 113 | G113F | 0.97 | 0.76 | 0.71 | 0.86 | 0.91 | 0.94 | 0.95 | 0.90 | 0.82 |
| 113 | G113H | 0.86 | 0.81 | 0.55 | 1.07 | 1.04 | 0.89 | 1.09 | 0.89 | 1.08 |
| 113 | G113I | 1.04 | 0.84 | 0.40 | 0.79 | 0.98 | 1.18 | 0.76 | 0.83 | 0.68 |
| 113 | G113K | 0.82 | 0.61 | 0.37 | 0.93 | 1.02 | 1.16 | 1.03 | 0.86 | 0.90 |
| 113 | G113L | 1.02 | 0.67 | 0.48 | 0.77 | 0.92 | 0.87 | 0.79 | 0.78 | 0.79 |
| 113 | G113M | 1.25 | 0.82 | 0.67 | 0.89 | 0.82 | 0.88 | 1.01 | 0.84 | 0.85 |
| 113 | G113N | 1.08 | 0.67 | 0.57 | 0.99 | 1.04 | 0.94 | 0.94 | 0.98 | 1.01 |
| 113 | G113Q | 1.33 | 0.97 | 0.76 | 1.09 | 1.40 | 1.09 | 1.06 | 0.95 | 1.03 |
| 113 | G113R | 0.72 | 0.62 | 0.30 | 0.90 | 0.96 | 1.16 | 1.04 | 0.97 | 1.01 |
| 113 | G113S | 0.74 | 0.67 | 0.66 | 0.90 | 0.96 | 0.92 | 0.90 | 0.87 | 0.96 |
| 113 | G113T | 1.25 | 0.78 | 0.57 | 0.84 | 0.77 | 1.00 | 1.13 | 0.91 | 0.83 |
| 113 | G113V | 1.23 | 0.98 | 0.51 | 0.95 | 0.97 | 1.04 | 1.08 | 0.94 | 0.78 |
| 113 | G113W | 1.14 | 0.59 | 0.58 | 0.77 | 0.80 | 0.94 | 0.90 | 0.87 | 0.79 |
| 113 | G113Y | 1.05 | 0.45 | 0.74 | 0.80 | 0.93 | 1.08 | 0.92 | 0.90 | 0.81 |
| 114 | T114A | 0.68 | 0.61 | 0.18 | 0.62 | 0.88 | 0.87 | 0.67 | 0.98 | 1.08 |
| 114 | T114C | 0.87 | 1.23 | 0.28 | 1.35 | 0.79 | 0.51 | 0.55 | 0.99 | 0.84 |
| 114 | T114D | 0.98 | 0.49 | 0.23 | 0.48 | 0.84 | 0.53 | 0.98 | 0.98 | 1.03 |
| 114 | T114E | 0.83 | 0.61 | 0.17 | 0.63 | 0.81 | 0.63 | 0.83 | 1.01 | 1.00 |
| 114 | T114F | 0.80 | 0.56 | 0.33 | 0.54 | 0.82 | 0.77 | 1.03 | 1.05 | 0.90 |
| 114 | T114G | 0.68 | 0.96 | 0.16 | 0.94 | 0.86 | 0.70 | 1.02 | 1.01 | 1.06 |
| 114 | T114H | 0.64 | 0.71 | 0.14 | 0.70 | 0.87 | 0.82 | 0.99 | 1.02 | 1.08 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 114 | T114I | 0.75 | 0.91 | 0.27 | 0.90 | 0.77 | 0.86 | 0.91 | 0.99 | 0.92 |
| 114 | T114K | 0.77 | 1.14 | 0.12 | 1.31 | 0.81 | 1.02 | 1.02 | 0.94 | 1.08 |
| 114 | T114L | 0.94 | 1.48 | 0.49 | 1.54 | 0.83 | 0.68 | 0.98 | 1.02 | 0.92 |
| 114 | T114M | 0.92 | 0.90 | 0.28 | 0.98 | 0.90 | 0.75 | 0.81 | 1.02 | 0.90 |
| 114 | T114N | 0.79 | 0.46 | 0.18 | 0.48 | 0.86 | 0.93 | 0.84 | 0.96 | 1.01 |
| 114 | T114P | 0.89 | 0.45 | 0.19 | 0.55 | 0.78 | 0.92 | 0.76 | 0.90 | 0.97 |
| 114 | T114Q | 0.82 | 1.59 | 0.15 | 1.71 | 0.92 | 0.76 | 1.08 | 1.04 | 0.92 |
| 114 | T114R | 0.80 | 1.27 | 0.11 | 1.52 | 0.96 | 0.98 | 1.02 | 1.01 | 1.08 |
| 114 | T114S | 0.74 | 0.53 | 0.23 | 0.54 | 0.90 | 0.77 | 0.80 | 0.96 | 1.02 |
| 114 | T114V | 0.72 | 1.07 | 0.39 | 1.04 | 0.93 | 0.98 | 1.08 | 1.01 | 0.85 |
| 114 | T114W | 0.90 | 0.46 | 0.30 | 0.46 | 0.75 | 0.64 | 1.05 | 1.05 | 0.94 |
| 114 | T114Y | 0.87 | 0.39 | 0.37 | 0.45 | 0.80 | 0.82 | 0.99 | 0.98 | 0.87 |
| 115 | E115C | 0.29 | 0.35 | 0.15 | 0.38 | 1.04 | 0.89 | 0.69 | 1.11 | 0.69 |
| 115 | E115D | 0.35 | 0.64 | 0.09 | 0.56 | 0.89 | 1.17 | 0.82 | 1.09 | 0.97 |
| 115 | E115Q | 0.49 | 0.89 | 0.10 | 0.84 | 0.99 | 1.17 | 1.04 | 1.06 | 0.98 |
| 116 | F116A | 0.57 | 1.23 | 0.36 | 1.15 | 0.86 | 0.81 | 0.93 | 0.89 | 1.03 |
| 116 | F116C | 0.81 | 1.00 | 1.05 | 0.92 | 0.97 | 0.73 | 0.68 | 0.95 | 0.87 |
| 116 | F116D | 0.82 | 1.10 | 0.58 | 0.94 | 1.03 | 0.62 | 0.88 | 0.98 | 1.00 |
| 116 | F116E | 0.79 | 1.14 | 0.78 | 0.99 | 0.98 | 0.76 | 0.81 | 1.01 | 0.96 |
| 116 | F116G | 0.58 | 1.26 | 0.28 | 1.17 | 1.05 | 1.01 | 0.94 | 1.07 | 0.90 |
| 116 | F116H | 0.73 | 1.25 | 0.44 | 1.05 | 1.06 | 1.00 | 0.85 | 1.03 | 0.98 |
| 116 | F116I | 0.78 | 1.01 | 0.71 | 1.00 | 1.04 | 1.01 | 0.90 | 1.07 | 0.95 |
| 116 | F116K | 0.71 | 1.00 | 0.39 | 0.98 | 1.09 | 1.08 | 1.01 | 1.04 | 0.87 |
| 116 | F116L | 0.70 | 1.05 | 0.87 | 0.93 | 1.01 | 0.93 | 0.72 | 0.99 | 0.98 |
| 116 | F116M | 0.83 | 0.97 | 0.88 | 0.96 | 1.01 | 0.67 | 0.95 | 1.02 | 0.99 |
| 116 | F116N | 0.81 | 1.08 | 0.52 | 1.04 | 1.00 | 0.63 | 0.77 | 1.06 | 1.09 |
| 116 | F116P | 0.58 | 1.13 | 0.40 | 1.11 | 1.06 | 1.00 | 0.92 | 0.99 | 1.02 |
| 116 | F116Q | 0.74 | 1.12 | 0.55 | 1.09 | 1.01 | 1.05 | 1.15 | 1.05 | 0.99 |
| 116 | F116R | 1.43 | 1.08 | 0.22 | 1.09 | 1.21 | 1.21 | 0.90 | 1.05 | 1.00 |
| 116 | F116S | 0.66 | 1.15 | 0.35 | 1.17 | 1.04 | 1.05 | 0.91 | 1.01 | 1.08 |
| 116 | F116T | 0.75 | 1.01 | 0.65 | 1.05 | 1.03 | 0.94 | 0.87 | 0.97 | 1.01 |
| 116 | F116V | 0.77 | 0.99 | 0.82 | 0.97 | 0.97 | 0.88 | 0.95 | 0.99 | 1.03 |
| 116 | F116W | 0.96 | 1.07 | 2.02 | 1.00 | 1.11 | 0.90 | 0.91 | 0.96 | 1.01 |
| 116 | F116Y | 0.77 | 1.20 | 0.93 | 1.00 | 1.08 | 0.88 | 0.84 | 1.05 | 0.98 |
| 118 | D118A | 0.60 | 1.16 | 0.23 | 1.02 | 1.06 | 1.59 | 0.47 | 0.99 | 0.60 |
| 118 | D118C | 1.05 | 0.54 | 2.15 | 0.46 | 0.54 | 0.73 | 0.62 | 0.77 | 0.55 |
| 118 | D118E | 0.66 | 0.87 | 0.79 | 0.86 | 0.93 | 1.01 | 0.94 | 0.90 | 0.81 |
| 118 | D118F | 0.76 | 0.58 | 0.64 | 0.54 | 0.76 | 1.03 | 0.64 | 0.63 | 0.61 |
| 118 | D118G | 0.54 | 0.63 | 0.09 | 0.61 | 0.79 | 1.32 | 0.60 | 0.84 | 0.57 |
| 118 | D118H | 0.55 | 0.82 | 0.25 | 0.81 | 0.89 | 1.23 | 0.68 | 0.93 | 0.82 |
| 118 | D118I | 0.38 | 0.40 | 0.14 | 0.41 | 0.69 | 1.26 | 0.60 | 0.78 | 0.47 |
| 118 | D118K | 0.71 | 0.79 | 0.13 | 0.80 | 0.96 | 1.55 | 0.84 | 1.01 | 0.71 |
| 118 | D118L | 0.73 | 0.49 | 0.65 | 0.51 | 0.88 | 1.29 | 0.41 | 0.84 | 0.49 |
| 118 | D118M | 0.72 | 0.41 | 0.96 | 0.43 | 0.77 | 0.91 | 0.57 | 0.77 | 0.49 |
| 118 | D118N | 0.62 | 1.07 | 0.36 | 0.96 | 0.88 | 1.29 | 0.79 | 0.86 | 0.97 |
| 118 | D118P | 1.05 | 0.98 | 0.59 | 1.01 | 0.92 | 1.24 | 0.89 | 0.91 | 0.89 |
| 118 | D118Q | 0.60 | 0.83 | 0.37 | 0.81 | 0.89 | 1.10 | 0.75 | 0.90 | 0.83 |
| 118 | D118S | 0.60 | 0.77 | 0.26 | 0.79 | 0.88 | 1.10 | 0.71 | 0.92 | 0.86 |
| 118 | D118T | 0.47 | 0.64 | 0.18 | 0.66 | 0.79 | 0.99 | 0.92 | 0.97 | 0.62 |
| 118 | D118V | 0.39 | 0.22 | 0.14 | 0.21 | 0.71 | 0.92 | 0.53 | 0.60 | 0.26 |
| 118 | D118W | 0.74 | 0.66 | 1.23 | 0.63 | 0.95 | 1.38 | 0.83 | 0.91 | 0.60 |
| 118 | D118Y | 0.65 | 0.41 | 0.53 | 0.43 | 0.82 | 0.77 | 0.61 | 0.81 | 0.49 |
| 121 | E121Q | 0.51 | 0.69 | 0.09 | 0.77 | 0.84 | 1.02 | 0.90 | 1.00 | 0.76 |
| 121 | E121T | 0.82 | 0.65 | 0.20 | 0.70 | 0.85 | 0.95 | 0.86 | 1.03 | 0.74 |
| 123 | D123A | 0.71 | 1.14 | 0.42 | 1.07 | 0.91 | 1.20 | 0.97 | 1.03 | 1.01 |
| 123 | D123E | 0.73 | 1.07 | 0.35 | 1.04 | 0.97 | 0.98 | 0.84 | 0.86 | 0.99 |
| 123 | D123H | 0.61 | 0.99 | 0.37 | 0.98 | 0.97 | 1.14 | 0.72 | 0.89 | 0.97 |
| 123 | D123K | 0.57 | 0.89 | 0.13 | 0.93 | 0.83 | 1.21 | 0.71 | 0.83 | 0.98 |
| 123 | D123L | 0.82 | 0.86 | 0.32 | 0.88 | 1.00 | 0.98 | 1.04 | 0.99 | 0.77 |
| 123 | D123M | 0.62 | 0.94 | 0.29 | 0.91 | 0.87 | 1.12 | 0.90 | 0.87 | 0.89 |
| 123 | D123Q | 0.54 | 0.92 | 0.12 | 0.98 | 0.91 | 1.17 | 0.85 | 0.91 | 0.95 |
| 123 | D123R | 0.42 | 0.91 | 0.07 | 0.90 | 0.78 | 1.89 | 0.71 | 0.82 | 0.90 |
| 123 | D123S | 0.79 | 0.90 | 0.59 | 0.92 | 0.83 | 1.28 | 0.74 | 0.85 | 0.90 |
| 123 | D123W | 0.34 | 0.71 | 0.06 | 0.69 | 0.85 | 1.16 | 0.72 | 0.89 | 0.73 |
| 125 | S125A | 0.96 | 0.93 | 1.19 | 0.92 | 1.16 | 1.05 | 0.69 | 1.13 | 1.03 |
| 125 | S125C | 0.72 | 0.69 | 1.34 | 0.60 | 1.05 | 0.63 | 0.89 | 1.03 | 0.70 |
| 125 | S125D | 0.47 | 0.90 | 0.61 | 0.81 | 1.08 | 0.84 | 0.90 | 0.97 | 0.93 |
| 125 | S125E | 0.93 | 1.36 | 0.74 | 1.25 | 1.01 | 0.73 | 0.89 | 1.08 | 0.95 |
| 125 | S125F | 0.96 | 1.01 | 1.52 | 0.88 | 1.04 | 0.96 | 0.81 | 1.02 | 0.96 |
| 125 | S125G | 0.92 | 0.89 | 0.78 | 0.92 | 1.12 | 0.98 | 0.91 | 1.04 | 0.99 |
| 125 | S125H | 0.91 | 0.89 | 1.23 | 0.93 | 1.11 | 1.09 | 0.79 | 0.94 | 0.99 |
| 125 | S125I | 0.56 | 0.88 | 0.40 | 0.91 | 1.07 | 0.95 | 0.72 | 1.03 | 0.92 |
| 125 | S125K | 0.93 | 1.08 | 1.58 | 0.89 | 1.01 | 1.06 | 0.76 | 0.96 | 1.02 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 125 | S125L | 0.84 | 0.55 | 1.41 | 0.50 | 1.06 | 0.74 | 0.75 | 0.94 | 0.46 |
| 125 | S125M | 1.01 | 0.69 | 1.37 | 0.77 | 0.83 | 0.91 | 1.05 | 0.91 | 0.82 |
| 125 | S125N | 0.88 | 0.89 | 1.28 | 0.86 | 1.03 | 0.96 | 0.96 | 0.86 | 0.98 |
| 125 | S125Q | 0.89 | 0.94 | 1.11 | 0.94 | 0.97 | 1.07 | 0.74 | 1.06 | 0.95 |
| 125 | S125R | 0.88 | 1.01 | 1.23 | 0.92 | 0.97 | 1.32 | 0.51 | 0.95 | 1.05 |
| 125 | S125T | 0.89 | 0.81 | 1.43 | 0.74 | 1.01 | 0.91 | 0.86 | 0.98 | 0.72 |
| 125 | S125V | 0.57 | 0.78 | 0.56 | 0.81 | 1.07 | 0.86 | 0.66 | 0.98 | 0.82 |
| 125 | S125W | 0.64 | 0.64 | 0.44 | 0.62 | 1.04 | 0.86 | 0.60 | 1.07 | 0.57 |
| 125 | S125Y | 0.97 | 1.23 | 1.32 | 1.02 | 1.09 | 1.29 | 0.94 | 0.96 | 0.94 |
| 126 | N126C | 0.37 | 0.86 | 0.08 | 0.81 | 0.77 | 0.39 | 0.84 | 1.19 | 0.72 |
| 126 | N126D | 1.84 | 1.04 | 1.52 | 0.96 | 0.81 | 0.82 | 0.98 | 0.94 | 0.99 |
| 126 | N126E | 0.63 | 1.10 | 0.10 | 1.03 | 0.97 | 0.80 | 0.79 | 1.02 | 0.93 |
| 128 | N128C | 3.90 | 0.70 | 2.31 | 0.69 | 0.94 | 0.36 | 1.41 | 1.56 | 0.66 |
| 128 | N128D | 0.84 | 1.05 | 0.62 | 0.93 | 0.99 | 0.74 | 0.99 | 1.04 | 0.94 |
| 128 | N128E | 0.91 | 0.98 | 0.69 | 0.97 | 1.07 | 0.41 | 1.09 | 1.42 | 0.87 |
| 128 | N128L | 0.43 | 0.89 | 0.76 | 0.92 | 1.15 | 0.35 | 1.32 | 1.30 | 0.83 |
| 128 | N128M | 0.41 | 0.89 | 0.59 | 0.91 | 1.05 | 0.40 | 1.26 | 1.25 | 0.82 |
| 128 | N128Q | 0.18 | 0.96 | 0.08 | 0.97 | 1.23 | 0.70 | 1.09 | 1.45 | 0.93 |
| 128 | N128T | 0.25 | 0.86 | 0.21 | 0.89 | 1.10 | 0.56 | 0.85 | 1.26 | 0.89 |
| 128 | N128V | 0.15 | 0.90 | 0.08 | 0.91 | 1.16 | 0.49 | 1.27 | 1.29 | 0.82 |
| 128 | N128W | 1.43 | 1.14 | 0.88 | 1.00 | 1.12 | 1.17 | 1.14 | 0.95 | 0.87 |
| 128 | N128Y | 2.25 | 0.96 | 0.95 | 0.95 | 1.15 | 0.55 | 1.21 | 1.34 | 0.82 |
| 129 | Q129A | 0.49 | 0.58 | 0.86 | 0.58 | 0.68 | 0.53 | 1.00 | 0.76 | 0.62 |
| 129 | Q129C | 0.98 | 0.49 | 2.59 | 0.47 | 0.80 | 0.40 | 0.99 | 1.15 | 0.48 |
| 129 | Q129D | 0.65 | 0.81 | 0.38 | 0.77 | 0.86 | 0.68 | 1.12 | 0.95 | 0.84 |
| 129 | Q129E | 0.94 | 0.52 | 0.49 | 0.56 | 1.02 | 0.37 | 0.99 | 1.12 | 0.52 |
| 129 | Q129F | 0.75 | 0.92 | 0.80 | 0.85 | 0.91 | 0.88 | 1.04 | 0.98 | 0.77 |
| 129 | Q129H | 0.60 | 0.58 | 1.05 | 0.73 | 0.87 | 0.69 | 0.91 | 0.91 | 0.84 |
| 129 | Q129I | 1.28 | 0.91 | 1.78 | 0.85 | 0.91 | 0.70 | 0.88 | 0.94 | 0.87 |
| 129 | Q129K | 0.79 | 0.76 | 1.10 | 0.79 | 0.84 | 0.93 | 1.01 | 0.90 | 0.82 |
| 129 | Q129L | 1.07 | 0.78 | 1.48 | 0.75 | 1.02 | 0.93 | 0.91 | 1.04 | 0.71 |
| 129 | Q129M | 0.92 | 0.80 | 1.25 | 0.78 | 0.97 | 0.73 | 1.03 | 0.97 | 0.74 |
| 129 | Q129N | 0.88 | 0.92 | 0.89 | 0.90 | 0.82 | 0.86 | 1.01 | 0.91 | 1.03 |
| 129 | Q129R | 0.76 | 0.91 | 1.18 | 0.79 | 0.90 | 1.13 | 0.79 | 1.01 | 0.67 |
| 129 | Q129S | 0.48 | 0.56 | 0.41 | 0.75 | 0.97 | 0.95 | 0.84 | 1.05 | 0.52 |
| 129 | Q129T | 0.76 | 0.76 | 0.62 | 0.78 | 1.05 | 0.82 | 1.04 | 1.04 | 0.71 |
| 129 | Q129V | 1.17 | 0.54 | 1.94 | 0.80 | 0.99 | 0.91 | 1.07 | 1.02 | 0.67 |
| 129 | Q129W | 0.69 | 0.78 | 0.48 | 0.80 | 0.89 | 1.03 | 0.83 | 1.02 | 0.77 |
| 130 | E130A | 1.32 | 0.70 | 0.29 | 0.75 | 1.05 | 0.51 | 0.99 | 1.19 | 0.87 |
| 130 | E130C | 1.43 | 0.70 | 0.39 | 0.63 | 0.94 | 0.23 | 1.03 | 1.31 | 0.75 |
| 130 | E130G | 0.75 | 0.79 | 0.11 | 0.74 | 0.99 | 0.53 | 0.95 | 1.04 | 1.01 |
| 130 | E130H | 0.90 | 0.75 | 0.08 | 0.80 | 0.94 | 0.73 | 0.90 | 1.05 | 0.99 |
| 130 | E130I | 0.89 | 0.89 | 0.17 | 0.87 | 1.07 | 0.62 | 1.00 | 1.06 | 0.83 |
| 130 | E130K | 1.75 | 0.73 | 0.75 | 0.85 | 0.96 | 0.65 | 0.92 | 1.15 | 1.01 |
| 130 | E130M | 0.84 | 0.81 | 0.09 | 0.79 | 1.01 | 0.44 | 0.90 | 1.08 | 0.99 |
| 130 | E130N | 0.50 | 0.87 | 0.09 | 0.79 | 0.86 | 0.64 | 0.99 | 1.02 | 1.02 |
| 130 | E130Q | 0.53 | 0.93 | 0.06 | 0.92 | 1.01 | 0.71 | 1.02 | 1.12 | 1.03 |
| 130 | E130R | 0.73 | 0.86 | 0.21 | 0.80 | 0.80 | 1.01 | 0.98 | 0.88 | 0.99 |
| 130 | E130S | 0.60 | 0.74 | 0.09 | 0.74 | 1.03 | 0.55 | 1.12 | 1.03 | 0.95 |
| 130 | E130T | 0.50 | 0.94 | 0.09 | 0.81 | 0.99 | 0.57 | 0.95 | 1.09 | 0.96 |
| 130 | E130W | 0.85 | 0.70 | 0.11 | 0.63 | 0.90 | 0.81 | 1.00 | 1.10 | 0.83 |
| 130 | E130Y | 0.66 | 0.68 | 0.08 | 0.68 | 0.96 | 0.52 | 1.13 | 1.14 | 0.85 |
| 131 | T131A | 0.40 | 1.02 | 0.14 | 0.96 | 1.08 | 0.92 | 1.06 | 0.97 | 1.03 |
| 131 | T131C | 0.66 | 0.85 | 0.63 | 0.82 | 0.90 | 0.70 | 0.84 | 1.03 | 0.84 |
| 131 | T131I | 1.68 | 0.94 | 2.12 | 0.98 | 1.03 | 0.91 | 1.04 | 0.96 | 0.90 |
| 131 | T131K | 0.50 | 0.32 | 0.25 | 0.32 | 1.11 | 1.08 | 0.69 | 1.00 | 0.21 |
| 131 | T131M | 0.89 | 0.85 | 0.93 | 0.93 | 1.17 | 1.02 | 1.01 | 0.86 | 0.85 |
| 131 | T131N | 0.38 | 0.96 | 0.12 | 0.95 | 0.95 | 0.86 | 1.08 | 0.96 | 0.99 |
| 131 | T131Q | 0.58 | 0.94 | 0.26 | 0.94 | 0.96 | 0.86 | 1.12 | 0.94 | 0.90 |
| 131 | T131R | 0.43 | 1.03 | 0.21 | 0.99 | 1.08 | 1.22 | 0.82 | 0.89 | 1.04 |
| 131 | T131S | 0.53 | 0.96 | 0.15 | 0.99 | 1.06 | 0.87 | 0.97 | 0.94 | 0.94 |
| 131 | T131V | 1.42 | 0.46 | 1.23 | 0.52 | 1.08 | 0.95 | 1.17 | 1.07 | 0.40 |
| 131 | T131W | 0.43 | 1.02 | 0.08 | 0.98 | 1.07 | 1.08 | 0.99 | 0.94 | 0.84 |
| 132 | S132T | 0.65 | 0.88 | 0.29 | 0.88 | 0.83 | 0.88 | 0.99 | 0.98 | 1.01 |
| 134 | T134A | 0.98 | 1.09 | 0.80 | 0.98 | 1.17 | 1.30 | 1.02 | 1.04 | 1.09 |
| 134 | T134C | 1.53 | 0.81 | 1.17 | 0.78 | 0.98 | 0.74 | 0.67 | 1.08 | 0.88 |
| 134 | T134D | 1.40 | 0.98 | 0.59 | 1.03 | 0.92 | 0.82 | 0.76 | 1.04 | 1.14 |
| 134 | T134E | 1.03 | 0.96 | 0.76 | 0.94 | 1.03 | 0.74 | 1.01 | 1.06 | 1.03 |
| 134 | T134G | 0.92 | 0.88 | 0.29 | 0.93 | 1.18 | 0.64 | 0.89 | 1.14 | 1.08 |
| 134 | T134H | 0.64 | 0.87 | 0.14 | 0.95 | 1.12 | 0.74 | 0.93 | 1.14 | 1.20 |
| 134 | T134I | 0.92 | 0.89 | 1.05 | 0.84 | 1.04 | 0.88 | 0.81 | 0.94 | 1.04 |
| 134 | T134K | 0.45 | 1.10 | 0.12 | 0.93 | 1.05 | 0.92 | 0.97 | 0.89 | 1.25 |
| 134 | T134L | 0.52 | 0.80 | 0.25 | 0.84 | 1.02 | 0.81 | 1.15 | 0.90 | 1.01 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 134 | T134M | 0.77 | 0.90 | 0.57 | 0.85 | 1.10 | 0.78 | 0.86 | 0.93 | 1.01 |
| 134 | T134N | 0.77 | 1.09 | 0.26 | 1.05 | 1.19 | 0.78 | 1.04 | 1.01 | 1.22 |
| 134 | T134P | 1.52 | 1.03 | 1.86 | 1.01 | 0.96 | 0.78 | 0.97 | 0.95 | 1.37 |
| 134 | T134Q | 0.80 | 1.07 | 0.49 | 1.02 | 1.17 | 0.87 | 1.15 | 1.07 | 1.18 |
| 134 | T134S | 0.80 | 1.02 | 0.48 | 0.95 | 1.13 | 0.94 | 0.89 | 0.98 | 1.07 |
| 134 | T134Y | 0.16 | 0.87 | 0.06 | 0.83 | 1.08 | 0.82 | 1.02 | 1.04 | 0.89 |
| 135 | Y135C | 0.20 | 0.43 | 0.13 | 0.80 | 1.08 | 0.73 | 1.00 | 0.76 | 1.07 |
| 135 | Y135E | 0.19 | 0.57 | 0.06 | 1.04 | 1.03 | 0.86 | 1.08 | 0.95 | 1.31 |
| 135 | Y135F | 0.35 | 0.48 | 0.25 | 0.96 | 1.13 | 0.90 | 1.05 | 0.99 | 1.05 |
| 135 | Y135H | 0.30 | 0.77 | 0.07 | 1.02 | 1.00 | 0.90 | 1.05 | 0.92 | 1.44 |
| 135 | Y135I | 0.24 | 0.43 | 0.50 | 0.89 | 1.18 | 1.08 | 0.88 | 0.98 | 0.94 |
| 135 | Y135K | 0.29 | 0.79 | 0.09 | 1.05 | 0.98 | 0.98 | 1.06 | 0.87 | 1.42 |
| 135 | Y135L | 0.47 | 0.84 | 0.34 | 0.87 | 1.12 | 0.90 | 1.23 | 1.04 | 0.94 |
| 135 | Y135M | 0.24 | 0.45 | 0.35 | 0.85 | 1.07 | 0.96 | 1.02 | 0.92 | 1.03 |
| 135 | Y135Q | 0.24 | 0.51 | 0.12 | 1.06 | 1.09 | 1.01 | 1.04 | 0.99 | 1.41 |
| 135 | Y135V | 0.42 | 0.67 | 0.23 | 0.88 | 1.09 | 0.97 | 0.93 | 0.98 | 0.84 |
| 136 | Q136A | 0.75 | 0.93 | 0.37 | 0.99 | 1.07 | 1.04 | 1.09 | 0.72 | 1.17 |
| 136 | Q136C | 1.03 | 0.82 | 1.05 | 0.77 | 0.89 | 0.60 | 0.92 | 0.96 | 1.00 |
| 136 | Q136D | 0.78 | 1.01 | 0.24 | 1.02 | 0.93 | 0.73 | 0.85 | 0.97 | 1.25 |
| 136 | Q136E | 1.03 | 0.96 | 0.89 | 0.85 | 0.79 | 0.64 | 1.07 | 0.95 | 1.07 |
| 136 | Q136F | 0.58 | 0.89 | 0.10 | 0.83 | 0.92 | 0.71 | 1.10 | 0.90 | 1.19 |
| 136 | Q136G | 0.77 | 1.16 | 0.30 | 1.10 | 1.04 | 0.90 | 1.22 | 0.96 | 1.38 |
| 136 | Q136H | 0.59 | 0.96 | 0.13 | 0.92 | 1.10 | 0.86 | 1.42 | 1.02 | 1.22 |
| 136 | Q136I | 0.84 | 0.72 | 0.83 | 0.69 | 1.04 | 0.84 | 1.22 | 0.80 | 0.96 |
| 136 | Q136K | 0.87 | 1.03 | 1.10 | 1.00 | 0.95 | 0.96 | 1.21 | 0.83 | 1.42 |
| 136 | Q136L | 0.90 | 0.57 | 0.84 | 0.55 | 0.90 | 0.73 | 0.65 | 0.88 | 0.75 |
| 136 | Q136M | 0.92 | 0.82 | 0.94 | 0.77 | 0.93 | 0.74 | 0.95 | 0.90 | 1.15 |
| 136 | Q136N | 0.88 | 1.05 | 0.44 | 0.99 | 0.99 | 0.78 | 1.16 | 0.90 | 1.46 |
| 140 | W140I | 0.64 | 0.15 | 0.18 | 0.16 | 0.12 | 0.18 | 0.64 | 1.09 | 0.59 |
| 140 | W140M | 0.56 | 0.39 | 0.16 | 0.40 | 0.18 | 0.22 | 0.95 | 1.32 | 0.63 |
| 140 | W140N | 0.68 | 0.24 | 0.15 | 0.27 | 0.25 | 0.07 | 1.02 | 1.24 | 0.81 |
| 140 | W140P | 0.39 | 0.23 | 0.07 | 0.25 | 0.21 | 0.06 | 1.08 | 1.21 | 0.84 |
| 140 | W140R | 0.41 | 0.75 | 0.13 | 0.83 | 0.66 | 0.15 | 0.98 | 1.37 | 0.72 |
| 140 | W140S | 0.61 | 0.20 | 0.14 | 0.22 | 0.21 | 0.23 | 1.12 | 1.38 | 0.65 |
| 140 | W140T | 0.62 | 0.11 | 0.13 | 0.13 | 0.17 | 0.09 | 0.90 | 1.30 | 0.59 |
| 140 | W140V | 0.70 | 0.14 | 0.19 | 0.16 | 0.16 | 0.26 | 0.90 | 1.16 | 0.74 |
| 140 | W140Y | 0.85 | 2.17 | 0.30 | 2.27 | 1.01 | 0.45 | 1.16 | 1.17 | 0.67 |
| 142 | K142A | 1.20 | 0.89 | 0.68 | 0.91 | 1.02 | 0.84 | 0.97 | 1.00 | 0.83 |
| 142 | K142C | 1.43 | 1.02 | 0.85 | 0.94 | 0.93 | 0.63 | 1.03 | 0.97 | 0.70 |
| 142 | K142D | 0.82 | 0.87 | 0.23 | 0.81 | 0.65 | 0.70 | 0.89 | 0.95 | 0.71 |
| 142 | K142E | 1.19 | 0.91 | 0.58 | 0.83 | 0.93 | 0.68 | 0.95 | 0.98 | 0.75 |
| 142 | K142F | 1.06 | 1.11 | 0.60 | 1.01 | 0.98 | 0.86 | 1.03 | 0.84 | 0.72 |
| 142 | K142G | 0.97 | 0.92 | 0.37 | 0.94 | 0.94 | 0.69 | 0.86 | 0.90 | 0.84 |
| 142 | K142H | 1.00 | 1.10 | 0.44 | 1.05 | 0.97 | 0.73 | 0.96 | 0.99 | 0.90 |
| 142 | K142I | 1.12 | 1.13 | 0.74 | 0.98 | 1.01 | 0.70 | 0.87 | 1.04 | 0.86 |
| 142 | K142L | 1.21 | 1.04 | 0.93 | 0.90 | 1.05 | 0.88 | 1.06 | 1.05 | 0.66 |
| 142 | K142M | 1.02 | 0.99 | 0.84 | 0.86 | 0.97 | 0.76 | 0.88 | 1.03 | 0.73 |
| 142 | K142N | 0.73 | 0.98 | 0.30 | 0.89 | 1.01 | 0.87 | 0.99 | 1.02 | 0.85 |
| 142 | K142P | 1.51 | 1.60 | 0.46 | 1.53 | 0.85 | 0.35 | 1.14 | 0.89 | 0.54 |
| 142 | K142Q | 1.22 | 1.13 | 0.71 | 1.09 | 1.00 | 0.75 | 0.80 | 1.03 | 0.85 |
| 142 | K142S | 1.15 | 0.83 | 0.59 | 0.81 | 0.99 | 1.03 | 1.22 | 1.03 | 0.68 |
| 142 | K142T | 0.91 | 0.72 | 0.36 | 0.71 | 1.04 | 0.61 | 1.06 | 0.95 | 0.71 |
| 142 | K142V | 1.18 | 0.93 | 0.94 | 0.91 | 1.03 | 0.72 | 1.09 | 0.92 | 0.83 |
| 142 | K142W | 1.22 | 1.04 | 0.72 | 0.96 | 0.94 | 0.76 | 0.98 | 0.92 | 0.77 |
| 142 | K142Y | 0.96 | 0.96 | 0.74 | 0.91 | 1.01 | 0.98 | 1.03 | 1.03 | 0.69 |
| 144 | D144A | 0.64 | 0.90 | 0.09 | 0.97 | 0.95 | 1.11 | 1.03 | 1.00 | 1.13 |
| 144 | D144C | 0.72 | 0.76 | 0.56 | 0.74 | 0.84 | 0.69 | 0.81 | 0.82 | 0.82 |
| 144 | D144E | 1.00 | 0.74 | 0.57 | 0.84 | 0.88 | 0.94 | 0.98 | 0.91 | 0.90 |
| 144 | D144F | 0.73 | 1.00 | 0.17 | 1.00 | 0.90 | 1.10 | 1.02 | 0.99 | 1.02 |
| 144 | D144G | 0.82 | 0.79 | 0.11 | 0.93 | 0.95 | 1.15 | 0.93 | 0.94 | 1.05 |
| 144 | D144H | 0.73 | 0.80 | 0.13 | 0.88 | 0.80 | 1.09 | 0.91 | 0.90 | 1.11 |
| 144 | D144I | 0.72 | 0.85 | 0.19 | 0.90 | 0.95 | 1.11 | 0.95 | 1.03 | 0.98 |
| 144 | D144K | 0.87 | 0.73 | 0.13 | 0.85 | 0.79 | 1.50 | 0.79 | 0.81 | 1.13 |
| 144 | D144L | 0.70 | 0.80 | 0.18 | 0.89 | 0.90 | 1.04 | 0.91 | 0.93 | 1.08 |
| 144 | D144M | 0.77 | 0.85 | 0.18 | 0.90 | 0.92 | 1.07 | 0.90 | 0.91 | 1.12 |
| 144 | D144N | 0.90 | 0.93 | 0.28 | 0.97 | 0.96 | 1.09 | 1.06 | 1.00 | 1.15 |
| 144 | D144P | 0.90 | 0.35 | 0.12 | 0.40 | 0.60 | 0.86 | 0.63 | 0.77 | 0.59 |
| 144 | D144R | 0.74 | 0.78 | 0.09 | 0.82 | 0.89 | 1.37 | 0.74 | 0.87 | 1.02 |
| 144 | D144S | 0.74 | 0.74 | 0.15 | 0.87 | 0.79 | 0.94 | 0.77 | 1.02 | 0.99 |
| 144 | D144T | 0.78 | 0.80 | 0.26 | 0.88 | 0.88 | 0.97 | 0.87 | 0.96 | 0.95 |
| 144 | D144V | 0.81 | 0.75 | 0.23 | 0.86 | 0.92 | 1.03 | 0.87 | 0.86 | 1.05 |
| 144 | D144W | 0.78 | 0.95 | 0.25 | 0.96 | 0.91 | 1.20 | 0.83 | 1.05 | 1.26 |
| 144 | D144Y | 0.72 | 0.80 | 0.20 | 0.85 | 1.16 | 1.18 | 0.63 | 0.94 | 1.00 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 147 | G147A | 0.91 | 0.97 | 0.43 | 0.96 | 0.98 | 0.75 | 0.52 | 0.89 | 0.68 |
| 147 | G147C | 0.92 | 0.75 | 0.45 | 0.72 | 0.79 | 0.61 | 0.74 | 0.54 | 0.55 |
| 147 | G147D | 1.02 | 0.97 | 0.49 | 0.96 | 0.95 | 0.64 | 0.86 | 0.77 | 0.70 |
| 147 | G147E | 1.05 | 0.84 | 0.48 | 0.93 | 0.90 | 0.68 | 0.78 | 0.68 | 0.70 |
| 147 | G147F | 0.94 | 1.00 | 0.38 | 0.93 | 1.01 | 0.85 | 0.79 | 0.88 | 0.68 |
| 147 | G147H | 0.95 | 1.01 | 0.35 | 0.98 | 0.85 | 1.26 | 0.72 | 0.90 | 0.78 |
| 147 | G147K | 0.93 | 0.85 | 0.30 | 0.84 | 0.98 | 0.94 | 0.96 | 0.85 | 0.71 |
| 147 | G147L | 0.82 | 0.93 | 0.34 | 0.86 | 1.09 | 0.80 | 0.85 | 0.77 | 0.67 |
| 147 | G147M | 0.92 | 0.92 | 0.42 | 0.90 | 0.90 | 0.83 | 0.79 | 0.79 | 0.71 |
| 147 | G147N | 0.99 | 0.93 | 0.49 | 0.94 | 0.94 | 0.83 | 0.79 | 0.83 | 0.84 |
| 147 | G147P | 0.94 | 0.69 | 0.33 | 0.71 | 0.95 | 0.85 | 0.92 | 0.85 | 0.57 |
| 147 | G147Q | 0.92 | 0.72 | 0.43 | 0.75 | 1.04 | 0.91 | 0.85 | 1.08 | 0.51 |
| 147 | G147R | 0.86 | 0.93 | 0.27 | 0.85 | 1.05 | 1.30 | 0.81 | 0.87 | 0.75 |
| 147 | G147S | 1.04 | 0.78 | 0.39 | 0.88 | 0.91 | 0.87 | 0.94 | 0.81 | 0.68 |
| 147 | G147T | 0.83 | 0.96 | 0.39 | 0.88 | 1.04 | 0.87 | 0.93 | 0.81 | 0.63 |
| 147 | G147V | 0.89 | 0.86 | 0.37 | 0.82 | 0.91 | 0.80 | 0.94 | 0.86 | 0.65 |
| 147 | G147W | 1.01 | 0.90 | 0.35 | 0.88 | 0.99 | 0.95 | 1.21 | 0.89 | 0.69 |
| 147 | G147Y | 0.88 | 1.08 | 0.37 | 0.96 | 0.87 | 0.96 | 0.81 | 0.84 | 0.66 |
| 149 | G149A | 0.90 | 1.02 | 0.73 | 1.02 | 1.12 | 1.07 | 1.03 | 0.98 | 0.89 |
| 149 | G149C | 0.85 | 0.62 | 0.68 | 0.56 | 0.88 | 0.63 | 0.70 | 0.73 | 0.54 |
| 149 | G149D | 0.96 | 0.97 | 0.87 | 0.92 | 0.98 | 0.73 | 0.90 | 0.77 | 0.98 |
| 149 | G149E | 0.97 | 0.93 | 0.76 | 0.94 | 0.79 | 0.68 | 0.87 | 0.74 | 0.97 |
| 149 | G149F | 0.93 | 1.04 | 0.59 | 0.98 | 0.92 | 0.79 | 0.96 | 0.77 | 0.98 |
| 149 | G149H | 0.94 | 1.00 | 0.57 | 1.03 | 0.98 | 0.98 | 0.85 | 0.81 | 1.12 |
| 149 | G149I | 0.85 | 0.99 | 0.40 | 0.96 | 1.24 | 1.03 | 0.96 | 0.92 | 0.92 |
| 149 | G149L | 1.08 | 0.91 | 0.51 | 1.04 | 1.14 | 0.91 | 0.84 | 0.85 | 0.98 |
| 149 | G149M | 0.99 | 1.02 | 0.67 | 1.03 | 1.12 | 0.81 | 0.79 | 0.90 | 1.01 |
| 149 | G149N | 0.96 | 1.06 | 0.89 | 1.03 | 1.12 | 0.72 | 0.85 | 0.84 | 1.16 |
| 149 | G149P | 0.79 | 0.86 | 0.30 | 0.90 | 0.94 | 0.81 | 0.76 | 0.79 | 1.06 |
| 149 | G149Q | 0.92 | 1.01 | 0.63 | 1.07 | 0.98 | 0.84 | 0.78 | 0.86 | 1.07 |
| 149 | G149R | 1.11 | 0.95 | 0.49 | 0.99 | 1.11 | 1.18 | 1.04 | 0.99 | 0.95 |
| 149 | G149S | 0.87 | 0.50 | 0.63 | 0.48 | 0.92 | 0.58 | 0.83 | 0.58 | 0.50 |
| 149 | G149V | 0.87 | 1.03 | 0.45 | 0.98 | 1.19 | 0.95 | 0.89 | 0.80 | 0.90 |
| 149 | G149W | 1.11 | 1.00 | 0.47 | 1.04 | 1.11 | 0.90 | 0.85 | 0.92 | 1.03 |
| 149 | G149Y | 0.92 | 1.19 | 0.51 | 1.08 | 1.04 | 0.97 | 0.84 | 0.90 | 0.99 |
| 150 | N150A | 0.87 | 0.94 | 0.53 | 0.97 | 0.93 | 0.95 | 0.83 | 0.84 | 0.94 |
| 150 | N150C | 0.82 | 0.91 | 0.68 | 0.76 | 0.83 | 0.58 | 0.81 | 1.01 | 0.83 |
| 150 | N150D | 0.98 | 1.04 | 1.21 | 0.97 | 0.95 | 0.78 | 1.01 | 0.92 | 1.13 |
| 150 | N150E | 1.02 | 0.84 | 0.97 | 0.91 | 0.85 | 0.79 | 1.08 | 0.96 | 0.96 |
| 150 | N150F | 1.06 | 0.93 | 0.48 | 0.93 | 1.03 | 0.80 | 1.16 | 1.07 | 0.95 |
| 150 | N150G | 0.99 | 0.92 | 0.66 | 0.98 | 0.98 | 0.80 | 1.11 | 1.02 | 1.07 |
| 150 | N150H | 0.95 | 1.04 | 0.53 | 1.04 | 0.91 | 0.87 | 0.89 | 1.07 | 1.08 |
| 150 | N150I | 0.92 | 0.79 | 0.51 | 0.83 | 0.95 | 0.93 | 0.83 | 1.02 | 0.83 |
| 150 | N150K | 0.89 | 0.96 | 0.39 | 0.95 | 0.92 | 0.84 | 0.95 | 1.02 | 1.08 |
| 150 | N150M | 1.07 | 0.81 | 0.57 | 0.88 | 0.91 | 0.86 | 0.83 | 1.14 | 0.93 |
| 150 | N150P | 0.80 | 0.48 | 0.35 | 0.50 | 0.88 | 0.69 | 0.50 | 0.80 | 0.52 |
| 150 | N150Q | 0.88 | 1.03 | 0.55 | 1.04 | 1.00 | 0.88 | 1.00 | 0.99 | 1.10 |
| 150 | N150S | 0.95 | 0.91 | 0.64 | 0.96 | 0.93 | 0.89 | 0.90 | 1.02 | 1.03 |
| 150 | N150T | 0.96 | 0.86 | 0.63 | 0.93 | 0.88 | 0.76 | 1.10 | 1.08 | 0.96 |
| 150 | N150V | 0.99 | 0.80 | 0.60 | 0.83 | 0.95 | 0.96 | 0.83 | 1.04 | 0.89 |
| 150 | N150W | 0.93 | 0.92 | 0.40 | 0.88 | 1.01 | 0.90 | 0.98 | 0.65 | 1.04 |
| 152 | Y152A | 0.79 | 0.81 | 0.28 | 0.77 | 0.97 | 0.95 | 0.92 | 0.88 | 0.68 |
| 152 | Y152D | 0.80 | 0.58 | 0.35 | 0.54 | 0.87 | 0.91 | 0.77 | 0.91 | 0.49 |
| 152 | Y152E | 1.00 | 0.60 | 0.37 | 0.58 | 0.97 | 0.87 | 0.84 | 0.95 | 0.61 |
| 152 | Y152G | 0.75 | 0.84 | 0.29 | 0.77 | 0.94 | 0.94 | 0.99 | 1.09 | 0.65 |
| 152 | Y152H | 1.14 | 0.97 | 0.51 | 0.91 | 0.89 | 0.93 | 0.87 | 1.02 | 1.01 |
| 152 | Y152I | 0.94 | 0.70 | 0.31 | 0.67 | 0.78 | 1.10 | 0.89 | 0.95 | 0.84 |
| 152 | Y152K | 0.96 | 0.45 | 0.25 | 0.43 | 0.93 | 0.97 | 0.69 | 0.89 | 0.54 |
| 152 | Y152L | 0.84 | 0.69 | 0.31 | 0.69 | 0.90 | 0.98 | 0.88 | 1.07 | 0.86 |
| 152 | Y152M | 0.84 | 0.44 | 0.34 | 0.44 | 0.81 | 0.87 | 0.82 | 0.93 | 0.51 |
| 152 | Y152N | 0.92 | 0.94 | 0.36 | 0.84 | 0.94 | 0.91 | 0.86 | 0.96 | 0.88 |
| 152 | Y152P | 0.86 | 0.75 | 0.33 | 0.69 | 0.86 | 0.80 | 0.82 | 0.88 | 0.75 |
| 152 | Y152Q | 0.79 | 0.61 | 0.28 | 0.58 | 0.92 | 0.95 | 1.49 | 1.01 | 0.59 |
| 152 | Y152R | 0.76 | 0.60 | 0.18 | 0.61 | 1.00 | 1.20 | 0.98 | 1.02 | 0.66 |
| 152 | Y152S | 0.77 | 0.85 | 0.31 | 0.75 | 0.88 | 0.98 | 0.85 | 0.98 | 0.65 |
| 152 | Y152T | 0.83 | 0.61 | 0.31 | 0.56 | 0.94 | 1.09 | 0.82 | 0.99 | 0.64 |
| 152 | Y152V | 0.96 | 0.61 | 0.33 | 0.60 | 0.93 | 1.03 | 0.80 | 1.02 | 0.68 |
| 152 | Y152W | 0.93 | 0.88 | 0.42 | 0.81 | 0.96 | 0.95 | 0.85 | 1.05 | 0.82 |
| 154 | S154A | 0.89 | 1.20 | 1.11 | 1.11 | 1.11 | 1.02 | 1.37 | 1.18 | 1.33 |
| 154 | S154C | 1.01 | 0.91 | 0.95 | 0.88 | 0.86 | 0.90 | 0.96 | 1.08 | 0.98 |
| 154 | S154D | 1.06 | 1.03 | 1.26 | 0.96 | 0.93 | 1.04 | 1.05 | 0.89 | 1.18 |
| 154 | S154E | 1.12 | 0.95 | 1.07 | 0.93 | 0.99 | 0.88 | 1.02 | 0.99 | 1.11 |
| 154 | S154F | 1.09 | 0.97 | 0.63 | 1.00 | 0.92 | 1.04 | 1.33 | 1.11 | 1.21 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 154 | S154G | 0.98 | 1.08 | 0.82 | 1.03 | 1.02 | 0.96 | 1.24 | 1.08 | 1.24 |
| 154 | S154H | 0.96 | 1.04 | 0.66 | 1.00 | 1.05 | 1.10 | 1.14 | 0.99 | 1.09 |
| 154 | S154I | 0.86 | 0.94 | 0.63 | 0.88 | 1.05 | 1.18 | 1.18 | 1.09 | 1.07 |
| 154 | S154K | 0.90 | 1.02 | 0.69 | 0.99 | 1.02 | 1.17 | 1.09 | 1.10 | 1.17 |
| 154 | S154L | 0.90 | 1.07 | 0.59 | 1.02 | 0.98 | 1.07 | 1.22 | 1.11 | 1.19 |
| 154 | S154M | 1.02 | 0.94 | 0.71 | 0.95 | 0.94 | 1.04 | 0.97 | 1.03 | 1.10 |
| 154 | S154N | 1.00 | 1.28 | 0.91 | 1.15 | 1.00 | 1.09 | 1.43 | 1.04 | 1.39 |
| 154 | S154Q | 0.95 | 1.02 | 0.69 | 1.02 | 0.96 | 1.09 | 1.10 | 1.06 | 1.10 |
| 154 | S154R | 1.01 | 1.02 | 0.62 | 1.05 | 1.07 | 1.22 | 1.06 | 1.03 | 1.30 |
| 154 | S154T | 0.99 | 0.89 | 0.98 | 0.86 | 0.93 | 1.13 | 1.32 | 1.03 | 1.02 |
| 154 | S154V | 0.94 | 0.96 | 0.68 | 0.92 | 0.98 | 0.98 | 1.24 | 1.03 | 1.12 |
| 154 | S154W | 1.04 | 0.98 | 0.59 | 0.97 | 1.00 | 1.07 | 1.16 | 0.99 | 1.26 |
| 154 | S154Y | 0.92 | 0.87 | 0.60 | 0.84 | 0.90 | 1.06 | 1.06 | 1.05 | 1.06 |
| 156 | K156A | 0.91 | 0.85 | 0.28 | 0.92 | 1.06 | 0.95 | 1.19 | 0.97 | 1.04 |
| 156 | K156C | 0.94 | 0.79 | 0.29 | 0.74 | 0.86 | 0.70 | 1.01 | 0.92 | 0.83 |
| 156 | K156D | 0.93 | 0.85 | 0.20 | 0.89 | 1.11 | 0.86 | 1.14 | 0.90 | 1.01 |
| 156 | K156E | 0.84 | 0.72 | 0.21 | 0.82 | 0.85 | 0.77 | 0.70 | 0.84 | 0.88 |
| 156 | K156F | 1.56 | 0.85 | 0.56 | 0.93 | 0.92 | 0.68 | 1.05 | 0.91 | 1.12 |
| 156 | K156G | 0.91 | 0.72 | 0.29 | 0.78 | 0.97 | 0.63 | 0.88 | 0.97 | 0.99 |
| 156 | K156H | 0.95 | 0.84 | 0.36 | 0.87 | 0.91 | 0.83 | 0.90 | 0.89 | 1.07 |
| 156 | K156I | 0.78 | 0.92 | 0.26 | 0.95 | 0.97 | 0.91 | 0.79 | 0.87 | 0.99 |
| 156 | K156L | 1.11 | 0.76 | 0.49 | 0.79 | 0.95 | 0.67 | 0.80 | 0.99 | 0.94 |
| 156 | K156M | 0.96 | 0.75 | 0.32 | 0.82 | 0.99 | 0.70 | 0.94 | 0.87 | 0.97 |
| 156 | K156N | 0.93 | 0.88 | 0.29 | 0.95 | 1.09 | 0.68 | 0.85 | 1.02 | 1.10 |
| 156 | K156P | 1.13 | 0.86 | 0.39 | 0.90 | 0.94 | 0.72 | 0.85 | 0.92 | 1.06 |
| 156 | K156Q | 0.89 | 0.89 | 0.36 | 0.91 | 0.89 | 0.66 | 0.86 | 0.99 | 1.02 |
| 156 | K156R | 0.90 | 0.91 | 0.42 | 0.94 | 1.00 | 0.96 | 1.02 | 0.95 | 1.13 |
| 156 | K156V | 0.99 | 0.67 | 0.40 | 0.69 | 0.89 | 0.74 | 1.00 | 1.36 | 0.76 |
| 156 | K156W | 1.04 | 0.89 | 0.33 | 0.92 | 0.92 | 0.79 | 1.13 | 1.03 | 0.97 |
| 156 | K156Y | 1.35 | 0.74 | 0.52 | 0.79 | 0.94 | 0.59 | 1.09 | 1.02 | 0.93 |
| 158 | R158A | 0.95 | 1.02 | 0.36 | 0.97 | 0.97 | 0.93 | 0.81 | 1.00 | 0.74 |
| 158 | R158C | 1.17 | 0.85 | 0.49 | 0.80 | 0.89 | 0.83 | 0.84 | 0.89 | 0.65 |
| 158 | R158D | 0.92 | 1.12 | 0.29 | 1.02 | 0.91 | 0.46 | 1.09 | 1.06 | 0.73 |
| 158 | R158E | 0.82 | 0.81 | 0.25 | 0.82 | 0.89 | 0.72 | 0.81 | 0.92 | 0.64 |
| 158 | R158G | 1.03 | 1.06 | 0.44 | 1.01 | 1.05 | 0.75 | 0.87 | 1.03 | 0.73 |
| 158 | R158H | 0.78 | 0.98 | 0.32 | 0.91 | 0.83 | 0.83 | 0.87 | 0.95 | 0.85 |
| 158 | R158I | 0.75 | 0.73 | 0.23 | 0.73 | 0.89 | 0.98 | 0.86 | 0.78 | 0.65 |
| 158 | R158K | 0.74 | 0.88 | 0.25 | 0.93 | 0.86 | 1.01 | 0.77 | 0.93 | 0.86 |
| 158 | R158L | 1.06 | 0.88 | 0.39 | 0.90 | 0.82 | 0.86 | 0.81 | 0.87 | 0.78 |
| 158 | R158M | 0.87 | 0.75 | 0.29 | 0.81 | 0.85 | 0.95 | 0.82 | 0.90 | 0.66 |
| 158 | R158Q | 0.79 | 1.04 | 0.33 | 0.94 | 0.94 | 0.98 | 0.92 | 0.96 | 0.69 |
| 158 | R158S | 1.06 | 0.87 | 0.46 | 0.91 | 0.89 | 0.94 | 0.91 | 1.01 | 0.68 |
| 158 | R158T | 0.82 | 0.85 | 0.36 | 0.82 | 0.90 | 0.95 | 0.62 | 0.90 | 0.59 |
| 158 | R158V | 0.89 | 0.69 | 0.36 | 0.68 | 0.95 | 1.03 | 0.87 | 0.85 | 0.57 |
| 158 | R158W | 1.30 | 1.09 | 0.60 | 1.04 | 0.88 | 0.87 | 0.91 | 0.97 | 0.72 |
| 158 | R158Y | 1.23 | 1.03 | 0.70 | 0.91 | 0.90 | 1.01 | 0.80 | 0.93 | 0.67 |
| 159 | W159D | 0.33 | 0.95 | 0.14 | 0.40 | 0.80 | 0.18 | 1.13 | 1.17 | 0.76 |
| 159 | W159F | 0.22 | 1.00 | 0.16 | 0.39 | 1.07 | 0.30 | 1.29 | 1.27 | 0.80 |
| 159 | W159H | 0.29 | 1.03 | 0.17 | 0.43 | 0.97 | 0.19 | 1.04 | 1.22 | 0.95 |
| 159 | W159N | 0.31 | 0.90 | 0.09 | 0.43 | 1.00 | 0.25 | 1.06 | 1.14 | 1.04 |
| 160 | Y160A | 1.05 | 0.95 | 0.56 | 0.92 | 1.01 | 0.44 | 1.06 | 1.17 | 1.01 |
| 160 | Y160D | 1.77 | 1.21 | 1.00 | 1.06 | 0.71 | 0.25 | 1.56 | 1.20 | 1.05 |
| 160 | Y160E | 1.71 | 1.06 | 1.27 | 1.03 | 0.70 | 0.18 | 1.23 | 1.31 | 1.04 |
| 160 | Y160F | 1.31 | 0.99 | 0.97 | 1.08 | 0.88 | 0.95 | 0.66 | 0.94 | 1.05 |
| 160 | Y160I | 1.92 | 0.96 | 1.42 | 0.90 | 1.09 | 0.56 | 1.07 | 1.30 | 0.82 |
| 160 | Y160K | 0.93 | 0.93 | 0.39 | 0.94 | 0.99 | 0.36 | 1.25 | 1.34 | 1.19 |
| 160 | Y160L | 1.58 | 0.87 | 0.81 | 0.93 | 0.95 | 0.36 | 1.16 | 1.34 | 1.06 |
| 160 | Y160M | 1.18 | 0.87 | 0.79 | 0.89 | 0.96 | 0.41 | 1.03 | 0.95 | 1.05 |
| 160 | Y160N | 1.05 | 1.20 | 0.57 | 1.14 | 0.88 | 0.25 | 1.00 | 1.28 | 1.22 |
| 160 | Y160P | 1.01 | 0.94 | 0.61 | 1.02 | 0.91 | 0.51 | 1.32 | 1.12 | 1.30 |
| 160 | Y160Q | 1.31 | 1.09 | 0.80 | 1.17 | 0.91 | 0.34 | 1.40 | 1.19 | 1.19 |
| 160 | Y160R | 1.05 | 0.75 | 0.45 | 0.79 | 1.00 | 0.34 | 1.22 | 1.30 | 1.13 |
| 160 | Y160S | 1.10 | 0.96 | 0.50 | 1.00 | 0.78 | 0.31 | 1.07 | 1.27 | 1.14 |
| 160 | Y160T | 1.24 | 0.92 | 0.74 | 0.91 | 0.99 | 0.32 | 1.24 | 1.30 | 0.95 |
| 160 | Y160V | 1.65 | 0.85 | 1.27 | 0.85 | 0.96 | 0.55 | 0.98 | 1.19 | 0.84 |
| 160 | Y160W | 1.45 | 1.34 | 0.96 | 1.30 | 0.98 | 1.06 | 1.04 | 0.97 | 1.25 |
| 161 | H161A | 1.15 | 0.47 | 0.42 | 0.46 | 0.93 | 0.69 | 1.04 | 0.99 | 0.37 |
| 161 | H161C | 0.86 | 0.70 | 0.35 | 0.70 | 1.00 | 0.42 | 1.10 | 1.02 | 0.58 |
| 161 | H161D | 1.52 | 0.60 | 0.56 | 0.59 | 1.04 | 0.44 | 1.14 | 0.94 | 0.47 |
| 161 | H161E | 2.81 | 0.17 | 0.40 | 0.18 | 0.83 | 0.14 | 1.05 | 0.82 | 0.17 |
| 161 | H161F | 0.55 | 0.82 | 0.16 | 0.85 | 1.02 | 1.08 | 1.29 | 0.99 | 0.48 |
| 161 | H161G | 1.24 | 0.08 | 0.28 | 0.09 | 0.84 | 0.60 | 1.48 | 0.67 | 0.09 |
| 161 | H161K | 0.40 | 0.19 | 0.06 | 0.20 | 1.00 | 0.45 | 1.10 | 1.00 | 0.18 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 161 | H161L | 0.89 | 0.78 | 0.34 | 0.80 | 0.99 | 1.09 | 0.91 | 1.07 | 0.55 |
| 161 | H161N | 0.48 | 0.88 | 0.24 | 0.83 | 1.10 | 0.59 | 1.06 | 1.12 | 0.57 |
| 161 | H161Q | 0.59 | 0.66 | 0.16 | 0.70 | 1.12 | 0.74 | 1.00 | 0.93 | 0.44 |
| 161 | H161S | 1.46 | 0.34 | 0.54 | 0.38 | 1.04 | 0.75 | 1.30 | 0.87 | 0.25 |
| 161 | H161T | 0.64 | 0.42 | 0.16 | 0.44 | 1.00 | 0.51 | 1.11 | 1.19 | 0.32 |
| 161 | H161V | 0.26 | 0.43 | 0.07 | 0.45 | 1.04 | 0.76 | 1.35 | 1.21 | 0.28 |
| 161 | H161Y | 0.54 | 0.79 | 0.21 | 0.81 | 1.02 | 0.95 | 1.04 | 0.91 | 0.55 |
| 162 | F162K | 0.25 | 0.09 | 0.07 | 0.07 | 0.23 | 0.31 | 0.08 | 0.60 | 0.18 |
| 162 | F162W | 1.52 | 0.50 | 0.25 | 0.51 | 0.65 | 0.52 | 0.61 | 0.85 | 0.96 |
| 162 | F162Y | 1.19 | 1.03 | 0.32 | 1.14 | 0.88 | 0.90 | 1.01 | 1.03 | 1.06 |
| 165 | T165A | 0.46 | 0.75 | 0.16 | 0.76 | 0.86 | 0.90 | 0.84 | 0.85 | 1.33 |
| 165 | T165C | 0.88 | 0.56 | 1.55 | 0.49 | 0.70 | 0.79 | 0.91 | 0.77 | 0.99 |
| 165 | T165D | 0.83 | 0.28 | 0.10 | 0.27 | 0.16 | 0.08 | 0.85 | 0.99 | 0.98 |
| 165 | T165E | 0.71 | 0.79 | 0.11 | 0.82 | 0.28 | 0.10 | 0.94 | 0.94 | 0.99 |
| 165 | T165H | 0.58 | 0.48 | 0.07 | 0.45 | 0.66 | 1.05 | 0.83 | 0.74 | 1.30 |
| 165 | T165I | 2.76 | 0.28 | 2.59 | 0.37 | 0.63 | 0.58 | 0.79 | 1.12 | 1.06 |
| 165 | T165L | 0.72 | 0.45 | 0.19 | 0.44 | 0.67 | 0.57 | 0.87 | 0.88 | 0.92 |
| 165 | T165M | 0.69 | 0.86 | 0.12 | 0.88 | 0.89 | 0.91 | 1.08 | 1.06 | 0.97 |
| 165 | T165N | 0.58 | 0.21 | 0.11 | 0.23 | 0.44 | 0.44 | 0.63 | 0.77 | 1.20 |
| 165 | T165P | 1.34 | 0.10 | 2.27 | 0.09 | 1.02 | 1.62 | 1.47 | 0.98 | 0.11 |
| 165 | T165Q | 0.64 | 0.69 | 0.07 | 0.73 | 0.99 | 0.92 | 0.78 | 1.16 | 1.10 |
| 165 | T165S | 0.50 | 0.77 | 0.16 | 0.79 | 0.85 | 0.96 | 0.99 | 0.99 | 1.11 |
| 165 | T165V | 1.61 | 0.60 | 2.68 | 0.56 | 0.87 | 1.17 | 0.81 | 0.93 | 1.04 |
| 165 | T165Y | 0.64 | 0.25 | 0.09 | 0.27 | 0.58 | 0.27 | 0.83 | 0.79 | 0.96 |
| 166 | D166N | 1.36 | 0.20 | 0.49 | 0.25 | 0.65 | 0.56 | 0.90 | 0.93 | 1.24 |
| 167 | W167A | 0.46 | 0.59 | 0.08 | 0.65 | 1.06 | 0.25 | 1.37 | 1.35 | 0.83 |
| 167 | W167C | 0.65 | 0.29 | 0.29 | 0.30 | 0.71 | 0.27 | 0.98 | 1.12 | 0.77 |
| 167 | W167E | 0.72 | 0.21 | 0.15 | 0.24 | 0.51 | 0.17 | 1.08 | 1.27 | 0.84 |
| 167 | W167F | 0.67 | 0.65 | 0.61 | 0.66 | 1.08 | 0.79 | 1.21 | 1.11 | 0.92 |
| 167 | W167I | 0.59 | 0.32 | 0.19 | 0.31 | 0.94 | 0.60 | 0.78 | 1.21 | 0.82 |
| 167 | W167K | 0.45 | 0.18 | 0.11 | 0.23 | 1.03 | 0.66 | 0.82 | 0.93 | 0.81 |
| 167 | W167L | 0.66 | 0.53 | 0.26 | 0.52 | 1.08 | 0.55 | 1.12 | 1.12 | 0.87 |
| 167 | W167N | 0.52 | 0.44 | 0.09 | 0.43 | 1.13 | 0.31 | 1.24 | 1.24 | 0.83 |
| 167 | W167R | 0.42 | 0.35 | 0.18 | 0.47 | 1.11 | 1.02 | 0.99 | 1.00 | 0.88 |
| 167 | W167S | 0.41 | 0.54 | 0.09 | 0.61 | 0.86 | 0.29 | 1.20 | 1.21 | 0.89 |
| 167 | W167T | 0.56 | 0.43 | 0.19 | 0.39 | 1.08 | 0.67 | 0.99 | 1.01 | 0.83 |
| 167 | W167V | 0.76 | 0.26 | 0.23 | 0.25 | 1.08 | 0.73 | 1.05 | 1.11 | 0.75 |
| 167 | W167Y | 0.74 | 0.50 | 0.77 | 0.55 | 1.03 | 1.69 | 0.91 | 1.00 | 0.87 |
| 168 | D168C | 1.17 | 0.73 | 0.22 | 0.84 | 1.06 | 1.10 | 0.61 | 0.97 | 0.93 |
| 168 | D168N | 0.58 | 0.66 | 0.06 | 0.77 | 1.32 | 1.30 | 0.96 | 0.84 | 1.14 |
| 169 | E169A | 0.71 | 0.98 | 0.18 | 1.10 | 1.07 | 1.17 | 0.99 | 1.02 | 0.87 |
| 169 | E169C | 0.82 | 1.21 | 0.18 | 1.13 | 0.78 | 0.37 | 0.81 | 0.95 | 0.80 |
| 169 | E169D | 0.67 | 0.89 | 0.25 | 0.88 | 0.99 | 0.84 | 0.81 | 0.85 | 0.85 |
| 169 | E169F | 0.77 | 0.95 | 0.15 | 1.17 | 1.10 | 0.81 | 1.04 | 0.99 | 0.90 |
| 169 | E169G | 0.66 | 0.72 | 0.08 | 0.88 | 1.01 | 1.03 | 1.15 | 0.86 | 0.84 |
| 169 | E169H | 0.80 | 0.60 | 0.23 | 0.68 | 0.95 | 1.23 | 1.07 | 0.77 | 0.86 |
| 169 | E169I | 0.89 | 1.57 | 0.14 | 1.64 | 0.86 | 0.50 | 0.87 | 1.07 | 0.96 |
| 169 | E169K | 0.68 | 1.42 | 0.12 | 1.99 | 0.97 | 0.87 | 1.00 | 1.00 | 1.23 |
| 169 | E169L | 1.00 | 1.66 | 0.14 | 1.84 | 0.87 | 0.47 | 1.07 | 1.07 | 1.03 |
| 169 | E169M | 0.77 | 1.07 | 0.12 | 1.23 | 1.02 | 0.81 | 0.91 | 0.87 | 0.80 |
| 169 | E169N | 0.73 | 1.01 | 0.16 | 1.09 | 1.01 | 1.04 | 1.02 | 0.96 | 0.90 |
| 169 | E169Q | 0.85 | 0.63 | 0.22 | 0.83 | 1.09 | 1.17 | 1.04 | 0.97 | 0.76 |
| 169 | E169S | 0.66 | 0.95 | 0.13 | 1.03 | 1.04 | 1.06 | 0.90 | 0.96 | 0.76 |
| 169 | E169T | 0.81 | 1.14 | 0.11 | 1.46 | 1.01 | 0.90 | 0.93 | 1.07 | 0.79 |
| 169 | E169V | 0.99 | 1.78 | 0.18 | 1.87 | 1.03 | 0.54 | 0.93 | 1.03 | 0.91 |
| 169 | E169W | 0.69 | 0.79 | 0.15 | 0.74 | 1.06 | 0.86 | 0.74 | 0.90 | 0.94 |
| 169 | E169Y | 0.83 | 0.82 | 0.16 | 1.08 | 1.03 | 0.74 | 0.99 | 1.09 | 0.85 |
| 170 | S170A | 0.74 | 0.84 | 0.58 | 0.90 | 0.97 | 0.85 | 0.97 | 1.04 | 1.05 |
| 170 | S170C | 1.07 | 0.79 | 1.14 | 0.80 | 0.80 | 0.49 | 0.94 | 0.98 | 0.94 |
| 170 | S170D | 0.82 | 0.81 | 0.49 | 0.80 | 1.05 | 0.55 | 0.96 | 0.98 | 0.93 |
| 170 | S170E | 0.80 | 0.78 | 0.64 | 0.81 | 0.96 | 0.51 | 0.83 | 0.97 | 0.94 |
| 170 | S170F | 0.41 | 1.02 | 0.09 | 0.98 | 1.30 | 1.15 | 1.11 | 1.10 | 0.85 |
| 170 | S170G | 0.74 | 0.99 | 0.42 | 1.06 | 1.25 | 0.89 | 1.07 | 1.08 | 1.00 |
| 170 | S170H | 0.75 | 0.93 | 0.60 | 0.91 | 1.00 | 0.81 | 0.82 | 1.01 | 1.02 |
| 170 | S170K | 0.87 | 0.78 | 0.62 | 0.84 | 1.05 | 0.85 | 0.91 | 0.99 | 1.04 |
| 170 | S170L | 1.25 | 0.51 | 1.38 | 0.53 | 0.88 | 0.50 | 1.07 | 0.98 | 0.65 |
| 170 | S170M | 0.88 | 0.93 | 1.25 | 0.94 | 0.89 | 0.78 | 0.94 | 0.96 | 1.11 |
| 170 | S170N | 0.77 | 0.78 | 0.79 | 0.79 | 1.04 | 0.82 | 0.99 | 1.03 | 1.05 |
| 170 | S170Q | 0.92 | 1.05 | 0.83 | 1.05 | 1.20 | 0.88 | 0.90 | 1.04 | 1.12 |
| 170 | S170R | 0.61 | 0.85 | 0.45 | 0.83 | 1.16 | 1.25 | 0.86 | 1.05 | 1.00 |
| 170 | S170T | 0.84 | 0.76 | 0.91 | 0.82 | 1.06 | 0.84 | 1.03 | 0.99 | 0.94 |
| 170 | S170V | 0.73 | 0.67 | 0.53 | 0.70 | 1.12 | 0.58 | 0.88 | 0.90 | 0.96 |
| 170 | S170W | 1.10 | 0.96 | 0.92 | 1.04 | 1.09 | 0.89 | 0.84 | 1.01 | 1.16 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 170 | S170Y | 0.85 | 0.95 | 0.90 | 0.97 | 1.15 | 0.88 | 1.01 | 0.94 | 1.05 |
| 171 | R171A | 0.68 | 0.93 | 0.20 | 0.97 | 1.00 | 0.62 | 0.98 | 0.98 | 0.62 |
| 171 | R171C | 0.70 | 0.94 | 0.25 | 0.88 | 0.79 | 0.32 | 0.94 | 0.89 | 0.69 |
| 171 | R171D | 0.72 | 1.00 | 0.12 | 1.10 | 0.77 | 0.53 | 0.94 | 0.91 | 0.79 |
| 171 | R171E | 0.68 | 0.90 | 0.17 | 0.87 | 0.78 | 0.52 | 1.00 | 0.80 | 0.64 |
| 171 | R171F | 0.57 | 0.88 | 0.13 | 0.83 | 0.80 | 0.75 | 0.90 | 0.83 | 0.77 |
| 171 | R171G | 0.73 | 0.99 | 0.22 | 0.90 | 0.95 | 0.55 | 1.04 | 0.98 | 0.66 |
| 171 | R171H | 0.67 | 0.85 | 0.16 | 0.89 | 0.87 | 0.72 | 0.96 | 0.92 | 0.72 |
| 171 | R171K | 0.55 | 1.01 | 0.30 | 0.94 | 0.89 | 0.75 | 0.99 | 0.99 | 0.65 |
| 171 | R171L | 0.69 | 0.96 | 0.23 | 0.91 | 0.99 | 0.65 | 1.06 | 0.93 | 0.63 |
| 171 | R171M | 0.79 | 0.87 | 0.24 | 0.97 | 0.82 | 0.71 | 0.91 | 0.95 | 0.63 |
| 171 | R171N | 0.46 | 0.82 | 0.22 | 0.94 | 0.84 | 0.69 | 1.06 | 0.88 | 0.68 |
| 171 | R171Q | 0.76 | 0.86 | 0.27 | 0.91 | 0.79 | 0.66 | 0.83 | 0.93 | 0.68 |
| 171 | R171S | 0.75 | 0.82 | 0.31 | 0.87 | 0.94 | 0.59 | 0.88 | 1.00 | 0.59 |
| 171 | R171T | 0.70 | 0.78 | 0.35 | 0.72 | 0.83 | 0.69 | 0.98 | 1.01 | 0.60 |
| 171 | R171W | 0.65 | 0.80 | 0.11 | 0.82 | 0.91 | 0.68 | 0.81 | 0.92 | 0.64 |
| 171 | R171Y | 0.64 | 0.78 | 0.12 | 0.80 | 0.91 | 0.51 | 0.98 | 0.90 | 0.63 |
| 172 | K172A | 0.78 | 1.15 | 0.40 | 1.02 | 1.01 | 0.79 | 1.06 | 0.96 | 0.64 |
| 172 | K172C | 0.94 | 0.96 | 0.62 | 0.87 | 0.84 | 0.28 | 1.01 | 0.97 | 0.55 |
| 172 | K172D | 0.78 | 1.01 | 0.21 | 0.87 | 0.98 | 1.03 | 1.11 | 0.89 | 0.55 |
| 172 | K172E | 0.94 | 0.87 | 0.33 | 0.82 | 0.94 | 0.58 | 1.02 | 0.99 | 0.56 |
| 172 | K172F | 0.89 | 1.21 | 0.29 | 1.14 | 1.00 | 0.74 | 0.92 | 0.97 | 0.74 |
| 172 | K172G | 1.17 | 0.79 | 0.69 | 0.86 | 1.05 | 0.83 | 1.12 | 1.31 | 0.40 |
| 172 | K172H | 0.85 | 1.05 | 0.61 | 0.97 | 1.01 | 0.89 | 0.93 | 1.02 | 0.63 |
| 172 | K172I | 0.61 | 0.97 | 0.12 | 0.84 | 0.95 | 0.78 | 0.95 | 0.92 | 0.68 |
| 172 | K172L | 0.97 | 0.87 | 0.30 | 0.92 | 1.02 | 0.74 | 1.01 | 0.85 | 0.67 |
| 172 | K172N | 0.86 | 1.12 | 0.41 | 1.02 | 1.05 | 0.95 | 1.12 | 1.02 | 0.61 |
| 172 | K172P | 0.84 | 0.64 | 0.09 | 0.47 | 0.99 | 0.74 | 0.96 | 0.90 | 0.63 |
| 172 | K172Q | 1.21 | 0.95 | 0.83 | 0.98 | 0.96 | 0.79 | 1.08 | 0.91 | 0.65 |
| 172 | K172R | 0.76 | 1.36 | 0.68 | 1.15 | 1.05 | 1.14 | 1.19 | 0.99 | 0.66 |
| 172 | K172S | 0.90 | 0.96 | 0.43 | 0.96 | 1.04 | 0.55 | 0.99 | 1.03 | 0.62 |
| 172 | K172T | 0.83 | 0.75 | 0.22 | 0.81 | 1.03 | 0.69 | 1.05 | 0.99 | 0.57 |
| 172 | K172V | 0.71 | 0.85 | 0.16 | 0.83 | 0.82 | 0.74 | 1.05 | 0.91 | 0.63 |
| 172 | K172W | 1.01 | 1.07 | 0.28 | 1.09 | 0.80 | 0.93 | 0.81 | 0.86 | 0.74 |
| 172 | K172Y | 0.86 | 1.03 | 0.29 | 0.98 | 1.02 | 0.88 | 0.95 | 0.94 | 0.60 |
| 174 | N174A | 0.88 | 0.78 | 0.90 | 0.87 | 1.14 | 0.81 | 0.90 | 1.03 | 0.91 |
| 174 | N174C | 1.29 | 0.35 | 0.89 | 0.43 | 0.87 | 0.45 | 0.72 | 0.97 | 0.81 |
| 174 | N174D | 0.78 | 0.69 | 0.26 | 0.75 | 1.07 | 0.63 | 0.70 | 1.00 | 0.80 |
| 174 | N174E | 1.19 | 0.77 | 0.55 | 0.83 | 0.74 | 0.52 | 0.74 | 1.01 | 0.77 |
| 174 | N174F | 0.89 | 0.52 | 0.54 | 0.52 | 0.95 | 0.85 | 0.84 | 0.76 | 0.80 |
| 174 | N174H | 0.92 | 0.74 | 1.04 | 0.71 | 1.05 | 0.90 | 0.73 | 0.81 | 0.83 |
| 174 | N174I | 0.94 | 0.58 | 0.42 | 0.63 | 0.87 | 0.94 | 0.74 | 0.74 | 0.62 |
| 174 | N174L | 0.88 | 0.40 | 0.47 | 0.44 | 0.58 | 0.76 | 0.50 | 0.57 | 0.64 |
| 174 | N174M | 1.02 | 0.47 | 0.81 | 0.55 | 0.91 | 0.86 | 0.80 | 0.73 | 0.68 |
| 174 | N174Q | 1.01 | 0.90 | 0.92 | 0.91 | 0.98 | 0.80 | 0.86 | 0.90 | 0.83 |
| 174 | N174R | 0.84 | 0.54 | 1.43 | 0.67 | 0.99 | 0.87 | 0.88 | 0.86 | 0.89 |
| 174 | N174S | 1.06 | 0.76 | 1.05 | 0.86 | 1.01 | 0.95 | 0.85 | 0.89 | 0.83 |
| 174 | N174T | 1.01 | 0.77 | 0.71 | 0.79 | 1.05 | 0.83 | 0.86 | 0.99 | 0.71 |
| 174 | N174V | 0.91 | 0.68 | 0.53 | 0.70 | 0.95 | 0.96 | 0.90 | 0.89 | 0.59 |
| 174 | N174W | 0.90 | 0.70 | 0.49 | 0.67 | 0.91 | 1.21 | 0.59 | 0.89 | 0.82 |
| 174 | N174Y | 0.87 | 0.51 | 0.57 | 0.53 | 0.94 | 0.85 | 0.67 | 0.67 | 0.74 |
| 175 | R175A | 0.88 | 0.83 | 0.63 | 0.89 | 1.00 | 0.39 | 1.09 | 1.14 | 1.01 |
| 175 | R175C | 0.68 | 0.73 | 0.23 | 0.78 | 1.03 | 0.47 | 1.02 | 1.08 | 0.89 |
| 175 | R175E | 0.59 | 0.99 | 0.10 | 0.87 | 0.99 | 0.66 | 1.26 | 0.99 | 1.11 |
| 175 | R175F | 0.66 | 0.94 | 0.11 | 0.97 | 1.02 | 0.79 | 1.25 | 0.97 | 0.94 |
| 175 | R175G | 0.51 | 0.81 | 0.26 | 0.82 | 0.99 | 0.35 | 0.91 | 0.97 | 1.08 |
| 175 | R175H | 0.88 | 0.95 | 0.31 | 0.99 | 1.53 | 0.65 | 1.08 | 1.05 | 1.15 |
| 175 | R175I | 0.50 | 0.64 | 0.07 | 0.64 | 0.92 | 0.77 | 1.01 | 0.96 | 0.99 |
| 175 | R175K | 0.92 | 0.91 | 0.79 | 1.00 | 0.99 | 0.78 | 0.76 | 1.01 | 1.06 |
| 175 | R175L | 0.69 | 0.78 | 0.17 | 0.78 | 0.91 | 0.64 | 0.65 | 0.94 | 1.09 |
| 175 | R175M | 0.67 | 0.79 | 0.11 | 0.86 | 1.00 | 0.73 | 1.07 | 1.01 | 0.98 |
| 175 | R175N | 0.96 | 1.03 | 0.42 | 1.01 | 1.03 | 0.69 | 1.15 | 1.15 | 1.13 |
| 175 | R175P | 0.90 | 0.71 | 0.34 | 0.72 | 1.01 | 0.57 | 0.91 | 1.08 | 1.12 |
| 175 | R175S | 0.57 | 1.03 | 0.22 | 1.06 | 1.09 | 0.47 | 0.93 | 1.12 | 1.17 |
| 175 | R175T | 0.54 | 0.71 | 0.13 | 0.76 | 0.99 | 0.64 | 1.20 | 1.03 | 0.93 |
| 175 | R175V | 0.63 | 0.63 | 0.15 | 0.64 | 0.96 | 0.66 | 1.11 | 0.94 | 0.83 |
| 175 | R175W | 0.53 | 0.70 | 0.09 | 0.95 | 1.07 | 0.55 | 0.95 | 0.91 | 1.28 |
| 175 | R175Y | 0.76 | 0.95 | 0.13 | 0.92 | 0.97 | 0.80 | 0.99 | 1.06 | 1.08 |
| 176 | I176L | 0.44 | 0.68 | 0.11 | 0.76 | 0.87 | 0.78 | 0.91 | 0.94 | 1.15 |
| 176 | I176V | 0.71 | 0.85 | 0.24 | 0.92 | 0.91 | 0.88 | 1.04 | 0.92 | 0.97 |
| 177 | Y177F | 1.22 | 1.00 | 1.37 | 1.12 | 1.00 | 0.96 | 0.90 | 1.00 | 1.11 |
| 177 | Y177L | 0.59 | 0.87 | 0.15 | 0.83 | 1.05 | 0.92 | 0.98 | 1.01 | 0.66 |
| 177 | Y177M | 0.67 | 0.44 | 0.08 | 0.46 | 1.09 | 1.13 | 1.64 | 0.93 | 0.38 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 177 | Y177R | 0.24 | 0.71 | 0.09 | 0.78 | 1.15 | 1.18 | 1.12 | 1.05 | 0.73 |
| 177 | Y177W | 1.12 | 1.19 | 0.57 | 1.27 | 1.02 | 0.99 | 1.10 | 1.00 | 0.92 |
| 178 | K178A | 0.96 | 0.65 | 0.57 | 0.63 | 1.07 | 0.22 | 1.35 | 1.17 | 0.60 |
| 178 | K178C | 1.15 | 0.50 | 0.60 | 0.53 | 1.12 | 0.26 | 1.73 | 1.35 | 0.43 |
| 178 | K178E | 0.12 | 0.55 | 0.12 | 0.57 | 1.61 | 0.17 | 1.93 | 1.33 | 0.49 |
| 178 | K178G | 1.66 | 0.67 | 0.96 | 0.68 | 0.90 | 0.31 | 1.53 | 0.94 | 0.63 |
| 178 | K178I | 2.39 | 0.60 | 0.64 | 0.68 | 1.09 | 1.34 | 1.63 | 1.34 | 0.45 |
| 178 | K178L | 7.94 | 0.77 | 3.22 | 0.82 | 1.12 | 0.35 | 1.60 | 1.35 | 0.57 |
| 178 | K178M | 2.13 | 0.70 | 1.36 | 0.73 | 1.09 | 0.37 | 1.94 | 1.18 | 0.53 |
| 178 | K178Q | 2.12 | 0.69 | 1.18 | 0.78 | 1.27 | 0.30 | 1.64 | 1.10 | 0.61 |
| 178 | K178R | 0.65 | 0.73 | 0.69 | 0.73 | 1.09 | 0.85 | 1.52 | 1.12 | 0.69 |
| 178 | K178V | 0.30 | 0.56 | 0.09 | 0.58 | 1.25 | 0.35 | 1.80 | 1.45 | 0.46 |
| 182 | T182A | 1.69 | 0.94 | 2.01 | 0.96 | 1.18 | 0.64 | 1.15 | 1.09 | 1.08 |
| 182 | T182C | 4.67 | 0.65 | 2.66 | 0.72 | 0.85 | 0.23 | 1.19 | 1.11 | 0.70 |
| 182 | T182D | 2.63 | 0.84 | 2.15 | 0.94 | 0.94 | 0.68 | 1.18 | 1.06 | 1.03 |
| 182 | T182E | 3.03 | 0.85 | 2.46 | 0.94 | 1.01 | 0.72 | 1.19 | 0.93 | 1.02 |
| 182 | T182F | 1.78 | 0.93 | 1.39 | 0.98 | 0.84 | 1.21 | 1.14 | 0.93 | 1.08 |
| 182 | T182G | 5.64 | 0.79 | 3.12 | 0.97 | 0.98 | 0.26 | 1.66 | 1.36 | 1.14 |
| 182 | T182H | 1.70 | 1.00 | 1.34 | 0.99 | 0.87 | 0.92 | 0.98 | 0.88 | 1.16 |
| 182 | T182I | 1.65 | 0.86 | 1.46 | 0.90 | 0.94 | 1.02 | 1.02 | 1.02 | 1.02 |
| 182 | T182K | 0.23 | 0.81 | 0.38 | 0.93 | 0.92 | 0.91 | 1.15 | 0.86 | 1.16 |
| 182 | T182L | 2.23 | 0.78 | 1.88 | 0.86 | 0.98 | 0.78 | 0.93 | 0.96 | 0.96 |
| 182 | T182M | 2.41 | 0.85 | 1.98 | 0.93 | 0.81 | 0.73 | 1.24 | 1.03 | 1.02 |
| 182 | T182N | 2.41 | 1.01 | 1.97 | 1.06 | 1.04 | 0.62 | 1.49 | 1.22 | 1.19 |
| 182 | T182P | 2.20 | 0.91 | 2.30 | 1.02 | 1.05 | 0.73 | 1.28 | 1.16 | 1.19 |
| 182 | T182Q | 1.82 | 0.97 | 1.74 | 1.01 | 1.10 | 0.64 | 1.17 | 1.01 | 1.07 |
| 182 | T182R | 1.11 | 1.03 | 1.05 | 0.95 | 0.97 | 1.13 | 1.13 | 0.97 | 1.11 |
| 182 | T182V | 1.31 | 0.79 | 1.25 | 0.89 | 0.70 | 0.95 | 1.18 | 0.90 | 0.89 |
| 182 | T182W | 1.62 | 0.91 | 1.27 | 0.95 | 0.76 | 1.53 | 0.99 | 0.86 | 1.02 |
| 182 | T182Y | 1.65 | 0.79 | 1.29 | 0.93 | 0.95 | 1.07 | 1.04 | 0.90 | 1.02 |
| 183 | G183A | 0.80 | 0.95 | 0.20 | 0.99 | 1.16 | 0.24 | 1.05 | 1.38 | 0.99 |
| 183 | G183C | 1.47 | 0.69 | 0.87 | 0.74 | 0.79 | 0.19 | 1.08 | 1.33 | 0.77 |
| 183 | G183E | 0.93 | 0.94 | 0.60 | 0.97 | 0.83 | 0.21 | 1.16 | 1.41 | 0.98 |
| 183 | G183F | 0.97 | 1.01 | 0.22 | 1.00 | 1.12 | 0.47 | 1.02 | 1.09 | 0.96 |
| 183 | G183L | 1.13 | 0.94 | 0.17 | 0.95 | 1.06 | 0.44 | 1.01 | 1.20 | 1.00 |
| 183 | G183M | 1.01 | 0.92 | 0.25 | 0.91 | 0.98 | 0.30 | 1.02 | 1.21 | 1.01 |
| 183 | G183N | 1.13 | 1.01 | 0.74 | 1.04 | 1.00 | 0.24 | 1.21 | 1.28 | 1.15 |
| 183 | G183P | 1.80 | 1.02 | 0.28 | 1.07 | 0.88 | 0.22 | 1.35 | 1.33 | 1.16 |
| 183 | G183Q | 0.76 | 0.93 | 0.13 | 1.03 | 1.06 | 0.22 | 1.28 | 1.36 | 1.08 |
| 183 | G183S | 0.40 | 0.93 | 0.16 | 0.92 | 1.11 | 0.31 | 1.05 | 1.30 | 0.98 |
| 183 | G183T | 0.47 | 0.87 | 0.11 | 0.90 | 1.05 | 0.21 | 1.14 | 1.35 | 0.94 |
| 183 | G183W | 1.18 | 0.96 | 0.26 | 0.93 | 1.25 | 0.44 | 0.95 | 1.21 | 0.96 |
| 185 | A185C | 1.39 | 0.75 | 0.83 | 0.79 | 0.89 | 0.32 | 1.03 | 1.02 | 0.74 |
| 185 | A185D | 2.88 | 0.87 | 2.60 | 0.92 | 0.94 | 0.38 | 1.17 | 1.01 | 0.81 |
| 185 | A185E | 2.40 | 0.89 | 2.18 | 1.00 | 0.93 | 0.31 | 1.12 | 1.05 | 0.81 |
| 185 | A185G | 0.61 | 0.86 | 1.06 | 0.91 | 0.96 | 0.68 | 1.07 | 0.93 | 0.89 |
| 185 | A185K | 0.56 | 0.96 | 0.09 | 1.01 | 1.00 | 0.77 | 0.75 | 0.81 | 0.93 |
| 185 | A185M | 0.55 | 0.86 | 0.34 | 0.97 | 1.02 | 0.91 | 1.05 | 0.85 | 0.77 |
| 185 | A185N | 0.67 | 0.98 | 1.19 | 0.99 | 1.39 | 0.63 | 1.04 | 0.91 | 0.91 |
| 185 | A185Q | 0.62 | 1.13 | 0.86 | 1.06 | 1.11 | 0.75 | 1.15 | 1.03 | 0.86 |
| 185 | A185R | 0.50 | 0.94 | 0.06 | 0.95 | 1.03 | 0.59 | 1.07 | 0.86 | 0.89 |
| 185 | A185S | 0.71 | 0.84 | 0.97 | 0.92 | 1.03 | 0.59 | 1.01 | 0.97 | 0.77 |
| 185 | A185T | 0.58 | 0.87 | 0.61 | 0.96 | 1.16 | 0.54 | 1.22 | 1.03 | 0.76 |
| 189 | E189K | 0.72 | 0.81 | 0.52 | 0.92 | 0.77 | 0.86 | 0.72 | 0.33 | 1.23 |
| 189 | E189P | 5.13 | 0.93 | 2.56 | 0.94 | 0.82 | 0.81 | 0.92 | 1.42 | 1.50 |
| 191 | D191C | 0.89 | 0.55 | 0.84 | 0.54 | 1.04 | 0.66 | 1.32 | 1.17 | 0.56 |
| 192 | T192C | 0.56 | 0.72 | 0.33 | 0.74 | 0.97 | 0.58 | 1.02 | 0.99 | 0.78 |
| 192 | T192D | 1.22 | 1.16 | 1.65 | 1.07 | 0.90 | 0.66 | 1.16 | 1.01 | 0.90 |
| 192 | T192E | 0.14 | 0.90 | 0.21 | 0.98 | 0.89 | 1.02 | 0.87 | 1.05 | 0.80 |
| 192 | T192I | 0.71 | 0.84 | 0.19 | 0.79 | 1.05 | 0.86 | 0.98 | 1.02 | 0.81 |
| 192 | T192N | 0.48 | 1.15 | 0.62 | 1.01 | 1.02 | 0.82 | 1.02 | 0.95 | 0.98 |
| 192 | T192S | 0.45 | 0.94 | 0.28 | 0.88 | 1.09 | 0.89 | 0.94 | 0.97 | 0.81 |
| 192 | T192V | 0.85 | 0.68 | 0.22 | 0.79 | 0.93 | 0.89 | 0.83 | 1.02 | 0.79 |
| 193 | E193C | 0.99 | 0.17 | 0.56 | 0.19 | 0.56 | 0.12 | 0.73 | 1.09 | 0.99 |
| 193 | E193D | 0.42 | 0.24 | 0.39 | 0.25 | 0.93 | 0.40 | 0.82 | 1.13 | 1.27 |
| 193 | E193Q | 0.57 | 0.19 | 0.08 | 0.25 | 0.94 | 0.68 | 0.80 | 0.89 | 1.22 |
| 193 | E193T | 0.36 | 0.09 | 0.06 | 0.14 | 0.78 | 0.20 | 0.98 | 1.12 | 0.81 |
| 195 | G195A | 1.22 | 1.02 | 0.15 | 1.08 | 1.00 | 0.82 | 0.83 | 1.05 | 1.18 |
| 195 | G195C | 2.92 | 1.04 | 0.46 | 0.93 | 0.99 | 0.46 | 1.28 | 0.98 | 0.99 |
| 195 | G195H | 1.45 | 1.21 | 0.19 | 1.12 | 0.94 | 0.89 | 1.06 | 0.95 | 1.41 |
| 195 | G195M | 0.92 | 0.97 | 0.07 | 0.96 | 0.87 | 0.78 | 1.14 | 0.96 | 1.16 |
| 195 | G195Q | 0.71 | 1.17 | 0.07 | 1.12 | 0.91 | 0.73 | 1.12 | 1.02 | 1.29 |
| 195 | G195V | 2.70 | 1.02 | 0.34 | 1.03 | 0.96 | 0.54 | 1.14 | 1.01 | 1.23 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 197 | Y197A | 0.32 | 0.10 | 1.13 | 0.10 | 0.70 | 0.31 | 1.12 | 1.05 | 0.97 |
| 197 | Y197C | 0.31 | 0.08 | 0.35 | 0.07 | 0.47 | 0.08 | 0.70 | 1.01 | 0.74 |
| 197 | Y197D | 1.14 | 0.11 | 1.63 | 0.11 | 0.53 | 0.16 | 1.12 | 1.08 | 0.95 |
| 197 | Y197F | 1.17 | 0.64 | 1.08 | 0.61 | 0.86 | 0.86 | 1.15 | 0.99 | 0.91 |
| 197 | Y197G | 0.21 | 0.06 | 0.11 | 0.06 | 0.51 | 0.20 | 0.96 | 0.99 | 0.72 |
| 197 | Y197N | 0.51 | 0.09 | 1.37 | 0.08 | 0.66 | 0.27 | 0.90 | 1.12 | 0.88 |
| 197 | Y197S | 0.16 | 0.08 | 0.58 | 0.08 | 0.70 | 0.29 | 1.04 | 1.06 | 0.78 |
| 199 | Y199I | 0.06 | 0.09 | 0.08 | 0.09 | 0.19 | 0.17 | 0.67 | 0.58 | 0.75 |
| 200 | L200A | 0.46 | 0.08 | 0.08 | 0.06 | 0.15 | 0.06 | 0.69 | 0.83 | 1.17 |
| 200 | L200M | 0.38 | 0.11 | 0.09 | 0.11 | 0.40 | 0.08 | 0.52 | 0.63 | 1.06 |
| 200 | L200V | 0.69 | 0.10 | 0.45 | 0.10 | 0.38 | 0.23 | 0.41 | 0.37 | 0.96 |
| 201 | M201A | 0.77 | 0.14 | 0.49 | 0.13 | 0.51 | 0.42 | 0.85 | 0.81 | 1.34 |
| 201 | M201C | 1.15 | 0.18 | 1.18 | 0.21 | 0.58 | 0.36 | 0.53 | 0.68 | 1.17 |
| 201 | M201I | 0.79 | 0.32 | 0.35 | 0.33 | 0.65 | 0.63 | 0.70 | 0.72 | 1.16 |
| 201 | M201L | 0.68 | 0.30 | 0.21 | 0.30 | 0.79 | 0.56 | 0.98 | 0.74 | 1.16 |
| 201 | M201T | 0.73 | 0.15 | 0.27 | 0.17 | 0.29 | 0.28 | 0.80 | 0.76 | 1.41 |
| 201 | M201V | 0.78 | 0.08 | 0.47 | 0.09 | 0.34 | 0.19 | 0.47 | 0.67 | 1.15 |
| 202 | F202A | 0.84 | 0.36 | 0.67 | 0.38 | 0.69 | 0.29 | 1.06 | 0.88 | 1.47 |
| 202 | F202G | 0.82 | 0.15 | 0.86 | 0.13 | 0.31 | 0.08 | 0.72 | 0.93 | 1.32 |
| 202 | F202H | 1.29 | 0.97 | 1.19 | 0.91 | 0.89 | 0.50 | 0.83 | 1.02 | 1.39 |
| 202 | F202L | 1.01 | 0.22 | 0.26 | 0.21 | 0.34 | 0.07 | 0.88 | 1.01 | 0.91 |
| 202 | F202M | 0.94 | 0.21 | 0.39 | 0.19 | 0.40 | 0.18 | 0.79 | 0.92 | 1.27 |
| 202 | F202N | 1.14 | 0.78 | 0.41 | 0.80 | 0.76 | 0.51 | 0.99 | 0.99 | 1.55 |
| 202 | F202S | 0.90 | 0.36 | 0.31 | 0.35 | 0.82 | 0.29 | 0.82 | 0.97 | 1.34 |
| 202 | F202Y | 1.01 | 0.81 | 1.54 | 0.76 | 1.08 | 0.83 | 1.05 | 1.08 | 1.33 |
| 203 | A203C | 0.73 | 0.12 | 1.84 | 0.12 | 0.73 | 0.70 | 0.88 | 0.89 | 0.77 |
| 203 | A203E | 1.67 | 0.40 | 0.80 | 0.41 | 0.29 | 0.11 | 0.66 | 0.87 | 0.94 |
| 203 | A203G | 0.50 | 0.83 | 0.11 | 0.88 | 0.80 | 0.76 | 1.16 | 0.83 | 1.04 |
| 203 | A203L | 0.25 | 0.06 | 1.19 | 0.06 | 0.34 | 0.25 | 0.90 | 0.89 | 0.84 |
| 203 | A203P | 0.90 | 0.06 | 0.08 | 0.07 | 0.76 | 0.33 | 0.92 | 0.89 | 0.72 |
| 203 | A203V | 0.45 | 0.17 | 1.41 | 0.16 | 0.63 | 0.54 | 0.93 | 1.12 | 0.68 |
| 207 | M207F | 0.81 | 0.95 | 1.10 | 0.97 | 0.97 | 0.87 | 0.88 | 0.89 | 0.85 |
| 207 | M207L | 0.07 | 1.30 | 0.08 | 1.20 | 1.18 | 0.92 | 1.17 | 1.05 | 1.03 |
| 207 | M207Y | 1.40 | 0.93 | 0.48 | 0.92 | 0.99 | 0.93 | 0.91 | 0.84 | 0.79 |
| 210 | P210C | 1.77 | 0.77 | 1.02 | 0.75 | 1.04 | 0.97 | 0.84 | 1.17 | 0.49 |
| 210 | P210D | 1.46 | 1.04 | 1.21 | 0.96 | 0.98 | 0.80 | 1.06 | 1.02 | 0.81 |
| 210 | P210E | 1.69 | 0.88 | 1.24 | 0.96 | 0.99 | 0.93 | 1.09 | 0.98 | 0.76 |
| 210 | P210F | 1.16 | 0.67 | 0.61 | 0.73 | 1.06 | 1.02 | 0.70 | 1.05 | 0.60 |
| 210 | P210G | 1.37 | 0.88 | 0.83 | 0.87 | 1.00 | 0.89 | 1.23 | 1.07 | 0.69 |
| 210 | P210H | 1.19 | 0.89 | 0.73 | 0.91 | 1.04 | 1.07 | 0.98 | 1.06 | 0.82 |
| 210 | P210I | 1.02 | 0.69 | 0.52 | 0.71 | 1.05 | 1.09 | 1.10 | 1.09 | 0.57 |
| 210 | P210K | 0.80 | 1.02 | 0.33 | 1.09 | 0.98 | 1.06 | 0.85 | 1.09 | 0.91 |
| 210 | P210L | 1.34 | 0.71 | 0.69 | 0.73 | 1.10 | 0.92 | 1.06 | 0.91 | 0.66 |
| 210 | P210M | 1.47 | 0.70 | 0.83 | 0.74 | 0.99 | 0.90 | 0.80 | 0.95 | 0.67 |
| 210 | P210N | 1.26 | 0.87 | 0.79 | 0.99 | 0.96 | 0.79 | 1.26 | 1.13 | 0.79 |
| 210 | P210Q | 1.36 | 0.98 | 0.80 | 1.05 | 0.93 | 1.12 | 1.08 | 1.06 | 0.82 |
| 210 | P210R | 0.82 | 1.07 | 0.28 | 1.10 | 0.93 | 1.13 | 0.97 | 0.95 | 0.99 |
| 210 | P210S | 1.02 | 0.10 | 0.69 | 0.10 | 0.70 | 0.59 | 0.34 | 0.94 | 0.11 |
| 210 | P210T | 1.30 | 0.76 | 0.68 | 0.86 | 1.00 | 1.18 | 1.08 | 1.15 | 0.64 |
| 210 | P210V | 1.07 | 0.76 | 0.63 | 0.73 | 0.93 | 0.88 | 0.82 | 1.05 | 0.58 |
| 210 | P210W | 1.33 | 0.81 | 0.64 | 0.87 | 0.99 | 1.10 | 1.09 | 1.12 | 0.74 |
| 214 | T214A | 0.87 | 0.96 | 1.24 | 0.88 | 1.16 | 0.94 | 0.81 | 0.95 | 0.95 |
| 214 | T214C | 1.16 | 0.78 | 1.17 | 0.76 | 1.25 | 0.79 | 0.78 | 0.93 | 0.75 |
| 214 | T214D | 1.24 | 0.69 | 1.56 | 0.69 | 0.96 | 0.81 | 1.05 | 0.88 | 0.90 |
| 214 | T214E | 1.33 | 0.93 | 1.78 | 0.94 | 1.06 | 0.72 | 0.82 | 0.87 | 1.15 |
| 214 | T214F | 1.09 | 0.81 | 0.81 | 0.78 | 1.08 | 0.95 | 0.58 | 0.89 | 0.89 |
| 214 | T214G | 0.98 | 0.92 | 0.88 | 0.91 | 1.03 | 0.92 | 0.81 | 0.93 | 0.98 |
| 214 | T214I | 1.11 | 0.70 | 0.85 | 0.73 | 1.15 | 1.22 | 0.92 | 1.00 | 0.69 |
| 214 | T214K | 0.91 | 0.92 | 0.87 | 0.97 | 1.12 | 0.96 | 1.10 | 0.85 | 1.04 |
| 214 | T214L | 0.95 | 0.60 | 0.96 | 0.57 | 1.09 | 1.02 | 1.03 | 0.74 | 0.60 |
| 214 | T214P | 0.69 | 1.04 | 0.59 | 1.04 | 0.96 | 0.90 | 0.78 | 0.91 | 1.06 |
| 214 | T214Q | 1.08 | 1.02 | 1.61 | 1.05 | 1.12 | 0.89 | 0.74 | 1.00 | 1.18 |
| 214 | T214R | 0.75 | 0.76 | 0.81 | 0.89 | 1.10 | 1.04 | 0.95 | 0.90 | 1.00 |
| 214 | T214S | 1.04 | 0.85 | 1.05 | 0.89 | 1.15 | 0.97 | 0.68 | 0.95 | 0.98 |
| 214 | T214V | 0.96 | 0.78 | 0.92 | 0.75 | 1.03 | 0.87 | 0.63 | 1.07 | 0.70 |
| 214 | T214W | 1.18 | 0.91 | 1.10 | 0.87 | 1.11 | 0.96 | 0.76 | 0.97 | 0.95 |
| 214 | T214Y | 1.09 | 0.75 | 0.82 | 0.77 | 1.04 | 0.90 | 0.75 | 0.91 | 0.87 |
| 217 | K217A | 1.25 | 0.92 | 0.68 | 0.95 | 0.88 | 0.70 | 1.11 | 0.75 | 1.03 |
| 217 | K217C | 1.43 | 0.67 | 0.76 | 0.73 | 0.86 | 0.58 | 1.11 | 0.89 | 0.66 |
| 217 | K217D | 1.47 | 0.72 | 0.48 | 0.78 | 0.84 | 0.58 | 1.38 | 0.88 | 0.75 |
| 217 | K217E | 1.51 | 0.76 | 0.66 | 0.84 | 0.93 | 0.63 | 1.05 | 0.82 | 0.84 |
| 217 | K217F | 1.13 | 0.89 | 0.80 | 0.93 | 0.83 | 0.56 | 1.63 | 0.84 | 0.76 |
| 217 | K217G | 1.54 | 0.69 | 0.51 | 0.75 | 0.96 | 0.75 | 1.20 | 0.95 | 0.73 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 217 | K217H | 1.21 | 0.79 | 0.61 | 0.89 | 0.90 | 0.59 | 1.23 | 0.84 | 0.84 |
| 217 | K217L | 1.15 | 0.75 | 0.69 | 0.82 | 0.81 | 0.56 | 1.23 | 0.85 | 0.69 |
| 217 | K217M | 1.58 | 0.29 | 0.86 | 0.34 | 1.28 | 0.93 | 1.27 | 1.38 | 0.13 |
| 217 | K217N | 1.08 | 0.93 | 0.60 | 0.93 | 0.96 | 0.71 | 1.23 | 0.98 | 0.81 |
| 217 | K217P | 2.41 | 0.32 | 0.95 | 0.41 | 0.88 | 0.86 | 1.17 | 0.79 | 0.27 |
| 217 | K217Q | 1.23 | 0.75 | 0.50 | 0.88 | 0.99 | 0.72 | 1.13 | 0.94 | 0.82 |
| 217 | K217R | 0.50 | 0.86 | 0.34 | 0.92 | 0.93 | 0.88 | 1.27 | 0.83 | 1.09 |
| 217 | K217S | 1.09 | 0.80 | 0.55 | 0.79 | 0.90 | 0.72 | 1.48 | 0.89 | 0.69 |
| 217 | K217T | 1.05 | 0.21 | 0.52 | 0.23 | 1.51 | 0.49 | 1.56 | 1.19 | 0.08 |
| 217 | K217V | 1.12 | 0.70 | 0.31 | 0.77 | 0.99 | 0.77 | 1.25 | 0.95 | 0.79 |
| 217 | K217W | 1.12 | 0.75 | 0.50 | 0.85 | 0.85 | 0.57 | 1.03 | 0.79 | 0.73 |
| 217 | K217Y | 0.60 | 0.66 | 0.61 | 0.73 | 0.92 | 0.61 | 0.93 | 0.84 | 0.68 |
| 221 | T221A | 0.94 | 0.90 | 0.66 | 1.04 | 1.04 | 1.07 | 1.10 | 1.03 | 1.04 |
| 221 | T221C | 0.94 | 0.72 | 0.61 | 0.72 | 0.93 | 0.94 | 1.04 | 0.92 | 0.64 |
| 221 | T221D | 1.14 | 0.88 | 0.70 | 0.94 | 0.91 | 0.96 | 1.09 | 0.82 | 1.08 |
| 221 | T221E | 1.28 | 0.80 | 0.91 | 0.94 | 0.97 | 0.82 | 0.92 | 0.94 | 1.02 |
| 221 | T221F | 1.16 | 0.79 | 0.73 | 0.82 | 0.88 | 1.02 | 0.76 | 0.93 | 0.85 |
| 221 | T221G | 1.03 | 0.89 | 0.60 | 0.94 | 0.95 | 0.80 | 1.20 | 0.85 | 0.96 |
| 221 | T221H | 1.10 | 0.83 | 0.65 | 0.94 | 0.99 | 0.89 | 0.86 | 0.89 | 1.06 |
| 221 | T221K | 0.66 | 0.71 | 0.68 | 0.96 | 0.93 | 1.01 | 1.19 | 1.04 | 1.06 |
| 221 | T221M | 1.11 | 0.65 | 0.74 | 0.73 | 0.93 | 1.46 | 1.12 | 0.95 | 0.81 |
| 221 | T221N | 1.10 | 0.98 | 0.64 | 0.99 | 1.21 | 1.05 | 1.11 | 1.02 | 1.09 |
| 221 | T221P | 1.03 | 0.85 | 1.04 | 0.97 | 0.91 | 0.82 | 0.99 | 0.94 | 1.13 |
| 221 | T221Q | 1.67 | 0.69 | 0.65 | 0.99 | 0.94 | 0.98 | 0.96 | 1.04 | 1.03 |
| 221 | T221R | 0.77 | 0.66 | 0.57 | 1.01 | 1.06 | 1.02 | 1.09 | 0.97 | 1.09 |
| 221 | T221S | 0.79 | 0.76 | 0.61 | 0.96 | 1.04 | 1.00 | 1.02 | 0.86 | 0.99 |
| 221 | T221V | 1.03 | 0.66 | 2.11 | 0.80 | 1.04 | 1.09 | 1.19 | 0.98 | 0.78 |
| 221 | T221W | 1.01 | 0.88 | 0.64 | 0.92 | 1.04 | 1.07 | 1.03 | 0.96 | 0.91 |
| 221 | T221Y | 1.12 | 0.83 | 0.73 | 0.86 | 1.07 | 1.04 | 0.95 | 0.94 | 0.82 |
| 228 | N228A | 0.67 | 0.89 | 0.78 | 0.91 | 1.08 | 1.02 | 0.99 | 0.80 | 0.90 |
| 228 | N228C | 0.87 | 0.85 | 0.85 | 0.79 | 0.95 | 0.98 | 0.95 | 0.96 | 0.69 |
| 228 | N228D | 0.94 | 1.11 | 1.17 | 0.98 | 0.96 | 0.98 | 1.07 | 0.81 | 0.96 |
| 228 | N228E | 1.06 | 0.92 | 0.92 | 0.92 | 0.87 | 0.65 | 0.74 | 0.94 | 0.91 |
| 228 | N228F | 1.06 | 0.99 | 0.65 | 0.99 | 1.03 | 1.13 | 1.08 | 0.96 | 0.95 |
| 228 | N228G | 0.97 | 1.03 | 1.13 | 1.00 | 0.99 | 1.10 | 0.71 | 0.96 | 0.86 |
| 228 | N228H | 1.05 | 0.90 | 0.71 | 0.96 | 0.97 | 0.87 | 0.90 | 0.90 | 1.00 |
| 228 | N228I | 1.03 | 0.83 | 0.61 | 0.82 | 1.12 | 1.09 | 1.00 | 0.84 | 0.82 |
| 228 | N228L | 0.92 | 0.86 | 0.68 | 0.89 | 1.04 | 0.99 | 0.94 | 0.92 | 0.90 |
| 228 | N228M | 0.98 | 0.93 | 0.77 | 0.99 | 1.10 | 0.98 | 1.01 | 0.89 | 0.95 |
| 228 | N228P | 1.10 | 0.67 | 0.68 | 0.75 | 1.01 | 0.90 | 0.92 | 0.90 | 1.08 |
| 228 | N228Q | 1.14 | 0.90 | 0.83 | 0.99 | 0.87 | 1.09 | 1.04 | 0.93 | 1.01 |
| 228 | N228R | 0.92 | 0.90 | 0.64 | 0.90 | 0.98 | 1.11 | 0.92 | 0.91 | 0.96 |
| 228 | N228S | 1.01 | 0.88 | 0.74 | 0.94 | 1.01 | 1.07 | 0.85 | 0.95 | 0.92 |
| 228 | N228T | 0.94 | 0.90 | 0.65 | 0.88 | 1.05 | 1.06 | 0.92 | 0.93 | 0.87 |
| 228 | N228V | 0.89 | 0.46 | 0.66 | 0.50 | 0.94 | 0.79 | 0.92 | 0.81 | 0.55 |
| 228 | N228W | 1.02 | 0.56 | 0.63 | 0.58 | 0.96 | 1.00 | 0.59 | 0.83 | 0.58 |
| 228 | N228Y | 0.95 | 0.86 | 0.61 | 0.86 | 1.06 | 0.99 | 0.83 | 0.91 | 0.83 |
| 234 | L234A | 2.32 | 0.76 | 1.23 | 0.77 | 1.00 | 0.69 | 1.39 | 1.08 | 1.45 |
| 234 | L234C | 1.41 | 0.53 | 0.86 | 0.47 | 0.82 | 1.42 | 1.07 | 0.96 | 0.91 |
| 234 | L234D | 1.16 | 0.17 | 0.48 | 0.15 | 0.80 | 0.50 | 0.79 | 0.98 | 0.30 |
| 234 | L234G | 1.75 | 0.59 | 0.65 | 0.61 | 0.95 | 0.89 | 1.21 | 0.98 | 1.12 |
| 234 | L234H | 1.18 | 0.50 | 0.38 | 0.53 | 0.92 | 0.74 | 1.04 | 0.96 | 1.11 |
| 234 | L234I | 0.68 | 0.67 | 0.37 | 0.74 | 1.06 | 0.82 | 1.16 | 1.07 | 1.44 |
| 234 | L234M | 1.08 | 0.82 | 1.10 | 0.83 | 1.01 | 0.97 | 1.05 | 0.97 | 1.34 |
| 234 | L234N | 1.79 | 0.56 | 0.80 | 0.59 | 0.94 | 0.77 | 1.17 | 0.97 | 0.94 |
| 234 | L234P | 1.18 | 0.12 | 0.36 | 0.13 | 0.86 | 0.43 | 1.12 | 0.80 | 1.17 |
| 234 | L234Q | 1.22 | 0.57 | 0.41 | 0.63 | 0.88 | 0.65 | 1.07 | 0.94 | 1.04 |
| 234 | L234S | 1.45 | 0.58 | 0.53 | 0.56 | 0.91 | 0.77 | 1.15 | 1.00 | 1.01 |
| 234 | L234T | 1.28 | 0.59 | 0.40 | 0.61 | 1.05 | 0.94 | 1.42 | 1.17 | 1.09 |
| 234 | L234V | 0.87 | 0.74 | 0.41 | 0.70 | 1.03 | 0.85 | 1.28 | 1.16 | 1.23 |
| 234 | L234W | 0.59 | 0.49 | 0.15 | 0.52 | 1.06 | 0.70 | 1.29 | 0.96 | 1.05 |
| 234 | L234Y | 0.61 | 0.43 | 0.22 | 0.48 | 1.02 | 1.39 | 1.20 | 1.07 | 1.12 |
| 236 | A236G | 1.06 | 0.06 | 1.17 | 0.06 | 0.46 | 0.29 | 0.47 | 0.17 | 0.91 |
| 236 | A236T | 0.47 | 0.19 | 0.13 | 0.18 | 0.78 | 0.63 | 0.32 | 0.29 | 0.86 |
| 237 | V237A | 0.76 | 1.12 | 0.22 | 1.04 | 1.02 | 0.57 | 0.90 | 0.91 | 1.07 |
| 237 | V237C | 1.02 | 0.16 | 0.74 | 0.16 | 0.75 | 0.32 | 1.06 | 1.03 | 0.22 |
| 237 | V237D | 0.33 | 0.72 | 0.18 | 0.75 | 0.80 | 0.07 | 1.14 | 0.93 | 0.84 |
| 237 | V237G | 0.98 | 0.71 | 0.16 | 0.68 | 0.78 | 0.64 | 1.39 | 0.95 | 1.04 |
| 237 | V237I | 0.89 | 0.66 | 0.47 | 0.75 | 1.47 | 0.91 | 1.01 | 0.99 | 0.95 |
| 237 | V237L | 0.44 | 0.59 | 0.24 | 0.66 | 1.02 | 0.62 | 1.80 | 1.08 | 0.93 |
| 237 | V237N | 0.92 | 1.11 | 0.20 | 1.15 | 0.91 | 0.54 | 1.24 | 0.97 | 1.10 |
| 237 | V237P | 0.47 | 0.16 | 0.06 | 0.15 | 1.11 | 0.68 | 1.48 | 0.79 | 1.03 |
| 237 | V237T | 0.90 | 0.85 | 0.25 | 0.89 | 0.89 | 0.74 | 1.23 | 0.88 | 0.97 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 240 | I240V | 0.68 | 0.94 | 0.23 | 1.04 | 0.95 | 0.98 | 1.10 | 0.95 | 1.21 |
| 243 | S243A | 2.52 | 0.68 | 1.35 | 0.71 | 1.16 | 0.97 | 0.90 | 0.91 | 0.53 |
| 243 | S243C | 4.02 | 0.63 | 0.91 | 0.68 | 0.98 | 0.93 | 0.94 | 0.89 | 0.45 |
| 243 | S243D | 6.78 | 0.92 | 2.18 | 0.90 | 0.95 | 0.86 | 0.82 | 0.79 | 0.73 |
| 243 | S243E | 8.88 | 0.83 | 2.59 | 1.00 | 1.01 | 0.71 | 0.86 | 0.83 | 0.76 |
| 243 | S243F | 1.52 | 0.64 | 0.12 | 0.71 | 1.05 | 1.16 | 0.98 | 0.89 | 0.53 |
| 243 | S243G | 1.02 | 0.96 | 0.55 | 0.97 | 0.93 | 0.98 | 0.87 | 0.81 | 0.77 |
| 243 | S243H | 0.89 | 0.64 | 0.06 | 0.81 | 0.86 | 1.01 | 0.87 | 0.90 | 0.64 |
| 243 | S243I | 2.19 | 0.58 | 0.44 | 0.60 | 1.02 | 1.12 | 0.98 | 0.88 | 0.46 |
| 243 | S243K | 0.41 | 0.97 | 0.09 | 0.93 | 0.97 | 1.14 | 0.78 | 0.78 | 0.81 |
| 243 | S243L | 2.01 | 0.70 | 0.48 | 0.62 | 1.00 | 1.00 | 0.90 | 0.93 | 0.52 |
| 243 | S243M | 1.95 | 0.53 | 0.49 | 0.63 | 0.85 | 0.93 | 0.81 | 0.79 | 0.53 |
| 243 | S243Q | 5.93 | 0.79 | 1.93 | 0.77 | 1.02 | 1.06 | 1.01 | 1.00 | 0.69 |
| 243 | S243T | 1.45 | 0.66 | 0.77 | 0.74 | 0.91 | 1.18 | 0.92 | 0.84 | 0.61 |
| 243 | S243V | 1.79 | 0.50 | 0.40 | 0.56 | 0.97 | 0.95 | 1.08 | 0.84 | 0.41 |
| 246 | P246A | 2.26 | 1.15 | 0.80 | 1.19 | 0.83 | 0.99 | 0.75 | 0.91 | 0.88 |
| 246 | P246C | 1.41 | 0.99 | 0.20 | 0.99 | 1.09 | 0.88 | 0.78 | 0.72 | 0.74 |
| 246 | P246D | 2.41 | 1.24 | 0.67 | 1.23 | 1.00 | 0.98 | 0.76 | 0.94 | 0.96 |
| 246 | P246E | 2.78 | 1.10 | 1.07 | 1.15 | 0.90 | 0.94 | 0.82 | 0.93 | 0.88 |
| 246 | P246F | 2.61 | 1.09 | 0.84 | 1.06 | 1.02 | 0.94 | 0.67 | 0.83 | 0.79 |
| 246 | P246G | 1.06 | 1.19 | 0.32 | 1.20 | 1.01 | 0.92 | 0.61 | 0.88 | 0.95 |
| 246 | P246I | 0.69 | 0.96 | 0.12 | 0.97 | 1.05 | 0.91 | 0.76 | 0.91 | 0.80 |
| 246 | P246K | 1.34 | 1.18 | 0.36 | 1.25 | 1.01 | 0.93 | 0.71 | 0.80 | 1.05 |
| 246 | P246M | 1.41 | 1.11 | 0.23 | 1.06 | 0.90 | 0.93 | 0.68 | 0.86 | 0.79 |
| 246 | P246N | 0.63 | 1.15 | 0.14 | 1.19 | 0.94 | 0.97 | 0.79 | 0.98 | 0.97 |
| 246 | P246Q | 2.14 | 1.16 | 0.54 | 1.34 | 1.01 | 0.97 | 0.84 | 1.00 | 0.92 |
| 246 | P246R | 1.39 | 1.25 | 0.36 | 1.21 | 1.03 | 0.90 | 0.63 | 0.69 | 0.99 |
| 246 | P246S | 2.01 | 1.14 | 0.62 | 1.21 | 0.92 | 1.09 | 0.71 | 0.93 | 0.93 |
| 246 | P246T | 1.21 | 1.12 | 0.40 | 1.13 | 1.06 | 0.99 | 0.70 | 0.89 | 0.93 |
| 246 | P246V | 1.28 | 1.06 | 0.73 | 1.03 | 0.97 | 0.90 | 0.74 | 0.81 | 0.83 |
| 246 | P246W | 2.51 | 1.08 | 0.75 | 1.03 | 0.97 | 0.94 | 0.63 | 0.83 | 0.80 |
| 246 | P246Y | 2.46 | 1.10 | 1.07 | 1.01 | 0.95 | 0.92 | 0.77 | 0.86 | 0.80 |
| 250 | T250A | 0.79 | 1.00 | 1.15 | 0.87 | 1.08 | 0.97 | 0.84 | 1.00 | 0.90 |
| 250 | T250C | 1.10 | 0.81 | 1.01 | 0.72 | 0.90 | 0.89 | 0.85 | 1.03 | 0.60 |
| 250 | T250D | 1.00 | 0.94 | 1.39 | 0.80 | 0.86 | 0.74 | 0.91 | 1.08 | 0.76 |
| 250 | T250E | 1.18 | 0.84 | 1.46 | 0.82 | 0.90 | 0.87 | 0.89 | 1.05 | 0.82 |
| 250 | T250F | 0.71 | 0.72 | 0.85 | 0.76 | 0.90 | 0.92 | 0.83 | 0.98 | 0.71 |
| 250 | T250G | 0.95 | 1.04 | 0.93 | 0.90 | 0.86 | 0.73 | 0.64 | 0.89 | 1.29 |
| 250 | T250H | 0.98 | 1.03 | 0.85 | 0.88 | 0.82 | 0.77 | 0.74 | 0.91 | 1.04 |
| 250 | T250I | 1.02 | 0.88 | 0.73 | 0.81 | 1.01 | 0.84 | 0.86 | 0.97 | 0.87 |
| 250 | T250K | 0.76 | 0.94 | 0.76 | 0.91 | 0.95 | 0.95 | 0.98 | 1.06 | 0.87 |
| 250 | T250L | 0.82 | 1.05 | 0.84 | 0.77 | 0.81 | 0.84 | 1.10 | 0.95 | 0.74 |
| 250 | T250P | 0.49 | 0.81 | 0.31 | 0.72 | 0.94 | 0.85 | 0.90 | 0.95 | 0.90 |
| 250 | T250Q | 0.94 | 1.04 | 0.98 | 0.87 | 0.94 | 0.88 | 0.89 | 1.22 | 0.85 |
| 250 | T250R | 0.64 | 1.01 | 0.69 | 0.92 | 0.96 | 0.94 | 0.89 | 0.98 | 0.92 |
| 250 | T250W | 0.99 | 1.00 | 0.85 | 0.82 | 0.84 | 1.04 | 1.17 | 1.01 | 0.77 |
| 250 | T250Y | 1.11 | 0.87 | 0.87 | 0.82 | 0.87 | 0.92 | 0.70 | 1.05 | 0.86 |
| 254 | N254A | 0.91 | 0.95 | 1.04 | 0.97 | 0.89 | 0.84 | 0.83 | 1.00 | 0.69 |
| 254 | N254C | 0.97 | 0.79 | 1.03 | 0.74 | 0.92 | 0.74 | 0.38 | 1.13 | 0.44 |
| 254 | N254D | 1.07 | 0.74 | 1.11 | 0.80 | 0.81 | 0.73 | 1.00 | 1.00 | 0.57 |
| 254 | N254E | 1.17 | 0.84 | 1.42 | 0.90 | 0.77 | 0.71 | 0.91 | 0.93 | 0.67 |
| 254 | N254F | 1.09 | 0.80 | 0.93 | 0.84 | 0.77 | 0.75 | 0.85 | 0.85 | 0.66 |
| 254 | N254G | 1.07 | 0.89 | 0.91 | 0.96 | 0.86 | 0.98 | 0.75 | 0.94 | 0.73 |
| 254 | N254H | 1.10 | 0.91 | 0.84 | 0.92 | 0.80 | 0.89 | 0.95 | 0.92 | 0.70 |
| 254 | N254I | 0.84 | 0.88 | 0.92 | 0.84 | 0.86 | 0.93 | 0.86 | 1.16 | 0.15 |
| 254 | N254K | 0.83 | 1.01 | 1.10 | 0.95 | 0.82 | 0.94 | 0.59 | 0.91 | 0.72 |
| 254 | N254L | 0.97 | 0.87 | 0.89 | 0.91 | 0.82 | 0.76 | 0.65 | 0.91 | 0.76 |
| 254 | N254M | 0.87 | 0.98 | 1.03 | 0.93 | 0.77 | 0.82 | 0.85 | 0.88 | 0.79 |
| 254 | N254P | 1.05 | 0.73 | 0.53 | 0.77 | 0.90 | 0.87 | 0.67 | 1.06 | 0.61 |
| 254 | N254Q | 1.20 | 0.88 | 1.12 | 0.95 | 0.89 | 0.81 | 0.81 | 0.97 | 0.70 |
| 254 | N254R | 0.84 | 1.00 | 0.92 | 0.96 | 0.92 | 1.01 | 0.86 | 0.96 | 0.75 |
| 254 | N254S | 0.97 | 0.72 | 1.11 | 0.78 | 0.80 | 0.88 | 0.60 | 0.98 | 0.58 |
| 254 | N254T | 1.08 | 0.87 | 1.28 | 0.87 | 0.92 | 0.86 | 0.95 | 1.01 | 0.65 |
| 254 | N254V | 1.04 | 0.82 | 0.96 | 0.82 | 0.80 | 0.88 | 0.93 | 1.00 | 0.46 |
| 254 | N254W | 1.01 | 0.90 | 0.71 | 0.87 | 0.86 | 0.87 | 0.83 | 0.93 | 0.68 |
| 254 | N254Y | 1.00 | 0.77 | 0.77 | 0.79 | 0.86 | 0.97 | 0.97 | 0.95 | 0.58 |
| 255 | Q255A | 0.77 | 0.81 | 1.05 | 0.82 | 0.92 | 0.74 | 0.74 | 1.00 | 0.65 |
| 255 | Q255C | 0.95 | 0.55 | 0.90 | 0.59 | 1.27 | 0.13 | 1.37 | 1.42 | 0.23 |
| 255 | Q255D | 1.07 | 0.75 | 0.69 | 0.79 | 0.88 | 0.44 | 0.74 | 0.86 | 0.62 |
| 255 | Q255E | 0.67 | 0.68 | 1.01 | 0.84 | 0.85 | 0.67 | 0.72 | 0.85 | 0.66 |
| 255 | Q255F | 0.89 | 0.87 | 0.72 | 0.80 | 0.93 | 0.77 | 0.70 | 0.82 | 0.64 |
| 255 | Q255I | 0.93 | 0.94 | 0.66 | 0.99 | 0.94 | 0.85 | 0.87 | 1.05 | 0.82 |
| 255 | Q255K | 0.83 | 0.92 | 0.92 | 0.88 | 0.90 | 0.68 | 0.69 | 0.88 | 0.71 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 255 | Q255L | 0.91 | 0.78 | 0.72 | 0.82 | 0.83 | 0.59 | 0.64 | 0.94 | 0.61 |
| 255 | Q255M | 1.00 | 0.71 | 0.93 | 0.78 | 0.93 | 0.54 | 0.94 | 0.92 | 0.60 |
| 255 | Q255N | 0.85 | 0.79 | 0.87 | 0.78 | 0.88 | 0.57 | 0.92 | 1.05 | 0.62 |
| 255 | Q255P | 1.09 | 0.53 | 0.77 | 0.51 | 0.90 | 0.57 | 0.95 | 1.04 | 0.39 |
| 255 | Q255R | 0.78 | 0.99 | 0.78 | 0.95 | 0.99 | 1.04 | 0.95 | 1.04 | 0.72 |
| 255 | Q255S | 0.92 | 0.72 | 1.01 | 0.81 | 0.80 | 0.57 | 0.83 | 0.97 | 0.68 |
| 255 | Q255T | 0.74 | 0.54 | 1.03 | 0.76 | 0.96 | 0.63 | 1.07 | 1.23 | 0.46 |
| 255 | Q255V | 0.97 | 0.71 | 0.91 | 0.77 | 0.89 | 0.53 | 0.90 | 0.96 | 0.58 |
| 255 | Q255W | 1.02 | 0.78 | 0.68 | 0.77 | 0.94 | 0.49 | 0.86 | 1.01 | 0.60 |
| 255 | Q255Y | 0.94 | 0.78 | 0.79 | 0.78 | 1.00 | 0.82 | 0.96 | 1.20 | 0.53 |
| 257 | G257C | 1.08 | 0.55 | 0.74 | 0.60 | 1.16 | 1.02 | 1.04 | 0.91 | 0.55 |
| 257 | G257D | 1.05 | 0.78 | 0.74 | 0.82 | 0.89 | 0.95 | 0.86 | 0.93 | 0.97 |
| 257 | G257E | 1.09 | 0.59 | 0.50 | 0.66 | 0.96 | 1.07 | 0.81 | 0.93 | 0.94 |
| 257 | G257F | 1.12 | 0.59 | 0.65 | 0.67 | 0.92 | 0.87 | 1.32 | 0.94 | 0.77 |
| 257 | G257H | 0.91 | 0.82 | 0.73 | 0.84 | 0.92 | 0.98 | 0.92 | 0.93 | 1.00 |
| 257 | G257I | 0.84 | 0.50 | 0.56 | 0.52 | 1.03 | 1.02 | 0.85 | 0.94 | 0.53 |
| 257 | G257K | 1.02 | 0.81 | 0.85 | 0.89 | 0.98 | 1.03 | 0.92 | 0.89 | 1.00 |
| 257 | G257L | 0.85 | 0.67 | 0.64 | 0.64 | 0.91 | 0.93 | 0.99 | 0.94 | 0.75 |
| 257 | G257M | 0.97 | 0.75 | 0.79 | 0.74 | 0.94 | 0.94 | 0.92 | 0.84 | 0.85 |
| 257 | G257N | 1.11 | 0.86 | 0.88 | 0.92 | 1.00 | 0.93 | 0.94 | 0.97 | 1.04 |
| 257 | G257P | 0.89 | 0.78 | 0.63 | 0.75 | 0.92 | 0.93 | 0.94 | 0.96 | 0.98 |
| 257 | G257R | 0.95 | 0.86 | 0.69 | 0.91 | 1.10 | 1.07 | 0.99 | 1.09 | 1.07 |
| 257 | G257S | 0.95 | 0.80 | 0.72 | 0.83 | 0.95 | 1.00 | 0.78 | 0.88 | 1.00 |
| 257 | G257T | 1.02 | 0.81 | 0.67 | 0.82 | 0.92 | 0.74 | 0.89 | 0.88 | 1.00 |
| 257 | G257V | 1.01 | 0.61 | 0.63 | 0.66 | 0.91 | 0.84 | 0.88 | 0.83 | 0.85 |
| 257 | G257W | 0.99 | 0.63 | 0.62 | 0.68 | 0.94 | 1.01 | 0.95 | 0.95 | 0.77 |
| 257 | G257Y | 0.91 | 0.70 | 0.66 | 0.69 | 0.93 | 0.82 | 0.72 | 0.96 | 0.87 |
| 259 | N259C | 0.72 | 1.03 | 0.87 | 0.83 | 1.74 | 2.31 | 2.93 | 2.03 | 0.26 |
| 259 | N259D | 0.80 | 1.33 | 0.95 | 1.28 | 1.21 | 1.23 | 1.10 | 0.96 | 1.12 |
| 259 | N259E | 0.88 | 1.25 | 0.92 | 1.17 | 1.04 | 1.21 | 1.14 | 0.97 | 0.99 |
| 259 | N259G | 0.81 | 1.23 | 0.73 | 1.15 | 1.00 | 1.17 | 1.07 | 0.97 | 0.99 |
| 259 | N259H | 0.84 | 1.28 | 0.80 | 1.31 | 1.00 | 1.06 | 0.83 | 0.95 | 1.32 |
| 259 | N259K | 0.78 | 1.32 | 0.88 | 1.19 | 1.08 | 1.24 | 1.00 | 1.08 | 1.03 |
| 259 | N259P | 0.99 | 1.09 | 0.91 | 1.23 | 1.04 | 1.06 | 1.05 | 1.03 | 1.09 |
| 259 | N259Q | 0.74 | 1.47 | 0.83 | 1.30 | 0.93 | 1.03 | 0.94 | 0.99 | 1.30 |
| 259 | N259R | 0.72 | 1.20 | 0.82 | 1.17 | 0.99 | 1.29 | 1.02 | 1.08 | 1.07 |
| 259 | N259S | 0.79 | 1.40 | 0.79 | 1.38 | 0.97 | 1.10 | 1.04 | 0.94 | 1.21 |
| 259 | N259T | 0.89 | 1.01 | 0.85 | 1.12 | 1.04 | 1.00 | 0.87 | 0.96 | 1.00 |
| 259 | N259Y | 0.93 | 1.03 | 0.77 | 1.13 | 0.96 | 1.03 | 1.00 | 0.92 | 1.08 |
| 264 | G264D | 0.69 | 0.73 | 0.17 | 0.62 | 0.88 | 0.53 | 0.83 | 0.85 | 0.88 |
| 264 | G264N | 1.10 | 0.56 | 0.29 | 0.55 | 1.00 | 0.50 | 0.99 | 0.88 | 0.72 |
| 264 | G264P | 0.76 | 0.06 | 0.26 | 0.07 | 1.14 | 0.58 | 0.89 | 0.93 | 0.48 |
| 264 | G264R | 0.34 | 0.21 | 0.06 | 0.18 | 0.60 | 0.39 | 0.42 | 0.79 | 0.25 |
| 264 | G264S | 1.06 | 0.74 | 0.56 | 0.64 | 0.88 | 1.11 | 0.83 | 0.88 | 0.91 |
| 264 | G264T | 0.83 | 0.62 | 0.22 | 0.59 | 0.78 | 0.63 | 1.04 | 0.92 | 0.74 |
| 264 | G264V | 0.76 | 0.37 | 0.16 | 0.38 | 0.87 | 0.46 | 0.91 | 0.79 | 0.55 |
| 266 | F266Y | 0.20 | 0.95 | 0.53 | 0.96 | 1.05 | 1.04 | 1.05 | 1.14 | 1.05 |
| 267 | W267F | 1.11 | 0.32 | 0.45 | 0.36 | 0.42 | 0.58 | 0.25 | 0.51 | 0.49 |
| 268 | S268A | 0.72 | 0.71 | 0.44 | 0.68 | 0.96 | 0.76 | 1.08 | 1.05 | 0.67 |
| 268 | S268D | 0.08 | 0.39 | 0.12 | 0.34 | 0.80 | 0.36 | 1.00 | 0.78 | 0.91 |
| 268 | S268G | 0.41 | 0.29 | 0.15 | 0.27 | 0.93 | 0.60 | 1.20 | 1.14 | 0.31 |
| 268 | S268H | 0.52 | 0.35 | 0.27 | 0.35 | 0.93 | 0.57 | 1.02 | 0.85 | 0.73 |
| 268 | S268N | 0.84 | 0.22 | 0.40 | 0.22 | 0.69 | 0.46 | 0.88 | 0.94 | 0.89 |
| 268 | S268T | 0.83 | 0.89 | 0.83 | 0.84 | 1.08 | 1.41 | 1.04 | 0.95 | 0.74 |
| 268 | S268V | 0.45 | 0.20 | 0.17 | 0.20 | 0.71 | 0.45 | 0.78 | 0.83 | 0.37 |
| 269 | Y269A | 0.63 | 0.56 | 0.36 | 0.40 | 0.90 | 0.71 | 1.11 | 0.99 | 0.91 |
| 269 | Y269C | 0.82 | 0.31 | 0.32 | 0.24 | 0.31 | 0.19 | 0.99 | 1.25 | 0.41 |
| 269 | Y269D | 0.53 | 0.64 | 0.29 | 0.45 | 0.81 | 0.45 | 0.98 | 1.06 | 0.83 |
| 269 | Y269E | 0.56 | 0.63 | 0.22 | 0.48 | 0.69 | 0.23 | 1.13 | 1.08 | 0.89 |
| 269 | Y269F | 0.94 | 0.48 | 0.94 | 0.39 | 0.84 | 0.81 | 1.20 | 0.99 | 0.76 |
| 269 | Y269G | 0.70 | 0.87 | 0.42 | 0.76 | 0.96 | 1.04 | 1.39 | 1.04 | 0.79 |
| 269 | Y269H | 0.74 | 0.82 | 0.44 | 0.69 | 0.88 | 0.61 | 0.92 | 0.99 | 0.70 |
| 269 | Y269I | 4.55 | 0.13 | 0.26 | 0.13 | 0.76 | 0.75 | 0.58 | 0.93 | 0.77 |
| 269 | Y269K | 0.62 | 0.23 | 0.28 | 0.17 | 0.71 | 0.43 | 0.80 | 0.94 | 0.83 |
| 269 | Y269L | 0.38 | 0.35 | 0.20 | 0.23 | 0.82 | 0.83 | 0.95 | 0.91 | 0.80 |
| 269 | Y269M | 0.73 | 0.43 | 0.41 | 0.37 | 0.86 | 0.67 | 1.04 | 0.81 | 0.68 |
| 269 | Y269N | 0.59 | 0.55 | 0.43 | 0.51 | 0.80 | 0.66 | 1.01 | 0.98 | 0.85 |
| 269 | Y269P | 0.73 | 0.44 | 0.48 | 0.35 | 0.86 | 0.44 | 1.47 | 1.03 | 0.79 |
| 269 | Y269Q | 0.50 | 0.34 | 0.31 | 0.31 | 0.86 | 0.50 | 0.92 | 1.05 | 0.68 |
| 269 | Y269R | 0.92 | 0.25 | 0.36 | 0.25 | 0.62 | 0.57 | 0.66 | 0.81 | 0.69 |
| 269 | Y269S | 3.35 | 0.32 | 0.36 | 0.36 | 0.74 | 0.56 | 1.52 | 0.99 | 0.83 |
| 269 | Y269T | 0.56 | 0.20 | 0.34 | 0.20 | 0.74 | 0.61 | 0.84 | 1.01 | 0.94 |
| 269 | Y269V | 58.10 | 0.17 | 0.34 | 0.15 | 0.64 | 0.58 | 0.46 | 0.95 | 0.81 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 269 | Y269W | 0.57 | 0.31 | 0.52 | 0.32 | 0.76 | 1.16 | 0.89 | 0.95 | 0.64 |
| 270 | D270A | 0.80 | 0.17 | 0.59 | 0.20 | 1.14 | 0.91 | 0.85 | 1.11 | 0.18 |
| 270 | D270C | 1.08 | 0.16 | 0.73 | 0.17 | 2.40 | 0.49 | 4.26 | 3.04 | 0.08 |
| 270 | D270E | 1.20 | 0.54 | 0.87 | 0.61 | 1.11 | 0.56 | 1.18 | 1.18 | 0.70 |
| 270 | D270G | 0.61 | 0.11 | 0.37 | 0.12 | 1.61 | 0.06 | 2.08 | 1.34 | 0.09 |
| 270 | D270H | 0.81 | 0.25 | 0.60 | 0.27 | 0.98 | 0.39 | 0.59 | 0.90 | 0.30 |
| 270 | D270K | 0.53 | 0.32 | 0.42 | 0.38 | 0.89 | 0.82 | 0.80 | 0.84 | 0.46 |
| 270 | D270N | 0.69 | 0.90 | 0.75 | 0.87 | 0.96 | 1.18 | 0.83 | 1.04 | 0.92 |
| 270 | D270R | 0.49 | 0.23 | 0.31 | 0.26 | 0.69 | 0.67 | 0.73 | 0.52 | 0.33 |
| 270 | D270S | 0.73 | 0.60 | 0.57 | 0.64 | 1.05 | 1.03 | 0.79 | 1.00 | 0.64 |
| 270 | D270T | 0.76 | 0.14 | 0.69 | 0.14 | 1.36 | 0.14 | 1.08 | 0.66 | 0.13 |
| 272 | N272A | 1.01 | 1.05 | 0.99 | 1.01 | 0.99 | 0.95 | 1.11 | 0.95 | 1.02 |
| 272 | N272C | 1.16 | 0.49 | 1.03 | 0.50 | 1.07 | 0.77 | 1.28 | 1.10 | 0.40 |
| 272 | N272D | 0.94 | 0.98 | 0.95 | 0.92 | 1.01 | 0.86 | 1.17 | 0.99 | 0.94 |
| 272 | N272E | 0.86 | 1.11 | 1.00 | 0.99 | 0.98 | 0.88 | 0.93 | 0.88 | 1.00 |
| 272 | N272F | 1.06 | 0.65 | 0.86 | 0.64 | 0.85 | 0.80 | 1.01 | 0.92 | 0.61 |
| 272 | N272H | 1.15 | 0.93 | 0.89 | 0.97 | 0.98 | 0.94 | 1.02 | 0.96 | 0.98 |
| 272 | N272I | 0.80 | 0.86 | 0.59 | 0.85 | 1.11 | 0.79 | 1.21 | 1.06 | 0.77 |
| 272 | N272K | 0.90 | 1.03 | 1.02 | 0.98 | 0.98 | 0.87 | 1.12 | 0.98 | 1.08 |
| 272 | N272L | 0.99 | 0.70 | 0.59 | 0.64 | 1.19 | 0.89 | 1.29 | 1.04 | 0.60 |
| 272 | N272M | 0.96 | 0.97 | 0.96 | 0.87 | 1.01 | 0.92 | 0.97 | 0.91 | 0.87 |
| 272 | N272P | 1.27 | 0.60 | 0.78 | 0.57 | 1.09 | 0.80 | 1.15 | 0.93 | 0.51 |
| 272 | N272Q | 0.95 | 1.07 | 0.98 | 1.01 | 1.08 | 0.98 | 1.00 | 0.92 | 0.99 |
| 272 | N272R | 0.88 | 0.96 | 0.87 | 1.00 | 0.79 | 1.10 | 0.84 | 0.89 | 1.04 |
| 272 | N272S | 1.04 | 0.98 | 1.07 | 0.95 | 0.98 | 0.90 | 1.04 | 0.94 | 1.00 |
| 272 | N272T | 0.85 | 0.82 | 1.03 | 0.85 | 0.92 | 0.83 | 0.96 | 0.93 | 0.90 |
| 272 | N272V | 0.86 | 0.89 | 0.71 | 0.91 | 0.99 | 0.89 | 1.16 | 0.97 | 0.86 |
| 272 | N272W | 1.36 | 0.71 | 1.14 | 0.66 | 0.83 | 0.92 | 0.83 | 0.84 | 0.73 |
| 272 | N272Y | 1.10 | 0.70 | 0.89 | 0.74 | 0.94 | 0.98 | 1.10 | 0.90 | 0.75 |
| 273 | K273R | 0.51 | 1.33 | 0.30 | 1.06 | 0.96 | 0.92 | 0.83 | 1.03 | 0.85 |
| 275 | H275A | 0.49 | 1.26 | 0.46 | 1.20 | 1.13 | 0.75 | 1.18 | 1.22 | 1.00 |
| 275 | H275C | 0.52 | 0.45 | 0.61 | 0.50 | 1.31 | 0.76 | 1.77 | 1.12 | 0.22 |
| 275 | H275D | 0.97 | 0.93 | 0.46 | 1.10 | 1.14 | 0.66 | 1.35 | 1.07 | 0.86 |
| 275 | H275E | 0.84 | 1.16 | 0.63 | 1.12 | 1.13 | 0.67 | 1.25 | 1.12 | 1.00 |
| 275 | H275F | 1.12 | 0.72 | 0.94 | 0.81 | 1.00 | 0.77 | 1.34 | 1.08 | 0.70 |
| 275 | H275G | 0.77 | 1.11 | 0.54 | 1.17 | 1.29 | 0.86 | 1.52 | 1.16 | 0.72 |
| 275 | H275I | 0.50 | 0.94 | 0.86 | 1.05 | 1.06 | 0.78 | 0.89 | 1.26 | 0.86 |
| 275 | H275K | 0.49 | 1.09 | 1.32 | 1.15 | 0.99 | 0.77 | 1.41 | 1.19 | 1.08 |
| 275 | H275L | 0.43 | 1.19 | 1.13 | 1.17 | 1.30 | 0.96 | 1.40 | 1.15 | 0.73 |
| 275 | H275M | 0.60 | 0.69 | 0.99 | 0.76 | 1.04 | 0.72 | 1.08 | 1.03 | 0.57 |
| 275 | H275N | 0.43 | 1.44 | 0.83 | 1.31 | 1.14 | 0.76 | 1.24 | 1.17 | 1.13 |
| 275 | H275Q | 0.62 | 1.34 | 0.85 | 1.28 | 1.17 | 0.76 | 1.19 | 1.19 | 1.06 |
| 275 | H275R | 0.67 | 1.24 | 0.68 | 1.28 | 1.19 | 0.90 | 0.97 | 1.04 | 1.18 |
| 275 | H275S | 0.42 | 0.97 | 0.50 | 1.08 | 0.89 | 0.74 | 1.24 | 1.00 | 0.94 |
| 275 | H275T | 0.36 | 0.99 | 0.78 | 1.05 | 1.05 | 0.71 | 1.16 | 1.09 | 0.91 |
| 275 | H275V | 0.41 | 0.94 | 0.84 | 1.05 | 1.14 | 0.70 | 1.36 | 1.09 | 0.84 |
| 275 | H275W | 1.22 | 0.69 | 0.71 | 0.78 | 1.19 | 0.71 | 1.27 | 1.04 | 0.55 |
| 275 | H275Y | 0.98 | 0.77 | 0.73 | 0.89 | 1.13 | 0.69 | 1.26 | 1.17 | 0.77 |
| 279 | T279A | 0.81 | 0.61 | 1.15 | 0.65 | 1.01 | 0.88 | 0.11 | 1.09 | 0.66 |
| 279 | T279D | 0.82 | 0.84 | 0.31 | 0.80 | 1.06 | 1.18 | 0.12 | 1.09 | 0.87 |
| 279 | T279E | 0.76 | 1.13 | 1.17 | 1.01 | 1.01 | 0.74 | 0.09 | 1.12 | 1.04 |
| 279 | T279H | 1.02 | 0.86 | 0.98 | 0.93 | 1.22 | 0.97 | 0.64 | 1.12 | 0.93 |
| 279 | T279K | 0.84 | 1.03 | 1.10 | 0.98 | 1.17 | 1.21 | 0.09 | 1.18 | 0.93 |
| 279 | T279L | 1.17 | 0.81 | 1.13 | 0.79 | 1.08 | 0.83 | 0.12 | 1.17 | 0.75 |
| 279 | T279N | 1.15 | 1.14 | 1.22 | 1.10 | 1.24 | 0.92 | 0.12 | 1.21 | 1.18 |
| 279 | T279Q | 0.74 | 0.72 | 1.24 | 1.04 | 1.10 | 0.88 | 1.18 | 1.14 | 1.03 |
| 279 | T279R | 0.81 | 1.00 | 0.95 | 1.01 | 1.09 | 1.10 | 0.45 | 1.13 | 1.10 |
| 279 | T279S | 0.90 | 0.94 | 0.93 | 0.95 | 1.03 | 0.93 | 0.15 | 1.09 | 0.97 |
| 279 | T279Y | 1.19 | 0.74 | 1.10 | 0.74 | 1.01 | 1.09 | 0.59 | 1.08 | 0.74 |
| 283 | G283A | 0.97 | 0.99 | 0.96 | 0.97 | 1.02 | 1.55 | 1.18 | 1.12 | 0.77 |
| 283 | G283C | 1.18 | 0.39 | 0.93 | 0.40 | 1.29 | 0.76 | 1.88 | 1.44 | 0.22 |
| 283 | G283D | 0.81 | 0.74 | 0.52 | 0.67 | 1.11 | 0.63 | 1.20 | 1.13 | 0.59 |
| 283 | G283E | 1.26 | 0.93 | 0.89 | 0.96 | 1.08 | 0.70 | 1.15 | 0.99 | 0.99 |
| 283 | G283F | 1.03 | 0.90 | 0.84 | 0.87 | 1.04 | 0.77 | 1.04 | 1.06 | 0.23 |
| 283 | G283H | 1.02 | 0.96 | 0.94 | 0.92 | 0.95 | 0.68 | 1.13 | 1.04 | 0.94 |
| 283 | G283K | 0.96 | 1.11 | 0.97 | 1.02 | 1.02 | 0.88 | 1.31 | 1.03 | 1.00 |
| 283 | G283M | 1.11 | 0.84 | 0.96 | 0.81 | 1.14 | 0.93 | 1.38 | 0.99 | 0.18 |
| 283 | G283N | 1.05 | 1.01 | 0.80 | 1.02 | 1.12 | 0.88 | 1.19 | 1.05 | 0.90 |
| 283 | G283P | 0.58 | 0.25 | 0.14 | 0.27 | 1.21 | 0.75 | 1.40 | 1.32 | 0.22 |
| 283 | G283Q | 1.08 | 0.99 | 0.91 | 0.99 | 0.89 | 0.73 | 1.03 | 1.07 | 0.91 |
| 283 | G283R | 0.89 | 1.19 | 1.00 | 1.07 | 1.16 | 0.92 | 1.13 | 1.05 | 0.94 |
| 283 | G283S | 1.13 | 0.81 | 0.93 | 0.84 | 0.96 | 0.81 | 1.03 | 0.91 | 0.87 |
| 283 | G283T | 1.12 | 0.56 | 0.66 | 0.62 | 1.15 | 0.83 | 1.17 | 1.08 | 0.54 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 283 | G283V | 0.97 | 0.29 | 0.44 | 0.30 | 1.41 | 0.81 | 1.16 | 1.52 | 0.17 |
| 283 | G283Y | 0.97 | 0.96 | 0.91 | 0.91 | 1.05 | 0.77 | 1.07 | 1.10 | 0.64 |
| 284 | S284C | 0.98 | 0.53 | 1.38 | 0.60 | 0.69 | 0.96 | 0.87 | 0.85 | 0.48 |
| 284 | S284D | 1.17 | 0.86 | 0.62 | 0.98 | 0.90 | 0.84 | 0.94 | 0.91 | 0.96 |
| 284 | S284E | 1.43 | 0.88 | 0.87 | 1.03 | 0.90 | 0.74 | 0.87 | 0.93 | 1.01 |
| 284 | S284F | 0.88 | 0.57 | 0.51 | 0.66 | 0.87 | 0.88 | 0.80 | 0.70 | 0.72 |
| 284 | S284G | 0.80 | 0.74 | 0.45 | 0.82 | 0.95 | 0.75 | 0.83 | 0.94 | 0.90 |
| 284 | S284H | 0.94 | 0.85 | 0.61 | 0.97 | 0.87 | 0.90 | 0.83 | 0.93 | 0.91 |
| 284 | S284I | 0.79 | 0.77 | 1.10 | 0.89 | 0.79 | 0.89 | 0.86 | 0.87 | 0.90 |
| 284 | S284K | 0.95 | 0.91 | 0.55 | 1.04 | 0.97 | 0.94 | 0.82 | 0.88 | 0.99 |
| 284 | S284L | 1.18 | 0.80 | 1.03 | 0.90 | 0.86 | 0.80 | 0.81 | 0.78 | 0.83 |
| 284 | S284M | 1.42 | 0.74 | 1.33 | 0.89 | 0.91 | 0.75 | 0.85 | 0.78 | 0.92 |
| 284 | S284N | 1.15 | 0.87 | 0.60 | 1.05 | 1.01 | 0.95 | 0.86 | 0.92 | 0.99 |
| 284 | S284P | 0.54 | 0.24 | 0.15 | 0.25 | 0.78 | 0.57 | 0.85 | 0.72 | 0.24 |
| 284 | S284Q | 1.14 | 1.03 | 0.89 | 1.09 | 1.07 | 0.91 | 0.88 | 0.92 | 0.98 |
| 284 | S284R | 0.78 | 0.92 | 0.39 | 1.00 | 0.93 | 0.84 | 0.77 | 0.98 | 1.01 |
| 284 | S284T | 0.93 | 0.86 | 1.07 | 1.03 | 0.92 | 0.83 | 0.80 | 0.86 | 0.92 |
| 284 | S284V | 1.00 | 0.73 | 1.30 | 0.93 | 0.92 | 0.89 | 0.71 | 0.84 | 0.91 |
| 284 | S284W | 1.19 | 0.67 | 0.57 | 0.77 | 0.88 | 0.86 | 0.95 | 0.87 | 0.75 |
| 284 | S284Y | 1.09 | 0.77 | 0.66 | 0.87 | 0.84 | 0.90 | 0.89 | 0.91 | 0.86 |
| 298 | T298C | 0.84 | 0.69 | 0.47 | 0.68 | 1.08 | 0.88 | 0.89 | 0.96 | 0.60 |
| 298 | T298D | 1.01 | 0.82 | 0.31 | 0.83 | 1.07 | 0.89 | 1.15 | 1.02 | 1.00 |
| 298 | T298E | 1.00 | 0.94 | 0.45 | 0.91 | 1.12 | 0.92 | 1.27 | 1.11 | 0.87 |
| 298 | T298F | 0.97 | 0.56 | 0.31 | 0.54 | 0.86 | 1.10 | 0.84 | 0.80 | 0.59 |
| 298 | T298G | 0.97 | 0.78 | 0.30 | 0.78 | 0.84 | 1.08 | 1.16 | 0.92 | 0.88 |
| 298 | T298H | 1.09 | 0.75 | 0.36 | 0.88 | 0.82 | 1.08 | 0.80 | 1.00 | 1.05 |
| 298 | T298I | 0.95 | 0.94 | 0.56 | 0.89 | 1.08 | 1.14 | 1.17 | 1.00 | 0.94 |
| 298 | T298K | 0.89 | 1.05 | 0.41 | 1.04 | 0.94 | 0.95 | 1.07 | 1.01 | 1.19 |
| 298 | T298L | 0.99 | 0.84 | 0.44 | 0.84 | 0.98 | 1.00 | 1.11 | 0.95 | 0.85 |
| 298 | T298M | 0.90 | 0.73 | 0.54 | 0.73 | 0.91 | 0.92 | 1.03 | 0.90 | 0.77 |
| 298 | T298N | 1.01 | 0.98 | 0.43 | 0.95 | 0.95 | 1.20 | 1.20 | 1.04 | 1.03 |
| 298 | T298Q | 0.86 | 1.13 | 0.47 | 1.03 | 1.01 | 1.14 | 1.26 | 1.05 | 1.08 |
| 298 | T298R | 0.91 | 0.94 | 0.38 | 0.97 | 0.90 | 1.21 | 1.04 | 0.86 | 1.05 |
| 298 | T298S | 1.11 | 0.81 | 0.33 | 0.91 | 0.91 | 1.06 | 1.13 | 0.90 | 0.99 |
| 298 | T298V | 0.95 | 0.91 | 0.51 | 0.91 | 0.97 | 1.24 | 1.18 | 1.02 | 0.79 |
| 298 | T298W | 1.05 | 0.56 | 0.37 | 0.62 | 0.73 | 1.62 | 0.77 | 0.79 | 0.52 |
| 298 | T298Y | 1.01 | 0.59 | 0.30 | 0.65 | 0.84 | 0.80 | 0.92 | 0.75 | 0.73 |
| 301 | K301C | 1.04 | 0.30 | 0.75 | 0.32 | 0.67 | 0.49 | 0.97 | 0.97 | 0.44 |
| 301 | K301D | 1.11 | 0.61 | 0.70 | 0.63 | 0.75 | 0.54 | 0.92 | 1.05 | 0.85 |
| 301 | K301E | 1.19 | 0.64 | 0.80 | 0.69 | 0.96 | 0.78 | 0.99 | 0.96 | 0.92 |
| 301 | K301F | 1.20 | 0.57 | 0.77 | 0.58 | 0.90 | 0.83 | 1.04 | 1.11 | 0.70 |
| 301 | K301G | 1.06 | 0.73 | 0.79 | 0.71 | 0.82 | 0.66 | 0.79 | 1.04 | 0.87 |
| 301 | K301H | 0.99 | 0.78 | 0.87 | 0.76 | 0.86 | 1.28 | 0.93 | 1.01 | 0.95 |
| 301 | K301I | 1.02 | 0.76 | 1.02 | 0.78 | 1.03 | 0.94 | 0.99 | 1.14 | 0.89 |
| 301 | K301L | 1.10 | 0.65 | 0.78 | 0.70 | 0.82 | 0.94 | 0.89 | 0.92 | 0.87 |
| 301 | K301M | 1.17 | 0.74 | 0.85 | 0.76 | 0.86 | 0.86 | 0.91 | 1.10 | 0.87 |
| 301 | K301N | 1.28 | 0.86 | 0.82 | 0.88 | 0.88 | 0.91 | 0.85 | 1.15 | 1.03 |
| 301 | K301Q | 1.11 | 0.85 | 0.93 | 0.88 | 0.86 | 1.02 | 0.96 | 1.09 | 0.98 |
| 301 | K301R | 0.98 | 0.89 | 0.82 | 0.92 | 0.85 | 0.95 | 0.95 | 0.98 | 1.14 |
| 301 | K301S | 1.07 | 0.83 | 0.75 | 0.83 | 0.86 | 0.62 | 0.99 | 1.05 | 1.01 |
| 301 | K301T | 1.16 | 0.80 | 0.97 | 0.80 | 0.90 | 0.80 | 1.05 | 1.18 | 0.95 |
| 301 | K301V | 1.37 | 0.54 | 0.82 | 0.61 | 0.83 | 0.56 | 1.15 | 1.10 | 0.70 |
| 301 | K301W | 1.25 | 0.55 | 0.73 | 0.59 | 0.85 | 0.85 | 0.97 | 0.92 | 0.68 |
| 301 | K301Y | 1.12 | 0.60 | 0.78 | 0.61 | 0.74 | 0.79 | 1.08 | 0.99 | 0.76 |
| 303 | S303A | 0.82 | 0.95 | 1.04 | 0.93 | 0.95 | 0.79 | 0.84 | 1.07 | 0.91 |
| 303 | S303C | 0.89 | 0.66 | 1.10 | 0.65 | 1.10 | 0.32 | 1.17 | 1.49 | 0.53 |
| 303 | S303D | 1.00 | 0.85 | 1.18 | 0.96 | 1.00 | 0.57 | 0.91 | 1.25 | 0.99 |
| 303 | S303E | 0.95 | 0.89 | 1.31 | 0.90 | 0.86 | 1.00 | 1.05 | 1.20 | 0.91 |
| 303 | S303F | 0.98 | 0.72 | 1.11 | 0.73 | 0.75 | 0.91 | 0.91 | 0.97 | 0.64 |
| 303 | S303G | 1.04 | 0.84 | 1.54 | 0.90 | 0.77 | 0.90 | 0.84 | 0.98 | 0.96 |
| 303 | S303H | 0.81 | 0.58 | 1.51 | 0.86 | 0.84 | 0.99 | 0.95 | 0.87 | 0.79 |
| 303 | S303I | 0.92 | 0.69 | 0.70 | 0.75 | 1.12 | 0.72 | 0.81 | 1.29 | 0.69 |
| 303 | S303K | 0.95 | 0.83 | 1.19 | 0.92 | 0.88 | 0.94 | 0.53 | 0.85 | 0.85 |
| 303 | S303L | 0.96 | 0.64 | 0.92 | 0.73 | 1.08 | 0.64 | 0.73 | 1.07 | 0.45 |
| 303 | S303M | 0.93 | 0.64 | 1.32 | 0.65 | 0.97 | 0.82 | 0.78 | 0.96 | 0.66 |
| 303 | S303N | 1.06 | 0.95 | 1.51 | 1.01 | 0.85 | 0.78 | 0.93 | 1.08 | 1.02 |
| 303 | S303P | 0.97 | 0.80 | 0.83 | 0.87 | 0.97 | 0.26 | 1.44 | 1.70 | 0.79 |
| 303 | S303Q | 1.06 | 0.93 | 1.42 | 0.97 | 1.00 | 0.77 | 0.86 | 1.12 | 0.86 |
| 303 | S303R | 0.93 | 0.80 | 1.01 | 0.90 | 0.85 | 0.90 | 0.72 | 0.81 | 0.93 |
| 303 | S303T | 0.96 | 0.83 | 0.85 | 0.85 | 0.89 | 0.77 | 0.99 | 1.15 | 0.82 |
| 303 | S303V | 1.10 | 0.60 | 0.90 | 0.73 | 0.93 | 0.69 | 0.66 | 1.05 | 0.65 |
| 303 | S303Y | 0.94 | 0.87 | 1.25 | 0.87 | 0.93 | 0.76 | 0.66 | 0.87 | 0.80 |
| 305 | Y305A | 0.85 | 1.26 | 1.44 | 1.17 | 1.14 | 0.54 | 1.52 | 1.26 | 1.33 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 305 | Y305C | 0.97 | 0.51 | 1.11 | 0.52 | 1.09 | 0.18 | 1.37 | 1.42 | 0.42 |
| 305 | Y305D | 0.91 | 1.20 | 1.57 | 1.14 | 1.16 | 0.29 | 1.57 | 1.33 | 1.27 |
| 305 | Y305E | 0.96 | 1.26 | 1.59 | 1.21 | 1.20 | 0.40 | 1.76 | 1.39 | 1.18 |
| 305 | Y305F | 0.98 | 1.08 | 1.07 | 0.98 | 1.01 | 0.84 | 0.93 | 0.89 | 0.94 |
| 305 | Y305G | 0.98 | 1.28 | 1.25 | 1.25 | 1.22 | 0.61 | 1.39 | 1.30 | 1.34 |
| 305 | Y305H | 0.85 | 1.22 | 1.08 | 1.11 | 1.19 | 0.71 | 1.43 | 1.19 | 1.15 |
| 305 | Y305I | 0.88 | 1.11 | 0.81 | 1.02 | 1.14 | 0.50 | 1.22 | 1.30 | 1.12 |
| 305 | Y305K | 0.93 | 1.14 | 1.38 | 1.16 | 1.25 | 0.66 | 1.44 | 1.30 | 1.30 |
| 305 | Y305L | 1.07 | 0.94 | 1.23 | 1.01 | 1.14 | 0.56 | 1.53 | 1.30 | 1.03 |
| 305 | Y305M | 0.95 | 1.06 | 1.38 | 1.03 | 1.16 | 0.56 | 1.36 | 1.27 | 1.03 |
| 305 | Y305N | 0.98 | 1.35 | 1.61 | 1.22 | 1.17 | 0.63 | 1.44 | 1.26 | 1.22 |
| 305 | Y305P | 1.04 | 0.88 | 0.72 | 0.93 | 0.91 | 0.25 | 1.88 | 1.53 | 0.87 |
| 305 | Y305Q | 0.98 | 1.18 | 1.43 | 1.20 | 1.13 | 0.58 | 1.60 | 1.33 | 1.22 |
| 305 | Y305R | 0.96 | 1.23 | 1.16 | 1.21 | 1.35 | 0.76 | 1.37 | 1.33 | 1.28 |
| 305 | Y305S | 0.97 | 1.26 | 1.38 | 1.17 | 1.18 | 0.52 | 1.60 | 1.37 | 1.22 |
| 305 | Y305T | 1.01 | 1.10 | 1.32 | 1.07 | 1.19 | 0.45 | 1.50 | 1.31 | 1.19 |
| 305 | Y305V | 1.01 | 1.01 | 0.99 | 0.99 | 1.16 | 0.43 | 1.55 | 1.23 | 1.03 |
| 305 | Y305W | 0.97 | 0.99 | 0.96 | 0.93 | 1.13 | 0.70 | 1.15 | 1.11 | 0.90 |
| 306 | F306A | 0.52 | 0.43 | 0.67 | 0.86 | 1.01 | 0.97 | 0.79 | 0.92 | 0.91 |
| 306 | F306C | 1.05 | 0.43 | 0.67 | 0.40 | 0.97 | 0.66 | 1.98 | 0.93 | 0.38 |
| 306 | F306D | 1.03 | 0.23 | 0.65 | 0.22 | 1.04 | 0.96 | 3.32 | 0.63 | 0.19 |
| 306 | F306E | 0.91 | 0.29 | 0.70 | 0.31 | 0.92 | 0.56 | 2.22 | 0.71 | 0.30 |
| 306 | F306G | 0.77 | 0.43 | 0.71 | 0.60 | 0.89 | 0.82 | 1.44 | 0.88 | 0.58 |
| 306 | F306H | 1.19 | 0.79 | 0.71 | 0.81 | 0.97 | 1.01 | 1.23 | 0.93 | 0.66 |
| 306 | F306I | 1.06 | 0.38 | 0.62 | 0.41 | 1.03 | 0.91 | 1.49 | 0.89 | 0.40 |
| 306 | F306K | 0.91 | 0.26 | 0.65 | 0.43 | 0.79 | 0.86 | 1.47 | 0.68 | 0.42 |
| 306 | F306L | 0.96 | 0.33 | 0.62 | 0.44 | 0.92 | 0.87 | 1.30 | 0.72 | 0.47 |
| 306 | F306M | 0.92 | 0.50 | 0.72 | 0.72 | 0.91 | 0.96 | 1.27 | 0.83 | 0.79 |
| 306 | F306N | 1.21 | 0.38 | 0.69 | 0.38 | 0.83 | 0.79 | 1.83 | 0.64 | 0.38 |
| 306 | F306Q | 0.80 | 0.38 | 0.69 | 0.50 | 1.05 | 0.79 | 1.55 | 0.95 | 0.47 |
| 306 | F306R | 0.83 | 0.18 | 0.59 | 0.25 | 0.77 | 1.20 | 2.42 | 0.62 | 0.21 |
| 306 | F306S | 0.45 | 0.40 | 0.65 | 0.65 | 0.92 | 0.89 | 0.72 | 0.84 | 0.71 |
| 306 | F306T | 0.97 | 0.38 | 0.67 | 0.55 | 0.95 | 0.84 | 1.33 | 0.92 | 0.57 |
| 306 | F306V | 1.14 | 0.35 | 0.69 | 0.37 | 0.94 | 0.79 | 2.14 | 0.88 | 0.34 |
| 306 | F306W | 1.28 | 0.90 | 0.66 | 0.95 | 0.94 | 1.11 | 0.90 | 0.85 | 0.93 |
| 310 | Y310A | 0.94 | 0.93 | 1.20 | 0.85 | 1.09 | 0.91 | 1.04 | 0.95 | 0.91 |
| 310 | Y310C | 1.04 | 0.93 | 1.29 | 0.96 | 0.99 | 0.92 | 0.84 | 1.01 | 0.87 |
| 310 | Y310D | 1.11 | 1.21 | 1.41 | 1.19 | 1.33 | 1.10 | 1.52 | 1.23 | 0.66 |
| 310 | Y310E | 0.99 | 1.09 | 1.57 | 1.02 | 1.07 | 0.87 | 1.13 | 1.12 | 1.15 |
| 310 | Y310F | 1.10 | 0.97 | 1.03 | 0.94 | 0.86 | 1.37 | 1.03 | 1.25 | 0.20 |
| 310 | Y310G | 1.20 | 1.07 | 1.10 | 1.06 | 0.71 | 0.93 | 1.00 | 1.12 | 0.33 |
| 310 | Y310H | 1.02 | 1.12 | 1.02 | 1.05 | 1.13 | 1.19 | 1.32 | 1.10 | 1.15 |
| 310 | Y310I | 0.93 | 1.07 | 0.84 | 1.06 | 1.13 | 1.17 | 1.44 | 1.25 | 0.94 |
| 310 | Y310K | 0.90 | 1.20 | 1.25 | 1.04 | 0.94 | 1.05 | 1.13 | 1.08 | 1.06 |
| 310 | Y310L | 0.88 | 1.08 | 1.30 | 0.94 | 1.07 | 0.88 | 0.97 | 0.96 | 1.48 |
| 310 | Y310M | 1.03 | 0.97 | 1.37 | 0.91 | 0.95 | 0.95 | 0.92 | 1.08 | 1.27 |
| 310 | Y310N | 1.17 | 1.14 | 1.47 | 1.13 | 0.91 | 1.03 | 1.50 | 1.18 | 1.19 |
| 310 | Y310Q | 1.10 | 1.04 | 1.24 | 1.09 | 1.13 | 1.02 | 1.32 | 1.06 | 1.28 |
| 310 | Y310R | 0.97 | 1.07 | 1.06 | 1.08 | 0.90 | 1.33 | 0.91 | 0.90 | 1.12 |
| 310 | Y310S | 1.05 | 1.02 | 1.16 | 1.03 | 0.97 | 0.84 | 0.84 | 1.10 | 1.31 |
| 310 | Y310T | 1.06 | 0.96 | 1.51 | 0.96 | 0.94 | 1.07 | 0.96 | 0.96 | 1.19 |
| 310 | Y310V | 1.10 | 0.89 | 0.93 | 0.95 | 1.04 | 1.12 | 1.20 | 1.07 | 1.16 |
| 311 | L311C | 0.93 | 0.44 | 0.68 | 0.46 | 0.99 | 0.75 | 0.74 | 0.93 | 0.39 |
| 311 | L311F | 1.00 | 0.79 | 0.58 | 0.81 | 0.95 | 0.80 | 0.81 | 0.81 | 0.70 |
| 311 | L311G | 1.04 | 0.09 | 0.66 | 0.10 | 1.25 | 0.50 | 1.18 | 1.04 | 0.07 |
| 311 | L311I | 0.70 | 0.75 | 1.34 | 0.96 | 0.94 | 0.98 | 1.00 | 0.92 | 0.94 |
| 311 | L311M | 0.93 | 1.00 | 0.82 | 0.92 | 0.94 | 0.82 | 0.80 | 0.95 | 0.83 |
| 311 | L311Q | 0.90 | 0.23 | 0.67 | 0.22 | 1.00 | 0.49 | 0.88 | 0.85 | 0.20 |
| 311 | L311S | 0.66 | 0.42 | 0.61 | 0.54 | 1.17 | 0.89 | 1.00 | 1.29 | 0.41 |
| 311 | L311T | 1.03 | 0.67 | 0.78 | 0.71 | 1.03 | 0.90 | 0.98 | 0.97 | 0.64 |
| 311 | L311V | 1.18 | 0.73 | 0.95 | 0.79 | 1.05 | 0.80 | 0.85 | 0.90 | 0.76 |
| 314 | N314A | 0.79 | 1.13 | 0.68 | 1.05 | 0.95 | 0.89 | 0.91 | 1.12 | 1.21 |
| 314 | N314C | 0.95 | 0.65 | 0.75 | 0.61 | 1.00 | 0.53 | 0.93 | 1.24 | 0.75 |
| 314 | N314D | 0.93 | 1.07 | 0.94 | 0.98 | 0.94 | 0.72 | 0.97 | 1.18 | 1.22 |
| 314 | N314E | 0.92 | 1.06 | 0.85 | 0.95 | 1.01 | 0.66 | 0.76 | 1.11 | 1.34 |
| 314 | N314F | 0.94 | 0.96 | 0.74 | 0.80 | 0.87 | 0.94 | 0.82 | 1.04 | 0.99 |
| 314 | N314G | 0.98 | 1.22 | 1.25 | 1.10 | 0.91 | 0.91 | 1.01 | 1.12 | 1.27 |
| 314 | N314H | 0.90 | 1.06 | 0.78 | 0.94 | 0.94 | 0.87 | 0.91 | 1.02 | 1.32 |
| 314 | N314I | 0.92 | 0.59 | 0.64 | 0.50 | 0.95 | 0.85 | 0.83 | 1.05 | 0.57 |
| 314 | N314K | 0.83 | 0.94 | 0.74 | 0.93 | 0.86 | 0.78 | 0.84 | 0.97 | 1.18 |
| 314 | N314L | 0.95 | 0.79 | 0.67 | 0.75 | 1.05 | 0.83 | 0.85 | 1.18 | 1.01 |
| 314 | N314M | 0.87 | 0.86 | 0.76 | 0.80 | 0.88 | 0.80 | 0.81 | 1.02 | 1.09 |
| 314 | N314P | 0.95 | 0.45 | 0.57 | 0.37 | 0.90 | 0.74 | 0.83 | 1.01 | 0.36 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 314 | N314Q | 0.92 | 1.00 | 0.78 | 0.91 | 0.87 | 0.89 | 0.83 | 1.16 | 1.26 |
| 314 | N314R | 0.79 | 1.00 | 0.65 | 0.93 | 0.84 | 0.96 | 0.90 | 0.86 | 1.23 |
| 314 | N314S | 0.88 | 0.98 | 0.75 | 0.92 | 0.92 | 0.72 | 0.83 | 1.14 | 1.18 |
| 314 | N314V | 0.92 | 0.82 | 0.68 | 0.70 | 0.88 | 0.88 | 0.82 | 1.00 | 0.73 |
| 314 | N314W | 0.98 | 0.84 | 0.68 | 0.77 | 0.96 | 0.93 | 0.94 | 0.92 | 0.89 |
| 314 | N314Y | 0.94 | 0.93 | 0.72 | 0.85 | 0.86 | 0.88 | 0.90 | 1.07 | 1.10 |
| 318 | K318A | 0.83 | 1.07 | 0.79 | 1.00 | 1.13 | 1.03 | 1.00 | 1.12 | 1.04 |
| 318 | K318C | 0.87 | 0.70 | 0.63 | 0.58 | 1.04 | 0.75 | 0.85 | 1.06 | 0.67 |
| 318 | K318D | 1.05 | 0.70 | 0.53 | 0.69 | 1.03 | 0.95 | 0.96 | 1.26 | 0.68 |
| 318 | K318E | 1.14 | 0.94 | 0.60 | 1.02 | 1.02 | 1.09 | 1.02 | 1.09 | 0.94 |
| 318 | K318G | 0.96 | 0.81 | 0.73 | 0.84 | 1.09 | 0.97 | 0.84 | 1.15 | 0.93 |
| 318 | K318H | 0.97 | 1.00 | 0.80 | 0.92 | 1.00 | 0.96 | 0.76 | 1.10 | 1.12 |
| 318 | K318I | 1.13 | 0.89 | 0.52 | 1.00 | 1.10 | 0.93 | 1.01 | 1.20 | 1.03 |
| 318 | K318L | 1.18 | 0.79 | 0.78 | 0.83 | 1.12 | 0.97 | 1.14 | 1.11 | 0.86 |
| 318 | K318M | 1.05 | 0.88 | 0.73 | 0.87 | 0.97 | 0.93 | 1.02 | 1.06 | 0.98 |
| 318 | K318N | 1.09 | 0.92 | 0.78 | 0.94 | 0.97 | 0.91 | 0.69 | 1.14 | 1.15 |
| 318 | K318P | 0.84 | 0.46 | 0.50 | 0.47 | 0.96 | 0.71 | 0.98 | 1.26 | 0.46 |
| 318 | K318Q | 1.16 | 0.91 | 0.71 | 1.00 | 1.04 | 1.00 | 0.98 | 1.12 | 1.06 |
| 318 | K318R | 1.06 | 0.97 | 0.89 | 1.01 | 1.07 | 1.17 | 0.68 | 1.15 | 1.15 |
| 318 | K318S | 0.96 | 1.04 | 0.70 | 0.98 | 1.12 | 1.05 | 0.91 | 1.06 | 1.06 |
| 318 | K318T | 0.89 | 0.99 | 0.52 | 0.97 | 1.14 | 0.79 | 1.05 | 1.20 | 1.00 |
| 318 | K318Y | 1.32 | 0.81 | 0.67 | 0.88 | 0.96 | 0.93 | 1.04 | 1.24 | 0.99 |
| 319 | D319A | 0.69 | 1.01 | 0.54 | 1.00 | 1.04 | 0.91 | 1.46 | 1.20 | 0.91 |
| 319 | D319E | 0.94 | 1.13 | 1.18 | 1.08 | 0.95 | 0.86 | 1.23 | 0.99 | 1.07 |
| 319 | D319F | 0.79 | 1.01 | 0.63 | 0.93 | 1.01 | 0.60 | 1.04 | 1.03 | 0.84 |
| 319 | D319H | 0.85 | 0.99 | 0.79 | 1.03 | 1.11 | 1.02 | 1.09 | 1.04 | 0.86 |
| 319 | D319I | 0.38 | 0.87 | 0.44 | 0.89 | 1.20 | 1.53 | 1.46 | 0.87 | 0.96 |
| 319 | D319K | 0.38 | 0.98 | 0.30 | 1.00 | 1.13 | 0.65 | 0.82 | 1.07 | 0.95 |
| 319 | D319M | 0.63 | 0.92 | 0.64 | 0.90 | 0.89 | 0.60 | 1.18 | 1.09 | 0.95 |
| 319 | D319N | 0.96 | 0.95 | 0.91 | 1.00 | 1.18 | 0.94 | 1.21 | 1.02 | 1.05 |
| 319 | D319P | 0.81 | 0.46 | 0.55 | 0.45 | 1.03 | 0.33 | 1.01 | 0.97 | 0.33 |
| 319 | D319Q | 0.69 | 0.97 | 0.69 | 1.02 | 1.03 | 1.05 | 1.38 | 1.00 | 1.04 |
| 319 | D319R | 0.29 | 1.16 | 0.28 | 1.06 | 1.03 | 1.27 | 1.20 | 0.85 | 1.02 |
| 319 | D319S | 0.89 | 0.95 | 0.95 | 0.98 | 1.14 | 0.86 | 1.41 | 1.04 | 0.95 |
| 319 | D319T | 0.89 | 0.90 | 1.13 | 0.95 | 1.17 | 0.66 | 1.42 | 1.09 | 1.02 |
| 319 | D319V | 0.36 | 0.94 | 0.44 | 0.93 | 1.37 | 0.99 | 1.49 | 1.30 | 0.71 |
| 319 | D319W | 0.56 | 0.90 | 0.45 | 0.83 | 1.00 | 0.52 | 1.23 | 0.90 | 0.84 |
| 319 | D319Y | 0.78 | 0.87 | 0.61 | 0.93 | 0.94 | 0.56 | 1.40 | 1.05 | 0.83 |
| 320 | Q320A | 0.94 | 0.70 | 1.15 | 0.84 | 1.20 | 0.77 | 0.76 | 0.95 | 0.72 |
| 320 | Q320C | 0.88 | 0.50 | 1.77 | 0.51 | 1.33 | 0.88 | 1.66 | 1.62 | 0.31 |
| 320 | Q320D | 0.93 | 0.86 | 0.77 | 0.95 | 1.09 | 0.63 | 1.27 | 1.23 | 0.86 |
| 320 | Q320E | 1.06 | 0.93 | 0.95 | 0.98 | 1.22 | 0.68 | 1.28 | 1.14 | 0.81 |
| 320 | Q320F | 1.32 | 0.78 | 1.51 | 0.87 | 1.12 | 0.56 | 1.46 | 1.21 | 0.79 |
| 320 | Q320G | 0.87 | 0.71 | 0.61 | 0.79 | 1.20 | 0.80 | 1.26 | 1.11 | 0.67 |
| 320 | Q320H | 0.86 | 0.98 | 1.20 | 0.95 | 1.14 | 0.70 | 1.31 | 1.05 | 0.86 |
| 320 | Q320I | 0.98 | 0.71 | 1.10 | 0.79 | 1.23 | 0.76 | 0.98 | 1.24 | 0.70 |
| 320 | Q320K | 0.96 | 0.84 | 1.16 | 0.97 | 1.17 | 0.74 | 1.25 | 1.06 | 0.95 |
| 320 | Q320L | 0.84 | 0.77 | 1.05 | 0.77 | 1.15 | 0.67 | 0.93 | 1.11 | 0.66 |
| 320 | Q320M | 0.91 | 0.87 | 1.25 | 0.83 | 1.06 | 0.74 | 1.03 | 1.12 | 0.77 |
| 320 | Q320N | 1.08 | 0.87 | 1.41 | 0.97 | 1.31 | 0.69 | 1.35 | 1.09 | 0.85 |
| 320 | Q320R | 0.78 | 0.99 | 1.06 | 0.98 | 1.29 | 0.83 | 1.18 | 1.06 | 0.92 |
| 320 | Q320S | 0.95 | 0.88 | 0.87 | 0.98 | 1.17 | 0.71 | 1.14 | 1.08 | 0.83 |
| 320 | Q320T | 1.12 | 0.77 | 1.00 | 0.89 | 1.09 | 0.66 | 0.96 | 1.10 | 0.80 |
| 320 | Q320V | 1.15 | 0.75 | 1.26 | 0.83 | 1.12 | 0.66 | 1.22 | 1.05 | 0.74 |
| 320 | Q320W | 1.06 | 0.80 | 1.07 | 0.88 | 1.03 | 0.60 | 2.41 | 1.09 | 0.73 |
| 320 | Q320Y | 1.12 | 0.85 | 1.61 | 0.88 | 1.14 | 0.56 | 1.35 | 1.08 | 0.80 |
| 322 | S322A | 0.90 | 1.09 | 0.97 | 1.01 | 1.04 | 1.06 | 1.14 | 1.05 | 0.99 |
| 322 | S322D | 0.91 | 1.04 | 1.27 | 0.92 | 1.11 | 0.87 | 1.30 | 1.09 | 0.80 |
| 322 | S322E | 0.96 | 1.23 | 1.22 | 1.04 | 0.91 | 0.78 | 1.06 | 0.95 | 1.04 |
| 322 | S322F | 0.87 | 0.89 | 0.87 | 0.76 | 0.89 | 0.92 | 0.73 | 0.94 | 0.70 |
| 322 | S322G | 0.68 | 0.88 | 1.08 | 1.03 | 0.95 | 0.83 | 1.00 | 0.98 | 1.00 |
| 322 | S322H | 0.51 | 0.52 | 1.24 | 0.94 | 1.05 | 0.72 | 1.00 | 0.96 | 0.96 |
| 322 | S322I | 0.83 | 0.96 | 0.71 | 0.81 | 1.02 | 0.94 | 1.07 | 1.03 | 0.80 |
| 322 | S322L | 0.78 | 0.99 | 0.90 | 0.82 | 1.12 | 0.85 | 1.13 | 1.04 | 0.74 |
| 322 | S322M | 0.75 | 1.39 | 0.97 | 1.10 | 1.18 | 0.83 | 1.18 | 1.09 | 0.91 |
| 322 | S322N | 1.04 | 1.13 | 1.34 | 1.06 | 1.02 | 0.88 | 1.02 | 1.08 | 0.96 |
| 322 | S322P | 0.95 | 0.89 | 0.87 | 0.82 | 0.86 | 0.83 | 1.26 | 1.01 | 0.74 |
| 322 | S322Q | 0.82 | 0.83 | 1.21 | 1.02 | 1.07 | 0.81 | 1.04 | 1.06 | 1.03 |
| 322 | S322R | 0.78 | 1.25 | 0.89 | 1.01 | 1.06 | 1.22 | 1.34 | 1.07 | 0.88 |
| 322 | S322T | 0.91 | 1.04 | 1.09 | 0.94 | 0.97 | 1.10 | 1.02 | 0.79 | 0.89 |
| 322 | S322V | 1.00 | 0.88 | 0.90 | 0.85 | 0.93 | 1.07 | 1.00 | 0.85 | 0.80 |
| 322 | S322W | 0.90 | 0.91 | 0.92 | 0.75 | 0.95 | 0.87 | 0.94 | 0.87 | 0.71 |
| 322 | S322Y | 0.97 | 0.89 | 0.96 | 0.87 | 0.83 | 1.02 | 0.93 | 0.81 | 0.84 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 323 | L323A | 0.66 | 0.97 | 0.56 | 0.98 | 1.10 | 0.87 | 1.13 | 1.09 | 0.95 |
| 323 | L323C | 0.68 | 0.48 | 0.47 | 0.48 | 1.10 | 0.85 | 0.81 | 1.04 | 0.40 |
| 323 | L323D | 0.67 | 0.66 | 0.42 | 0.67 | 1.00 | 0.69 | 0.96 | 1.17 | 0.70 |
| 323 | L323E | 0.68 | 0.86 | 0.45 | 0.85 | 0.82 | 0.70 | 1.02 | 0.98 | 1.04 |
| 323 | L323F | 0.79 | 0.98 | 0.93 | 0.95 | 1.01 | 0.83 | 1.09 | 1.13 | 1.00 |
| 323 | L323G | 0.76 | 0.87 | 0.38 | 0.91 | 0.96 | 0.76 | 1.00 | 1.09 | 0.93 |
| 323 | L323H | 0.65 | 0.81 | 0.65 | 1.05 | 0.97 | 0.84 | 0.81 | 1.20 | 1.09 |
| 323 | L323K | 0.76 | 1.15 | 0.78 | 1.13 | 1.01 | 0.91 | 1.08 | 0.97 | 1.13 |
| 323 | L323M | 1.02 | 0.81 | 0.79 | 0.90 | 1.00 | 0.99 | 0.99 | 1.01 | 0.88 |
| 323 | L323N | 0.86 | 0.98 | 0.44 | 1.04 | 0.98 | 0.80 | 1.23 | 1.20 | 1.07 |
| 323 | L323P | 0.69 | 0.39 | 0.41 | 0.41 | 0.94 | 0.63 | 0.94 | 1.09 | 0.43 |
| 323 | L323Q | 0.84 | 1.04 | 0.49 | 1.06 | 1.02 | 0.89 | 1.06 | 1.15 | 1.07 |
| 323 | L323R | 0.77 | 0.56 | 0.46 | 0.58 | 1.10 | 1.02 | 1.12 | 0.93 | 0.57 |
| 323 | L323S | 0.73 | 1.07 | 0.48 | 1.03 | 1.02 | 0.92 | 1.21 | 1.08 | 0.98 |
| 323 | L323T | 0.86 | 0.58 | 0.50 | 0.60 | 0.92 | 0.45 | 1.05 | 1.01 | 0.62 |
| 323 | L323V | 0.91 | 0.93 | 0.62 | 0.86 | 0.99 | 0.76 | 1.00 | 0.91 | 0.95 |
| 323 | L323W | 0.67 | 0.83 | 0.47 | 0.77 | 0.83 | 0.81 | 0.99 | 0.96 | 0.76 |
| 336 | G336A | 0.77 | 0.83 | 0.57 | 0.74 | 0.86 | 0.81 | 1.18 | 1.01 | 0.86 |
| 336 | G336C | 0.93 | 0.44 | 0.68 | 0.42 | 0.89 | 0.59 | 1.01 | 1.03 | 0.47 |
| 336 | G336E | 0.95 | 0.89 | 0.67 | 0.84 | 0.90 | 0.67 | 1.16 | 0.98 | 0.92 |
| 336 | G336F | 1.00 | 0.75 | 0.73 | 0.73 | 0.88 | 0.95 | 1.26 | 0.84 | 0.53 |
| 336 | G336H | 0.88 | 0.99 | 0.70 | 0.90 | 0.89 | 1.02 | 1.02 | 0.93 | 0.86 |
| 336 | G336I | 0.97 | 0.41 | 0.51 | 0.39 | 0.84 | 0.39 | 1.13 | 0.93 | 0.49 |
| 336 | G336K | 0.95 | 0.86 | 0.56 | 0.90 | 0.68 | 0.62 | 1.33 | 0.85 | 0.94 |
| 336 | G336M | 0.91 | 0.73 | 0.70 | 0.72 | 0.90 | 0.82 | 1.38 | 1.01 | 0.73 |
| 336 | G336N | 0.87 | 0.30 | 0.74 | 0.28 | 0.76 | 0.69 | 1.14 | 0.92 | 0.32 |
| 336 | G336P | 1.22 | 0.09 | 0.70 | 0.08 | 0.37 | 0.12 | 1.28 | 1.00 | 0.66 |
| 336 | G336Q | 0.98 | 0.92 | 0.64 | 0.86 | 0.93 | 0.71 | 1.16 | 0.97 | 0.93 |
| 336 | G336R | 0.90 | 0.83 | 0.49 | 0.75 | 0.74 | 0.87 | 0.67 | 0.81 | 0.88 |
| 336 | G336S | 0.94 | 0.71 | 0.60 | 0.70 | 0.83 | 0.68 | 1.11 | 0.92 | 0.91 |
| 336 | G336T | 1.00 | 0.66 | 0.57 | 0.68 | 0.76 | 0.62 | 1.04 | 0.91 | 0.90 |
| 336 | G336W | 0.88 | 0.98 | 0.60 | 0.82 | 0.90 | 0.99 | 1.00 | 0.92 | 0.66 |
| 336 | G336Y | 1.04 | 0.99 | 0.73 | 0.98 | 0.95 | 0.95 | 1.00 | 1.02 | 0.79 |
| 337 | Q337A | 0.97 | 0.37 | 1.18 | 0.38 | 1.02 | 1.02 | 0.65 | 0.91 | 0.83 |
| 337 | Q337E | 1.27 | 0.56 | 0.55 | 0.61 | 0.24 | 0.17 | 0.94 | 0.93 | 0.99 |
| 337 | Q337G | 1.18 | 0.46 | 1.74 | 0.47 | 0.91 | 0.55 | 0.59 | 0.78 | 0.88 |
| 337 | Q337N | 1.20 | 0.11 | 0.91 | 0.12 | 0.68 | 0.38 | 1.01 | 0.80 | 0.95 |
| 337 | Q337S | 0.97 | 0.22 | 1.18 | 0.21 | 0.83 | 0.52 | 0.46 | 0.77 | 0.72 |
| 337 | Q337T | 1.04 | 0.06 | 0.87 | 0.06 | 0.56 | 0.33 | 0.81 | 0.77 | 0.77 |
| 338 | S338A | 1.01 | 0.54 | 1.00 | 0.57 | 0.93 | 0.95 | 0.96 | 0.97 | 1.03 |
| 338 | S338C | 1.07 | 0.06 | 0.87 | 0.06 | 0.31 | 0.13 | 0.89 | 0.82 | 0.52 |
| 338 | S338D | 1.14 | 0.14 | 0.91 | 0.14 | 0.75 | 0.18 | 1.03 | 0.91 | 1.02 |
| 338 | S338E | 1.05 | 0.06 | 0.92 | 0.06 | 0.50 | 0.11 | 1.46 | 0.74 | 1.11 |
| 338 | S338G | 1.03 | 0.27 | 0.83 | 0.28 | 0.75 | 0.86 | 0.97 | 0.96 | 0.81 |
| 338 | S338K | 0.72 | 0.06 | 1.13 | 0.06 | 0.59 | 0.41 | 0.97 | 0.82 | 1.07 |
| 338 | S338M | 1.01 | 0.09 | 0.88 | 0.10 | 0.63 | 0.28 | 0.88 | 0.67 | 0.93 |
| 338 | S338N | 1.01 | 0.08 | 0.86 | 0.08 | 0.66 | 0.26 | 1.06 | 0.88 | 1.09 |
| 338 | S338P | 0.99 | 0.15 | 1.70 | 0.15 | 0.74 | 0.42 | 0.90 | 0.70 | 0.92 |
| 338 | S338Q | 1.01 | 0.14 | 0.80 | 0.15 | 0.62 | 0.29 | 0.91 | 0.89 | 1.07 |
| 338 | S338T | 1.05 | 0.08 | 0.80 | 0.09 | 0.47 | 0.30 | 0.80 | 0.64 | 0.92 |
| 338 | S338Y | 0.96 | 0.09 | 0.78 | 0.09 | 0.30 | 0.13 | 0.74 | 0.60 | 0.83 |
| 339 | L339G | 1.07 | 0.09 | 0.90 | 0.10 | 0.31 | 0.13 | 0.35 | 0.61 | 1.18 |
| 339 | L339H | 0.65 | 0.22 | 0.78 | 0.26 | 0.61 | 0.38 | 0.34 | 0.84 | 1.39 |
| 339 | L339I | 2.08 | 0.08 | 0.68 | 0.15 | 0.66 | 0.29 | 0.78 | 0.65 | 1.17 |
| 339 | L339M | 1.16 | 0.28 | 1.27 | 0.30 | 0.82 | 0.42 | 0.66 | 0.71 | 1.29 |
| 339 | L339Q | 0.87 | 0.57 | 0.78 | 0.49 | 0.77 | 0.56 | 0.45 | 1.04 | 1.36 |
| 339 | L339V | 0.99 | 0.13 | 0.76 | 0.13 | 0.45 | 0.22 | 0.78 | 0.74 | 1.26 |
| 340 | Q340A | 0.90 | 0.67 | 0.80 | 0.68 | 1.01 | 0.99 | 0.97 | 0.97 | 0.87 |
| 340 | Q340C | 0.97 | 0.33 | 0.88 | 0.33 | 1.12 | 0.32 | 1.18 | 1.14 | 0.39 |
| 340 | Q340D | 1.01 | 0.70 | 0.81 | 0.68 | 0.87 | 0.33 | 1.06 | 0.96 | 0.99 |
| 340 | Q340E | 1.02 | 0.98 | 1.53 | 0.97 | 1.02 | 0.99 | 1.08 | 0.96 | 1.07 |
| 340 | Q340F | 0.89 | 0.79 | 0.72 | 0.67 | 1.11 | 1.04 | 0.98 | 0.93 | 0.51 |
| 340 | Q340G | 0.93 | 0.62 | 0.74 | 0.56 | 0.68 | 0.18 | 0.94 | 0.92 | 0.91 |
| 340 | Q340H | 1.01 | 0.74 | 0.70 | 0.72 | 0.87 | 0.69 | 0.92 | 0.92 | 0.94 |
| 340 | Q340I | 0.98 | 0.30 | 0.63 | 0.27 | 0.59 | 0.18 | 0.95 | 0.83 | 0.53 |
| 340 | Q340K | 0.87 | 0.64 | 0.56 | 0.56 | 0.65 | 0.31 | 0.62 | 0.77 | 1.09 |
| 340 | Q340L | 0.97 | 0.42 | 0.63 | 0.37 | 0.47 | 0.07 | 1.10 | 0.92 | 0.45 |
| 340 | Q340M | 0.99 | 0.73 | 0.83 | 0.67 | 0.86 | 0.77 | 1.02 | 0.85 | 0.54 |
| 340 | Q340N | 1.07 | 0.60 | 0.80 | 0.60 | 0.88 | 0.40 | 1.19 | 0.93 | 0.91 |
| 340 | Q340R | 0.97 | 0.53 | 0.52 | 0.54 | 0.57 | 0.50 | 0.58 | 0.76 | 0.91 |
| 340 | Q340S | 1.01 | 0.51 | 0.87 | 0.54 | 0.86 | 0.70 | 0.94 | 0.92 | 1.01 |
| 340 | Q340T | 1.13 | 0.55 | 0.81 | 0.55 | 0.99 | 1.07 | 1.21 | 0.96 | 1.10 |
| 340 | Q340V | 1.15 | 0.58 | 0.75 | 0.64 | 0.89 | 0.69 | 0.82 | 0.79 | 0.86 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 340 | Q340W | 0.90 | 0.59 | 0.59 | 0.52 | 0.71 | 0.53 | 0.54 | 0.72 | 0.46 |
| 340 | Q340Y | 1.00 | 0.86 | 0.70 | 0.87 | 1.05 | 1.36 | 1.00 | 0.85 | 0.65 |
| 344 | E344A | 0.96 | 1.01 | 0.70 | 1.01 | 0.82 | 1.08 | 0.68 | 0.69 | 1.28 |
| 344 | E344C | 0.85 | 0.83 | 0.87 | 0.76 | 0.91 | 0.90 | 1.04 | 0.99 | 0.87 |
| 344 | E344D | 0.90 | 0.92 | 0.84 | 0.82 | 0.87 | 0.90 | 0.83 | 0.93 | 1.17 |
| 344 | E344F | 0.96 | 0.70 | 0.67 | 0.64 | 0.73 | 0.77 | 0.71 | 0.77 | 0.95 |
| 344 | E344G | 0.98 | 0.73 | 0.67 | 0.76 | 0.87 | 0.76 | 0.49 | 0.78 | 1.11 |
| 344 | E344H | 0.95 | 0.80 | 0.64 | 0.76 | 0.80 | 0.99 | 0.54 | 0.94 | 1.13 |
| 344 | E344K | 0.99 | 1.08 | 0.71 | 1.14 | 0.63 | 0.98 | 0.38 | 0.51 | 1.60 |
| 344 | E344L | 0.90 | 0.90 | 0.72 | 0.87 | 0.81 | 0.83 | 0.18 | 0.60 | 1.18 |
| 344 | E344M | 0.85 | 0.70 | 0.81 | 0.67 | 0.59 | 1.02 | 0.20 | 0.59 | 0.97 |
| 344 | E344N | 1.14 | 0.75 | 0.69 | 0.79 | 0.78 | 0.80 | 0.53 | 0.83 | 1.11 |
| 344 | E344P | 1.08 | 0.54 | 0.71 | 0.61 | 0.63 | 0.88 | 0.34 | 0.60 | 1.14 |
| 344 | E344R | 0.83 | 1.14 | 0.62 | 1.13 | 0.67 | 1.11 | 0.51 | 0.56 | 1.42 |
| 344 | E344S | 0.85 | 0.78 | 0.73 | 0.81 | 0.77 | 1.03 | 0.28 | 0.61 | 1.09 |
| 344 | E344T | 0.97 | 0.75 | 0.70 | 0.80 | 0.86 | 0.93 | 0.34 | 0.69 | 1.10 |
| 344 | E344V | 1.08 | 0.71 | 0.68 | 0.75 | 0.65 | 0.73 | 0.40 | 0.62 | 1.09 |
| 359 | Q359A | 0.92 | 0.96 | 1.04 | 1.02 | 1.01 | 0.87 | 0.81 | 1.20 | 1.01 |
| 359 | Q359C | 0.92 | 0.23 | 0.76 | 0.28 | 1.63 | 1.13 | 3.36 | 1.55 | 0.12 |
| 359 | Q359D | 1.02 | 0.92 | 0.79 | 0.93 | 1.01 | 0.83 | 1.02 | 0.94 | 0.95 |
| 359 | Q359E | 1.06 | 0.83 | 0.95 | 0.93 | 1.00 | 0.83 | 0.81 | 0.92 | 0.93 |
| 359 | Q359F | 1.11 | 0.93 | 0.75 | 1.06 | 0.96 | 0.93 | 0.90 | 0.93 | 1.00 |
| 359 | Q359G | 0.99 | 0.87 | 0.78 | 0.99 | 0.87 | 0.82 | 0.80 | 0.91 | 1.01 |
| 359 | Q359I | 0.89 | 0.74 | 0.90 | 0.78 | 0.95 | 0.82 | 0.71 | 0.93 | 0.77 |
| 359 | Q359M | 1.00 | 0.81 | 0.85 | 0.85 | 1.10 | 0.85 | 0.84 | 0.88 | 0.88 |
| 359 | Q359N | 1.03 | 1.06 | 0.81 | 1.15 | 1.02 | 0.86 | 0.83 | 0.94 | 1.19 |
| 359 | Q359S | 0.94 | 0.93 | 0.89 | 1.02 | 0.93 | 0.92 | 0.93 | 0.88 | 1.00 |
| 359 | Q359T | 0.99 | 0.79 | 0.83 | 0.92 | 1.13 | 0.97 | 0.79 | 0.91 | 0.93 |
| 359 | Q359V | 0.96 | 0.80 | 0.82 | 0.84 | 1.05 | 0.81 | 0.89 | 0.94 | 0.87 |
| 359 | Q359W | 0.88 | 0.99 | 0.75 | 1.00 | 1.08 | 0.98 | 0.95 | 0.95 | 0.97 |
| 359 | Q359Y | 0.89 | 0.98 | 0.74 | 0.98 | 1.05 | 0.90 | 0.92 | 0.97 | 0.95 |
| 374 | P374A | 0.83 | 0.75 | 1.39 | 0.70 | 0.97 | 0.84 | 1.09 | 0.92 | 0.70 |
| 374 | P374D | 0.94 | 0.80 | 1.25 | 0.81 | 1.09 | 0.81 | 1.25 | 0.96 | 0.68 |
| 374 | P374E | 0.93 | 0.77 | 1.77 | 0.71 | 0.96 | 0.86 | 1.24 | 0.90 | 0.73 |
| 374 | P374F | 1.07 | 0.29 | 1.27 | 0.33 | 1.24 | 1.03 | 1.80 | 1.40 | 0.23 |
| 374 | P374H | 0.97 | 0.75 | 1.25 | 0.72 | 0.97 | 0.96 | 0.98 | 0.97 | 0.67 |
| 374 | P374I | 0.95 | 0.43 | 1.81 | 0.42 | 1.03 | 1.11 | 1.33 | 1.07 | 0.45 |
| 374 | P374K | 0.91 | 0.82 | 1.25 | 0.80 | 0.96 | 1.08 | 1.21 | 0.98 | 0.70 |
| 374 | P374L | 0.94 | 0.41 | 1.60 | 0.40 | 1.01 | 0.90 | 1.47 | 0.94 | 0.39 |
| 374 | P374M | 0.96 | 0.53 | 1.67 | 0.53 | 0.87 | 1.06 | 1.35 | 0.92 | 0.49 |
| 374 | P374N | 1.03 | 0.84 | 1.30 | 0.82 | 1.06 | 0.95 | 1.23 | 0.89 | 0.72 |
| 374 | P374Q | 0.97 | 0.67 | 1.71 | 0.72 | 0.99 | 0.98 | 1.12 | 1.03 | 0.73 |
| 374 | P374R | 0.84 | 0.76 | 1.16 | 0.76 | 0.99 | 1.20 | 1.08 | 1.00 | 0.75 |
| 374 | P374S | 0.85 | 0.69 | 1.36 | 0.66 | 0.92 | 1.03 | 1.15 | 0.84 | 0.62 |
| 374 | P374T | 0.82 | 0.64 | 1.44 | 0.60 | 0.92 | 1.00 | 0.86 | 0.88 | 0.68 |
| 374 | P374V | 0.76 | 0.50 | 1.98 | 0.43 | 1.01 | 0.90 | 1.28 | 0.90 | 0.48 |
| 374 | P374W | 0.99 | 0.35 | 1.37 | 0.35 | 1.02 | 1.05 | 1.27 | 1.06 | 0.31 |
| 374 | P374Y | 0.98 | 0.34 | 1.34 | 0.33 | 1.04 | 0.79 | 1.23 | 0.93 | 0.29 |
| 375 | K375A | 0.98 | 0.87 | 0.99 | 0.79 | 0.83 | 0.54 | 1.30 | 0.98 | 0.72 |
| 375 | K375C | 1.03 | 0.08 | 0.81 | 0.07 | 0.36 | 0.19 | 1.47 | 0.95 | 0.09 |
| 375 | K375D | 1.26 | 0.86 | 0.78 | 0.84 | 0.81 | 1.10 | 1.11 | 0.87 | 0.76 |
| 375 | K375E | 1.11 | 1.03 | 0.86 | 0.97 | 0.87 | 0.81 | 1.27 | 0.78 | 0.74 |
| 375 | K375F | 1.05 | 0.44 | 0.89 | 0.38 | 0.70 | 0.44 | 1.06 | 0.85 | 0.39 |
| 375 | K375G | 1.29 | 0.72 | 0.83 | 0.74 | 0.87 | 0.62 | 0.98 | 0.87 | 0.68 |
| 375 | K375H | 1.07 | 0.85 | 0.78 | 0.81 | 0.89 | 0.57 | 1.07 | 0.89 | 0.74 |
| 375 | K375I | 1.04 | 0.66 | 0.72 | 0.61 | 0.86 | 0.60 | 1.26 | 0.93 | 0.63 |
| 375 | K375L | 1.03 | 0.66 | 0.75 | 0.58 | 0.83 | 0.73 | 2.17 | 0.86 | 0.56 |
| 375 | K375N | 1.16 | 0.88 | 0.89 | 0.82 | 0.90 | 0.73 | 1.14 | 0.92 | 0.75 |
| 375 | K375P | 1.22 | 0.67 | 0.75 | 0.65 | 0.84 | 0.57 | 1.20 | 0.83 | 0.64 |
| 375 | K375Q | 1.12 | 0.97 | 0.80 | 0.92 | 0.80 | 0.71 | 1.30 | 0.86 | 0.88 |
| 375 | K375R | 0.88 | 0.99 | 0.79 | 0.86 | 0.98 | 1.14 | 1.22 | 0.96 | 0.80 |
| 375 | K375S | 1.06 | 0.90 | 1.03 | 0.80 | 0.83 | 0.64 | 1.15 | 0.81 | 0.68 |
| 375 | K375T | 1.03 | 1.00 | 1.08 | 0.87 | 0.66 | 0.65 | 0.96 | 0.75 | 0.70 |
| 375 | K375V | 1.12 | 0.72 | 0.89 | 0.73 | 0.87 | 0.61 | 1.12 | 0.87 | 0.68 |
| 375 | K375W | 1.10 | 0.63 | 0.72 | 0.57 | 0.85 | 0.55 | 1.08 | 0.85 | 0.54 |
| 375 | K375Y | 0.98 | 0.40 | 0.86 | 0.39 | 0.72 | 0.52 | 1.17 | 0.93 | 0.38 |
| 376 | Y376A | 1.32 | 1.15 | 0.76 | 1.36 | 0.97 | 0.82 | 0.76 | 1.01 | 1.04 |
| 376 | Y376C | 1.11 | 0.21 | 0.64 | 0.24 | 2.09 | 0.57 | 1.45 | 1.82 | 0.09 |
| 376 | Y376D | 1.13 | 1.18 | 0.61 | 1.29 | 1.00 | 0.85 | 0.76 | 1.04 | 0.97 |
| 376 | Y376E | 1.28 | 1.34 | 0.73 | 1.46 | 1.01 | 0.72 | 0.86 | 1.10 | 1.20 |
| 376 | Y376F | 1.20 | 1.10 | 0.79 | 1.16 | 1.02 | 0.75 | 1.02 | 0.97 | 0.86 |
| 376 | Y376G | 1.16 | 1.17 | 0.69 | 1.26 | 1.00 | 0.82 | 0.78 | 0.96 | 0.96 |
| 376 | Y376H | 0.99 | 0.71 | 1.00 | 0.99 | 1.07 | 0.88 | 0.91 | 1.04 | 0.90 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 376 | Y376I | 1.08 | 1.03 | 0.59 | 1.12 | 0.98 | 0.87 | 0.77 | 0.99 | 0.88 |
| 376 | Y376K | 1.22 | 1.10 | 0.70 | 1.44 | 0.83 | 0.79 | 0.42 | 0.80 | 1.25 |
| 376 | Y376M | 1.09 | 1.19 | 0.75 | 1.26 | 0.96 | 0.88 | 0.95 | 1.11 | 0.93 |
| 376 | Y376N | 1.13 | 1.15 | 0.71 | 1.22 | 0.93 | 0.83 | 0.81 | 0.98 | 1.02 |
| 376 | Y376P | 1.21 | 0.82 | 0.51 | 0.89 | 0.96 | 0.64 | 0.75 | 0.86 | 0.65 |
| 376 | Y376Q | 1.12 | 1.21 | 0.86 | 1.34 | 1.03 | 0.93 | 0.91 | 1.03 | 1.01 |
| 376 | Y376R | 1.12 | 1.06 | 0.91 | 1.28 | 0.90 | 1.78 | 0.51 | 0.81 | 1.16 |
| 376 | Y376S | 1.20 | 1.09 | 0.75 | 1.18 | 0.96 | 0.72 | 0.78 | 1.00 | 0.98 |
| 376 | Y376T | 1.13 | 0.95 | 0.67 | 0.99 | 0.99 | 0.79 | 0.93 | 1.00 | 0.84 |
| 376 | Y376V | 1.13 | 0.98 | 0.69 | 1.07 | 0.89 | 0.80 | 0.60 | 1.06 | 0.88 |
| 376 | Y376W | 1.05 | 0.84 | 0.98 | 0.86 | 0.98 | 0.90 | 0.87 | 1.06 | 0.63 |
| 377 | N377A | 0.94 | 0.76 | 0.81 | 0.86 | 1.01 | 0.87 | 0.72 | 1.09 | 0.93 |
| 377 | N377C | 0.91 | 0.26 | 0.87 | 0.27 | 0.66 | 0.46 | 0.71 | 0.74 | 0.34 |
| 377 | N377D | 0.97 | 0.91 | 1.06 | 0.95 | 0.96 | 0.77 | 0.73 | 1.12 | 1.08 |
| 377 | N377E | 1.03 | 0.83 | 0.98 | 0.92 | 0.95 | 0.72 | 0.89 | 1.17 | 1.02 |
| 377 | N377F | 0.97 | 0.62 | 0.81 | 0.59 | 0.93 | 0.84 | 0.79 | 1.05 | 0.62 |
| 377 | N377G | 1.16 | 0.73 | 1.03 | 0.82 | 0.98 | 0.89 | 0.92 | 1.13 | 0.79 |
| 377 | N377H | 1.07 | 0.78 | 0.83 | 0.89 | 1.02 | 0.93 | 0.87 | 0.90 | 0.94 |
| 377 | N377K | 0.92 | 1.02 | 0.83 | 1.16 | 0.93 | 0.96 | 1.08 | 1.07 | 1.35 |
| 377 | N377L | 0.89 | 0.67 | 0.80 | 0.69 | 0.89 | 0.78 | 0.95 | 0.98 | 0.81 |
| 377 | N377M | 0.92 | 0.66 | 0.88 | 0.72 | 1.00 | 0.80 | 0.97 | 0.96 | 0.79 |
| 377 | N377P | 1.09 | 0.43 | 0.52 | 0.49 | 0.82 | 0.68 | 0.60 | 0.88 | 0.45 |
| 377 | N377Q | 0.94 | 0.86 | 0.87 | 0.92 | 0.98 | 0.93 | 1.10 | 1.27 | 0.93 |
| 377 | N377R | 0.79 | 1.08 | 0.74 | 1.02 | 1.05 | 1.13 | 1.01 | 1.19 | 1.00 |
| 377 | N377S | 0.88 | 0.84 | 0.90 | 0.91 | 0.94 | 0.93 | 0.98 | 1.05 | 0.97 |
| 377 | N377T | 0.98 | 0.54 | 0.85 | 0.65 | 0.80 | 0.79 | 0.85 | 0.90 | 0.68 |
| 377 | N377V | 0.89 | 0.48 | 0.83 | 0.53 | 0.89 | 0.84 | 0.93 | 1.02 | 0.50 |
| 377 | N377W | 1.04 | 0.52 | 0.81 | 0.52 | 0.82 | 0.77 | 0.86 | 0.79 | 0.65 |
| 377 | N377Y | 0.95 | 0.58 | 0.84 | 0.64 | 0.91 | 0.91 | 1.03 | 1.08 | 0.71 |
| 379 | P379A | 1.02 | 1.01 | 0.97 | 1.13 | 1.03 | 0.90 | 1.17 | 1.02 | 1.15 |
| 379 | P379C | 0.81 | 0.31 | 0.85 | 0.28 | 0.90 | 0.60 | 0.60 | 0.88 | 0.35 |
| 379 | P379E | 1.01 | 1.36 | 1.17 | 1.34 | 0.97 | 0.84 | 0.89 | 1.07 | 1.27 |
| 379 | P379F | 0.96 | 0.55 | 0.83 | 0.53 | 0.96 | 0.62 | 0.89 | 0.99 | 0.51 |
| 379 | P379G | 0.90 | 0.91 | 0.95 | 0.85 | 1.10 | 0.83 | 0.82 | 1.02 | 0.80 |
| 379 | P379H | 0.98 | 1.10 | 0.82 | 1.14 | 1.05 | 1.03 | 1.05 | 1.10 | 1.10 |
| 379 | P379I | 0.63 | 1.02 | 0.18 | 0.98 | 1.08 | 0.84 | 0.93 | 1.09 | 0.90 |
| 379 | P379K | 1.03 | 1.18 | 0.93 | 1.25 | 1.01 | 1.00 | 0.89 | 1.04 | 1.24 |
| 379 | P379L | 0.95 | 0.76 | 0.89 | 0.77 | 1.03 | 0.98 | 1.00 | 0.95 | 0.76 |
| 379 | P379M | 1.13 | 0.82 | 0.95 | 0.94 | 1.03 | 0.90 | 0.95 | 0.99 | 0.89 |
| 379 | P379Q | 0.90 | 1.22 | 0.91 | 1.19 | 1.04 | 0.96 | 0.95 | 1.05 | 1.11 |
| 379 | P379R | 0.98 | 1.23 | 0.84 | 1.26 | 1.13 | 1.19 | 0.98 | 1.01 | 1.10 |
| 379 | P379T | 1.02 | 1.08 | 0.97 | 1.13 | 1.01 | 0.98 | 1.13 | 0.87 | 1.13 |
| 379 | P379V | 1.00 | 1.14 | 0.92 | 1.14 | 0.96 | 0.82 | 1.00 | 0.95 | 1.22 |
| 379 | P379W | 0.94 | 0.64 | 0.80 | 0.63 | 0.90 | 1.10 | 0.69 | 0.76 | 0.64 |
| 379 | P379Y | 0.88 | 0.88 | 0.81 | 0.81 | 1.00 | 1.02 | 0.91 | 1.12 | 0.78 |
| 381 | L381A | 0.94 | 1.09 | 0.65 | 1.12 | 1.02 | 1.21 | 1.22 | 1.04 | 1.23 |
| 381 | L381D | 1.14 | 0.85 | 0.71 | 0.94 | 1.02 | 0.95 | 0.97 | 0.89 | 1.20 |
| 381 | L381E | 0.97 | 1.06 | 0.78 | 1.01 | 1.03 | 0.91 | 1.11 | 1.31 | 1.31 |
| 381 | L381F | 0.99 | 0.84 | 0.92 | 0.78 | 1.32 | 0.96 | 0.93 | 0.86 | 0.99 |
| 381 | L381G | 1.02 | 1.00 | 0.83 | 1.02 | 0.97 | 1.05 | 1.09 | 0.97 | 1.21 |
| 381 | L381H | 0.99 | 1.00 | 0.75 | 1.10 | 1.02 | 1.10 | 1.10 | 0.98 | 1.23 |
| 381 | L381I | 0.94 | 0.85 | 0.77 | 0.86 | 1.05 | 1.06 | 1.17 | 0.93 | 1.14 |
| 381 | L381K | 1.05 | 0.66 | 0.76 | 0.72 | 0.89 | 0.94 | 0.86 | 0.96 | 1.07 |
| 381 | L381M | 0.98 | 0.99 | 1.08 | 0.96 | 1.00 | 1.00 | 1.10 | 0.97 | 1.31 |
| 381 | L381N | 0.98 | 1.16 | 0.78 | 1.11 | 1.00 | 1.04 | 0.90 | 0.94 | 1.36 |
| 381 | L381P | 1.03 | 0.43 | 0.58 | 0.42 | 0.75 | 0.20 | 0.73 | 0.62 | 0.52 |
| 381 | L381Q | 0.99 | 1.16 | 0.82 | 1.18 | 1.09 | 1.10 | 0.97 | 0.99 | 1.36 |
| 381 | L381R | 1.04 | 0.67 | 0.63 | 0.71 | 0.91 | 1.11 | 0.91 | 0.93 | 0.94 |
| 381 | L381S | 0.89 | 1.08 | 0.71 | 1.03 | 1.06 | 1.03 | 1.06 | 0.91 | 1.29 |
| 381 | L381T | 0.99 | 0.81 | 0.73 | 0.82 | 0.96 | 1.06 | 1.10 | 0.99 | 1.14 |
| 381 | L381V | 1.18 | 0.78 | 0.74 | 0.88 | 0.97 | 0.90 | 1.18 | 0.86 | 1.19 |
| 381 | L381W | 0.97 | 0.91 | 0.79 | 0.87 | 0.99 | 0.99 | 1.03 | 0.98 | 0.95 |
| 381 | L381Y | 1.10 | 0.88 | 0.86 | 0.95 | 0.97 | 1.01 | 1.11 | 0.90 | 1.35 |
| 382 | K382A | 0.89 | 0.74 | 0.78 | 0.72 | 1.13 | 0.68 | 0.99 | 0.77 | 0.69 |
| 382 | K382D | 1.01 | 0.68 | 0.86 | 0.69 | 1.12 | 0.67 | 1.29 | 0.85 | 0.60 |
| 382 | K382E | 0.87 | 0.95 | 0.86 | 0.85 | 0.90 | 0.76 | 1.25 | 0.84 | 0.78 |
| 382 | K382F | 0.98 | 0.44 | 0.90 | 0.38 | 0.87 | 0.47 | 1.08 | 0.79 | 0.41 |
| 382 | K382G | 1.05 | 0.83 | 0.86 | 0.81 | 1.02 | 0.77 | 1.33 | 0.88 | 0.79 |
| 382 | K382H | 0.70 | 0.62 | 0.92 | 0.75 | 1.01 | 0.69 | 1.14 | 0.86 | 0.75 |
| 382 | K382L | 0.91 | 0.43 | 0.77 | 0.41 | 0.97 | 0.42 | 0.73 | 0.74 | 0.41 |
| 382 | K382M | 1.04 | 0.56 | 0.94 | 0.61 | 1.09 | 0.78 | 1.06 | 0.70 | 0.54 |
| 382 | K382N | 0.93 | 0.86 | 0.95 | 0.80 | 1.07 | 0.75 | 1.19 | 0.81 | 0.79 |
| 382 | K382P | 1.09 | 0.51 | 0.84 | 0.53 | 1.01 | 0.51 | 1.21 | 0.77 | 0.62 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 382 | K382Q | 0.93 | 0.88 | 1.05 | 0.87 | 0.99 | 0.76 | 1.15 | 0.86 | 0.84 |
| 382 | K382R | 0.99 | 0.74 | 0.84 | 0.80 | 0.98 | 0.81 | 1.39 | 0.91 | 0.80 |
| 382 | K382T | 0.96 | 0.59 | 0.83 | 0.61 | 1.01 | 0.64 | 1.20 | 0.87 | 0.58 |
| 382 | K382V | 1.03 | 0.46 | 0.85 | 0.47 | 1.01 | 0.52 | 1.14 | 0.76 | 0.47 |
| 382 | K382W | 0.97 | 0.39 | 0.94 | 0.36 | 0.98 | 0.56 | 0.93 | 0.84 | 0.36 |
| 382 | K382Y | 0.98 | 0.55 | 0.96 | 0.53 | 0.91 | 0.60 | 1.04 | 0.81 | 0.54 |
| 393 | R393A | 0.97 | 0.90 | 0.56 | 0.93 | 0.87 | 1.03 | 1.10 | 0.85 | 0.75 |
| 393 | R393C | 0.93 | 0.64 | 0.58 | 0.63 | 0.94 | 0.95 | 1.00 | 0.88 | 0.51 |
| 393 | R393D | 0.95 | 0.72 | 0.60 | 0.71 | 0.85 | 0.91 | 0.99 | 0.83 | 0.62 |
| 393 | R393E | 0.91 | 0.69 | 0.64 | 0.63 | 0.94 | 0.86 | 1.05 | 0.86 | 0.51 |
| 393 | R393F | 1.06 | 0.43 | 0.62 | 0.46 | 0.91 | 0.75 | 0.96 | 0.82 | 0.36 |
| 393 | R393G | 1.04 | 0.62 | 0.66 | 0.66 | 0.87 | 0.79 | 0.91 | 0.88 | 0.55 |
| 393 | R393H | 0.93 | 0.97 | 0.61 | 1.03 | 1.03 | 1.05 | 0.81 | 0.96 | 0.85 |
| 393 | R393I | 1.03 | 0.75 | 0.58 | 0.77 | 1.02 | 1.07 | 1.03 | 0.92 | 0.59 |
| 393 | R393K | 0.89 | 0.97 | 0.78 | 0.98 | 1.00 | 0.94 | 1.11 | 0.96 | 0.85 |
| 393 | R393L | 0.93 | 0.66 | 0.64 | 0.67 | 0.96 | 0.89 | 1.26 | 0.83 | 0.60 |
| 393 | R393M | 1.22 | 0.68 | 0.71 | 0.76 | 0.81 | 0.76 | 0.94 | 0.88 | 0.67 |
| 393 | R393N | 1.00 | 0.97 | 0.62 | 1.01 | 0.92 | 0.98 | 1.00 | 0.87 | 0.85 |
| 393 | R393Q | 1.04 | 0.98 | 0.66 | 1.05 | 1.03 | 1.09 | 1.03 | 0.91 | 0.67 |
| 393 | R393T | 1.17 | 0.89 | 0.66 | 1.00 | 0.87 | 1.05 | 1.09 | 1.00 | 0.78 |
| 393 | R393V | 0.99 | 0.88 | 0.65 | 0.86 | 0.86 | 0.93 | 1.07 | 0.83 | 0.69 |
| 393 | R393W | 0.99 | 0.31 | 0.63 | 0.31 | 1.09 | 0.91 | 0.92 | 0.88 | 0.24 |
| 394 | D394A | 0.91 | 1.21 | 0.52 | 1.27 | 1.11 | 1.33 | 1.25 | 0.98 | 1.42 |
| 394 | D394C | 1.06 | 0.57 | 0.60 | 0.66 | 0.87 | 1.00 | 1.20 | 0.86 | 0.75 |
| 394 | D394E | 1.03 | 0.99 | 0.71 | 1.07 | 0.90 | 1.09 | 0.94 | 0.94 | 1.34 |
| 394 | D394F | 0.98 | 0.69 | 0.62 | 0.77 | 0.92 | 1.54 | 1.01 | 0.79 | 1.03 |
| 394 | D394G | 0.86 | 1.10 | 0.63 | 1.03 | 1.12 | 1.09 | 0.93 | 0.99 | 1.24 |
| 394 | D394H | 0.67 | 0.79 | 0.61 | 0.99 | 0.98 | 1.24 | 0.99 | 0.92 | 1.20 |
| 394 | D394K | 0.90 | 1.09 | 0.58 | 1.13 | 0.99 | 1.20 | 1.18 | 0.92 | 1.37 |
| 394 | D394L | 0.93 | 0.89 | 0.61 | 0.91 | 0.98 | 1.23 | 1.16 | 0.95 | 0.96 |
| 394 | D394M | 1.01 | 0.89 | 0.63 | 0.99 | 0.96 | 1.14 | 0.96 | 0.94 | 1.34 |
| 394 | D394N | 0.58 | 0.36 | 0.07 | 0.33 | 0.74 | 0.42 | 0.96 | 0.90 | 0.51 |
| 394 | D394Q | 1.05 | 1.07 | 0.65 | 1.18 | 1.11 | 1.20 | 1.04 | 0.91 | 1.37 |
| 394 | D394R | 0.75 | 0.93 | 0.52 | 0.95 | 1.14 | 1.30 | 1.02 | 1.04 | 1.10 |
| 394 | D394S | 0.92 | 1.00 | 0.57 | 1.15 | 1.05 | 1.22 | 0.94 | 0.99 | 1.40 |
| 394 | D394T | 0.83 | 1.13 | 0.61 | 1.13 | 1.07 | 1.20 | 1.22 | 0.98 | 1.47 |
| 394 | D394V | 0.84 | 0.91 | 0.66 | 0.91 | 0.92 | 1.17 | 1.11 | 0.85 | 1.23 |
| 394 | D394W | 0.81 | 0.83 | 0.61 | 0.77 | 0.89 | 1.50 | 1.15 | 0.86 | 1.14 |
| 399 | T399A | 0.98 | 1.03 | 0.72 | 1.07 | 0.96 | 0.85 | 1.12 | 1.02 | 1.15 |
| 399 | T399C | 1.05 | 0.65 | 0.77 | 0.74 | 0.81 | 0.59 | 1.26 | 0.83 | 0.88 |
| 399 | T399E | 1.07 | 1.10 | 1.16 | 1.10 | 0.95 | 0.75 | 0.77 | 0.94 | 1.21 |
| 399 | T399F | 1.10 | 0.88 | 1.05 | 0.91 | 1.13 | 0.98 | 1.18 | 0.87 | 0.85 |
| 399 | T399G | 1.15 | 1.03 | 0.93 | 1.15 | 0.94 | 0.77 | 1.05 | 0.91 | 1.21 |
| 399 | T399H | 1.02 | 0.84 | 1.00 | 0.81 | 1.06 | 0.81 | 0.99 | 1.15 | 0.67 |
| 399 | T399I | 1.06 | 0.89 | 0.67 | 1.00 | 1.09 | 0.77 | 1.20 | 0.98 | 1.01 |
| 399 | T399K | 1.02 | 1.03 | 0.82 | 1.08 | 0.96 | 0.81 | 0.79 | 0.87 | 1.19 |
| 399 | T399L | 1.12 | 0.82 | 0.92 | 0.93 | 0.88 | 0.83 | 0.88 | 1.02 | 1.05 |
| 399 | T399M | 1.12 | 0.84 | 1.02 | 0.96 | 0.87 | 0.74 | 1.09 | 0.91 | 1.09 |
| 399 | T399P | 1.09 | 1.01 | 1.22 | 1.06 | 0.93 | 0.83 | 1.09 | 0.97 | 1.20 |
| 399 | T399Q | 1.23 | 0.94 | 1.09 | 1.12 | 0.97 | 0.88 | 0.71 | 0.98 | 1.23 |
| 399 | T399R | 0.99 | 1.07 | 0.58 | 1.10 | 1.05 | 0.95 | 0.90 | 0.95 | 1.27 |
| 399 | T399S | 0.96 | 1.05 | 0.80 | 1.09 | 1.02 | 0.85 | 1.10 | 0.89 | 1.19 |
| 399 | T399W | 1.13 | 0.82 | 0.93 | 0.88 | 0.96 | 0.96 | 0.97 | 0.95 | 0.99 |
| 399 | T399Y | 1.08 | 0.91 | 1.03 | 0.95 | 0.95 | 1.28 | 0.68 | 0.93 | 1.03 |
| 401 | R401A | 1.11 | 0.94 | 0.62 | 1.06 | 0.90 | 0.82 | 1.00 | 1.18 | 0.87 |
| 401 | R401C | 1.05 | 0.72 | 0.71 | 0.84 | 0.94 | 0.56 | 0.96 | 1.14 | 0.74 |
| 401 | R401D | 1.04 | 0.77 | 0.71 | 0.86 | 0.87 | 0.67 | 1.00 | 1.19 | 0.70 |
| 401 | R401E | 1.10 | 0.96 | 0.76 | 1.10 | 0.77 | 0.83 | 0.99 | 1.14 | 0.94 |
| 401 | R401G | 1.25 | 1.22 | 0.75 | 1.31 | 0.84 | 0.96 | 0.96 | 1.02 | 1.06 |
| 401 | R401H | 0.94 | 0.70 | 1.55 | 0.96 | 0.81 | 0.81 | 0.71 | 1.13 | 0.84 |
| 401 | R401I | 0.89 | 0.97 | 0.67 | 1.04 | 0.75 | 0.95 | 0.82 | 1.05 | 0.89 |
| 401 | R401K | 1.05 | 1.05 | 0.72 | 1.10 | 0.77 | 0.92 | 1.00 | 1.15 | 0.99 |
| 401 | R401L | 1.28 | 1.04 | 0.72 | 1.21 | 0.76 | 0.83 | 1.07 | 1.25 | 1.02 |
| 401 | R401M | 1.24 | 0.90 | 0.80 | 1.04 | 0.74 | 0.73 | 1.02 | 1.17 | 0.91 |
| 401 | R401N | 1.26 | 0.90 | 1.00 | 1.03 | 0.90 | 0.67 | 0.88 | 1.17 | 0.89 |
| 401 | R401Q | 1.16 | 0.95 | 0.81 | 1.14 | 0.78 | 0.91 | 0.98 | 1.07 | 0.93 |
| 401 | R401S | 0.99 | 0.96 | 0.70 | 1.04 | 0.79 | 0.93 | 0.90 | 1.03 | 0.87 |
| 401 | R401T | 1.04 | 0.99 | 0.77 | 1.10 | 0.78 | 0.87 | 0.95 | 1.20 | 0.93 |
| 401 | R401W | 1.05 | 0.81 | 1.08 | 0.81 | 0.82 | 0.89 | 1.02 | 1.25 | 0.64 |
| 401 | R401Y | 1.26 | 0.69 | 1.22 | 0.86 | 0.77 | 0.89 | 0.86 | 1.07 | 0.69 |
| 407 | Q407A | 0.92 | 1.03 | 0.73 | 1.06 | 1.05 | 0.81 | 1.32 | 1.07 | 0.91 |
| 407 | Q407C | 1.09 | 0.81 | 0.80 | 0.90 | 0.82 | 0.52 | 1.21 | 1.04 | 0.81 |
| 407 | Q407D | 1.11 | 0.83 | 0.80 | 0.89 | 1.04 | 0.65 | 1.71 | 1.19 | 0.81 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 407 | Q407E | 1.05 | 0.93 | 1.17 | 0.99 | 0.76 | 0.80 | 1.20 | 0.89 | 0.91 |
| 407 | Q407F | 1.07 | 0.88 | 0.73 | 0.87 | 0.76 | 1.22 | 1.01 | 0.86 | 0.72 |
| 407 | Q407G | 1.03 | 0.80 | 0.74 | 0.86 | 0.93 | 0.95 | 1.42 | 1.07 | 0.72 |
| 407 | Q407I | 0.95 | 0.89 | 0.62 | 0.88 | 0.88 | 1.02 | 0.93 | 0.96 | 0.80 |
| 407 | Q407K | 0.98 | 0.98 | 0.73 | 1.01 | 1.05 | 0.99 | 1.54 | 1.20 | 0.83 |
| 407 | Q407M | 1.13 | 0.77 | 0.80 | 0.87 | 0.84 | 0.90 | 1.19 | 0.97 | 0.75 |
| 407 | Q407N | 1.06 | 0.97 | 0.77 | 0.95 | 0.90 | 1.02 | 1.24 | 1.05 | 0.78 |
| 407 | Q407P | 1.06 | 0.96 | 1.36 | 0.98 | 0.81 | 0.83 | 1.32 | 1.05 | 0.88 |
| 407 | Q407R | 1.11 | 0.93 | 0.63 | 1.03 | 0.83 | 1.06 | 1.19 | 0.83 | 0.85 |
| 407 | Q407S | 1.01 | 0.77 | 0.73 | 0.80 | 0.88 | 0.85 | 0.73 | 0.94 | 0.70 |
| 407 | Q407T | 1.06 | 0.64 | 0.70 | 0.71 | 1.01 | 1.02 | 1.25 | 1.14 | 0.54 |
| 407 | Q407V | 1.01 | 0.85 | 0.75 | 0.87 | 0.87 | 1.12 | 1.27 | 1.00 | 0.67 |
| 407 | Q407W | 1.16 | 0.78 | 0.81 | 0.85 | 0.80 | 1.26 | 1.25 | 0.92 | 0.71 |
| 408 | D408A | 0.89 | 0.16 | 0.62 | 0.16 | 1.04 | 0.43 | 1.01 | 1.86 | 0.20 |
| 408 | D408C | 0.65 | 0.16 | 0.58 | 0.14 | 0.90 | 0.75 | 0.90 | 1.68 | 0.17 |
| 408 | D408H | 0.82 | 0.44 | 0.70 | 0.56 | 1.15 | 0.71 | 1.37 | 1.32 | 0.70 |
| 408 | D408N | 1.08 | 0.80 | 0.79 | 0.85 | 1.08 | 1.08 | 1.45 | 1.10 | 1.12 |
| 408 | D408Q | 0.97 | 0.21 | 0.73 | 0.22 | 0.99 | 0.64 | 0.94 | 1.39 | 0.30 |
| 408 | D408S | 0.78 | 0.46 | 0.74 | 0.40 | 1.06 | 0.78 | 1.09 | 1.03 | 0.53 |
| 408 | D408T | 0.99 | 0.13 | 0.70 | 0.14 | 0.99 | 0.61 | 0.78 | 1.69 | 0.18 |
| 419 | T419A | 0.99 | 0.91 | 0.98 | 1.04 | 0.96 | 0.93 | 0.99 | 0.90 | 1.00 |
| 419 | T419C | 1.06 | 0.84 | 1.10 | 0.98 | 1.02 | 1.68 | 1.03 | 0.94 | 0.84 |
| 419 | T419D | 1.06 | 0.73 | 1.19 | 0.81 | 0.94 | 0.91 | 1.04 | 0.93 | 0.82 |
| 419 | T419E | 1.20 | 0.82 | 1.37 | 0.99 | 1.00 | 0.88 | 1.04 | 0.92 | 0.97 |
| 419 | T419F | 1.06 | 0.77 | 0.86 | 0.81 | 0.96 | 0.90 | 1.06 | 0.93 | 0.69 |
| 419 | T419G | 1.09 | 0.99 | 0.98 | 1.09 | 0.96 | 0.87 | 1.01 | 0.79 | 0.96 |
| 419 | T419H | 1.10 | 0.93 | 0.89 | 0.99 | 0.96 | 0.85 | 0.89 | 0.98 | 0.89 |
| 419 | T419I | 1.05 | 0.78 | 0.81 | 0.88 | 1.04 | 1.01 | 1.26 | 1.04 | 0.74 |
| 419 | T419K | 1.01 | 1.05 | 0.86 | 1.06 | 1.16 | 0.97 | 1.03 | 0.99 | 0.90 |
| 419 | T419L | 1.12 | 0.83 | 0.93 | 0.91 | 1.06 | 1.57 | 1.02 | 0.92 | 0.73 |
| 419 | T419M | 1.13 | 0.84 | 0.98 | 0.93 | 1.04 | 0.94 | 1.14 | 0.90 | 0.85 |
| 419 | T419N | 1.13 | 1.08 | 0.98 | 1.10 | 0.96 | 0.89 | 0.91 | 0.89 | 1.11 |
| 419 | T419P | 1.08 | 0.89 | 0.88 | 0.98 | 1.01 | 1.02 | 1.19 | 0.85 | 0.91 |
| 419 | T419Q | 1.01 | 1.04 | 1.00 | 1.04 | 0.96 | 0.86 | 0.77 | 0.94 | 0.98 |
| 419 | T419R | 0.95 | 0.96 | 0.78 | 1.00 | 1.09 | 1.12 | 1.03 | 0.96 | 0.88 |
| 419 | T419S | 1.09 | 1.32 | 1.03 | 1.42 | 1.08 | 1.19 | 1.18 | 0.96 | 1.20 |
| 419 | T419V | 1.07 | 0.85 | 0.96 | 0.92 | 1.09 | 1.09 | 1.01 | 0.94 | 0.76 |
| 419 | T419W | 1.20 | 0.78 | 0.83 | 0.84 | 0.98 | 0.90 | 0.97 | 0.90 | 0.91 |
| 419 | T419Y | 1.03 | 0.86 | 0.85 | 0.87 | 0.95 | 0.98 | 1.08 | 0.83 | 0.82 |
| 433 | P433A | 0.84 | 1.06 | 1.07 | 1.01 | 1.12 | 0.70 | 1.16 | 1.02 | 0.89 |
| 433 | P433D | 0.93 | 1.01 | 1.13 | 0.94 | 1.05 | 0.81 | 1.39 | 1.30 | 0.83 |
| 433 | P433E | 0.80 | 1.12 | 1.32 | 0.96 | 0.90 | 0.40 | 1.31 | 1.21 | 0.88 |
| 433 | P433H | 0.87 | 0.97 | 0.80 | 0.90 | 1.03 | 0.69 | 0.88 | 1.06 | 0.76 |
| 433 | P433I | 0.82 | 1.05 | 1.18 | 0.96 | 1.12 | 0.57 | 1.22 | 1.36 | 0.82 |
| 433 | P433K | 0.84 | 1.01 | 0.95 | 0.96 | 1.06 | 0.68 | 0.91 | 1.17 | 0.92 |
| 433 | P433L | 0.77 | 1.07 | 0.99 | 0.91 | 1.06 | 0.52 | 0.97 | 1.14 | 0.85 |
| 433 | P433M | 0.72 | 0.68 | 1.13 | 0.88 | 1.05 | 0.55 | 1.24 | 1.23 | 0.83 |
| 433 | P433N | 0.94 | 1.12 | 0.92 | 1.05 | 0.95 | 0.70 | 1.05 | 1.23 | 0.88 |
| 433 | P433Q | 0.83 | 1.12 | 0.97 | 1.00 | 1.05 | 0.59 | 1.15 | 1.24 | 0.90 |
| 433 | P433R | 0.76 | 1.08 | 0.90 | 0.95 | 1.06 | 1.00 | 0.69 | 1.00 | 0.90 |
| 433 | P433S | 0.79 | 1.01 | 0.96 | 0.95 | 1.19 | 0.76 | 1.14 | 1.14 | 0.83 |
| 433 | P433T | 0.89 | 0.99 | 0.98 | 0.93 | 1.10 | 0.59 | 1.13 | 1.29 | 0.83 |
| 433 | P433V | 0.87 | 1.04 | 1.22 | 0.98 | 1.16 | 0.53 | 1.23 | 1.42 | 0.74 |
| 433 | P433W | 0.85 | 0.89 | 0.81 | 0.77 | 1.04 | 0.87 | 0.95 | 0.95 | 0.57 |
| 436 | S436A | 0.86 | 0.86 | 0.88 | 0.92 | 0.97 | 0.83 | 1.01 | 0.96 | 0.76 |
| 436 | S436C | 0.77 | 0.85 | 0.94 | 0.84 | 0.87 | 0.70 | 0.85 | 0.83 | 0.74 |
| 436 | S436D | 0.97 | 0.81 | 0.89 | 0.89 | 0.87 | 0.65 | 0.60 | 0.90 | 0.79 |
| 436 | S436E | 1.02 | 0.86 | 1.02 | 0.92 | 0.82 | 0.72 | 0.81 | 0.83 | 0.78 |
| 436 | S436F | 1.02 | 0.88 | 0.96 | 0.92 | 0.95 | 0.81 | 0.94 | 0.89 | 0.77 |
| 436 | S436G | 0.96 | 0.94 | 1.00 | 0.93 | 0.89 | 0.86 | 1.06 | 0.88 | 0.76 |
| 436 | S436H | 0.91 | 0.26 | 0.72 | 0.27 | 0.99 | 1.02 | 0.92 | 0.93 | 0.19 |
| 436 | S436I | 0.86 | 0.90 | 0.80 | 0.92 | 0.99 | 0.94 | 1.06 | 0.82 | 0.75 |
| 436 | S436K | 0.82 | 1.32 | 0.79 | 1.30 | 0.90 | 1.05 | 0.93 | 0.93 | 0.88 |
| 436 | S436L | 0.82 | 0.79 | 0.87 | 0.77 | 0.91 | 0.92 | 1.05 | 0.97 | 0.62 |
| 436 | S436M | 0.91 | 0.85 | 0.96 | 0.86 | 0.79 | 0.90 | 0.94 | 0.98 | 0.70 |
| 436 | S436N | 0.92 | 1.02 | 1.03 | 0.97 | 0.93 | 1.25 | 1.04 | 0.90 | 0.82 |
| 436 | S436P | 0.93 | 0.96 | 0.92 | 0.97 | 0.87 | 0.95 | 1.04 | 0.92 | 0.69 |
| 436 | S436Q | 0.98 | 0.93 | 1.00 | 0.95 | 1.00 | 0.90 | 0.72 | 0.91 | 0.76 |
| 436 | S436R | 0.76 | 0.93 | 0.76 | 0.90 | 1.02 | 1.06 | 0.86 | 0.97 | 0.68 |
| 436 | S436T | 1.02 | 0.87 | 1.03 | 0.91 | 0.80 | 0.82 | 1.06 | 0.91 | 0.80 |
| 436 | S436V | 0.94 | 0.99 | 0.99 | 0.97 | 0.95 | 0.85 | 0.87 | 0.86 | 0.82 |
| 436 | S436W | 1.00 | 0.79 | 0.90 | 0.84 | 0.98 | 0.86 | 0.88 | 0.88 | 0.67 |
| 436 | S436Y | 0.74 | 0.15 | 0.91 | 0.14 | 0.97 | 0.79 | 0.71 | 0.64 | 0.13 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 438 | W438C | 0.97 | 1.00 | 1.14 | 1.00 | 1.01 | 0.35 | 1.12 | 1.00 | 1.01 |
| 438 | W438F | 0.98 | 1.09 | 1.01 | 1.06 | 0.97 | 0.61 | 1.12 | 1.07 | 1.03 |
| 438 | W438G | 1.00 | 1.05 | 0.83 | 1.11 | 0.97 | 0.51 | 1.03 | 1.22 | 1.12 |
| 438 | W438H | 1.04 | 1.04 | 0.84 | 1.14 | 0.99 | 0.57 | 1.09 | 1.16 | 1.17 |
| 438 | W438I | 0.93 | 0.93 | 0.99 | 0.99 | 1.01 | 0.59 | 1.14 | 1.13 | 0.97 |
| 438 | W438K | 0.94 | 0.97 | 0.97 | 1.04 | 0.96 | 0.50 | 1.12 | 1.08 | 1.09 |
| 438 | W438L | 0.99 | 0.95 | 0.91 | 1.02 | 0.99 | 0.38 | 1.23 | 1.05 | 1.02 |
| 438 | W438M | 0.94 | 1.01 | 1.02 | 1.03 | 0.93 | 0.52 | 1.19 | 1.08 | 1.11 |
| 438 | W438N | 1.05 | 1.08 | 0.95 | 1.11 | 1.07 | 0.54 | 1.23 | 1.08 | 1.12 |
| 438 | W438P | 1.05 | 1.02 | 0.88 | 1.09 | 1.09 | 0.61 | 0.99 | 1.13 | 1.12 |
| 438 | W438Q | 4.28 | 0.80 | 0.82 | 1.19 | 1.14 | 0.55 | 1.16 | 1.13 | 1.20 |
| 438 | W438R | 0.90 | 1.09 | 0.93 | 1.09 | 0.94 | 0.79 | 1.05 | 1.26 | 1.03 |
| 438 | W438S | 0.94 | 1.01 | 0.93 | 1.08 | 0.96 | 0.57 | 1.12 | 1.19 | 1.13 |
| 438 | W438T | 0.96 | 1.18 | 0.97 | 1.17 | 1.10 | 0.64 | 1.18 | 1.15 | 1.17 |
| 438 | W438V | 0.95 | 1.03 | 0.96 | 1.04 | 0.97 | 0.45 | 0.89 | 1.14 | 1.04 |
| 438 | W438Y | 1.00 | 0.96 | 0.93 | 1.04 | 1.06 | 0.57 | 1.16 | 1.17 | 1.00 |
| 444 | K444C | 1.14 | 0.89 | 0.84 | 0.99 | 0.90 | 0.74 | 0.82 | 0.98 | 1.20 |
| 444 | K444D | 1.03 | 1.03 | 0.90 | 1.02 | 0.94 | 0.79 | 0.81 | 1.14 | 1.17 |
| 444 | K444F | 1.18 | 0.95 | 0.89 | 1.05 | 0.92 | 0.97 | 0.93 | 1.04 | 1.13 |
| 444 | K444G | 1.10 | 1.01 | 0.95 | 1.08 | 0.96 | 0.87 | 0.96 | 1.01 | 1.21 |
| 444 | K444H | 0.91 | 0.88 | 0.98 | 0.85 | 0.99 | 0.81 | 0.84 | 0.97 | 0.97 |
| 444 | K444I | 1.02 | 1.05 | 0.85 | 1.06 | 0.96 | 0.93 | 0.95 | 1.09 | 1.18 |
| 444 | K444L | 1.18 | 0.82 | 0.87 | 0.99 | 0.93 | 0.86 | 0.94 | 1.03 | 1.26 |
| 444 | K444M | 1.01 | 1.01 | 0.97 | 1.03 | 0.86 | 1.02 | 1.15 | 1.07 | 1.07 |
| 444 | K444N | 1.20 | 0.98 | 1.03 | 1.10 | 0.89 | 0.94 | 0.85 | 1.02 | 1.27 |
| 444 | K444P | 1.23 | 0.92 | 0.91 | 1.10 | 0.90 | 0.94 | 0.98 | 1.01 | 1.31 |
| 444 | K444Q | 1.14 | 0.92 | 1.01 | 1.08 | 0.95 | 1.01 | 1.02 | 0.99 | 1.23 |
| 444 | K444R | 1.05 | 0.81 | 1.13 | 0.92 | 1.00 | 1.01 | 0.92 | 1.03 | 1.07 |
| 444 | K444S | 1.16 | 0.89 | 0.94 | 1.01 | 0.94 | 0.90 | 1.04 | 1.05 | 1.20 |
| 444 | K444T | 1.10 | 0.91 | 0.98 | 0.99 | 0.94 | 0.88 | 0.74 | 1.00 | 1.14 |
| 444 | K444V | 1.17 | 0.87 | 0.96 | 0.99 | 1.01 | 0.83 | 0.97 | 0.99 | 1.12 |
| 444 | K444W | 1.13 | 0.98 | 0.92 | 0.99 | 0.91 | 0.90 | 1.13 | 1.07 | 1.03 |
| 444 | K444Y | 1.21 | 0.89 | 0.90 | 1.04 | 0.99 | 1.03 | 1.04 | 1.09 | 1.08 |
| 447 | G447A | 1.06 | 0.99 | 0.75 | 1.06 | 1.03 | 1.11 | 0.91 | 1.20 | 1.01 |
| 447 | G447C | 1.09 | 0.97 | 0.87 | 0.93 | 0.92 | 0.79 | 0.86 | 0.93 | 0.98 |
| 447 | G447D | 1.09 | 1.02 | 0.85 | 1.00 | 0.98 | 0.81 | 0.76 | 0.89 | 1.08 |
| 447 | G447F | 1.10 | 0.94 | 0.87 | 0.88 | 0.97 | 1.00 | 0.89 | 0.90 | 0.95 |
| 447 | G447H | 1.26 | 0.96 | 0.83 | 1.02 | 1.10 | 0.96 | 0.86 | 1.03 | 1.01 |
| 447 | G447I | 1.13 | 0.69 | 0.67 | 0.67 | 1.02 | 0.86 | 0.79 | 1.08 | 0.67 |
| 447 | G447K | 1.07 | 0.94 | 0.77 | 0.92 | 1.03 | 1.12 | 0.74 | 0.83 | 0.98 |
| 447 | G447L | 1.18 | 0.95 | 0.79 | 0.92 | 1.02 | 0.94 | 0.79 | 0.86 | 1.03 |
| 447 | G447M | 1.23 | 0.89 | 0.86 | 0.91 | 0.98 | 0.93 | 0.77 | 0.87 | 1.03 |
| 447 | G447N | 1.16 | 1.14 | 0.95 | 1.06 | 1.10 | 0.99 | 0.96 | 0.96 | 1.17 |
| 447 | G447P | 1.18 | 0.80 | 0.73 | 0.79 | 0.99 | 0.85 | 0.78 | 0.95 | 0.88 |
| 447 | G447Q | 0.90 | 0.73 | 0.76 | 1.01 | 1.15 | 1.05 | 0.77 | 1.05 | 0.99 |
| 447 | G447R | 0.93 | 0.59 | 0.80 | 0.60 | 0.94 | 1.10 | 0.77 | 1.04 | 0.58 |
| 447 | G447S | 1.13 | 0.77 | 0.54 | 0.82 | 1.05 | 1.08 | 0.64 | 0.93 | 0.95 |
| 447 | G447T | 1.12 | 1.01 | 0.79 | 0.97 | 1.02 | 0.96 | 0.84 | 0.85 | 1.05 |
| 447 | G447V | 1.07 | 0.46 | 0.84 | 0.48 | 0.68 | 0.67 | 0.73 | 0.83 | 0.79 |
| 447 | G447W | 1.16 | 1.03 | 0.80 | 0.98 | 1.01 | 1.02 | 0.88 | 0.97 | 1.05 |
| 447 | G447Y | 1.10 | 1.03 | 0.83 | 0.98 | 0.91 | 0.93 | 0.84 | 1.07 | 1.02 |
| 448 | K448A | 0.92 | 1.27 | 0.61 | 1.23 | 0.92 | 1.06 | 1.13 | 1.03 | 1.29 |
| 448 | K448C | 0.90 | 1.42 | 0.59 | 1.33 | 0.94 | 1.11 | 1.10 | 0.97 | 1.26 |
| 448 | K448D | 0.98 | 1.17 | 0.68 | 1.14 | 0.97 | 1.11 | 0.96 | 1.01 | 1.19 |
| 448 | K448E | 1.15 | 1.01 | 0.79 | 1.12 | 0.96 | 1.03 | 0.99 | 1.08 | 1.23 |
| 448 | K448F | 1.10 | 1.02 | 0.70 | 1.04 | 0.97 | 0.93 | 1.00 | 1.39 | 1.23 |
| 448 | K448G | 1.14 | 1.16 | 0.71 | 1.29 | 0.95 | 0.96 | 1.01 | 1.11 | 1.32 |
| 448 | K448H | 0.98 | 1.15 | 0.70 | 1.13 | 0.89 | 0.98 | 1.05 | 0.85 | 1.23 |
| 448 | K448L | 1.03 | 0.88 | 0.66 | 0.90 | 0.98 | 1.01 | 0.72 | 1.03 | 0.88 |
| 448 | K448N | 1.02 | 1.32 | 0.73 | 1.22 | 0.95 | 1.04 | 1.05 | 0.96 | 1.34 |
| 448 | K448P | 0.95 | 0.24 | 0.69 | 0.25 | 0.87 | 0.84 | 0.81 | 0.98 | 0.29 |
| 448 | K448Q | 0.97 | 1.09 | 0.77 | 1.09 | 0.90 | 0.97 | 1.05 | 1.03 | 1.15 |
| 448 | K448R | 0.85 | 0.85 | 0.66 | 0.90 | 0.96 | 1.37 | 0.93 | 1.01 | 0.98 |
| 448 | K448S | 1.05 | 1.15 | 0.67 | 1.14 | 0.82 | 1.02 | 1.01 | 0.98 | 1.16 |
| 448 | K448T | 1.12 | 1.03 | 0.70 | 1.11 | 0.93 | 0.90 | 1.21 | 1.01 | 1.17 |
| 448 | K448V | 1.08 | 1.03 | 0.70 | 1.05 | 0.89 | 0.95 | 1.14 | 0.97 | 1.11 |
| 448 | K448W | 1.03 | 1.03 | 0.68 | 0.99 | 0.94 | 0.97 | 1.35 | 1.15 | 0.96 |
| 451 | Y451A | 0.99 | 1.09 | 0.63 | 1.03 | 0.92 | 1.03 | 1.15 | 1.02 | 0.92 |
| 451 | Y451C | 1.10 | 0.94 | 0.69 | 1.02 | 0.85 | 1.04 | 1.12 | 0.95 | 0.88 |
| 451 | Y451D | 0.97 | 1.05 | 0.69 | 1.00 | 1.03 | 0.84 | 0.99 | 0.91 | 1.00 |
| 451 | Y451E | 1.14 | 1.06 | 0.76 | 1.07 | 0.97 | 0.90 | 1.29 | 0.90 | 1.06 |
| 451 | Y451F | 1.03 | 1.07 | 0.94 | 0.94 | 0.94 | 0.94 | 1.06 | 0.90 | 0.93 |
| 451 | Y451G | 1.08 | 1.06 | 0.77 | 1.04 | 0.94 | 0.88 | 0.87 | 0.90 | 1.04 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 451 | Y451K | 1.15 | 0.98 | 0.71 | 1.08 | 1.00 | 1.00 | 1.08 | 0.95 | 1.06 |
| 451 | Y451L | 1.09 | 1.04 | 0.62 | 1.02 | 1.00 | 0.91 | 1.02 | 0.90 | 1.08 |
| 451 | Y451M | 1.14 | 0.98 | 0.83 | 0.96 | 0.98 | 0.85 | 1.23 | 0.98 | 0.89 |
| 451 | Y451N | 1.14 | 1.27 | 0.75 | 1.16 | 1.12 | 1.04 | 1.26 | 0.96 | 1.04 |
| 451 | Y451P | 1.18 | 0.22 | 0.69 | 0.24 | 1.01 | 0.72 | 1.25 | 0.95 | 0.25 |
| 451 | Y451Q | 1.09 | 1.12 | 0.77 | 1.14 | 1.00 | 0.94 | 1.16 | 0.97 | 1.10 |
| 451 | Y451R | 0.97 | 0.98 | 0.66 | 1.02 | 1.10 | 1.14 | 1.22 | 0.99 | 1.00 |
| 451 | Y451S | 0.99 | 1.02 | 0.69 | 1.04 | 0.90 | 0.89 | 1.24 | 0.92 | 1.04 |
| 451 | Y451T | 1.17 | 0.96 | 0.75 | 1.01 | 0.87 | 1.07 | 1.18 | 0.98 | 0.98 |
| 451 | Y451V | 1.07 | 1.07 | 0.82 | 1.00 | 1.06 | 1.03 | 1.14 | 0.84 | 0.93 |
| 453 | L453A | 1.16 | 1.11 | 0.74 | 1.31 | 1.11 | 1.08 | 0.91 | 1.15 | 1.40 |
| 453 | L453C | 0.95 | 1.20 | 0.81 | 1.20 | 1.14 | 0.92 | 1.01 | 1.13 | 1.25 |
| 453 | L453D | 0.99 | 1.01 | 0.82 | 1.07 | 1.04 | 1.02 | 0.90 | 1.00 | 1.21 |
| 453 | L453E | 0.96 | 1.23 | 0.80 | 1.22 | 0.92 | 0.92 | 0.80 | 0.93 | 1.70 |
| 453 | L453F | 1.04 | 1.11 | 0.97 | 1.10 | 0.93 | 1.00 | 0.91 | 0.98 | 1.41 |
| 453 | L453G | 1.18 | 0.94 | 0.80 | 1.10 | 1.18 | 1.09 | 0.87 | 1.07 | 1.29 |
| 453 | L453H | 0.97 | 0.88 | 0.90 | 0.93 | 1.04 | 1.15 | 0.89 | 1.02 | 1.07 |
| 453 | L453I | 0.93 | 1.04 | 0.87 | 1.06 | 1.14 | 1.07 | 1.02 | 1.15 | 1.08 |
| 453 | L453K | 0.92 | 1.44 | 0.81 | 1.34 | 1.16 | 0.92 | 0.94 | 1.00 | 1.47 |
| 453 | L453M | 1.16 | 0.19 | 0.63 | 0.20 | 0.28 | 0.25 | 0.38 | 0.28 | 0.21 |
| 453 | L453N | 1.10 | 1.49 | 0.80 | 1.55 | 1.03 | 1.00 | 1.23 | 1.21 | 1.49 |
| 453 | L453P | 1.06 | 0.40 | 0.80 | 0.48 | 0.94 | 0.72 | 0.90 | 1.14 | 0.54 |
| 453 | L453Q | 1.00 | 1.29 | 0.78 | 1.34 | 1.11 | 1.12 | 0.95 | 1.11 | 1.32 |
| 453 | L453R | 1.00 | 1.46 | 0.73 | 1.43 | 1.19 | 1.21 | 1.12 | 1.10 | 1.47 |
| 453 | L453S | 0.97 | 1.26 | 0.79 | 1.28 | 0.97 | 0.86 | 1.00 | 1.13 | 1.29 |
| 453 | L453T | 0.89 | 1.08 | 0.70 | 1.12 | 1.13 | 1.04 | 0.95 | 1.06 | 1.26 |
| 453 | L453V | 1.06 | 1.10 | 0.84 | 1.14 | 1.15 | 1.06 | 0.95 | 1.10 | 1.17 |
| 453 | L453W | 1.17 | 0.98 | 0.99 | 1.03 | 1.11 | 1.06 | 0.71 | 1.10 | 1.13 |
| 453 | L453Y | 0.98 | 1.14 | 0.91 | 1.09 | 1.06 | 1.11 | 0.96 | 1.08 | 1.16 |
| 459 | D459A | 0.86 | 0.86 | 0.63 | 0.94 | 1.01 | 1.07 | 1.01 | 0.94 | 1.01 |
| 459 | D459C | 1.00 | 1.04 | 0.65 | 1.13 | 1.07 | 0.82 | 0.84 | 0.96 | 1.18 |
| 459 | D459E | 1.01 | 1.16 | 0.75 | 1.27 | 1.05 | 0.88 | 1.04 | 0.97 | 1.40 |
| 459 | D459F | 0.99 | 0.95 | 0.73 | 1.01 | 0.89 | 0.95 | 0.99 | 0.94 | 1.12 |
| 459 | D459G | 0.92 | 1.42 | 0.70 | 1.58 | 1.14 | 1.08 | 1.16 | 0.92 | 1.57 |
| 459 | D459H | 1.01 | 1.15 | 0.71 | 1.25 | 1.08 | 1.10 | 0.94 | 1.02 | 1.31 |
| 459 | D459I | 0.99 | 1.00 | 0.58 | 1.14 | 1.11 | 1.00 | 0.90 | 0.95 | 1.18 |
| 459 | D459K | 1.03 | 1.07 | 0.63 | 1.20 | 0.83 | 0.98 | 0.62 | 0.77 | 1.38 |
| 459 | D459L | 0.95 | 0.96 | 0.59 | 1.05 | 1.03 | 1.00 | 0.85 | 0.87 | 1.12 |
| 459 | D459M | 0.87 | 1.17 | 0.70 | 1.14 | 0.96 | 1.01 | 0.55 | 0.91 | 1.30 |
| 459 | D459N | 1.04 | 1.25 | 0.72 | 1.34 | 1.07 | 0.97 | 0.91 | 0.90 | 1.51 |
| 459 | D459P | 0.92 | 1.10 | 0.72 | 1.15 | 1.16 | 0.95 | 0.75 | 0.96 | 1.31 |
| 459 | D459Q | 1.08 | 1.09 | 0.72 | 1.28 | 1.03 | 1.00 | 0.85 | 0.87 | 1.40 |
| 459 | D459R | 0.94 | 1.29 | 0.56 | 1.31 | 0.90 | 1.25 | 0.86 | 0.67 | 1.39 |
| 459 | D459S | 0.90 | 1.20 | 0.65 | 1.22 | 1.02 | 1.05 | 0.88 | 0.92 | 1.37 |
| 459 | D459T | 1.01 | 1.08 | 0.68 | 1.17 | 1.11 | 0.97 | 0.79 | 0.96 | 1.28 |
| 459 | D459V | 1.06 | 1.10 | 0.69 | 1.21 | 1.07 | 0.95 | 0.67 | 0.87 | 1.32 |
| 459 | D459W | 0.93 | 0.92 | 0.70 | 0.94 | 0.90 | 1.00 | 0.70 | 0.72 | 1.46 |
| 459 | D459Y | 0.95 | 0.84 | 0.71 | 0.87 | 1.06 | 0.88 | 0.89 | 0.90 | 1.00 |
| 465 | A465C | 1.00 | 0.88 | 1.06 | 0.84 | 0.94 | 0.85 | 1.19 | 1.15 | 0.82 |
| 465 | A465F | 1.10 | 1.10 | 0.87 | 1.01 | 1.06 | 1.00 | 0.89 | 1.18 | 1.03 |
| 465 | A465G | 1.19 | 0.94 | 0.94 | 1.05 | 0.90 | 1.01 | 1.11 | 1.02 | 1.07 |
| 465 | A465H | 1.24 | 0.69 | 0.46 | 0.66 | 0.61 | 0.19 | 1.20 | 1.21 | 0.95 |
| 465 | A465I | 1.08 | 0.90 | 0.86 | 0.92 | 0.99 | 0.92 | 0.95 | 1.19 | 0.95 |
| 465 | A465K | 1.07 | 0.86 | 0.97 | 0.88 | 0.88 | 0.94 | 0.98 | 1.08 | 0.99 |
| 465 | A465L | 1.16 | 0.88 | 0.86 | 0.94 | 0.89 | 0.91 | 1.07 | 1.16 | 0.97 |
| 465 | A465M | 1.17 | 0.88 | 1.00 | 0.93 | 0.97 | 0.92 | 1.08 | 1.15 | 1.01 |
| 465 | A465N | 1.07 | 1.01 | 1.02 | 0.99 | 0.98 | 0.93 | 1.04 | 1.17 | 1.08 |
| 465 | A465P | 1.11 | 1.13 | 0.93 | 1.17 | 0.95 | 0.94 | 0.92 | 1.17 | 1.23 |
| 465 | A465Q | 1.07 | 0.96 | 0.92 | 1.03 | 0.93 | 0.92 | 1.10 | 1.13 | 1.07 |
| 465 | A465S | 1.05 | 0.89 | 1.02 | 0.89 | 1.03 | 1.13 | 1.17 | 1.24 | 0.82 |
| 465 | A465T | 1.07 | 0.94 | 0.96 | 0.91 | 0.92 | 0.95 | 1.08 | 1.19 | 0.98 |
| 465 | A465V | 1.17 | 0.85 | 0.91 | 0.91 | 0.94 | 0.96 | 0.94 | 1.10 | 0.98 |
| 465 | A465W | 1.08 | 0.99 | 0.86 | 0.99 | 1.00 | 1.09 | 1.01 | 1.19 | 0.97 |
| 465 | A465Y | 1.09 | 1.01 | 0.85 | 1.03 | 1.10 | 1.04 | 1.17 | 1.09 | 1.10 |
| 470 | E470A | 0.82 | 1.02 | 0.61 | 1.02 | 1.10 | 1.07 | 0.90 | 0.92 | 1.17 |
| 470 | E470C | 1.01 | 0.87 | 1.33 | 0.94 | 1.04 | 0.73 | 0.98 | 1.00 | 0.93 |
| 470 | E470D | 0.88 | 1.02 | 1.04 | 0.96 | 1.05 | 0.82 | 0.91 | 0.89 | 1.04 |
| 470 | E470F | 1.07 | 0.91 | 0.87 | 0.96 | 1.07 | 1.00 | 1.07 | 1.02 | 0.88 |
| 470 | E470G | 1.09 | 0.88 | 0.83 | 0.95 | 1.07 | 1.30 | 0.81 | 0.83 | 1.08 |
| 470 | E470H | 1.07 | 0.96 | 0.92 | 1.01 | 1.05 | 1.08 | 0.81 | 0.85 | 1.19 |
| 470 | E470I | 0.91 | 0.96 | 0.86 | 1.00 | 1.12 | 0.94 | 1.02 | 0.93 | 1.03 |
| 470 | E470K | 1.01 | 1.10 | 0.88 | 1.08 | 0.97 | 0.99 | 0.80 | 0.65 | 1.29 |
| 470 | E470L | 1.01 | 0.87 | 0.86 | 0.95 | 1.03 | 1.06 | 0.73 | 0.67 | 0.96 |

TABLE 7-1-continued

Performance Indices of BASE Variants (3,408 alpha-amylases)

| Position | Variant | DET STAB Pi | (DET) BPNPG7 initial Activity Pi | THER STAB Pi | (THER) BPNPG7 initial Activity Pi | CS28 pH 10 32 Pi | CS28 pH 10 50 Pi | CS28 pH 8 16 Pi | CS28 pH 8 32 Pi | HPLC PROT Pi |
|---|---|---|---|---|---|---|---|---|---|---|
| 470 | E470N | 1.08 | 0.97 | 0.95 | 0.97 | 1.02 | 1.30 | 0.57 | 0.84 | 1.13 |
| 470 | E470P | 0.99 | 1.05 | 0.81 | 1.03 | 1.04 | 1.07 | 0.88 | 0.80 | 1.20 |
| 470 | E470Q | 0.97 | 1.06 | 0.84 | 1.03 | 0.96 | 1.13 | 0.87 | 0.84 | 1.19 |
| 470 | E470R | 0.87 | 1.11 | 0.88 | 1.04 | 0.89 | 1.29 | 0.86 | 0.77 | 1.22 |
| 470 | E470S | 0.97 | 0.96 | 0.88 | 0.98 | 1.05 | 0.75 | 0.75 | 0.88 | 1.08 |
| 470 | E470T | 0.95 | 0.94 | 0.89 | 0.98 | 0.98 | 0.76 | 0.99 | 1.05 | 1.08 |
| 470 | E470W | 1.06 | 0.91 | 0.88 | 0.96 | 0.99 | 1.42 | 0.85 | 1.02 | 1.00 |
| 470 | E470Y | 1.05 | 0.95 | 0.89 | 1.02 | 0.98 | 1.23 | 0.82 | 0.85 | 1.09 |
| 475 | G475A | 0.89 | 1.30 | 1.24 | 1.11 | 1.14 | 0.41 | 1.48 | 1.52 | 1.20 |
| 475 | G475C | 1.04 | 0.92 | 1.12 | 0.88 | 0.87 | 0.09 | 1.90 | 1.40 | 0.96 |
| 475 | G475D | 1.00 | 1.16 | 1.75 | 1.09 | 0.98 | 0.23 | 1.39 | 1.48 | 1.24 |
| 475 | G475E | 1.01 | 1.05 | 1.24 | 1.00 | 0.90 | 0.11 | 1.76 | 1.41 | 1.00 |
| 475 | G475F | 1.04 | 0.93 | 0.92 | 0.89 | 1.08 | 0.21 | 2.02 | 1.78 | 0.83 |
| 475 | G475H | 1.02 | 1.14 | 0.92 | 1.13 | 1.17 | 0.26 | 1.96 | 1.45 | 1.29 |
| 475 | G475I | 1.03 | 0.89 | 0.84 | 0.86 | 1.20 | 0.17 | 1.77 | 1.80 | 0.80 |
| 475 | G475K | 0.95 | 1.25 | 0.94 | 1.12 | 1.15 | 0.28 | 1.93 | 1.51 | 1.36 |
| 475 | G475L | 0.95 | 0.89 | 0.80 | 0.82 | 1.17 | 0.22 | 1.97 | 1.66 | 0.82 |
| 475 | G475N | 1.04 | 1.26 | 1.17 | 1.13 | 1.13 | 0.44 | 1.92 | 1.65 | 1.09 |
| 475 | G475P | 1.02 | 1.05 | 1.09 | 1.03 | 1.12 | 0.40 | 1.53 | 1.36 | 1.16 |
| 475 | G475Q | 1.05 | 1.19 | 0.97 | 1.16 | 1.08 | 0.22 | 1.94 | 1.59 | 1.22 |
| 475 | G475R | 0.90 | 1.33 | 0.92 | 1.16 | 1.28 | 0.41 | 1.82 | 1.58 | 1.35 |
| 475 | G475S | 0.87 | 1.29 | 1.19 | 1.08 | 1.21 | 0.32 | 1.56 | 1.48 | 1.20 |
| 475 | G475T | 1.05 | 1.16 | 1.12 | 1.13 | 1.14 | 0.24 | 2.09 | 1.70 | 1.22 |
| 475 | G475V | 0.96 | 1.00 | 0.87 | 0.93 | 1.08 | 0.15 | 1.76 | 1.77 | 0.89 |
| 475 | G475W | 1.05 | 0.95 | 0.87 | 0.90 | 1.24 | 0.37 | 1.77 | 1.76 | 0.77 |
| 476 | G476A | 0.72 | 1.00 | 1.19 | 0.86 | 1.07 | 0.33 | 2.52 | 1.49 | 1.03 |
| 476 | G476C | 0.79 | 0.40 | 1.42 | 0.33 | 0.52 | 0.24 | 3.02 | 2.48 | 0.31 |
| 476 | G476D | 0.75 | 1.64 | 0.84 | 1.36 | 1.00 | 0.34 | 2.69 | 1.62 | 1.32 |
| 476 | G476H | 0.71 | 1.02 | 0.99 | 0.80 | 0.98 | 0.24 | 2.65 | 1.65 | 0.85 |
| 476 | G476I | 0.55 | 0.59 | 1.04 | 0.48 | 0.83 | 0.19 | 1.87 | 2.10 | 0.53 |
| 476 | G476K | 0.76 | 0.96 | 1.32 | 0.76 | 1.22 | 0.35 | 1.83 | 1.70 | 0.82 |
| 476 | G476L | 0.75 | 0.80 | 1.05 | 0.64 | 0.84 | 0.26 | 3.83 | 2.01 | 0.56 |
| 476 | G476M | 0.89 | 0.69 | 1.35 | 0.67 | 0.88 | 0.28 | 3.25 | 1.95 | 0.68 |
| 476 | G476N | 0.87 | 1.18 | 1.09 | 1.03 | 1.11 | 0.22 | 2.83 | 1.83 | 1.17 |
| 476 | G476P | 0.80 | 1.35 | 0.91 | 1.14 | 1.18 | 0.39 | 2.13 | 1.59 | 1.21 |
| 476 | G476Q | 0.77 | 1.22 | 1.34 | 1.04 | 1.08 | 0.34 | 2.67 | 1.64 | 1.24 |
| 476 | G476T | 0.80 | 1.21 | 1.26 | 1.05 | 1.08 | 0.28 | 2.90 | 1.76 | 1.15 |
| 476 | G476V | 0.81 | 1.01 | 1.00 | 0.91 | 0.93 | 0.23 | 2.68 | 1.68 | 1.55 |
| 476 | G476W | 0.77 | 0.28 | 1.15 | 0.24 | 0.86 | 0.37 | 2.58 | 2.33 | 0.25 |
| 476 | G476Y | 1.05 | 0.49 | 1.14 | 0.45 | 0.97 | 0.19 | 4.48 | 2.24 | 0.38 |
| 483 | A483C | 0.91 | 1.28 | 0.84 | 1.04 | 0.98 | 0.82 | 1.34 | 1.06 | 1.12 |
| 483 | A483D | 0.97 | 1.16 | 0.82 | 1.05 | 0.99 | 0.83 | 0.97 | 0.77 | 1.38 |
| 483 | A483E | 1.03 | 1.18 | 0.95 | 1.03 | 1.00 | 0.84 | 0.89 | 1.00 | 1.09 |
| 483 | A483F | 1.11 | 1.21 | 0.92 | 1.09 | 0.97 | 0.88 | 0.86 | 1.04 | 1.33 |
| 483 | A483G | 1.17 | 1.10 | 1.01 | 1.11 | 0.97 | 0.89 | 0.89 | 1.09 | 1.35 |
| 483 | A483H | 0.93 | 0.70 | 0.91 | 0.62 | 0.90 | 0.70 | 0.88 | 1.03 | 0.75 |
| 483 | A483I | 1.04 | 1.08 | 0.70 | 1.04 | 1.04 | 0.98 | 1.02 | 1.13 | 1.14 |
| 483 | A483K | 1.08 | 1.09 | 0.80 | 1.03 | 0.96 | 0.88 | 1.05 | 1.03 | 1.29 |
| 483 | A483M | 1.12 | 0.95 | 0.93 | 0.90 | 0.90 | 0.83 | 0.97 | 0.98 | 1.15 |
| 483 | A483N | 0.96 | 0.81 | 0.99 | 0.79 | 0.94 | 0.80 | 0.76 | 0.99 | 1.05 |
| 483 | A483P | 1.20 | 0.94 | 1.31 | 0.93 | 0.93 | 0.83 | 0.98 | 1.02 | 1.26 |
| 483 | A483Q | 1.02 | 1.07 | 1.05 | 0.96 | 0.98 | 0.84 | 0.93 | 1.04 | 1.20 |
| 483 | A483R | 0.85 | 1.07 | 0.73 | 0.94 | 0.93 | 1.04 | 1.03 | 1.10 | 1.02 |
| 483 | A483S | 1.04 | 0.96 | 0.98 | 0.92 | 0.95 | 0.83 | 0.84 | 1.03 | 1.33 |
| 483 | A483T | 1.04 | 1.06 | 0.90 | 0.94 | 0.96 | 0.88 | 1.13 | 1.38 | 1.10 |
| 483 | A483V | 1.11 | 1.12 | 0.86 | 1.04 | 0.95 | 1.03 | 1.09 | 1.09 | 1.28 |
| 483 | A483W | 1.09 | 1.03 | 0.86 | 1.00 | 0.95 | 0.87 | 1.03 | 1.00 | 1.71 |
| 483 | A483Y | 1.03 | 1.13 | 0.85 | 1.10 | 0.96 | 0.90 | 0.81 | 1.17 | 1.38 |
| 484 | K484A | 0.85 | 0.95 | 0.78 | 0.99 | 0.77 | 0.93 | 1.02 | 0.92 | 0.87 |
| 484 | K484C | 0.78 | 0.94 | 0.84 | 0.93 | 0.78 | 0.76 | 0.90 | 0.87 | 0.81 |
| 484 | K484D | 0.81 | 1.13 | 0.80 | 1.11 | 0.80 | 0.99 | 1.20 | 0.90 | 0.95 |
| 484 | K484E | 0.85 | 1.07 | 0.88 | 1.08 | 0.83 | 0.91 | 1.06 | 0.81 | 0.99 |
| 484 | K484F | 0.92 | 0.77 | 0.89 | 0.78 | 0.85 | 0.90 | 0.89 | 0.89 | 0.68 |
| 484 | K484G | 0.96 | 0.96 | 0.98 | 1.03 | 0.92 | 0.97 | 1.08 | 0.93 | 0.87 |
| 484 | K484H | 0.70 | 0.91 | 0.99 | 0.90 | 0.91 | 0.80 | 0.87 | 0.87 | 0.86 |
| 484 | K484I | 0.74 | 0.90 | 0.68 | 0.94 | 1.01 | 1.13 | 1.04 | 1.12 | 0.65 |
| 484 | K484L | 0.88 | 0.72 | 0.86 | 0.76 | 0.77 | 0.85 | 0.83 | 0.96 | 0.63 |
| 484 | K484M | 0.88 | 0.82 | 0.98 | 0.86 | 0.86 | 0.80 | 0.95 | 0.86 | 0.75 |
| 484 | K484N | 0.95 | 1.07 | 0.90 | 1.06 | 0.94 | 0.81 | 1.12 | 0.87 | 0.93 |

The other 821 mutations of the BASE SEL members present in Table 3-2, but absent in Table 7-1 are less suitable for inclusion in combinatorial variants of a parent alpha-amylase. Likewise residues of naturally occurring alpha-amylases at positions corresponding to SEQ ID NO: 2 that are identical to the 821 non-combinable mutations are contemplated to be present in underperforming naturally occurring alpha-amylases, and thus are candidates for mutagenesis. As such, the present disclosure provides a detailed recipe for producing variant alpha-amylases that have a desired set of properties Example 8

Restrictive and Non-Restrictive Positions in Alpha-Amylases

Results of experiments conducted to determine wash performance (CS-28 microswatch assay at pH 10/32° C., pH 10/50° C., pH 8/16° C. and pH 8/32° C.), detergent stability, thermostability, BPNPG7 amylase activity and HPLC protein concentration (tests of properties of interest) of BASE and variants thereof are described. The results were obtained using the methods described in Example 1. As described throughout, functionality of BASE variants was quantified as a performance index (PI), which is the ratio of performance of a variant to a parent or reference amylase. Various terms set forth below are used to describe the mutation: up mutations have a PI>1; neutral mutations have a PI>0.5, non-deleterious mutations have a PI>0.05; deleterious mutations have a PI≤0.05; combinable mutations are those mutations for which the variant has PI≥0.5 for at least one property, and >0.05 for all properties. Combinable mutations are mutations that can be combined to deliver proteins with appropriate PIs for one or more desired properties.

Positions at which mutations occur are classed as follows: non-restrictive positions have ≥20% neutral mutations for at least one property; and restrictive positions have <20% neutral mutations for activity and stability. Table 8-1 shows the restrictive positions where less than 20% neutral mutations (PI>0.5) for activity and stability were detected. Table 8-2 shows the non-restrictive positions where ≥20% neutral mutations (PI>0.5) for at least one property tested were detected. %=percent of variants evaluated that meet definition of neutral mutation.

TABLE 8-1

Restrictive Positions <20% Neutral Mutations for Activity and Stability

| Position | # mutants | Detergent stability PI > 0.5 | Detergent initial PI % > 0.5 | Thermo-stability PI > 0.5 | Thermo-stability initial PI > 0.5 | CS28 pH 10 32 ° C. PI > 0.5 | CS28 pH 10 50° C. PI > 0.5 | CS28 Ph 8 16° C. PI > 0.5 | CS28 pH 8 32° C. PI > 0.5 | HPLC Protein PI > 0.5 |
|---|---|---|---|---|---|---|---|---|---|---|
| 58 | 19 | 11 | 5 | 0 | 5 | 11 | 5 | 0 | 5 | 84 |
| 236 | 18 | 6 | 0 | 6 | 0 | 6 | 6 | 0 | 0 | 100 |

TABLE 8-2

Non-restrictive Positions ≥20% Neutral Mutations for at least One Property

| Position | # mutants | Detergent stability PI > 0.5 | Detergent initial PI % > 0.5 | Thermo-stability PI > 0.5 | Thermo-stability initial PI > 0.5 | CS28 pH 10 32° C. PI > 0.5 | CS28 pH 10 50° C. PI > 0.5 | CS28 Ph 8 16° C. PI > 0.5 | CS28 pH 8 32° C. PI > 0.5 | HPLC Protein PI > 0.5 |
|---|---|---|---|---|---|---|---|---|---|---|
| 1 | 19 | 74% | 53% | 74% | 0% | 84% | 84% | 84% | 74% | 68% |
| 2 | 15 | 100% | 87% | 100% | 87% | 100% | 100% | 93% | 100% | 93% |
| 3 | 19 | 95% | 89% | 95% | 89% | 95% | 95% | 95% | 95% | 74% |
| 4 | 16 | 100% | 94% | 100% | 94% | 100% | 100% | 100% | 100% | 81% |
| 5 | 16 | 100% | 100% | 100% | 100% | 100% | 100% | 100% | 100% | 100% |
| 7 | 19 | 100% | 100% | 100% | 95% | 95% | 100% | 100% | 100% | 100% |
| 15 | 19 | 58% | 11% | 47% | 11% | 11% | 0% | 42% | 63% | 89% |
| 16 | 18 | 100% | 6% | 78% | 11% | 94% | 67% | 89% | 94% | 39% |
| 17 | 19 | 100% | 89% | 58% | 100% | 100% | 89% | 100% | 100% | 95% |
| 18 | 18 | 100% | 89% | 89% | 89% | 100% | 100% | 94% | 100% | 94% |
| 19 | 19 | 95% | 42% | 26% | 58% | 95% | 95% | 95% | 95% | 89% |
| 22 | 18 | 94% | 94% | 89% | 94% | 94% | 94% | 94% | 94% | 94% |
| 25 | 18 | 100% | 94% | 100% | 94% | 100% | 100% | 100% | 89% | 100% |
| 26 | 19 | 100% | 84% | 95% | 89% | 100% | 89% | 100% | 100% | 79% |
| 28 | 18 | 89% | 89% | 89% | 89% | 89% | 94% | 89% | 89% | 83% |
| 29 | 18 | 94% | 83% | 94% | 94% | 94% | 94% | 94% | 94% | 89% |
| 30 | 17 | 94% | 53% | 94% | 53% | 100% | 82% | 100% | 94% | 53% |
| 32 | 16 | 100% | 100% | 100% | 100% | 100% | 100% | 100% | 100% | 100% |
| 35 | 17 | 100% | 71% | 94% | 71% | 100% | 100% | 100% | 100% | 71% |
| 36 | 18 | 94% | 83% | 94% | 83% | 94% | 94% | 94% | 94% | 89% |
| 37 | 18 | 100% | 89% | 100% | 89% | 100% | 100% | 100% | 100% | 78% |
| 50 | 19 | 63% | 42% | 11% | 42% | 37% | 21% | 53% | 74% | 79% |
| 51 | 17 | 94% | 29% | 71% | 29% | 76% | 65% | 100% | 88% | 88% |
| 52 | 19 | 100% | 89% | 68% | 89% | 95% | 79% | 100% | 100% | 100% |
| 53 | 19 | 74% | 68% | 21% | 79% | 89% | 95% | 95% | 89% | 84% |
| 54 | 19 | 95% | 95% | 84% | 95% | 95% | 95% | 100% | 100% | 89% |
| 55 | 17 | 71% | 6% | 0% | 6% | 35% | 24% | 41% | 82% | 100% |
| 56 | 19 | 95% | 53% | 42% | 53% | 74% | 68% | 95% | 95% | 95% |
| 57 | 16 | 13% | 6% | 0% | 6% | 13% | 6% | 25% | 56% | 19% |
| 59 | 18 | 28% | 11% | 22% | 11% | 17% | 0% | 22% | 50% | 89% |
| 60 | 19 | 84% | 63% | 53% | 74% | 95% | 89% | 95% | 100% | 84% |

TABLE 8-2-continued

Non-restrictive Positions ≥20% Neutral Mutations for at least One Property

| Position | # mutants | Detergent stability PI > 0.5 | Detergent initial PI % > 0.5 | Thermo-stability PI > 0.5 | Thermo-stability initial PI > 0.5 | CS28 pH 10 32° C. PI > 0.5 | CS28 pH 10 50° C. PI > 0.5 | CS28 Ph 8 16° C. PI > 0.5 | CS28 pH 8 32° C. PI > 0.5 | HPLC Protein PI > 0.5 |
|---|---|---|---|---|---|---|---|---|---|---|
| 70 | 19 | 100% | 100% | 100% | 100% | 100% | 100% | 100% | 100% | 95% |
| 71 | 19 | 100% | 95% | 11% | 95% | 100% | 95% | 100% | 100% | 63% |
| 72 | 16 | 94% | 94% | 0% | 94% | 94% | 50% | 94% | 94% | 94% |
| 73 | 19 | 84% | 79% | 58% | 79% | 84% | 84% | 79% | 84% | 74% |
| 75 | 18 | 100% | 100% | 94% | 100% | 100% | 100% | 100% | 100% | 100% |
| 78 | 19 | 79% | 58% | 0% | 53% | 68% | 21% | 84% | 84% | 53% |
| 82 | 18 | 100% | 94% | 100% | 89% | 100% | 100% | 100% | 100% | 94% |
| 83 | 19 | 100% | 100% | 100% | 100% | 100% | 100% | 100% | 100% | 100% |
| 87 | 19 | 95% | 95% | 95% | 95% | 95% | 84% | 95% | 95% | 100% |
| 90 | 19 | 100% | 95% | 100% | 95% | 100% | 100% | 100% | 100% | 95% |
| 91 | 18 | 100% | 94% | 100% | 94% | 100% | 100% | 89% | 100% | 94% |
| 93 | 16 | 88% | 31% | 75% | 31% | 88% | 88% | 88% | 94% | 6% |
| 94 | 19 | 89% | 74% | 89% | 74% | 84% | 79% | 84% | 89% | 79% |
| 95 | 18 | 100% | 94% | 100% | 100% | 100% | 100% | 100% | 100% | 100% |
| 103 | 17 | 82% | 53% | 6% | 53% | 94% | 88% | 82% | 82% | 71% |
| 104 | 19 | 37% | 5% | 5% | 5% | 26% | 11% | 32% | 26% | 84% |
| 105 | 18 | 78% | 94% | 0% | 94% | 94% | 89% | 94% | 100% | 94% |
| 107 | 19 | 11% | 0% | 0% | 0% | 5% | 0% | 16% | 32% | 79% |
| 108 | 14 | 100% | 93% | 14% | 93% | 100% | 79% | 100% | 100% | 79% |
| 110 | 17 | 88% | 53% | 6% | 47% | 88% | 59% | 94% | 100% | 94% |
| 112 | 17 | 94% | 6% | 0% | 6% | 94% | 24% | 100% | 100% | 82% |
| 113 | 19 | 89% | 79% | 68% | 89% | 89% | 89% | 89% | 89% | 89% |
| 114 | 19 | 100% | 74% | 0% | 79% | 100% | 100% | 100% | 100% | 100% |
| 115 | 16 | 0% | 56% | 0% | 38% | 100% | 100% | 100% | 100% | 100% |
| 116 | 19 | 100% | 100% | 63% | 100% | 100% | 100% | 100% | 100% | 100% |
| 118 | 19 | 79% | 68% | 42% | 68% | 95% | 95% | 84% | 95% | 68% |
| 121 | 17 | 12% | 100% | 0% | 100% | 100% | 100% | 100% | 100% | 100% |
| 123 | 17 | 47% | 100% | 6% | 100% | 100% | 100% | 100% | 100% | 100% |
| 125 | 19 | 89% | 100% | 84% | 100% | 100% | 100% | 100% | 100% | 95% |
| 126 | 17 | 12% | 100% | 6% | 100% | 100% | 88% | 100% | 100% | 94% |
| 127 | 14 | 0% | 21% | 0% | 36% | 100% | 36% | 100% | 100% | 93% |
| 128 | 18 | 28% | 100% | 39% | 100% | 100% | 67% | 100% | 100% | 100% |
| 129 | 18 | 78% | 89% | 67% | 89% | 100% | 83% | 100% | 100% | 89% |
| 130 | 19 | 74% | 84% | 5% | 84% | 89% | 68% | 84% | 84% | 84% |
| 131 | 18 | 33% | 89% | 22% | 94% | 100% | 100% | 100% | 100% | 89% |
| 132 | 17 | 6% | 94% | 0% | 94% | 100% | 71% | 100% | 100% | 94% |
| 134 | 17 | 76% | 100% | 41% | 100% | 100% | 100% | 100% | 100% | 100% |
| 135 | 19 | 11% | 74% | 5% | 100% | 100% | 95% | 100% | 100% | 100% |
| 136 | 19 | 100% | 100% | 53% | 100% | 100% | 100% | 100% | 100% | 100% |
| 138 | 17 | 94% | 100% | 29% | 100% | 100% | 94% | 100% | 100% | 100% |
| 140 | 18 | 72% | 22% | 0% | 22% | 22% | 0% | 94% | 100% | 100% |
| 142 | 18 | 100% | 100% | 67% | 100% | 100% | 94% | 100% | 100% | 100% |
| 144 | 18 | 100% | 94% | 11% | 94% | 100% | 100% | 100% | 100% | 100% |
| 147 | 18 | 100% | 100% | 0% | 100% | 100% | 100% | 100% | 100% | 100% |
| 149 | 19 | 89% | 84% | 63% | 84% | 89% | 95% | 89% | 89% | 89% |
| 150 | 17 | 94% | 88% | 71% | 94% | 94% | 94% | 88% | 94% | 94% |
| 152 | 17 | 100% | 88% | 6% | 88% | 100% | 100% | 100% | 100% | 94% |
| 154 | 18 | 100% | 100% | 100% | 100% | 100% | 100% | 100% | 100% | 100% |
| 156 | 17 | 100% | 100% | 12% | 100% | 100% | 100% | 100% | 100% | 100% |
| 158 | 16 | 100% | 100% | 13% | 100% | 100% | 94% | 100% | 100% | 100% |
| 159 | 16 | 0% | 94% | 0% | 0% | 94% | 0% | 94% | 94% | 94% |
| 160 | 16 | 100% | 100% | 81% | 100% | 100% | 31% | 100% | 100% | 100% |
| 161 | 17 | 65% | 47% | 12% | 47% | 100% | 76% | 100% | 100% | 29% |
| 162 | 15 | 13% | 33% | 0% | 40% | 87% | 60% | 73% | 93% | 53% |
| 164 | 5 | 0% | 0% | 0% | 0% | 40% | 0% | 60% | 80% | 60% |
| 165 | 18 | 78% | 50% | 22% | 44% | 72% | 67% | 89% | 94% | 94% |
| 166 | 16 | 6% | 0% | 0% | 0% | 19% | 13% | 50% | 75% | 94% |
| 167 | 17 | 53% | 29% | 12% | 29% | 82% | 47% | 88% | 88% | 82% |
| 168 | 17 | 12% | 41% | 0% | 41% | 100% | 71% | 71% | 100% | 100% |
| 169 | 19 | 89% | 95% | 0% | 95% | 95% | 79% | 95% | 95% | 95% |
| 170 | 19 | 84% | 95% | 68% | 95% | 95% | 89% | 100% | 95% | 95% |
| 171 | 17 | 88% | 94% | 0% | 100% | 100% | 94% | 100% | 100% | 100% |
| 172 | 18 | 100% | 100% | 28% | 94% | 100% | 94% | 100% | 100% | 94% |
| 174 | 16 | 100% | 81% | 75% | 88% | 100% | 94% | 100% | 100% | 100% |
| 175 | 19 | 95% | 95% | 11% | 95% | 95% | 74% | 95% | 95% | 95% |
| 176 | 19 | 5% | 84% | 0% | 95% | 95% | 74% | 100% | 95% | 95% |
| 177 | 15 | 40% | 80% | 13% | 80% | 100% | 100% | 100% | 100% | 80% |
| 178 | 18 | 61% | 83% | 44% | 94% | 100% | 11% | 100% | 100% | 56% |
| 179 | 15 | 7% | 67% | 0% | 73% | 93% | 27% | 93% | 93% | 67% |
| 182 | 18 | 94% | 100% | 94% | 100% | 100% | 89% | 100% | 100% | 100% |
| 183 | 16 | 81% | 100% | 19% | 100% | 100% | 0% | 100% | 100% | 100% |
| 185 | 17 | 59% | 94% | 47% | 94% | 100% | 76% | 100% | 100% | 94% |
| 186 | 15 | 0% | 13% | 0% | 13% | 47% | 13% | 80% | 93% | 20% |
| 188 | 18 | 0% | 89% | 0% | 100% | 100% | 83% | 100% | 100% | 100% |

TABLE 8-2-continued

Non-restrictive Positions ≥20% Neutral Mutations for at least One Property

| Position | # mutants | Detergent stability PI > 0.5 | Detergent initial PI % > 0.5 | Thermo-stability PI > 0.5 | Thermo-stability initial PI > 0.5 | CS28 pH 10 32 °C. PI > 0.5 | CS28 pH 10 50° C. PI > 0.5 | CS28 Ph 8 16° C. PI > 0.5 | CS28 Ph 8 32° C. PI > 0.5 | HPLC Protein PI > 0.5 |
|---|---|---|---|---|---|---|---|---|---|---|
| 189 | 18 | 22% | 83% | 11% | 100% | 100% | 94% | 94% | 83% | 100% |
| 190 | 16 | 0% | 44% | 0% | 44% | 50% | 38% | 88% | 100% | 44% |
| 191 | 16 | 6% | 31% | 6% | 31% | 88% | 56% | 100% | 100% | 94% |
| 192 | 19 | 21% | 100% | 11% | 100% | 100% | 100% | 100% | 100% | 100% |
| 193 | 17 | 12% | 0% | 6% | 0% | 88% | 12% | 82% | 94% | 94% |
| 195 | 17 | 65% | 88% | 0% | 88% | 94% | 82% | 100% | 100% | 94% |
| 197 | 17 | 18% | 6% | 29% | 6% | 82% | 12% | 100% | 100% | 94% |
| 199 | 19 | 0% | 0% | 0% | 0% | 16% | 0% | 58% | 79% | 63% |
| 200 | 15 | 7% | 0% | 0% | 0% | 0% | 0% | 13% | 40% | 100% |
| 201 | 19 | 32% | 0% | 5% | 0% | 21% | 11% | 53% | 53% | 84% |
| 202 | 19 | 53% | 16% | 21% | 16% | 26% | 11% | 63% | 79% | 100% |
| 203 | 19 | 21% | 5% | 21% | 5% | 32% | 26% | 84% | 89% | 79% |
| 207 | 15 | 13% | 93% | 7% | 100% | 100% | 100% | 100% | 100% | 100% |
| 210 | 17 | 100% | 94% | 88% | 94% | 100% | 100% | 94% | 100% | 88% |
| 214 | 16 | 100% | 100% | 100% | 100% | 100% | 100% | 100% | 100% | 100% |
| 217 | 18 | 94% | 83% | 83% | 83% | 100% | 94% | 100% | 100% | 83% |
| 221 | 17 | 100% | 100% | 100% | 100% | 100% | 100% | 100% | 100% | 100% |
| 228 | 18 | 100% | 94% | 100% | 100% | 100% | 100% | 100% | 100% | 100% |
| 234 | 15 | 100% | 73% | 40% | 73% | 100% | 87% | 100% | 100% | 93% |
| 237 | 19 | 32% | 53% | 5% | 47% | 84% | 47% | 84% | 84% | 74% |
| 238 | 17 | 6% | 0% | 6% | 0% | 0% | 0% | 35% | 41% | 100% |
| 239 | 17 | 0% | 0% | 0% | 0% | 0% | 0% | 53% | 53% | 71% |
| 240 | 16 | 6% | 75% | 0% | 88% | 94% | 44% | 100% | 100% | 88% |
| 243 | 16 | 81% | 94% | 44% | 100% | 100% | 100% | 100% | 100% | 81% |
| 246 | 19 | 89% | 89% | 47% | 89% | 89% | 89% | 89% | 89% | 89% |
| 250 | 15 | 93% | 100% | 93% | 100% | 100% | 100% | 100% | 100% | 100% |
| 254 | 19 | 100% | 100% | 100% | 100% | 100% | 100% | 95% | 100% | 84% |
| 255 | 17 | 100% | 100% | 100% | 100% | 100% | 82% | 100% | 100% | 82% |
| 257 | 17 | 100% | 94% | 94% | 100% | 100% | 100% | 100% | 100% | 100% |
| 259 | 13 | 92% | 92% | 92% | 92% | 92% | 92% | 92% | 92% | 85% |
| 264 | 17 | 41% | 24% | 6% | 24% | 94% | 35% | 94% | 100% | 41% |
| 266 | 19 | 0% | 53% | 5% | 53% | 95% | 84% | 84% | 100% | 74% |
| 267 | 4 | 50% | 0% | 0% | 0% | 0% | 75% | 0% | 100% | 0% |
| 268 | 19 | 21% | 11% | 5% | 11% | 79% | 42% | 89% | 95% | 32% |
| 269 | 19 | 95% | 32% | 11% | 16% | 95% | 68% | 95% | 100% | 95% |
| 270 | 10 | 90% | 30% | 70% | 30% | 100% | 60% | 100% | 100% | 30% |
| 272 | 18 | 100% | 94% | 100% | 100% | 100% | 100% | 100% | 100% | 94% |
| 273 | 15 | 7% | 100% | 0% | 93% | 100% | 100% | 100% | 100% | 67% |
| 275 | 18 | 61% | 94% | 89% | 100% | 100% | 100% | 100% | 100% | 94% |
| 279 | 16 | 100% | 100% | 94% | 100% | 100% | 100% | 19% | 100% | 94% |
| 283 | 16 | 100% | 81% | 88% | 81% | 100% | 100% | 100% | 100% | 69% |
| 284 | 18 | 100% | 94% | 83% | 94% | 100% | 100% | 100% | 100% | 89% |
| 298 | 17 | 100% | 100% | 18% | 100% | 100% | 100% | 100% | 100% | 100% |
| 301 | 17 | 100% | 94% | 100% | 94% | 100% | 94% | 100% | 100% | 94% |
| 303 | 18 | 100% | 100% | 100% | 100% | 100% | 89% | 100% | 100% | 94% |
| 305 | 19 | 100% | 100% | 100% | 100% | 100% | 63% | 100% | 100% | 95% |
| 306 | 17 | 94% | 12% | 100% | 41% | 100% | 100% | 100% | 100% | 41% |
| 310 | 19 | 95% | 89% | 95% | 89% | 89% | 89% | 89% | 89% | 89% |
| 311 | 9 | 100% | 56% | 100% | 67% | 100% | 89% | 100% | 100% | 56% |
| 314 | 19 | 95% | 89% | 95% | 84% | 95% | 95% | 95% | 95% | 89% |
| 318 | 16 | 100% | 94% | 100% | 94% | 100% | 100% | 100% | 100% | 94% |
| 319 | 17 | 76% | 88% | 71% | 88% | 100% | 88% | 100% | 100% | 88% |
| 320 | 18 | 100% | 100% | 100% | 100% | 100% | 100% | 100% | 100% | 94% |
| 322 | 17 | 100% | 100% | 100% | 100% | 100% | 100% | 100% | 100% | 100% |
| 323 | 17 | 100% | 88% | 41% | 88% | 100% | 94% | 100% | 100% | 88% |
| 336 | 16 | 100% | 75% | 94% | 75% | 94% | 88% | 100% | 100% | 81% |
| 337 | 16 | 38% | 6% | 38% | 6% | 38% | 19% | 63% | 88% | 100% |
| 338 | 17 | 71% | 6% | 82% | 6% | 59% | 12% | 100% | 94% | 100% |
| 339 | 18 | 33% | 6% | 33% | 0% | 28% | 6% | 22% | 56% | 89% |
| 340 | 19 | 100% | 79% | 100% | 79% | 89% | 58% | 100% | 100% | 84% |
| 344 | 16 | 100% | 94% | 94% | 94% | 94% | 94% | 44% | 100% | 94% |
| 359 | 14 | 100% | 93% | 100% | 93% | 100% | 100% | 100% | 100% | 93% |
| 374 | 17 | 100% | 65% | 100% | 65% | 100% | 100% | 100% | 100% | 59% |
| 375 | 19 | 95% | 79% | 95% | 79% | 89% | 84% | 95% | 95% | 79% |
| 376 | 18 | 100% | 94% | 100% | 94% | 100% | 100% | 94% | 100% | 94% |
| 377 | 18 | 100% | 83% | 100% | 89% | 100% | 94% | 100% | 100% | 83% |
| 379 | 16 | 100% | 94% | 94% | 94% | 100% | 100% | 100% | 100% | 94% |
| 381 | 19 | 95% | 89% | 95% | 89% | 95% | 89% | 95% | 95% | 95% |
| 382 | 19 | 84% | 63% | 84% | 63% | 84% | 74% | 84% | 84% | 63% |
| 393 | 17 | 94% | 82% | 94% | 82% | 94% | 94% | 94% | 94% | 82% |
| 394 | 16 | 100% | 94% | 94% | 94% | 100% | 94% | 100% | 100% | 100% |
| 399 | 17 | 94% | 94% | 94% | 94% | 94% | 94% | 100% | 94% | 94% |
| 401 | 16 | 100% | 100% | 100% | 100% | 100% | 100% | 100% | 100% | 100% |
| 407 | 16 | 100% | 100% | 100% | 100% | 100% | 100% | 100% | 100% | 100% |

TABLE 8-2-continued

Non-restrictive Positions ≥20% Neutral Mutations for at least One Property

| Position | # mutants | Detergent stability PI > 0.5 | Detergent initial PI % > 0.5 | Thermo-stability PI > 0.5 | Thermo-stability initial PI > 0.5 | CS28 pH 10 32 °C. PI > 0.5 | CS28 pH 10 50° C. PI > 0.5 | CS28 Ph 8 16° C. PI > 0.5 | CS28 pH 8 32° C. PI > 0.5 | HPLC Protein PI > 0.5 |
|---|---|---|---|---|---|---|---|---|---|---|
| 408 | 13 | 54% | 8% | 54% | 15% | 54% | 46% | 54% | 54% | 23% |
| 419 | 19 | 100% | 100% | 100% | 100% | 100% | 100% | 100% | 100% | 100% |
| 433 | 16 | 100% | 94% | 94% | 94% | 100% | 94% | 100% | 100% | 94% |
| 436 | 19 | 100% | 89% | 100% | 89% | 100% | 100% | 100% | 100% | 89% |
| 438 | 16 | 100% | 100% | 100% | 100% | 100% | 75% | 100% | 100% | 100% |
| 444 | 17 | 100% | 100% | 100% | 100% | 100% | 100% | 100% | 100% | 100% |
| 447 | 18 | 100% | 94% | 100% | 94% | 100% | 100% | 100% | 100% | 100% |
| 448 | 16 | 100% | 94% | 100% | 94% | 100% | 100% | 100% | 100% | 94% |
| 451 | 16 | 100% | 94% | 100% | 94% | 100% | 100% | 100% | 100% | 94% |
| 453 | 19 | 100% | 89% | 100% | 89% | 95% | 95% | 95% | 95% | 95% |
| 459 | 19 | 100% | 100% | 100% | 100% | 100% | 100% | 100% | 100% | 100% |
| 465 | 16 | 100% | 100% | 94% | 100% | 100% | 94% | 100% | 100% | 100% |
| 470 | 17 | 100% | 100% | 100% | 100% | 100% | 100% | 100% | 100% | 100% |
| 475 | 17 | 100% | 100% | 100% | 100% | 100% | 0% | 100% | 100% | 100% |
| 476 | 16 | 94% | 75% | 94% | 69% | 94% | 0% | 94% | 94% | 75% |
| 483 | 18 | 100% | 100% | 100% | 100% | 100% | 100% | 100% | 100% | 100% |
| 484 | 18 | 100% | 100% | 100% | 100% | 100% | 100% | 100% | 100% | 100% |

In general, restrictive positions should not be mutated, as there are only few substitutions at these positions that are neutral for any property. When these positions must be changed, they require that the amino acid replacement be a conservative replacement. For example two mutations at position 58, i.e., A58G and A58T, are combinable, and two mutations at position 236, i.e., Y236F and Y236W, are combinable. Non-restrictive positions are the positions that are most suitable for use in constructing combinatorial libraries, since they have a large number of combinable mutations. Since homologous proteins share the same structure, restrictive positions are restrictive in all homologous amylases, since they are important for the structure and/or function of the protein. As demonstrated in the present disclosure, restrictive positions can only be identified by testing the possible amino acid mutations and measuring the properties of one of the proteins (e.g., alpha-amylase). Note that the two restrictive sites are conserved in the sequence alignment in FIG. 1, but that conservation itself is not an indicator that a position is restrictive. For example, Q71, K72, and G73 are all conserved in the sequence alignment, but all three positions have several mutations that are better than the parent for activity, stability, or both. Non-restrictive positions with more than 20% neutral mutations for each property are generally very good choices for combinatorial mutations. There are 115 positions out of the 198 positions tested in alpha-amylase that meet this condition.

Example 9

Detergent Stability of ACE-Q Amylase Variants

The detergent stability of ACE-Q (ACE-S243Q) amylase variants was measured after incubation under defined conditions in the presence of 10% detergent (commercial detergent; inactivated) at 70° C., and the initial and residual amylase activities were determined using the Ceralpha method (BPNPG7) as described in Example 1. The numbering of amino acid residues corresponds to that of the BASE alpha-amylase. The results in Table 9-1 below are shown as a performance index (PI) for each variant in relation to ACE alpha mylase.

TABLE 9-1

Detergent Stability of ACE-Q Variants with PI ≥ 0.5

| Position | Variant | PI |
|---|---|---|
| 127 | R127C | 0.58 |
| 305 | Y305A | 4.05 |
| 305 | Y305C | 4.12 |
| 305 | Y305D | 4.53 |
| 305 | Y305E | 3.86 |
| 305 | Y305G | 3.97 |
| 305 | Y305H | 3.96 |
| 305 | Y305L | 4.27 |
| 305 | Y305N | 4.20 |
| 305 | Y305P | 4.36 |
| 305 | Y305Q | 3.95 |
| 305 | Y305R | 3.92 |
| 305 | Y305S | 4.01 |
| 305 | Y305T | 4.12 |
| 305 | Y305V | 3.92 |
| 305 | Y305W | 4.18 |
| 320 | Q320A | 3.96 |
| 320 | Q320C | 3.78 |
| 320 | Q320D | 3.93 |
| 320 | Q320E | 3.88 |
| 320 | Q320F | 3.73 |
| 320 | Q320G | 3.58 |
| 320 | Q320H | 4.05 |
| 320 | Q320I | 4.00 |
| 320 | Q320L | 3.78 |
| 320 | Q320M | 3.83 |
| 320 | Q320N | 4.01 |
| 320 | Q320P | 3.68 |
| 320 | Q320R | 4.28 |
| 320 | Q320S | 3.76 |
| 320 | Q320T | 3.82 |
| 320 | Q320V | 4.03 |
| 320 | Q320W | 3.55 |
| 320 | Q320Y | 3.80 |
| 379 | P379A | 4.54 |
| 379 | P379C | 4.27 |
| 379 | P379E | 3.82 |
| 379 | P379F | 3.88 |
| 379 | P379G | 4.04 |
| 379 | P379H | 3.99 |
| 379 | P379L | 3.85 |
| 379 | P379N | 3.87 |
| 379 | P379Q | 4.17 |
| 379 | P379R | 4.39 |
| 379 | P379S | 4.09 |
| 379 | P379T | 3.98 |
| 379 | P379V | 4.30 |

TABLE 9-1-continued

Detergent Stability of ACE-Q Variants with PI ≥ 0.5

| Position | Variant | PI |
|---|---|---|
| 379 | P379W | 3.79 |
| 379 | P379Y | 4.17 |
| 419 | T419A | 3.78 |
| 419 | T419C | 3.88 |
| 419 | T419D | 3.59 |
| 419 | T419E | 4.06 |
| 419 | T419F | 3.64 |
| 419 | T419G | 3.71 |
| 419 | T419H | 3.69 |
| 419 | T419K | 3.58 |
| 419 | T419L | 3.65 |
| 419 | T419M | 3.66 |
| 419 | T419N | 3.69 |
| 419 | T419P | 3.87 |
| 419 | T419Q | 3.93 |
| 419 | T419R | 3.78 |
| 419 | T419S | 3.64 |
| 419 | T419V | 3.68 |
| 419 | T419W | 3.92 |
| 419 | T419Y | 4.14 |
| 453 | L453A | 4.18 |
| 453 | L453C | 4.14 |
| 453 | L453D | 4.12 |
| 453 | L453F | 4.41 |
| 453 | L453G | 4.21 |
| 453 | L453H | 4.26 |
| 453 | L453I | 4.20 |
| 453 | L453K | 4.09 |
| 453 | L453M | 4.52 |
| 453 | L453N | 4.08 |
| 453 | L453P | 4.24 |
| 453 | L453Q | 4.14 |
| 453 | L453R | 4.31 |
| 453 | L453S | 4.09 |
| 453 | L453T | 4.34 |
| 453 | L453V | 4.01 |
| 453 | L453W | 4.03 |
| 453 | L453Y | 4.05 |
| 475 | G475A | 3.74 |
| 475 | G475D | 3.40 |
| 475 | G475E | 3.36 |
| 475 | G475H | 3.43 |
| 475 | G475I | 3.49 |
| 475 | G475K | 3.41 |
| 475 | G475L | 3.33 |
| 475 | G475M | 3.40 |
| 475 | G475N | 3.40 |
| 475 | G475P | 3.49 |
| 475 | G475Q | 3.56 |
| 475 | G475R | 3.87 |
| 475 | G475S | 3.42 |
| 475 | G475T | 3.39 |
| 475 | G475V | 3.47 |
| 475 | G475W | 3.42 |

The variants shown are the combinable mutations identified in the SEL data. Only variants with a PI≥0.5 are shown. These mutations can be combined to give a desired combination of stability and activity.

Example 10

Cleaning Performance of ACE-Q Variants

The wash performance of ACE-Q (ACE-S243Q) amylase variants was measured using CS28 microswatches under four different conditions pH 8/16° C., pH 8/32° C., pH 10/32° C. and pH 10/50° C. as described in Example 1. The numbering of amino acid residues corresponds to that of the BASE alpha-amylase. The results in Tables 10-1 to 10-4 below are shown as a performance index (PI) for each variant in relation to ACE alpha amylase.

TABLE 10-1

ACE-Q Variants (118) with PI ≥ 0.5 for CS-28, pH 8, 16° C. Wash Performance

| Position | Variant | PI |
|---|---|---|
| 127 | R127A | 1.22 |
| 127 | R127C | 1.28 |
| 127 | R127D | 1.28 |
| 127 | R127E | 1.14 |
| 127 | R127F | 1.13 |
| 127 | R127G | 0.86 |
| 127 | R127H | 0.97 |
| 127 | R127I | 1.20 |
| 127 | R127K | 1.26 |
| 127 | R127L | 1.27 |
| 127 | R127M | 1.03 |
| 127 | R127P | 1.06 |
| 127 | R127Q | 1.25 |
| 127 | R127S | 1.23 |
| 127 | R127T | 1.24 |
| 127 | R127V | 1.29 |
| 127 | R127W | 1.43 |
| 127 | R127Y | 1.01 |
| 305 | Y305A | 1.54 |
| 305 | Y305C | 1.63 |
| 305 | Y305D | 1.65 |
| 305 | Y305E | 1.61 |
| 305 | Y305G | 1.58 |
| 305 | Y305H | 1.48 |
| 305 | Y305L | 1.65 |
| 305 | Y305N | 1.61 |
| 305 | Y305P | 1.91 |
| 305 | Y305Q | 1.78 |
| 305 | Y305R | 1.44 |
| 305 | Y305S | 1.49 |
| 305 | Y305T | 1.68 |
| 305 | Y305V | 1.68 |
| 305 | Y305W | 1.44 |
| 320 | Q320A | 1.29 |
| 320 | Q320C | 1.28 |
| 320 | Q320D | 1.27 |
| 320 | Q320E | 1.25 |
| 320 | Q320F | 1.28 |
| 320 | Q320G | 1.53 |
| 320 | Q320H | 1.29 |
| 320 | Q320I | 1.16 |
| 320 | Q320L | 1.32 |
| 320 | Q320M | 1.28 |
| 320 | Q320N | 1.28 |
| 320 | Q320P | 2.36 |
| 320 | Q320R | 1.20 |
| 320 | Q320S | 1.09 |
| 320 | Q320T | 1.10 |
| 320 | Q320V | 1.09 |
| 320 | Q320W | 1.02 |
| 320 | Q320Y | 1.27 |
| 379 | P379A | 0.96 |
| 379 | P379C | 0.90 |
| 379 | P379E | 1.00 |
| 379 | P379F | 0.99 |
| 379 | P379G | 1.00 |
| 379 | P379H | 0.97 |
| 379 | P379L | 1.05 |
| 379 | P379N | 0.98 |
| 379 | P379Q | 1.10 |
| 379 | P379R | 0.81 |
| 379 | P379S | 1.01 |
| 379 | P379T | 1.04 |
| 379 | P379V | 1.00 |
| 379 | P379W | 0.86 |
| 379 | P379Y | 0.95 |
| 419 | T419A | 1.21 |
| 419 | T419C | 1.08 |
| 419 | T419D | 1.19 |
| 419 | T419E | 1.17 |
| 419 | T419F | 1.27 |
| 419 | T419G | 1.14 |
| 419 | T419H | 1.42 |
| 419 | T419K | 1.13 |
| 419 | T419L | 1.01 |

TABLE 10-1-continued

ACE-Q Variants (118) with PI ≥ 0.5 for CS-28, pH 8, 16° C. Wash Performance

| Position | Variant | PI |
|---|---|---|
| 419 | T419M | 1.20 |
| 419 | T419N | 1.13 |
| 419 | T419P | 1.29 |
| 419 | T419Q | 1.18 |
| 419 | T419R | 1.32 |
| 419 | T419S | 1.18 |
| 419 | T419V | 1.23 |
| 419 | T419W | 1.20 |
| 419 | T419Y | 1.02 |
| 453 | L453A | 0.97 |
| 453 | L453C | 0.93 |
| 453 | L453D | 0.80 |
| 453 | L453F | 0.92 |
| 453 | L453G | 0.85 |
| 453 | L453H | 1.05 |
| 453 | L453I | 0.91 |
| 453 | L453K | 1.02 |
| 453 | L453M | 0.82 |
| 453 | L453N | 1.00 |
| 453 | L453P | 0.76 |
| 453 | L453Q | 1.02 |
| 453 | L453R | 0.96 |
| 453 | L453S | 0.95 |
| 453 | L453T | 0.95 |
| 453 | L453V | 1.02 |
| 453 | L453W | 0.88 |
| 453 | L453Y | 0.89 |
| 475 | G475A | 1.88 |
| 475 | G475D | 1.91 |
| 475 | G475E | 1.92 |
| 475 | G475H | 1.73 |
| 475 | G475I | 2.31 |
| 475 | G475K | 1.93 |
| 475 | G475L | 2.20 |
| 475 | G475M | 2.17 |
| 475 | G475N | 1.86 |
| 475 | G475P | 1.78 |
| 475 | G475Q | 1.99 |
| 475 | G475R | 1.92 |
| 475 | G475S | 1.75 |
| 475 | G475T | 2.06 |
| 475 | G475V | 2.10 |
| 475 | G475W | 2.11 |

TABLE 10-2

ACE-Q Variants (118) with PI ≥ 0.5 for CS-28, pH 8, 32° C. Wash Performance

| Position | Variant | PI |
|---|---|---|
| 127 | R127A | 0.64 |
| 127 | R127C | 0.95 |
| 127 | R127D | 0.82 |
| 127 | R127E | 0.83 |
| 127 | R127F | 0.90 |
| 127 | R127G | 0.75 |
| 127 | R127H | 0.81 |
| 127 | R127I | 1.24 |
| 127 | R127K | 0.86 |
| 127 | R127L | 1.12 |
| 127 | R127M | 1.05 |
| 127 | R127P | 1.05 |
| 127 | R127Q | 1.16 |
| 127 | R127S | 0.88 |
| 127 | R127T | 1.19 |
| 127 | R127V | 1.26 |
| 127 | R127W | 1.14 |
| 127 | R127Y | 1.11 |
| 305 | Y305A | 1.17 |
| 305 | Y305C | 1.19 |
| 305 | Y305D | 1.09 |

TABLE 10-2-continued

ACE-Q Variants (118) with PI ≥ 0.5 for CS-28, pH 8, 32° C. Wash Performance

| Position | Variant | PI |
|---|---|---|
| 305 | Y305E | 1.08 |
| 305 | Y305G | 1.19 |
| 305 | Y305H | 1.11 |
| 305 | Y305L | 1.21 |
| 305 | Y305N | 1.20 |
| 305 | Y305P | 1.16 |
| 305 | Y305Q | 1.23 |
| 305 | Y305R | 1.20 |
| 305 | Y305S | 1.14 |
| 305 | Y305T | 1.18 |
| 305 | Y305V | 1.18 |
| 305 | Y305W | 1.11 |
| 320 | Q320A | 1.12 |
| 320 | Q320C | 1.18 |
| 320 | Q320D | 1.21 |
| 320 | Q320E | 1.17 |
| 320 | Q320F | 1.23 |
| 320 | Q320G | 1.32 |
| 320 | Q320H | 1.13 |
| 320 | Q320I | 1.18 |
| 320 | Q320L | 1.15 |
| 320 | Q320M | 1.23 |
| 320 | Q320N | 1.32 |
| 320 | Q320P | 1.64 |
| 320 | Q320R | 1.22 |
| 320 | Q320S | 1.11 |
| 320 | Q320T | 1.20 |
| 320 | Q320V | 1.15 |
| 320 | Q320W | 1.05 |
| 320 | Q320Y | 1.15 |
| 379 | P379A | 1.11 |
| 379 | P379C | 0.89 |
| 379 | P379E | 1.05 |
| 379 | P379F | 1.09 |
| 379 | P379G | 1.08 |
| 379 | P379H | 1.05 |
| 379 | P379L | 1.03 |
| 379 | P379N | 1.05 |
| 379 | P379Q | 1.06 |
| 379 | P379R | 1.03 |
| 379 | P379S | 1.13 |
| 379 | P379T | 1.14 |
| 379 | P379V | 1.11 |
| 379 | P379W | 0.99 |
| 379 | P379Y | 1.07 |
| 419 | T419A | 0.79 |
| 419 | T419C | 0.79 |
| 419 | T419D | 0.82 |
| 419 | T419E | 0.70 |
| 419 | T419F | 0.81 |
| 419 | T419G | 0.71 |
| 419 | T419H | 0.85 |
| 419 | T419K | 0.78 |
| 419 | T419L | 0.77 |
| 419 | T419M | 1.01 |
| 419 | T419N | 1.01 |
| 419 | T419P | 1.03 |
| 419 | T419Q | 0.84 |
| 419 | T419R | 0.86 |
| 419 | T419S | 0.98 |
| 419 | T419V | 1.01 |
| 419 | T419W | 1.09 |
| 419 | T419Y | 1.04 |
| 453 | L453A | 1.02 |
| 453 | L453C | 0.96 |
| 453 | L453D | 0.93 |
| 453 | L453F | 1.02 |
| 453 | L453G | 1.01 |
| 453 | L453H | 1.00 |
| 453 | L453I | 0.98 |
| 453 | L453K | 0.99 |
| 453 | L453M | 0.96 |
| 453 | L453N | 1.01 |
| 453 | L453P | 0.96 |
| 453 | L453Q | 1.07 |

TABLE 10-2-continued

ACE-Q Variants (118) with PI ≥ 0.5 for CS-28, pH 8, 32° C. Wash Performance

| Position | Variant | PI |
|---|---|---|
| 453 | L453R | 1.04 |
| 453 | L453S | 0.95 |
| 453 | L453T | 1.05 |
| 453 | L453V | 0.98 |
| 453 | L453W | 0.95 |
| 453 | L453Y | 0.99 |
| 475 | G475A | 1.24 |
| 475 | G475D | 1.22 |
| 475 | G475E | 1.12 |
| 475 | G475H | 1.21 |
| 475 | G475I | 1.44 |
| 475 | G475K | 1.41 |
| 475 | G475L | 1.26 |
| 475 | G475M | 1.42 |
| 475 | G475N | 1.25 |
| 475 | G475P | 1.26 |
| 475 | G475Q | 1.25 |
| 475 | G475R | 1.39 |
| 475 | G475S | 1.26 |
| 475 | G475T | 1.26 |
| 475 | G475V | 1.30 |
| 475 | G475W | 1.36 |

TABLE 10-3

ACE-Q Variants (87) with PI ≥ 0.5 for CS-28, pH 10, 32° C. Wash Performance

| Position | Variant | PI |
|---|---|---|
| 127 | R127A | 0.55 |
| 127 | R127C | 0.76 |
| 127 | R127F | 0.63 |
| 127 | R127G | 0.60 |
| 127 | R127H | 0.66 |
| 127 | R127I | 0.64 |
| 127 | R127K | 0.90 |
| 127 | R127L | 0.55 |
| 127 | R127M | 0.79 |
| 127 | R127Q | 0.76 |
| 127 | R127S | 0.74 |
| 127 | R127T | 0.83 |
| 127 | R127V | 0.51 |
| 127 | R127W | 0.72 |
| 127 | R127Y | 0.77 |
| 305 | Y305H | 0.61 |
| 305 | Y305L | 0.52 |
| 305 | Y305N | 0.55 |
| 305 | Y305Q | 0.65 |
| 305 | Y305R | 0.84 |
| 305 | Y305W | 0.90 |
| 320 | Q320A | 0.55 |
| 320 | Q320C | 0.67 |
| 320 | Q320D | 0.61 |
| 320 | Q320E | 0.51 |
| 320 | Q320F | 0.55 |
| 320 | Q320G | 0.88 |
| 320 | Q320H | 0.65 |
| 320 | Q320I | 0.57 |
| 320 | Q320M | 0.79 |
| 320 | Q320N | 0.94 |
| 320 | Q320R | 0.79 |
| 320 | Q320S | 0.64 |
| 320 | Q320T | 0.79 |
| 320 | Q320V | 0.60 |
| 320 | Q320Y | 0.56 |
| 379 | P379A | 0.91 |
| 379 | P379C | 0.97 |
| 379 | P379E | 0.83 |
| 379 | P379F | 1.22 |
| 379 | P379G | 1.03 |
| 379 | P379H | 0.95 |

TABLE 10-3-continued

ACE-Q Variants (87) with PI ≥ 0.5 for CS-28, pH 10, 32° C. Wash Performance

| Position | Variant | PI |
|---|---|---|
| 379 | P379L | 1.09 |
| 379 | P379N | 1.15 |
| 379 | P379Q | 1.07 |
| 379 | P379R | 1.20 |
| 379 | P379S | 1.12 |
| 379 | P379T | 1.06 |
| 379 | P379V | 1.05 |
| 379 | P379W | 1.13 |
| 379 | P379Y | 1.01 |
| 419 | T419A | 1.11 |
| 419 | T419C | 0.85 |
| 419 | T419D | 1.03 |
| 419 | T419E | 1.09 |
| 419 | T419F | 1.18 |
| 419 | T419G | 1.03 |
| 419 | T419H | 1.33 |
| 419 | T419K | 1.11 |
| 419 | T419L | 0.93 |
| 419 | T419M | 1.08 |
| 419 | T419N | 1.13 |
| 419 | T419P | 1.22 |
| 419 | T419Q | 1.11 |
| 419 | T419R | 1.60 |
| 419 | T419S | 1.11 |
| 419 | T419V | 1.16 |
| 419 | T419W | 1.17 |
| 419 | T419Y | 1.06 |
| 453 | L453A | 0.94 |
| 453 | L453C | 0.91 |
| 453 | L453D | 0.93 |
| 453 | L453F | 1.17 |
| 453 | L453G | 1.05 |
| 453 | L453H | 1.22 |
| 453 | L453I | 1.06 |
| 453 | L453K | 1.06 |
| 453 | L453M | 1.14 |
| 453 | L453N | 0.96 |
| 453 | L453P | 0.84 |
| 453 | L453Q | 1.04 |
| 453 | L453R | 1.00 |
| 453 | L453S | 0.99 |
| 453 | L453T | 1.03 |
| 453 | L453V | 1.05 |
| 453 | L453W | 1.00 |
| 453 | L453Y | 1.16 |

TABLE 10-4

ACE-Q Variants (73) with PI ≥ 0.5 for CS-28, pH 10, 50° C. Wash Performance

| Position | Variant | PI |
|---|---|---|
| 127 | R127C | 0.72 |
| 127 | R127G | 0.71 |
| 305 | Y305A | 1.79 |
| 305 | Y305E | 1.56 |
| 305 | Y305G | 0.74 |
| 305 | Y305L | 2.96 |
| 305 | Y305N | 0.64 |
| 305 | Y305R | 2.44 |
| 305 | Y305S | 0.68 |
| 305 | Y305W | 2.61 |
| 320 | Q320C | 2.58 |
| 320 | Q320D | 4.81 |
| 320 | Q320E | 4.25 |
| 320 | Q320H | 4.88 |
| 320 | Q320I | 1.47 |
| 320 | Q320M | 2.20 |
| 320 | Q320N | 2.12 |
| 320 | Q320R | 1.87 |
| 320 | Q320Y | 0.83 |

TABLE 10-4-continued

ACE-Q Variants (73) with PI ≥ 0.5 for CS-28, pH 10, 50° C. Wash Performance

| Position | Variant | PI |
|---|---|---|
| 379 | P379A | 0.90 |
| 379 | P379C | 0.93 |
| 379 | P379E | 0.74 |
| 379 | P379F | 0.89 |
| 379 | P379G | 1.02 |
| 379 | P379H | 0.81 |
| 379 | P379L | 0.83 |
| 379 | P379N | 1.03 |
| 379 | P379Q | 0.95 |
| 379 | P379R | 1.11 |
| 379 | P379S | 0.81 |
| 379 | P379T | 1.08 |
| 379 | P379V | 1.01 |
| 379 | P379W | 0.97 |
| 379 | P379Y | 0.86 |
| 419 | T419A | 0.83 |
| 419 | T419C | 0.51 |
| 419 | T419D | 0.59 |
| 419 | T419E | 0.58 |
| 419 | T419F | 0.69 |
| 419 | T419G | 0.64 |
| 419 | T419H | 0.92 |
| 419 | T419K | 0.70 |
| 419 | T419L | 0.77 |
| 419 | T419M | 0.77 |
| 419 | T419N | 0.68 |
| 419 | T419P | 0.82 |
| 419 | T419Q | 0.67 |
| 419 | T419R | 0.56 |
| 419 | T419S | 0.62 |
| 419 | T419V | 0.91 |
| 419 | T419W | 0.82 |
| 419 | T419Y | 0.90 |
| 453 | L453A | 1.41 |
| 453 | L453C | 1.43 |
| 453 | L453D | 1.39 |
| 453 | L453F | 1.20 |
| 453 | L453G | 1.50 |
| 453 | L453H | 2.01 |
| 453 | L453I | 1.17 |
| 453 | L453K | 1.60 |
| 453 | L453M | 1.66 |
| 453 | L453N | 1.48 |
| 453 | L453P | 1.36 |
| 453 | L453Q | 1.53 |
| 453 | L453R | 2.03 |
| 453 | L453S | 1.61 |
| 453 | L453T | 1.90 |
| 453 | L453V | 1.71 |
| 453 | L453W | 2.12 |
| 453 | L453Y | 2.62 |
| 475 | G475H | 0.53 |
| 475 | G475L | 0.51 |
| 475 | G475W | 0.73 |

Example 11

Thermostability of BASE Single-Mutation Variants

Twenty-three single mutation variants of BASE were selected from the SEL screen for accurate $T_{50}\%$ determination in heat-inactivated 100% Persil (Henkel) HDL. Heat inactivation of commercial detergents serves to destroy the activity of any enzymatic components while retaining the properties of non-enzymatic components. The selection was based on improved performance indices in the thermostability and 10% Persil HDL stability assays, as performed in the SEL screen. The selected variants with their respective $T_{50}\%$ values in 100% Persil HDL are listed in Table 11-1.

TABLE 11-1

Thermostability of Amylase Variants Having Single Substitutions

| BASE Variant No. | Mutation | $T_{50\%}$ in 100% Persil HDL (° C.) |
|---|---|---|
| 1 | Wild Type BASE | 35.4 |
| 2 | N128C | 40.3 |
| 3 | T131I | 38.1 |
| 4 | T134P | 36.8 |
| 5 | Q138E | 36.8 |
| 6 | Y160I | 38.7 |
| 7 | T165I | 39.3 |
| 8 | T165V | 37.8 |
| 9 | K178L | 44.7 |
| 10 | T182A | 38.2 |
| 11 | T182C | 41.0 |
| 12 | T182D | 37.2 |
| 13 | T182M | 38.3 |
| 14 | T182F | 36.5 |
| 15 | T182N | 36.5 |
| 16 | T182G | 42.0 |
| 17 | T182P | 38.9 |
| 18 | T182Q | 38.4 |
| 19 | A185D | 40.4 |
| 20 | A185E | 37.3 |
| 21 | E189P | 35.4 |
| 22 | S243D | 40.4 |
| 23 | S243E | 44.1 |
| 24 | S243Q | 42.7 |

Example 12

Thermostability of BASE Combinatorial Variants

Five positions (N128C, K178L, T182G, A185D, and S243Q) of the BASE reference amylase were chosen for the construction of a combinatorial library as described in Example 5. Of the possible 32 variants of this combinatorial library (designated BASE-S1 to BASE-S32), 30 variants were assayed for stability in heat-inactivated Persil HDL. The variants, their respective mutations and the measured $T_{50}\%$ in Persil HDL are listed in Table 12-1 in comparison to wild type BASE (reference amylase), ACE, and ACE-S243Q amylase variants.

TABLE 12-1

Thermostability of Amylase Variants

| Variant | Amino acid positions mutated | | | | | $T_{50\%}$ in 100% Persil HDL (° C.) |
|---|---|---|---|---|---|---|
| | N128 | K178 | T182 | A185 | S243 | |
| BASE-WT | | | | | | 36.3 |
| BASE-S1 | | | G | D | | 45.9 |
| BASE-S2 | | | G | | | 45.6 |
| BASE-S3 | | L | G | D | | 49.8 |
| BASE-S4 | | L | G | | | 52.7 |
| BASE-S5 | | | | D | | 40.4 |
| BASE-S6 | | | | | | 40.1 |
| BASE-S7 | | L | | D | | 43.9 |
| BASE-S8 | | L | | | | 39.9 |
| BASE-S9 | | | G | D | Q | 48.1 |
| BASE-S10 | | | G | | Q | 51.1 |
| BASE-S11 | | L | G | D | Q | 53.7 |
| BASE-S12 | | L | G | | Q | 57.1 |
| BASE-S13 | | | | D | Q | 42.7 |
| BASE-S14 | | | | | Q | 45.3 |
| BASE-S15 | | L | | D | Q | 53.2 |
| BASE-S16 | | L | | | Q | 48.9 |
| BASE-S17 | C | | G | D | | 45.8 |
| BASE-S18 | C | | G | | | 47.8 |
| BASE-S19 | C | L | G | D | | 51.4 |
| BASE-S20 | C | L | G | | | 56.3 |
| BASE-S21 | C | | | D | | 42.5 |

TABLE 12-1-continued

Thermostability of Amylase Variants

| Variant | Amino acid positions mutated | | | | | $T_{50\%}$ in 100% Persil HDL (° C.) |
|---|---|---|---|---|---|---|
| | N128 | K178 | T182 | A185 | S243 | |
| BASE-S23 | C | L | | D | | 48.2 |
| BASE-S24 | C | L | | | | 44.0 |
| BASE-S25 | C | | G | D | Q | 51.5 |
| BASE-S26 | C | | G | | Q | 55.9 |
| BASE-S27 | C | L | G | D | Q | 57.3 |
| BASE-S28 | C | L | G | | Q | 63.2 |
| BASE-S29 | C | | | D | Q | 48.1 |
| BASE-S31 | C | L | | D | Q | 56.4 |
| ACE | | | | | | 60.1 |
| ACE-S243Q | | | | | | 64.0 |

The results show that ACE and ACE-S243Q have significantly increased thermostability compared to WT BASE. Moreover, several combinatorial variants also demonstrated significantly increased thermostability, with six variants (BASE-S26, BASE-S20, BASE-S31, BASE-S12, BASE-S27, BASE-S28) showing more than a 50% increase in stability.

Example 13

Cleaning Performance and Thermostability of BASE Combinatorial Variants

Thirteen combinatorial BASE variants were constructed as described in Example 5, incorporating performance enhancing mutations and stability enhancing mutations. The alpha-amylase variants BASE-W1 to BASE-W13 were assayed for cleaning performance (PI or performance index) on CS28 microswatches under two different conditions (pH 8, 16° C., and pH 8, 32° C.) and for thermostability ($T_{50\%}$) in MOPS buffer and in 100% Persil HDL as shown in Table 13-1.

TABLE 13-1

Cleaning Performance and Thermostability of Amylase Variants

| Variant | PI CS28, pH 8 16° C. | PI CS28, pH 8 32° C. | $T_{50\%}$ MOPS (° C.) | $T_{50\%}$ Persil HDL (° C.) |
|---|---|---|---|---|
| BASE-WT | 1.0 | 1.0 | 62 | 36 |
| BASE-W1 | 2.4 | 1.7 | 86 | 63 |
| BASE-W2 | 2.8 | 1.4 | 86 | 64 |
| BASE-W3 | 2.8 | 1.8 | 76 | 52 |
| BASE-W4 | 2.8 | 1.5 | 87 | 64 |
| BASE-W5 | 1.9 | 0.5 | 88 | 66 |
| BASE-W6 | 2.5 | 1.7 | 87 | 64 |
| BASE-W7 | 2.2 | 1.6 | 84 | 60 |
| BASE-W8 | 2.7 | 1.5 | 87 | 64 |
| BASE-W9 | 3.7 | 2.1 | 86 | 64 |
| BASE-W10* | 3.8 | 2.0 | 86 | 64 |
| BASE-W11 | 3.4 | 2.3 | 86 | 64 |
| BASE-W12 | 3.0 | 1.9 | 84 | 59 |
| BASE-W13 | 2.7 | 1.9 | 86 | 63 |

*The BASE-W10 variant further comprises a F202Y substitution.

The results show that several combinatorial variants demonstrate significantly increased cleaning performance and detergent stability compared to WT BASE. Three of the variants, BASE-W9, BASE-W10, and BASE-W11, show more than three fold improvement in low temperature cleaning, while at the same time showing more than 1.75 fold improved detergent stability.

Example 14

Cleaning Performance of BASE Variants W9, W10, W11, and ACE-QK

The wash performance of BASE variants W9, W10 and W11, and ACE-QK was tested in a laundry detergent application. Stain removal was measured on CFT CS-28 rice starch on cotton (Center for Testmaterials BV, Vlaardingen, Netherlands) and EMPA161 starch on cotton (Test materials AG, St. Gallen, Switzerland) in launder-o-meter experiments using heat inactivated Ariel detergent (Proctor and Gamble), purchased from the local supermarket. Ariel detergent was inactivated at 90° C. to 100° C. in a Brother Hi-Speed microwave for 8 minutes. The detergent was allowed to cool down to less than 50° C. and then heated again in the microwave for 7 min. This step was repeated once.

EMPA swatches were measured before and after treatment by optical reflectance using a Tristimulus Minolta Meter CR-400. The difference in the L, a, b values was converted to total color difference (dE), as defined by the CIE-LAB color space. Cleaning of the stains is expressed as percent stain removal index (% SRI) by taking a ratio between the color difference before and after washing and comparing it to the difference of unwashed soils (before wash) to unsoiled fabric.

Figure 5:
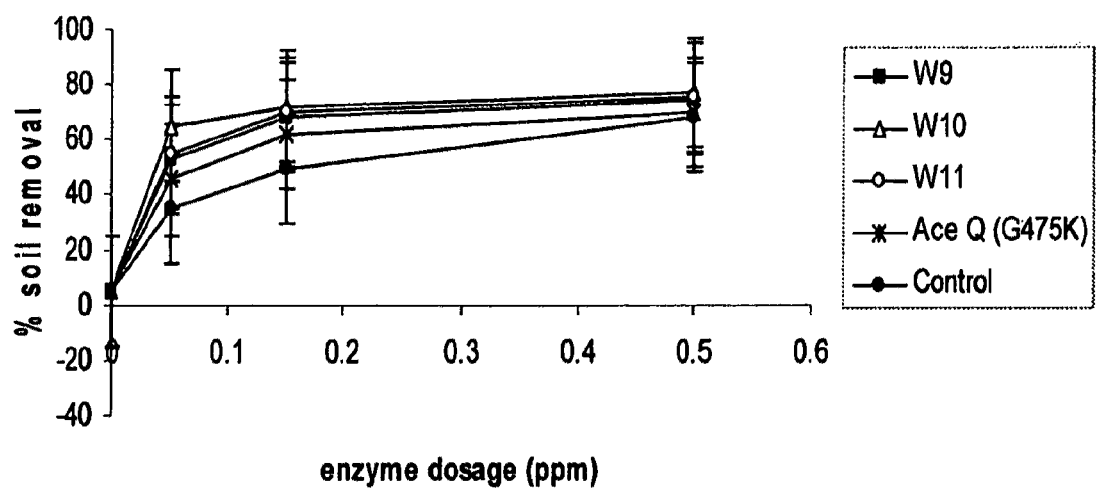
FIG. 5 provides a graph showing the wash performance of multiple alpha-amylases in a laundry detergent application. The enzymes tested were as follows: W9 (BASE-S125A–N128C–K178L–T182G–S243Q–T279N–D319T–Q320N–G475R); W10 (BASE-N128C–K178L–T182G–S243Q–Y305R–D319T–G475R; W11 (BASE-S125A–N128C–K178L–T182G–S243Q–Y305R–G475R; and ACE-S243Q–G475K.

Wash treatment was conducted in a launder-o-meter at 30° C. The wash time was 45 minutes (15 minutes to reach 30° C., then 30 minutes at 30° C.) with a rinse time of 5 minutes with cold tap water. The water hardness was adjusted to 8.5° GH and heat inactivated Ariel was used at 4.5 ml/L. The soil load consisted of 2 ea. EMPA 161 and 2 CFT CS-28 swatches per beaker plus 6 steal balls. After the wash treatment, all swatches were spin-dried followed by air drying and read for optical reflectance as described above. The control consisted of a benchmark commercial enzyme. The results are shown in FIG. 5.

Generally, the presence of BASE variant in an amount of from about 0.05 to about 0.5 ppm improved performance compared to the control, with the relative performance of the BASE variants following the pattern W10>W11>W9>ACE-Q.

Example 15

Cleaning Performance of BASE Variants X8C, W10EK, and ACE-QK

The wash performance of additional BASE variants BASE-X8C (i.e., W11-T131I-T165I), BASE-W10EK (i.e., BASE-N128C-K178L-T182G-S243E-Y305R-D319T-G475K), and ACE-S243Q-G475K (i.e., ACE-QK) was tested in a laundry detergent application using a Terg-o-tometer. The performance evaluation was conducted at 16° C. The soil load consisted of 2 ea. CS-28 Rice Starch (Center for Testmaterials BV, Vlaardingen, Netherlands), 2 ea. AS-10 Pigment Oil Milk (CFT of Holland), 2 ea. EMPA 161 Maize Starch, 2 ea. EMPA 160 Chocolate Cream, and 2 ea. EMPA 163 Porridge (EMPA Testmaterials AG, St. Gallen, Switzerland) swatches per beaker of the Terg-o-tometer, which was filled with 1 L of DI water. The water hardness was adjusted to 6 grains per gallon and heat-inactivated Great Value (Walmart) detergent was used at 1.0 ml/L. The wash time was 15 minutes. After the wash treatment, all swatches were spin-dried followed by air drying.

Each stain was measured before and after treatment by optical reflectance using a Minolta Reflectometer Chroma Meter Model CR-410 (Konica Minolta) set to a D65 (6500°

Figure 6:
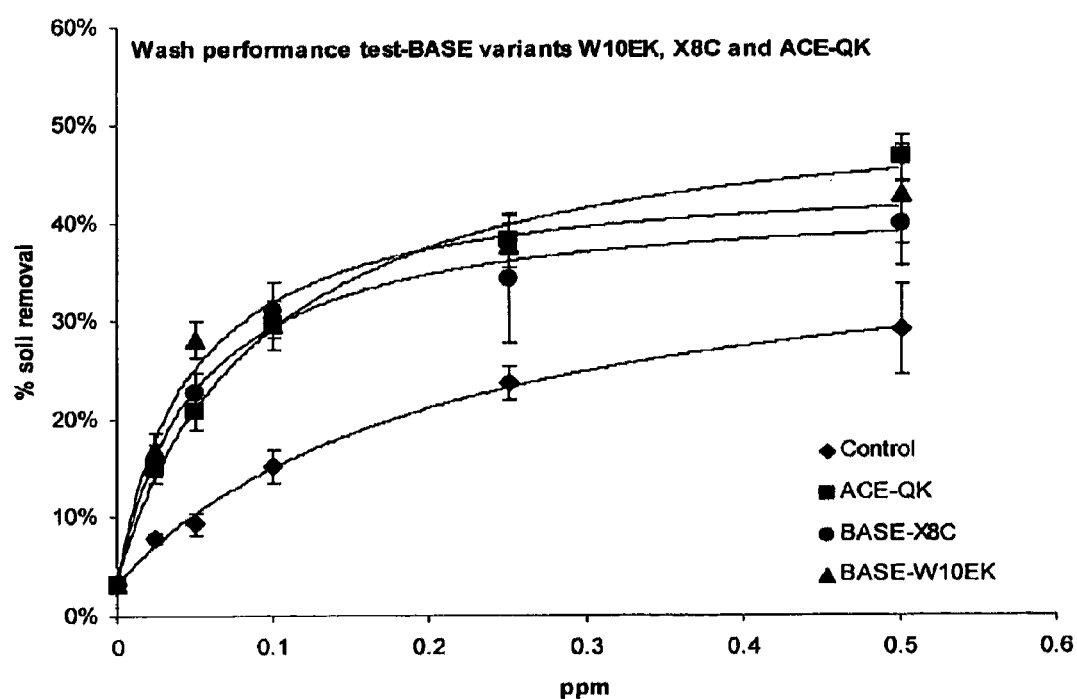
FIG. 6 provides a graph showing the wash performance of multiple alpha-amylases in a laundry detergent application. The enzymes tested were as follows: BASE-X8C, BASE-W10EK, ACE-QK and control (benchmark commercial enzyme).

K) standard illuminant. The difference in the L, a, b values was converted to total color difference (dE), as defined by the CIE-LAB color space. Cleaning of the stains was expressed as stain removal index (SRI) by taking a ratio between the color difference before and after washing. Results for the cleaning of EMPA 160 swatches are shown in FIG. 6. All tested BASE variants showed effective cleaning compared to the control.

Example 16

Laundry Application Synergy Between BASE Variants and Subtilisin Protease

The synergy between BASE and subtilisin protease (*B. amyloliquefaciens* subtilisin BPN'-Y217L; BPN' Swissprot Accession Number P00782) for stain removal was measured on chocolate cream-stained EMPA 160 and porridge-stained EMPA 163 swatches in a full scale laundry application. Stain removal from EMPA 160 and EMPA 163 swatches was tested in buffered 5 mM HEPES (Sigma, H4034) pH 8.0, and heat-inactivated TIDE® 2× coldwater detergent (Proctor & Gamble, Cincinnati, Ohio). Heat inactivation of commercial detergents serves to destroy the activity of enzymatic components while retaining the properties of nonenzymatic components. Heat inactivation was performed by placing pre-weighed liquid detergent (in a glass bottle) in a water bath at 95° C. for 2 hours. The detergent was purchased from local supermarkets. Both unheated and heated detergents were assayed within 5 minutes of dissolving the detergent, to accurately determine the percentage deactivated. Enzyme activity was tested by AAPF and Ceralpha assays.

EMPA swatches were measured before and after treatment by optical reflectance using a Minolta Reflectometer CR-410 set to a D65 (6500° K) standard illuminant. The difference in the L, a, b values was converted to total color difference (dE), as defined by the CIE-LAB color space. Cleaning of the stains was expressed as percent stain removal index (% SRI) by taking a ratio between the color difference before and after washing and comparing it to the difference of unwashed soils (before wash) to unsoiled fabric. Wash treatment was conducted in 44 L in a Kenmore Washing Machine. The washing machine was filled using the 'Cold Auto Temperature' setting and the water hardness was adjusted to 6 gpg using a 15,000 gpg 3:1 Ca:Mg water hardness stock solution. TIDE® coldwater inactivated detergent (43.12 g) was added and the temperature adjusted to 32° C. Subtilisin protease was added to a final concentration of 0.6 ppm and ACE amylase was added to a final concentration of 0.1 ppm. Four swatches were used per wash condition and bleached cotton interlock knit was added as ballast to provide 40 g/L total fabric load. The wash conditions were as follows: normal cycle (15.5 min) with second rinse (3 min), wash/rinse temperature of 89.6° F./32° C., fast agitation, and fast spin. After washing, the swatches were machine dried on low heat and read by optical reflectance as described above.

Figure 7A:
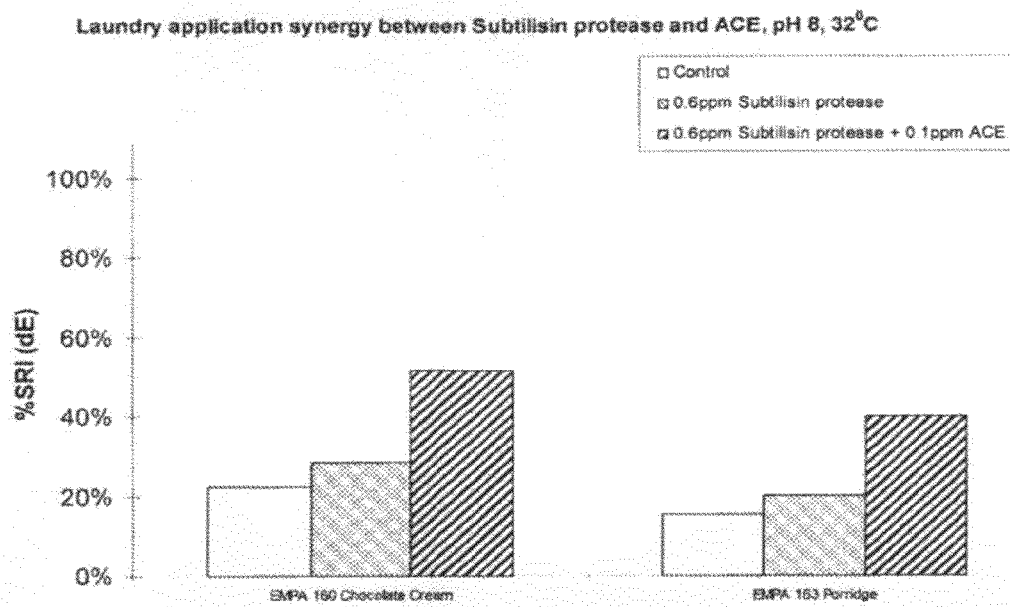
FIG. 7A provides a graph showing the synergy between ACE alpha-amylase and the BPN'Y217L subtilisin protease in laundry applications.
Figure 7B:
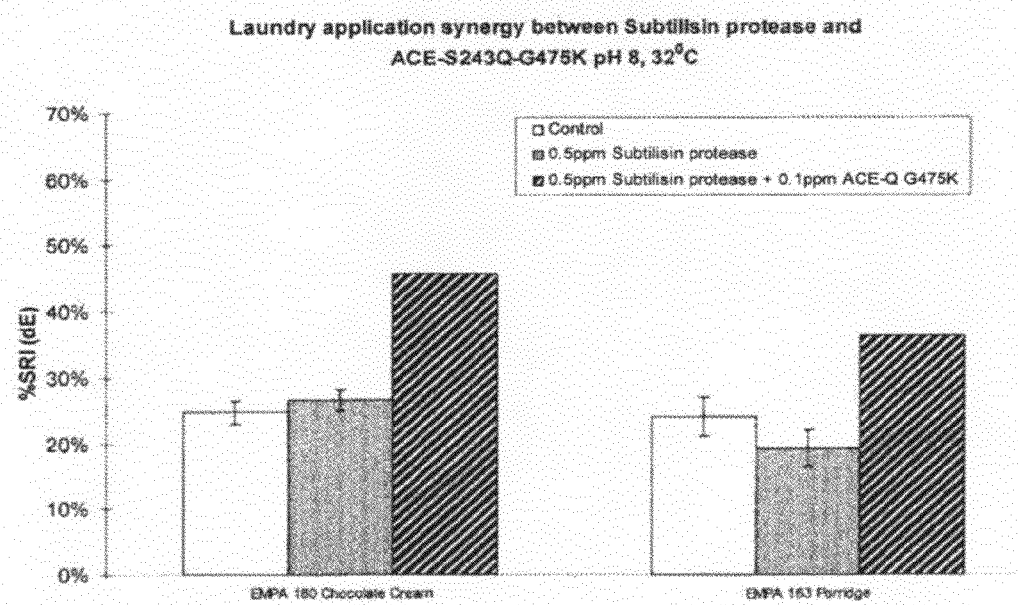
FIG. 7B provides a graph showing the synergy between the ACE-S243Q–G475K (ACE-QK) alpha-amylase and the BPN'Y217L subtilisin protease in a laundry applications.

As shown in FIG. 7A, the ACE alpha-amylase and the BPN'Y217L subtilisin protease produced a synergistic cleaning effect in laundry applications. Similar laundry application synergy tests were done with ACE-S243Q–G475K (ACE-QK) alpha-amylase and subtilisin protease (*B. amyloliquefaciens* subtilisin BPN'-Y217L variant). As shown in FIG. 7B, the ACE-S243Q–G475K (ACE-QK) alpha-amylase and the BPN'Y217L subtilisin protease produced a synergistic cleaning effect in laundry applications, suggesting that BASE variants and proteases can be used in combination for superior cleaning in laundry applications.

Example 17

Dose Effects of BASE Variants and Subtilisin Protease

A dose efficiency curve of selected concentrations of ACE-S243Q and subtilisin protease (*B. amyloliquefaciens* subtilisin BPN'-Y217L; BPN' Swissprot Accession Number P00782) were generated using a Terg-o-tometer. The performance evaluation was conducted at both 20° C. and 40° C. Typically, 2 ea. swatches of CS-28 Rice Starch (Center for Testmaterials BV, Vlaardingen, Netherlands), AS-10 Pigment Oil Milk (CFT of Holland), EMPA 161 Maize Starch, EMPA 160 Chocolate Cream, and EMPA 163 Porridge, (EMPA Testmaterials AG, St. Gallen, Switzerland) were placed in the steel container of the Terg-o-tometer, which was filled with 1 L of DI water and 1.0 g of commercial WISK® (Sun Products, purchased in USA) laundry detergent or 4.5 g OMO™ (Unilever, purchased in Denmark) laundry detergent. Two replicates were run at the same time. Unless otherwise stated, the tests were carried out for 12 minutes and the swatches were rinsed for 3 minutes. After washing, the swatches were air-dried.

Each stain was measured before and after treatment by optical reflectance using a Minolta Reflectometer Chroma Meter Model CR-410 (Konica Minolta) set to a D65 (6500° K) standard illuminant. The difference in the L, a, b values was converted to total color difference (dE), as defined by the CIE-LAB color space. Cleaning of the stains was expressed as stain removal index (SRI) by taking a ratio between the color difference before and after washing.

The results shown in Table 17-1 demonstrate that the combination of the BASE variant and protease produced significant cleaning benefits on several technical cleaning soils. These data demonstrate that a unique cleaning benefit is obtained using BASE variant in combination with a protease.

TABLE 17-1

Cleaning performance of ACE-S243Q with Protease

| ACE-S243Q (ppm) | Protease (ppm) | EMPA161 SRI(dL) | CS-28 SRI(dE) | C-10 POM SRI(dE) | EMPA160 Choco SRI(dE) | EMPA163 Porridge SRI(dE) |
|---|---|---|---|---|---|---|
| 0 | 0 | −0.0317 | 0.2638 | 0.0846 | 0.125 | 0.0584 |
| 0 | 0 | −0.0305 | 0.2634 | 0.1039 | 0.1105 | 0.0734 |
| 0 | 0 | −0.023 | 0.2667 | 0.1297 | 0.1277 | 0.0991 |
| 0 | 0 | −0.0326 | 0.2667 | 0.1112 | 0.1221 | 0.0953 |
| 0 | 0 | −0.0426 | 0.256 | 0.08 | 0.1351 | 0.0569 |
| 0 | 0 | −0.0338 | 0.2652 | 0.0951 | 0.1198 | 0.0572 |
| 0 | 0 | −0.0262 | 0.2674 | 0.1036 | 0.1748 | 0.0982 |
| 0 | 0 | −0.045 | 0.2744 | 0.0871 | 0.1201 | 0.0832 |

TABLE 17-1-continued

Cleaning performance of ACE-S243Q with Protease

| ACE-S243Q (ppm) | Protease (ppm) | EMPA161 SRI(dL) | CS-28 SRI(dE) | C-10 POM SRI(dE) | EMPA160 Choco SRI(dE) | EMPA163 Porridge SRI(dE) |
|---|---|---|---|---|---|---|
| 0.025 | 0.1 | 0.0941 | 0.4659 | 0.125 | 0.3105 | 0.1405 |
| 0.025 | 0.1 | 0.0924 | 0.472 | 0.125 | 0.2764 | 0.1496 |
| 0.025 | 0.1 | 0.0635 | 0.4515 | 0.1599 | 0.2836 | 0.1736 |
| 0.025 | 0.1 | 0.0696 | 0.4502 | 0.1668 | 0.2741 | 0.1915 |
| 0.025 | 0.1 | 0.0892 | 0.4752 | 0.1253 | 0.2989 | 0.1357 |
| 0.025 | 0.1 | 0.0945 | 0.468 | 0.1341 | 0.2571 | 0.1493 |
| 0.025 | 0.1 | 0.0481 | 0.4509 | 0.1216 | 0.1705 | 0.0854 |
| 0.025 | 0.1 | 0.0289 | 0.4503 | 0.1555 | 0.1645 | 0.1027 |
| 0.05 | 0.1 | 0.1269 | 0.5335 | 0.118 | 0.2627 | 0.1658 |
| 0.05 | 0.1 | 0.0679 | 0.5345 | 0.1202 | 0.2838 | 0.1457 |
| 0.05 | 0.1 | 0.0877 | 0.4801 | 0.1326 | 0.1666 | 0.1763 |
| 0.05 | 0.1 | 0.0847 | 0.4912 | 0.1288 | 0.1684 | 0.1426 |
| 0.05 | 0.1 | 0.1287 | 0.4941 | 0.1647 | 0.2747 | 0.1522 |
| 0.05 | 0.1 | 0.1485 | 0.4936 | 0.1752 | 0.2893 | 0.1709 |
| 0.05 | 0.1 | 0.1573 | 0.4516 | 0.1163 | 0.2708 | 0.1692 |
| 0.05 | 0.1 | 0.0691 | 0.4769 | 0.1446 | 0.2478 | 0.2253 |
| 0.1 | 0.1 | 0.1783 | 0.5517 | 0.1142 | 0.2292 | 0.1887 |
| 0.1 | 0.1 | 0.1162 | 0.5434 | 0.0983 | 0.2159 | 0.2012 |
| 0.1 | 0.1 | 0.1727 | 0.5376 | 0.1801 | 0.2397 | 0.2531 |
| 0.1 | 0.1 | 0.1691 | 0.531 | 0.1898 | 0.2349 | 0.2028 |
| 0.1 | 0.1 | 0.1521 | 0.5573 | 0.0993 | 0.2364 | 0.1533 |
| 0.1 | 0.1 | 0.1801 | 0.5637 | 0.1044 | 0.207 | 0.142 |
| 0.1 | 0.1 | 0.1308 | 0.5347 | 0.1027 | 0.2872 | 0.2478 |
| 0.1 | 0.1 | 0.1707 | 0.5418 | 0.1035 | 0.2893 | 0.2757 |
| 0.2 | 0.1 | 0.2517 | 0.5683 | 0.1457 | 0.171 | 0.1027 |
| 0.2 | 0.1 | 0.2308 | 0.5607 | 0.1336 | 0.1701 | 0.1243 |
| 0.2 | 0.1 | 0.1529 | 0.599 | 0.1891 | 0.2939 | 0.2218 |
| 0.2 | 0.1 | 0.1517 | 0.5998 | 0.1825 | 0.3002 | 0.2319 |
| 0.2 | 0.1 | 0.2836 | 0.545 | 0.1719 | 0.2939 | 0.199 |
| 0.2 | 0.1 | 0.2602 | 0.551 | 0.1602 | 0.2824 | 0.2124 |
| 0.2 | 0.1 | 0.2778 | 0.5795 | 0.1427 | 0.2494 | 0.1844 |
| 0.2 | 0.1 | 0.2722 | 0.5759 | 0.117 | 0.2897 | 0.1684 |
| 0.025 | 0.25 | 0.0897 | 0.4656 | 0.1653 | 0.2815 | 0.2177 |
| 0.025 | 0.25 | 0.0884 | 0.4726 | 0.1748 | 0.2942 | 0.1982 |
| 0.025 | 0.25 | 0.0281 | 0.4853 | 0.1637 | 0.3068 | 0.1646 |
| 0.025 | 0.25 | 0.0568 | 0.4647 | 0.1689 | 0.32 | 0.1591 |
| 0.025 | 0.25 | 0.0261 | 0.4335 | 0.1734 | 0.2168 | 0.1189 |
| 0.025 | 0.25 | 0.0225 | 0.4272 | 0.1437 | 0.255 | 0.1714 |
| 0.025 | 0.25 | 0.0537 | 0.4875 | 0.1489 | 0.2697 | 0.21 |
| 0.025 | 0.25 | 0.0559 | 0.4747 | 0.1466 | 0.2958 | 0.2055 |
| 0.05 | 0.25 | 0.0762 | 0.4241 | 0.1381 | 0.2479 | 0.236 |
| 0.05 | 0.25 | 0.0794 | 0.4164 | 0.1418 | 0.2423 | 0.162 |
| 0.05 | 0.25 | 0.1164 | 0.4943 | 0.2099 | 0.327 | 0.2089 |
| 0.05 | 0.25 | 0.1471 | 0.4842 | 0.1907 | 0.3064 | 0.2044 |
| 0.05 | 0.25 | 0.0312 | 0.4733 | 0.1543 | 0.2584 | 0.185 |
| 0.05 | 0.25 | 0.0557 | 0.4611 | 0.1556 | 0.2958 | 0.2273 |
| 0.05 | 0.25 | 0.0906 | 0.4782 | 0.1635 | 0.2914 | 0.1589 |
| 0.05 | 0.25 | 0.0697 | 0.4747 | 0.1693 | 0.2698 | 0.2226 |
| 0.1 | 0.25 | 0.255 | 0.4986 | 0.1794 | 0.2805 | 0.2547 |
| 0.1 | 0.25 | 0.2447 | 0.5058 | 0.1858 | 0.31 | 0.2679 |
| 0.1 | 0.25 | 0.153 | 0.5276 | 0.163 | 0.2489 | 0.2432 |
| 0.1 | 0.25 | 0.1541 | 0.5416 | 0.1647 | 0.2585 | 0.2319 |
| 0.1 | 0.25 | 0.1735 | 0.5578 | 0.1359 | 0.2877 | 0.144 |
| 0.1 | 0.25 | 0.1567 | 0.5608 | 0.1353 | 0.3235 | 0.1351 |
| 0.1 | 0.25 | 0.0987 | 0.561 | 0.1419 | 0.2798 | 0.2194 |
| 0.1 | 0.25 | 0.1201 | 0.5542 | 0.1334 | 0.2491 | 0.1942 |
| 0.2 | 0.25 | 0.2803 | 0.5574 | 0.1839 | 0.2461 | 0.2486 |
| 0.2 | 0.25 | 0.2197 | 0.577 | 0.1748 | 0.2125 | 0.2301 |
| 0.2 | 0.25 | 0.214 | 0.5644 | 0.1732 | 0.3019 | 0.1514 |
| 0.2 | 0.25 | 0.1824 | 0.5827 | 0.1926 | 0.2925 | 0.1492 |
| 0.2 | 0.25 | 0.2513 | 0.5869 | 0.1629 | 0.3038 | 0.2395 |
| 0.2 | 0.25 | 0.2354 | 0.5877 | 0.1467 | 0.2961 | 0.2396 |
| 0.2 | 0.25 | 0.2589 | 0.5823 | 0.151 | 0.3097 | 0.2109 |
| 0.2 | 0.25 | 0.2176 | 0.5652 | 0.1526 | 0.3123 | 0.1749 |
| 0.025 | 0.5 | 0.0754 | 0.4867 | 0.1756 | 0.261 | 0.1599 |
| 0.025 | 0.5 | 0.0645 | 0.4902 | 0.2003 | 0.2744 | 0.1638 |
| 0.025 | 0.5 | 0.0578 | 0.4306 | 0.2164 | 0.2246 | 0.1775 |
| 0.025 | 0.5 | 0.0629 | 0.4232 | 0.2266 | 0.2339 | 0.1971 |
| 0.025 | 0.5 | 0.0261 | 0.3563 | 0.1708 | 0.2715 | 0.1783 |
| 0.025 | 0.5 | 0.0433 | 0.3837 | 0.1746 | 0.3044 | 0.171 |
| 0.025 | 0.5 | 0.084 | 0.4094 | 0.1793 | 0.3157 | 0.1723 |
| 0.025 | 0.5 | 0.1339 | 0.4221 | 0.1921 | 0.3159 | 0.1576 |
| 0.05 | 0.5 | 0.1018 | 0.4777 | 0.178 | 0.313 | 0.2437 |
| 0.05 | 0.5 | 0.1068 | 0.4955 | 0.171 | 0.2915 | 0.2507 |

TABLE 17-1-continued

Cleaning performance of ACE-S243Q with Protease

| ACE-S243Q (ppm) | Protease (ppm) | EMPA161 SRI(dL) | CS-28 SRI(dE) | C-10 POM SRI(dE) | EMPA160 Choco SRI(dE) | EMPA163 Porridge SRI(dE) |
|---|---|---|---|---|---|---|
| 0.05 | 0.5 | 0.1313 | 0.4776 | 0.2014 | 0.2261 | 0.1646 |
| 0.05 | 0.5 | 0.1468 | 0.4737 | 0.2122 | 0.2926 | 0.186 |
| 0.05 | 0.5 | 0.0959 | 0.4573 | 0.2034 | 0.2519 | 0.2163 |
| 0.05 | 0.5 | 0.1652 | 0.4721 | 0.1935 | 0.2562 | 0.1837 |
| 0.05 | 0.5 | 0.0732 | 0.4849 | 0.1834 | 0.3303 | 0.1187 |
| 0.05 | 0.5 | 0.0845 | 0.4961 | 0.2198 | 0.3601 | 0.1213 |
| 0.1 | 0.5 | 0.1838 | 0.5488 | 0.2121 | 0.2669 | 0.2804 |
| 0.1 | 0.5 | 0.1763 | 0.5582 | 0.1892 | 0.2824 | 0.2767 |
| 0.1 | 0.5 | 0.2292 | 0.5212 | 0.2358 | 0.2773 | 0.2334 |
| 0.1 | 0.5 | 0.2217 | 0.5137 | 0.2441 | 0.2902 | 0.1984 |
| 0.1 | 0.5 | 0.2083 | 0.5468 | 0.1476 | 0.2162 | 0.0908 |
| 0.1 | 0.5 | 0.2082 | 0.5448 | 0.1403 | 0.2113 | 0.0992 |
| 0.1 | 0.5 | 0.2037 | 0.5514 | 0.2085 | 0.1865 | 0.1317 |
| 0.1 | 0.5 | 0.14 | 0.527 | 0.2297 | 0.2348 | 0.1383 |
| 0.2 | 0.5 | 0.2851 | 0.5694 | 0.1949 | 0.2853 | 0.2283 |
| 0.2 | 0.5 | 0.316 | 0.5664 | 0.1852 | 0.2861 | 0.2113 |
| 0.2 | 0.5 | 0.2059 | 0.597 | 0.2343 | 0.3013 | 0.2598 |
| 0.2 | 0.5 | 0.2227 | 0.5838 | 0.237 | 0.3184 | 0.2889 |
| 0.2 | 0.5 | 0.3379 | 0.5854 | 0.1716 | 0.2117 | 0.2698 |
| 0.2 | 0.5 | 0.3356 | 0.588 | 0.1762 | 0.2159 | 0.2599 |
| 0.2 | 0.5 | 0.2862 | 0.5867 | 0.2147 | 0.2314 | 0.1106 |
| 0.2 | 0.5 | 0.2693 | 0.5893 | 0.1964 | 0.2658 | 0.1203 |
| 0.025 | 1 | 0.0873 | 0.4258 | 0.1974 | 0.3064 | 0.1162 |
| 0.025 | 1 | 0.0751 | 0.4501 | 0.1789 | 0.2839 | 0.1214 |
| 0.025 | 1 | 0.0882 | 0.4631 | 0.2165 | 0.3237 | 0.2614 |
| 0.025 | 1 | 0.0819 | 0.4879 | 0.2068 | 0.34 | 0.2637 |
| 0.025 | 1 | 0.123 | 0.4284 | 0.2148 | 0.2782 | 0.1592 |
| 0.025 | 1 | 0.0524 | 0.4391 | 0.2232 | 0.2916 | 0.2253 |
| 0.025 | 1 | 0.021 | 0.4215 | 0.2235 | 0.2801 | 0.1232 |
| 0.025 | 1 | 0.0376 | 0.4478 | 0.2031 | 0.2564 | 0.1307 |
| 0.05 | 1 | 0.1742 | 0.5086 | 0.1707 | 0.2801 | 0.1726 |
| 0.05 | 1 | 0.1647 | 0.5138 | 0.1614 | 0.2746 | 0.1651 |
| 0.05 | 1 | 0.1588 | 0.529 | 0.3072 | 0.2718 | 0.2403 |
| 0.05 | 1 | 0.1597 | 0.5241 | 0.261 | 0.2598 | 0.2451 |
| 0.05 | 1 | 0.1846 | 0.4865 | 0.2127 | 0.2889 | 0.1236 |
| 0.05 | 1 | 0.1018 | 0.4942 | 0.2157 | 0.3268 | 0.1537 |
| 0.05 | 1 | 0.1215 | 0.4998 | 0.1923 | 0.2883 | 0.2071 |
| 0.05 | 1 | 0.101 | 0.4956 | 0.1961 | 0.3312 | 0.1918 |
| 0.1 | 1 | 0.1312 | 0.5636 | 0.2155 | 0.3115 | 0.2694 |
| 0.1 | 1 | 0.1378 | 0.542 | 0.2202 | 0.3166 | 0.2764 |
| 0.1 | 1 | 0.1452 | 0.533 | 0.2445 | 0.3908 | 0.1793 |
| 0.1 | 1 | 0.1184 | 0.5202 | 0.2501 | 0.3644 | 0.1741 |
| 0.1 | 1 | 0.1635 | 0.5755 | 0.2163 | 0.3158 | 0.1417 |
| 0.1 | 1 | 0.2388 | 0.5909 | 0.2233 | 0.351 | 0.1628 |
| 0.1 | 1 | 0.1531 | 0.5478 | 0.2591 | 0.2813 | 0.2639 |
| 0.1 | 1 | 0.1577 | 0.5626 | 0.2561 | 0.2801 | 0.2355 |
| 0.2 | 1 | 0.2264 | 0.5704 | 0.2121 | 0.2499 | 0.1882 |
| 0.2 | 1 | 0.2565 | 0.5849 | 0.2178 | 0.2291 | 0.172 |
| 0.2 | 1 | 0.3134 | 0.5953 | 0.2341 | 0.3278 | 0.2834 |
| 0.2 | 1 | 0.2699 | 0.6076 | 0.2487 | 0.3373 | 0.3069 |
| 0.2 | 1 | 0.2516 | 0.5654 | 0.2298 | 0.2916 | 0.3055 |
| 0.2 | 1 | 0.2486 | 0.5815 | 0.2341 | 0.2906 | 0.2825 |
| 0.2 | 1 | 0.2545 | 0.5617 | 0.2738 | 0.2637 | 0.1517 |
| 0.2 | 1 | 0.3077 | 0.5693 | 0.2667 | 0.2681 | 0.1791 |

Figure 8:
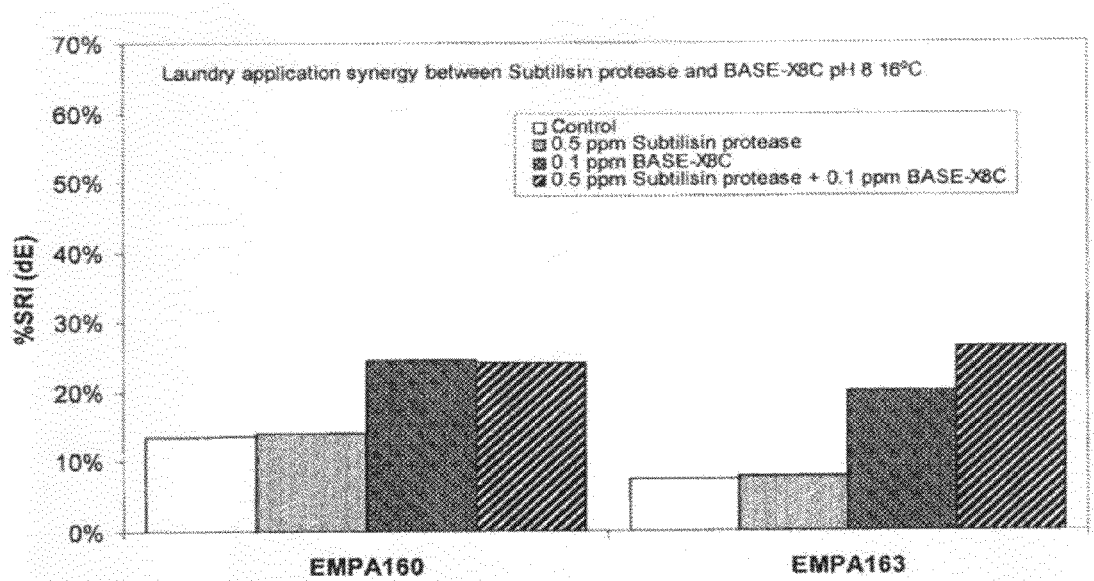
FIG. 8 provides a graph showing the synergy between BASE-X8C (W11-T131I–T165I) alpha-amylase and the BPN'Y217L subtilisin protease in laundry applications.
Figure 9:
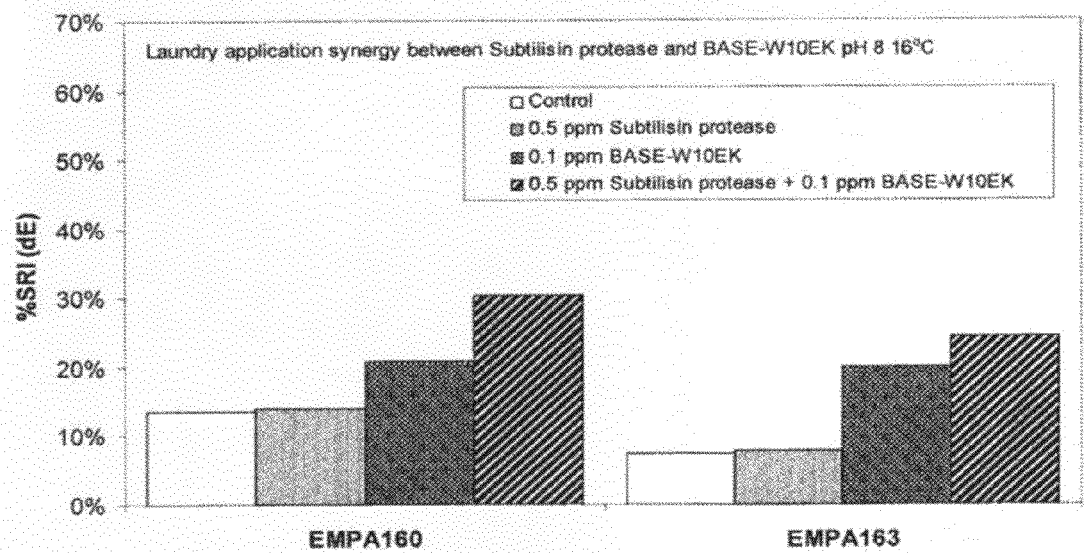
FIG. 9 provides a graph showing the synergy between BASE W 10EK (BASE-N128C–K178L–T182G–S243E–Y305R–D319T–G475K) alpha-amylase and the BPN'Y217L subtilisin protease in laundry applications.
Figure 10:
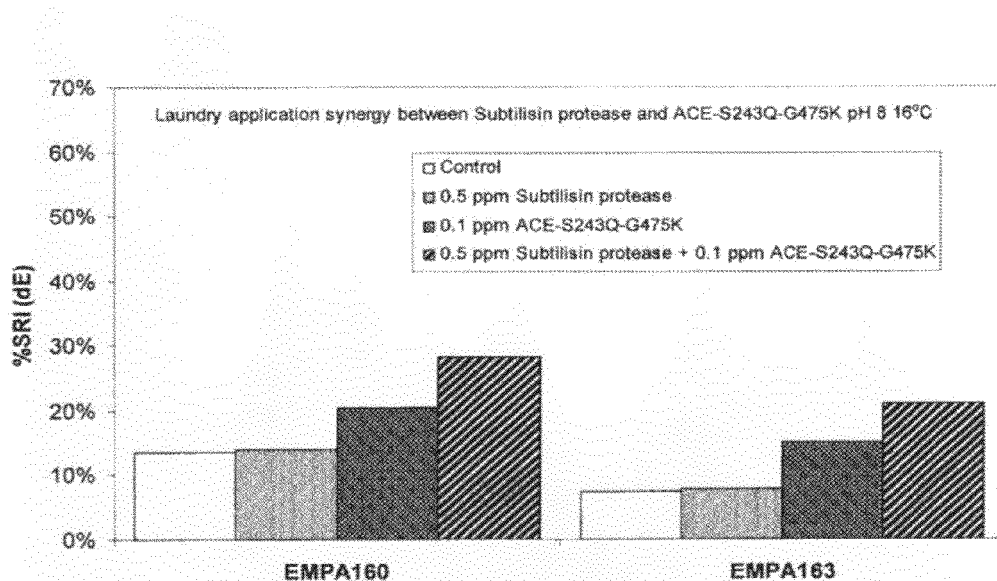
FIG. 10 provides a graph showing the synergy between ACE-S243Q-G475K (ACE-QK) alpha-amylase and the BPN'Y217L subtilisin protease in laundry applications.

The laundry application synergies between additional BASE variants [i.e., BASE-X8C (i.e., W11-T131I-T165I), BASE W10EK (i.e., BASE-N128C-K178L-T182G-S243E-Y305R-D319T-G475K), and ACE-S243Q-G475K (i.e., ACE-QK) in combination with the BPN'Y217L subtilisin protease were further tested on EMPA 160 and EMPA 163 swatches as described above. The results are shown in FIG. 8 (BASE-X8C), FIG. 9 (BASE W10EK), and FIG. 10 (ACE-QK). These data demonstrate that a unique cleaning benefit is obtained using BASE variants in combination with a protease.

All patents and publications mentioned in the specification are indicative of the levels of those skilled in the art to which the disclosure pertains. Those of skill in the art readily appreciate that the present disclosure is well adapted to carry out the objects and obtain the ends and advantages mentioned, as well as those inherent therein. The compositions and methods described herein are representative of preferred embodiments, are exemplary, and are not intended as limitations on the scope of the disclosure. It is readily apparent to one skilled in the art that varying substitutions and modifications may be made to the disclosure disclosed herein without departing from the scope and spirit of the disclosure.

The disclosure illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by herein.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not excised material is specifically recited herein.

What is claimed is:

1. An isolated alpha-amylase variant, wherein said variant is a mature form of alpha-amylase having amylase activity, and comprising a substitution at one or more positions selected from the group consisting of 1, 2, 3, 4, 5, 7, 15, 16, 17, 18, 19, 22, 25, 26, 28, 29, 30, 32, 35, 36, 37, 50, 51, 52, 53, 54, 55, 56, 59, 60, 70, 71, 72, 73, 75, 78, 83, 87, 90, 91, 93, 94, 95, 104, 105, 107, 108, 110, 112, 113, 116, 118, 125, 126, 128, 129, 130, 131, 134, 136, 138, 142, 144, 147, 149, 150, 152, 154, 156, 158, 160, 161, 162, 165, 166, 168, 169, 170, 172, 174, 177, 178, 182, 183, 185, 189, 192, 195, 197, 201, 202, 203, 207, 210, 214, 217, 221, 228, 234, 236, 237, 246, 250, 254, 255, 257, 264, 267, 269, 270, 272, 275, 279, 283, 284, 298, 301, 303, 305, 306, 310, 311, 314, 318, 319, 320, 322, 323, 336, 337, 338, 339, 340, 344, 359, 374, 375, 376, 377, 379, 381, 382, 393, 394, 399, 401, 407, 408, 419, 433, 436, 438, 444, 447, 448, 451, 453, 459, 465, 470, 475, 476, 483, and 484;

wherein the positions correspond to amino acid residues in the amino acid sequence set forth in SEQ ID NO: 2;

wherein the variant has at least 90% amino acid sequence identity to SEQ ID NO: 2, and wherein the substitution of the naturally-occurring amino acid residue at the one or more positions for a different amino acid residue produces an alpha-amylase variant having a performance index >1.0 for a measure of stability, and a performance index >1.0 for a measure of activity.

2. The isolated alpha-amylase variant of claim 1, comprising a substitution at one or more positions selected from the group consisting of 7, 29, 35, 53, 60, 72, 87, 108, 116, 126, 128, 129, 130, 131, 134, 136, 138, 142, 156, 161, 165, 178, 182, 185, 189, 192, 195, 197, 202, 210, 214, 217, 221, 234, 246, 269, 303, 310, 337, 340, 374, 401, and 438, and wherein the substitution of the naturally-occurring amino acid residue for a different amino acid residue, produces an alpha-amylase variant having a performance index >1.5 for a measure of activity and a performance index >1.0 for a measure of stability.

3. The isolated alpha-amylase variant of claim 1, comprising a substitution at one or more positions selected from the group consisting of 2, 7, 22, 25, 28, 30, 37, 70, 75, 83, 87, 91, 93, 108, 128, 160, 165, 178, 182, 183, 217, 269, 270, 279, 283, 298, 305, 306, 310, 320, 374, 375, 376, 407, 419, 475, and 476, wherein the substitution of the naturally-occurring amino acid residue for a different amino acid residue, produces an alpha-amylase variant having a performance index >1.5 for a measure of stability and a performance index >1.0 for a measure of activity.

4. The isolated alpha-amylase variant of claim 1, comprising a substitution at one or more positions selected from the group consisting of 83, 125, 128, 131, 160, 178, 182, 183, 185, 189, 279, 305, 319, 320, 379, 407, 433, 453, 475, 476, and 483.

5. The isolated alpha-amylase variant of claim 1, wherein the different amino acid residue is selected from the group consisting of A, C, D, E, F, G, H, I, K, L, M, N, P, Q, R, S, T, V, W, and Y, with the proviso that the different amino acid residue is different from the naturally-occurring amino acid residue.

6. The isolated alpha-amylase variant of claim 1, further comprising a substitution at position 243 corresponding to the amino acid sequence set forth in SEQ ID NO: 2.

7. The isolated alpha-amylase variant of claim 1, further comprising a deletion at position 180 and/or position 181, corresponding to the amino acid sequence set forth in SEQ ID NO: 2.

8. The alpha-amylase variant of claim 1, wherein the alpha-amylase variant is derived from a parent alpha-amylase having an amino acid sequence that is at least 75% identical to an amino acid sequence selected from the group consisting of SEQ ID NO: 2, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

9. The isolated alpha-amylase variant of claim 1, wherein the alpha-amylase variant has at least 75% sequence identity with the amino acid sequence set forth in SEQ ID NO: 2.

10. The isolated alpha-amylase variant of claim 1, wherein the alpha-amylase variant has at least 80% sequence identity with the amino acid sequence set forth in SEQ ID NO: 2.

11. The alpha-amylase variant of claim 1, wherein the variant comprises a substitution at one or more positions selected from the group consisting of 128, 178, 182, 185, and 189 corresponding to the amino acid sequence set forth in SEQ ID: 2, wherein the substitution provides improved cleaning performance or improved detergent stability.

12. The alpha-amylase variant of claim 1, wherein the alpha-amylase variant comprises:
(a) an alanine at position 125,
    a cysteine at position 128,
    an isoleucine at position 131,
    an isoleucine at position 165,
    a leucine at position 178,
    a glycine at position 182,
    a tyrosine at position 202,
    an arginine at position 305,
    a threonine at position 319, or
    an arginine at position 475;
(b) the substitutions N128C+K178L+T182G+Y305R+G475K, and
    at least one additional substitution selected from the group consisting of S125A, T131I, T165I, F202Y, and D319T; or
(c) the substitutions
    N128C+K178L+T182G+F202Y+Y305R+D319T+G475K,
    S125A+N128C+K178L+T182G+Y305R+G475K, or
    S125A+N128C+T131I+T165I+K178L+T182G+Y305R+G475K;
wherein the variant optionally further comprises a substitution at position 243 and/or a deletion at position 180 and/or position 181; and
wherein the positions correspond to the amino acid sequence set forth in SEQ ID NO: 2.

13. The alpha-amylase variant of claim 1, wherein said alpha-amylase variant comprises a substitution at position 475.

14. The alpha-amylase variant of claim 13, wherein said alpha-amylase variant comprises an arginine at position 475.

15. The alpha-amylase variant of claim 13, further comprising a substitution at position 243 and/or a deletion at position 180 and/or position 181.

16. The alpha-amylase variant of claim 1, wherein said substitution at one or more positions is a substitution at 1, 2, 3, 4, 5, 6, 7, 8, 9, or 10 positions.

17. The alpha-amylase variant of claim 1, wherein the alpha-amylase variant is derived from a parent alpha-amylase selected from the group consisting of BASE, ACE, ACE-Q, and ACE-QK.

18. A cleaning composition comprising the alpha-amylase variant of claim 1.

19. The cleaning composition of claim 18, further comprising at least one additional enzyme selected from the group consisting of a protease, a lipase, a cutinase, a carbohydrase, a cellulase, a pectinase, a mannanase, an arabinase, a galactanase, a xylanase, an oxidase, a perhydrolase, a pectate lyase, and a peroxidase.

20. The cleaning composition of claim 19, wherein the at least one additional enzyme is a protease.

21. The cleaning composition of claim 20, wherein the at least one additional enzyme is a subtilisin.

22. The cleaning composition of claim 21, wherein the at least one additional enzyme is subtilisin BPN' or a variant, thereof.

23. The cleaning composition of claim 22, wherein the at least one additional enzyme is subtilisin BPN'Y217L or a variant, thereof.

* * * * *

SEQUENCE LISTING

```
<160> NUMBER OF SEQ ID NOS: 70

<210> SEQ ID NO 1
<211> LENGTH: 583
<212> TYPE: PRT
<213> ORGANISM: Bacillus sp.

<400> SEQUENCE: 1

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
                100                 105                 110

Gly Thr Glu Phe Val Asp Ala Val Glu Val Asp Pro Ser Asn Arg Asn
            115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
```

```
                290                 295                 300
Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
                340                 345                 350

Ala Phe Ile Leu Thr Arg Gln Glu Gly Tyr Pro Cys Val Phe Tyr Gly
                355                 360                 365

Asp Tyr Tyr Gly Ile Pro Lys Tyr Asn Ile Pro Gly Leu Lys Ser Lys
                370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
                435                 440                 445

Val Phe Tyr Asp Leu Thr Gly Asn Arg Ser Asp Thr Val Thr Ile Asn
                450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
                485                 490                 495

Thr Thr Ser Gly Gln Asn Val Tyr Val Val Ala Asn Ile Pro Glu Leu
                500                 505                 510

Gly Asn Trp Asn Thr Ala Asn Ala Ile Lys Met Asn Pro Ser Ser Tyr
                515                 520                 525

Pro Thr Trp Lys Ala Thr Ile Ala Leu Pro Gln Gly Lys Ala Ile Glu
                530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
                565                 570                 575

Thr Ala Ser Trp Asn Val Pro
                580

<210> SEQ ID NO 2
<211> LENGTH: 484
<212> TYPE: PRT
<213> ORGANISM: Bacillus sp.

<400> SEQUENCE: 2

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
        50                  55                  60

Asp Leu Gly Glu Phe Asn Gln Lys Gly Thr Ile Arg Thr Lys Tyr Gly
65                  70                  75                  80
```

```
Thr Lys Thr Gln Tyr Ile Gln Ala Ile Gln Ala Ala Lys Ala Ala Gly
                85                  90                  95
Met Gln Val Tyr Ala Asp Val Val Phe Asn His Lys Ala Gly Ala Asp
            100                 105                 110
Gly Thr Glu Phe Val Asp Ala Val Glu Val Asp Pro Ser Asn Arg Asn
        115                 120                 125
Gln Glu Thr Ser Gly Thr Tyr Gln Ile Gln Ala Trp Thr Lys Phe Asp
    130                 135                 140
Phe Pro Gly Arg Gly Asn Thr Tyr Ser Ser Phe Lys Trp Arg Trp Tyr
145                 150                 155                 160
His Phe Asp Gly Thr Asp Trp Asp Glu Ser Arg Lys Leu Asn Arg Ile
                165                 170                 175
Tyr Lys Phe Arg Ser Thr Gly Lys Ala Trp Asp Trp Glu Val Asp Thr
            180                 185                 190
Glu Asn Gly Asn Tyr Asp Tyr Leu Met Phe Ala Asp Leu Asp Met Asp
        195                 200                 205
His Pro Glu Val Val Thr Glu Leu Lys Asn Trp Gly Thr Trp Tyr Val
    210                 215                 220
Asn Thr Thr Asn Ile Asp Gly Phe Arg Leu Asp Ala Val Lys His Ile
225                 230                 235                 240
Lys Tyr Ser Phe Phe Pro Asp Trp Leu Thr Tyr Val Arg Asn Gln Thr
                245                 250                 255
Gly Lys Asn Leu Phe Ala Val Gly Glu Phe Trp Ser Tyr Asp Val Asn
            260                 265                 270
Lys Leu His Asn Tyr Ile Thr Lys Thr Asn Gly Ser Met Ser Leu Phe
        275                 280                 285
Asp Ala Pro Leu His Asn Asn Phe Tyr Thr Ala Ser Lys Ser Ser Gly
    290                 295                 300
Tyr Phe Asp Met Arg Tyr Leu Leu Asn Asn Thr Leu Met Lys Asp Gln
305                 310                 315                 320
Pro Ser Leu Ala Val Thr Leu Val Asp Asn His Asp Thr Gln Pro Gly
                325                 330                 335
Gln Ser Leu Gln Ser Trp Val Glu Pro Trp Phe Lys Pro Leu Ala Tyr
            340                 345                 350
Ala Phe Ile Leu Thr Arg Gln Glu Gly Tyr Pro Cys Val Phe Tyr Gly
        355                 360                 365
Asp Tyr Tyr Gly Ile Pro Lys Tyr Asn Ile Pro Gly Leu Lys Ser Lys
    370                 375                 380
Ile Asp Pro Leu Leu Ile Ala Arg Arg Asp Tyr Ala Tyr Gly Thr Gln
385                 390                 395                 400
Arg Asp Tyr Ile Asp His Gln Asp Ile Ile Gly Trp Thr Arg Glu Gly
                405                 410                 415
Ile Asp Thr Lys Pro Asn Ser Gly Leu Ala Ala Leu Ile Thr Asp Gly
            420                 425                 430
Pro Gly Gly Ser Lys Trp Met Tyr Val Gly Lys Lys His Ala Gly Lys
        435                 440                 445
Val Phe Tyr Asp Leu Thr Gly Asn Arg Ser Asp Thr Val Thr Ile Asn
    450                 455                 460
Ala Asp Gly Trp Gly Glu Phe Lys Val Asn Gly Gly Ser Val Ser Ile
465                 470                 475                 480

Trp Val Ala Lys

<210> SEQ ID NO 3
```

<211> LENGTH: 1752
<212> TYPE: DNA
<213> ORGANISM: Artificial Sequence
<220> FEATURE:
<223> OTHER INFORMATION: Synthetic DNA: codon-modified nucleic acid sequence encoding the mature form of AmyTS23

<400> SEQUENCE: 3

| | | |
|---|---|---|
| aatacggcgc cgatcaacga aacgatgatg cagtattttg aatgggatct gccgaatgat | 60 | |
| ggaacgctgt ggacgaaagt caaaaacgaa gcggcgaatc ttagcagcct gggaatcaca | 120 | |
| gcactttggc ttccgccggc atataaagga acgagccaaa gcgatgtcgg ctatggcgtc | 180 | |
| tatgatctgt atgacctggg cgaatttaac caaaaaggca cgatccggac gaaatatggc | 240 | |
| acgaaaacac agtatatcca agcgatccag gcagcaaaag cagcaggcat gcaagtctat | 300 | |
| gccgacgtcg tctttaatca taaagcggga cggatggca cagaatttgt cgatgccgtc | 360 | |
| gaagttgatc cgagcaacag aaaccaagaa acgagcggca cgtatcaaat ccaagcgtgg | 420 | |
| acgaaatttg attttccggg cagaggcaat acgtatagca gctttaaatg gcgctggtat | 480 | |
| cattttgacg gcacggattg ggatgaaagc agaaaactga accggatcta taaatttcgg | 540 | |
| agcacgggca agcatggga ttgggaagtc gatacggaaa acggcaacta tgactatctg | 600 | |
| atgtttgccg atctggatat ggatcatccg aagtcgtca cggaactgaa aaattggggc | 660 | |
| acgtggtatg ttaatacgac gaacatcgat ggctttagac tggatgccgt caaacatatc | 720 | |
| aaatatagct tttttccgga ctggctgacg tatgtcagaa accagacggg caaaaacctt | 780 | |
| tttgccgtcg cgaattttg gagctatgac gtcaacaaac ttcataacta tatcacgaaa | 840 | |
| acgaacggca gcatgagcct tttttgatgcc ccgcttcata caactttta tcggcgagc | 900 | |
| aaaagctcag gctattttga tatgagatat ctgctgaaca cacgctgat gaaagatcaa | 960 | |
| ccgagcctgg cagtcacact ggtcgataac catgatacac aaccgggcca agccttcaa | 1020 | |
| agctgggtcg aaccgtggtt taaaccgctg gcgtatgcct ttatcctgac gagacaagaa | 1080 | |
| gggtatcctt gcgtcttta tggcgactat tatggcatcc gaaatataa tatcccgggc | 1140 | |
| ctgaaaagca aaatcgatcc gctgctgatc gccagacggg attatgccta tggcacacag | 1200 | |
| cgggattata tcgaccatca ggacatcatc ggctggacaa gagaaggcat cgatacgaaa | 1260 | |
| ccgaatagcg gactggcagc actgattaca gatggaccgg gcggaagcaa atggatgtat | 1320 | |
| gtcggcaaaa aacatgccgg caaagtcttt tatgatctga cgggcaacag aagcgatacg | 1380 | |
| gtcacgatca atgctgatgg ctggggagaa tttaaagtca atggcggcag cgtttcaatc | 1440 | |
| tgggtcgcca aaacgagcaa tgtcacgttt acggtcaaca atgccacgac aacgagcggc | 1500 | |
| caaaatgtct atgtcgtcgc caatatcccg gaactgggca attggaatac ggcgaacgca | 1560 | |
| atcaaaatga acccgagcag ctatccgaca tggaaagcga caatcgctct gccgcaagga | 1620 | |
| aaagcgatcg aatttaaatt tatcaaaaaa gaccaggcgg gcaatgttat ttgggaaagc | 1680 | |
| acgagcaata aacgtatac ggtcccgttt agcagcacag aagctatac agcgagctgg | 1740 | |
| aatgttccgt ga | 1752 | |

<210> SEQ ID NO 4
<211> LENGTH: 1479
<212> TYPE: DNA
<213> ORGANISM: Artificial Sequence
<220> FEATURE:
<223> OTHER INFORMATION: Synthetic DNA - codon-modified nucleic acid sequence produced by GENEART, encoding the mature form of BASE (AmyTS23t)

<400> SEQUENCE: 4

```
tctgcagctt cagcaaacac cgcgccgatt aacgaaacca tgatgcagta tttcgaatgg    60
gatctgccga acgatggcac cctgtggacc aaagtgaaaa acgaagcggc gaacctgagc   120
agcctgggca ttaccgcgct gtggctgccg ccggcatata aaggcaccag ccagagcgat   180
gtgggctatg gcgtgtatga tctgtacgat ctgggcgaat ttaaccagaa aggcaccatt   240
cgtaccaaat atggcaccaa aacccagtat attcaggcga tccaggcggc gaaagcggcg   300
ggtatgcagg tgtatgcgga tgtggtgttt aaccataaag cgggtgcgga tggcaccgaa   360
tttgtggatg cggtggaagt ggatccgagc aaccgtaacc aggaaaccag cggcaccctat   420
cagattcagg cgtggaccaa atttgatttt cccggccgtg caacaccta tagcagcttt   480
aaatggcgct ggtatcattt tgatggcacc gattgggatg aaagccgtaa actgaaccgc   540
atctataaat ttcgtagcac cggcaaagcg tgggattggg aagtggatac cgaaaacggc   600
aactatgatt acctgatgtt cgcagacctg gatatggatc atccggaagt ggtgaccgaa   660
ctgaaaaact ggggcaccctg gtatgtgaac accaccaaca ttgatggctt tcgtctggat   720
gcggtgaaac acatcaaata cagcttttt ccggattggc tgacctatgt gcgtaaccag   780
accggcaaaa acctgtttgc ggtgggcgaa ttttggagct atgatgtgaa caaactgcac   840
aactacatca ccaaaaccaa cggcagcatg agcctgtttg atgcgccgct gcataacaac   900
ttttataccg cgagcaaaag cagcggctat tttgatatgc gttatctgct gaacaacacc   960
ctgatgaaag atcagccgag cctggccgtg accctggtgg ataaccatga tacccagccg  1020
ggccagagcc tgcaaagctg ggtggaaccg tggtttaaac cgctggccta cgcgtttatt  1080
ctgacccgtc aagagggcta tccgtgcgtt ttttatggcg attattacgg catcccgaaa  1140
tataacattc cgggcctgaa aagcaaaatt gatccgctgc tgattgcgcg tcgtgattat  1200
gcgtatggca cccagcgtga ttatattgat caccaggata ttattggctg gacccgtgaa  1260
ggcattgata ccaaaccgaa cagcggcctg ccgcgctga ttaccgatgg cccgggtggc  1320
agcaaatgga tgtatgtggg caaaaaacat gcgggcaaag tgttttatga tctgaccggc  1380
aaccgtagcg ataccgtgac cattaacgcg atggctggg gtgagtttaa agtgaacggc  1440
ggcagcgtga gcatttgggt ggcgaaataa gttaacaga                         1479
```

<210> SEQ ID NO 5
<211> LENGTH: 483
<212> TYPE: PRT
<213> ORGANISM: B. licheniformis

<400> SEQUENCE: 5

```
Ala Asn Leu Asn Gly Thr Leu Met Gln Tyr Phe Glu Trp Tyr Met Pro
 1               5                  10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
```

```
            100                 105                 110
Glu Asp Val Thr Ala Val Glu Val Asp Pro Ala Asp Arg Asn Arg Val
            115                 120                 125

Ile Ser Gly Glu His Leu Ile Lys Ala Trp Thr His Phe His Phe Pro
            130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
                195                 200                 205

Ala Ala Glu Ile Lys Arg Trp Gly Thr Trp Tyr Ala Asn Glu Leu Gln
                210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Gly Tyr Asp Met
                290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
                370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
                450                 455                 460

Glu Gly Trp Gly Glu Phe His Val Asn Gly Gly Ser Val Ser Ile Tyr
465                 470                 475                 480

Val Gln Arg

<210> SEQ ID NO 6
<211> LENGTH: 515
<212> TYPE: PRT
<213> ORGANISM: Geobacillus stearothermophilus
```

```
<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Asn Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Ser Thr Leu Met Asn Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415
```

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Trp Pro Ile Thr Thr
            485                 490                 495

Arg Pro Trp Thr Gly Glu Phe Val Arg Trp Thr Glu Pro Arg Leu Val
            500                 505                 510

Ala Trp Pro
        515

<210> SEQ ID NO 7
<211> LENGTH: 483
<212> TYPE: PRT
<213> ORGANISM: B. amyloliquefaciens

<400> SEQUENCE: 7

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
        50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn

```
            260                 265                 270
Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 8
<211> LENGTH: 485
<212> TYPE: PRT
<213> ORGANISM: Bacillus sp.

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
```

```
                145                 150                 155                 160
His Phe Asp Gly Val Asp Trp Asp Gln Ser Arg Arg Leu Asn Asn Arg
                    165                 170                 175

Ile Tyr Lys Phe Arg Gly His Gly Lys Ala Trp Asp Trp Glu Val Asp
                    180                 185                 190

Thr Glu Asn Gly Asn Tyr Asp Tyr Leu Met Tyr Ala Asp Ile Asp Met
                    195                 200                 205

Asp His Pro Glu Val Val Asn Glu Leu Arg Asn Trp Gly Val Trp Tyr
                    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                    245                 250                 255

Thr Gly Lys Asn Met Phe Ala Val Ala Glu Phe Trp Lys Asn Asp Leu
                    260                 265                 270

Gly Ala Ile Glu Asn Tyr Leu Gln Lys Thr Asn Trp Asn His Ser Val
                    275                 280                 285

Phe Asp Val Pro Leu His Tyr Asn Leu Tyr Asn Ala Ser Lys Ser Gly
                    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                    325                 330                 335

Glu Glu Ala Leu Glu Ser Phe Val Glu Trp Phe Lys Pro Leu Ala
                    340                 345                 350

Tyr Ala Leu Thr Leu Thr Arg Glu Gln Gly Tyr Pro Ser Val Phe Tyr
                    355                 360                 365

Gly Asp Tyr Tyr Gly Ile Pro Thr His Gly Val Pro Ala Met Arg Ser
                    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                    405                 410                 415

Gly Asn Thr Ala His Pro Asn Ser Gly Leu Ala Thr Ile Met Ser Asp
                    420                 425                 430

Gly Ala Gly Gly Ser Lys Trp Met Phe Val Gly Arg Asn Lys Ala Gly
                    435                 440                 445

Gln Val Trp Ser Asp Ile Thr Gly Asn Arg Thr Gly Thr Val Thr Ile
                    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 9
<211> LENGTH: 486
<212> TYPE: PRT
<213> ORGANISM: B. megaterium

<400> SEQUENCE: 9

Asp Thr Val Asn Gly Thr Leu Met Gln Tyr Phe Glu Trp Tyr Ala
1                   5                   10                  15

Pro Asn Asp Gly Asn His Trp Asn Arg Leu Arg Thr Asp Ala Glu Asn
                    20                  25                  30
```

-continued

```
Leu Ala Gln Lys Gly Ile Thr Ser Val Trp Ile Pro Ala Tyr Lys
         35                  40                  45

Gly Thr Thr Gln Asn Asp Val Gly Tyr Gly Ala Tyr Asp Leu Tyr Asp
 50                  55                  60

Leu Gly Glu Phe Asn Gln Lys Gly Thr Val Arg Thr Lys Tyr Gly Thr
 65                  70                  75                  80

Lys Ala Gln Leu Lys Ser Ala Ile Asp Ala Leu His Lys Lys Asn Ile
                 85                  90                  95

Asp Val Tyr Gly Asp Val Val Met Asn His Lys Gly Ala Asp Tyr
                100                 105                 110

Thr Glu Thr Val Thr Ala Val Glu Val Asp Pro Ser Asn Arg Asn Val
                115                 120                 125

Glu Val Ser Gly Asp Tyr Glu Ile Ser Ala Trp Thr Gly Phe Asn Phe
                130                 135                 140

Pro Gly Arg Gly Asp Ser Tyr Ser Asn Phe Lys Trp Lys Trp Tyr His
145                 150                 155                 160

Phe Asp Gly Thr Asp Trp Asp Glu Gly Arg Lys Leu Asn Arg Ile Tyr
                165                 170                 175

Lys Phe Arg Gly Ile Gly Lys Ala Trp Asp Trp Glu Val Ser Ser Glu
                180                 185                 190

Asn Gly Asn Tyr Asp Tyr Leu Met Tyr Ala Asp Leu Asp Phe Asp His
                195                 200                 205

Pro Asp Val Ala Asn Glu Met Lys Lys Trp Gly Thr Trp Tyr Ala Asn
                210                 215                 220

Glu Leu Asn Leu Asp Gly Phe Arg Leu Asp Ala Val Lys His Ile Asp
225                 230                 235                 240

His Glu Tyr Leu Arg Asp Trp Val Asn His Val Arg Gln Gln Thr Gly
                245                 250                 255

Lys Glu Met Phe Ala Val Ala Glu Tyr Trp Gln Asn Asp Ile Gln Thr
                260                 265                 270

Leu Asn Asn Tyr Leu Ala Lys Val Asn Tyr Asn Gln Ser Val Phe Asp
                275                 280                 285

Ala Pro Leu His Tyr Asn Phe His Tyr Ala Ser Lys Gly Asn Gly Asn
                290                 295                 300

Tyr Asp Met Arg Asn Ile Leu Lys Gly Thr Val Val Ala Asn His Pro
305                 310                 315                 320

Thr Leu Ala Val Thr Leu Val Glu Asn His Asp Ser Gln Pro Gly Gln
                325                 330                 335

Ser Leu Glu Ser Val Val Ser Pro Trp Phe Lys Pro Leu Ala Tyr Ala
                340                 345                 350

Phe Ile Leu Thr Arg Ala Glu Gly Tyr Pro Ser Val Phe Tyr Gly Asp
                355                 360                 365

Tyr Tyr Gly Thr Lys Gly Asn Ser Asn Tyr Glu Ile Pro Ala Leu Lys
                370                 375                 380

Asp Lys Ile Asp Pro Ile Leu Thr Ala Arg Lys Asn Tyr Ala Tyr Gly
385                 390                 395                 400

Thr Gln Arg Asp Tyr Phe Asp His Pro Asp Val Ile Gly Trp Thr Arg
                405                 410                 415

Glu Gly Asp Ser Val His Ala Asn Ser Gly Leu Ala Thr Leu Ile Ser
                420                 425                 430

Asp Gly Pro Gly Gly Ala Lys Trp Met Asp Val Gly Lys Asn Asn Ala
                435                 440                 445

Gly Glu Ile Trp Tyr Asp Ile Thr Gly Asn Gln Thr Asn Thr Val Thr
```

Ile Asn Lys Asp Gly Trp Gly Gln Phe Gln Val Ser Gly Gly Ser Val
465                 470                 475                 480

Ser Ile Tyr Val Gln Arg
                485

<210> SEQ ID NO 10
<211> LENGTH: 485
<212> TYPE: PRT
<213> ORGANISM: Bacillus sp.

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

-continued

```
Glu Glu Ala Leu Glu Ser Phe Val Glu Trp Phe Lys Pro Leu Ala
                340                 345                 350

Tyr Ala Leu Thr Leu Thr Arg Asp Gln Gly Tyr Pro Ser Val Phe Tyr
            355                 360                 365

Gly Asp Tyr Tyr Gly Ile Pro Thr His Gly Val Pro Ala Met Lys Ser
        370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 11
<211> LENGTH: 485
<212> TYPE: PRT
<213> ORGANISM: B. halmapalus

<400> SEQUENCE: 11

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
        130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220
```

```
Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
        260                 265                 270

Gly Ala Leu Glu Asn Tyr Leu Asn Lys Thr Asn Trp Asn His Ser Val
    275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
        450                 455                 460

Asn Ala Asp Gly Trp Ala Asn Phe Ser Val Asn Gly Gly Ser Val Ser
465                 470                 475                 480

Ile Trp Val Lys Arg
            485

<210> SEQ ID NO 12
<211> LENGTH: 485
<212> TYPE: PRT
<213> ORGANISM: Bacillus sp.

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
```

```
            100                 105                 110
Ala Thr Glu Met Val Arg Ala Glu Val Asn Pro Asn Arg Asn
            115                 120             125
Gln Glu Val Ser Gly Glu Tyr Thr Ile Glu Ala Trp Thr Lys Phe Asp
        130                 135             140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Lys Leu Asn Asn Arg
                    165                 170                 175
Ile Tyr Lys Phe Arg Gly Asp Gly Lys Gly Trp Asp Trp Glu Val Asp
                180                 185                 190
Thr Glu Asn Gly Asn Tyr Asp Tyr Leu Met Tyr Ala Asp Ile Asp Met
            195                 200                 205
Asp His Pro Glu Val Val Asn Glu Leu Arg Asn Trp Gly Val Trp Tyr
        210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Ile Asn His Val Arg Ser Ala
                245                 250                 255
Thr Gly Lys Asn Met Phe Ala Val Ala Glu Phe Trp Lys Asn Asp Leu
                260                 265                 270
Gly Ala Ile Glu Asn Tyr Leu Asn Lys Thr Asn Trp Asn His Ser Val
            275                 280                 285
Phe Asp Val Pro Leu His Tyr Asn Leu Tyr Asn Ala Ser Lys Ser Gly
        290                 295                 300
Gly Asn Tyr Asp Met Arg Gln Ile Phe Asn Gly Thr Val Val Gln Arg
305                 310                 315                 320
His Pro Met His Ala Val Thr Phe Val Asp Asn His Asp Ser Gln Pro
                325                 330                 335
Glu Glu Ala Leu Glu Ser Phe Val Glu Glu Trp Phe Lys Pro Leu Ala
                340                 345                 350
Tyr Ala Leu Thr Leu Thr Arg Glu Gln Gly Tyr Pro Ser Val Phe Tyr
            355                 360                 365
Gly Asp Tyr Tyr Gly Ile Pro Thr His Gly Val Pro Ala Met Lys Ser
        370                 375                 380
Lys Ile Asp Pro Ile Leu Glu Ala Arg Gln Lys Tyr Ala Tyr Gly Arg
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
                420                 425                 430
Gly Ala Gly Gly Asn Lys Trp Met Phe Val Gly Arg Asn Lys Ala Gly
            435                 440                 445
Gln Val Trp Thr Asp Ile Thr Gly Asn Arg Ala Gly Thr Val Thr Ile
        450                 455                 460
Asn Ala Asp Gly Trp Gly Asn Phe Ser Val Asn Gly Gly Ser Val Ser
465                 470                 475                 480

Ile Trp Val Asn Lys
            485

<210> SEQ ID NO 13
<211> LENGTH: 485
<212> TYPE: PRT
<213> ORGANISM: Bacillus sp.
```

<400> SEQUENCE: 13

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Met Val Asn Ala Val Glu Val Asn Arg Ser Asn Arg Asn
        115                 120                 125

Gln Glu Ile Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Ile Glu Asn Gly Asn Tyr Asp Tyr Leu Met Tyr Ala Asp Ile Asp Met
        195                 200                 205

Asp His Pro Glu Val Ile Asn Glu Leu Arg Asn Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
    290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Gly Val Pro Ser Met Lys Ser
    370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu

```
                    405                 410                 415
Gly Asp Ser Ser His Pro Asn Ser Gly Leu Ala Thr Ile Met Ser Asp
                420                 425                 430

Gly Pro Gly Gly Asn Lys Trp Met Tyr Val Gly Lys His Lys Ala Gly
            435                 440                 445

Gln Val Trp Arg Asp Ile Thr Gly Asn Arg Ser Gly Thr Val Thr Ile
        450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 14
<211> LENGTH: 480
<212> TYPE: PRT
<213> ORGANISM: Bacillus sp.

<400> SEQUENCE: 14

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285
```

```
Asn Tyr Asn Phe Tyr Arg Ala Ser Gln Gln Gly Gly Ser Tyr Asp Met
    290                 295                 300
Arg Asn Ile Leu Arg Gly Ser Leu Val Glu Ala His Pro Met His Ala
305                 310                 315                 320
Val Thr Phe Val Asp Asn His Asp Thr Gln Pro Gly Glu Ser Leu Glu
                325                 330                 335
Ser Trp Val Ala Asp Trp Phe Lys Pro Leu Ala Tyr Ala Thr Ile Leu
            340                 345                 350
Thr Arg Glu Gly Gly Tyr Pro Asn Val Phe Tyr Gly Asp Tyr Tyr Gly
        355                 360                 365
Ile Pro Asn Asp Asn Ile Ser Ala Lys Lys Asp Met Ile Asp Glu Leu
370                 375                 380
Leu Asp Ala Arg Gln Asn Tyr Ala Tyr Gly Thr Gln His Asp Tyr Phe
385                 390                 395                 400
Asp His Trp Asp Val Val Gly Trp Thr Arg Glu Gly Ser Ser Ser Arg
                405                 410                 415
Pro Asn Ser Gly Leu Ala Thr Ile Met Ser Asn Gly Pro Gly Gly Ser
            420                 425                 430
Lys Trp Met Tyr Val Gly Arg Gln Asn Ala Gly Gln Thr Trp Thr Asp
        435                 440                 445
Leu Thr Gly Asn Asn Gly Ala Ser Val Thr Ile Asn Gly Asp Gly Trp
    450                 455                 460
Gly Glu Phe Phe Thr Asn Gly Gly Ser Val Ser Val Tyr Val Asn Gln
465                 470                 475                 480

<210> SEQ ID NO 15
<211> LENGTH: 87
<212> TYPE: DNA
<213> ORGANISM: Artificial Sequence
<220> FEATURE:
<223> OTHER INFORMATION: Synthetic DNA - coding region for the LAT
      signal peptide

<400> SEQUENCE: 15
atgaaacaac aaaaacggct ttacgcccga ttgctgacgc tgttatttgc gctcatcttc      60
ttgctgcctc attctgcagc ttcagca                                         87

<210> SEQ ID NO 16
<211> LENGTH: 29
<212> TYPE: PRT
<213> ORGANISM: Artificial Sequence
<220> FEATURE:
<223> OTHER INFORMATION: Synthetic peptide - amino acid sequence of the
      LAT signal peptide

<400> SEQUENCE: 16

Met Lys Gln Gln Lys Arg Leu Tyr Ala Arg Leu Leu Thr Leu Leu Phe
1               5                   10                  15
Ala Leu Ile Phe Leu Leu Pro His Ser Ala Ala Ser Ala
            20                  25

<210> SEQ ID NO 17
<211> LENGTH: 33
<212> TYPE: DNA
<213> ORGANISM: Artificial Sequence
<220> FEATURE:
<223> OTHER INFORMATION: Synthetic primer: N128C_FW (128-FW)

<400> SEQUENCE: 17
gatccgagca accgttgcca ggaaaccagc ggc                                   33
```

<210> SEQ ID NO 18
<211> LENGTH: 33
<212> TYPE: DNA
<213> ORGANISM: Artificial Sequence
<220> FEATURE:
<223> OTHER INFORMATION: Synthetic primer: N128C_RV (128-RV)

<400> SEQUENCE: 18
gccgctggtt tcctggcaac ggttgctcgg atc                            33

<210> SEQ ID NO 19
<211> LENGTH: 44
<212> TYPE: DNA
<213> ORGANISM: Artificial Sequence
<220> FEATURE:
<223> OTHER INFORMATION: Synthetic primer: KGA/D_FW (KGA/D-FW)

<400> SEQUENCE: 19
ccgcatctat aaatttcgta gcggaggcaa agmytgggat tggg                44

<210> SEQ ID NO 20
<211> LENGTH: 44
<212> TYPE: DNA
<213> ORGANISM: Artificial Sequence
<220> FEATURE:
<223> OTHER INFORMATION: Synthetic primer: KGA/D_RV (KGA/D-RV)

<400> SEQUENCE: 20
cccaatccca rkctttgcct ccgctacgaa atttatagat gcgg                44

<210> SEQ ID NO 21
<211> LENGTH: 44
<212> TYPE: DNA
<213> ORGANISM: Artificial Sequence
<220> FEATURE:
<223> OTHER INFORMATION: Synthetic primer: LGA/D_FW (LGA/D-FW)

<400> SEQUENCE: 21
ccgcatctat ttatttcgta gcggaggcaa agmytgggat tggg                44

<210> SEQ ID NO 22
<211> LENGTH: 44
<212> TYPE: DNA
<213> ORGANISM: Artificial Sequence
<220> FEATURE:
<223> OTHER INFORMATION: Synthetic primer: LGA/D_RV (LGA/D-RV)

<400> SEQUENCE: 22
cccaatccca rkctttgcct ccgctacgaa ataaatagat gcgg                44

<210> SEQ ID NO 23
<211> LENGTH: 44
<212> TYPE: DNA
<213> ORGANISM: Artificial Sequence
<220> FEATURE:
<223> OTHER INFORMATION: Synthetic primer: KTA/D_FW (KTA/D-FW)

<400> SEQUENCE: 23
ccgcatctat aaatttcgta gcaccggcaa agmytgggat tggg                44

<210> SEQ ID NO 24
<211> LENGTH: 44
<212> TYPE: DNA
<213> ORGANISM: Artificial Sequence
<220> FEATURE:

<223> OTHER INFORMATION: Synthetic primer: KTA/D_RV (KTA/D-RV)

<400> SEQUENCE: 24
cccaatccca rkctttgccg gtgctacgaa atttatagat gcgg                44

<210> SEQ ID NO 25
<211> LENGTH: 44
<212> TYPE: DNA
<213> ORGANISM: Artificial Sequence
<220> FEATURE:
<223> OTHER INFORMATION: Synthetic primer: LTA/D_FW (LTA/D-FW)

<400> SEQUENCE: 25
ccgcatctat ttatttcgta gcaccggcaa agmytgggat tggg                44

<210> SEQ ID NO 26
<211> LENGTH: 44
<212> TYPE: DNA
<213> ORGANISM: Artificial Sequence
<220> FEATURE:
<223> OTHER INFORMATION: Synthetic primer: LTA/D_RV (LTA/D-RV)

<400> SEQUENCE: 26
cccaatccca rkctttgccg gtgctacgaa ataaatagat gcgg                44

<210> SEQ ID NO 27
<211> LENGTH: 25
<212> TYPE: DNA
<213> ORGANISM: Artificial Sequence
<220> FEATURE:
<223> OTHER INFORMATION: Synthetic primer: BASE-PstI-FW (PstI-Fw)

<400> SEQUENCE: 27
gctgcctcat tctgcagctt cagca                                     25

<210> SEQ ID NO 28
<211> LENGTH: 24
<212> TYPE: DNA
<213> ORGANISM: Artificial Sequence
<220> FEATURE:
<223> OTHER INFORMATION: Synthetic primer: BASE-HindIII-RV (HindIII-Rv)

<400> SEQUENCE: 28
ctgttttatc ctttaccttg tctc                                      24

<210> SEQ ID NO 29
<211> LENGTH: 34
<212> TYPE: DNA
<213> ORGANISM: Artificial Sequence
<220> FEATURE:
<223> OTHER INFORMATION: Synthetic primer: BASE-N128C-FW (Pr1)

<400> SEQUENCE: 29
ggatccgagc aaccgttgcc aggaaaccag cggc                           34

<210> SEQ ID NO 30
<211> LENGTH: 34
<212> TYPE: DNA
<213> ORGANISM: Artificial Sequence
<220> FEATURE:
<223> OTHER INFORMATION: Synthetic primer: BASE-N128C-RV (Pr2)

<400> SEQUENCE: 30
gccgctggtt tcctggcaac ggttgctcgg atcc                           34

```
<210> SEQ ID NO 31
<211> LENGTH: 34
<212> TYPE: DNA
<213> ORGANISM: Artificial Sequence
<220> FEATURE:
<223> OTHER INFORMATION: Synthetic primer: BASE-S125A-N128C-FW (Pr3)

<400> SEQUENCE: 31
ggatccggcc aaccgttgcc aggaaaccag cggc                                34

<210> SEQ ID NO 32
<211> LENGTH: 34
<212> TYPE: DNA
<213> ORGANISM: Artificial Sequence
<220> FEATURE:
<223> OTHER INFORMATION: Synthetic primer: BASE-S125A-N128C-RV (Pr4)

<400> SEQUENCE: 32
gccgctggtt tcctggcaac ggttggccgg atcc                                34

<210> SEQ ID NO 33
<211> LENGTH: 43
<212> TYPE: DNA
<213> ORGANISM: Artificial Sequence
<220> FEATURE:
<223> OTHER INFORMATION: Synthetic primer: BASE-K178L-T182G-FW (Pr5)

<400> SEQUENCE: 33
gaaccgcatc tatctatttc gtagcggcgg caaagcgtgg gat                      43

<210> SEQ ID NO 34
<211> LENGTH: 43
<212> TYPE: DNA
<213> ORGANISM: Artificial Sequence
<220> FEATURE:
<223> OTHER INFORMATION: Synthetic primer: BASE-K178L-T182G-RV (Pr6)

<400> SEQUENCE: 34
atcccacgct ttgccgccgc tacgaaatag atagatgcgg ttc                      43

<210> SEQ ID NO 35
<211> LENGTH: 43
<212> TYPE: DNA
<213> ORGANISM: Artificial Sequence
<220> FEATURE:
<223> OTHER INFORMATION: Synthetic primer: BASE-K178L-T182G-G183N-FW
     (Pr7)

<400> SEQUENCE: 35
gaaccgcatc tatctatttc gtagcggcaa caaagcgtgg gat                      43

<210> SEQ ID NO 36
<211> LENGTH: 43
<212> TYPE: DNA
<213> ORGANISM: Artificial Sequence
<220> FEATURE:
<223> OTHER INFORMATION: Synthetic primer: BASE-K178L-T182G-G183N-RV
     (Pr8)

<400> SEQUENCE: 36
atcccacgct ttgttgccgc tacgaaatag atagatgcgg ttc                      43

<210> SEQ ID NO 37
<211> LENGTH: 43
<212> TYPE: DNA
<213> ORGANISM: Artificial Sequence
<220> FEATURE:
```

<223> OTHER INFORMATION: Synthetic primer: BASE-K178L-T182A-FW (Pr9)

<400> SEQUENCE: 37
gaaccgcatc tatctatttc gtagcgccgg caaagcgtgg gat         43

<210> SEQ ID NO 38
<211> LENGTH: 43
<212> TYPE: DNA
<213> ORGANISM: Artificial Sequence
<220> FEATURE:
<223> OTHER INFORMATION: Synthetic primer: BASE-K178L-T182A-RV (Pr10)

<400> SEQUENCE: 38
atcccacgct ttgccggcgc tacgaaatag atagatgcgg ttc         43

<210> SEQ ID NO 39
<211> LENGTH: 40
<212> TYPE: DNA
<213> ORGANISM: Artificial Sequence
<220> FEATURE:
<223> OTHER INFORMATION: Synthetic primer: BASE-S243Q-FW (Pr11)

<400> SEQUENCE: 39
ggtgaaacac atcaaatacc aattttttcc ggattggctg              40

<210> SEQ ID NO 40
<211> LENGTH: 40
<212> TYPE: DNA
<213> ORGANISM: Artificial Sequence
<220> FEATURE:
<223> OTHER INFORMATION: Synthetic primer: BASE-S243Q-RV (Pr12)

<400> SEQUENCE: 40
cagccaatcc ggaaaaaatt ggtatttgat gtgtttcacc              40

<210> SEQ ID NO 41
<211> LENGTH: 43
<212> TYPE: DNA
<213> ORGANISM: Artificial Sequence
<220> FEATURE:
<223> OTHER INFORMATION: Synthetic primer: BASE-T182G-FW (Pr13)

<400> SEQUENCE: 41
gaaccgcatc tataaatttc gtagcggcgg caaagcgtgg gat         43

<210> SEQ ID NO 42
<211> LENGTH: 43
<212> TYPE: DNA
<213> ORGANISM: Artificial Sequence
<220> FEATURE:
<223> OTHER INFORMATION: Synthetic primer: BASE-T182G-RV (Pr14)

<400> SEQUENCE: 42
atcccacgct ttgccgccgc tacgaaattt atagatgcgg ttc         43

<210> SEQ ID NO 43
<211> LENGTH: 43
<212> TYPE: DNA
<213> ORGANISM: Artificial Sequence
<220> FEATURE:
<223> OTHER INFORMATION: Synthetic primer: BASE-T182G-G182N-FW (Pr15)

<400> SEQUENCE: 43
gaaccgcatc tataaatttc gtagcggcaa caaagcgtgg gat         43

```
<210> SEQ ID NO 44
<211> LENGTH: 43
<212> TYPE: DNA
<213> ORGANISM: Artificial Sequence
<220> FEATURE:
<223> OTHER INFORMATION: Synthetic primer: BASE-T182G-G182N-RV (Pr16)

<400> SEQUENCE: 44
atcccacgct tgttgccgc tacgaaattt atagatgcgg ttc                          43

<210> SEQ ID NO 45
<211> LENGTH: 43
<212> TYPE: DNA
<213> ORGANISM: Artificial Sequence
<220> FEATURE:
<223> OTHER INFORMATION: Synthetic primer: BASE-T182A-FW  (Pr17)

<400> SEQUENCE: 45
gaaccgcatc tataaatttc gtagcgccgg caaagcgtgg gat                         43

<210> SEQ ID NO 46
<211> LENGTH: 43
<212> TYPE: DNA
<213> ORGANISM: Artificial Sequence
<220> FEATURE:
<223> OTHER INFORMATION: Synthetic primer: BASE-T182A-RV  (Pr18)

<400> SEQUENCE: 46
atcccacgct tgccggcgc tacgaaattt atagatgcgg ttc                          43

<210> SEQ ID NO 47
<211> LENGTH: 25
<212> TYPE: DNA
<213> ORGANISM: Artificial Sequence
<220> FEATURE:
<223> OTHER INFORMATION: Synthetic primer: BASE-PstI-FW  (Pr19)

<400> SEQUENCE: 47
gctgcctcat tctgcagctt cagca                                             25

<210> SEQ ID NO 48
<211> LENGTH: 25
<212> TYPE: DNA
<213> ORGANISM: Artificial Sequence
<220> FEATURE:
<223> OTHER INFORMATION: Synthetic primer: BASE-HindIII-RV  (Pr20)

<400> SEQUENCE: 48
gctgttttat cctttacctt gtctc                                             25

<210> SEQ ID NO 49
<211> LENGTH: 29
<212> TYPE: DNA
<213> ORGANISM: Artificial Sequence
<220> FEATURE:
<223> OTHER INFORMATION: Synthetic primer: pHPLT-PstI-FW

<400> SEQUENCE: 49
ctcattctgc agcttcagca aatacggcg                                         29

<210> SEQ ID NO 50
<211> LENGTH: 35
<212> TYPE: DNA
<213> ORGANISM: Artificial Sequence
<220> FEATURE:
<223> OTHER INFORMATION: Synthetic primer: pHPLT-HpaI-RV
```

<400> SEQUENCE: 50
ctctgttaac tcatttggcg acccagattg aaacg					35

<210> SEQ ID NO 51
<211> LENGTH: 31
<212> TYPE: DNA
<213> ORGANISM: Artificial Sequence
<220> FEATURE:
<223> OTHER INFORMATION: Synthetic primer: TS-delRS-FW

<400> SEQUENCE: 51
ctataaattt acgggcaaag catgggattg g					31

<210> SEQ ID NO 52
<211> LENGTH: 33
<212> TYPE: DNA
<213> ORGANISM: Artificial Sequence
<220> FEATURE:
<223> OTHER INFORMATION: Synthetic primer: TS-delRS-RV

<400> SEQUENCE: 52
tgctttgccc gtaaatttat agatccggtt cag					33

<210> SEQ ID NO 53
<211> LENGTH: 33
<212> TYPE: DNA
<213> ORGANISM: Artificial Sequence
<220> FEATURE:
<223> OTHER INFORMATION: Synthetic primer: ACE-S243Q-FW

<400> SEQUENCE: 53
caaacatatc aaatatcaat tttttccgga ctg					33

<210> SEQ ID NO 54
<211> LENGTH: 33
<212> TYPE: DNA
<213> ORGANISM: Artificial Sequence
<220> FEATURE:
<223> OTHER INFORMATION: Synthetic primer: ACE-S243Q-RV

<400> SEQUENCE: 54
cagtccggaa aaaattgata tttgatatgt ttg					33

<210> SEQ ID NO 55
<211> LENGTH: 32
<212> TYPE: DNA
<213> ORGANISM: Artificial Sequence
<220> FEATURE:
<223> OTHER INFORMATION: Synthetic primer: ACE-Q-R127-FW
<220> FEATURE:
<221> NAME/KEY: misc_feature
<222> LOCATION: (16)..(17)
<223> OTHER INFORMATION: n is a, c, g, or t

<400> SEQUENCE: 55
gttgatccga gcaacnnsaa ccaagaaacg ag					32

<210> SEQ ID NO 56
<211> LENGTH: 32
<212> TYPE: DNA
<213> ORGANISM: Artificial Sequence
<220> FEATURE:
<223> OTHER INFORMATION: Synthetic primer: ACE-Q-R127-RV
<220> FEATURE:
<221> NAME/KEY: misc_feature
<222> LOCATION: (16)..(17)
<223> OTHER INFORMATION: n is a, c, g, or t

<400> SEQUENCE: 56
ctcgtttctt ggttsnngtt gctcggatca ac                                      32

<210> SEQ ID NO 57
<211> LENGTH: 33
<212> TYPE: DNA
<213> ORGANISM: Artificial Sequence
<220> FEATURE:
<223> OTHER INFORMATION: Synthetic primer: ACE-Q-Y305-FW
<220> FEATURE:
<221> NAME/KEY: misc_feature
<222> LOCATION: (15)..(16)
<223> OTHER INFORMATION: n is a, c, g, or t

<400> SEQUENCE: 57
gcaaaagctc aggcnnsttt gatatgagat atc                                     33

<210> SEQ ID NO 58
<211> LENGTH: 33
<212> TYPE: DNA
<213> ORGANISM: Artificial Sequence
<220> FEATURE:
<223> OTHER INFORMATION: Synthetic primer: ACE-Q-Y305-RV
<220> FEATURE:
<221> NAME/KEY: misc_feature
<222> LOCATION: (18)..(19)
<223> OTHER INFORMATION: n is a, c, g, or t

<400> SEQUENCE: 58
gatatctcat atcaaasnng cctgagcttt tgc                                     33

<210> SEQ ID NO 59
<211> LENGTH: 32
<212> TYPE: DNA
<213> ORGANISM: Artificial Sequence
<220> FEATURE:
<223> OTHER INFORMATION: Synthetic primer: ACE-Q-Q320-FW
<220> FEATURE:
<221> NAME/KEY: misc_feature
<222> LOCATION: (15)..(16)
<223> OTHER INFORMATION: n is a, c, g, or t

<400> SEQUENCE: 59
cgctgatgaa agatnnsccg agcctggcag tc                                      32

<210> SEQ ID NO 60
<211> LENGTH: 32
<212> TYPE: DNA
<213> ORGANISM: Artificial Sequence
<220> FEATURE:
<223> OTHER INFORMATION: Synthetic primer: ACE-Q-Q320-RV
<220> FEATURE:
<221> NAME/KEY: misc_feature
<222> LOCATION: (17)..(18)
<223> OTHER INFORMATION: n is a, c, g, or t

<400> SEQUENCE: 60
gactgccagg ctcggsnnat ctttcatcag cg                                      32

<210> SEQ ID NO 61
<211> LENGTH: 29
<212> TYPE: DNA
<213> ORGANISM: Artificial Sequence
<220> FEATURE:
<223> OTHER INFORMATION: Synthetic primer: ACE-Q-P379-FW
<220> FEATURE:
<221> NAME/KEY: misc_feature
<222> LOCATION: (15)..(16)

<223> OTHER INFORMATION: n is a, c, g, or t

<400> SEQUENCE: 61
cgaaatataa tatcnnsggc ctgaaaagc                                               29

<210> SEQ ID NO 62
<211> LENGTH: 29
<212> TYPE: DNA
<213> ORGANISM: Artificial Sequence
<220> FEATURE:
<223> OTHER INFORMATION: Synthetic primer: ACE-Q-P379-RV
<220> FEATURE:
<221> NAME/KEY: misc_feature
<222> LOCATION: (14)..(15)
<223> OTHER INFORMATION: n is a, c, g, or t

<400> SEQUENCE: 62
gcttttcagg ccsnngatat tatatttcg                                               29

<210> SEQ ID NO 63
<211> LENGTH: 30
<212> TYPE: DNA
<213> ORGANISM: Artificial Sequence
<220> FEATURE:
<223> OTHER INFORMATION: Synthetic primer: ACE-Q-T419-FW
<220> FEATURE:
<221> NAME/KEY: misc_feature
<222> LOCATION: (15)..(16)
<223> OTHER INFORMATION: n is a, c, g, or t

<400> SEQUENCE: 63
gagaaggcat cgatnnsaaa ccgaatagcg                                              30

<210> SEQ ID NO 64
<211> LENGTH: 30
<212> TYPE: DNA
<213> ORGANISM: Artificial Sequence
<220> FEATURE:
<223> OTHER INFORMATION: Synthetic primer: ACE-Q-T419-RV
<220> FEATURE:
<221> NAME/KEY: misc_feature
<222> LOCATION: (15)..(16)
<223> OTHER INFORMATION: n is a, c, g, or t

<400> SEQUENCE: 64
cgctattcgg tttsnnatcg atgccttctc                                              30

<210> SEQ ID NO 65
<211> LENGTH: 34
<212> TYPE: DNA
<213> ORGANISM: Artificial Sequence
<220> FEATURE:
<223> OTHER INFORMATION: Synthetic primer: ACE-Q-L453-FW
<220> FEATURE:
<221> NAME/KEY: misc_feature
<222> LOCATION: (17)..(18)
<223> OTHER INFORMATION: n is a, c, g, or t

<400> SEQUENCE: 65 caaagtctttt tatgatnnsa cgggcaacag aagc                                        34

<210> SEQ ID NO 66
<211> LENGTH: 34
<212> TYPE: DNA
<213> ORGANISM: Artificial Sequence
<220> FEATURE:
<223> OTHER INFORMATION: Synthetic primer: ACE-Q-L453-RV
<220> FEATURE:
<221> NAME/KEY: misc_feature -continued

```
<222> LOCATION: (17)..(18)
<223> OTHER INFORMATION: n is a, c, g, or t

<400> SEQUENCE: 66
gcttctgttg cccgtsnnat cataaaagac tttg                    34

<210> SEQ ID NO 67
<211> LENGTH: 33
<212> TYPE: DNA
<213> ORGANISM: Artificial Sequence
<220> FEATURE:
<223> OTHER INFORMATION: Synthetic primer: ACE-Q-G475-FW
<220> FEATURE:
<221> NAME/KEY: misc_feature
<222> LOCATION: (16)..(17)
<223> OTHER INFORMATION: n is a, c, g, or t

<400> SEQUENCE: 67
gaatttaaag tcaatnnsgg cagcgtttca atc                     33

<210> SEQ ID NO 68
<211> LENGTH: 33
<212> TYPE: DNA
<213> ORGANISM: Artificial Sequence
<220> FEATURE:
<223> OTHER INFORMATION: Synthetic primer: ACE-Q-G475-RV
<220> FEATURE:
<221> NAME/KEY: misc_feature
<222> LOCATION: (17)..(18)
<223> OTHER INFORMATION: n is a, c, g, or t

<400> SEQUENCE: 68
gattgaaacg ctgccsnnat tgactttaaa ttc                     33

<210> SEQ ID NO 69
<211> LENGTH: 29
<212> TYPE: DNA
<213> ORGANISM: Artificial Sequence
<220> FEATURE:
<223> OTHER INFORMATION: Synthetic primer: pHPLT-BglII-FW

<400> SEQUENCE: 69
gcaatcagat cttccttcag gttatgacc                          29

<210> SEQ ID NO 70
<211> LENGTH: 30
<212> TYPE: DNA
<213> ORGANISM: Artificial Sequence
<220> FEATURE:
<223> OTHER INFORMATION: Synthetic primer: pHPLT-BglII-RV

<400> SEQUENCE: 70
gcatcgaaga tctgattgct taactgcttc                         30
```